United States Patent
Tuna et al.

(10) Patent No.: US 12,312,408 B2
(45) Date of Patent: May 27, 2025

(54) MULTISPECIFIC ANTI-TCR DELTA VARIABLE 1 ANTIBODIES

(71) Applicants: GammaDelta Therapeutics Ltd, London (GB); F-star Therapeutics Limited, Cambridge (GB)

(72) Inventors: Mihriban Tuna, Cambridge (GB); Mark Uden, London (GB); Joshua Freedman, London (GB); Natalie Mount, London (GB)

(73) Assignees: GammaDelta Therapeutics Ltd, London (GB); F-star Therapeutics Limited, Cambridge (GB)

( * ) Notice: Subject to any disclaimer, the term of this patent is extended or adjusted under 35 U.S.C. 154(b) by 0 days.

(21) Appl. No.: 18/451,047

(22) Filed: Aug. 16, 2023

(65) Prior Publication Data

US 2024/0132599 A1   Apr. 25, 2024

Related U.S. Application Data

(63) Continuation of application No. PCT/EP2022/054011, filed on Feb. 17, 2022.

(30) Foreign Application Priority Data

Feb. 17, 2021   (GB) ..................... 2102224
Aug. 14, 2021   (GB) ..................... 2111685

(51) Int. Cl.
*C07K 16/28*   (2006.01)

(52) U.S. Cl.
CPC ...... *C07K 16/2863* (2013.01); *C07K 16/2809* (2013.01); *C07K 2317/31* (2013.01)

(58) Field of Classification Search
CPC ........... C07K 16/2863; C07K 16/2809; C07K 2317/31
USPC ..................................... 424/136.1
See application file for complete search history.

(56) References Cited

U.S. PATENT DOCUMENTS

| | | | | |
|---|---|---|---|---|
| 9,334,331 | B2 * | 5/2016 | Igawa | C07K 16/36 |
| 10,421,807 | B2 * | 9/2019 | Gonzales | A61P 17/08 |
| 11,629,193 | B2 * | 4/2023 | Tuna | C07K 16/2863 |
| | | | | 424/136.1 |
| 2019/0119634 | A1 | 4/2019 | Jakobovits et al. | |
| 2022/0403025 | A1 | 12/2022 | Mount et al. | |
| 2023/0028110 | A1 * | 1/2023 | Tuna | C07K 16/2863 |
| 2023/0090901 | A1 | 3/2023 | Polyakova et al. | |
| 2024/0376215 | A1 * | 11/2024 | Tuna | C07K 16/30 |

FOREIGN PATENT DOCUMENTS

| | | |
|---|---|---|
| JP | 2019-519210 A | 7/2019 |
| WO | WO 03/080672 A1 | 10/2003 |
| WO | WO 2016/166544 A1 | 10/2016 |
| WO | WO 2016/198480 A1 | 12/2016 |
| WO | WO 2017/197347 A1 | 11/2017 |
| WO | WO 2019/147735 A1 | 8/2019 |
| WO | WO 2020/060406 A1 | 3/2020 |
| WO | WO 2020/159368 A1 | 8/2020 |
| WO | WO 2021/032960 A1 | 2/2021 |
| WO | WO 2021/032961 A1 | 2/2021 |
| WO | WO 2021/032963 A1 | 2/2021 |
| WO | WO 2022/175414 A1 | 8/2022 |

OTHER PUBLICATIONS

Al Qaraghuli et al. (2020, Nature Scientific Reports 10:13969).*
Edwards et al. (2003, JMB 334:103-118).*
Lloyd et al. (2009, Protein Engineering, Eng. Design & Selection 22(3): 159-168).*
Goel et al. (2004, J. Immunol. 173: 7358-7367).*
Khan et al. (2014, J. Immunol. 192: 5398-5405).*
Poosarla et al. (2017, Biotechn. Bioeng. 114(6): 1331-1342).*
International Search Report and Written Opinion for Application No. PCT/GB2020/051959, mailed Mar. 3, 2022.
International Preliminary Report on Patentability for Application No. PCT/GB2020/051959, mailed Oct. 30, 2020.
International Search Report and Written Opinion for Application No. PCT/EP2022/054011, mailed May 30, 2022.
International Preliminary Report on Patentability for Application No. PCT/EP2022/054011, mailed Aug. 31, 2023.
International Search Report and Written Opinion for Application No. PCT/EP2022/054004, mailed May 24, 2022.
International Preliminary Report on Patentability for Application No. PCT/EP2022/054004, mailed Aug. 31, 2023.
Almagro et al., Progress and Challenges in the Design and Clinical Development of Antibodies for Cancer Therapy. Front Immunol. Jan. 4, 2018;8:1751. doi: 10.3389/fimmu.2017.01751. eCollection 2017.
Brown et al., Tolerance of single, but not multiple, amino acid replacements in antibody VH CDR 2: a means of minimizing B cell wastage from somatic hypermutation? J Immunol. May 1, 1996;156(9):3285-91.
Chitadze et al., The Ambiguous Role of γδ T Lymphocytes in Antitumor Immunity. Trends Immunol. Sep. 2017;38(9):668-678. doi: 10.1016/j.it.2017.06.004. Epub Jul. 11, 2017.
Chiu et al., Antibody Structure and Function: The Basis for Engineering Therapeutics. Antibodies (Basel). Dec. 3, 2019;8(4):55. doi: 10.3390/antib8040055.
Davey et al., Clonal selection in the human Vδ1 T cell repertoire indicates γδ TCR-dependent adaptive immune surveillance. Nat Commun. Mar. 1, 2017;8:14760. doi: 10.1038/ncomms14760.

(Continued)

*Primary Examiner* — Lynn A Bristol
(74) *Attorney, Agent, or Firm* — Wolf, Greenfield & Sacks, P.C.

(57) ABSTRACT

The present invention provides multispecific antibodies comprising a Fab region and an Fc region, wherein the Fab region comprises a binding site specific for an epitope of the variable delta 1 (Vδ1) chain of a γδ T cell receptor (TCR); and the Fc region comprises an EGFR binding site. The present invention also provides compositions and pharmaceutical compositions comprising such multispecific antibodies, and method of making such multispecific antibodies. The present invention also provides methods of treatment and medical uses involving the multispecific antibodies.

14 Claims, 91 Drawing Sheets

Specification includes a Sequence Listing.

(56) References Cited

OTHER PUBLICATIONS

De Bruin et al., A bispecific nanobody approach to leverage the potent and widely applicable tumor cytolytic capacity of Vγ9Vδ2-T cells. Oncoimmunology. Oct. 20, 2017;7(1):e1375641. doi: 10.1080/2162402X.2017.1375641. eCollection 2017.
De Weerdt et al., A Bispecific Single-Domain Antibody Boosts Autologous Vγ9Vδ2-T Cell Responses Toward CD1d in Chronic Lymphocytic Leukemia. Clin Cancer Res. Mar. 15, 2021;27(6):1744-1755. doi: 10.1158/1078-0432.CCR-20-4576. Epub Jan. 15, 2021.
Deniger et al., Clinical applications of gamma delta T cells with multivalent immunity. Front Immunol. Dec. 11, 2014;5:636. doi: 10.3389/fimmu.2014.00636. eCollection 2014.
Fisher et al., Engineering Approaches in Human Gamma Delta T Cells for Cancer Immunotherapy. Front Immunol. Jun. 26, 2018;9:1409. doi: 10.3389/fimmu.2018.01409. eCollection 2018.
Garber, γδ T cells bring unconventional cancer-targeting to the clinic—again. Nat Biotechnol. Apr. 2020;38(4):389-391. doi: 10.1038/s41587-020-0487-2.
Knight et al., Human Vdeltal gamma-delta T cells exert potent specific cytotoxicity against primary multiple myeloma cells. Cytotherapy. Oct. 2012;14(9):1110-8. doi: 10.3109/14653249.2012.700766. Epub Jul. 17, 2012.
Oberg et al., Bispecific antibodies enhance tumor-infiltrating T cell cytotoxicity against autologous HER-2-expressing high-grade ovarian tumors. J Leukoc Biol. Jun. 2020;107(6):1081-1095. doi: 10.1002/JLB.5MA1119-265R. Epub Dec. 13, 2019.
Oberg et al., Novel bispecific antibodies increase γδ T-cell cytotoxicity against pancreatic cancer cells. Cancer Res. Mar. 1, 2014;74(5):1349-60. doi: 10.1158/0008-5472.CAN-13-0675. Epub Jan. 21, 2014.
Romagné et al., Structural analysis of γδ TCR using a novel set of TCR γ and δ chain-specific monoclonal antibodies generated against soluble γδ TCR: Evidence for a specific conformation adopted by the Jδ2 region and for a Vδ1 polymorphism. J Immunol Methods. Jan. 16, 1996;189(1):25-36. doi: 10.1016/0022-1759(95)00224-3.
Rudikoff et al., Single amino acid substitution altering antigen-binding specificity. Proc Natl Acad Sci U S A. Mar. 1982;79(6):1979-83. doi: 10.1073/pnas.79.6.1979.
Sebestyen et al., Translating gammadelta (γδ) T cells and their receptors into cancer cell therapies. Nat Rev Drug Discov. Mar. 2020;19(3):169-184. doi: 10.1038/s41573-019-0038-z. Epub Sep. 6, 2019.
Siegers et al., Cytotoxic and regulatory properties of circulating Vδ1+ γδ T cells: a new player on the cell therapy field? Mol Ther. Aug. 2014;22(8):1416-1422. doi: 10.1038/mt.2014.104. Epub Jun. 4, 2014.
Invitation to Pay Additional Fees for Application No. PCT/GB2021/050459, mailed Jun. 7, 2021.
International Search Report and Written Opinion for Application No. PCT/GB2021/050459, mailed Jul. 28, 2021.
International Preliminary Report on Patentability for Application No. PCT/GB2021/050459, mailed Sep. 9, 2022.
Abeler-Dörner et al., Butyrophilins: an emerging family of immune regulators. Trends Immunol. Jan. 2012;33(1):34-41. doi: 10.1016/j.it.2011.09.007. Epub Oct. 24, 2011.
Almeida et al., Delta One T Cells for Immunotherapy of Chronic Lymphocytic Leukemia: Clinical-Grade Expansion/Differentiation and Preclinical Proof of Concept. Clin Cancer Res. Dec. 1, 2016;22(23):5795-5804. doi: 10.1158/1078-0432.CCR-16-0597. Epub Jun. 15, 2016.
Aruda et al., Impact of gd T cells on clinical outcome of hematopoietic stem cell transplantation: systematic review and meta-analysis. Blood Adv. 2019; 3 (21): 3436-3448. https://doi.org/10.1182/bloodadvances.2019000682.
Blink et al., γδ T cell subsets play opposing roles in regulating experimental autoimmune encephalomyelitis. Cell Immunol. Jul. 2014;290(1):39-51. doi: 10.1016/j.cellimm.2014.04.013. Epub May 10, 2014. Author Manuscript (29 pages).

Catellani et al., Expansion of Vdeltal T lymphocytes producing IL-4 in low-grade non-Hodgkin lymphomas expressing UL-16-binding proteins. Blood. Mar. 1, 2007;109(5):2078-85. doi: 10.1182/blood-2006-06-028985. Epub Sep. 14, 2006.
Cordova et al., Characterization of human γδ T lymphocytes infiltrating primary malignant melanomas. Plos ONE. 2012;7(11):e49878. doi: 10.1371/journal.pone.0049878. Epub Nov. 26, 2012.
Davodeau et al., Surface expression of two distinct functional antigen receptors on human gamma delta T cells. Science. Jun. 18, 1993;260(5115):1800-2. doi: 10.1126/science.8390096.
De Libero et al., Selection by two powerful antigens may account for the presence of the major population of human peripheral gamma/delta T cells. J Exp Med. Jun. 1, 1991;173(6):1311-22. doi: 10.1084/jem.173.6.1311.
Di Lorenzo et al., Broad Cytotoxic Targeting of Acute Myeloid Leukemia by Polyclonal Delta One T Cells. Cancer Immunol Res. Apr. 2019;7(4):552-558. doi: 10.1158/2326-6066.CIR-18-0647. Epub Mar. 20, 2019.
Dondelinger et al., Understanding the Significance and Implications of Antibody Numbering and Antigen-Binding Surface/Residue Definition. Front Immunol. Oct. 16, 2018;9:2278. doi: 10.3389/fimmu.2018.02278. eCollection 2018.
Dutta et al., Apoptosis Induced via Gamma Delta T Cell Antigen Receptor "Blocking" Antibodies: A Cautionary Tale. Front Immunol. Jun. 30, 2017;8:776. doi: 10.3389/fimmu.2017.00776. eCollection 2017.
Ferrarini et al., Killing of laminin receptor-positive human lung cancers by tumor-infiltrating lymphocytes bearing γσ+ T-cell receptors. J Natl Cancer Inst. Apr. 3, 1996;88(7):436-41. doi: 10.1093/jnci/88.7.436.
Fisher et al., Neuroblastoma killing properties of Vδ2 and Vδ2-negative γδT cells following expansion by artificial antigen-presenting cells. Clin Cancer Res. Nov. 15, 2014;20(22):5720-32. doi: 10.1158/1078-0432.CCR-13-3464. Epub Jun. 3, 2014.
Gentles et al., The prognostic landscape of genes and infiltrating immune cells across human cancers. Nat Med. Author manuscript; available in PMC May 2, 2016. Published in final edited form as: Nat Med. Aug. 2015; 21(8): 938-945. Published online Jul. 20, 2015. doi: 10.1038/nm.3909.
Godder et al., Long term disease-free survival in acute leukemia patients recovering with increased gammadelta T cells after partially mismatched related donor bone marrow transplantation. Bone Marrow Transplant. Jun. 2007;39(12):751-7. doi: 10.1038/sj.bmt.1705650. Epub Apr. 23, 2007.
Groh et al., Broad tumor-associated expression and recognition by tumor-derived gamma delta T cells of MICA and MICB. Proc Natl Acad Sci U S A. Jun. 8, 1999;96(12):6879-84. doi: 10.1073/pnas.96.12.6879.
Jefferis et al., Human immunoglobulin allotypes: possible implications for immunogenicity. Mabs. Jul.-Aug. 2009;1(4):332-8. doi: 10.4161/mabs.1.4.9122.
Khairallah et al., γδ T cells confer protection against murine cytomegalovirus (MCMV). PLoS Pathog. Mar. 6, 2015;11(3):e1004702. doi: 10.1371/journal.ppat.1004702. eCollection Mar. 2015.
Kim et al., Spectrum of EGFR Gene Copy No. Changes and KRAS Gene Mutation Status in Korean Triple Negative Breast Cancer Patients. PLoS One. Oct. 30, 2013;8(10):e79014. doi: 10.1371/journal.pone.0079014. eCollection 2013.
Kitayama et al., Functional analysis of TCR gamma delta+ T cells in tumour-infiltrating lymphocytes (TIL) of human pancreatic cancer. Clin Exp Immunol. Sep. 1993;93(3):442-7. doi: 10.1111/j.1365-2249.1993.tb08198.x.
Langerak et al., Immunophenotypic and immunogenotypic characteristics of TCRgammadelta+ T cell acute lymphoblastic leukemia. Leukemia. Feb. 1999;13(2):206-14. doi: 10.1038/sj.leu.2401276.
Licitra et al., Evaluation of EGFR gene copy No. as a predictive biomarker for the efficacy of cetuximab in combination with chemotherapy in the first-line treatment of recurrent and/or metastatic squamous cell carcinoma of the head and neck: Extreme study. Ann Oncol. May 2011;22(5):1078-1087. doi: 10.1093/annonc/mdq588. Epub Nov. 3, 2010.
Luoma et al., Crystal structure of Vδ1 T cell receptor in complex with CD1d-sulfatide shows MHC-like recognition of a self-lipid by

(56) References Cited

OTHER PUBLICATIONS human γδ T cells. Immunity. Dec. 12, 2013;39(6):1032-42. doi: 10.1016/j.immuni.2013.11.001. Epub Nov. 14, 2013.
Maeurer et al., Human intestinal Vdelta1+ lymphocytes recognize tumor cells of epithelial origin. J Exp Med. Apr. 1, 1996;183(4):1681-96. doi: 10.1084/jem.183.4.1681.
Mahvi et al., Overexpression of 27-kDa heat-shock protein in MCF-7 breast cancer cells: effects on lymphocyte-mediated killing by natural killer and gamma delta T cells. Cancer Immunol Immunother. Aug. 1993;37(3):181-6. doi: 10.1007/BF01525433.
Mayassi et al., Chronic Inflammation Permanently Reshapes Tissue-Resident Immunity in Celiac Disease. Cell. Feb. 21, 2019;176(5):967-981.e19. doi: 10.1016/j.cell.2018.12.039. Epub Feb. 7, 2019.
Mikulak et al., NKp46-expressing human gut-resident intraepithelial VδT cell subpopulation exhibits high antitumor activity against colorectal cancer. JCI Insight. Dec. 19, 2019;4(24):e125884. doi: 10.1172/jci.insight.125884.
No Author Listed, Purified anti-mouse TCR V[gamma]4 Antibody Antigen. Biolegend. Version 1. Last revised: Aug. 10, 2020. Retrieved from the Internet: URL: https://www.biolegend.com/en-ie/global-elements/pdf-popup/purified-anti-mouse-tcr-vy4-antibody-19846?filename=Purified%20anti-mouse%20TCR%20Vgamma4%20Antibody.pdf&pdfgen=true. [retrieved on Sep. 29, 2022].
Poccia et al., Anti-severe acute respiratory syndrome coronavirus immune responses: the role played by V gamma 9V delta 2 T cells. J Infect Dis. May 1, 2006;193(9):1244-9. doi: 10.1086/502975. Epub Mar. 27, 2006.
Sela-Culang et al., The structural basis of antibody-antigen recognition. Front Immunol. Oct. 8, 2013;4:302. doi: 10.3389/fimmu.2013.00302.
Tamura et al., Structural Correlates of an Anticarcinoma Antibody: Identification of Specificity-Determining Residues (SDRs) and Development of a Minimally Immunogenic Antibody Variant by Retention of SDRs Only. J Immunol. Feb. 1, 2000;164(3):1432-41. doi: 10.4049/jimmunol.164.3.1432.
Van Dorp et al., Therapeutic Potential of Gammadelta T-Cells in Controlling CMV After Allogeneic Stem Cell Transplantation. Biology of Blood and Marrow Transplantation. 2011; 17(2): S217.
Wu et al., An innate-like Vδ1+ γδ T cell compartment in the human breast is associated with remission in triple-negative breast cancer. Sci Transl Med. Oct. 9, 2019;11(513):eaax9364. doi: 10.1126/scitranslmed.aax9364.
Wu et al., Ex vivo expanded human circulating Vδ1 γδT cells exhibit favorable therapeutic potential for colon cancer. OncoImmunology. Jan. 22, 2015;4(3):e992749. doi: 10.4161/2162402X.2014.992749. eCollection Mar. 2015.
Xu et al., Crystal structure of a γδ T-cell receptor specific for the human MHC class I homolog MICA. Proc Natl Acad Sci U S A. Feb. 8, 2011;108(6):2414-9. doi: 10.1073/pnas.1015433108. Epub Jan. 24, 2011.
Yamashiro et al., Stimulation of human butyrophilin 3 molecules results in negative regulation of cellular immunity. J Leukoc Biol. Oct. 2010;88(4):757-67. doi: 10.1189/jlb.0309156. Epub Jul. 7, 2010.
Zhang et al., Epidermal growth factor receptor expression and gene copy No. analysis in gastric carcinoma samples from Chinese patients. Oncol Lett. Jan. 2016;11(1):173-181. doi: 10.3892/ol.2015.3875. Epub Nov. 5, 2015.
Zhao et al., Protective Role of γ8 T Cells in Different Pathogen Infections and Its Potential Clinical Application. J Immunol Res. Jul. 10, 2018:2018:5081634. doi: 10.1155/2018/5081634. eCollection 2018.
An et al., IgG2m4, an engineered antibody isotype with reduced Fc function. MAbs. Nov.-Dec. 2009;1(6):572-9. doi: 10.4161/mabs.1.6.10185.
Crescioli et al., IgG4 Characteristics and Functions in Cancer Immunity. Curr Allergy Asthma Rep. Jan. 2016;16(1):7. doi: 10.1007/s11882-015-0580-7.
Gonzales et al., Minimizing the Immunogenicity of Antibodies for Clinical Application. Tumour Biol. Jan.-Feb. 2005;26(1):31-43. doi: 10.1159/000084184.
Kontermann, Strategies to Extend Plasma Half-Lives of Recombinant Antibodies. BioDrugs. 2009;23(2):93-109. doi: 10.2165/00063030-200923020-00003.
Kunik et al., Structural Consensus among Antibodies Defines the Antigen Binding Site. PLoS Comput Biol. 2012;8(2):e1002388. doi: 10.1371/journal.pcbi.1002388. Epub Feb. 23, 2012.
Liu, Pharmacokinetics of monoclonal antibodies and Fc-fusion proteins. Protein Cell. Jan. 2018;9(1):15-32. doi: 10.1007/s13238-017-0408-4. Epub Apr. 19, 2017.
Lucchese et al., How a single amino acid change may alter the immunological information of a peptide. Front Biosci (Elite Ed). Jan. 1, 2012;4(5):1843-52. doi: 10.2741/e506.
Mix et al., Immunoglobulins—Basic considerations. J Neurol. Sep. 2006:253 Suppl 5:V9-17. doi: 10.1007/s00415-006-5002-2.
Panka et al., Variable region framework differences result in decreased or increased affinity of variant anti-digoxin antibodies. Proc Natl Acad Sci U S A. May 1988;85(9):3080-4. doi: 10.1073/pnas.85.9.3080.
Strohl et al., Therapeutic antibody classes. Chapter 9 in: Therapeutic Antibody Engineering: Current and Future Advances Driving the Strongest Growth Area in the Pharmaceutical Industry. 1st edition. Woodhead Publishing Limited, eds. 2012; 197-223 and 459-595.
Ternant et al., Pharmacokinetics and concentration-effect relationships of therapeutic monoclonal antibodies and fusion proteins. Expert Opin Biol Ther. Sep. 2005:5 Suppl 1:S37-47. doi: 10.1517/14712598.5.1.s37.
Vidarsson et al., IgG subclasses and allotypes: from structure to effector functions. Front Immunol. Oct. 20, 2014;5:520. doi: 10.3389/fimmu.2014.00520. eCollection 2014.
Wark et al., Latest technologies for the enhancement of antibody affinityB. Adv Drug Deliv Rev. Aug. 7, 2006;58(5-6):657-70. doi: 10.1016/j.addr.2006.01.025. Epub May 22, 2006.
Wu et al., Humanization of a Murine Monoclonal Antibody by Simultaneous Optimization of Framework and CDR Residues. J Mol Biol. Nov. 19, 1999;294(1):151-62. doi: 10.1006/jmbi.1999.3141.
Xenaki et al., Antibody or Antibody Fragments: Implications for Molecular Imaging and Targeted Therapy of Solid Tumors. Front Immunol. Oct. 12, 2017;8:1287. doi: 10.3389/fimmu.2017.01287. eCollection 2017.

\* cited by examiner

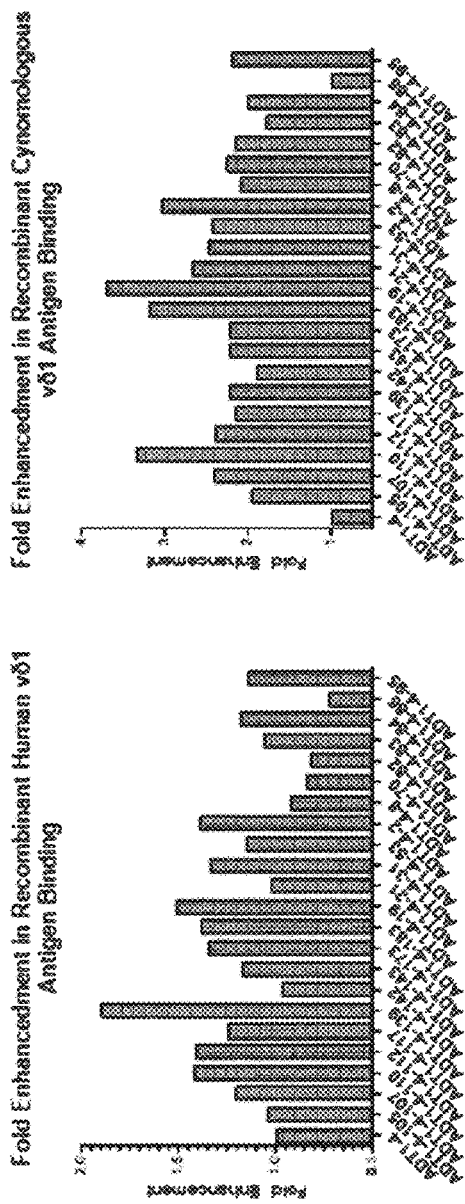
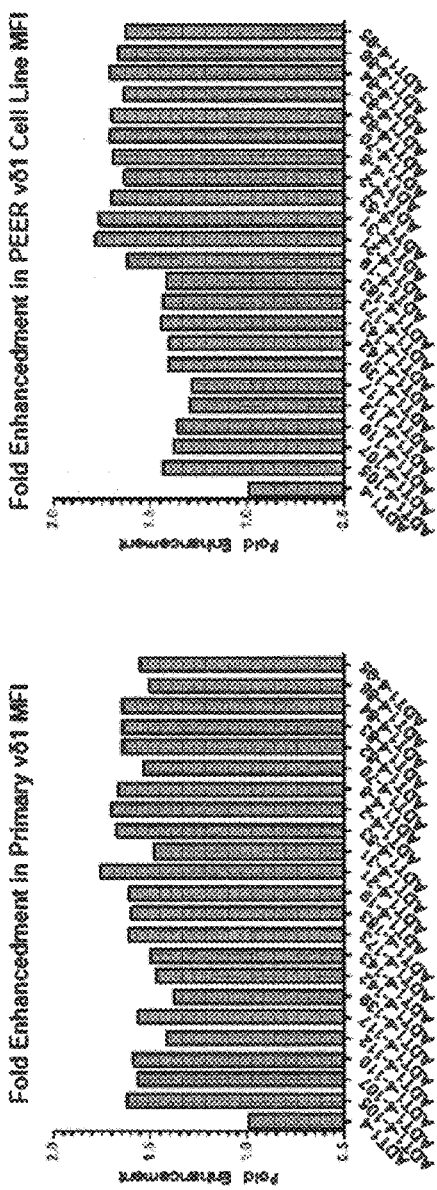
FIG. 5A
FIG. 5B
FIG. 5C
FIG. 5D

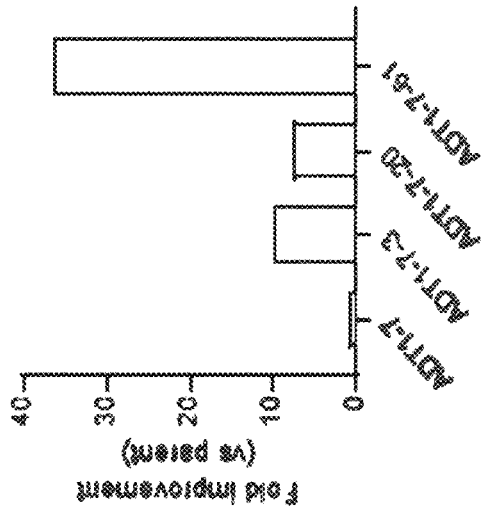
| Clone | Avg KD (M) | Fold-change |
|---|---|---|
| ADT1-7 | 3.81E-08 | 1.00 |
| ADT1-7-3 | 3.78E-09 | 10.07 |
| ADT1-7-20 | 4.99E-09 | 7.63 |
| ADT1-7-61 | 1.04E-09 | 36.62 |
FIG. 9D
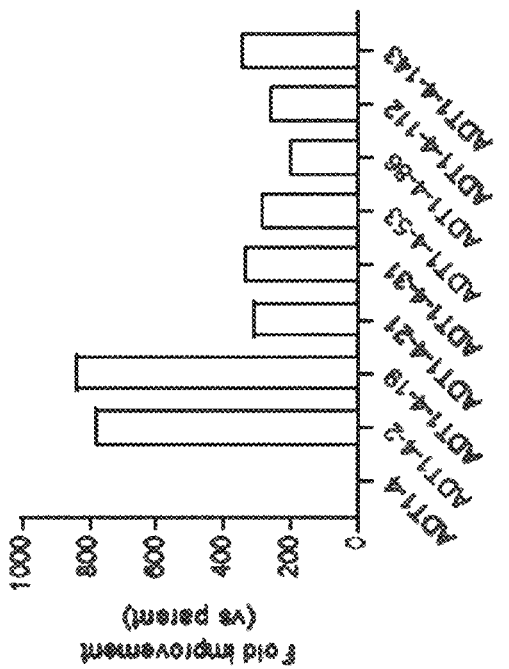
FIG. 9F
| Clone | Avg KD (M) | Fold-change |
|---|---|---|
| ADT1-4 | 1.49E-07 | 1.00 |
| ADT1-4-2 | 1.90E-10 | 784.21 |
| ADT1-4-19 | 1.77E-10 | 841.81 |
| ADT1-4-21 | 4.74E-10 | 314.35 |
| ADT1-4-31 | 4.42E-10 | 337.49 |
| ADT1-4-53 | 5.07E-10 | 294.18 |
| ADT1-4-86 | 7.16E-10 | 208.25 |
| ADT1-4-112 | 5.65E-10 | 263.95 |
| ADT1-4-143 | 4.24E-10 | 351.42 |
FIG. 9C
FIG. 9E

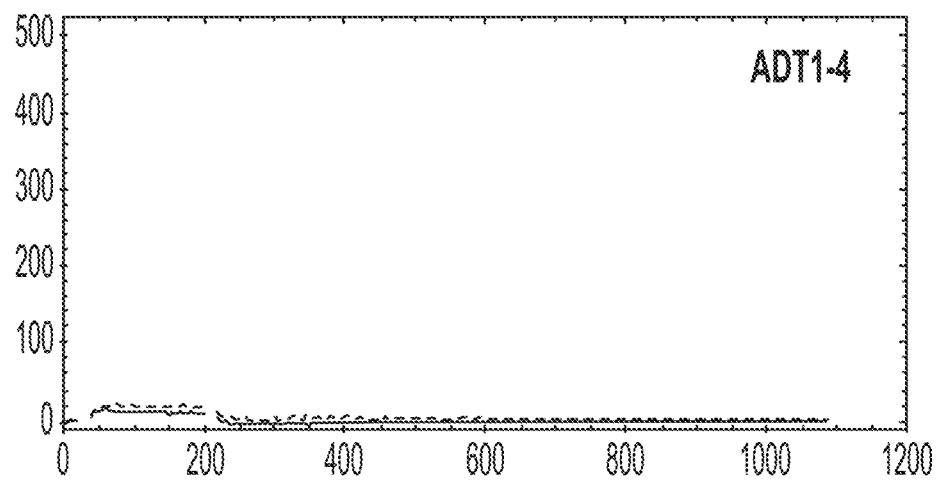
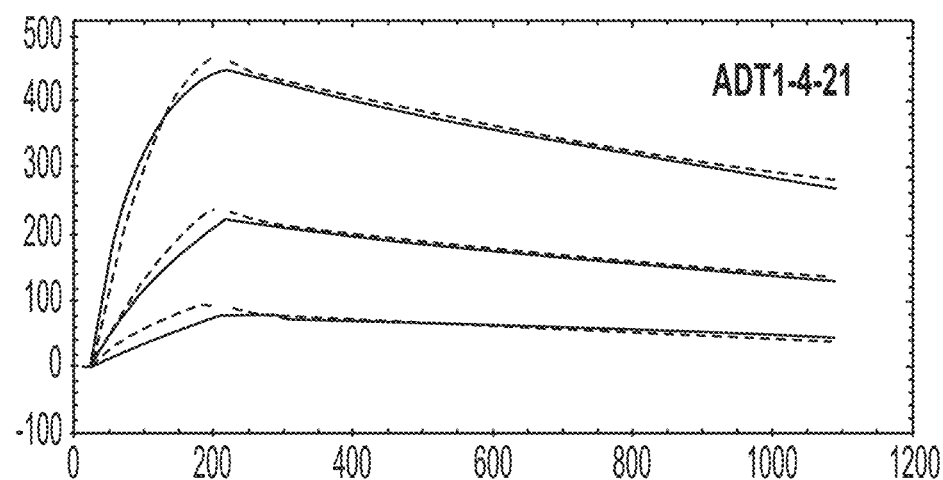
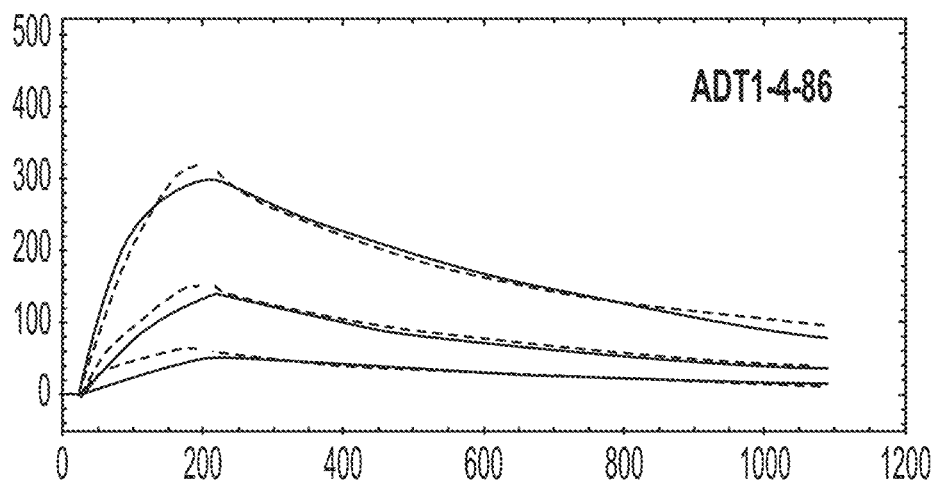
FIG. 10A

| Clone | Avg KD (M) |
|---|---|
| ADT1-4 | No binding |
| ADT1-4-2 | 1.92E-09 |
| ADT1-4-19 | 2.25E-09 |
| ADT1-4-21 | 4.38E-09 |
| ADT1-4-31 | 6.45E-09 |
| ADT1-4-53 | 4.01E-09 |
| ADT1-4-86 | 9.22E-09 |
| ADT1-4-112 | 8.27E-09 |
| ADT1-4-143 | 7.61E-09 |

FIG. 10D

| mAb | Donor 1 (ATS006) | Donor 2 (TS164) | HEK293T | Raji | CD8 (PBMC) | CD4 (PBMC) | CD56 (PBMC) | CD19 (PBMC) | CD14 (PBMC) |
|---|---|---|---|---|---|---|---|---|---|
| | | | | IC50 (nM) | | | | | |
| ADT1-4 | 107.7 | 575.9 | No binding | No binding | No binding | No binding | No binding | No binding | No binding |
| ADT1-4-2 | 2.164 | 1.703 | No binding | No binding | No binding | No binding | No binding | No binding | No binding |
| ADT1-4-19 | 2.375 | 2.456 | No binding | No binding | No binding | No binding | No binding | No binding | No binding |
| ADT1-4-21 | 2.536 | 1.675 | No binding | No binding | No binding | No binding | No binding | No binding | No binding |
| ADT1-4-31 | 3.33 | 2.63 | No binding | No binding | No binding | No binding | No binding | No binding | No binding |
| ADT1-4-53 | 2.228 | 2.456 | No binding | No binding | No binding | No binding | No binding | No binding | No binding |
| ADT1-4-86 | 5.357 | 2.34 | No binding | No binding | No binding | No binding | No binding | No binding | No binding |
| ADT1-4-112 | 2.621 | 2.436 | No binding | No binding | No binding | No binding | No binding | No binding | No binding |
| ADT1-4-143 | 2.819 | 3.066 | No binding | No binding | No binding | No binding | No binding | No binding | No binding |

| mAb | Donor 1 (ATS006) | Donor 2 (TS164) | HEK293T | Raji | CD8 (PBMC) | CD4 (PBMC) | CD56 (PBMC) | CD19 (PBMC) | CD14 (PBMC) |
|---|---|---|---|---|---|---|---|---|---|
| | | | | IC50 (nM) | | | | | |
| ADT1-7 | >100 | 225.6 | No binding | No binding | No binding | No binding | No binding | No binding | No binding |
| ADT1-7-3 | 5.153 | 0.9517 | No binding | No binding | No binding | No binding | No binding | No binding | No binding |
| ADT1-7-20 | 37.22 | 2.684 | No binding | No binding | No binding | No binding | No binding | No binding | No binding |
| ADT1-7-61 | 93.01 | 195.7 | No binding | No binding | No binding | No binding | No binding | No binding | No binding |

| mAb | Donor 1 (ATS006) | CD8 (PBMC) | CD4 (PBMC) | CD56 (PBMC) | CD19 (PBMC) | CD14 (PBMC) |
|---|---|---|---|---|---|---|
| | IC50 (nM) | | | | | |
| OKT3 | 2.889 | 0.252 | 0.1906 | No binding | No binding | No binding |
| RSV (IgG control) | No binding | No binding | No binding | No binding | No binding | No binding |

FIG. 11D

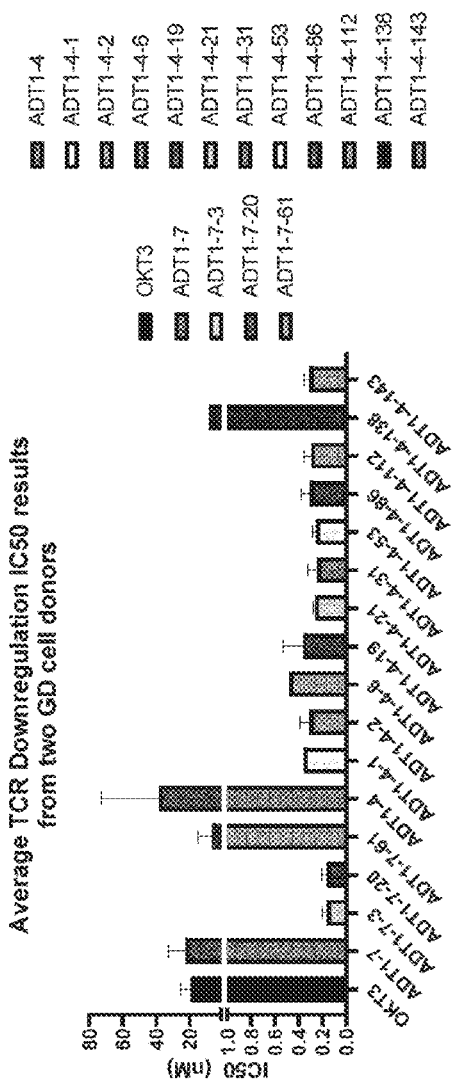
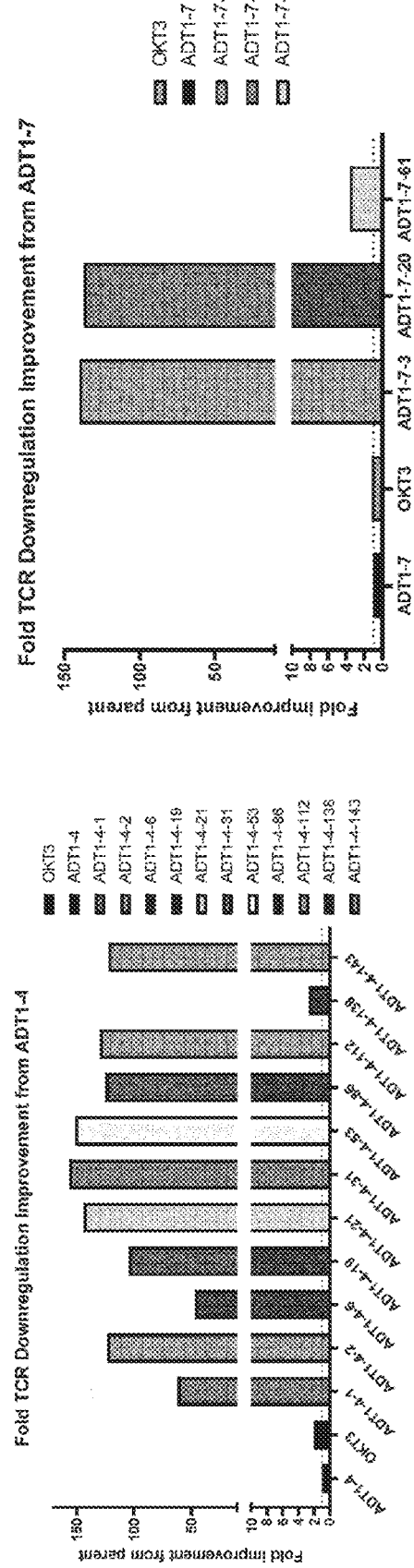
FIG. 12C
FIG. 12D
FIG. 12E

| | IC50 | % improvement in IC50 |
|---|---|---|
| ADT1-4 | 38.28 | 100 |
| OKT3 | 19.43 | 197 |
| ADT1-4-2 | 0.31 | 12348 |
| ADT1-4-31 | 0.24 | 15630 |
| ADT1-4-21 | 0.27 | 14372 |
| ADT1-4-86 | 0.31 | 12472 |
| ADT1-4-143 | 0.31 | 12219 |
| ADT1-4-19 | 0.37 | 10420 |
| ADT1-4-53 | 0.25 | 15090 |
| ADT1-4-112 | 0.30 | 12964 |
| ADT1-4-1 | 0.36 | 6185 |
| ADT1-4-6 | 0.48 | 4648 |
| ADT1-4-138 | 8.38 | 266 |

FIG. 12F

| | IC50 | % improvement in IC50 |
|---|---|---|
| ADT1-7 | 22.42 | 100 |
| OKT3 | 19.43 | 115 |
| ADT1-7-3 | 0.16 | 13968 |
| ADT1-7-20 | 0.16 | 13697 |
| ADT1-7-61 | 6.26 | 358 |

| | IC50 | Fold improvement in IC50 |
|---|---|---|
| ADT1-4 | 38.28 | 1 |
| OKT3 | 19.43 | 2 |
| ADT1-4-1 | 0.36 | 62 |
| ADT1-4-2 | 0.31 | 123 |
| ADT1-4-6 | 0.48 | 46 |
| ADT1-4-19 | 0.37 | 104 |
| ADT1-4-21 | 0.27 | 144 |
| ADT1-4-31 | 0.24 | 156 |
| ADT1-4-53 | 0.25 | 151 |
| ADT1-4-86 | 0.31 | 125 |
| ADT1-4-112 | 0.30 | 130 |
| ADT1-4-138 | 8.38 | 3 |
| ADT1-4-143 | 0.31 | 122 |

| | IC50 | Fold improvement in IC50 |
|---|---|---|
| ADT1-7 | 22.42 | 1 |
| OKT3 | 19.43 | 1 |
| ADT1-7-3 | 0.16 | 140 |
| ADT1-7-20 | 0.16 | 137 |
| ADT1-7-61 | 6.26 | 4 |

FIG. 12G

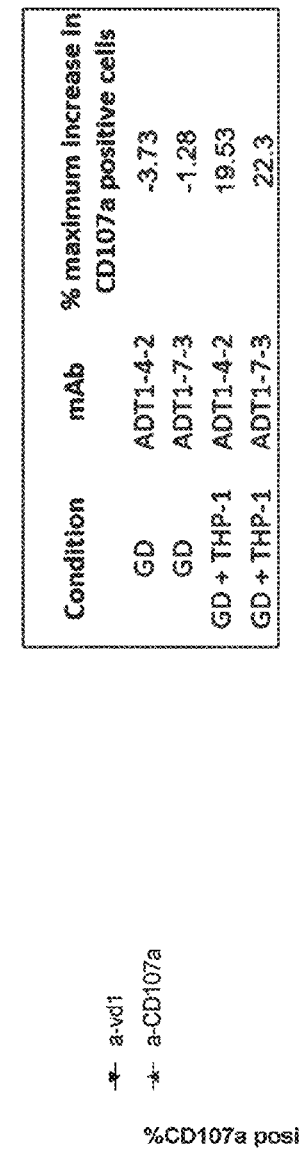
FIG. 13E
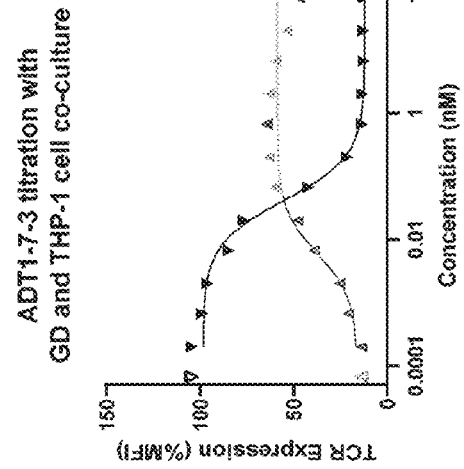
FIG. 13F
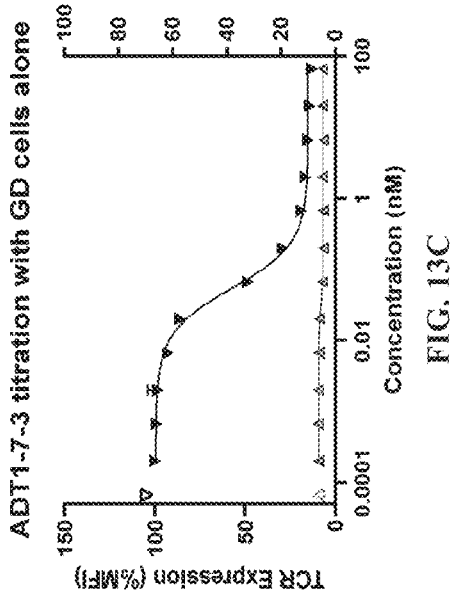
FIG. 13C
FIG. 13D

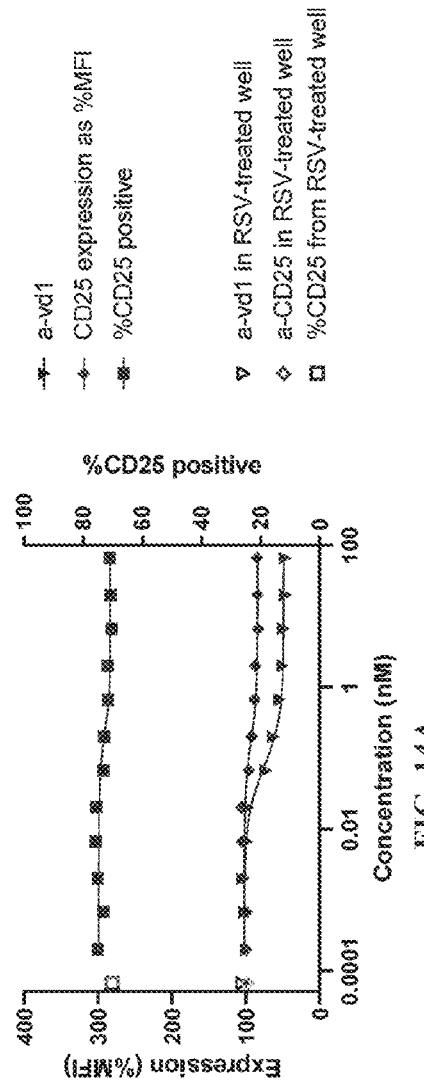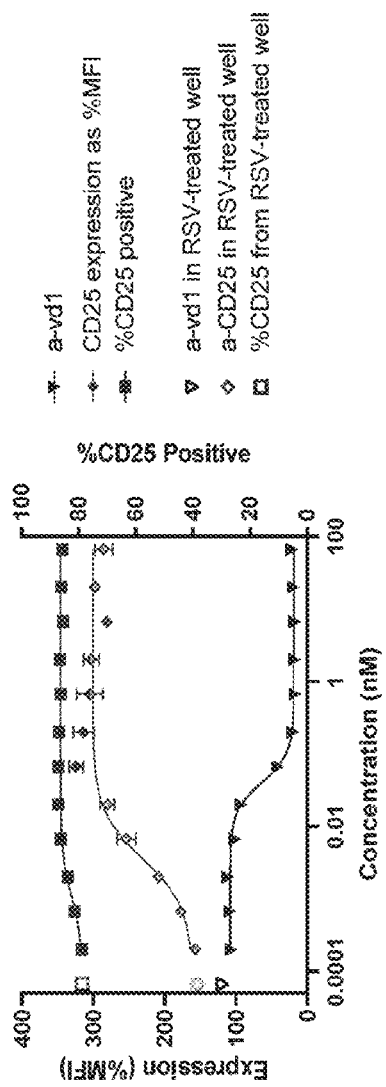
FIG. 14A
FIG. 14B

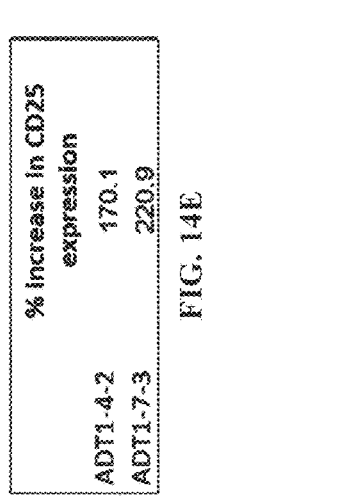
FIG. 14E
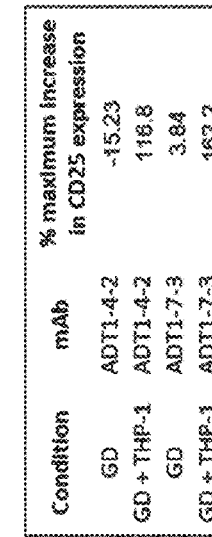
FIG. 14F
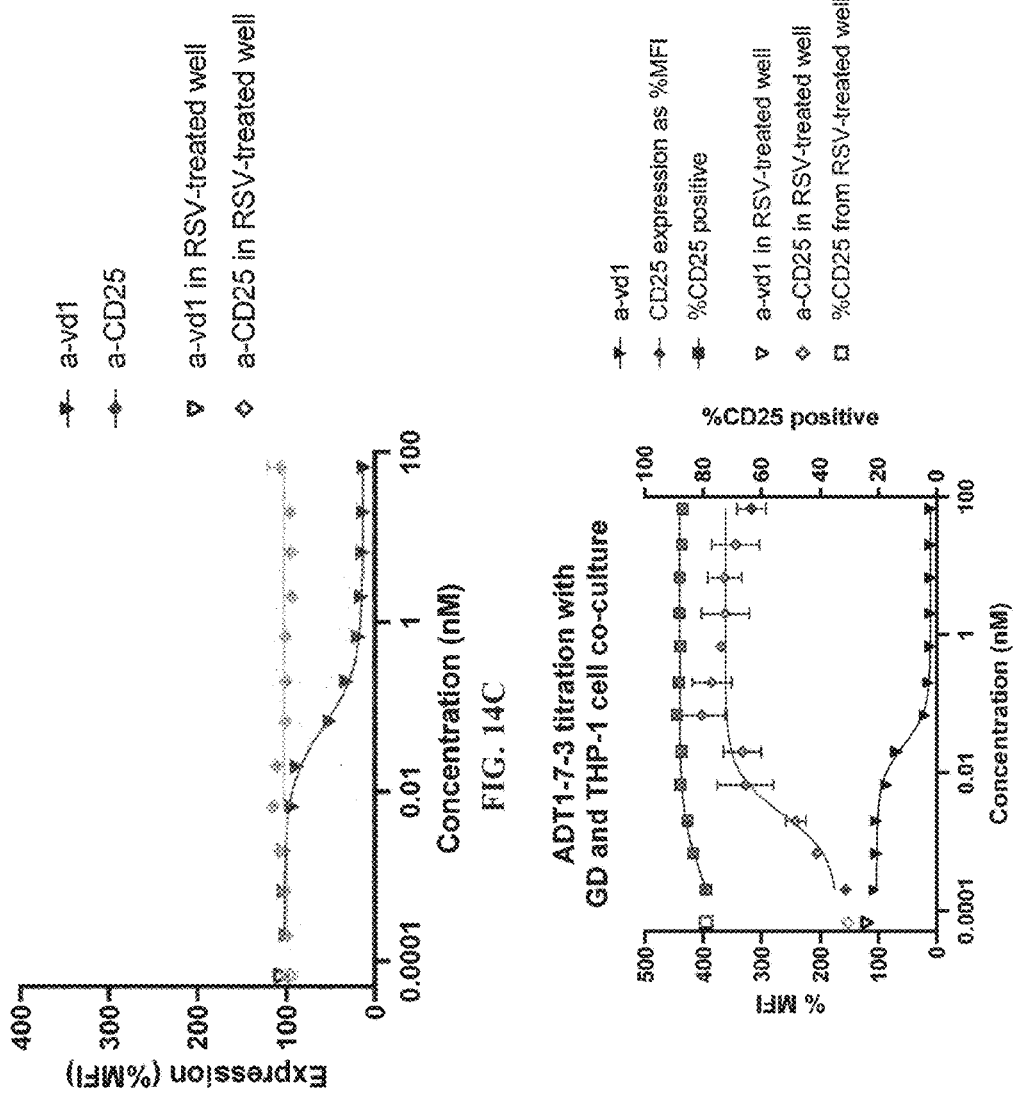
FIG. 14C
FIG. 14D

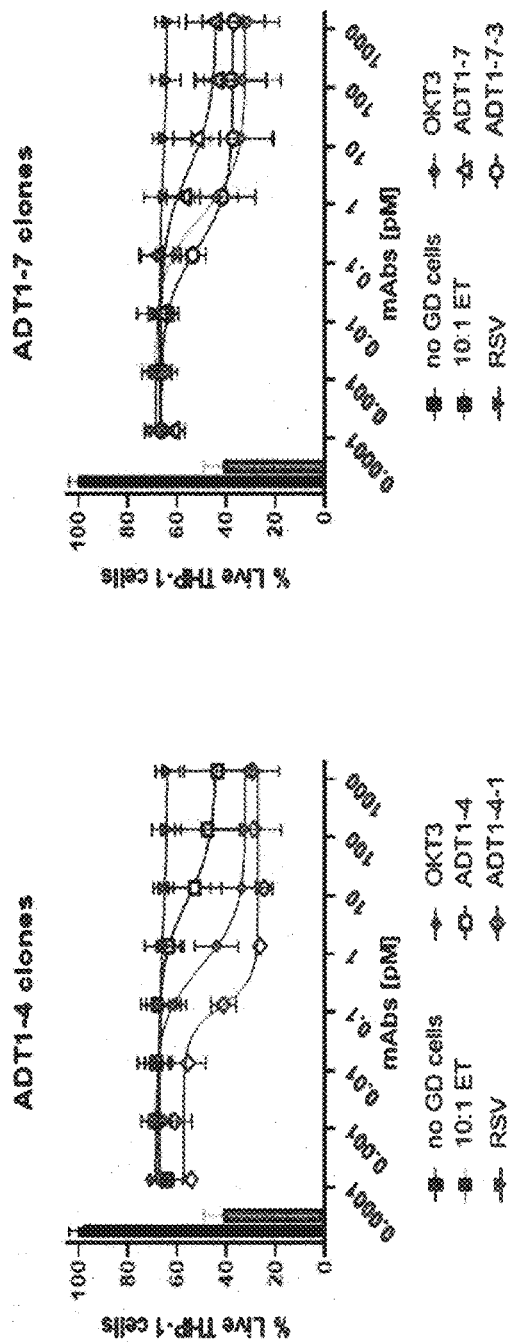
FIG. 16A
FIG. 16B
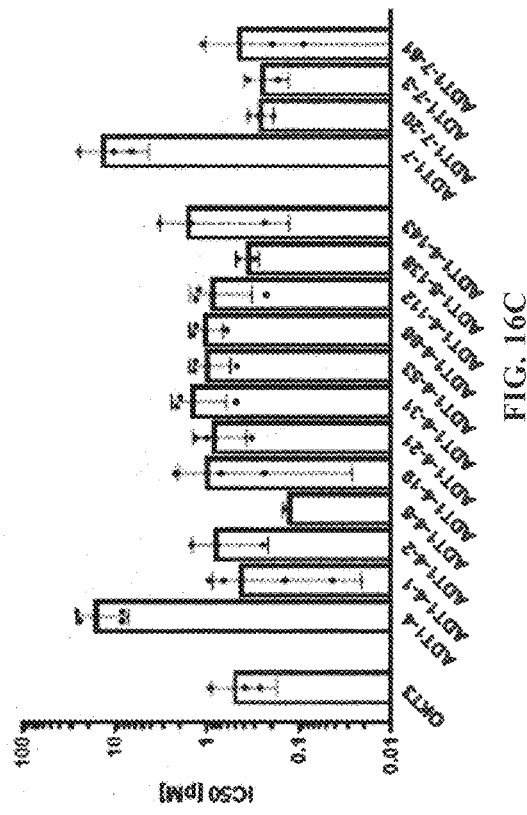
FIG. 16C

| Clone ID | THP-1 killing assay EC50 [pM] (average of ≥3 donors) | Standard deviation | Fold improvement | % improvement over parent |
|---|---|---|---|---|
| OKT3 (anti CD3) | 3.53 | 2.40 | | |
| ADT1-4 | 121.47 | 136.80 | 1.0 | 100% |
| ADT1-4-1 | 3.00 | 2.87 | 40.5 | 4049% |
| ADT1-4-2 | 6.33 | 3.67 | 19.2 | 1918% |
| ADT1-4-6 | 0.93 | 0.07 | 130.1 | 13014% |
| ADT1-4-19 | 8.33 | 6.13 | 14.6 | 1458% |
| ADT1-4-21 | 6.13 | 2.93 | 19.8 | 1980% |
| ADT1-4-31 | 10.93 | 4.73 | 11.1 | 1111% |
| ADT1-4-53 | 7.40 | 3.13 | 16.4 | 1641% |
| ADT1-4-86 | 7.60 | 2.87 | 16.0 | 1598% |
| ADT1-4-112 | 6.47 | 3.53 | 18.8 | 1878% |
| ADT1-6-138 | 2.53 | 0.73 | 47.9 | 4795% |
| ADT1-4-143 | 13.07 | 9.27 | 9.3 | 930% |
| ADT1-7 | 65.20 | 54.80 | 1.0 | 100% |
| ADT1-7-20 | 1.87 | 0.53 | 34.9 | 3493% |
| ADT1-7-3 | 1.33 | 0.87 | 48.9 | 4890% |
| ADT1-7-61 | 3.60 | 3.60 | 18.1 | 1811% |

FIG. 16D

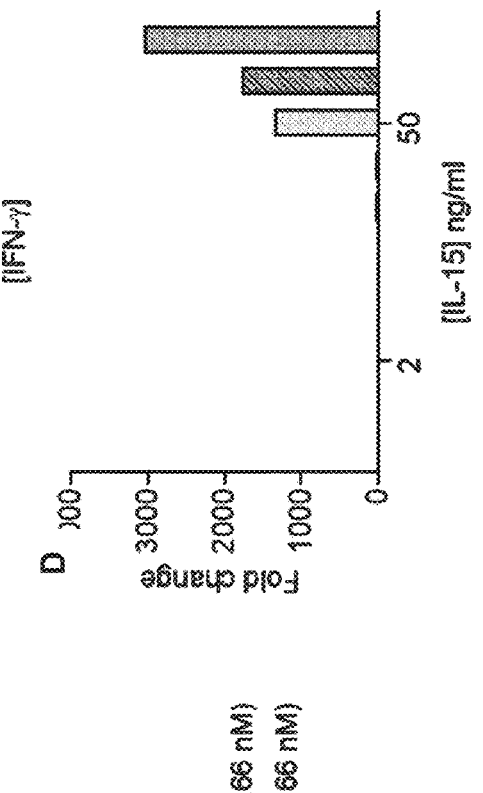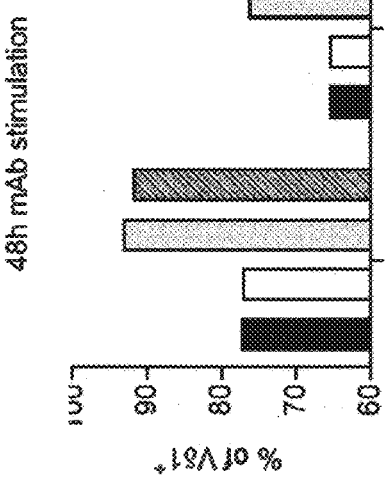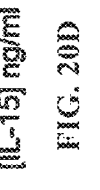
FIG. 20A
FIG. 20B
FIG. 20C
FIG. 20D

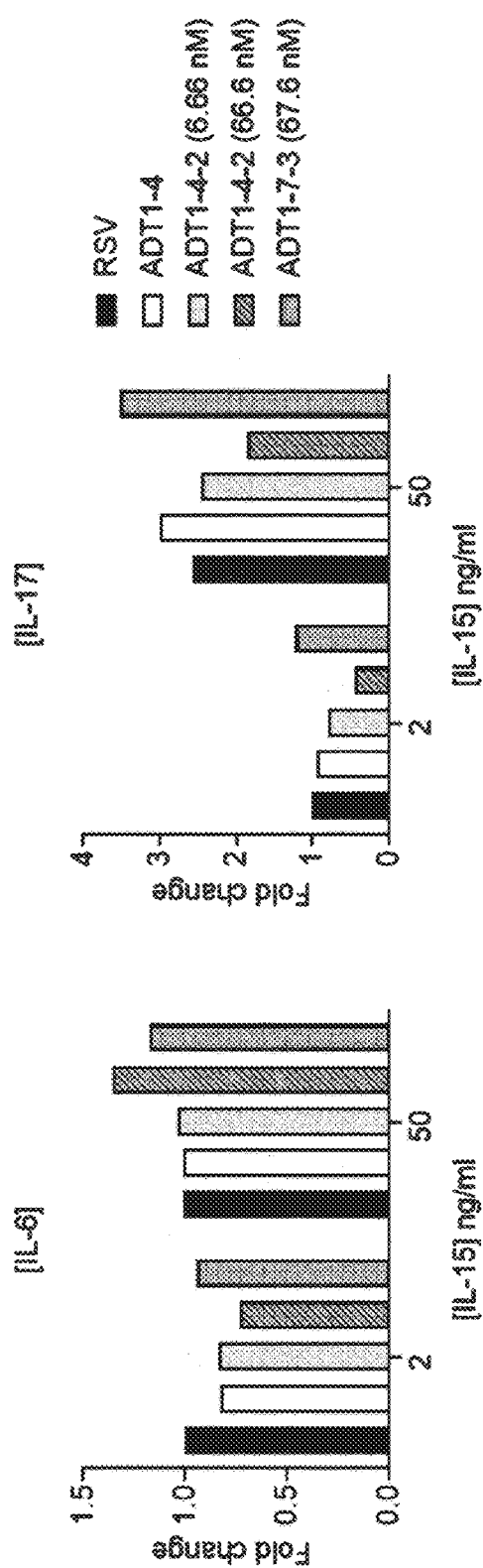
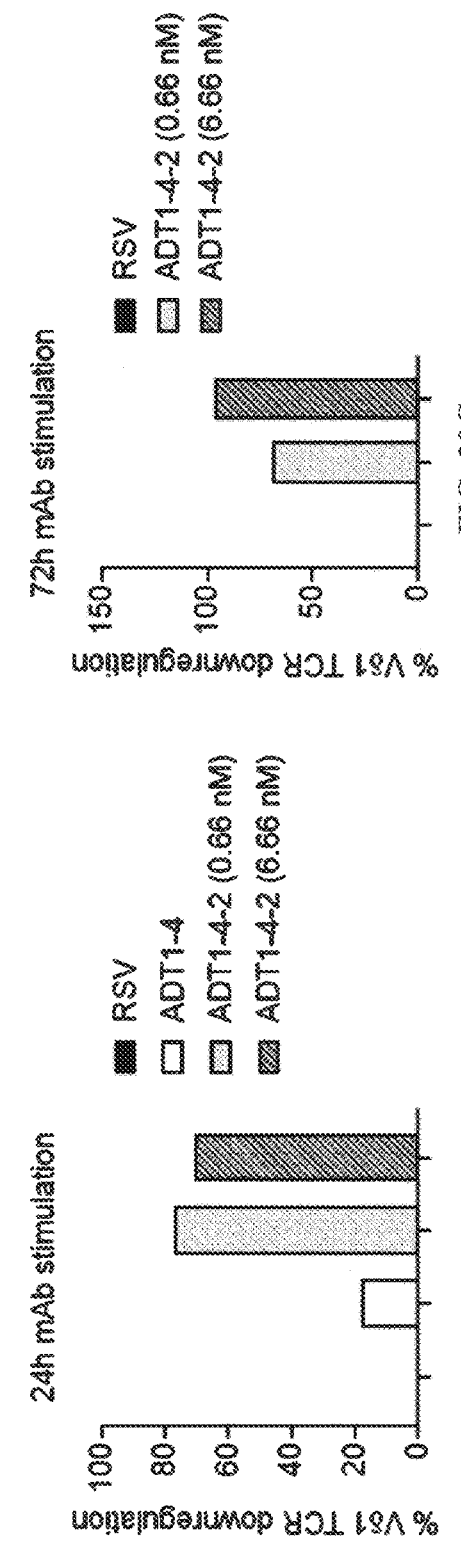
FIG. 20E
FIG. 20F
FIG. 20G

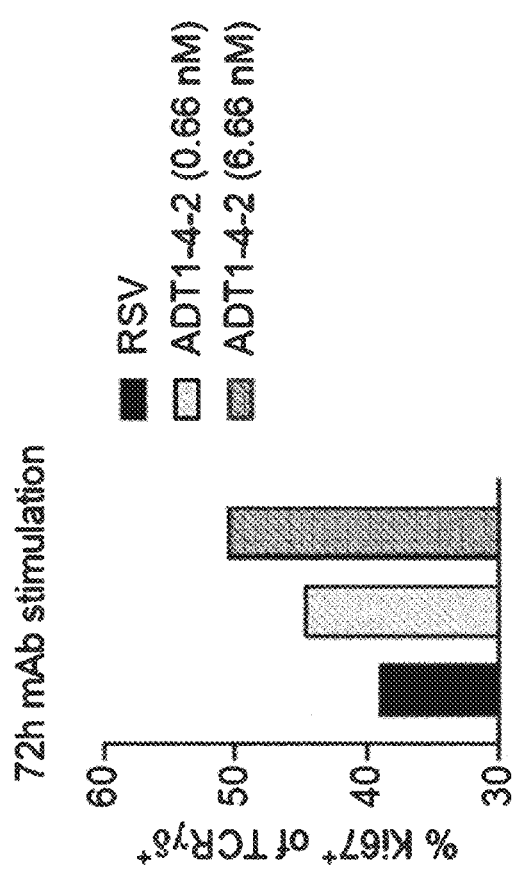
FIG. 20H
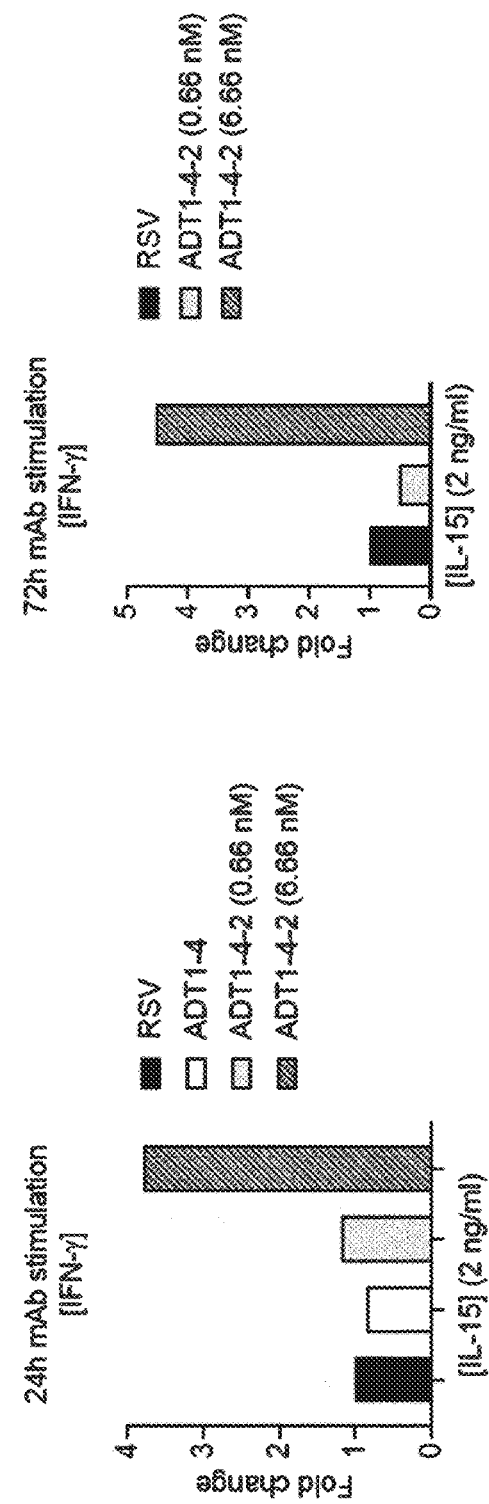
FIG. 20I
FIG. 20J

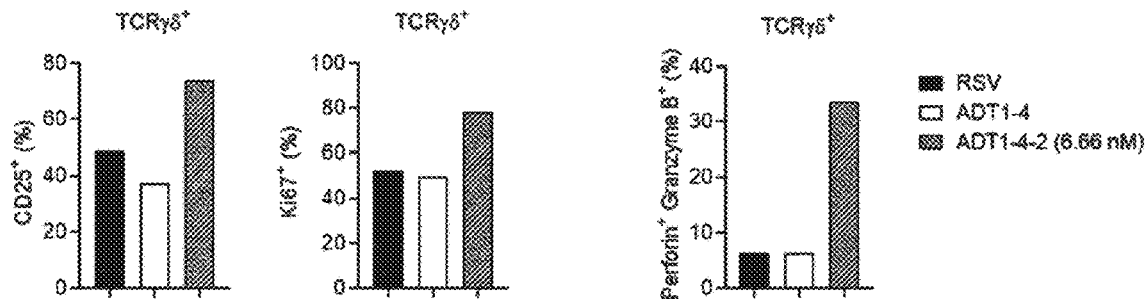
FIG. 21A
FIG. 21B
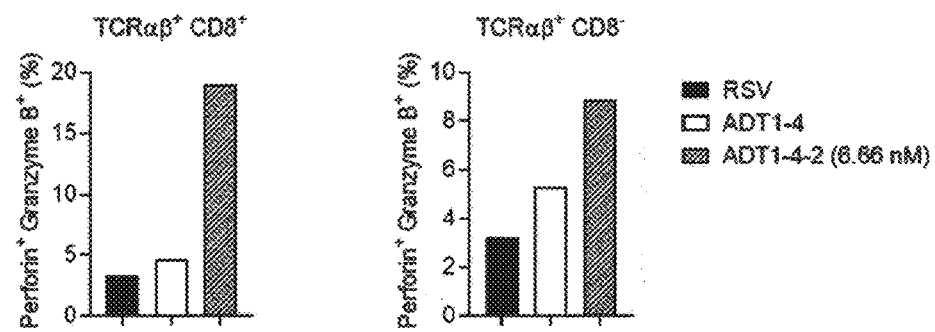
FIG. 21C
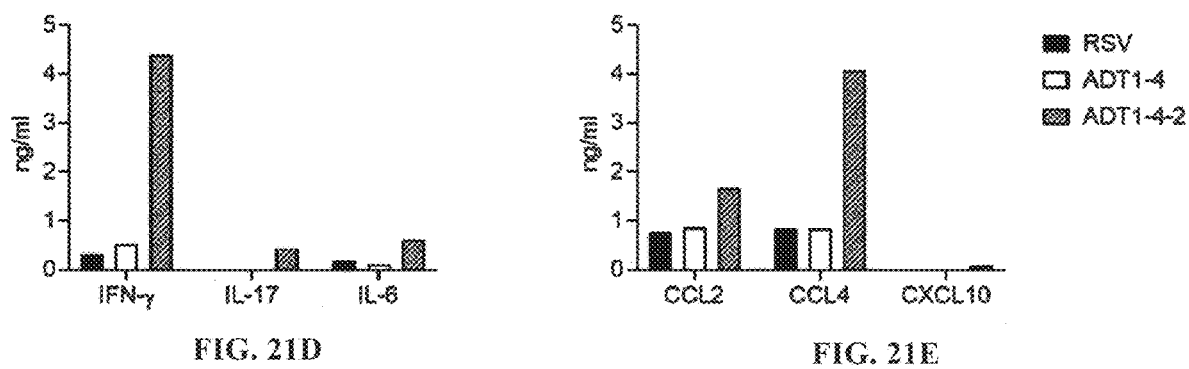
FIG. 21D
FIG. 21E

| ADT1-4-105 | 2499_01_D07 |
| --- | --- |

DIQMTQSPPALSASVGDRVTITCRASQDINDWLAWYQHKPGKAPKLLIYDASSLESGVPLRFSGSGSGTEFTLTISSLQPDDFATYYCQQKYSTPQITFGQGTRLEIK

| ADT1-4-107 | 2499_01_F07 |
| --- | --- |

DIQMTQSPPALSASVGDRVTITCRASQDINDWLAWYQHKPGKAPKLLIYDASSLESGVPLRFSGSGSGTEFTLTISSLQPDDFATYYCQQRYSTPQITFGQGTRLEIK

| ADT1-4-110 | 2499_02_A02 |
| --- | --- |

DIQMTQSPPALSASVGDRVTITCRASQDINDWLAWYQHKPGKAPKLLIYDASSLESGVPLRFSGSGSGTEFTLTISSLQPDDFATYYCQQKYSTPQVTFGAGTRLEIK

| ADT1-4-112 | 2499_02_B04 |
| --- | --- |

DIQMTQSPPALSASVGDRVTITCRASQDINDWLAWYQHKPGKAPKLLIYDASSLESGVPLRFSGSGSGTEFTLTISSLQPDDFATYYCQQKYSQFQVTFGQGTRLEIK

| ADT1-4-117 | 2499_02_F12 |
| --- | --- |

DIQMTQSPPALSASVGDRVTITCRASQDINDWLAWYQHKPGKAPKLLIYDASSLESGVPLRFSGSGSGTEFTLTISSLQPDDFATYYCQQKYSTPPVTFGQGTRLEIK

| ADT1-4-19 | 2501_01_H01 |
| --- | --- |

DIQMTQSPPALSASVGDRVTITCRASQDINDWLAWYQHKPGKAPKLLIYDASSLESGVPLRFSGSGSGTEFTLTISSLQPDDFATYYCQQKYSTPKVTFGQGTRLEIK

| ADT1-4-21 | 2501_02_A05 |
| --- | --- |

DIQMTQSPPALSASVGDRVTITCRASQDINDWLAWYQHKPGKAPKLLIYDASSLESGVPLRFSGSGSGTEFTLTISSLQPDDFATYYCQQKYSTPNVTFGQGTRLEIK

| ADT1-4-31 | 2501_02_G09 |
| --- | --- |

DIQMTQSPPALSASVGDRVTITCRASQDINDWLAWYQHKPGKAPKLLIYDASSLESGVPLRFSGSGSGTEFTLTISSLQPDDFATYYCQQKYSTPPVTFGQGTRLEIK

| ADT1-4-139 | 2502_01_C07 |
| --- | --- |

DIQMTQSPPALSASVGDRVTITCRASQDINDWLAWYQHKPGKAPKLLIYDASSLESGVPLRFSGSGSGTEFTLTISSLQPDDFATYYCQQKYSTPQLTFGQGTRLEIK

| ADT1-4-4 | 2502_01_E01 |
| --- | --- |

DIQMTQSPPALSASVGDRVTITCRASQDINDWLAWYQHKPGKAPKLLIYDASSLESGVPLRFSGSGSGTEFTLTISSLQPDDFATYYCQQKYSTPWVTFGQGTRLEIK

| ADT1-4-143 | 2502_01_E05 |
| --- | --- |

DIQMTQSPPALSASVGDRVTITCRASQDINDWLAWYQHKPGKAPKLLIYDASSLESGVPLRFSGSGSGTEFTLTISSLQPDDFATYYCQQKYSTHQVTFGQGTRLEIK

| ADT1-4-53 | 2505_02_E12 |
| --- | --- |

DIQMTQSPPALSASVGDRVTITCRASQDINDWLAWYQHKPGKAPKLLIYDASSLESGVPLRFSGSGSGTEFTLTISSLQPDDFATYYCQQKYSTPQLTFGQGTRLVIK

FIG. 22A

| ADT1-4-173 | 2505_02_G11 |
| ADT1-4-2 | 2506_01_B10 |
| ADT1-4-8 | 2506_01_B11 |
| ADT1-4-82 | 2506_02_B09 |
| ADT1-4-83 | 2506_02_B10 |
| ADT1-4-3 | 2506_02_C01 |
| ADT1-4-84 | 2506_02_C02 |
| ADT1-4-86 | 2506_02_C12 |
| ADT1-4-95 | 2506_02_H04 |
| ADT1-4-1 | 2501_01_C09 |
| ADT1-4-6 | 2506_1_B06 |
| ADT1-4-138 | 2502_01_B03 |

DIQMTQSPPALSASVGDRVTITCRASQDINDWLAWYQHKPGKAPKLLIYDASSLESGVPLRFSGSGSGTEFTLTISSLQPDDFATYYCQQKYSAPQVTFGQGTRLEIK

DIQMTQSPPALSASVGDRVTITCRASQDINDWLAWYQHKPGKAPKLLIYDASSLESGVPLRFSGSGSGTEFTLTISSLQPDDFATYYCQQKYSAPQVTFGQGTRLEIK

DIQMTQSPPALSASVGDRVTITCRASQDINDWLAWYQHKPGKAPKLLIYDASSLESGVPLRFSGSGSGTEFTLTISSLQPDDFATYYCQQKYSAPQVTFGQGTRLEIK

DIQMTQSPPALSASVGDRVTITCRASQDINDWLAWYQHKPGKAPKLLIYDASSLESGVPLRFSGSGSGTEFTLTISSLQPDDFATYYCQQKYSAPQVTFGQGTRLEIK

DIQMTQSPPALSASVGDRVTITCRASQDINDWLAWYQHKPGKAPKLLIYDASSLESGVPLRFSGSGSGTEFTLTISSLQPDDFATYYCQQRYSTPQITFGQGTRLEIK

DIQMTQSPPALSASVGDRVTITCRASQDINDWLAWYQHKPGKAPKLLIYDASSLESGVPLRFSGSGSGTEFTLTISSLQPDDFATYYCQQKYSEPQVTFGQGTRLEIK

DIQMTQSPPALSASVGDRVTITCRASQDINDWLAWYQHKFGKAPKLLIYDASSLESGVPLRFSGSGSGTEFTLTISSLQPDDFATYYCQQKYSTPEVTFGQGTRLEIK

DIQMTQSPPALSASVGDRVTITCRASQDINDWLAWYQHKPGKAPKLLIYDASSLESGVPLRFSGSGSGTEFTLTISSLQPDDFATYYCQQKYSSDPQVTFGQGTRLEIK

DIQMTQSPPALSASVGDRVTITCRASQDINDWLAWYQHKPGKAPKLLIYDASSLESGVPLRFSGSGSGTEFTLNISSLQPDDFATYYCQQRYSTPIVTFGQGTRLEIK

DIQMTQSPPALSASVGDRVTITCRASQDINDWLAWYQHKPGKAPKLLIYDASSLESGVPLRFSGSGSGTEFTLTISSLQPDDFATYYCQQKYKTPQVTFGQGTRLEIK

DIQMTQSPPALSASVGDRVTITCRASQDINDWLAWYQHKPGKAPKLLIYDASSLESGVPSRPSGSGSGTEFTLNISSLQPDDFATYYCQQRYSTDQVTFGQGTRLEIK

FIG. 22B

| ADT1-4-105 | 2499_01_D07 |
EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVGYVDVWGQGTLVTVSS

| ADT1-4-107 | 2499_01_F07 |
EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVGYVDVWGQGTLVTVSS

| ADT1-4-110 | 2499_02_A02 |
EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVGYVDVWGQGTLVTVSS

| ADT1-4-112 | 2499_02_B04 |
EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVGYVDVWGQGTLVTVSS

| ADT1-4-117 | 2499_02_F12 |
EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVGYVEYVDYWGQGTLVTVSS

| ADT1-4-19 | 2501_01_H01 |
EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVGYVDVWGQGTLVTVSS

| ADT1-4-21 | 2501_02_A05 |
EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVGYVDRWGQGTLVTVSS

| ADT1-4-31 | 2501_02_G09 |
EVQLQQSGPGLVKPSQTLSLTCAISGDSVSSKSVAWNWIRQSPSRGLEWLGRTYYRSKWSTDYAASVKSRITINPDTSKNQLSLQLNSVTPEDTAVYYCARTWADYVDYWGQGTLVTVSS

| ADT1-4-139 | 2502_01_C07 |
EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVGYADVWGQGTLVTVSS

| ADT1-4-4 | 2502_01_E01 |
EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVGYVDVWGQGTLVTVSS

| ADT1-4-143 | 2502_01_E05 |
EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVGYADVWGQGTLVTVSS

| ADT1-4-53 | 2505_02_E12 |
EVQLQQSGPGLVKPSQTLSLTCAISGDSVSSKSVAWNWIRQSPSRGLEWLGRTYYRSKWSTDYAASVKSRITINPDTSKNQLSLQLNSVTPEDTAVYYCARTWADYVDVWGQGTLVTVSS

FIG. 23A

| ADT1-4-173 | 2505_02_G11 |
| --- | --- |

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWAGYFDVWGQGTLVTVSS

| ADT1-4-2 | 2506_01_B10 |
| --- | --- |

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVGYTVDRWGQGTLVTVSS

| ADT1-4-8 | 2506_01_B11 |
| --- | --- |

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVGYADVWGQGTLVTVSS

| ADT1-4-82 | 2506_02_B09 |
| --- | --- |

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARSWVGYVDVWGQGTLVTVSS

| ADT1-4-83 | 2506_02_B10 |
| --- | --- |

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARSWVGYVDVWGQGTLVTVSS

| ADT1-4-3 | 2506_02_C01 |
| --- | --- |

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWADYVDVWGQGTLVTVSS

| ADT1-4-84 | 2506_02_C02 |
| --- | --- |

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWLGNVDVWGQGTLVTVSS

| ADT1-4-86 | 2506_02_C12 |
| --- | --- |

EVQLQQSGPGLVKPSQTLSLTCAISGDSVSSKSVAWNWIRQSPSRGLEWLGRTYYRSKWSTDYAASVKSRITINPDTSKNQLSLQLNSVTPEDTAVYYCARTWVGYADVWGQGTLVTVSS

| ADT1-4-95 | 2506_02_H04 |
| --- | --- |

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVGYADVWGQGTLVTVSS

| ADT1-4-1 | 2501_01_C09 |
| --- | --- |

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWAGYFDVWGQGTLVTVSS

| ADT1-4-6 | 2506_1_B06 |
| --- | --- |

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWVGYADVWGQGTLVTVSS

| ADT1-4-138 | 2502_01_B03 |
| --- | --- |

EVQLQQSGPGLVKPSQTLSLTCAISGDSVSSKSAAWNWIRQSPSRGLEWLGRTYYRSKWSTDYAASVKSRITINPDTSKNQLSLQLNSVTPEDTAVYYCARTWADYVDVWGQGTLVTVSS

FIG. 23B

| ADT1-7-10 | 2503_1_C12 | DIQMTQSPSSLSASVGDRVTIACRAGQSIGTYLNWYQQKPGKAPKLLIYVASSLQSGVPSRFSGSGSGTEFTLTISSLQPEDFATYYCQQTASTLLTFGRGTKVEIK |
| ADT1-7-15 | 2503_1_F01 | DIQMTQSPSSLSASVGDRVTIACRAGQSIGTYLNWYQQKPGKAPKLLIYVASSLQSGVPSRFSGSGSGTEFTLTISSLQPEDFATYYCQQSADTLLTFGRGTKVEIK |
| ADT1-7-17 | 2503_1_G05 | DIQMTQSPSSLSASVGDRVTIACRAGQSIGTYLNWYQQKPGKAPKLLIYVASSLQSGVPSRFSGSGSGTEFTLTISSLQPEDFATYYCQQSGSELLTFGRGTKVEIK |
| ADT1-7-18 | 2503_1_G06 | DIQMTQSPSSLSASVGDRVTIACRVGQSIGTYLNWYQQKPGKAPKLLIYVASSLQSGVPSRFSGSGSGTEFTLTISSLQPEDFATYYCQQSASELLTFGRGTKVEIK |
| ADT1-7-19 | 2503_1_G10 | DIQMTQSPSSLSASVGDRVTIACRAGQSIGTYLNWYQQKPGKAPKLLIYVASSLQSGVPSRFSGSGSGTEFTLTISSLQPEDFATYYCQQSYSGLDTFGRGTKVEIK |
| ADT1-7-20 | 2503_1_H02 | DIQMTQSPSSLSASVGDRVTIACRAGQSIGTYLNWYQQKPGKAPKLLIYVASSLQSGVPSRFSGSGSGTEFTLTISSLQPEDFATYYCQQSASELLTFGRGTKVEIK |
| ADT1-7-22 | 2503_2_A02 | DIQMTQSPSSLSASVGDRVTIACRAGQSIGTYLNWYQQKPGKAPKLLIYVASSLQSGVPSRFSGSGSGTEFTLTISSLQPEDFATYYCQQSYSGLDTFGRGTKVEIK |
| ADT1-7-23 | 2503_2_A07 | DIQMTQSPSSLSASVGDRVTIACRAGQSIGTYLNWYQQKPGKAPKLLIYVASSLQSGVPSRFSGSGSGTEFTLTISSLQPEDFATYYCQQSGSELLTFGRGTKVEIK |
| ADT1-7-42 | 2503_2_H06 | DIQMTQSPSSLSASVGDRVTIACRAGQSIGTYLNWYQQKPGKAPKLLIYVASSLQSGVPSRFSGSGSGTEFTLTISSLQPEDFATYYCQQSYSGLDTFGRGTKVEIK |
| ADT1-7-3  | 2504_1_A01 | DIQMTQSPSSLSASVGDRVTIACRAGQSIGTYLNWYQQKPGKAPKLLIYVASSLQSGVPSRFSGSGSGTEFTLTISSLQPEDFATYYCQQSASELLTFGRGTKVEIK |
| ADT1-7-61 | 2504_1_F02 | DIQMTQSPSSLSASVGDRVTIACRAGQSIGTYLNWYQQKPGKAPKLLIYVASSLQSGVPSRFSGSGSGTEFTLTISSLQPEDFATYYCQQSASELLTFGRGTKVEIK |

FIG. 24

ADT1-7-10_2503_1_C12
EVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARDYNDAFDIWGQGTLVTVSS

ADT1-7-15_2503_1_F01
EVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARDYNDAFDIWGQGTLVTVSS

ADT1-7-17_2503_1_G05
EVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARIDYEDAFDIWGQGTLVTVSS

ADT1-7-18_2503_1_G06
EVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARVSYDDAFDIWGQGTLVTVSS

ADT1-7-19_2503_1_G10
EVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARIDYEDAFDIWGQGTLVTVSS

ADT1-7-20_2503_1_H02
EVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARVDYQEAFDIWGQGTLVTVSS

ADT1-7-22_2503_2_A02
EVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARDDYNDAFDIWGQGTLVTVSS

ADT1-7-23_2503_2_A07
EVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARVDYNEAFDIWGQGTLVTVSS

ADT1-7-42_2503_2_H06
EVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARVYYEAFDIWGQGTLVTVSS

ADT1-7-3_2504_1_A01
EVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARVSYAEAFDIWGQGTLVTVSS

ADT1-7-61_2504_1_F02
EVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARDYDDAFDIWGQGTLVTVSS

FIG. 25

Human VD1
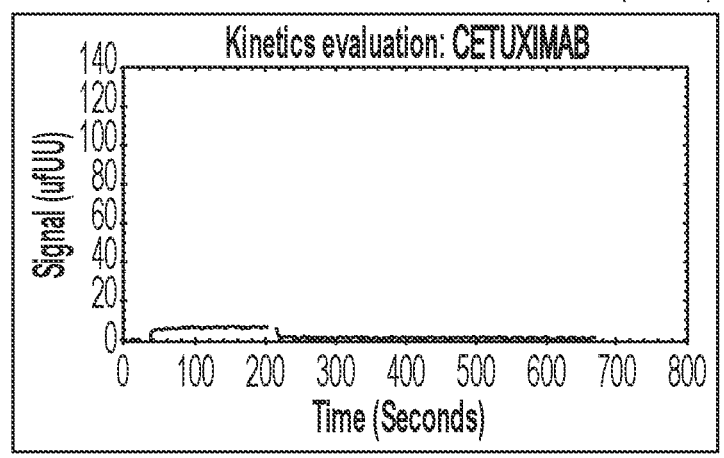
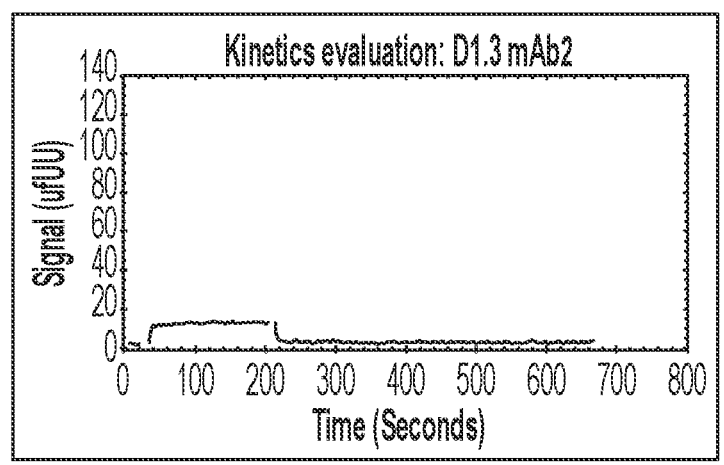
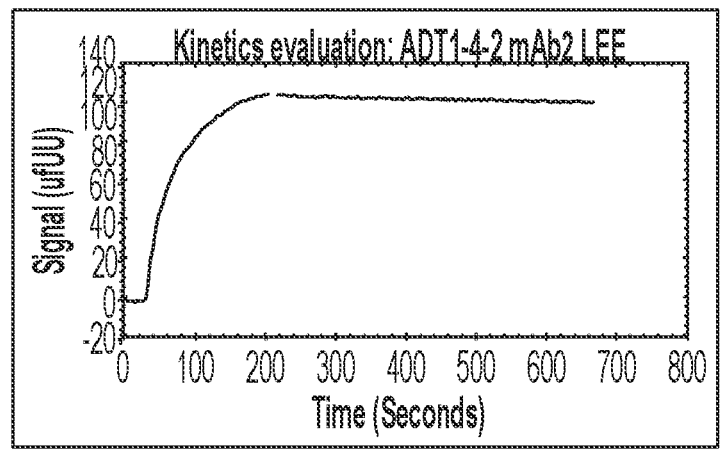
FIG. 26C

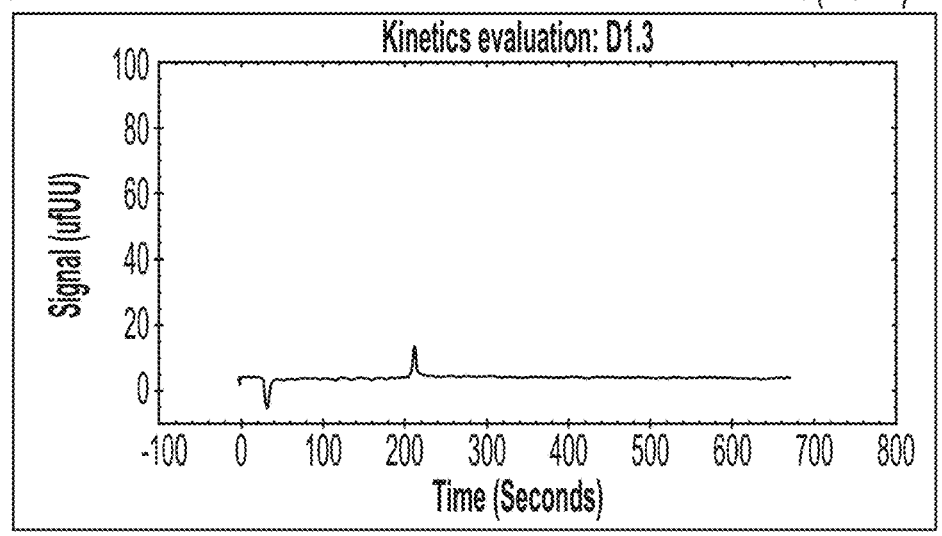
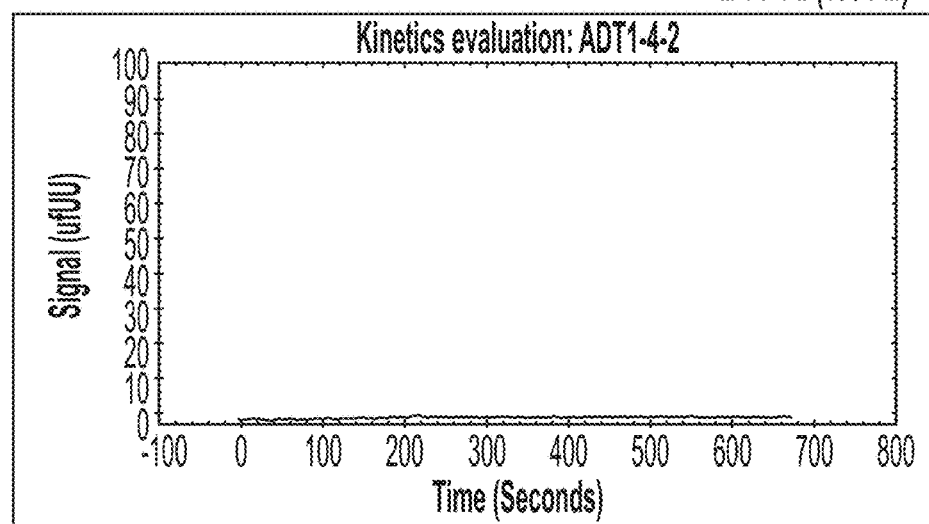
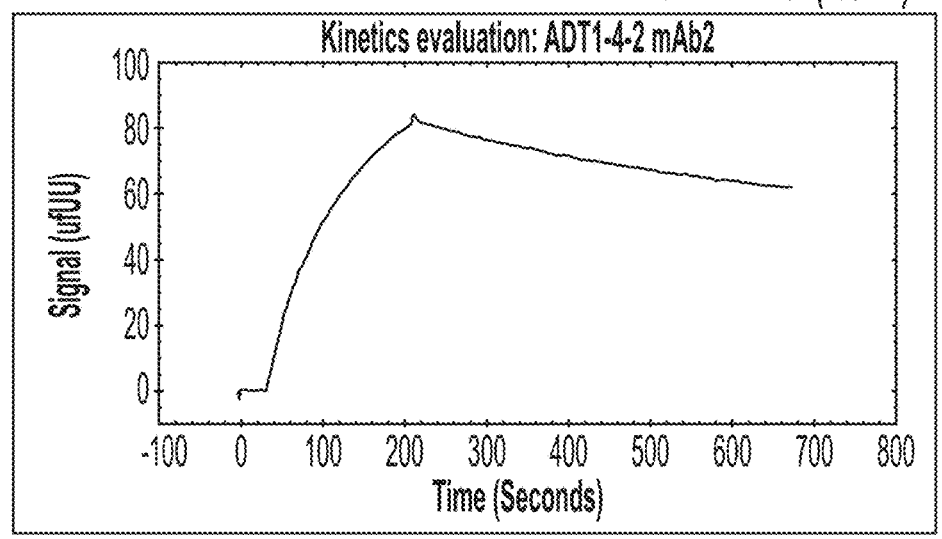
FIG. 26E

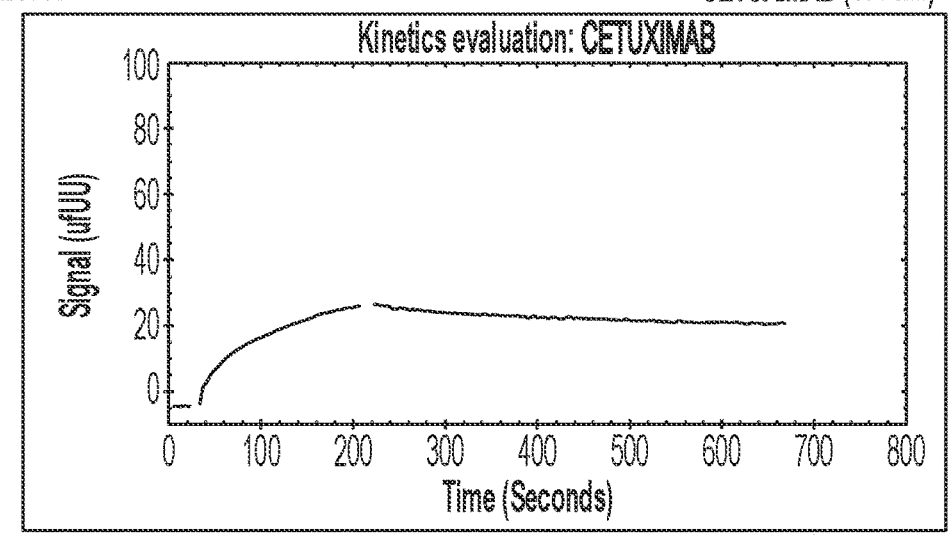
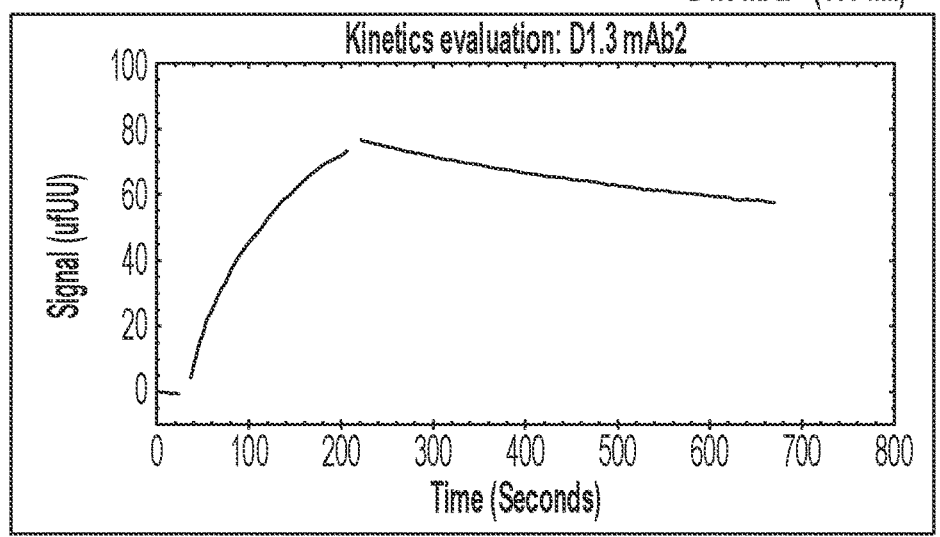
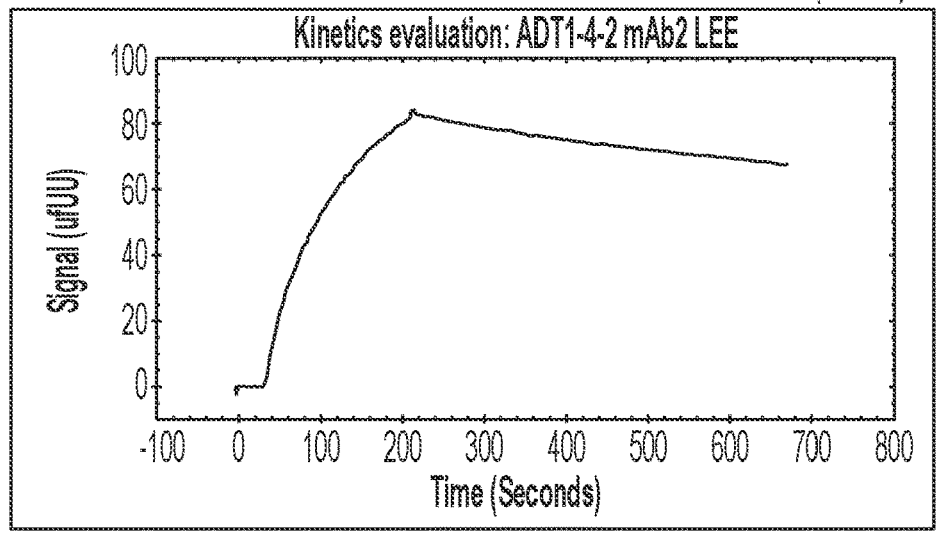
FIG. 26F

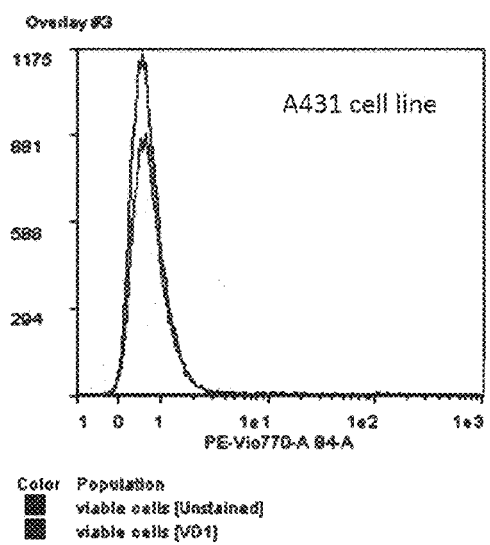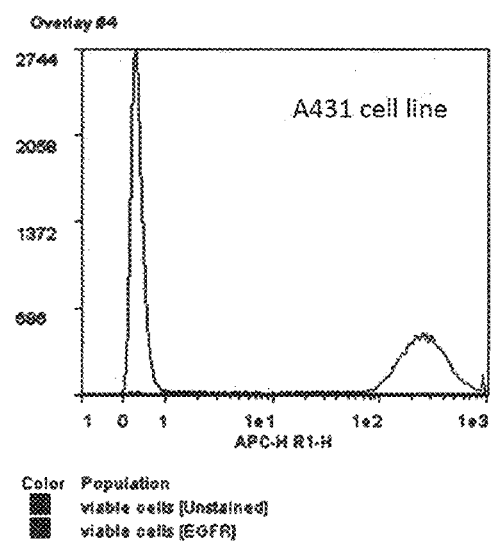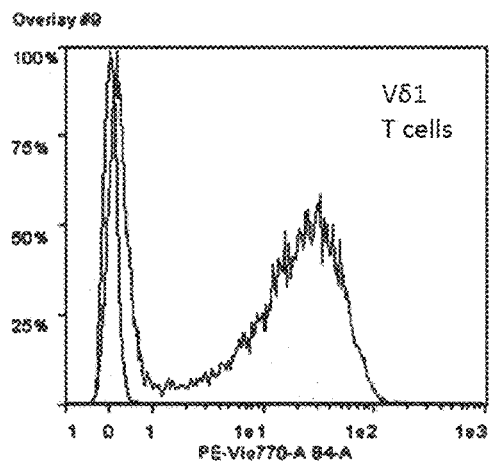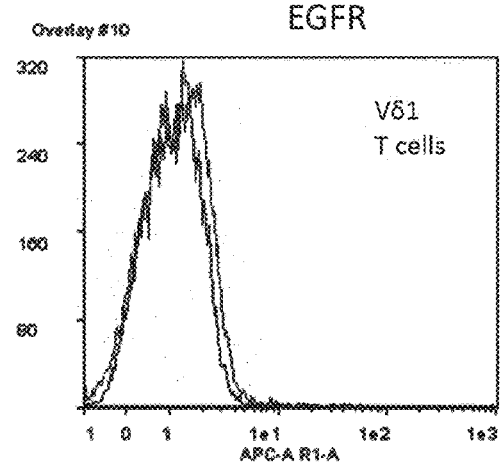
FIG. 27A

| | 5 hrs | 12 hrs | 24 hrs |
|---|---|---|---|
| No mAb | 100% | 100% | 100% |
| D1.3 | 114% | 99% | 112% |
| D1.3 IgG LAGA | 106% | 96% | 113% |
| D1.3 FS1-67 | 149% | 143% | 147% |
| CETUXIMAB | 121% | 110% | 126% |
| C08- LAGA | 99% | 84% | 101% |
| E07-LAGA | 115% | 117% | 127% |
| G04-LAGA | 141% | 128% | 163% |
| C08 FS1-67 | 467% | 424% | 371% |
| E07 FS1-67 | 303% | 292% | 259% |
| G04 FS1-67 | 254% | 232% | 212% |
FIG. 31D
| | 5 hrs | 12 hrs | 24 hrs |
|---|---|---|---|
| No mAb | 100% | 100% | 100% |
| D1.3 | 114% | 99% | 112% |
| D1.3 IgG LAGA | 106% | 96% | 113% |
| D1.3 LAGA CETUXIMAB | 132% | 123% | 118% |
| CETUXIMAB | 121% | 110% | 126% |
| C08- LAGA | 99% | 84% | 101% |
| E07-LAGA | 115% | 117% | 127% |
| G04-LAGA | 141% | 128% | 163% |
| C08 LAGA CETUXIMAB | 334% | 313% | 245% |
| E07 LAGA CETUXIMAB | 208% | 216% | 187% |
| G04 LAGA CETUXIMAB | 197% | 210% | 158% |
FIG. 31H
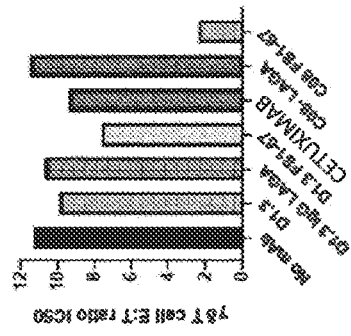
FIG. 31A
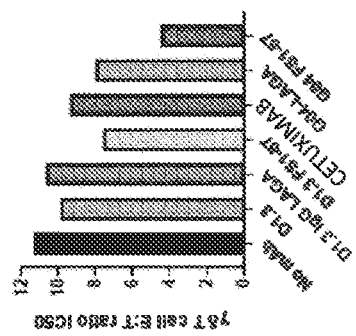
FIG. 31B
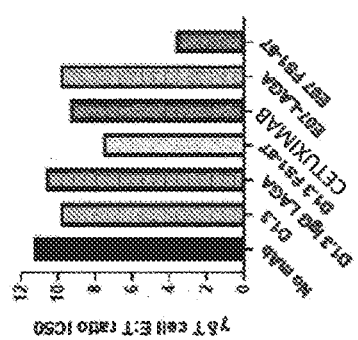
FIG. 31C
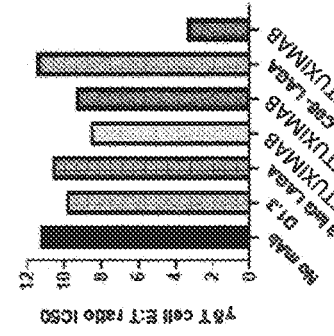
FIG. 31E
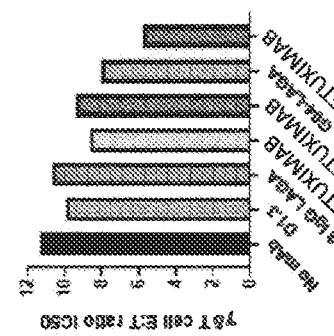
FIG. 31F
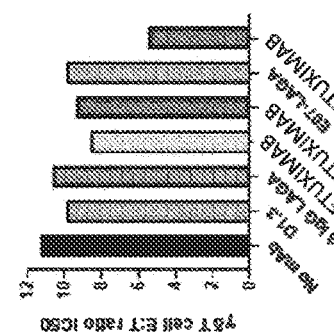
FIG. 31G EGFR binding domains (IgG1 CH1-CH2-CH3)

FS1-67 (SEQ ID NO: 385)

ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLY
SKLTVDKSRWQQGNVFSCSVMHEALHNHYTQKSLSLSPG

LEE (SEQ ID NO: 392)

ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESTYGPENNYKTTPPVLDSDGSFFLY
SKLTVDKSRWQQGNVFSCSVMHEALHNHYTQKSLSLSPG

LEE1 (SEQ ID NO: 509)

ASTKGPSVFPLAPSSKSTSGGTAALGCLVKDYFPEPVTVSWNSGALTSGVATSGVHTFPAVLQSSGLYSLSSVVTVPSSSLGTQTYICNVNHKPSNTKVDKRVEPKSCDKTHTCPPCPAPELAGAPSVFLFPPKPKDTLMISRTPEVTCV
VVDVSHEDPEVKFNWYVDGVEVHNAKTKPREEQYNSTYRVVSVLTVLHQDWLNGKEYKCKVSNKALPAPIEKTISKAKGQPREPQVYTLPPSRDENTKNQVSLTCLVKGFYPSDIAVEWESTYGPENNYKTTPPVLDSDGSFFLY
SKLTVSYSRWKYKGNVFSCSVMHEALHNHYTQKSLSLSPG

LEE2 (SEQ ID NO: 521)

ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCV
VVDVSHEDPEVKFMYVDGVEVHNAKTPREEQYNSTYRVVSVLTVLHQDWLNGKEEYKCKVSNKALPAPIEKTISKAKGQPREPQVYTLPPSRDIAVEWESNGQPENNYKTTPPVLDSDGSFFLY
SKLTVSYWMEQGGNVFSCSVMHEALHNHYTQKSLSLSPG

LEE3 (SEQ ID NO: 531)

ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEEYKCKVSNKALPAPIEKTISKAKGQPREPQVYTLPPSRDELEEGPVSLTCLVKGFYPSDIAVEWESNGQPENNYKTTPPVLDSDGSFFLY
SKLTVSYRMYTRGNVFSCSVMHEALHNHYTQKSLSLSPG

FS1-65 (SEQ ID NO: 540)

ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKENYKCKVSNKALPAPIEKTISKAKGQPREPQVYTLPPSRDELEEGGVSLSHAKGQPREPQVYTLPPSRDIAVEWESTYPSDIAVEWEZSTYPSDGSFFL
YSKLTVSMAYWMYKGNVPSCSVMHEAALHNHYTQKSLSLSPG 747 (SEQ ID NO: 551)

ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCV
VVDVSHEDPEVKFNWYVDGVEVHNARTKPREEQYNSTYRVVSVLTVLHQDWLNGKEYKCKVSNKALPAPIEKTISHAKGQPREPQVYTLPPSDETSGGVSLTCLVKGFYPSDIVWESKYGPENMYKTTPPVLDSDGSFFLY
SKLTVSNLEWTKGNVFSCSVMHEALHNHYTQKSLSLSPG

FIG. 32A

EGFR binding domains (IgG1 CH3 only, with EU numbering 341 through to 446 inclusive)

```
          34         35         36         37         38         39         40         41         42         43         44
          1234567890 1234567890 1234567890 1234567890 1234567890 1234567890 1234567890 1234567890 1234567890 1234567890 123456
IgG1      GQPREPQVYT LPPSRDELTKN QVSLTCLVKG FYPSDIAVEW ESNGQPENNY KTTPPVLDSD GSFFLYSKLT VDKSRWQQGN VFSCSVMHEA LHNHYTQKSL SLSPG
FS1-67    GQPREPQVYT LPPSRDEEEEG PVSLTCLVRG FYPSDIAVEW ESTYGPENNY KTTPPVLDSD GSFFLYSKLT VSMRWYKGN VFSCSVMHEA LHNHYTQKSL SLSPG
LEE       GQPREPQVYT LPPSRDEEEEG PVSLTCLVRG FYPSDIAVEW ESTYGPENNY KTTPPVLDSD GSFFLYSKLT VSMRWYKGN VFSCSVMHEA LHNHYTQKSL SLSPG
LEE1      GQPREPQVYT LPPSRDELTRN QVSLTCLVRG FYPSDIAVEW ESTYGPENNY KTTPPVLDSD GSFFLYSKLT VSMRWYKGN VFSCSVMHEA LHNHYTQKSL SLSPG
LEE2      GQPREPQVYT LPPSRDEEEEG PVSLTCLVRG FYPSDIAVEW ESNGQPENNY KTTPPVLDSD GSFFLYSKLT VSMRWYKGN VFSCSVMHEA LHNHYTQKSL SLSPG
LEE3      GQPREPQVYT LPPSRDEEKEG PVSLTCLVRG FYPSDIAVEW ESTYGPENNY KTTPPVLDSD GSFFLYSKLT VSMLRWYKGN VFSCSVMHEA LHNHYTQKSL SLSPG
747       GQPREPQVYT LPPSRDEEEEG PVSLTCLVRG FYPSDIVVEW ESKFGPENNY KTTPPVLDSD GSFFLYSKLT VSMRWYKGN QQGNVFSCSV MHEALHNHYT QKSLSLSPG
FS1-65    GQPREPQVYT LPPSRDENEG PVSITCLVRG FYPSDIAVEW ESTYGPENNY KTTPPVLDSR GSFFLYSKLT VSMRWYKGN VFSCSVMHRA LHNHYTQKSL SLSPG
```

Changes to IgG1 CH3 by EU numbering

| | AB LOOP | | CD LOOP | EF LOOP |
|---|---|---|---|---|
| FS1-67 | L358T, T359E, K360D, N361G, Q362P | | N384T, G385Y, Q386G | D413S, K414Y, S415W, Q418Y, Q419K |
| LEE | T359E, K360E, N361G, Q362P | | N384T, G385Y, Q386G | D413S, K414Y, S415W, Q418Y, Q419K |
| LEE1 | | | N384T, G385Y, Q386G | D413S, K414Y, S415W, Q418Y, Q419K |
| LEE2 | T359E, K360E, N361G, Q362P | | N384T, G385Y, Q386G | D413S, K414Y, S415W, Q418Y, Q419K |
| LEE3 | T359E, K360E, N361G, Q362P | | N384T, G385Y, Q386G | D413S, K414Y, S415W |
| 747 | L358T, T359E, K360S, N361G, Q362P | A378V | N384K, G385P, Q386G | D413S, K414N, S415L, Q418T, Q419K, N421H |
| FS1-65 | T359D, K360E, N361G, 361-1G, Q362P | | N384K, G385F, Q386G | D413S, K414Y, S415W, Q418V, Q419K |

FIG. 32B

| Human CH3 numbering convention (with cross-reference to IGHG1*01 wild-type) | | | | |
|---|---|---|---|---|
| CH3 Human Sequence IGHG1 amino acid translation J00228 (J00228 corresponds to the IGHG1*01 allele) | IMGT unique numbering for C-DOMAIN | IMGT CH3 exon numbering — see IMGT.Org (also for source of this adapted Table) | Eu numbering — see Edelman, G.M. et al., Proc. Natl. Acad. USA, 63, 78-85 (1969). | Kabat numbering — see Kabat, E.A. et al., NIH publication n° 91-3242, pp 662,680,689 (1991). |
| (G) | 1.4 | 1 | 341 | 361 |
| Q | 1.3 | 2 | 342 | 362 |
| P | 1.2 | 3 | 343 | 364 |
| R | 1.1 | 4 | 344 | 365 |
| E | 1 | 5 | 345 | 366 |
| P | 2 | 6 | 346 | 367 |
| Q | 3 | 7 | 347 | 368 |
| V | 4 | 8 | 348 | 369 |
| Y | 5 | 9 | 349 | 370 |
| T | 6 | 10 | 350 | 371 |
| L | 7 | 11 | 351 | 372 |
| P | 8 | 12 | 352 | 373 |
| P | 9 | 13 | 353 | 374 |
| S | 10 | 14 | 354 | 375 |
| R | 11 | 15 | 355 | 376 |
| D | 12 | 16 | 356 | 377 |
| E | 13 | 17 | 357 | 378 |
| L | 14 | 18 | 358 | 381 |
| T | 15 | 19 | 359 | 382 |
| K | 16 | 20 | 360 | 383 |
| N | 17 | 21 | 361 | 384 |
| (extra insert found in one example construct) | 17.1 | 21.1 | 361.1 | 384.1 |
| Q | 18 | 22 | 362 | 385 |
| V | 19 | 23 | 363 | 386 |
| S | 20 | 24 | 364 | 387 |
| L | 21 | 25 | 365 | 388 |
| T | 22 | 26 | 366 | 389 |
| C | 23 | 27 | 367 | 390 |
| L | 24 | 28 | 368 | 391 |
| V | 25 | 29 | 369 | 392 |
| K | 26 | 30 | 370 | 393 |
| G | 27 | 31 | 371 | 394 |
| F | 28 | 32 | 372 | 395 |
| Y | 29 | 33 | 373 | 396 |
| P | 30 | 34 | 374 | 397 |
| S | 35 | 35 | 375 | 398 |
| D | 36 | 36 | 376 | 399 |
| I | 37 | 37 | 377 | 400 |
| A | 38 | 38 | 378 | 401 |

FIG. 33A

| | | | | |
|---|---|---|---|---|
| V | 39 | 39 | 379 | 402 |
| E | 40 | 40 | 380 | 405 |
| W | 41 | 41 | 381 | 406 |
| E | 42 | 42 | 382 | 407 |
| S | 43 | 43 | 383 | 408 |
| N | 44 | 44 | 384 | 410 |
| G | 45 | 45 | 385 | 411 |
| Q | 45.1 | 46 | 386 | 414 |
| P | 45.2 | 47 | 387 | 415 |
| E | 45.3 | 48 | 388 | 416 |
| N | 45.4 | 49 | 389 | 417 |
| N | 77 | 50 | 390 | 418 |
| Y | 78 | 51 | 391 | 419 |
| K | 79 | 52 | 392 | 420 |
| T | 80 | 53 | 393 | 421 |
| T | 81 | 54 | 394 | 422 |
| P | 82 | 55 | 395 | 423 |
| P | 83 | 56 | 396 | 424 |
| V | 84 | 57 | 397 | 425 |
| L | 84.1 | 58 | 398 | 426 |
| D | 84.2 | 59 | 399 | 427 |
| S | 84.3 | 60 | 400 | 428 |
| D | 84.4 | 61 | 401 | 430 |
| G | 85.4 | 62 | 402 | 433 |
| S | 85.3 | 63 | 403 | 434 |
| F | 85.2 | 64 | 404 | 435 |
| F | 85.1 | 65 | 405 | 436 |
| L | 85 | 66 | 406 | 437 |
| Y | 86 | 67 | 407 | 438 |
| S | 87 | 68 | 408 | 439 |
| K | 88 | 69 | 409 | 440 |
| L | 89 | 70 | 410 | 441 |
| T | 90 | 71 | 411 | 442 |
| V | 91 | 72 | 412 | 443 |
| D | 92 | 73 | 413 | 444 |
| K | 93 | 74 | 414 | 445 |
| S | 94 | 75 | 415 | 446 |
| R | 95 | 76 | 416 | 447 |
| W | 96 | 77 | 417 | 448 |
| Q | 97 | 78 | 418 | 449 |
| Q | 98 | 79 | 419 | 450 |
| G | 99 | 80 | 420 | 451 |
| N | 100 | 81 | 421 | 452 |
| V | 101 | 82 | 422 | 453 |
| F | 102 | 83 | 423 | 454 |
| S | 103 | 84 | 424 | 455 |

FIG. 33B

| | | | | |
|---|---|---|---|---|
| C | 104 | 85 | 425 | 456 |
| S | 105 | 86 | 426 | 457 |
| V | 106 | 87 | 427 | 458 |
| M | 107 | 88 | 428 | 459 |
| H | 108 | 89 | 429 | 460 |
| E | 109 | 90 | 430 | 461 |
| A | 110 | 91 | 431 | 462 |
| L | 112 | 92 | 432 | 463 |
| H | 113 | 93 | 433 | 464 |
| N | 114 | 94 | 434 | 465 |
| H | 115 | 95 | 435 | 466 |
| Y | 116 | 96 | 436 | 467 |
| T | 117 | 97 | 437 | 468 |
| Q | 118 | 98 | 438 | 469 |
| K | 119 | 99 | 439 | 470 |
| S | 120 | 100 | 440 | 471 |
| L | 121 | 101 | 441 | 472 |
| S | 122 | 102 | 442 | 473 |
| L | 123 | 103 | 443 | 474 |
| S | 124 | 104 | 444 | 475 |
| P | 125 | 105 | 445 | 476 |
| G | 129 | CHS 106 | 446 | 477 |
| K | 130 | CHS 107 | 447 | 478 |

FIG. 33C

| Antibody (@37C for 48 hours) | % Basic time zero | % Basic at 48 hours | % Change |
|---|---|---|---|
| ADT1-4-2xLEE | 2.8 | 3.4 | +0.6 |
| ADT1-4-2xLEE2 | 2.6 | 3.1 | +0.5 |
| ADT1-4-2xLEE3 | 3.9 | 4.0 | +0.1 |
| ADT1-4-2xFS1-67 | 3.4 | 23.4 | +20.0 |
| ADT1-4-2xFS1-65 | 2.6 | 3.8 | +1.2 |

| Antibody | Tm onset (°C) | Tagg onset (°C) | Delta(°C) |
|---|---|---|---|
| ADT1-4-2xLEE | 63.8 | 63.8 | 0 |
| ADT1-4-2xLEE2 | 67.7 | 64.2 | -3.5 |
| ADT1-4-2xLEE3 | 67.8 | 64.4 | -3.4 |
| ADT1-4-2xFS1-67 | 68.9 | 65.7 | -3.2 |
| ADT1-4-2xFS1-65 | 74 | 57.6 | -16.4 |
FIG. 34C
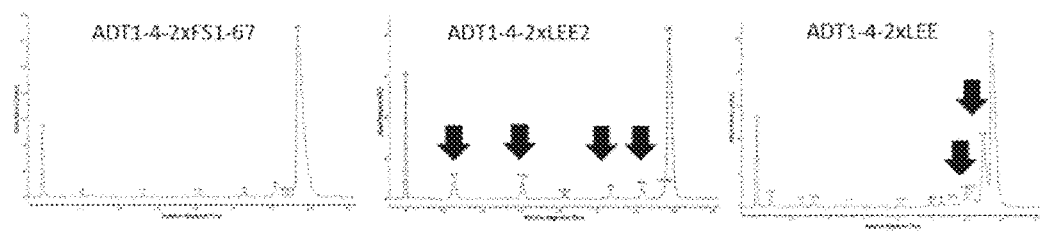
FIG. 34D
| Antibody @ 5mg/ml | % Monomer (time zero) | % Monomer (18 days, 37°C) | % change over 18-days |
|---|---|---|---|
| ADT1-4-2xLEE | 98.0 | 60.6 | -37.4 |
| ADT1-4-2xLEE2 | 97.7 | 74.0 | -23.7 |
| ADT1-4-2xLEE3 | 97.5 | 68.3 | -29.2 |
| ADT1-4-2xFS1-67 | 95.6 | 94.0 | -1.6 |
| ADT1-4-2xFS1-65 | 96.8 | 72.7 | -24.1 |
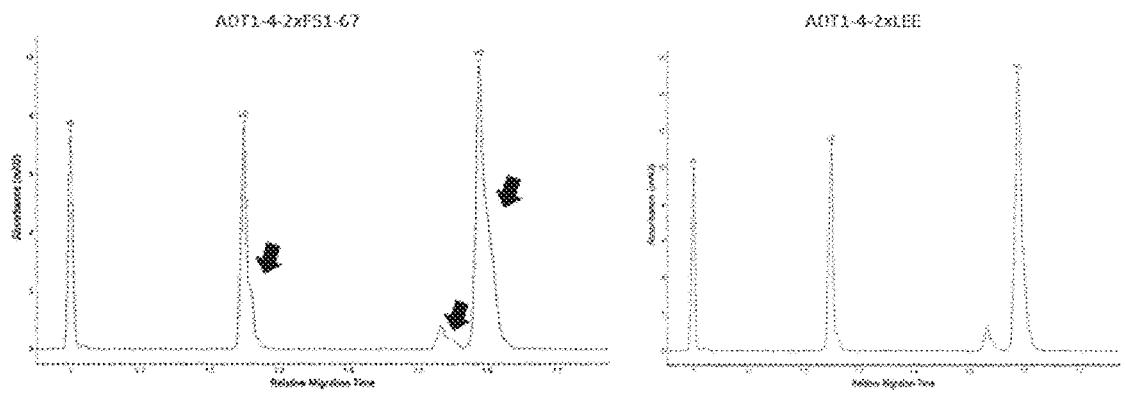
FIG. 34E

| Antibody | Yield | Stable Charge at 37C | Favorable Tm/agg delta | %Monomer 5mg/ml, 18d @ 37C (non-reduced) | Typical HC + LC profile at 5mg/ml 18 d @ 37C (reduced) | Total Score | AB loop modifications | BC loop modifications | EF loop modifications | No. of changes (and % identity) relative to human CH3 sequence P343 to G446 (117 residues) |
|---|---|---|---|---|---|---|---|---|---|---|
| ADT1-4-2xLEE | ++ | +++ | +++ | + | ++ | 11 | T359E,K360E,N361G, Q362P | N384T,G385Y,Q386G | D413S,K414Y,S415W,Q418Y,Q419K | 12 (89%) |
| ADT1-4-2xLEE2 | ++ | +++ | ++ | ++ | ++ | 11 | T359E,K360E,N361G, Q362P | No changes from wild-type | D413S,K414Y,S415W,Q418Y,Q419K | 9 (9.1%) |
| ADT1-4-2xLEE3 | ++ | +++ | +++ | ++ | ++ | 11 | T359E,K360E,N361G, Q362P | N384T,G385Y,Q386G | D413S,K414Y,S415W | 10 (90%) |
| ADT1-4-2xFS1-67 | + | + | ++ | +++ | - | 7 | L358T,T359D,K360D, N361G,Q362P | N384T,G385Y,Q386G | D413S,K414Y,S415W,Q418Y,Q419K | 13 (88%) |
| ADT1-4-2xFS1-65 | ++ | +++ | | ++ | ++ | 9 | T359D,K360D,N361G, 361G,Q362P | N384T,G385Y,Q386G | D413S,K414Y,S415W,Q418Y,Q419K | 13 (88%) |

FIG. 34F

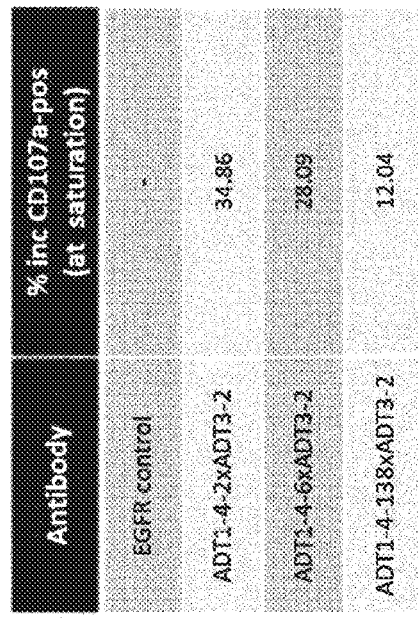
FIG. 35E
FIG. 35G
FIG. 35D
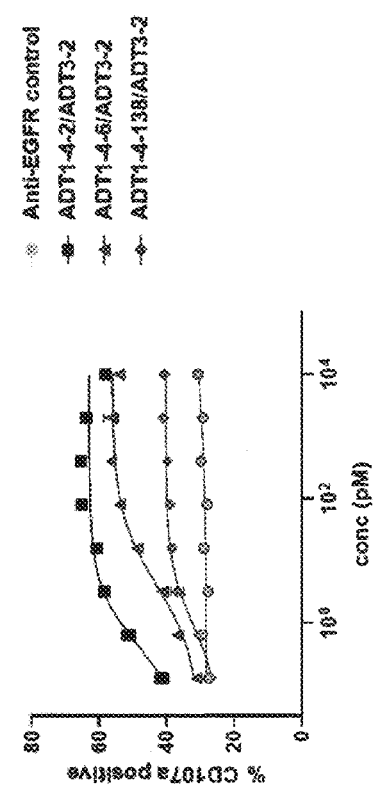
FIG. 35F

| Technical effect conferred on primary tissue-derived Vδ1+ by anti-Vδ1 TCR antibodies of this invention | Is this effect further enhanced by increasing the affinity of the antibody to less than 10nM ? | Can the diminished effect conferred by lower affinity molecules be compensated for by increasing conc. 100-fold or more ? |
|---|---|---|
| Binding (MFI) | YES | NO |
| Vδ1 TCR downregulation | YES | NO |
| CD107A upregulation | YES | NO |
| Cytoxicity | YES | NO |
| Proliferation | YES | YES |

| Antibody | Alias (if any) | Affinity to EGFR (nM) | No of changes vs wild-type immunoglobulin sequence | | |
|---|---|---|---|---|---|
| | | | AB loop | CD loop | EF loop |
| ADT1-4-2 | - | - | 0 | 0 | 0 |
| ADT1-4-2xADT3-1 | ADT1-4-2xFS1-67 | 1.37 | 5 | 3 | 5 |
| ADT1-4-2xADT3-2 | ADT1-4-2xLEE | 1.49 | 4 | 3 | 5 |
| ADT1-4-2xADT3-3 | ADT1-4-2xFS1-65 | 1.35 | 6 | 3 | 5 |
| ADT1-4-2xADT3-4 | ADT1-4-2x747 | 2.35 | 5(+1) | 3 | 6 |
| ADT1-4-2xADT3-5 | ADT1-4-2xLEE1 | 1.42 | 0 | 3 | 5 |
| ADT1-4-2xADT3-6 | ADT1-4-2xLEE2 | 19.2 | 4 | 0 | 5 |
| ADT1-4-2xADT3-7 | ADT1-4-2xLEE3 | 8.63 | 4 | 3 | 3 |

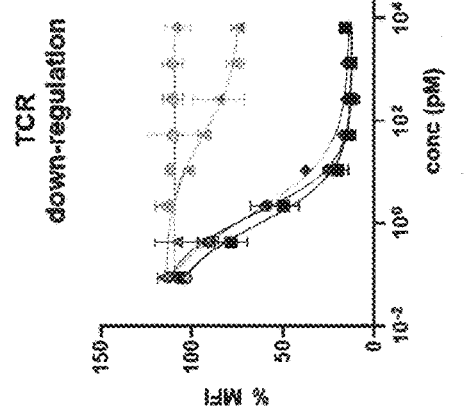
FIG. 36C
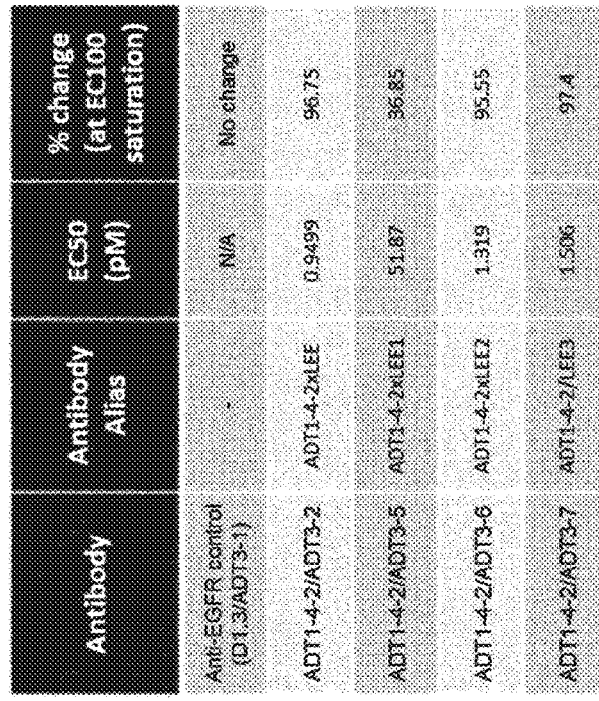
FIG. 36D
FIG. 36E

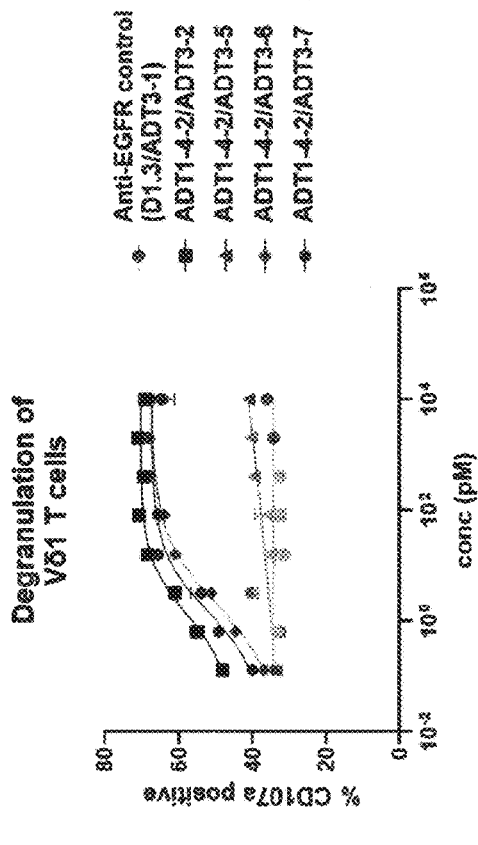
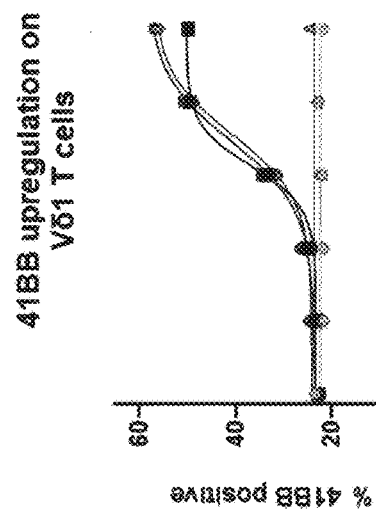
FIG. 36F
FIG. 36G
FIG. 36H
FIG. 36I

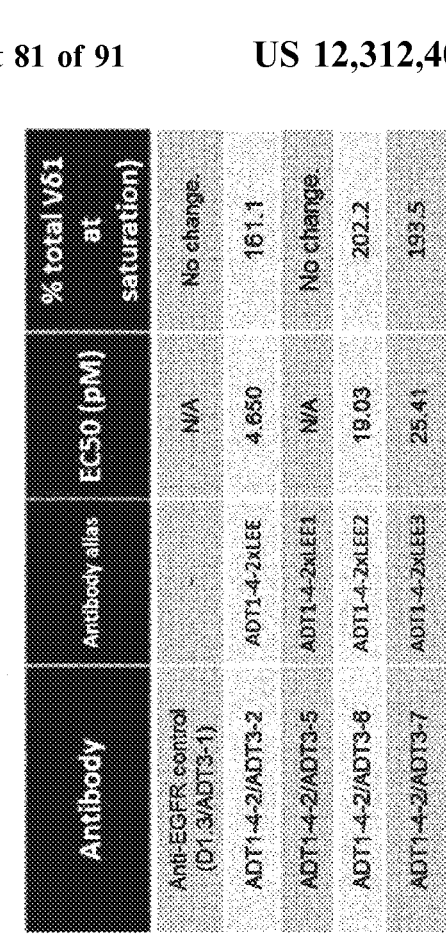
FIG. 36K
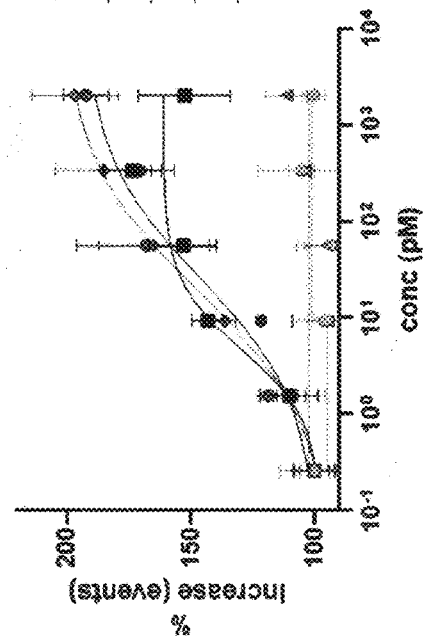
FIG. 36M
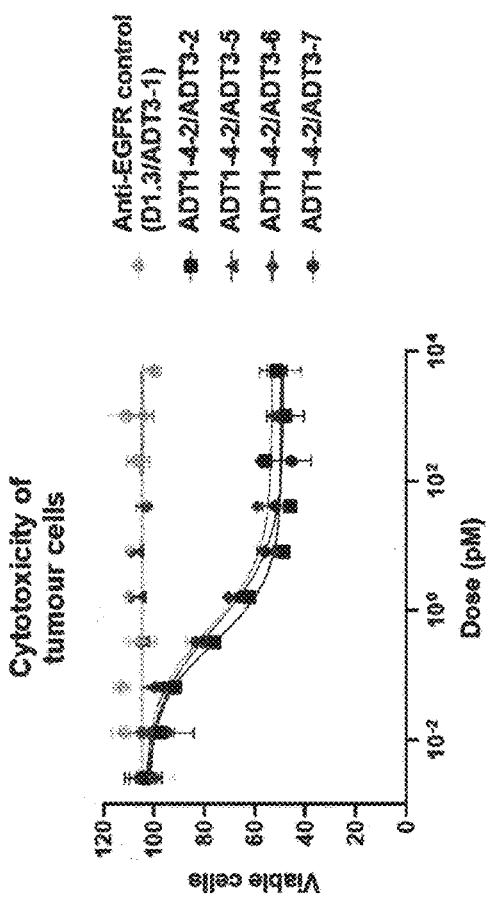
FIG. 36J
FIG. 36L

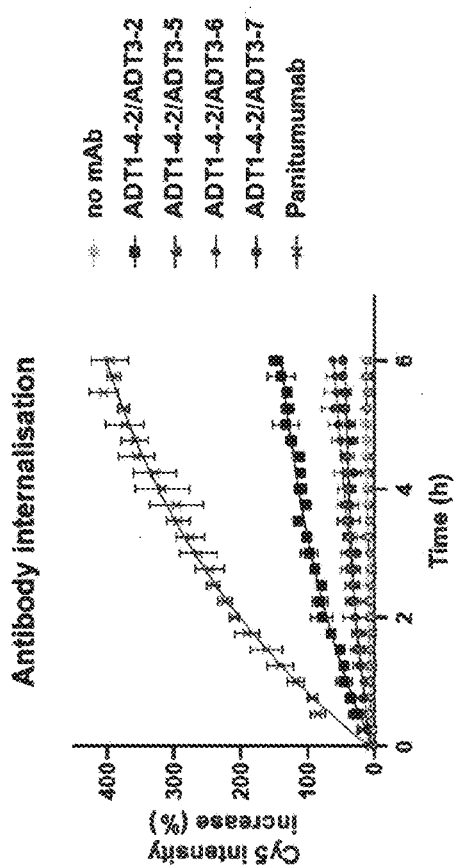
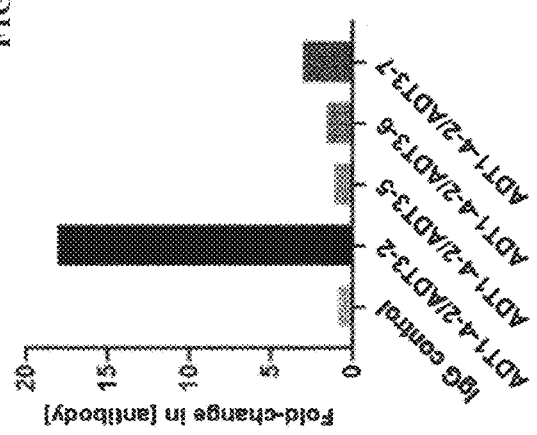
FIG. 38A
FIG. 38B
FIG. 38C
FIG. 38D

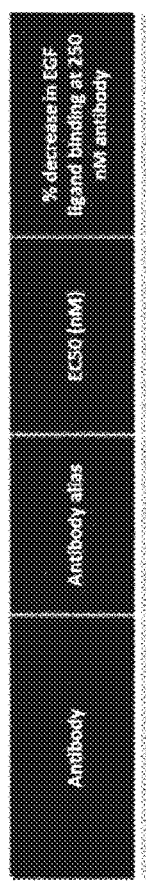
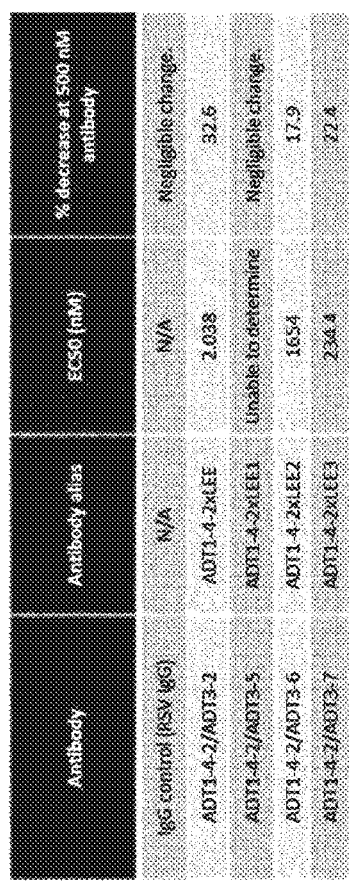
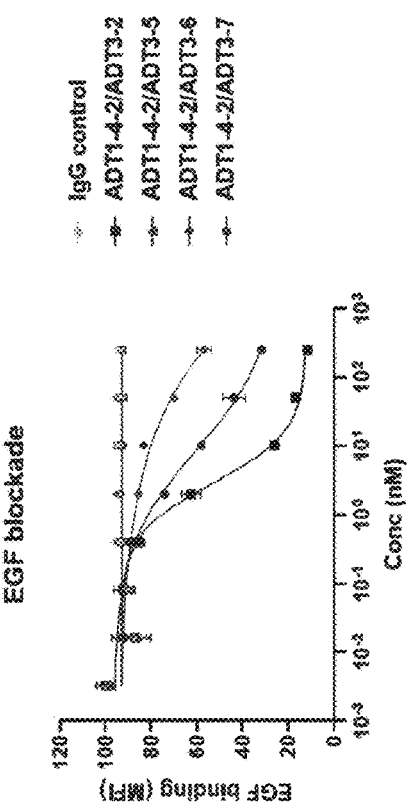
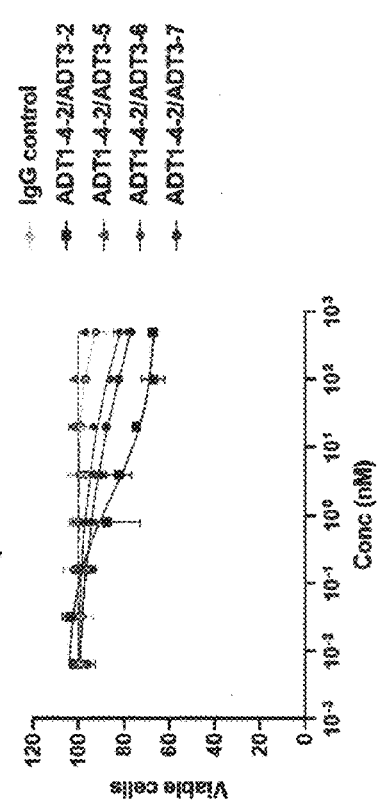
FIG. 39A
FIG. 39B
FIG. 39C
FIG. 39D

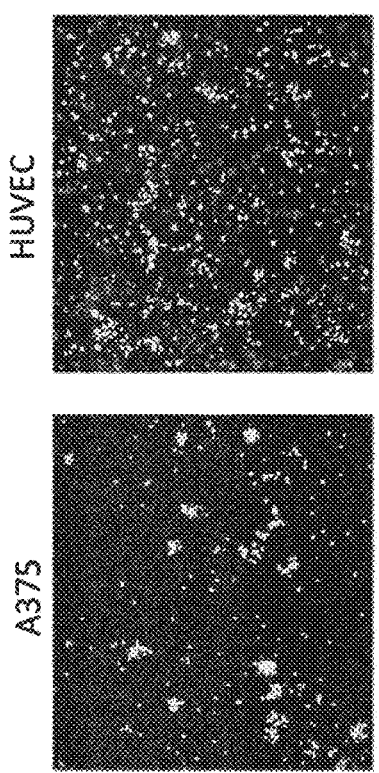
FIG. 40B
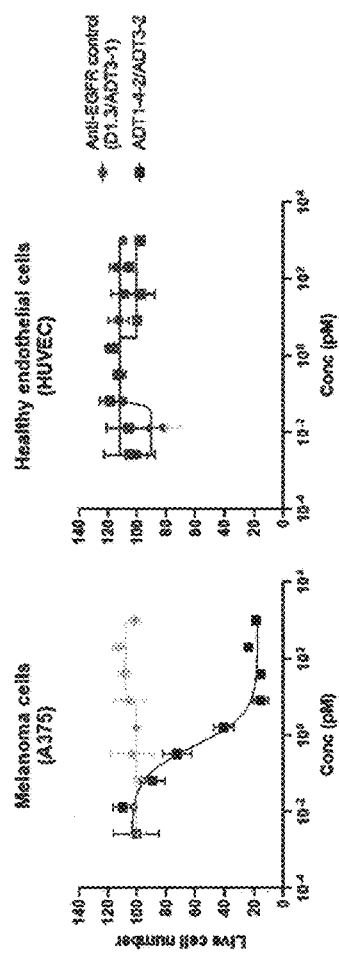
FIG. 40A
FIG. 40C

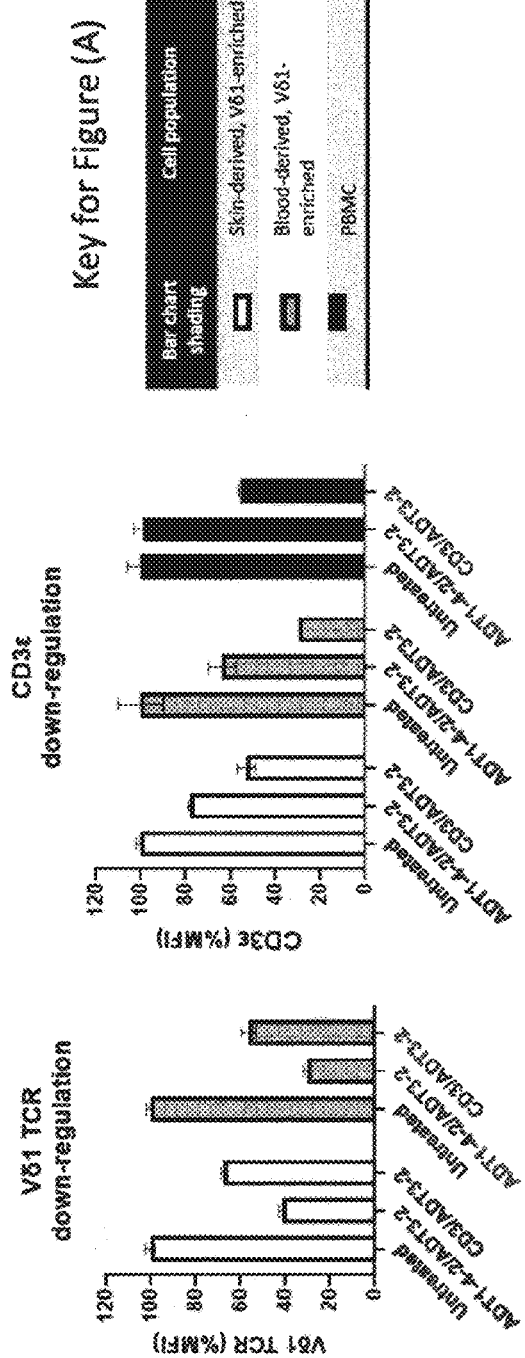
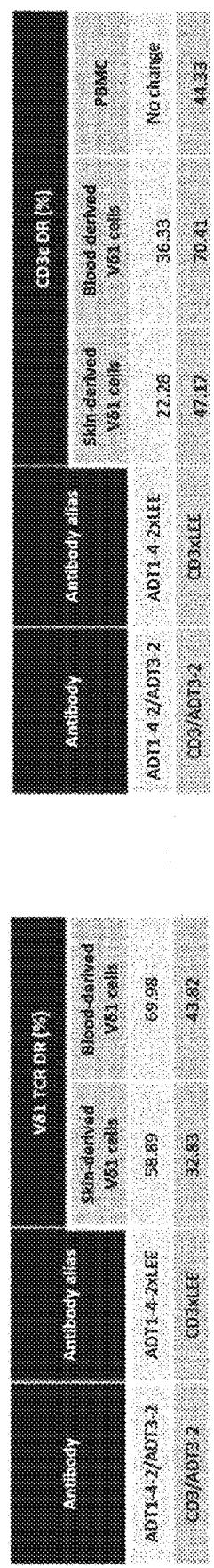
FIG. 42A
FIG. 42B
FIG. 42C

SEQUENCE LISTING

```
Sequence total quantity: 563
SEQ ID NO: 1                    moltype = AA  length = 120
FEATURE                         Location/Qualifiers
REGION                          1..120
                                note = ADT1-4 Variable Heavy
source                          1..120
                                mol_type = protein
                                organism = Homo sapiens
SEQUENCE: 1
QVQLQQSGPG LVKPSQTLSL TCAISGDSVS SKSAAWNWIR QSPSRGLEWL GRTYYRSKWS   60
TDYAASVKSR ITINPDTSKN QLSLQLNSVT PEDTAVYYCA RTWSGYVDVW GQGTLVTVSS  120

SEQ ID NO: 2                    moltype = AA  length = 120
FEATURE                         Location/Qualifiers
REGION                          1..120
                                note = ADT1-4-105 Variable Heavy
source                          1..120
                                mol_type = protein
                                organism = Homo sapiens
SEQUENCE: 2
EVQLQQSGPG LVKPSQTLSL TCAISGDSVS SKSAAWNWIR QSPSRGLEWL GRTYYRSKWS   60
TDYAASVKSR ITINPDTSKN QLSLQLNSVT PEDTAVYYCA RTWVGYVDVW GQGTLVTVSS  120

SEQ ID NO: 3                    moltype = AA  length = 120
FEATURE                         Location/Qualifiers
REGION                          1..120
                                note = ADT1-4-107 Variable Heavy
source                          1..120
                                mol_type = protein
                                organism = Homo sapiens
SEQUENCE: 3
EVQLQQSGPG LVKPSQTLSL TCAISGDSVS SKSAAWNWIR QSPSRGLEWL GRTYYRSKWS   60
TDYAASVKSR ITINPDTSKN QLSLQLNSVT PEDTAVYYCA RTWVGYADVW GQGTLVTVSS  120

SEQ ID NO: 4                    moltype = AA  length = 120
FEATURE                         Location/Qualifiers
REGION                          1..120
                                note = ADT1-4-110 Variable Heavy
source                          1..120
                                mol_type = protein
                                organism = Homo sapiens
SEQUENCE: 4
EVQLQQSGPG LVKPSQTLSL TCAISGDSVS SKSAAWNWIR QSPSRGLEWL GRTYYRSKWS   60
TDYAASVKSR ITINPDTSKN QLSLQLNSVT PEDTAVYYCA RTWVEYVDVW GQGTLVTVSS  120

SEQ ID NO: 5                    moltype = AA  length = 120
FEATURE                         Location/Qualifiers
REGION                          1..120
                                note = ADT1-4-112 Variable Heavy
source                          1..120
                                mol_type = protein
                                organism = Homo sapiens
SEQUENCE: 5
EVQLQQSGPG LVKPSQTLSL TCAISGDSVS SKSAAWNWIR QSPSRGLEWL GRTYYRSKWS   60
TDYAASVKSR ITINPDTSKN QLSLQLNSVT PEDTAVYYCA RTWVGYVDYW GQGTLVTVSS  120

SEQ ID NO: 6                    moltype = AA  length = 120
FEATURE                         Location/Qualifiers
REGION                          1..120
                                note = ADT1-4-117 Variable Heavy
source                          1..120
                                mol_type = protein
                                organism = Homo sapiens
SEQUENCE: 6
EVQLQQSGPG LVKPSQTLSL TCAISGDSVS SKSAAWNWIR QSPSRGLEWL GRTYYRSKWS   60
TDYAASVKSR ITINPDTSKN QLSLQLNSVT PEDTAVYYCA RTWVGYVDVW GQGTLVTVSS  120

SEQ ID NO: 7                    moltype = AA  length = 120
FEATURE                         Location/Qualifiers
REGION                          1..120
                                note = ADT1-4-19 Variable Heavy
source                          1..120
                                mol_type = protein
                                organism = Homo sapiens
SEQUENCE: 7
EVQLQQSGPG LVKPSQTLSL TCAISGDSVS SKSAAWNWIR QSPSRGLEWL GRTYYRSKWS   60
TDYAASVKSR ITINPDTSKN QLSLQLNSVT PEDTAVYYCA RTWVGYVDRW GQGTLVTVSS  120
```

```
SEQ ID NO: 8              moltype = AA  length = 120
FEATURE                   Location/Qualifiers
REGION                    1..120
                          note = ADT1-4-21 Variable Heavy
source                    1..120
                          mol_type = protein
                          organism = Homo sapiens
SEQUENCE: 8
EVQLQQSGPG LVKPSQTLSL TCAISGDSVS SKSVAWNWIR QSPSRGLEWL GRTYYRSKWS   60
TDYAASVKSR ITINPDTSKN QLSLQLNSVT PEDTAVYYCA RTWADYVDVW GQGTLVTVSS  120

SEQ ID NO: 9              moltype = AA  length = 120
FEATURE                   Location/Qualifiers
REGION                    1..120
                          note = ADT1-4-31 Variable Heavy
source                    1..120
                          mol_type = protein
                          organism = Homo sapiens
SEQUENCE: 9
EVQLQQSGPG LVKPSQTLSL TCAISGDSVS SKSAAWNWIR QSPSRGLEWL GRTYYRSKWS   60
TDYAASVKSR ITINPDTSKN QLSLQLNSVT PEDTAVYYCA RTWVGYADVW GQGTLVTVSS  120

SEQ ID NO: 10             moltype = AA  length = 120
FEATURE                   Location/Qualifiers
REGION                    1..120
                          note = ADT1-4-139 Variable Heavy
source                    1..120
                          mol_type = protein
                          organism = Homo sapiens
SEQUENCE: 10
EVQLQQSGPG LVKPSQTLSL TCAISGDSVS SKSAAWNWIR QSPSRGLEWL GRTYYRSKWS   60
TDYAASVKSR ITINPDTSKN QLSLQLNSVT PEDTAVYYCA RTWVGYVDYW GQGTLVTVSS  120

SEQ ID NO: 11             moltype = AA  length = 120
FEATURE                   Location/Qualifiers
REGION                    1..120
                          note = ADT1-4-4 Variable Heavy
source                    1..120
                          mol_type = protein
                          organism = Homo sapiens
SEQUENCE: 11
EVQLQQSGPG LVKPSQTLSL TCAISGDSVS SKSAAWNWIR QSPSRGLEWL GRTYYRSKWS   60
TDYAASVKSR ITINPDTSKN QLSLQLNSVT PEDTAVYYCA RTWVGYADVW GQGTLVTVSS  120

SEQ ID NO: 12             moltype = AA  length = 120
FEATURE                   Location/Qualifiers
REGION                    1..120
                          note = ADT1-4-143 Variable Heavy
source                    1..120
                          mol_type = protein
                          organism = Homo sapiens
SEQUENCE: 12
EVQLLQSGPG LVKPSQTLSL TCAISGDSVS SKSAAWNWIR QSPSRGLEWL GRTYYRSKWS   60
TDYAASVKSR ITINPDTSKN QLSLQLNSVT PEDTAVYYCA RTWVGYADVW GQGTLVTVSS  120

SEQ ID NO: 13             moltype = AA  length = 120
FEATURE                   Location/Qualifiers
REGION                    1..120
                          note = ADT1-4-53 Variable Heavy
source                    1..120
                          mol_type = protein
                          organism = Homo sapiens
SEQUENCE: 13
EVQLQQSGPG LVKPSQTLSL TCAISGDSVS SKSVAWNWIR QSPSRGLEWL GRTYYRSKWS   60
TDYAASVKSR ITINPDTSKN QLSLQLNSVT PEDTAVYYCA RTWADYVDVW GQGTLVTVSS  120

SEQ ID NO: 14             moltype = AA  length = 120
FEATURE                   Location/Qualifiers
REGION                    1..120
                          note = ADT1-4-173 Variable Heavy
source                    1..120
                          mol_type = protein
                          organism = Homo sapiens
SEQUENCE: 14
EVQLQQSGPG LVKPSQTLSL TCAISGDSVS SKSAAWNWIR QSPSRGLEWL GRTYYRSKWS   60
TDYAASVKSR ITINPDTSKN QLSLQLNSVT PEDTAVYYCA RTWAGYPDVW GQGTLVTVSS  120

SEQ ID NO: 15             moltype = AA  length = 120
FEATURE                   Location/Qualifiers
```

```
REGION              1..120
                    note = ADT1-4-2 Variable Heavy
source              1..120
                    mol_type = protein
                    organism = Homo sapiens
SEQUENCE: 15
EVQLQQSGPG LVKPSQTLSL TCAISGDSVS SKSAAWNWIR QSPSRGLEWL GRTYYRSKWS    60
TDYAASVKSR ITINPDTSKN QLSLQLNSVT PEDTAVYYCA RTWVGYVDRW GQGTLVTVSS   120

SEQ ID NO: 16       moltype = AA   length = 120
FEATURE             Location/Qualifiers
REGION              1..120
                    note = ADT1-4-8 Variable Heavy
source              1..120
                    mol_type = protein
                    organism = Homo sapiens
SEQUENCE: 16
EVQLQQSGPG LVKPSQTLSL TCAISGDSVS SKSAAWNWIR QSPSRGLEWL GRTYYRSKWS    60
TDYAASVKSR ITINPDTSKN QLSLQLNSVT PEDTAVYYCA RSWVGYVDVW GQGTLVTVSS   120

SEQ ID NO: 17       moltype = AA   length = 120
FEATURE             Location/Qualifiers
REGION              1..120
                    note = ADT1-4-82 Variable Heavy
source              1..120
                    mol_type = protein
                    organism = Homo sapiens
SEQUENCE: 17
EVQLQQSGPG LVKPSQTLSL TCAISGDSVS SKSAAWNWIR QSPSRGLEWL GRTYYRSKWS    60
TDYAASVKSR ITINPDTSKN QLSLQLNSVT PEDTAVYYCA RSWVGYVDVW GQGTLVTVSS   120

SEQ ID NO: 18       moltype = AA   length = 120
FEATURE             Location/Qualifiers
REGION              1..120
                    note = ADT1-4-83 Variable Heavy
source              1..120
                    mol_type = protein
                    organism = Homo sapiens
SEQUENCE: 18
EVQLQQSGPG LVKPSQTLSL TCAISGDSVS SKSAAWNWIR QSPSRGLEWL GRTYYRSKWS    60
TDYAASVKSR ITINPDTSKN QLSLQLNSVT PEDTAVYYCA RSWVGYVDVW GQGTLVTVSS   120

SEQ ID NO: 19       moltype = AA   length = 120
FEATURE             Location/Qualifiers
REGION              1..120
                    note = ADT1-4-3 Variable Heavy
source              1..120
                    mol_type = protein
                    organism = Homo sapiens
SEQUENCE: 19
EVQLQQSGPG LVKPSQTLSL TCAISGDSVS SKSAAWNWIR QSPSRGLEWL GRTYYRSKWS    60
TDYAASVKSR ITINPDTSKN QLSLQLNSVT PEDTAVYYCA RTWADYVDVW GQGTLVTVSS   120

SEQ ID NO: 20       moltype = AA   length = 120
FEATURE             Location/Qualifiers
REGION              1..120
                    note = ADT1-4-84 Variable Heavy
source              1..120
                    mol_type = protein
                    organism = Homo sapiens
SEQUENCE: 20
EVQLQQSGPG LVKPSQTLSL TCAISGDSVS SKSAAWNWIR QSPSRGLEWL GRTYYRSKWS    60
TDYAASVKSR ITINPDTSKN QLSLQLNSVT PEDTAVYYCA RTWVGYADVW GQGTLVTVSS   120

SEQ ID NO: 21       moltype = AA   length = 120
FEATURE             Location/Qualifiers
REGION              1..120
                    note = ADT1-4-86 Variable Heavy
source              1..120
                    mol_type = protein
                    organism = Homo sapiens
SEQUENCE: 21
EVQLQQSGPG LVKPSQTLSL TCAISGDSVS SKSVAWNWIR QSPSRGLEWL GRTYYRSKWS    60
TDYAASVKSR ITINPDTSKN QLSLQLNSVT PEDTAVYYCA RTWLGNVDVW GQGTLVTVSS   120

SEQ ID NO: 22       moltype = AA   length = 120
FEATURE             Location/Qualifiers
REGION              1..120
                    note = ADT1-4-95 Variable Heavy
```

```
                        -continued
source                  1..120
                        mol_type = protein
                        organism = Homo sapiens
SEQUENCE: 22
EVQLQQSGPG LVKPSQTLSL TCAISGDSVS SKSAAWNWIR QSPSRGLEWL GRTYYRSKWS    60
TDYAASVKSR ITINPDTSKN QLSLQLNSVT PEDTAVYYCA RTWVGYADVW GQGTLVTVSS   120

SEQ ID NO: 23           moltype = AA  length = 120
FEATURE                 Location/Qualifiers
REGION                  1..120
                        note = ADT1-4-1 Variable Heavy
source                  1..120
                        mol_type = protein
                        organism = Homo sapiens
SEQUENCE: 23
EVQLQQSGPG LVKPSQTLSL TCAISGDSVS SKSAAWNWIR QSPSRGLEWL GRTYYRSKWS    60
TDYAASVKSR ITINPDTSKN QLSLQLNSVT PEDTAVYYCA RTWVGYADVW GQGTLVTVSS   120

SEQ ID NO: 24           moltype = AA  length = 120
FEATURE                 Location/Qualifiers
REGION                  1..120
                        note = ADT1-4-6 Variable Heavy
source                  1..120
                        mol_type = protein
                        organism = Homo sapiens
SEQUENCE: 24
EVQLQQSGPG LVKPSQTLSL TCAISGDSVS SKSAAWNWIR QSPSRGLEWL GRTYYRSKWS    60
TDYAASVKSR ITINPDTSKN QLSLQLNSVT PEDTAVYYCA RTWAGYPDVW GQGTLVTVSS   120

SEQ ID NO: 25           moltype = AA  length = 120
FEATURE                 Location/Qualifiers
REGION                  1..120
                        note = ADT1-4-138 Variable Heavy
source                  1..120
                        mol_type = protein
                        organism = Homo sapiens
SEQUENCE: 25
EVQLQQSGPG LVKPSQTLSL TCAISGDSVS SKSAAWNWIR QSPSRGLEWL GRTYYRSKWS    60
TDYAASVKSR ITINPDTSKN QLSLQLNSVT PEDTAVYYCA RTWADYVDVW GQGTLVTVSS   120

SEQ ID NO: 26           moltype = AA  length = 110
FEATURE                 Location/Qualifiers
REGION                  1..110
                        note = ADT1-4 Variable Light
source                  1..110
                        mol_type = protein
                        organism = Homo sapiens
SEQUENCE: 26
ASDIQMTQSP PALSASVGDR VTITCRASQD INDWLAWYQH KPGKAPKLLI YDASSLESGV    60
PSRFSGSGSG TEFTLTISSL QPDDFATYYC QQSYSTPQVT FGQGTRLEIK              110

SEQ ID NO: 27           moltype = AA  length = 108
FEATURE                 Location/Qualifiers
REGION                  1..108
                        note = ADT1-4-105 Variable Light
source                  1..108
                        mol_type = protein
                        organism = Homo sapiens
SEQUENCE: 27
DIQMTQSPPA LSASVGDRVT ITCRASQDIN DWLAWYQHKP GKAPKLLIYD ASSLESGVPL    60
RFSGSGSGTE FTLTISSLQP DDFATYYCQQ KYSTPQITFG QGTRLEIK                108

SEQ ID NO: 28           moltype = AA  length = 108
FEATURE                 Location/Qualifiers
REGION                  1..108
                        note = ADT1-4-107 Variable Light
source                  1..108
                        mol_type = protein
                        organism = Homo sapiens
SEQUENCE: 28
DIQMTQSPPA LSASVGDRVT ITCRASQDIN DWLAWYQHKP GKAPKLLIYD ASSLESGVPL    60
RFSGSGSGTE FTLTISSLQP DDFATYYCQQ RYSTPQITFG QGTRLEIK                108

SEQ ID NO: 29           moltype = AA  length = 108
FEATURE                 Location/Qualifiers
REGION                  1..108
                        note = ADT1-4-110 Variable Light
source                  1..108
                        mol_type = protein
```

```
                                organism = Homo sapiens
SEQUENCE: 29
DIQMTQSPPA LSASVGDRVT ITCRASQDIN DWLAWYQHKP GKAPKLLIYD ASSLESGVPL    60
RFSGSGSGTE FTLTISSLQP DDFATYYCQQ KYSTPQVTFG AGTRLEIK                108

SEQ ID NO: 30               moltype = AA  length = 108
FEATURE                     Location/Qualifiers
REGION                      1..108
                            note = ADT1-4-112 Variable Light
source                      1..108
                            mol_type = protein
                            organism = Homo sapiens
SEQUENCE: 30
DIQMTQSPPA LSASVGDRVT ITCRASQDIN DWLAWYQHKP GKAPKLLIYD ASSLESGVPL    60
RFSGSGSGTE FTLTISSLQP DDFATYYCQQ KYSQPQVTFG QGTRLEIK                108

SEQ ID NO: 31               moltype = AA  length = 108
FEATURE                     Location/Qualifiers
REGION                      1..108
                            note = ADT1-4-117 Variable Light
source                      1..108
                            mol_type = protein
                            organism = Homo sapiens
SEQUENCE: 31
DIQMTQSPPA LSASVGDRVT ITCRASQDIN DWLAWYQHKP GKAPKLLIYD ASSLESGVPL    60
RFSGSGSGTE FTLTISSLQP DDFATYYCQQ RYSTPRVTFG QGTRLEIK                108

SEQ ID NO: 32               moltype = AA  length = 108
FEATURE                     Location/Qualifiers
REGION                      1..108
                            note = ADT1-4-19 Variable Light
source                      1..108
                            mol_type = protein
                            organism = Homo sapiens
SEQUENCE: 32
DIQMTQSPPA LSASVGDRVT ITCRASQDIN DWLAWYQHKP GKAPKLLIYD ASSLESGVPL    60
RFSGSGSGTE FTLTISSLQP DDFATYYCQQ KYSTPKVTFG QGTRLEIK                108

SEQ ID NO: 33               moltype = AA  length = 108
FEATURE                     Location/Qualifiers
REGION                      1..108
                            note = ADT1-4-21 Variable Light
source                      1..108
                            mol_type = protein
                            organism = Homo sapiens
SEQUENCE: 33
DIQMTQSPPA LSASVGDRVT ITCRASQDIN DWLAWYQHKP GKAPKLLIYD ASSLESGVPL    60
RFSGSGSGTE FTLTISSLQP DDFATYYCQQ KYSTPWVTFG QGTRLEIK                108

SEQ ID NO: 34               moltype = AA  length = 108
FEATURE                     Location/Qualifiers
REGION                      1..108
                            note = ADT1-4-31 Variable Light
source                      1..108
                            mol_type = protein
                            organism = Homo sapiens
SEQUENCE: 34
DIQMTQSPPA LSASVGDRVT ITCRASQDIN DWLAWYQHKP GKAPKLLIYD ASSLESGVPL    60
RFSGSGSGTE FTLTISSLQP DDFATYYCQQ RYSTPPVTFG QGTRLEIK                108

SEQ ID NO: 35               moltype = AA  length = 108
FEATURE                     Location/Qualifiers
REGION                      1..108
                            note = ADT1-4-139 Variable Light
source                      1..108
                            mol_type = protein
                            organism = Homo sapiens
SEQUENCE: 35
DIQMTQSPPA LSASVGDRVT ITCRASQDIN DWLAWYQHKP GKAPKLLIYD ASSLESGVPL    60
RFSGSGSGTE FTLTISSLQP DDFATYYCQQ GYSTPQLTFG QGTRLEIK                108

SEQ ID NO: 36               moltype = AA  length = 108
FEATURE                     Location/Qualifiers
REGION                      1..108
                            note = ADT1-4-4 Variable Light
source                      1..108
                            mol_type = protein
                            organism = Homo sapiens
SEQUENCE: 36
```

```
DIQMTQSPPA LSASVGDRVT ITCRASQDIN DWLAWYQHKP GKAPKLLIYD ASSLESGVPL   60
RFSGSGSGTE FTLTISSLQP DDFATYYCQQ KYSTPWVTFG QGTRLEIK              108

SEQ ID NO: 37              moltype = AA   length = 108
FEATURE                    Location/Qualifiers
REGION                     1..108
                           note = ADT1-4-143 Variable Light
source                     1..108
                           mol_type = protein
                           organism = Homo sapiens
SEQUENCE: 37
DIQMTQSPPA LSASVGDRVT ITCRASQDIN DWLAWYQHKP GKAPKLLIYD ASSLESGVPL   60
RFSGSGSGTE FTLTISSLQP DDFATYYCQQ RYSTHQVTFG QGTRLVIK              108

SEQ ID NO: 38              moltype = AA   length = 108
FEATURE                    Location/Qualifiers
REGION                     1..108
                           note = ADT1-4-53 Variable Light
source                     1..108
                           mol_type = protein
                           organism = Homo sapiens
SEQUENCE: 38
DIQMTQSPPA LSASVGDRVT ITCRASQDIN DWLAWYQHKP GKAPKLLIYD ASSLESGVPL   60
RFSGSGSGTE FTLTISSLQP DDFATYYCQQ KYSTPQLTFG QGTRLEIK              108

SEQ ID NO: 39              moltype = AA   length = 108
FEATURE                    Location/Qualifiers
REGION                     1..108
                           note = ADT1-4-173 Variable Light
source                     1..108
                           mol_type = protein
                           organism = Homo sapiens
SEQUENCE: 39
DIQMTQSPPA LSASVGDRVT ITCRASQDIN DWLAWYQHKP GKAPKLLIYD ASSLESGVPL   60
RFSGSGSGTE FTLTISSLQP DDFATYYCQQ KYSAPQVTFG QGTRLEIK              108

SEQ ID NO: 40              moltype = AA   length = 108
FEATURE                    Location/Qualifiers
REGION                     1..108
                           note = ADT1-4-2 Variable Light
source                     1..108
                           mol_type = protein
                           organism = Homo sapiens
SEQUENCE: 40
DIQMTQSPPA LSASVGDRVT ITCRASQDIN DWLAWYQHKP GKAPKLLIYD ASSLESGVPL   60
RFSGSGSGTE FTLTISSLQP DDFATYYCQQ KYSAPQVTFG QGTRLEIK              108

SEQ ID NO: 41              moltype = AA   length = 108
FEATURE                    Location/Qualifiers
REGION                     1..108
                           note = ADT1-4-8 Variable Light
source                     1..108
                           mol_type = protein
                           organism = Homo sapiens
SEQUENCE: 41
DIQMTQSPPA LSASVGDRVT ITCRASQDIN DWLAWYQHKP GKAPKLLIYD ASSLESGVPL   60
RFSGSGSGTE FTLTISSLQP DDFATYYCQQ KYSAPQVTFG QGTRLEIK              108

SEQ ID NO: 42              moltype = AA   length = 108
FEATURE                    Location/Qualifiers
REGION                     1..108
                           note = ADT1-4-82 Variable Light
source                     1..108
                           mol_type = protein
                           organism = Homo sapiens
SEQUENCE: 42
DIQMTQSPPA LSASVGDRVT ITCRASQDIN DWLAWYQHKP GKAPKLLIYD ASSLESGVPL   60
RFSGSGSGTE FTLTISSLQP DDFATYYCQQ RYSTPQITFG QGTRLEIK              108

SEQ ID NO: 43              moltype = AA   length = 108
FEATURE                    Location/Qualifiers
REGION                     1..108
                           note = ADT1-4-83 Variable Light
source                     1..108
                           mol_type = protein
                           organism = Homo sapiens
SEQUENCE: 43
DIQMTQSPPA LSASVGDRVT ITCRASQDIN DWLAWYQHKP GKAPKLLIYD ASSLESGVPL   60
RFSGSGSGTE FTLTISSLQP DDFATYYCQQ KYSEPQVTFG QGTRLEIK              108
```

```
SEQ ID NO: 44            moltype = AA   length = 108
FEATURE                  Location/Qualifiers
REGION                   1..108
                         note = ADT1-4-3 Variable Light
source                   1..108
                         mol_type = protein
                         organism = Homo sapiens
SEQUENCE: 44
DIQMTQSPPA LSASVGDRVT ITCRASQDIN DWLAWYQHKP GKAPKLLIYD ASSLESGVPL    60
RFSGSGSGTE FTLTISSLQP DDFATYYCQQ KYSTPEVTFG QGTRLEIK               108

SEQ ID NO: 45            moltype = AA   length = 108
FEATURE                  Location/Qualifiers
REGION                   1..108
                         note = ADT1-4-84 Variable Light
source                   1..108
                         mol_type = protein
                         organism = Homo sapiens
SEQUENCE: 45
DIQMTQSPPA LSASVGDRVT ITCRASQDIN DWLAWYQHKP GKAPKLLIYD ASSLESGVPL    60
RFSGSGSGTE FTLTISSLQP DDFATYYCQQ KYSDPQVTFG QGTRLEIK               108

SEQ ID NO: 46            moltype = AA   length = 108
FEATURE                  Location/Qualifiers
REGION                   1..108
                         note = ADT1-4-86 Variable Light
source                   1..108
                         mol_type = protein
                         organism = Homo sapiens
SEQUENCE: 46
DIQMTQSPPA LSASVGDRVT ITCRASQDIN DWLAWYQHKP GKAPKLLIYD ASSLESGVPL    60
RFSGSGSGTE FTLTISSLQP DDFATYYCQQ KYSEPQVTFG QGTRLEIK               108

SEQ ID NO: 47            moltype = AA   length = 108
FEATURE                  Location/Qualifiers
REGION                   1..108
                         note = ADT1-4-95 Variable Light
source                   1..108
                         mol_type = protein
                         organism = Homo sapiens
SEQUENCE: 47
DIQMTQSPPA LSASVGDRVT ITCRASQDIN DWLAWYQHKP GKAPKLLIYD ASSLESGVPL    60
RFSGSGSGTE FTLTISSLQP DDFATYYCQQ KYSTPQVTFG SGTRLEIK               108

SEQ ID NO: 48            moltype = AA   length = 108
FEATURE                  Location/Qualifiers
REGION                   1..108
                         note = ADT1-4-1 Variable Light
source                   1..108
                         mol_type = protein
                         organism = Homo sapiens
SEQUENCE: 48
DIQMTQSPPA LSASVGDRVT ITCRASQDIN DWLAWYQHKP GKAPKLLIYD ASSLESGVPL    60
RFSGSGSGTE FTLTISSLQP DDFATYYCQQ RYSTPIVTFG QGTRLEIK               108

SEQ ID NO: 49            moltype = AA   length = 108
FEATURE                  Location/Qualifiers
REGION                   1..108
                         note = ADT1-4-6 Variable Light
source                   1..108
                         mol_type = protein
                         organism = Homo sapiens
SEQUENCE: 49
DIQMTQSPPA LSASVGDRVT ITCRASQDIN DWLAWYQHKP GKAPKLLIYD ASSLESGVPL    60
RFSGSGSGTE FTLTISSLQP DDFATYYCQQ KYKTPQVTFG QGTRLEIK               108

SEQ ID NO: 50            moltype = AA   length = 108
FEATURE                  Location/Qualifiers
REGION                   1..108
                         note = ADT1-4-138 Variable Light
source                   1..108
                         mol_type = protein
                         organism = Homo sapiens
SEQUENCE: 50
DIQMTQSPPA LSASVGDRVT ITCRASQDIN DWLAWYQHKP GKAPKLLIYD ASSLESGVPS    60
RFSGSGSGTE FTLTISSLQP DDFATYYCQQ RYSTDQVTFG QGTRLEIK               108

SEQ ID NO: 51            moltype = AA   length = 10
```

```
FEATURE                    Location/Qualifiers
REGION                     1..10
                           note = ADT1-4 VHCDR1 (parental and affinity matured clones)
source                     1..10
                           mol_type = protein
                           organism = Homo sapiens
SEQUENCE: 51
GDSVSSKSAA                                                                    10

SEQ ID NO: 52              moltype = AA  length = 10
FEATURE                    Location/Qualifiers
REGION                     1..10
                           note = ADT1-4-21/ADT1-4-53/ADT1-4-86 VHCDR1
source                     1..10
                           mol_type = protein
                           organism = Homo sapiens
SEQUENCE: 52
GDSVSSKSVA                                                                    10

SEQ ID NO: 53              moltype = AA  length = 9
FEATURE                    Location/Qualifiers
REGION                     1..9
                           note = ADT1-4 VHCDR2 (parental and all affinity matured
                            clones)
source                     1..9
                           mol_type = protein
                           organism = Homo sapiens
SEQUENCE: 53
TYYRSKWST                                                                      9

SEQ ID NO: 54              moltype = AA  length = 8
FEATURE                    Location/Qualifiers
REGION                     1..8
                           note = ADT1-4 VHCDR3
source                     1..8
                           mol_type = protein
                           organism = Homo sapiens
SEQUENCE: 54
TWSGYVDV                                                                       8

SEQ ID NO: 55              moltype = AA  length = 8
FEATURE                    Location/Qualifiers
REGION                     1..8
                           note = ADT1-4-105 VHCDR3
source                     1..8
                           mol_type = protein
                           organism = Homo sapiens
SEQUENCE: 55
TWVGYVDV                                                                       8

SEQ ID NO: 56              moltype = AA  length = 8
FEATURE                    Location/Qualifiers
REGION                     1..8
                           note = ADT1-4-107 VHCDR3
source                     1..8
                           mol_type = protein
                           organism = Homo sapiens
SEQUENCE: 56
TWVGYADV                                                                       8

SEQ ID NO: 57              moltype = AA  length = 8
FEATURE                    Location/Qualifiers
REGION                     1..8
                           note = ADT1-4-110 VHCDR3
source                     1..8
                           mol_type = protein
                           organism = Homo sapiens
SEQUENCE: 57
TWVEYVDV                                                                       8

SEQ ID NO: 58              moltype = AA  length = 8
FEATURE                    Location/Qualifiers
REGION                     1..8
                           note = ADT1-4-112 VHCDR3
source                     1..8
                           mol_type = protein
                           organism = Homo sapiens
SEQUENCE: 58
TWVGYVDY                                                                       8
```

```
SEQ ID NO: 59           moltype = AA   length = 8
FEATURE                 Location/Qualifiers
REGION                  1..8
                        note = ADT1-4-117 VHCDR3
source                  1..8
                        mol_type = protein
                        organism = Homo sapiens
SEQUENCE: 59
TWVGYVDV                                                                   8

SEQ ID NO: 60           moltype = AA   length = 8
FEATURE                 Location/Qualifiers
REGION                  1..8
                        note = ADT1-4-19 VHCDR3
source                  1..8
                        mol_type = protein
                        organism = Homo sapiens
SEQUENCE: 60
TWVGYVDR                                                                   8

SEQ ID NO: 61           moltype = AA   length = 8
FEATURE                 Location/Qualifiers
REGION                  1..8
                        note = ADT1-4-21 VHCDR3
source                  1..8
                        mol_type = protein
                        organism = Homo sapiens
SEQUENCE: 61
TWADYVDV                                                                   8

SEQ ID NO: 62           moltype = AA   length = 8
FEATURE                 Location/Qualifiers
REGION                  1..8
                        note = ADT1-4-31 VHCDR3
source                  1..8
                        mol_type = protein
                        organism = Homo sapiens
SEQUENCE: 62
TWVGYADV                                                                   8

SEQ ID NO: 63           moltype = AA   length = 8
FEATURE                 Location/Qualifiers
REGION                  1..8
                        note = ADT1-4-139 VHCDR3
source                  1..8
                        mol_type = protein
                        organism = Homo sapiens
SEQUENCE: 63
TWVGYVDY                                                                   8

SEQ ID NO: 64           moltype = AA   length = 8
FEATURE                 Location/Qualifiers
REGION                  1..8
                        note = ADT1-4-4 VHCDR3
source                  1..8
                        mol_type = protein
                        organism = Homo sapiens
SEQUENCE: 64
TWVGYADV                                                                   8

SEQ ID NO: 65           moltype = AA   length = 8
FEATURE                 Location/Qualifiers
REGION                  1..8
                        note = ADT1-4-143 VHCDR3
source                  1..8
                        mol_type = protein
                        organism = Homo sapiens
SEQUENCE: 65
TWVGYADV                                                                   8

SEQ ID NO: 66           moltype = AA   length = 8
FEATURE                 Location/Qualifiers
REGION                  1..8
                        note = ADT1-4-53 VHCDR3
source                  1..8
                        mol_type = protein
                        organism = Homo sapiens
SEQUENCE: 66
```

TWADYVDV                                                                          8

SEQ ID NO: 67           moltype = AA   length = 8
FEATURE                 Location/Qualifiers
REGION                  1..8
                        note = ADT1-4-173 VHCDR3
source                  1..8
                        mol_type = protein
                        organism = Homo sapiens
SEQUENCE: 67
TWAGYPDV                                                                          8

SEQ ID NO: 68           moltype = AA   length = 8
FEATURE                 Location/Qualifiers
REGION                  1..8
                        note = ADT1-4-2 VHCDR3
source                  1..8
                        mol_type = protein
                        organism = Homo sapiens
SEQUENCE: 68
TWVGYVDR                                                                          8

SEQ ID NO: 69           moltype = AA   length = 8
FEATURE                 Location/Qualifiers
REGION                  1..8
                        note = ADT1-4-8 VHCDR3
source                  1..8
                        mol_type = protein
                        organism = Homo sapiens
SEQUENCE: 69
TWVGYADV                                                                          8

SEQ ID NO: 70           moltype = AA   length = 8
FEATURE                 Location/Qualifiers
REGION                  1..8
                        note = ADT1-4-82 VHCDR3
source                  1..8
                        mol_type = protein
                        organism = Homo sapiens
SEQUENCE: 70
SWVGYVDV                                                                          8

SEQ ID NO: 71           moltype = AA   length = 8
FEATURE                 Location/Qualifiers
REGION                  1..8
                        note = ADT1-4-83 VHCDR3
source                  1..8
                        mol_type = protein
                        organism = Homo sapiens
SEQUENCE: 71
SWVGYVDV                                                                          8

SEQ ID NO: 72           moltype = AA   length = 8
FEATURE                 Location/Qualifiers
REGION                  1..8
                        note = ADT1-4-3 VHCDR3
source                  1..8
                        mol_type = protein
                        organism = Homo sapiens
SEQUENCE: 72
TWADYVDV                                                                          8

SEQ ID NO: 73           moltype = AA   length = 8
FEATURE                 Location/Qualifiers
REGION                  1..8
                        note = ADT1-4-84 VHCDR3
source                  1..8
                        mol_type = protein
                        organism = Homo sapiens
SEQUENCE: 73
TWVGYADV                                                                          8

SEQ ID NO: 74           moltype = AA   length = 8
FEATURE                 Location/Qualifiers
REGION                  1..8
                        note = ADT1-4-86 VHCDR3
source                  1..8
                        mol_type = protein
                        organism = Homo sapiens

```
SEQUENCE: 74
TWLGNVDV                                                                    8

SEQ ID NO: 75           moltype = AA  length = 8
FEATURE                 Location/Qualifiers
REGION                  1..8
                        note = ADT1-4-95 VHCDR3
source                  1..8
                        mol_type = protein
                        organism = Homo sapiens
SEQUENCE: 75
TWVGYADV                                                                    8

SEQ ID NO: 76           moltype = AA  length = 8
FEATURE                 Location/Qualifiers
REGION                  1..8
                        note = ADT1-4-1 VHCDR3
source                  1..8
                        mol_type = protein
                        organism = Homo sapiens
SEQUENCE: 76
TWVGYADV                                                                    8

SEQ ID NO: 77           moltype = AA  length = 8
FEATURE                 Location/Qualifiers
REGION                  1..8
                        note = ADT1-4-6 VHCDR3
source                  1..8
                        mol_type = protein
                        organism = Homo sapiens
SEQUENCE: 77
TWAGYPDV                                                                    8

SEQ ID NO: 78           moltype = AA  length = 8
FEATURE                 Location/Qualifiers
REGION                  1..8
                        note = ADT1-4-138 VHCDR3
source                  1..8
                        mol_type = protein
                        organism = Homo sapiens
SEQUENCE: 78
TWADYVDV                                                                    8

SEQ ID NO: 79           moltype = AA  length = 6
FEATURE                 Location/Qualifiers
REGION                  1..6
                        note = ADT1-4 VLCDR1 (parental and all affinity matured
                         clones)
source                  1..6
                        mol_type = protein
                        organism = Homo sapiens
SEQUENCE: 79
QDINDW                                                                      6

SEQ ID NO: 80           moltype =   length =
SEQUENCE: 80
000

SEQ ID NO: 81           moltype = AA  length = 10
FEATURE                 Location/Qualifiers
REGION                  1..10
                        note = ADT1-4 VLCDR3
source                  1..10
                        mol_type = protein
                        organism = Homo sapiens
SEQUENCE: 81
QQSYSTPQVT                                                                 10

SEQ ID NO: 82           moltype = AA  length = 10
FEATURE                 Location/Qualifiers
REGION                  1..10
                        note = ADT1-4-105 VLCDR3
source                  1..10
                        mol_type = protein
                        organism = Homo sapiens
SEQUENCE: 82
QQKYSTPQIT                                                                 10

SEQ ID NO: 83           moltype = AA  length = 10
```

```
FEATURE                    Location/Qualifiers
REGION                     1..10
                           note = ADT1-4-107 VLCDR3
source                     1..10
                           mol_type = protein
                           organism = Homo sapiens
SEQUENCE: 83
QQRYSTPQIT                                                                          10

SEQ ID NO: 84              moltype = AA  length = 10
FEATURE                    Location/Qualifiers
REGION                     1..10
                           note = ADT1-4-110 VLCDR3
source                     1..10
                           mol_type = protein
                           organism = Homo sapiens
SEQUENCE: 84
QQKYSTPQVT                                                                          10

SEQ ID NO: 85              moltype = AA  length = 10
FEATURE                    Location/Qualifiers
REGION                     1..10
                           note = ADT1-4-112 VLCDR3
source                     1..10
                           mol_type = protein
                           organism = Homo sapiens
SEQUENCE: 85
QQKYSQPQVT                                                                          10

SEQ ID NO: 86              moltype = AA  length = 10
FEATURE                    Location/Qualifiers
REGION                     1..10
                           note = ADT1-4-117 VLCDR3
source                     1..10
                           mol_type = protein
                           organism = Homo sapiens
SEQUENCE: 86
QQRYSTPRVT                                                                          10

SEQ ID NO: 87              moltype = AA  length = 10
FEATURE                    Location/Qualifiers
REGION                     1..10
                           note = ADT1-4-19 VLCDR3
source                     1..10
                           mol_type = protein
                           organism = Homo sapiens
SEQUENCE: 87
QQKYSTPKVT                                                                          10

SEQ ID NO: 88              moltype = AA  length = 10
FEATURE                    Location/Qualifiers
REGION                     1..10
                           note = ADT1-4-21 VLCDR3
source                     1..10
                           mol_type = protein
                           organism = Homo sapiens
SEQUENCE: 88
QQKYSTPWVT                                                                          10

SEQ ID NO: 89              moltype = AA  length = 10
FEATURE                    Location/Qualifiers
REGION                     1..10
                           note = ADT1-4-31 VLCDR3
source                     1..10
                           mol_type = protein
                           organism = Homo sapiens
SEQUENCE: 89
QQRYSTPPVT                                                                          10

SEQ ID NO: 90              moltype = AA  length = 10
FEATURE                    Location/Qualifiers
REGION                     1..10
                           note = ADT1-4-139 VLCDR3
source                     1..10
                           mol_type = protein
                           organism = Homo sapiens
SEQUENCE: 90
QQGYSTPQLT                                                                          10
```

```
SEQ ID NO: 91          moltype = AA   length = 10
FEATURE                Location/Qualifiers
REGION                 1..10
                       note = ADT1-4-4 VLCDR3
source                 1..10
                       mol_type = protein
                       organism = Homo sapiens
SEQUENCE: 91
QQKYSTPWVT                                                                10

SEQ ID NO: 92          moltype = AA   length = 10
FEATURE                Location/Qualifiers
REGION                 1..10
                       note = ADT1-4-143 VLCDR3
source                 1..10
                       mol_type = protein
                       organism = Homo sapiens
SEQUENCE: 92
QQRYSTHQVT                                                                10

SEQ ID NO: 93          moltype = AA   length = 10
FEATURE                Location/Qualifiers
REGION                 1..10
                       note = ADT1-4-53 VLCDR3
source                 1..10
                       mol_type = protein
                       organism = Homo sapiens
SEQUENCE: 93
QQKYSTPQLT                                                                10

SEQ ID NO: 94          moltype = AA   length = 10
FEATURE                Location/Qualifiers
REGION                 1..10
                       note = ADT1-4-173 VLCDR3
source                 1..10
                       mol_type = protein
                       organism = Homo sapiens
SEQUENCE: 94
QQKYSAPQVT                                                                10

SEQ ID NO: 95          moltype = AA   length = 10
FEATURE                Location/Qualifiers
REGION                 1..10
                       note = ADT1-4-2 VLCDR3
source                 1..10
                       mol_type = protein
                       organism = Homo sapiens
SEQUENCE: 95
QQKYSAPQVT                                                                10

SEQ ID NO: 96          moltype = AA   length = 10
FEATURE                Location/Qualifiers
REGION                 1..10
                       note = ADT1-4-8 VLCDR3
source                 1..10
                       mol_type = protein
                       organism = Homo sapiens
SEQUENCE: 96
QQKYSAPQVT                                                                10

SEQ ID NO: 97          moltype = AA   length = 10
FEATURE                Location/Qualifiers
REGION                 1..10
                       note = ADT1-4-82 VLCDR3
source                 1..10
                       mol_type = protein
                       organism = Homo sapiens
SEQUENCE: 97
QQRYSTPQIT                                                                10

SEQ ID NO: 98          moltype = AA   length = 10
FEATURE                Location/Qualifiers
REGION                 1..10
                       note = ADT1-4-83 VLCDR3
source                 1..10
                       mol_type = protein
                       organism = Homo sapiens
SEQUENCE: 98
QQKYSEPQVT                                                                10
```

```
SEQ ID NO: 99              moltype = AA   length = 10
FEATURE                    Location/Qualifiers
REGION                     1..10
                           note = ADT1-4-3 VLCDR3
source                     1..10
                           mol_type = protein
                           organism = Homo sapiens
SEQUENCE: 99
QQKYSTPEVT                                                                    10

SEQ ID NO: 100             moltype = AA   length = 10
FEATURE                    Location/Qualifiers
REGION                     1..10
                           note = ADT1-4-84 VLCDR3
source                     1..10
                           mol_type = protein
                           organism = Homo sapiens
SEQUENCE: 100
QQKYSDPQVT                                                                    10

SEQ ID NO: 101             moltype = AA   length = 10
FEATURE                    Location/Qualifiers
REGION                     1..10
                           note = ADT1-4-86 VLCDR3
source                     1..10
                           mol_type = protein
                           organism = Homo sapiens
SEQUENCE: 101
QQKYSEPQVT                                                                    10

SEQ ID NO: 102             moltype = AA   length = 10
FEATURE                    Location/Qualifiers
REGION                     1..10
                           note = ADT1-4-95 VLCDR3
source                     1..10
                           mol_type = protein
                           organism = Homo sapiens
SEQUENCE: 102
QQKYSTPQVT                                                                    10

SEQ ID NO: 103             moltype = AA   length = 10
FEATURE                    Location/Qualifiers
REGION                     1..10
                           note = ADT1-4-1 VLCDR3
source                     1..10
                           mol_type = protein
                           organism = Homo sapiens
SEQUENCE: 103
QQRYSTPIVT                                                                    10

SEQ ID NO: 104             moltype = AA   length = 10
FEATURE                    Location/Qualifiers
REGION                     1..10
                           note = ADT1-4-6 VLCDR3
source                     1..10
                           mol_type = protein
                           organism = Homo sapiens
SEQUENCE: 104
QQKYKTPQVT                                                                    10

SEQ ID NO: 105             moltype = AA   length = 10
FEATURE                    Location/Qualifiers
REGION                     1..10
                           note = ADT1-4-138 VLCDR3
source                     1..10
                           mol_type = protein
                           organism = Homo sapiens
SEQUENCE: 105
QQRYSTDQVT                                                                    10

SEQ ID NO: 106             moltype = AA   length = 118
FEATURE                    Location/Qualifiers
REGION                     1..118
                           note = ADT1-7 Variable Heavy
source                     1..118
                           mol_type = protein
                           organism = Homo sapiens
SEQUENCE: 106
```

```
QVQLVESGGG LVKPGGSLRL SCAASGFTFS DYYMSWIRQA PGKGLEWVSY ISSSGSTIYY    60
ADSVKGRFTI SRDNAKNSLY LQMNSLRAED TAVYYCARVD YADAFDIWGQ GTLVTVSS    118

SEQ ID NO: 107          moltype = AA  length = 118
FEATURE                 Location/Qualifiers
REGION                  1..118
                        note = ADT1-7-10 Variable Heavy
source                  1..118
                        mol_type = protein
                        organism = Homo sapiens
SEQUENCE: 107
EVQLVESGGG LVKPGGSLRL SCAASGFTFS DYYMSWIRQA PGKGLEWVSY ISSSGSTIYY    60
ADSVKGRFTI SRDNAKNSLY LQMNSLRAED TAVYYCARDD YNDAFDIWGQ GTLVTVSS    118

SEQ ID NO: 108          moltype = AA  length = 118
FEATURE                 Location/Qualifiers
REGION                  1..118
                        note = ADT1-7-15 Variable Heavy
source                  1..118
                        mol_type = protein
                        organism = Homo sapiens
SEQUENCE: 108
EVQLVESGGG LVKPGGSLRL SCAASGFTFS DYYMSWIRQA PGKGLEWVSY ISSSGSTIYY    60
ADSVKGRFTI SRDNAKNSLY LQMNSLRAED TAVYYCARDD YNDAFDIWGQ GTLVTVSS    118

SEQ ID NO: 109          moltype = AA  length = 118
FEATURE                 Location/Qualifiers
REGION                  1..118
                        note = ADT1-7-17 Variable Heavy
source                  1..118
                        mol_type = protein
                        organism = Homo sapiens
SEQUENCE: 109
EVQLVESGGG LVKPGGSLRL SCAASGFTFS DYYMSWIRQA PGKGLEWVSY ISSSGSTIYY    60
ADSVKGRFTI SRDNAKNSLY LQMNSLRAED TAVYYCARID YEDAFDIWGQ GTLVTVSS    118

SEQ ID NO: 110          moltype = AA  length = 118
FEATURE                 Location/Qualifiers
REGION                  1..118
                        note = ADT1-7-18 Variable Heavy
source                  1..118
                        mol_type = protein
                        organism = Homo sapiens
SEQUENCE: 110
EVQLVESGGG LVKPGGSLRL SCAASGFTFS DYYMSWIRQA PGKGLEWVSY ISSSGSTIYY    60
ADSVKGRFTI SRDNAKNSLY LQMNSLRAED TAVYYCARVS YDDAFDIWGQ GTLVTVSS    118

SEQ ID NO: 111          moltype = AA  length = 118
FEATURE                 Location/Qualifiers
REGION                  1..118
                        note = ADT1-7-19 Variable Heavy
source                  1..118
                        mol_type = protein
                        organism = Homo sapiens
SEQUENCE: 111
EVQLVESGGG LVKPGGSLRL SCAASGFTFS DYYMSWIRQA PGKGLEWVSY ISSSGSTIYY    60
ADSVKGRFTI SRDNAKNSLY LQMNSLRAED TAVYYCARID YEDAFDIWGQ GTLVTVSS    118

SEQ ID NO: 112          moltype = AA  length = 118
FEATURE                 Location/Qualifiers
REGION                  1..118
                        note = ADT1-7-20 Variable Heavy
source                  1..118
                        mol_type = protein
                        organism = Homo sapiens
SEQUENCE: 112
EVQLVESGGG LVKPGGSLRL SCAASGFTFS DYYMSWIRQA PGKGLEWVSY ISSSGSTIYY    60
ADSVKGRFTI SRDNAKNSLY LQMNSLRAED TAVYYCARVD YQEAFDIWGQ GTLVTVSS    118

SEQ ID NO: 113          moltype = AA  length = 118
FEATURE                 Location/Qualifiers
REGION                  1..118
                        note = ADT1-7-22 Variable Heavy
source                  1..118
                        mol_type = protein
                        organism = Homo sapiens
SEQUENCE: 113
EVQLVESGGG LVKPGGSLRL SCAASGFTFS DYYMSWIRQA PGKGLEWVSY ISSSGSTIYY    60
ADSVKGRFTI SRDNAKNSLY LQMNSLRAED TAVYYCARDD YNDAFDIWGQ GTLVTVSS    118
```

```
SEQ ID NO: 114          moltype = AA   length = 118
FEATURE                 Location/Qualifiers
REGION                  1..118
                        note = ADT1-7-23 Variable Heavy
source                  1..118
                        mol_type = protein
                        organism = Homo sapiens
SEQUENCE: 114
EVQLVESGGG LVKPGGSLRL SCAASGFTFS DYYMSWIRQA PGKGLEWVSY ISSSGSTIYY    60
ADSVKGRFTI SRDNAKNSLY LQMNSLRAED TAVYYCARVD YNEAFDIWGQ GTLVTVSS    118

SEQ ID NO: 115          moltype = AA   length = 118
FEATURE                 Location/Qualifiers
REGION                  1..118
                        note = ADT1-7-42 Variable Heavy
source                  1..118
                        mol_type = protein
                        organism = Homo sapiens
SEQUENCE: 115
EVQLVESGGG LVKPGGSLRL SCAASGFTFS DYYMSWIRQA PGKGLEWVSY ISSSGSTIYY    60
ADSVKGRFTI SRDNAKNSLY LQMNSLRAED TAVYYCARDD YEDAFDIWGQ GTLVTVSS    118

SEQ ID NO: 116          moltype = AA   length = 118
FEATURE                 Location/Qualifiers
REGION                  1..118
                        note = ADT1-7-3 Variable Heavy
source                  1..118
                        mol_type = protein
                        organism = Homo sapiens
SEQUENCE: 116
EVQLVESGGG LVKPGGSLRL SCAASGFTFS DYYMSWIRQA PGKGLEWVSY ISSSGSTIYY    60
ADSVKGRFTI SRDNAKNSLY LQMNSLRAED TAVYYCARVS YAEAFDIWGQ GTLVTVSS    118

SEQ ID NO: 117          moltype = AA   length = 118
FEATURE                 Location/Qualifiers
REGION                  1..118
                        note = ADT1-7-61 Variable Heavy
source                  1..118
                        mol_type = protein
                        organism = Homo sapiens
SEQUENCE: 117
EVQLVESGGG LVKPGGSLRL SCAASGFTFS DYYMSWIRQA PGKGLEWVSY ISSSGSTIYY    60
ADSVKGRFTI SRDNAKNSLY LQMNSLRAED TAVYYCARDD YDDAFDIWGQ GTLVTVSS    118

SEQ ID NO: 118          moltype = AA   length = 109
FEATURE                 Location/Qualifiers
REGION                  1..109
                        note = ADT1-7 Variable Light
source                  1..109
                        mol_type = protein
                        organism = Homo sapiens
SEQUENCE: 118
ASDIQMTQSP SSLSASVGDR VTIACRAGQS IGTYLNWYQQ KPGKAPKLLI YVASSLQSGV    60
PSRFSGSGSG TEFTLTISSL QPEDFATYYC QQSYSTLLTF GRGTKVEIK              109

SEQ ID NO: 119          moltype = AA   length = 107
FEATURE                 Location/Qualifiers
REGION                  1..107
                        note = ADT1-7-10 Variable Light
source                  1..107
                        mol_type = protein
                        organism = Homo sapiens
SEQUENCE: 119
DIQMTQSPSS LSASVGDRVT IACRAGQSIG TYLNWYQQKP GKAPKLLIYV ASSLQSGVPS    60
RFSGSGSGTE FTLTISSLQP EDFATYYCQQ TASTLLTFGR GTKVEIK                107

SEQ ID NO: 120          moltype = AA   length = 107
FEATURE                 Location/Qualifiers
REGION                  1..107
                        note = ADT1-7-15 Variable Light
source                  1..107
                        mol_type = protein
                        organism = Homo sapiens
SEQUENCE: 120
DIQMTQSPSS LSASVGDRVT IACRAGQSIG TYLNWYQQKP GKAPKLLIYV ASSLQSGVPS    60
RFSGSGSGTE FTLTISSLQP EDFATYYCQQ SADTLLTFGR GTKVEIK                107

SEQ ID NO: 121          moltype = AA   length = 107
```

```
FEATURE              Location/Qualifiers
REGION               1..107
                     note = ADT1-7-17 Variable Light
source               1..107
                     mol_type = protein
                     organism = Homo sapiens
SEQUENCE: 121
DIQMTQSPSS LSASVGDRVT IACRAGQSIG TYLNWYQQKP GKAPKLLIYV ASSLQSGVPS   60
RFSGSGSGTE FTLTISSLQP EDFATYYCQQ SGSELLTFGR GTKVEIK               107

SEQ ID NO: 122       moltype = AA  length = 107
FEATURE              Location/Qualifiers
REGION               1..107
                     note = ADT1-7-18 Variable Light
source               1..107
                     mol_type = protein
                     organism = Homo sapiens
SEQUENCE: 122
DIQMTQSPSS LSASVGDRVT IACRVGQSIG TYLNWYQQKP GKAPKLLIYV ASSLQSGVPS   60
RFSGSGSGTE FTLTISSLQP EDFATYYCQQ SASELLTFGR GTKVEIK               107

SEQ ID NO: 123       moltype = AA  length = 107
FEATURE              Location/Qualifiers
REGION               1..107
                     note = ADT1-7-19 Variable Light
source               1..107
                     mol_type = protein
                     organism = Homo sapiens
SEQUENCE: 123
DIQMTQSPSS LSASVGDRVT IACRAGQSIG TYLNWYQQKP GKAPKLLIYV ASSLQSGVPS   60
RFSGSGSGTE FTLTISSLQP EDFATYYCQQ SASELLTFGR GTKVEIK               107

SEQ ID NO: 124       moltype = AA  length = 107
FEATURE              Location/Qualifiers
REGION               1..107
                     note = ADT1-7-20 Variable Light
source               1..107
                     mol_type = protein
                     organism = Homo sapiens
SEQUENCE: 124
DIQMTQSPSS LSASVGDRVT IACRAGQSIG TYLNWYQQKP GKAPKLLIYV ASSLQSGVPS   60
RFSGSGSGTE FTLTISSLQP EDFATYYCQQ SYSGLDTFGR GTKVEIK               107

SEQ ID NO: 125       moltype = AA  length = 107
FEATURE              Location/Qualifiers
REGION               1..107
                     note = ADT1-7-22 Variable Light
source               1..107
                     mol_type = protein
                     organism = Homo sapiens
SEQUENCE: 125
DIQMTQSPSS LSASVGDRVT IACRAGQSIG TYLNWYQQKP GKAPKLLIYV ASSLQSGVPS   60
RFSGSGSGTE FTLTISSLQP EDFATYYCQQ SASELLTFGR GTKVEIK               107

SEQ ID NO: 126       moltype = AA  length = 107
FEATURE              Location/Qualifiers
REGION               1..107
                     note = ADT1-7-23 Variable Light
source               1..107
                     mol_type = protein
                     organism = Homo sapiens
SEQUENCE: 126
DIQMTQSPSS LSASVGDRVT IACRAGQSIG TYLNWYQQKP GKAPKLLIYV ASSLQSGVPS   60
RFSGSGSGTE FTLTISSLQP EDFATYYCQQ SYSGLDTFGR GTKVEIK               107

SEQ ID NO: 127       moltype = AA  length = 107
FEATURE              Location/Qualifiers
REGION               1..107
                     note = ADT1-7-42 Variable Light
source               1..107
                     mol_type = protein
                     organism = Homo sapiens
SEQUENCE: 127
DIQMTQSPSS LSASVGDRVT IACRAGQSIG TYLNWYQQKP GKAPKLLIYV ASSLQSGVPS   60
RFSGSGSGTE FTLTISSLQP EDFATYYCQQ SSSELLTFGR GTKVEIK               107

SEQ ID NO: 128       moltype = AA  length = 107
FEATURE              Location/Qualifiers
REGION               1..107
```

```
                         note = ADT1-7-3 Variable Light
source                   1..107
                         mol_type = protein
                         organism = Homo sapiens
SEQUENCE: 128
DIQMTQSPSS LSASVGDRVT IACRAGQSIG TYLNWYQQKP GKAPKLLIYV ASSLQSGVPS    60
RFSGSGSGTE FTLTISSLQP EDFATYYCQQ SYSGLDTFGR GTKVEIK                 107

SEQ ID NO: 129           moltype = AA  length = 107
FEATURE                  Location/Qualifiers
REGION                   1..107
                         note = ADT1-7-61 Variable Light
source                   1..107
                         mol_type = protein
                         organism = Homo sapiens
SEQUENCE: 129
DIQMTQSPSS LSASVGDRVT IACRAGQSIG TYLNWYQQKP GKAPKLLIYV ASSLQSGVPS    60
RFSGSGSGTE FTLTISSLQP EDFATYYCQQ SASELLTFGR GTKVEIK                 107

SEQ ID NO: 130           moltype = AA  length = 8
FEATURE                  Location/Qualifiers
REGION                   1..8
                         note = ADT1-7 VHCDR1 (parental and all affinity matured
                          clones)
source                   1..8
                         mol_type = protein
                         organism = Homo sapiens
SEQUENCE: 130
GFTFSDYY                                                              8

SEQ ID NO: 131           moltype = AA  length = 8
FEATURE                  Location/Qualifiers
REGION                   1..8
                         note = ADT1-7 VHCDR2 (parental and all affinity matured
                          clones)
source                   1..8
                         mol_type = protein
                         organism = Homo sapiens
SEQUENCE: 131
ISSSGSTI                                                              8

SEQ ID NO: 132           moltype = AA  length = 9
FEATURE                  Location/Qualifiers
REGION                   1..9
                         note = ADT1-7 VHCDR3
source                   1..9
                         mol_type = protein
                         organism = Homo sapiens
SEQUENCE: 132
VDYADAFDI                                                             9

SEQ ID NO: 133           moltype = AA  length = 9
FEATURE                  Location/Qualifiers
REGION                   1..9
                         note = ADT1-7-10 VHCDR3
source                   1..9
                         mol_type = protein
                         organism = Homo sapiens
SEQUENCE: 133
DDYNDAFDI                                                             9

SEQ ID NO: 134           moltype = AA  length = 9
FEATURE                  Location/Qualifiers
REGION                   1..9
                         note = ADT1-7-15 VHCDR3
source                   1..9
                         mol_type = protein
                         organism = Homo sapiens
SEQUENCE: 134
DDYNDAFDI                                                             9

SEQ ID NO: 135           moltype = AA  length = 9
FEATURE                  Location/Qualifiers
REGION                   1..9
                         note = ADT1-7-17 VHCDR3
source                   1..9
                         mol_type = protein
                         organism = Homo sapiens
SEQUENCE: 135
```

```
IDYEDAFDI                                                                        9

SEQ ID NO: 136        moltype = AA   length = 9
FEATURE               Location/Qualifiers
REGION                1..9
                      note = ADT1-7-18 VHCDR3
source                1..9
                      mol_type = protein
                      organism = Homo sapiens
SEQUENCE: 136
VSYDDAFDI                                                                        9

SEQ ID NO: 137        moltype = AA   length = 9
FEATURE               Location/Qualifiers
REGION                1..9
                      note = ADT1-7-19 VHCDR3
source                1..9
                      mol_type = protein
                      organism = Homo sapiens
SEQUENCE: 137
IDYEDAFDI                                                                        9

SEQ ID NO: 138        moltype = AA   length = 9
FEATURE               Location/Qualifiers
REGION                1..9
                      note = ADT1-7-20 VHCDR3
source                1..9
                      mol_type = protein
                      organism = Homo sapiens
SEQUENCE: 138
VDYQEAFDI                                                                        9

SEQ ID NO: 139        moltype = AA   length = 9
FEATURE               Location/Qualifiers
REGION                1..9
                      note = ADT1-7-22 VHCDR3
source                1..9
                      mol_type = protein
                      organism = Homo sapiens
SEQUENCE: 139
DDYNDAFDI                                                                        9

SEQ ID NO: 140        moltype = AA   length = 9
FEATURE               Location/Qualifiers
REGION                1..9
                      note = ADT1-7-23 VHCDR3
source                1..9
                      mol_type = protein
                      organism = Homo sapiens
SEQUENCE: 140
VDYNEAFDI                                                                        9

SEQ ID NO: 141        moltype = AA   length = 9
FEATURE               Location/Qualifiers
REGION                1..9
                      note = ADT1-7-42 VHCDR3
source                1..9
                      mol_type = protein
                      organism = Homo sapiens
SEQUENCE: 141
DDYEDAFDI                                                                        9

SEQ ID NO: 142        moltype = AA   length = 9
FEATURE               Location/Qualifiers
REGION                1..9
                      note = ADT1-7-3 VHCDR3
source                1..9
                      mol_type = protein
                      organism = Homo sapiens
SEQUENCE: 142
VSYAEAFDI                                                                        9

SEQ ID NO: 143        moltype = AA   length = 9
FEATURE               Location/Qualifiers
REGION                1..9
                      note = ADT1-7-61 VHCDR3
source                1..9
                      mol_type = protein
                      organism = Homo sapiens
```

```
SEQUENCE: 143
DDYDDAFDI                                                                        9

SEQ ID NO: 144         moltype = AA  length = 6
FEATURE                Location/Qualifiers
REGION                 1..6
                       note = ADT1-7 VLCDR1 (parental and all affinity matured
                        clones)
source                 1..6
                       mol_type = protein
                       organism = Homo sapiens
SEQUENCE: 144
QSIGTY                                                                           6

SEQ ID NO: 145         moltype =    length =
SEQUENCE: 145
000

SEQ ID NO: 146         moltype = AA  length = 9
FEATURE                Location/Qualifiers
REGION                 1..9
                       note = ADT1-7 VLCDR3
source                 1..9
                       mol_type = protein
                       organism = Homo sapiens
SEQUENCE: 146
QQSYSTLLT                                                                        9

SEQ ID NO: 147         moltype = AA  length = 9
FEATURE                Location/Qualifiers
REGION                 1..9
                       note = ADT1-7-10 VLCDR3
source                 1..9
                       mol_type = protein
                       organism = Homo sapiens
SEQUENCE: 147
QQTASTLLT                                                                        9

SEQ ID NO: 148         moltype = AA  length = 9
FEATURE                Location/Qualifiers
REGION                 1..9
                       note = ADT1-7-15 VLCDR3
source                 1..9
                       mol_type = protein
                       organism = Homo sapiens
SEQUENCE: 148
QQSADTLLT                                                                        9

SEQ ID NO: 149         moltype = AA  length = 9
FEATURE                Location/Qualifiers
REGION                 1..9
                       note = ADT1-7-17 VLCDR3
source                 1..9
                       mol_type = protein
                       organism = Homo sapiens
SEQUENCE: 149
QQSGSELLT                                                                        9

SEQ ID NO: 150         moltype = AA  length = 9
FEATURE                Location/Qualifiers
REGION                 1..9
                       note = ADT1-7-18 VLCDR3
source                 1..9
                       mol_type = protein
                       organism = Homo sapiens
SEQUENCE: 150
QQSASELLT                                                                        9

SEQ ID NO: 151         moltype = AA  length = 9
FEATURE                Location/Qualifiers
REGION                 1..9
                       note = ADT1-7-19 VLCDR3
source                 1..9
                       mol_type = protein
                       organism = Homo sapiens
SEQUENCE: 151
QQSASELLT                                                                        9

SEQ ID NO: 152         moltype = AA  length = 9
```

```
FEATURE                 Location/Qualifiers
REGION                  1..9
                        note = ADT1-7-20 VLCDR3
source                  1..9
                        mol_type = protein
                        organism = Homo sapiens
SEQUENCE: 152
QQSYSGLDT                                                                        9

SEQ ID NO: 153          moltype = AA  length = 9
FEATURE                 Location/Qualifiers
REGION                  1..9
                        note = ADT1-7-22 VLCDR3
source                  1..9
                        mol_type = protein
                        organism = Homo sapiens
SEQUENCE: 153
QQSASELLT                                                                        9

SEQ ID NO: 154          moltype = AA  length = 9
FEATURE                 Location/Qualifiers
REGION                  1..9
                        note = ADT1-7-23 VLCDR3
source                  1..9
                        mol_type = protein
                        organism = Homo sapiens
SEQUENCE: 154
QQSYSGLDT                                                                        9

SEQ ID NO: 155          moltype = AA  length = 9
FEATURE                 Location/Qualifiers
REGION                  1..9
                        note = ADT1-7-42 VLCDR3
source                  1..9
                        mol_type = protein
                        organism = Homo sapiens
SEQUENCE: 155
QQSSSELLT                                                                        9

SEQ ID NO: 156          moltype = AA  length = 9
FEATURE                 Location/Qualifiers
REGION                  1..9
                        note = ADT1-7-3 VLCDR3
source                  1..9
                        mol_type = protein
                        organism = Homo sapiens
SEQUENCE: 156
QQSYSGLDT                                                                        9

SEQ ID NO: 157          moltype = AA  length = 9
FEATURE                 Location/Qualifiers
REGION                  1..9
                        note = ADT1-7-61 VLCDR3
source                  1..9
                        mol_type = protein
                        organism = Homo sapiens
SEQUENCE: 157
QQSASELLT                                                                        9

SEQ ID NO: 158          moltype = AA  length = 10
FEATURE                 Location/Qualifiers
REGION                  1..10
                        note = ADT1-4-derived anti-TCR delta variable 1 antibody or
                         antigen-binding fragment thereof: HCDR1
VARIANT                 9
                        note = Xaa can be any naturally occurring amino acid
source                  1..10
                        mol_type = protein
                        organism = Homo sapiens
SEQUENCE: 158
GDSVSSKSXA                                                                      10

SEQ ID NO: 159          moltype = AA  length = 10
FEATURE                 Location/Qualifiers
REGION                  1..10
                        note = ADT1-4-derived anti-TCR delta variable 1 antibody or
                         antigen-binding fragment thereof: HCDR1
VARIANT                 9
                        note = X is A or V
```

```
source                  1..10
                        mol_type = protein
                        organism = Homo sapiens
SEQUENCE: 159
GDSVSSKSXA                                                               10

SEQ ID NO: 160          moltype = AA  length = 10
FEATURE                 Location/Qualifiers
REGION                  1..10
                        note = ADT1-4-derived anti-TCR delta variable 1 antibody or
                         antigen-binding fragment thereof: HCDR1
VARIANT                 9
                        note = X is A or V
source                  1..10
                        mol_type = protein
                        organism = Homo sapiens
SEQUENCE: 160
GDSVSSKSXA                                                               10

SEQ ID NO: 161          moltype = AA  length = 10
FEATURE                 Location/Qualifiers
REGION                  1..10
                        note = ADT1-4-derived anti-TCR delta variable 1 antibody or
                         antigen-binding fragment thereof: HCDR1
VARIANT                 9
                        note = X is A or V
source                  1..10
                        mol_type = protein
                        organism = Homo sapiens
SEQUENCE: 161
GDSVSSKSXA                                                               10

SEQ ID NO: 162          moltype =    length =
SEQUENCE: 162
000

SEQ ID NO: 163          moltype =    length =
SEQUENCE: 163
000

SEQ ID NO: 164          moltype =    length =
SEQUENCE: 164
000

SEQ ID NO: 165          moltype =    length =
SEQUENCE: 165
000

SEQ ID NO: 166          moltype = AA  length = 10
FEATURE                 Location/Qualifiers
REGION                  1..10
                        note = ADT1-4-derived anti-TCR delta variable 1 antibody or
                         antigen-binding fragment thereof: LCDR3
VARIANT                 3
                        note = Xaa can be any naturally occurring amino acid
VARIANT                 5..9
                        note = Xaa can be any naturally occurring amino acid
source                  1..10
                        mol_type = protein
                        organism = Homo sapiens
SEQUENCE: 166
QQXYXXXXXT                                                               10

SEQ ID NO: 167          moltype = AA  length = 10
FEATURE                 Location/Qualifiers
REGION                  1..10
                        note = ADT1-4-derived anti-TCR delta variable 1 antibody or
                         antigen-binding fragment thereof: LCDR3
VARIANT                 3
                        note = X is K, R or G
VARIANT                 5
                        note = X is S or K
VARIANT                 6
                        note = X is T, Q, A, E or D
VARIANT                 7
                        note = X is P, H or D
VARIANT                 8
                        note = X is Q, R, K, W, P, E or I
VARIANT                 9
```

```
                        note = X is I, V or L
source                  1..10
                        mol_type = protein
                        organism = Homo sapiens
SEQUENCE: 167
QQXYXXXXXT                                                                   10

SEQ ID NO: 168          moltype = AA  length = 10
FEATURE                 Location/Qualifiers
REGION                  1..10
                        note = ADT1-4-derived anti-TCR delta variable 1 antibody or
                         antigen-binding fragment thereof: LCDR3
VARIANT                 3
                        note = X is K, R or G
VARIANT                 5
                        note = X is S or K
VARIANT                 6
                        note = X is T, Q, A, E or D
VARIANT                 7
                        note = X is P or H
VARIANT                 8
                        note = X is Q, R, K, W, P, E or I
VARIANT                 9
                        note = X is I, V or L
source                  1..10
                        mol_type = protein
                        organism = Homo sapiens
SEQUENCE: 168
QQXYXXXXXT                                                                   10

SEQ ID NO: 169          moltype = AA  length = 10
FEATURE                 Location/Qualifiers
REGION                  1..10
                        note = ADT1-4-derived anti-TCR delta variable 1 antibody or
                         antigen-binding fragment thereof: LCDR3
VARIANT                 3
                        note = X is K or R
VARIANT                 5
                        note = X is S or K
VARIANT                 6
                        note = X is T, Q, A or E
VARIANT                 7
                        note = X is P or H
VARIANT                 8
                        note = X is Q, K, W, P or I
VARIANT                 9
                        note = X is V or L
source                  1..10
                        mol_type = protein
                        organism = Homo sapiens
SEQUENCE: 169
QQXYXXXXXT                                                                   10

SEQ ID NO: 170          moltype = AA  length = 25
FEATURE                 Location/Qualifiers
REGION                  1..25
                        note = ADT1-4 HFR1 (parental and affinity matured clones)
source                  1..25
                        mol_type = protein
                        organism = Homo sapiens
SEQUENCE: 170
EVQLQQSGPG LVKPSQTLSL TCAIS                                                  25

SEQ ID NO: 171          moltype = AA  length = 25
FEATURE                 Location/Qualifiers
REGION                  1..25
                        note = ADT1-4-143 HFR1
source                  1..25
                        mol_type = protein
                        organism = Homo sapiens
SEQUENCE: 171
EVQLLQSGPG LVKPSQTLSL TCAIS                                                  25

SEQ ID NO: 172          moltype = AA  length = 17
FEATURE                 Location/Qualifiers
REGION                  1..17
                        note = ADT1-4 HFR2 (parental and all affinity matured
                         clones)
source                  1..17
```

```
                        mol_type = protein
                        organism = Homo sapiens
SEQUENCE: 172
WNWIRQSPSR GLEWLGR                                                           17

SEQ ID NO: 173          moltype = AA   length = 40
FEATURE                 Location/Qualifiers
REGION                  1..40
                        note = ADT1-4 HFR3 (parental and all affinity matured
                         clones)
source                  1..40
                        mol_type = protein
                        organism = Homo sapiens
SEQUENCE: 173
DYAASVKSRI TINPDTSKNQ LSLQLNSVTP EDTAVYYCAR                                  40

SEQ ID NO: 174          moltype = AA   length = 11
FEATURE                 Location/Qualifiers
REGION                  1..11
                        note = ADT1-4 HFR4 (parental and all affinity matured
                         clones)
source                  1..11
                        mol_type = protein
                        organism = Homo sapiens
SEQUENCE: 174
WGQGTLVTVS S                                                                 11

SEQ ID NO: 175          moltype = AA   length = 26
FEATURE                 Location/Qualifiers
REGION                  1..26
                        note = ADT1-4 LFR1 (parental and all affinity matured
                         clones)
source                  1..26
                        mol_type = protein
                        organism = Homo sapiens
SEQUENCE: 175
DIQMTQSPPA LSASVGDRVT ITCRAS                                                 26

SEQ ID NO: 176          moltype = AA   length = 17
FEATURE                 Location/Qualifiers
REGION                  1..17
                        note = ADT1-4 LFR2 (parental and all affinity matured
                         clones)
source                  1..17
                        mol_type = protein
                        organism = Homo sapiens
SEQUENCE: 176
LAWYQHKPGK APKLLIY                                                           17

SEQ ID NO: 177          moltype = AA   length = 36
FEATURE                 Location/Qualifiers
REGION                  1..36
                        note = ADT1-4 LFR3 (affinity matured clones)
source                  1..36
                        mol_type = protein
                        organism = Homo sapiens
SEQUENCE: 177
SLESGVPLRF SGSGSGTEFT LTISSLQPDD FATYYC                                      36

SEQ ID NO: 178          moltype = AA   length = 36
FEATURE                 Location/Qualifiers
REGION                  1..36
                        note = ADT1-4 parental clones and ADT1-4-138 LFR3
source                  1..36
                        mol_type = protein
                        organism = Homo sapiens
SEQUENCE: 178
SLESGVPSRF SGSGSGTEFT LTISSLQPDD FATYYC                                      36

SEQ ID NO: 179          moltype = AA   length = 10
FEATURE                 Location/Qualifiers
REGION                  1..10
                        note = ADT1-4 LFR4 (parental and affinity matured clones)
source                  1..10
                        mol_type = protein
                        organism = Homo sapiens
SEQUENCE: 179
FGQGTRLEIK                                                                   10
```

| | | |
|---|---|---|
| SEQ ID NO: 180 | moltype = AA  length = 10 | |
| FEATURE | Location/Qualifiers | |
| REGION | 1..10 | |
| | note = ADT1-4-110 LFR4 | |
| source | 1..10 | |
| | mol_type = protein | |
| | organism = Homo sapiens | |
| SEQUENCE: 180 | | |
| FGAGTRLEIK | | 10 |
| | | |
| SEQ ID NO: 181 | moltype = AA  length = 10 | |
| FEATURE | Location/Qualifiers | |
| REGION | 1..10 | |
| | note = ADT1-4-143 LFR4 | |
| source | 1..10 | |
| | mol_type = protein | |
| | organism = Homo sapiens | |
| SEQUENCE: 181 | | |
| FGQGTRLVIK | | 10 |
| | | |
| SEQ ID NO: 182 | moltype = AA  length = 10 | |
| FEATURE | Location/Qualifiers | |
| REGION | 1..10 | |
| | note = ADT1-4-95 LFR4 | |
| source | 1..10 | |
| | mol_type = protein | |
| | organism = Homo sapiens | |
| SEQUENCE: 182 | | |
| FGSGTRLEIK | | 10 |
| | | |
| SEQ ID NO: 183 | moltype = AA  length = 9 | |
| FEATURE | Location/Qualifiers | |
| REGION | 1..9 | |
| | note = ADT1-7-derived anti-TCR delta variable 1 antibody or antigen-binding fragment thereof: HCDR3 | |
| VARIANT | 1..2 | |
| | note = Xaa can be any naturally occurring amino acid | |
| VARIANT | 4..5 | |
| | note = Xaa can be any naturally occurring amino acid | |
| source | 1..9 | |
| | mol_type = protein | |
| | organism = Homo sapiens | |
| SEQUENCE: 183 | | |
| XXYXXAFDI | | 9 |
| | | |
| SEQ ID NO: 184 | moltype = AA  length = 9 | |
| FEATURE | Location/Qualifiers | |
| REGION | 1..9 | |
| | note = ADT1-7-derived anti-TCR delta variable 1 antibody or antigen-binding fragment thereof: HCDR3 | |
| VARIANT | 1 | |
| | note = X is D, I or V | |
| VARIANT | 2 | |
| | note = X is D or S | |
| VARIANT | 4 | |
| | note = X is N, E, D, Q or A | |
| VARIANT | 5 | |
| | note = X is D or E | |
| source | 1..9 | |
| | mol_type = protein | |
| | organism = Homo sapiens | |
| SEQUENCE: 184 | | |
| XXYXXAFDI | | 9 |
| | | |
| SEQ ID NO: 185 | moltype = AA  length = 9 | |
| FEATURE | Location/Qualifiers | |
| REGION | 1..9 | |
| | note = ADT1-7-derived anti-TCR delta variable 1 antibody or antigen-binding fragment thereof: HCDR3 | |
| VARIANT | 1 | |
| | note = X is D or V | |
| VARIANT | 2 | |
| | note = X is D or S | |
| VARIANT | 4 | |
| | note = X is D, Q or A | |
| VARIANT | 5 | |
| | note = X is D or E | |
| source | 1..9 | |
| | mol_type = protein | |

```
                             organism = Homo sapiens
SEQUENCE: 185
XXYXXAFDI                                                            9

SEQ ID NO: 186           moltype = AA  length = 9
FEATURE                  Location/Qualifiers
REGION                   1..9
                         note = ADT1-7-derived anti-TCR delta variable 1 antibody or
                          antigen-binding fragment thereof: LCDR3
VARIANT                  3..6
                         note = Xaa can be any naturally occurring amino acid
VARIANT                  8
                         note = Xaa can be any naturally occurring amino acid
source                   1..9
                         mol_type = protein
                         organism = Homo sapiens
SEQUENCE: 186
QQXXXXLXT                                                            9

SEQ ID NO: 187           moltype = AA  length = 9
FEATURE                  Location/Qualifiers
REGION                   1..9
                         note = ADT1-7-derived anti-TCR delta variable 1 antibody or
                          antigen-binding fragment thereof: LCDR3
VARIANT                  3
                         note = X is T or S
VARIANT                  4
                         note = X is A, G, Y or S
VARIANT                  5
                         note = X is S or D
VARIANT                  6
                         note = X is T, E or G
VARIANT                  8
                         note = X is L or D
source                   1..9
                         mol_type = protein
                         organism = Homo sapiens
SEQUENCE: 187
QQXXXXLXT                                                            9

SEQ ID NO: 188           moltype = AA  length = 9
FEATURE                  Location/Qualifiers
REGION                   1..9
                         note = ADT1-7-derived anti-TCR delta variable 1 antibody or
                          antigen-binding fragment thereof: LCDR3
VARIANT                  4
                         note = X is A or Y
VARIANT                  6
                         note = X is E or G
VARIANT                  8
                         note = X is L or D
source                   1..9
                         mol_type = protein
                         organism = Homo sapiens
SEQUENCE: 188
QQSXSXLXT                                                            9

SEQ ID NO: 189           moltype = AA  length = 25
FEATURE                  Location/Qualifiers
REGION                   1..25
                         note = ADT1-7 HFR1 (parental and all affinity matured
                          clones)
source                   1..25
                         mol_type = protein
                         organism = Homo sapiens
SEQUENCE: 189
EVQLVESGGG LVKPGGSLRL SCAAS                                         25

SEQ ID NO: 190           moltype = AA  length = 17
FEATURE                  Location/Qualifiers
REGION                   1..17
                         note = ADT1-7 HFR2 (parental and all affinity matured
                          clones)
source                   1..17
                         mol_type = protein
                         organism = Homo sapiens
SEQUENCE: 190
MSWIRQAPGK GLEWVSY                                                  17
```

```
SEQ ID NO: 191           moltype = AA  length = 40
FEATURE                  Location/Qualifiers
REGION                   1..40
                         note = ADT1-7 HFR3 (parental and all affinity matured
                         clones)
source                   1..40
                         mol_type = protein
                         organism = Homo sapiens
SEQUENCE: 191
YYADSVKGRF TISRDNAKNS LYLQMNSLRA EDTAVYYCAR                          40

SEQ ID NO: 192           moltype = AA  length = 11
FEATURE                  Location/Qualifiers
REGION                   1..11
                         note = ADT1-7 HFR4 (parental and all affinity matured
                         clones)
source                   1..11
                         mol_type = protein
                         organism = Homo sapiens
SEQUENCE: 192
WGQGTLVTVS S                                                         11

SEQ ID NO: 193           moltype = AA  length = 26
FEATURE                  Location/Qualifiers
REGION                   1..26
                         note = ADT1-7 LFR1 (parental and affinity matured clones)
source                   1..26
                         mol_type = protein
                         organism = Homo sapiens
SEQUENCE: 193
DIQMTQSPSS LSASVGDRVT IACRAG                                         26

SEQ ID NO: 194           moltype = AA  length = 26
FEATURE                  Location/Qualifiers
REGION                   1..26
                         note = ADT1-7-18 LFR1
source                   1..26
                         mol_type = protein
                         organism = Homo sapiens
SEQUENCE: 194
DIQMTQSPSS LSASVGDRVT IACRVG                                         26

SEQ ID NO: 195           moltype = AA  length = 17
FEATURE                  Location/Qualifiers
REGION                   1..17
                         note = ADT1-7 LFR2 (parental and all affinity matured
                         clones)
source                   1..17
                         mol_type = protein
                         organism = Homo sapiens
SEQUENCE: 195
LNWYQQKPGK APKLLIY                                                   17

SEQ ID NO: 196           moltype = AA  length = 36
FEATURE                  Location/Qualifiers
REGION                   1..36
                         note = ADT1-7 LFR3 (parental and all affinity matured
                         clones)
source                   1..36
                         mol_type = protein
                         organism = Homo sapiens
SEQUENCE: 196
SLQSGVPSRF SGSGSGTEFT LTISSLQPED FATYYC                              36

SEQ ID NO: 197           moltype = AA  length = 10
FEATURE                  Location/Qualifiers
REGION                   1..10
                         note = ADT1-7 LFR4 (parental and all affinity matured
                         clones)
source                   1..10
                         mol_type = protein
                         organism = Homo sapiens
SEQUENCE: 197
FGRGTKVEIK                                                           10

SEQ ID NO: 198           moltype = DNA  length = 360
FEATURE                  Location/Qualifiers
misc_feature             1..360
                         note = ADT1-4 Variable Heavy DNA
```

| source | 1..360 |
| --- | --- |
| | mol_type = genomic DNA |
| | organism = Homo sapiens |

SEQUENCE: 198

```
caggtacagc tgcagcagtc aggtccagga ctggtgaagc cctcgcagac cctctcactc   60
acctgtgcca tctccgggga cagtgtctcc agcaaaagtg ctgcttggaa ctggatcagg  120
cagtccccat cgagaggcct tgagtggctg ggaaggacat actacaggtc caagtggtct  180
actgattatg cagcatctgt gaaaagtcga ataaccatca cccagacac atccaagaac  240
cagctctccc tgcagttaaa ctctgtgact cccgaggaca cggctgtgta ttactgtgca  300
agaacgtgga gtggttatgt ggacgtctgg ggccaaggaa ccctggtcac cgtctcgagc  360
```

| SEQ ID NO: 199 | moltype = DNA   length = 360 |
| --- | --- |
| FEATURE | Location/Qualifiers |
| misc_feature | 1..360 |
| | note = ADT1-4-105 Variable Heavy DNA |
| source | 1..360 |
| | mol_type = genomic DNA |
| | organism = Homo sapiens |

SEQUENCE: 199

```
gaggtacagc tgcagcagtc aggtccagga ctggtgaagc cctcgcagac cctctcactc   60
acctgtgcca tctccgggga cagtgtctcc agcaaaagtg ctgcttggaa ctggatcagg  120
cagtccccat cgagaggcct tgagtggctg ggaaggacat actacaggtc caagtggtct  180
actgattatg cagcatctgt gaaaagtcga ataaccatca cccagacac atccaagaac  240
cagctctccc tgcagttaaa ctctgtgact cccgaggaca cggctgtgta ttactgtgca  300
agaacgtggg tgggttatgt ggacgtctgg ggccaaggaa ccctggtcac cgtctcgagc  360
```

| SEQ ID NO: 200 | moltype = DNA   length = 360 |
| --- | --- |
| FEATURE | Location/Qualifiers |
| misc_feature | 1..360 |
| | note = ADT1-4-107 Variable Heavy DNA |
| source | 1..360 |
| | mol_type = genomic DNA |
| | organism = Homo sapiens |

SEQUENCE: 200

```
gaggtacagc tgcagcagtc aggtccagga ctggtgaagc cctcgcagac cctctcactc   60
acctgtgcca tctccgggga cagtgtctcc agcaaaagtg ctgcttggaa ctggatcagg  120
cagtccccat cgagaggcct tgagtggctg ggaaggacat actacaggtc caagtggtct  180
actgattatg cagcatctgt gaaaagtcga ataaccatca cccagacac atccaagaac  240
cagctctccc tgcagttaaa ctctgtgact cccgaggaca cggctgtgta ttactgtgca  300
agaacgtggg tgggttatgc cgacgtctgg ggccaaggaa ccctggtcac cgtctcgagc  360
```

| SEQ ID NO: 201 | moltype = DNA   length = 360 |
| --- | --- |
| FEATURE | Location/Qualifiers |
| misc_feature | 1..360 |
| | note = ADT1-4-110 Variable Heavy DNA |
| source | 1..360 |
| | mol_type = genomic DNA |
| | organism = Homo sapiens |

SEQUENCE: 201

```
gaggtacagc tgcagcagtc aggtccagga ctggtgaagc cctcgcagac cctctcactc   60
acctgtgcga tctccgggga cagtgtctcc agcaaaagtg ctgcttggaa ctggatcagg  120
cagtccccat cgagaggcct tgagtggctg ggaaggacat actacaggtc caagtggtct  180
actgattatg cagcatctgt gaaaagtcga ataaccatca cccagacac atccaagaac  240
cagctctctc tgcagttaaa ctctgtgact cccgaggaca cggctgtgta ttactgtgca  300
agaacgtggg tggagtatgt ggacgtctgg ggccaaggaa ccctggtcac cgtctcgagc  360
```

| SEQ ID NO: 202 | moltype = DNA   length = 360 |
| --- | --- |
| FEATURE | Location/Qualifiers |
| misc_feature | 1..360 |
| | note = ADT1-4-112 Variable Heavy DNA |
| source | 1..360 |
| | mol_type = genomic DNA |
| | organism = Homo sapiens |

SEQUENCE: 202

```
gaggtacagc tgcagcagtc aggtccagga ctggtgaagc cctcgcagac cctctcactc   60
acctgtgcca tctccgggga cagtgtctcc agcaaaagtg ctgcttggaa ctggatcagg  120
cagtccccat cgagaggcct tgagtggctg ggaaggacat actacaggtc caagtggtct  180
actgattatg cagcatctgt gaaaagtcga ataaccatca cccagacac atccaagaac  240
cagctctccc tgcagttaaa ctctgtgact cccgaggaca cggctgtgta ttactgtgca  300
agaacgtggg tgggttatgt ggactactgg ggccaaggaa ccctggtcac cgtctcgagc  360
```

| SEQ ID NO: 203 | moltype = DNA   length = 360 |
| --- | --- |
| FEATURE | Location/Qualifiers |
| misc_feature | 1..360 |
| | note = ADT1-4-117 Variable Heavy DNA |
| source | 1..360 |
| | mol_type = genomic DNA |
| | organism = Homo sapiens |

SEQUENCE: 203

```
gaggtacagc tgcagcagtc aggtccagga ctggtgaagc cctcgcagac cctctcactc   60
acctgtgcca tctccgggga cagtgtctcc agcaaaagtg ctgcttggaa ctggatcagg  120
cagtccccat cgagaggcct tgagtggctg ggaaggacat actacaggtc caagtggtct  180
actgattatg cagcatctgt gaaaagtcga ataaccatca cccagacac atccaagaac   240
cagctctccc tgcagttaaa ctctgtgact cccgaggaca cggctgtgta ttactgtgca  300
agaacgtggg tgggttatgt ggacgtctgg ggccaaggaa ccctggtcac cgtctcgagc  360
```

SEQ ID NO: 204          moltype = DNA   length = 360
FEATURE                 Location/Qualifiers
misc_feature            1..360
                        note = ADT1-4-19 Variable Heavy DNA
source                  1..360
                        mol_type = genomic DNA
                        organism = Homo sapiens
SEQUENCE: 204
```
gaggtacagc tgcagcagtc aggtccagga ctggtgaagc cctcgcagac cctctcactc   60
acctgtgcca tctccgggga cagtgtctcc agcaaaagtg ctgcttggaa ctggatcagg  120
cagtccccat cgagaggcct tgagtggctg ggaaggacat actacaggtc caagtggtct  180
actgattatg cagcatctgt gaaaagtcga ataaccatca cccagacac atccaagaac   240
cagctctccc tgcagttaaa ctctgtgact cccgaggaca cggctgtgta ttactgtgca  300
agaacgtggg tgggttatgt ggacaggtgg ggccaaggaa ccctggtcac cgtctcgagc  360
```

SEQ ID NO: 205          moltype = DNA   length = 360
FEATURE                 Location/Qualifiers
misc_feature            1..360
                        note = ADT1-4-21 Variable Heavy DNA
source                  1..360
                        mol_type = genomic DNA
                        organism = Homo sapiens
SEQUENCE: 205
```
gaggtacagc tgcagcagtc aggtccagga ctggtgaagc cctcgcagac cctctcactc   60
acctgtgcca tctccgggga cagtgtctcc agcaaaagtg ttgcttggaa ctggatcagg  120
cagtccccat cgagaggcct tgagtggctg ggaaggacat actacaggtc caagtggtct  180
actgattatg cagcatctgt gaaaagtcga ataaccatca cccagacac atccaagaac   240
cagctctccc tgcagttaaa ctctgtgact cccgaggaca cggctgtgta ttactgtgca  300
agaacgtggg ccgactatgt ggacgtctgg ggccaaggaa ccctggtcac cgtctcgagc  360
```

SEQ ID NO: 206          moltype = DNA   length = 360
FEATURE                 Location/Qualifiers
misc_feature            1..360
                        note = ADT1-4-31 Variable Heavy DNA
source                  1..360
                        mol_type = genomic DNA
                        organism = Homo sapiens
SEQUENCE: 206
```
gaggtacagc tgcagcagtc aggtccagga ctggtgaagc cctcgcagac cctctcactc   60
acctgtgcca tctccgggga cagtgtctcc agcaaaagtg ctgcttggaa ctggatcagg  120
cagtccccat cgagaggcct tgagtggctg ggaaggacat actacaggtc caagtggtct  180
actgattatg cagcatctgt gaaaagtcga ataaccatca cccagacac atccaagaac   240
cagctctccc tgcagttaaa ctctgtgact cccgaggaca cggctgtgta ttactgtgca  300
agaacgtggg tgggttatgc cgacgtctgg ggccaaggaa ccctggtcac cgtctcgagc  360
```

SEQ ID NO: 207          moltype = DNA   length = 360
FEATURE                 Location/Qualifiers
misc_feature            1..360
                        note = ADT1-4-139 Variable Heavy DNA
source                  1..360
                        mol_type = genomic DNA
                        organism = Homo sapiens
SEQUENCE: 207
```
gaggtacagc tgcagcagtc aggtccagga ctggtgaagc cctcgcagac cctctcactc   60
acctgtgcca tctccgggga cagtgtctcc agcaaaagtg ctgcttggaa ctggatcagg  120
cagtcccat cgagaggcct tgagtggctg ggaaggacat actacaggtc caagtggtct   180
actgattatg cagcatctgt gaaaagtcga ataaccatca cccagacac atccaagaac   240
cagctctccc tgcagttaaa ctctgtgact cccgaggaca cggctgtgta ttactgtgca  300
agaacgtggg tgggttatgt ggactactgg ggccaaggaa ccctggtcac cgtctcgagc  360
```

SEQ ID NO: 208          moltype = DNA   length = 360
FEATURE                 Location/Qualifiers
misc_feature            1..360
                        note = ADT1-4-4 Variable Heavy DNA
source                  1..360
                        mol_type = genomic DNA
                        organism = Homo sapiens
SEQUENCE: 208
```
gaggtacagc tgcagcagtc aggtccagga ctggtgaagc cctcgcagac cctctcactc   60
acctgtgcca tctccgggga cagtgtctcc agcaaaagtg ctgcttggaa ctggatcagg  120
cagtccccat cgagaggcct tgagtggctg ggaaggacat actacaggtc caagtggtct  180
actgattatg cagcatctgt gaaaagtcga ataaccatca cccagacac atccaagaac   240
```

```
cagctctccc tgcagttaaa ctctgtgact cccgaggaca cggctgtgta ttactgtgca    300
agaacgtggg tgggttatgc cgacgtctgg ggccaaggaa ccctggtcac cgtctcgagc    360

SEQ ID NO: 209         moltype = DNA  length = 360
FEATURE                Location/Qualifiers
misc_feature           1..360
                       note = ADT1-4-143 Variable Heavy DNA
source                 1..360
                       mol_type = genomic DNA
                       organism = Homo sapiens
SEQUENCE: 209
gaggtacagc tgctgcagtc aggtccagga ctggtgaagc cctcgcagac cctctcactc    60
acctgtgcca tctccgggga cagtgtctcc agcaaaagtg ctgcttggaa ctggatcagg    120
cagtccccat cgagaggcct tgagtggctg ggaaggacat actacaggtc caagtggtct    180
actgattatg cagcatctgt gaaaagtcga ataaccatca acccagacac atccaagaac    240
cagctctccc tgcagttaaa ctctgtgact cccgaggaca cggctgtgta ttactgtgca    300
agaacgtggg tgggttatgc cgacgtctgg ggccaaggaa ccctggtcac cgtctcgagc    360

SEQ ID NO: 210         moltype = DNA  length = 360
FEATURE                Location/Qualifiers
misc_feature           1..360
                       note = ADT1-4-53 Variable Heavy DNA
source                 1..360
                       mol_type = genomic DNA
                       organism = Homo sapiens
SEQUENCE: 210
gaggtacagc tgcagcagtc aggtccagga ctggtgaagc cctcgcagac cctctcactc    60
acctgtgcca tctccgggga cagtgtctcc agcaaaagtg ttgcttggaa ctggatcagg    120
cagtccccat cgagaggcct tgagtggctg ggaaggacat actacaggtc caagtggtct    180
actgattatg cagcatctgt gaaaagtcga ataaccatca acccagacac atccaagaac    240
cagctctccc tgcagttaaa ctctgtgact cccgaggaca cggctgtgta ttactgtgca    300
agaacgtggg ccgactatgt ggacgtctgg ggccaaggaa ccctggtcac cgtctcgagc    360

SEQ ID NO: 211         moltype = DNA  length = 360
FEATURE                Location/Qualifiers
misc_feature           1..360
                       note = ADT1-4-173 Variable Heavy DNA
source                 1..360
                       mol_type = genomic DNA
                       organism = Homo sapiens
SEQUENCE: 211
gaggtacagc tgcagcagtc aggtccagga ctggtgaagc cctcgcagac cctctcactc    60
acctgtgcca tctccgggga cagtgtctcc agcaaaagtg ctgcttggaa ctggatcagg    120
cagtccccat cgagaggcct tgagtggctg ggaaggacat actacaggtc caagtggtct    180
actgattatg cagcatctgt gaaaagtcga ataaccatca acccagacac atccaagaac    240
cagctctccc tgcagttaaa ctctgtgact cccgaggaca cggctgtgta ttactgtgca    300
agaacgtggg ccggttatcc cgacgtctgg ggccaaggaa ccctggtcac cgtctcgagc    360

SEQ ID NO: 212         moltype = DNA  length = 360
FEATURE                Location/Qualifiers
misc_feature           1..360
                       note = ADT1-4-2 Variable Heavy DNA
source                 1..360
                       mol_type = genomic DNA
                       organism = Homo sapiens
SEQUENCE: 212
gaggtacagc tgcagcagtc aggtccagga ctggtgaagc cctcgcagac cctctcactc    60
acctgtgcca tctccgggga cagtgtctcc agcaaaagtg ctgcttggaa ctggatcagg    120
cagtccccat cgagaggcct tgagtggctg ggaaggacat actacaggtc caagtggtct    180
actgattatg cagcatctgt gaaaagtcga ataaccatca acccagacac atccaagaac    240
cagctctccc tgcagttaaa ctctgtgact cccgaggaca cggctgtgta ttactgtgca    300
agaacgtggg tgggttatgt ggacaggtgg ggccaaggaa ccctggtcac cgtctcgagc    360

SEQ ID NO: 213         moltype = DNA  length = 360
FEATURE                Location/Qualifiers
misc_feature           1..360
                       note = ADT1-4-8 Variable Heavy DNA
source                 1..360
                       mol_type = genomic DNA
                       organism = Homo sapiens
SEQUENCE: 213
gaggtacagc tgcagcagtc aggtccagga ctggtgaagc cctcgcagac cctctcactc    60
acctgtgcca tctccgggga cagtgtctcc agcaaaagtg ctgcttggaa ctggatcagg    120
cagtccccat cgagaggcct tgagtggctg ggaaggacat actacaggtc caagtggtct    180
actgattatg cagcatctgt gaaaagtcga ataaccatca acccagacac atccaagaac    240
cagctctccc tgcagttaaa ctctgtgact cccgaggaca cggctgtgta ttactgtgca    300
agaacgtggg tgggttatgc cgacgtctgg ggccaaggaa ccctggtcac cgtctcgagc    360

SEQ ID NO: 214         moltype = DNA  length = 360
```

| FEATURE | Location/Qualifiers |
|---|---|
| misc_feature | 1..360 |
| | note = ADT1-4-82 Variable Heavy DNA |
| source | 1..360 |
| | mol_type = genomic DNA |
| | organism = Homo sapiens |

SEQUENCE: 214
```
gaggtacagc tgcagcagtc aggtccagga ctggtgaagc cctcgcagac cctctcactc   60
acctgtgcca tctccgggga cagtgtctcc agcaaaagtg ctgcttggaa ctggatcagg  120
cagtccccat cgagaggcct tgagtggctg ggaaggacat actacaggtc caagtggtct  180
actgattatg cagcatctgt gaaaagtcga ataaccatca acccagacac atccaagaac  240
cagctctccc tgcagttaaa ctctgtgact cccgaggaca cggctgtgta ttactgtgca  300
agaagctggg tgggttatgt ggacgtctgg ggccaaggaa ccctggtcac cgtctcgagc  360
```

| SEQ ID NO: 215 | moltype = DNA length = 360 |
|---|---|
| FEATURE | Location/Qualifiers |
| misc_feature | 1..360 |
| | note = ADT1-4-83 Variable Heavy DNA |
| source | 1..360 |
| | mol_type = genomic DNA |
| | organism = Homo sapiens |

SEQUENCE: 215
```
gaggtacagc tgcagcagtc aggtccagga ctggtgaagc cctcgcagac cctctcactc   60
acctgtgcca tctccgggga cagtgtctcc agcaaaagtg ctgcttggaa ctggatcagg  120
cagtccccat cgagaggcct tgagtggctg ggaaggacat actacaggtc caagtggtct  180
actgattatg cagcatctgt gaaaagtcga ataaccatca acccagacac atccaagaac  240
cagctctccc tgcagttaaa ctctgtgact cccgaggaca cggctgtgta ttactgtgca  300
agaagctggg tgggttatgt ggacgtctgg ggccaaggaa ccctggtcac cgtctcgagc  360
```

| SEQ ID NO: 216 | moltype = DNA length = 360 |
|---|---|
| FEATURE | Location/Qualifiers |
| misc_feature | 1..360 |
| | note = ADT1-4-3 Variable Heavy DNA |
| source | 1..360 |
| | mol_type = genomic DNA |
| | organism = Homo sapiens |

SEQUENCE: 216
```
gaggtacagc tgcagcagtc aggtccagga ctggtgaagc cctcgcagac cctctcactc   60
acctgtgcca tctccgggga cagtgtctcc agcaaaagtg ctgcttggaa ctggatcagg  120
cagtccccat cgagaggcct tgagtggctg ggaaggacat actacaggtc caagtggtct  180
actgattatg cagcatctgt gaaaagtcga ataaccatca acccagacac atccaagaac  240
cagctctccc tgcagttaaa ctctgtgact cccgaggaca cggctgtgta ttactgtgca  300
agaacgtggg ccgactatgt ggacgtctgg ggccaaggaa ccctggtcac cgtctcgagc  360
```

| SEQ ID NO: 217 | moltype = DNA length = 360 |
|---|---|
| FEATURE | Location/Qualifiers |
| misc_feature | 1..360 |
| | note = ADT1-4-84 Variable Heavy DNA |
| source | 1..360 |
| | mol_type = genomic DNA |
| | organism = Homo sapiens |

SEQUENCE: 217
```
gaggtacagc tgcagcagtc aggtccagga ctggtgaagc cctcgcagac cctctcactc   60
acctgtgcca tctccgggga cagtgtctcc agcaaaagtg ctgcttggaa ctggatcagg  120
cagtccccat cgagaggcct tgagtggctg ggaaggacat actacaggtc caagtggtct  180
actgattatg cagcatctgt gaaaagtcga ataaccatca acccagacac atccaagaac  240
cagctctccc tgcagttaaa ctctgtgact cccgaggaca cggctgtgta ttactgtgca  300
agaacgtggg tgggttatgc cgacgtctgg ggccaaggaa ccctggtcac cgtctcgagc  360
```

| SEQ ID NO: 218 | moltype = DNA length = 360 |
|---|---|
| FEATURE | Location/Qualifiers |
| misc_feature | 1..360 |
| | note = ADT1-4-86 Variable Heavy DNA |
| source | 1..360 |
| | mol_type = genomic DNA |
| | organism = Homo sapiens |

SEQUENCE: 218
```
gaggtacagc tgcagcagtc aggtccagga ctggtgaagc cctcgcagac cctctcactc   60
acctgtgcca tctccgggga cagtgtctcc agcaaaagtg ttgcttggaa ctggatcagg  120
cagtccccat cgagaggcct tgagtggctg ggaaggacat actacaggtc caagtggtct  180
actgattatg cagcatctgt gaaaagtcga ataaccatca acccagacac atccaagaac  240
cagctctccc tgcagttaaa ctctgtgact cccgaggaca cggctgtgta ttactgtgca  300
agaacgtggg tgggtaacgt ggacgtctgg ggccaaggaa ccctggtcac cgtctcgagc  360
```

| SEQ ID NO: 219 | moltype = DNA length = 360 |
|---|---|
| FEATURE | Location/Qualifiers |
| misc_feature | 1..360 |
| | note = ADT1-4-95 Variable Heavy DNA |
| source | 1..360 |

```
                            mol_type = genomic DNA
                            organism = Homo sapiens
SEQUENCE: 219
gaggtacagc tgcagcagtc aggtccagga ctggtgaagc cctcgcagac cctctcactc  60
acctgtgcca tctccgggga cagtgtctcc agcaaaagtg ctgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctccc tgcagttaaa ctctgtgact cccgaggaca cggctgtgta ttactgtgca 300
agaacgtggg tgggttatgc cgacgtctgg ggccaaggaa ccctggtcac cgtctcgagc 360

SEQ ID NO: 220             moltype = DNA   length = 360
FEATURE                    Location/Qualifiers
misc_feature               1..360
                            note = ADT1-4-1 Variable Heavy DNA
source                     1..360
                            mol_type = genomic DNA
                            organism = Homo sapiens
SEQUENCE: 220
gaggtacagc tgcagcagtc aggtccagga ctggtgaagc cctcgcagac cctctcactc  60
acctgtgcca tctccgggga cagtgtctcc agcaaaagtg ctgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctccc tgcagttaaa ctctgtgact cccgaggaca cggctgtgta ttactgtgca 300
agaacgtggg tgggttatgc cgacgtctgg ggccaaggaa ccctggtcac cgtctcgagc 360

SEQ ID NO: 221             moltype = DNA   length = 360
FEATURE                    Location/Qualifiers
misc_feature               1..360
                            note = ADT1-4-6 Variable Heavy DNA
source                     1..360
                            mol_type = genomic DNA
                            organism = Homo sapiens
SEQUENCE: 221
gaggtacagc tgcagcagtc aggtccagga ctggtgaagc cctcgcagac cctctcactc  60
acctgtgcca tctccgggga cagtgtctcc agcaaaagtg ctgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctccc tgcagttaaa ctctgtgact cccgaggaca cggctgtgta ttactgtgca 300
agaacgtggg ccggttatcc cgacgtctgg ggccaaggaa ccctggtcac cgtctcgagc 360

SEQ ID NO: 222             moltype = DNA   length = 360
FEATURE                    Location/Qualifiers
misc_feature               1..360
                            note = ADT1-4-138 Variable Heavy DNA
source                     1..360
                            mol_type = genomic DNA
                            organism = Homo sapiens
SEQUENCE: 222
gaggtacagc tgcagcagtc aggtccagga ctggtgaagc cctcgcagac cctctcactc  60
acctgtgcca tctccgggga cagtgtctcc agcaaaagtg ctgcttggaa ctggatcagg 120
cagtccccat cgagaggcct tgagtggctg ggaaggacat actacaggtc caagtggtct 180
actgattatg cagcatctgt gaaaagtcga ataaccatca acccagacac atccaagaac 240
cagctctccc tgcagttaaa ctctgtgact cccgaggaca cggctgtgta ttactgtgca 300
agaacgtggg ccgactatgt ggacgtctgg ggccaaggaa ccctggtcac cgtctcgagc 360

SEQ ID NO: 223             moltype = DNA   length = 330
FEATURE                    Location/Qualifiers
misc_feature               1..330
                            note = ADT1-4 Variable Light DNA
source                     1..330
                            mol_type = genomic DNA
                            organism = Homo sapiens
SEQUENCE: 223
gctagcgaca tccagatgac ccagtcccct cccgccctgt ctgcatctgt gggagacaga  60
gtcaccatca cttgccgggc cagtcaagat attaatgact ggttggcctg gtatcagcat 120
aaacctggga agcccctaa gctcctgatc tatgatgcct ccagtttgga aagtggggtc 180
ccatcaaggt tcagcggcag tggatctggg acagaattca ctctcaccat cagcagcctg 240
cagcctgatg attttgcaac ttactactgt caacagagtt acagtacccc tcaggtcact 300
tttggccagg ggacacgact ggagatcaaa                                   330

SEQ ID NO: 224             moltype = DNA   length = 324
FEATURE                    Location/Qualifiers
misc_feature               1..324
                            note = ADT1-4-105 Variable Light DNA
source                     1..324
                            mol_type = genomic DNA
                            organism = Homo sapiens
SEQUENCE: 224
gacatccaga tgacccagtc cctcccgcc ctgtctgcat ctgtgggaga cagagtcacc  60
```

```
atcacttgcc gggccagtca agatattaat gactggttgg cctggtatca gcataaacct    120
gggaaagccc ctaagctcct gatctatgat gcctccagtt tggaaagtgg ggtcccatta    180
aggttcagcg gcagtggatc tgggacagaa ttcactctca ccatcagcag cctgcagcct    240
gatgattttg caacttacta ctgtcaacag aagtacagta cccctcagat cacttttggc    300
caggggacac gactggagat caaa                                           324

SEQ ID NO: 225          moltype = DNA  length = 324
FEATURE                 Location/Qualifiers
misc_feature            1..324
                        note = ADT1-4-107 Variable Light DNA
source                  1..324
                        mol_type = genomic DNA
                        organism = Homo sapiens
SEQUENCE: 225
gacatccaga tgacccagtc ccctcccgcc ctgtctgcat ctgtgggaga cagagtcacc     60
atcacttgcc gggccagtca agatattaat gactggttgg cctggtatca gcataaacct    120
gggaaagccc ctaagctcct gatctatgat gcctccagtt tggaaagtgg ggtcccatta    180
aggttcagcg gcagtggatc tgggacagaa ttcactctca ccatcagcag cctgcagcct    240
gatgattttg caacttacta ctgtcaacag cgctacagta cccctcagat cacttttggc    300
caggggacac gactggagat caaa                                           324

SEQ ID NO: 226          moltype = DNA  length = 324
FEATURE                 Location/Qualifiers
misc_feature            1..324
                        note = ADT1-4-110 Variable Light DNA
source                  1..324
                        mol_type = genomic DNA
                        organism = Homo sapiens
SEQUENCE: 226
gacatccaga tgacccagtc ccctcccgcc ctgtctgcat ctgtgggaga cagagtcacc     60
atcacttgcc gggccagtca agatattaat gactggttgg cctggtatca gcataaacct    120
gggaaagccc ctaagctcct gatctatgat gcctccagtt tggaaagtgg ggtcccatta    180
aggttcagcg gcagtggatc tgggacagaa ttcactctca ccatcagcag cctgcagcct    240
gatgattttg caacttacta ctgtcaacag aagtacagta cccctcaggt cacttttggc    300
gccgggacac gactggagat caaa                                           324

SEQ ID NO: 227          moltype = DNA  length = 324
FEATURE                 Location/Qualifiers
misc_feature            1..324
                        note = ADT1-4-112 Variable Light DNA
source                  1..324
                        mol_type = genomic DNA
                        organism = Homo sapiens
SEQUENCE: 227
gacatccaga tgacccagtc ccctcccgcc ctgtctgcat ctgtgggaga cagagtcacc     60
atcacttgcc gggccagtca agatattaat gactggttgg cctggtatca gcataaacct    120
gggaaagccc ctaagctcct gatctatgat gcctccagtt tggaaagtgg ggtcccatta    180
aggttcagcg gcagtggatc tgggacagaa ttcactctca ccatcagcag cctgcagcct    240
gatgattttg caacttacta ctgtcaacag aagtacagtc agcctcaggt cacttttggc    300
caggggacac gactggagat caaa                                           324

SEQ ID NO: 228          moltype = DNA  length = 324
FEATURE                 Location/Qualifiers
misc_feature            1..324
                        note = ADT1-4-117 Variable Light DNA
source                  1..324
                        mol_type = genomic DNA
                        organism = Homo sapiens
SEQUENCE: 228
gacatccaga tgacccagtc ccctcccgcc ctgtctgcat ctgtgggaga cagagtcacc     60
atcacttgcc gggccagtca agatattaat gactggttgg cctggtatca gcataaacct    120
gggaaagccc ctaagctcct gatctatgat gcctccagtt tggaaagtgg ggtcccatta    180
aggttcagcg gcagtggatc tgggacagaa ttcactctca ccatcagcag cctgcagcct    240
gatgattttg caacttacta ctgtcaacag cgctacagta ccctcgcgt cacttttggc     300
caggggacac gactggagat caaa                                           324

SEQ ID NO: 229          moltype = DNA  length = 324
FEATURE                 Location/Qualifiers
misc_feature            1..324
                        note = ADT1-4-19 Variable Light DNA
source                  1..324
                        mol_type = genomic DNA
                        organism = Homo sapiens
SEQUENCE: 229
gacatccaga tgacccagtc ccctcccgcc ctgtctgcat ctgtgggaga cagagtcacc     60
atcacttgcc gggccagtca agatattaat gactggttgg cctggtatca gcataaacct    120
gggaaagccc ctaagctcct gatctatgat gcctccagtt tggaaagtgg ggtcccatta    180
aggttcagcg gcagtggatc tgggacagaa ttcactctca ccatcagcag cctgcagcct    240
gatgattttg caacttacta ctgtcaacag aagtacagta cccctaaggt cacttttggc    300
```
caggggacac gactggagat caaa 324

SEQ ID NO: 230        moltype = DNA   length = 324
FEATURE               Location/Qualifiers
misc_feature          1..324
                      note = ADT1-4-21 Variable Light DNA
source                1..324
                      mol_type = genomic DNA
                      organism = Homo sapiens
SEQUENCE: 230
gacatccaga tgacccagtc ccctcccgcc ctgtctgcat ctgtgggaga cagagtcacc   60
atcacttgcc gggccagtca agatattaat gactggttgg cctggtatca gcataaacct  120
gggaaagccc ctaagctcct gatctatgat gcctccagtt tggaaagtgg ggtcccatta  180
aggttcagcg gcagtggatc tgggacagaa ttcactctca ccatcagcag cctgcagcct  240
gatgattttg caacttacta ctgtcaacag aagtacagta ccccttgggt cacttttggc  300
caggggacac gactggagat caaa                                         324

SEQ ID NO: 231        moltype = DNA   length = 324
FEATURE               Location/Qualifiers
misc_feature          1..324
                      note = ADT1-4-31 Variable Light DNA
source                1..324
                      mol_type = genomic DNA
                      organism = Homo sapiens
SEQUENCE: 231
gacatccaga tgacccagtc ccctcccgcc ctgtctgcat ctgtgggaga cagagtcacc   60
atcacttgcc gggccagtca agatattaat gactggttgg cctggtatca gcataaacct  120
gggaaagccc ctaagctcct gatctatgat gcctccagtt tggaaagtgg ggtcccatta  180
aggttcagcg gcagtggatc tgggacagaa ttcactctca ccatcagcag cctgcagcct  240
gatgattttg caacttacta ctgtcaacag cgctacagta ccccctcccgt cacttttggc  300
caggggacac gactggagat caaa                                         324

SEQ ID NO: 232        moltype = DNA   length = 324
FEATURE               Location/Qualifiers
misc_feature          1..324
                      note = ADT1-4-139 Variable Light DNA
source                1..324
                      mol_type = genomic DNA
                      organism = Homo sapiens
SEQUENCE: 232
gacatccaga tgacccagtc ccctcccgcc ctgtctgcat ctgtgggaga cagagtcacc   60
atcacttgcc gggccagtca agatattaat gactggttgg cctggtatca gcataaacct  120
gggaaagccc ctaagctcct gatctatgat gcctccagtt tggaaagtgg ggtcccatta  180
aggttcagcg gcagtggatc tgggacagaa ttcactctca ccatcagcag cctgcagcct  240
gatgattttg caacttacta ctgtcaacag ggctacagta ccccctcagct gacttttggc  300
caggggacac gactggagat caaa                                         324

SEQ ID NO: 233        moltype = DNA   length = 324
FEATURE               Location/Qualifiers
misc_feature          1..324
                      note = ADT1-4-4 Variable Light DNA
source                1..324
                      mol_type = genomic DNA
                      organism = Homo sapiens
SEQUENCE: 233
gacatccaga tgacccagtc ccctcccgcc ctgtctgcat ctgtgggaga cagagtcacc   60
atcacttgcc gggccagtca agatattaat gactggttgg cctggtatca gcataaacct  120
gggaaagccc ctaagctcct gatctatgat gcctccagtt tggaaagtgg ggtcccatta  180
aggttcagcg gcagtggatc tgggacagaa ttcactctca ccatcagcag cctgcagcct  240
gatgattttg caacttacta ctgtcaacag aagtacagta ccccttgggt cacttttggc  300
caggggacac gactggagat caaa                                         324

SEQ ID NO: 234        moltype = DNA   length = 324
FEATURE               Location/Qualifiers
misc_feature          1..324
                      note = ADT1-4-143 Variable Light DNA
source                1..324
                      mol_type = genomic DNA
                      organism = Homo sapiens
SEQUENCE: 234
gacatccaga tgacccagtc ccctcccgcc ctgtctgcat ctgtgggaga cagagtcacc   60
atcacttgcc gggccagtca agatattaat gactggttgg cctggtatca gcataaacct  120
gggaaagccc ctaagctcct gatctatgat gcctccagtt tggaaagtgg ggtcccatta  180
aggttcagcg gcagtggatc tgggacagaa ttcactctca ccatcagcag cctgcagcct  240
gatgattttg caacttacta ctgtcaacag cgctacagta cccaccaggt cacttttggc  300
caggggacac gactggtgat caaa                                         324

SEQ ID NO: 235        moltype = DNA   length = 324
FEATURE               Location/Qualifiers

```
misc_feature               1..324
                           note = ADT1-4-53 Variable Light DNA
source                     1..324
                           mol_type = genomic DNA
                           organism = Homo sapiens
SEQUENCE: 235
gacatccaga tgacccagtc ccctcccgcc ctgtctgcat ctgtgggaga cagagtcacc    60
atcacttgcc gggccagtca agatattaat gactggttgg cctggtatca gcataaacct   120
gggaaagccc ctaagctcct gatctatgat gcctccagtt tggaaagtgg ggtcccatta   180
aggttcagcg gcagtggatc tgggacagaa ttcactctca ccatcagcag cctgcagcct   240
gatgattttg caacttacta ctgtcaacag aagtacagta cccctcagct gacttttggc   300
caggggacac gactggagat caaa                                          324

SEQ ID NO: 236             moltype = DNA  length = 324
FEATURE                    Location/Qualifiers
misc_feature               1..324
                           note = ADT1-4-173 Variable Light DNA
source                     1..324
                           mol_type = genomic DNA
                           organism = Homo sapiens
SEQUENCE: 236
gacatccaga tgacccagtc ccctcccgcc ctgtctgcat ctgtgggaga cagagtcacc    60
atcacttgcc gggccagtca agatattaat gactggttgg cctggtatca gcataaacct   120
gggaaagccc ctaagctcct gatctatgat gcctccagtt tggaaagtgg ggtcccatta   180
aggttcagcg gcagtggatc tgggacagaa ttcactctca ccatcagcag cctgcagcct   240
gatgattttg caacttacta ctgtcaacag aagtacagtg cccctcaggt cacttttggc   300
caggggacac gactggagat caaa                                          324

SEQ ID NO: 237             moltype = DNA  length = 324
FEATURE                    Location/Qualifiers
misc_feature               1..324
                           note = ADT1-4-2 Variable Light DNA
source                     1..324
                           mol_type = genomic DNA
                           organism = Homo sapiens
SEQUENCE: 237
gacatccaga tgacccagtc ccctcccgcc ctgtctgcat ctgtgggaga cagagtcacc    60
atcacttgcc gggccagtca agatattaat gactggttgg cctggtatca gcataaacct   120
gggaaagccc ctaagctcct gatctatgat gcctccagtt tggaaagtgg ggtcccatta   180
aggttcagcg gcagtggatc tgggacagaa ttcactctca ccatcagcag cctgcagcct   240
gatgattttg caacttacta ctgtcaacag aagtacagtg cccctcaggt cacttttggc   300
caggggacac gactggagat caaa                                          324

SEQ ID NO: 238             moltype = DNA  length = 324
FEATURE                    Location/Qualifiers
misc_feature               1..324
                           note = ADT1-4-8 Variable Light DNA
source                     1..324
                           mol_type = genomic DNA
                           organism = Homo sapiens
SEQUENCE: 238
gacatccaga tgacccagtc ccctcccgcc ctgtctgcat ctgtgggaga cagagtcacc    60
atcacttgcc gggccagtca agatattaat gactggttgg cctggtatca gcataaacct   120
gggaaagccc ctaagctcct gatctatgat gcctccagtt tggaaagtgg ggtcccatta   180
aggttcagcg gcagtggatc tgggacagaa ttcactctca ccatcagcag cctgcagcct   240
gatgattttg caacttacta ctgtcaacag aagtacagtg cccctcaggt cacttttggc   300
caggggacac gactggagat caaa                                          324

SEQ ID NO: 239             moltype = DNA  length = 324
FEATURE                    Location/Qualifiers
misc_feature               1..324
                           note = ADT1-4-82 Variable Light DNA
source                     1..324
                           mol_type = genomic DNA
                           organism = Homo sapiens
SEQUENCE: 239
gacatccaga tgacccagtc ccctcccgcc ctgtctgcat ctgtgggaga cagagtcacc    60
atcacttgcc gggccagtca agatattaat gactggttgg cctggtatca gcataaacct   120
gggaaagccc ctaagctcct gatctatgat gcctccagtt tggaaagtgg ggtcccatta   180
aggttcagcg gcagtggatc tgggacagaa ttcactctca ccatcagcag cctgcagcct   240
gatgattttg caacttacta ctgtcaacag cgctacagta cccctcagat cacttttggc   300
caggggacac gactggagat caaa                                          324

SEQ ID NO: 240             moltype = DNA  length = 324
FEATURE                    Location/Qualifiers
misc_feature               1..324
                           note = ADT1-4-83 Variable Light DNA
source                     1..324
                           mol_type = genomic DNA
```

-continued

```
                        organism = Homo sapiens
SEQUENCE: 240
gacatccaga tgacccagtc ccctcccgcc ctgtctgcat ctgtgggaga cagagtcacc    60
atcacttgcc gggccagtca agatattaat gactggttgg cctggtatca gcataaacct   120
gggaaagccc ctaagctcct gatctatgat gcctccagtt tggaaagtgg ggtcccatta   180
aggttcagcg gcagtggatc tgggacagaa ttcactctca ccatcagcag cctgcagcct   240
gatgattttg caacttacta ctgtcaacag aagtacagtg agcctcaggt cacttttggc   300
caggggacac gactggagat caaa                                          324

SEQ ID NO: 241          moltype = DNA  length = 324
FEATURE                 Location/Qualifiers
misc_feature            1..324
                        note = ADT1-4-3 Variable Light DNA
source                  1..324
                        mol_type = genomic DNA
                        organism = Homo sapiens
SEQUENCE: 241
gacatccaga tgacccagtc ccctcccgcc ctgtctgcat ctgtgggaga cagagtcacc    60
atcacttgcc gggccagtca agatattaat gactggttgg cctggtatca gcataaacct   120
gggaaagccc ctaagctcct gatctatgat gcctccagtt tggaaagtgg ggtcccatta   180
aggttcagcg gcagtggatc tgggacagaa ttcactctca ccatcagcag cctgcagcct   240
gatgattttg caacttacta ctgtcaacag aagtacagta cccctgaggt cacttttggc   300
caggggacac gactggagat caaa                                          324

SEQ ID NO: 242          moltype = DNA  length = 324
FEATURE                 Location/Qualifiers
misc_feature            1..324
                        note = ADT1-4-84 Variable Light DNA
source                  1..324
                        mol_type = genomic DNA
                        organism = Homo sapiens
SEQUENCE: 242
gacatccaga tgacccagtc ccctcccgcc ctgtctgcat ctgtgggaga cagagtcacc    60
atcacttgcc gggccagtca agatattaat gactggttgg cctggtatca gcataaacct   120
gggaaagccc ctaagctcct gatctatgat gcctccagtt tggaaagtgg ggtcccatta   180
aggttcagcg gcagtggatc tgggacagaa ttcactctca ccatcagcag cctgcagcct   240
gatgattttg caacttacta ctgtcaacag aagtacagtg accctcaggt cacttttggc   300
caggggacac gactggagat caaa                                          324

SEQ ID NO: 243          moltype = DNA  length = 324
FEATURE                 Location/Qualifiers
misc_feature            1..324
                        note = ADT1-4-86 Variable Light DNA
source                  1..324
                        mol_type = genomic DNA
                        organism = Homo sapiens
SEQUENCE: 243
gacatccaga tgacccagtc ccctcccgcc ctgtctgcat ctgtgggaga cagagtcacc    60
atcacttgcc gggccagtca agatattaat gactggttgg cctggtatca gcataaacct   120
gggaaagccc ctaagctcct gatctatgat gcctccagtt tggaaagtgg ggtcccatta   180
aggttcagcg gcagtggatc tgggacagaa ttcactctca ccatcagcag cctgcagcct   240
gatgattttg caacttacta ctgtcaacag aagtacagtg agcctcaggt cacttttggc   300
caggggacac gactggagat caaa                                          324

SEQ ID NO: 244          moltype = DNA  length = 324
FEATURE                 Location/Qualifiers
misc_feature            1..324
                        note = ADT1-4-95 Variable Light DNA
source                  1..324
                        mol_type = genomic DNA
                        organism = Homo sapiens
SEQUENCE: 244
gacatccaga tgacccagtc ccctcccgcc ctgtctgcat ctgtgggaga cagagtcacc    60
atcacttgcc gggccagtca agatattaat gactggttgg cctggtatca gcataaacct   120
gggaaagccc ctaagctcct gatctatgat gcctccagtt tggaaagtgg ggtcccatta   180
aggttcagcg gcagtggatc tgggacagaa ttcactctca ccatcagcag cctgcagcct   240
gatgattttg caacttacta ctgtcaacag aagtacagta cccctcaggt cacttttggc   300
agcgggacac gactggagat caaa                                          324

SEQ ID NO: 245          moltype = DNA  length = 324
FEATURE                 Location/Qualifiers
misc_feature            1..324
                        note = ADT1-4-1 Variable Light DNA
source                  1..324
                        mol_type = genomic DNA
                        organism = Homo sapiens
SEQUENCE: 245
gacatccaga tgacccagtc ccctcccgcc ctgtctgcat ctgtgggaga cagagtcacc    60
atcacttgcc gggccagtca agatattaat gactggttgg cctggtatca gcataaacct   120
```

```
gggaaagccc ctaagctcct gatctatgat gcctccagtt tggaaagtgg ggtcccatta    180
aggttcagcg gcagtggatc tgggacagaa ttcactctca ccatcagcag cctgcagcct    240
gatgattttg caacttacta ctgtcaacag cgctacagta cccctatcgt cacttttggc    300
caggggacac gactggagat caaa                                           324

SEQ ID NO: 246          moltype = DNA  length = 324
FEATURE                 Location/Qualifiers
misc_feature            1..324
                        note = ADT1-4-6 Variable Light DNA
source                  1..324
                        mol_type = genomic DNA
                        organism = Homo sapiens
SEQUENCE: 246
gacatccaga tgacccagtc ccctcccgcc ctgtctgcat ctgtgggaga cagagtcacc    60
atcacttgcc gggccagtca agatattaat gactggttgg cctggtatca gcataaacct    120
gggaaagccc ctaagctcct gatctatgat gcctccagtt tggaaagtgg ggtcccatta    180
aggttcagcg gcagtggatc tgggacagaa ttcactctca ccatcagcag cctgcagcct    240
gatgattttg caacttacta ctgtcaacag aagtacaaga cccctcaggt cacttttggc    300
caggggacac gactggagat caaa                                           324

SEQ ID NO: 247          moltype = DNA  length = 324
FEATURE                 Location/Qualifiers
misc_feature            1..324
                        note = ADT1-4-138 Variable Light DNA
source                  1..324
                        mol_type = genomic DNA
                        organism = Homo sapiens
SEQUENCE: 247
gacatccaga tgacccagtc ccctcccgcc ctgtctgcat ctgtgggaga cagagtcacc    60
atcacttgcc gggccagtca agatattaat gactggttgg cctggtatca gcataaacct    120
gggaaagccc ctaagctcct gatctatgat gcctccagtt tggaaagtgg ggtcccatca    180
aggttcagcg gcagtggatc tgggacagaa ttcactctca ccatcagcag cctgcagcct    240
gatgattttg caacttacta ctgtcaacag cgctacagta ccgaccaggt cacttttggc    300
caggggacac gactggagat caaa                                           324

SEQ ID NO: 248          moltype = DNA  length = 354
FEATURE                 Location/Qualifiers
misc_feature            1..354
                        note = ADT1-7 Variable Heavy DNA
source                  1..354
                        mol_type = genomic DNA
                        organism = Homo sapiens
SEQUENCE: 248
caggtgcagc tggtggagtc tgggggaggc ttggtcaagc ctggagggtc cctgagactc    60
tcctgtgcag cctctggatt caccttcagt gactactaca tgagctggat ccgccaggct    120
ccagggaagg ggctggagtg ggtttcatac attagtagta gtggtagtac catatactac    180
gcagactctg tgaagggccg attcaccatc tccagggaca cgccaagaa ctcactgtat    240
ctgcaaatga acagcctgag agccgaggac acggctgtgt attactgtgc aagggtggac    300
tacgctgatg catttgatat ctggggccag ggcaccctgg tcaccgtctc gagc          354

SEQ ID NO: 249          moltype = DNA  length = 354
FEATURE                 Location/Qualifiers
misc_feature            1..354
                        note = ADT1-7-10 Variable Heavy DNA
source                  1..354
                        mol_type = genomic DNA
                        organism = Homo sapiens
SEQUENCE: 249
gaggtgcagc tggtggagtc tgggggaggc ttggtcaagc ctggagggtc cctgagactc    60
tcctgtgcag cctctggatt caccttcagt gactactaca tgagctggat ccgccaggct    120
ccagggaagg ggctggagtg ggtttcatac attagtagta gtggtagtac catatactac    180
gcagactctg tgaagggccg attcaccatc tccagggaca cgccaagaa ctcactgtat    240
ctgcaaatga acagcctgag agccgaggac acggctgtgt attactgtgc aagggacgac    300
tacaacgatg catttgatat ctggggccag ggcaccctgg tcaccgtctc gagc          354

SEQ ID NO: 250          moltype = DNA  length = 354
FEATURE                 Location/Qualifiers
misc_feature            1..354
                        note = ADT1-7-15 Variable Heavy DNA
source                  1..354
                        mol_type = genomic DNA
                        organism = Homo sapiens
SEQUENCE: 250
gaggtgcagc tggtggagtc tgggggaggc ttggtcaagc ctggagggtc cctgagactc    60
tcctgtgcag cctctggatt caccttcagt gactactaca tgagctggat ccgccaggct    120
ccagggaagg ggctggagtg ggtttcatac attagtagta gtggtagtac catatactac    180
gcagactctg tgaagggccg attcaccatc tccagggaca cgccaagaa ctcactgtat    240
ctgcaaatga acagcctgag agccgaggac acggctgtgt attactgtgc aagggacgac    300
tacaacgatg catttgatat ctggggccag ggcaccctgg tcaccgtctc gagc          354
```

| SEQ ID NO: 251 | moltype = DNA   length = 354 |
| --- | --- |
| FEATURE | Location/Qualifiers |
| misc_feature | 1..354 |
| | note = ADT1-7-17 Variable Heavy DNA |
| source | 1..354 |
| | mol_type = genomic DNA |
| | organism = Homo sapiens |

SEQUENCE: 251

```
gaggtgcagc tggtggagtc tgggggaggc ttggtcaagc ctggagggtc cctgagactc   60
tcctgtgcag cctctggatt caccttcagt gactactaca tgagctggat ccgccaggct  120
ccagggaagg ggctggagtg ggtttcatac attagtagta gtggtagtac catatactac  180
gcagactctg tgaagggccg attcaccatc tccagggaca acgccaagaa ctcactgtat  240
ctgcaaatga acagcctgag agccgaggac acggctgtgt attactgtgc aaggatcgac  300
tacgaggatg catttgatat ctggggccag ggcaccctgg tcaccgtctc gagc         354
```

| SEQ ID NO: 252 | moltype = DNA   length = 354 |
| --- | --- |
| FEATURE | Location/Qualifiers |
| misc_feature | 1..354 |
| | note = ADT1-7-18 Variable Heavy DNA |
| source | 1..354 |
| | mol_type = genomic DNA |
| | organism = Homo sapiens |

SEQUENCE: 252

```
gaggtgcagc tggtggagtc tgggggaggc ttggtcaagc ctggagggtc cctgagactc   60
tcctgtgcag cctctggatt caccttcagt gactactaca tgagctggat ccgccaggct  120
ccagggaagg ggctggagtg ggtttcatac attagtagta gtggtagtac catatactac  180
gcagactctg tgaagggccg attcaccatc tccagggaca acgccaagaa ctcactgtat  240
ctgcaaatga acagcctgag agccgaggac acggctgtgt attactgtgc aagggtgagc  300
tacgacgatg catttgatat ctggggccag ggcaccctgg tcaccgtctc gagc         354
```

| SEQ ID NO: 253 | moltype = DNA   length = 354 |
| --- | --- |
| FEATURE | Location/Qualifiers |
| misc_feature | 1..354 |
| | note = ADT1-7-19 Variable Heavy DNA |
| source | 1..354 |
| | mol_type = genomic DNA |
| | organism = Homo sapiens |

SEQUENCE: 253

```
gaggtgcagc tggtggagtc tgggggaggc ttggtcaagc ctggagggtc cctgagactc   60
tcctgtgcag cctctggatt caccttcagt gactactaca tgagctggat ccgccaggct  120
ccagggaagg ggctggagtg ggtttcatac attagtagta gtggtagtac catatactac  180
gcagactctg tgaagggccg attcaccatc tccagggaca acgccaagaa ctcactgtat  240
ctgcaaatga acagcctgag agccgaggac acggctgtgt attactgtgc aaggatcgac  300
tacgaggatg catttgatat ctggggccag ggcaccctgg tcaccgtctc gagc         354
```

| SEQ ID NO: 254 | moltype = DNA   length = 354 |
| --- | --- |
| FEATURE | Location/Qualifiers |
| misc_feature | 1..354 |
| | note = ADT1-7-20 Variable Heavy DNA |
| source | 1..354 |
| | mol_type = genomic DNA |
| | organism = Homo sapiens |

SEQUENCE: 254

```
gaggtgcagc tggtggagtc tgggggaggc ttggtcaagc ctggagggtc cctgagactc   60
tcctgtgcag cctctggatt caccttcagt gactactaca tgagctggat ccgccaggct  120
ccagggaagg ggctggagtg ggtttcatac attagtagta gtggtagtac catatactac  180
gcagactctg tgaagggccg attcaccatc tccagggaca acgccaagaa ttcactgtat  240
ctgcaaatga acagcctgag agccgaggac acggctgtgt attactgtgc aagggtggac  300
taccaggagg catttgatat ctggggccag ggcaccctgg tcaccgtctc gagc         354
```

| SEQ ID NO: 255 | moltype = DNA   length = 354 |
| --- | --- |
| FEATURE | Location/Qualifiers |
| misc_feature | 1..354 |
| | note = ADT1-7-22 Variable Heavy DNA |
| source | 1..354 |
| | mol_type = genomic DNA |
| | organism = Homo sapiens |

SEQUENCE: 255

```
gaggtgcagc tggtggagtc tgggggaggc ttggtcaagc ctggagggtc cctgagactc   60
tcctgtgcag cctctggatt caccttcagt gactactaca tgagctggat ccgccaggct  120
ccagggaagg ggctggagtg ggtttcatac attagtagta gtggtagtac catatactac  180
gcagactctg tgaagggccg attcaccatc tccagggaca acgccaagaa ctcactgtat  240
ctgcaaatga acagcctgag agccgaggac acggctgtgt attactgtgc aagggacgac  300
tacaacgatg catttgatat ctggggccag ggcaccctgg tcaccgtctc gagc         354
```

| SEQ ID NO: 256 | moltype = DNA   length = 354 |
| --- | --- |
| FEATURE | Location/Qualifiers |
| misc_feature | 1..354 |

```
                        note = ADT1-7-23 Variable Heavy DNA
source                  1..354
                        mol_type = genomic DNA
                        organism = Homo sapiens
SEQUENCE: 256
gaggtgcagc tggtggagtc tgggggaggc ttggtcaagc ctggagggtc cctgagactc    60
tcctgtgcag cctctggatt caccttcagt gactactaca tgagctggat ccgccaggct   120
ccagggaagg ggctggagtg ggtttcatac attagtagta gtggtagtac catatactac   180
gcagactctg tgaagggccg attcaccatc tccagggaca acgccaagaa ctcactgtat   240
ctgcaaatga acagcctgag agccgaggac acggctgtgt attactgtgc aagggtggac   300
tacaacgagg catttgatat ctggggccag ggcaccctgg tcaccgtctc gagc         354

SEQ ID NO: 257          moltype = DNA   length = 354
FEATURE                 Location/Qualifiers
misc_feature            1..354
                        note = ADT1-7-42 Variable Heavy DNA
source                  1..354
                        mol_type = genomic DNA
                        organism = Homo sapiens
SEQUENCE: 257
gaggtgcagc tggtggagtc tgggggaggc ttggtcaagc ctggagggtc cctgagactc    60
tcctgtgcag cctctggatt caccttcagt gactactaca tgagctggat ccgccaggct   120
ccagggaagg ggctggagtg ggtttcatac attagtagta gtggtagtac catatactac   180
gcagactctg tgaagggccg attcaccatc tccagggaca acgccaagaa ctcactgtat   240
ctgcaaatga acagcctgag agccgaggac acggctgtgt attactgtgc aagggacgac   300
tacgaggatg catttgatat ctggggccag ggcaccctgg tcaccgtctc gagc         354

SEQ ID NO: 258          moltype = DNA   length = 354
FEATURE                 Location/Qualifiers
misc_feature            1..354
                        note = ADT1-7-3 Variable Heavy DNA
source                  1..354
                        mol_type = genomic DNA
                        organism = Homo sapiens
SEQUENCE: 258
gaggtgcagc tggtggagtc tgggggaggc ttggtcaagc ctggagggtc cctgagactc    60
tcctgtgcag cctctggatt caccttcagt gactactaca tgagctggat ccgccaggct   120
ccagggaagg ggctggagtg ggtttcatac attagtagta gtggtagtac catatactac   180
gcagactctg tgaagggccg attcaccatc tccagggaca acgccaagaa ctcactgtat   240
ctgcaaatga acagcctgag agccgaggac acggctgtgt attactgtgc aagggtgagc   300
tacgctgagg catttgatat ctggggccag ggcaccctgg tcaccgtctc gagc         354

SEQ ID NO: 259          moltype = DNA   length = 354
FEATURE                 Location/Qualifiers
misc_feature            1..354
                        note = ADT1-7-61 Variable Heavy DNA
source                  1..354
                        mol_type = genomic DNA
                        organism = Homo sapiens
SEQUENCE: 259
gaggtgcagc tggtggagtc tgggggaggc ttggtcaagc ctggagggtc cctgagactc    60
tcctgtgcag cctctggatt caccttcagt gactactaca tgagctggat ccgccaggct   120
ccagggaagg ggctggagtg ggtttcatac attagtagta gtggtagtac catatactac   180
gcagactctg tgaagggccg attcaccatc tccagggaca acgccaagaa ctcactgtat   240
ctgcaaatga acagcctgag agccgaggac acggctgtgt attactgtgc aagggacgac   300
tacgacgatg catttgatat ctggggccag ggcaccctgg tcaccgtctc gagc         354

SEQ ID NO: 260          moltype = DNA   length = 327
FEATURE                 Location/Qualifiers
misc_feature            1..327
                        note = ADT1-7 Variable Light DNA
source                  1..327
                        mol_type = genomic DNA
                        organism = Homo sapiens
SEQUENCE: 260
gctagcgaca tccagatgac ccagtctcca tcctccctgt ctgcatctgt aggagacaga    60
gtcaccatcg cttgccgggc aggtcagagc attggcacct atttaaattg gtatcagcag   120
aaaccaggga aagcccctaa actcctgatc tatgttgcat ccagtttgca aagtggggtc   180
ccgtcacggt tcagtggcag tggatctggg acagaattca ctctcaccat cagcagtctg   240
caacctgaag attttgcaac ttactactgt caacagagtt acagtaccct cctcactttc   300
ggcagaggga ccaaggtgga aatcaaa                                       327

SEQ ID NO: 261          moltype = DNA   length = 321
FEATURE                 Location/Qualifiers
misc_feature            1..321
                        note = ADT1-7-10 Variable Light DNA
source                  1..321
                        mol_type = genomic DNA
                        organism = Homo sapiens
```

-continued

```
SEQUENCE: 261
gacatccaga tgacccagtc tccatcctcc ctgtctgcat ctgtaggaga cagagtcacc    60
atcgcttgcc gggcaggtca gagcattggc acctatttaa attggtatca gcagaaacca   120
gggaaagccc ctaaactcct gatctatgtt gcatccagtt tgcaaagtgg ggtcccgtca   180
cggttcagtg gcagtggatc tgggacagaa ttcactctca ccatcagcag tctgcaacct   240
gaagattttg caacttacta ctgtcaacag accgccagta ccctcctcac tttcggcaga   300
gggaccaagg tggaaatcaa a                                             321

SEQ ID NO: 262        moltype = DNA   length = 321
FEATURE               Location/Qualifiers
misc_feature          1..321
                      note = ADT1-7-15 Variable Light DNA
source                1..321
                      mol_type = genomic DNA
                      organism = Homo sapiens
SEQUENCE: 262
gacatccaga tgacccagtc tccatcctcc ctgtctgcat ctgtaggaga cagagtcacc    60
atcgcttgcc gggcaggtca gagcattggc acctatttaa attggtatca gcagaaacca   120
gggaaagccc ctaaactcct gatctatgtt gcatccagtt tgcaaagtgg ggtcccgtca   180
cggttcagtg gcagtggatc tgggacagaa ttcactctca ccatcagcag tctgcaacct   240
gaagattttg caacttacta ctgtcaacag agtgccgaca ccctcctcac tttcggcaga   300
gggaccaagg tggaaatcaa a                                             321

SEQ ID NO: 263        moltype = DNA   length = 321
FEATURE               Location/Qualifiers
misc_feature          1..321
                      note = ADT1-7-17 Variable Light DNA
source                1..321
                      mol_type = genomic DNA
                      organism = Homo sapiens
SEQUENCE: 263
gacatccaga tgacccagtc tccatcctcc ctgtctgcat ctgtaggaga cagagtcacc    60
atcgcttgcc gggcaggtca gagcattggc acctatttaa attggtatca gcagaaacca   120
gggaaagccc ctaaactcct gatctatgtt gcatccagtt tgcaaagtgg ggtcccgtca   180
cggttcagtg gcagtggatc tgggacagaa ttcactctca ccatcagcag tctgcaacct   240
gaagattttg caacttacta ctgtcaacag agtggcagtg agctcctcac tttcggcaga   300
gggaccaagg tggaaatcaa a                                             321

SEQ ID NO: 264        moltype = DNA   length = 321
FEATURE               Location/Qualifiers
misc_feature          1..321
                      note = ADT1-7-18 Variable Light DNA
source                1..321
                      mol_type = genomic DNA
                      organism = Homo sapiens
SEQUENCE: 264
gacatccaga tgacccagtc tccatcctcc ctgtctgcat ctgtaggaga cagagtcacc    60
atcgcttgcc gggtaggtca gagcattggc acctatttaa attggtatca gcagaaacca   120
gggaaagccc ctaaactcct gatctatgtt gcatccagtt tgcaaagtgg ggtcccgtca   180
cggttcagtg gcagtggatc tgggacagaa ttcactctca ccatcagcag tctgcaacct   240
gaagattttg caacttacta ctgtcaacag agtgccagtg agctcctcac tttcggcaga   300
gggaccaagg tggaaatcaa a                                             321

SEQ ID NO: 265        moltype = DNA   length = 321
FEATURE               Location/Qualifiers
misc_feature          1..321
                      note = ADT1-7-19 Variable Light DNA
source                1..321
                      mol_type = genomic DNA
                      organism = Homo sapiens
SEQUENCE: 265
gacatccaga tgacccagtc tccatcctcc ctgtctgcat ctgtaggaga cagagtcacc    60
atcgcttgcc gggcaggtca gagcattggc acctatttaa attggtatca gcagaaacca   120
gggaaagccc ctaaactcct gatctatgtt gcatccagtt tgcaaagtgg ggtcccgtca   180
cggttcagtg gcagtggatc tgggacagaa ttcactctca ccatcagcag tctgcaacct   240
gaagattttg caacttacta ctgtcaacag agtgccagtg agctcctcac tttcggcaga   300
gggaccaagg tggaaatcaa a                                             321

SEQ ID NO: 266        moltype = DNA   length = 321
FEATURE               Location/Qualifiers
misc_feature          1..321
                      note = ADT1-7-20 Variable Light DNA
source                1..321
                      mol_type = genomic DNA
                      organism = Homo sapiens
SEQUENCE: 266
gacatccaga tgacccagtc tccatcctcc ctgtctgcat ctgtaggaga cagagtcacc    60
atcgcttgcc gggcaggtca gagcattggc acctatttaa attggtatca gcagaaacca   120
gggaaagccc ctaaactcct gatctatgtt gcatccagtt tgcaaagtgg ggtcccgtca   180
```

```
cggttcagtg gcagtggatc tgggacagaa ttcactctca ccatcagcag tctgcaacct    240
gaagattttg caacttacta ctgtcaacag agttacagtg gcctcgacac tttcggcaga    300
gggaccaagg tggaaatcaa a                                              321

SEQ ID NO: 267          moltype = DNA   length = 321
FEATURE                 Location/Qualifiers
misc_feature            1..321
                        note = ADT1-7-22 Variable Light DNA
source                  1..321
                        mol_type = genomic DNA
                        organism = Homo sapiens
SEQUENCE: 267
gacatccaga tgacccagtc tccatcctcc ctgtctgcat ctgtaggaga cagagtcacc    60
atcgcttgcc gggcaggtca gagcattggc acctatttaa attggtatca gcagaaacca   120
gggaaagccc ctaaactcct gatctatgtt gcatccagtt tgcaaagtgg ggtcccgtca   180
cggttcagtg gcagtggatc tgggacagaa ttcactctca ccatcagcag tctgcaacct   240
gaagattttg caacttacta ctgtcaacag agtgccagtg agctcctcac tttcggcaga   300
gggaccaagg tggaaatcaa a                                             321

SEQ ID NO: 268          moltype = DNA   length = 321
FEATURE                 Location/Qualifiers
misc_feature            1..321
                        note = ADT1-7-23 Variable Light DNA
source                  1..321
                        mol_type = genomic DNA
                        organism = Homo sapiens
SEQUENCE: 268
gacatccaga tgacccagtc tccatcctcc ctgtctgcat ctgtaggaga cagagtcacc    60
atcgcttgcc gggcaggtca gagcattggc acctatttaa attggtatca gcagaaacca   120
gggaaagccc ctaaactcct gatctatgtt gcatccagtt tgcaaagtgg ggtcccgtca   180
cggttcagtg gcagtggatc tgggacagaa ttcactctca ccatcagcag tctgcaacct   240
gaagattttg caacttacta ctgtcaacag agttacagtg gcctcgacac tttcggcaga   300
gggaccaagg tggaaatcaa a                                             321

SEQ ID NO: 269          moltype = DNA   length = 321
FEATURE                 Location/Qualifiers
misc_feature            1..321
                        note = ADT1-7-42 Variable Light DNA
source                  1..321
                        mol_type = genomic DNA
                        organism = Homo sapiens
SEQUENCE: 269
gacatccaga tgacccagtc tccatcctcc ctgtctgcat ctgtaggaga cagagtcacc    60
atcgcttgcc gggcaggtca gagcattggc acctatttaa attggtatca gcagaaacca   120
gggaaagccc ctaaactcct gatctatgtt gcatccagtt tgcaaagtgg ggtcccgtca   180
cggttcagtg gcagtggatc tgggacagaa ttcactctca ccatcagcag tctgcaacct   240
gaagattttg caacttacta ctgtcaacag agtagcagtg agctcctcac tttcggcaga   300
gggaccaagg tggaaatcaa a                                             321

SEQ ID NO: 270          moltype = DNA   length = 321
FEATURE                 Location/Qualifiers
misc_feature            1..321
                        note = ADT1-7-3 Variable Light DNA
source                  1..321
                        mol_type = genomic DNA
                        organism = Homo sapiens
SEQUENCE: 270
gacatccaga tgacccagtc tccatcctcc ctgtctgcat ctgtaggaga cagagtcacc    60
atcgcttgcc gggcaggtca gagcattggc acctatttaa attggtatca gcagaaacca   120
gggaaagccc ctaaactcct gatctatgtt gcatccagtt tgcaaagtgg ggtcccgtca   180
cggttcagtg gcagtggatc tgggacagaa ttcactctca ccatcagcag tctgcaacct   240
gaagattttg caacttacta ctgtcaacag agttacagtg gcctcgacac tttcggcaga   300
gggaccaagg tggaaatcaa a                                             321

SEQ ID NO: 271          moltype = DNA   length = 321
FEATURE                 Location/Qualifiers
misc_feature            1..321
                        note = ADT1-7-61 Variable Light DNA
source                  1..321
                        mol_type = genomic DNA
                        organism = Homo sapiens
SEQUENCE: 271
gacatccaga tgacccagtc tccatcctcc ctgtctgcat ctgtaggaga cagagtcacc    60
atcgcttgcc gggcaggtca gagcattggc acctatttaa attggtatca gcagaaacca   120
gggaaagccc ctaaactcct gatctatgtt gcatccagtt tgcaaagtgg ggtcccgtca   180
cggttcagtg gcagtggatc tgggacagaa ttcactctca ccatcagcag tctgcaacct   240
gaagattttg caacttacta ctgtcaacag agtgccagtg agctcctcac tttcggcaga   300
gggaccaagg tggaaatcaa a                                             321
```

```
SEQ ID NO: 272          moltype = AA  length = 209
FEATURE                 Location/Qualifiers
REGION                  1..209
                        note = Human variable delta 1 (V delta 1) chain of a gamma
                         delta T cell receptor (TCR) - aka TRDV1
source                  1..209
                        mol_type = protein
                        organism = Homo sapiens
SEQUENCE: 272
AQKVTQAQSS VSMPVRKAVT LNCLYETSWW SYYIFWYKQL PSKEMIFLIR QGSDEQNAKS   60
GRYSVNFKKA AKSVALTISA LQLEDSAKYF CALGESLTRA DKLIFGKGTR VTVEPNIQNP  120
DPAVYQLRDS KSSDKSVCLF TDFDSQTNVS QSKDSDVYIT DKTVLDMRSM DFKSNSAVAW  180
SNKSDFACAN AFNNSIIPED TFFPSPESS                                    209

SEQ ID NO: 273          moltype = AA  length = 117
FEATURE                 Location/Qualifiers
REGION                  1..117
                        note = C08 Variable Heavy
source                  1..117
                        mol_type = protein
                        organism = Homo sapiens
SEQUENCE: 273
EVQLLESGGG LVQPGRSLRL SCAASGFTVS SNYMSWVRQA PGKGLEWVSV IYSGGSTYYA   60
DSVKGRFTIS RDNSKNTLYL QMNSLRAEDT AVYYCASPIE LGAFDIWGQG TLVTVSS    117

SEQ ID NO: 274          moltype = AA  length = 118
FEATURE                 Location/Qualifiers
REGION                  1..118
                        note = B07 Variable Heavy
source                  1..118
                        mol_type = protein
                        organism = Homo sapiens
SEQUENCE: 274
EVQLLESGGG LVKPGGSLRL SCAASGFTFS DYYMSWIRQA PGKGLEWVSY ISSSGSTIYY   60
ADSVKGRFTI SRDNAKNSLY LQMNSLRAED TAVYYCAREN YLNAFDIWGR GTLVTVSS   118

SEQ ID NO: 275          moltype = AA  length = 117
FEATURE                 Location/Qualifiers
REGION                  1..117
                        note = C05 Variable Heavy
source                  1..117
                        mol_type = protein
                        organism = Homo sapiens
SEQUENCE: 275
EVQLLESGGG LVQPGGSLRL SCAASGFTFS SYAMSWVRQA PGKGLEWVSA ISGGGGTTYS   60
SDSVKGRFTI SRDNSKNTLY LQMNSLRAED TAVYYCARDS GVAFDIWGQG TLVTVSS    117

SEQ ID NO: 276          moltype = AA  length = 120
FEATURE                 Location/Qualifiers
REGION                  1..120
                        note = E04 Variable Heavy
source                  1..120
                        mol_type = protein
                        organism = Homo sapiens
SEQUENCE: 276
QVQLQQSGPG LVKPSQTLSL TCAISGDSVS SNSAAWNWIR QSPSRGLEWL GRTYYRSKWY   60
NDYAVSVRSR ITINPDTSKN QFSLQLNSVT PEDTAVYYCA RSWNDAFDIW GQGTTVTVSS  120

SEQ ID NO: 277          moltype = AA  length = 120
FEATURE                 Location/Qualifiers
REGION                  1..120
                        note = F07 Variable Heavy
source                  1..120
                        mol_type = protein
                        organism = Homo sapiens
SEQUENCE: 277
QVQLQQSGPG LVKPSQTLSL TCVISGDSVS SNSAAWNWIR QSPSRGLEWL GRTYYRSKWY   60
NDYAVSVKSR ITINPDTSKN QFSLQLNSVT PEDTAVYYCA RDYYYSMDVW GQGTMVTVSS  120

SEQ ID NO: 278          moltype = AA  length = 118
FEATURE                 Location/Qualifiers
REGION                  1..118
                        note = G06 Variable Heavy
source                  1..118
                        mol_type = protein
                        organism = Homo sapiens
SEQUENCE: 278
QVQLVESGGG LVKPGGSLRL SCAASGFTFS DYYMSWIRQA PGKGLEWVSY ISSSGSTIYY   60
ADSVKGRFTI SRDNAKNSLY LQMNSLRAED TAVYYCARHS WNDAFDVWGQ GTLVTVSS   118
```

```
SEQ ID NO: 279          moltype = AA  length = 120
FEATURE                 Location/Qualifiers
REGION                  1..120
                        note = G09 Variable Heavy
source                  1..120
                        mol_type = protein
                        organism = Homo sapiens
SEQUENCE: 279
QVQLQQSGPG LVKPSQTLSL TCAISGDSVS SNSAAWNWIR QSPSRGLEWL GRTYYGSKWY    60
NEYALSVKSR IIINPDTSKN QFSLQLNSVT PEDTAVYYCA RDYYYSMDVW GQGTLVTVSS   120

SEQ ID NO: 280          moltype = AA  length = 118
FEATURE                 Location/Qualifiers
REGION                  1..118
                        note = B09 Variable Heavy
source                  1..118
                        mol_type = protein
                        organism = Homo sapiens
SEQUENCE: 280
EVQLLESGGG LVKPGGSLRL SCAASGFTFS DYYMSWIRQA PGKGLEWVSY ISSSGSTIYY    60
ADSVKGRFTI SRDNAKNSLY LQMNSLRAED TAVYYCARHS WSDAFDIWGQ GTLVTVSS    118

SEQ ID NO: 281          moltype = AA  length = 118
FEATURE                 Location/Qualifiers
REGION                  1..118
                        note = G10 Variable Heavy
source                  1..118
                        mol_type = protein
                        organism = Homo sapiens
SEQUENCE: 281
EVQLVESGGG LVQPGGSLRL SCAASGFTFS DYYMSWIRQA PGKGLEWVSY ISSSGSTIYY    60
ADSVKGRFTI SRDNAKNSLY LQMNSLRAED TAVYYCARHS WNDAFDIWGR GTLVTVSS    118

SEQ ID NO: 282          moltype = AA  length = 110
FEATURE                 Location/Qualifiers
REGION                  1..110
                        note = C08 Variable Light
source                  1..110
                        mol_type = protein
                        organism = Homo sapiens
SEQUENCE: 282
ASSYELTQPP SVSVAPGKTA RITCGGNNIG SQSVHWYQQK PGQAPMLVIY YDSDRPSGIP    60
ERFSGSNSGN TATLTISRVE AGDEADYYCQ VWDSSSDHVV FGGGTKLTVL             110

SEQ ID NO: 283          moltype = AA  length = 109
FEATURE                 Location/Qualifiers
REGION                  1..109
                        note = B07 Variable Light
source                  1..109
                        mol_type = protein
                        organism = Homo sapiens
SEQUENCE: 283
ASDIQMTQSP SSLSASVGDR VTITCRTSQS LSNYLNWYQQ KPGKAPKLLI YAASSLQSGV    60
PSRFSGSGSG TDFTLTISSL QPEDFATYYC QQSYSTPLTF GGGTKLEIK              109

SEQ ID NO: 284          moltype = AA  length = 109
FEATURE                 Location/Qualifiers
REGION                  1..109
                        note = C05 Variable Light
source                  1..109
                        mol_type = protein
                        organism = Homo sapiens
SEQUENCE: 284
ASDIQMTQSP SFLSASVGDR VTITCRASQN IRTWLAWYQQ KPGRAPKLLI YDASSLESGV    60
PSRFSGSGSG TDFTLTISSL QPEDFATYYC QQFKRYPPTF GLGTKVEIK              109

SEQ ID NO: 285          moltype = AA  length = 109
FEATURE                 Location/Qualifiers
REGION                  1..109
                        note = E04 Variable Light
source                  1..109
                        mol_type = protein
                        organism = Homo sapiens
SEQUENCE: 285
ASDIVMTQSP STLSASIGDR VTITCRAGQS ISTWLAWYQQ KPGKAPKLLI YDASSLESGV    60
PLRFSGSGSG TDFTLTISSL QPEDFATYYC QQSYSTPLTF GGGTKVEIK              109

SEQ ID NO: 286          moltype = AA  length = 109
```

```
FEATURE                 Location/Qualifiers
REGION                  1..109
                        note = F07 Variable Light
source                  1..109
                        mol_type = protein
                        organism = Homo sapiens
SEQUENCE: 286
ASDIQMTQSP STLSASVGDR VTITCRASQS ISSWLAWYQQ KPGKAPKLLI YDASSLESGV    60
PLRFSGSGSG TEFTLTISSL QPDDFATYYC QQSHSHPPTF GPGTKVDIK              109

SEQ ID NO: 287          moltype = AA  length = 109
FEATURE                 Location/Qualifiers
REGION                  1..109
                        note = G06 Variable Light
source                  1..109
                        mol_type = protein
                        organism = Homo sapiens
SEQUENCE: 287
ASDIQMTQSP SSLSASVGDR VSITCRASQS ISSYLNWYQQ KPGKAPKLLI YAASSLQSGV    60
PSRFSGSGSG TDFTLTISSL QPEDFATYYC QQSYSTPDTF GGGTKVEIK              109

SEQ ID NO: 288          moltype = AA  length = 109
FEATURE                 Location/Qualifiers
REGION                  1..109
                        note = G09 Variable Light
source                  1..109
                        mol_type = protein
                        organism = Homo sapiens
SEQUENCE: 288
ASDIVMTQSP STLSASIGDR VTITCRAGQS ISTWLAWYQQ KPGKAPKLLI YDASSLESGV    60
PLRFSGSGSG TEFTLAISSL QPDDFATYYC QQSYSTPVTF GQGTKVEIK              109

SEQ ID NO: 289          moltype = AA  length = 109
FEATURE                 Location/Qualifiers
REGION                  1..109
                        note = B09 Variable Light
source                  1..109
                        mol_type = protein
                        organism = Homo sapiens
SEQUENCE: 289
ASDIQMTQSP SSLSASVGDR VTITCQASQD ISNYLNWYQQ KPGKAPKLLI YDASNLETGV    60
PSRFSGSGSG TDFTLTISSL QPEDFATYYC QQSYSTPLTF GGGTKVEIK              109

SEQ ID NO: 290          moltype = AA  length = 109
FEATURE                 Location/Qualifiers
REGION                  1..109
                        note = G10 Variable Light
source                  1..109
                        mol_type = protein
                        organism = Homo sapiens
SEQUENCE: 290
ASDIQMTQSP SSLSASVGDR VTITCRASQS ISSHLNWYQQ KPGKAPKLLI YAASSLQSGV    60
PSRFSASGSG TDFTLTISSL QPEDFATYYC QQSYSTLLTF GGGTKVEIK              109

SEQ ID NO: 291          moltype = AA  length = 13
FEATURE                 Location/Qualifiers
REGION                  1..13
                        note = VH-VL linker
source                  1..13
                        mol_type = protein
                        organism = synthetic construct
SEQUENCE: 291
GGGGSGGGGS GGG                                                      13

SEQ ID NO: 292          moltype = AA  length = 12
FEATURE                 Location/Qualifiers
REGION                  1..12
                        note = Optional scFv tag sequence (kappa sequence + His tag)
source                  1..12
                        mol_type = protein
                        organism = synthetic construct
SEQUENCE: 292
RTAAASAHHH HH                                                       12

SEQ ID NO: 293          moltype = AA  length = 37
FEATURE                 Location/Qualifiers
REGION                  1..37
                        note = Optional scFv tag sequence (kappa sequence + His and
                        FLAG tag)
```

```
source                  1..37
                        mol_type = protein
                        organism = synthetic construct
SEQUENCE: 293
RTAAASAHHH HHHKLDYKDH DGDYKDHDID YKDDDDK                              37

SEQ ID NO: 294          moltype = AA  length = 13
FEATURE                 Location/Qualifiers
REGION                  1..13
                        note = Optional scFv tag sequence (lambda sequence + His
                         tag)
source                  1..13
                        mol_type = protein
                        organism = synthetic construct
SEQUENCE: 294
GQPAAASAHH HHH                                                        13

SEQ ID NO: 295          moltype = AA  length = 38
FEATURE                 Location/Qualifiers
REGION                  1..38
                        note = Optional scFv tag sequence (lambda sequence + His
                         and FLAG tag)
source                  1..38
                        mol_type = protein
                        organism = synthetic construct
SEQUENCE: 295
GQPAAASAHH HHHKLDYKD HDGDYKDHDI DYKDDDDK                              38

SEQ ID NO: 296          moltype = AA  length = 107
FEATURE                 Location/Qualifiers
REGION                  1..107
                        note = Constant domain (AD3 and AD4 full light constant
                         chain with RTVAAPS sequence instead of RTAAAPS)
source                  1..107
                        mol_type = protein
                        organism = Homo sapiens
SEQUENCE: 296
RTVAAPSVFI FPPSDEQLKS GTASVVCLLN NFYPREAKVQ WKVDNALQSG NSQESVTEQD     60
SKDSTYSLSS TLTLSKADYE KHKVYACEVT HQGLSSPVTK SFNRGEC                   107

SEQ ID NO: 297          moltype = AA  length = 330
FEATURE                 Location/Qualifiers
REGION                  1..330
                        note = Constant domain (AD3 full heavy constant domain
                         chain)
source                  1..330
                        mol_type = protein
                        organism = Homo sapiens
SEQUENCE: 297
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPELLGG     120
PSVFLFPPKP KDTLMISRTP EVTCVVVDVS HEDPEVKFNW YVDGVEVHNA KTKPREEQYN     180
STYRVVSVLT VLHQDWLNGK EYKCKVSNKA LPAPIEKTIS KAKGQPREPQ VYTLPPSRDE     240
LTKNQVSLTC LVKGFYPSDI AVEWESNGQP ENNYKTTPPV LDSDGSFFLY SKLTVDKSRW     300
QQGNVFSCSV MHEALHNHYT QKSLSLSPGK                                      330

SEQ ID NO: 298          moltype = AA  length = 330
FEATURE                 Location/Qualifiers
REGION                  1..330
                        note = Constant domain (AD4 full heavy constant domain
                         chain employed (with L235A, G237A modification))
source                  1..330
                        mol_type = protein
                        organism = Homo sapiens
SEQUENCE: 298
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPELAGA     120
PSVFLFPPKP KDTLMISRTP EVTCVVVDVS HEDPEVKFNW YVDGVEVHNA KTKPREEQYN     180
STYRVVSVLT VLHQDWLNGK EYKCKVSNKA LPAPIEKTIS KAKGQPREPQ VYTLPPSRDE     240
LTKNQVSLTC LVKGFYPSDI AVEWESNGQP ENNYKTTPPV LDSDGSFFLY SKLTVDKSRW     300
QQGNVFSCSV MHEALHNHYT QKSLSLSPGK                                      330

SEQ ID NO: 299          moltype = AA  length = 20
FEATURE                 Location/Qualifiers
REGION                  1..20
                        note = N-terminal leader sequence of the V delta 1 chain
source                  1..20
                        mol_type = protein
                        organism = Homo sapiens
```

```
SEQUENCE: 299
MLFSSLLCVF VAFSYSGSSV                                                  20

SEQ ID NO: 300          moltype = AA  length = 95
FEATURE                 Location/Qualifiers
REGION                  1..95
                        note = V region of the V delta 1 chain
source                  1..95
                        mol_type = protein
                        organism = Homo sapiens
SEQUENCE: 300
AQKVTQAQSS VSMPVRKAVT LNCLYETSWW SYYIFWYKQL PSKEMIFLIR QGSDEQNAKS       60
GRYSVNFKKA AKSVALTISA LQLEDSAKYF CALGE                                  95

SEQ ID NO: 301          moltype = AA  length = 16
FEATURE                 Location/Qualifiers
REGION                  1..16
                        note = J1*0 - one of the four J regions encoded in the
                         human delta one chain germline
source                  1..16
                        mol_type = protein
                        organism = Homo sapiens
SEQUENCE: 301
TDKLIFGKGT RVTVEP                                                      16

SEQ ID NO: 302          moltype = AA  length = 17
FEATURE                 Location/Qualifiers
REGION                  1..17
                        note = J2*0 - one of the four J regions encoded in the
                         human delta one chain germline
source                  1..17
                        mol_type = protein
                        organism = Homo sapiens
SEQUENCE: 302
LTAQLFFGKG TQLIVEP                                                     17

SEQ ID NO: 303          moltype = AA  length = 19
FEATURE                 Location/Qualifiers
REGION                  1..19
                        note = J3*0 - one of the four J regions encoded in the
                         human delta one chain germline
source                  1..19
                        mol_type = protein
                        organism = Homo sapiens
SEQUENCE: 303
SWDTRQMFFG TGIKLFVEP                                                   19

SEQ ID NO: 304          moltype = AA  length = 15
FEATURE                 Location/Qualifiers
REGION                  1..15
                        note = J4*0 - one of the four J regions encoded in the
                         human delta one chain germline
source                  1..15
                        mol_type = protein
                        organism = Homo sapiens
SEQUENCE: 304
RPLIFGKGTY LEVQQ                                                       15

SEQ ID NO: 305          moltype = AA  length = 153
FEATURE                 Location/Qualifiers
REGION                  1..153
                        note = C1*0 which contains the C-terminal
                         juxtamembrane/transmembrane regions
VARIANT                 1
                        note = Xaa can be any naturally occurring amino acid
source                  1..153
                        mol_type = protein
                        organism = Homo sapiens
SEQUENCE: 305
XSQPHTKPSV FVMKNGTNVA CLVKEFYPKD IRINLVSSKK ITEFDPAIVI SPSGKYNAVK       60
LGKYESNSVT CSVQHDNKTV HSTDFEVKTD STDHVKPKET ENTKQPSKSC HKPKAIVHTE      120
KVNMMSLTVL GLRMLFAKTV AVNFLLTAKL FFL                                   153

SEQ ID NO: 306          moltype = AA  length = 254
FEATURE                 Location/Qualifiers
REGION                  1..254
                        note = Human variable delta 1 (V delta 1) chain of a gamma
                         delta T cell receptor (TCR) polymorphic variant - aka
                         human TRDV1 polymorphic variant
```

```
                         -continued
source                   1..254
                         mol_type = protein
                         organism = Homo sapiens
SEQUENCE: 306
AQKVTQAQSS VSMPVRKAVT LNCLYETSWW SYYIFWYKQL PSKEMIFLIR QGSDEQNAKS     60
GRYSVNFKKA VKSVALTISA LQLEDSAKYF CALGESLTRA DKLIFGKGTR VTVEPNIQNP    120
DPAVYQLRDS KSSDKSVCLF TDFDSQTNVS QSKDSDVYIT DKTVLDMRSM DFKSNSAVAW    180
SNKSDFACAN AFNNSIIPED TFFPSPESSC TTAPSAQLKK KLQALKKKNA QLKWKLQALK    240
KKLAQGSGHH HHHH                                                     254

SEQ ID NO: 307           moltype = AA  length = 107
FEATURE                  Location/Qualifiers
REGION                   1..107
                         note = Constant domain (AD3 and AD4 full light constant
                          chain with RTAAAPS sequence)
source                   1..107
                         mol_type = protein
                         organism = Homo sapiens
SEQUENCE: 307
RTAAAPSVFI FPPSDEQLKS GTASVVCLLN NFYPREAKVQ WKVDNALQSG NSQESVTEQD     60
SKDSTYSLSS TLTLSKADYE KHKVYACEVT HQGLSSPVTK SFNRGEC                 107

SEQ ID NO: 308           moltype = AA  length = 92
FEATURE                  Location/Qualifiers
REGION                   1..92
                         note = Cyno variable delta 1 (V delta 1) chain of a gamma
                          delta T cell receptor (TCR) - aka cyno TRDV1 (minus leader)
source                   1..92
                         mol_type = protein
                         organism = Homo sapiens
SEQUENCE: 308
AQKVTQAQSS VSMPVEKAVT LNCQYETSSW SYDLFWYKQL PGKEMIFLIH QGSSQQNARN     60
GRYSVNFQKA ASSITLTISA LQLEDSATYF CA                                  92

SEQ ID NO: 309           moltype = AA  length = 101
FEATURE                  Location/Qualifiers
REGION                   1..101
                         note = Human variable gamma 4 chain (V gamma 4) of a gamma
                          delta T cell receptor (TCR) - aka human TRGV4 (minus
                          leader)
source                   1..101
                         mol_type = protein
                         organism = Homo sapiens
SEQUENCE: 309
KSSNLEGRTK SVIRQTGSSA EITCDLAEGS TGYIHWYLHQ EGKAPQRLLY YDSYTSSVVL     60
ESGISPGKYD TYGSTRKNLR MILRNLIEND SGVYYCATWD G                       101

SEQ ID NO: 310           moltype = AA  length = 96
FEATURE                  Location/Qualifiers
REGION                   1..96
                         note = Human variable delta 2 (V delta 2) chain of a gamma
                          delta T cell receptor (TCR) - aka TRDV2 (minus leader)
source                   1..96
                         mol_type = protein
                         organism = Homo sapiens
SEQUENCE: 310
AIELVPEHQT VPVSIGVPAT LRCSMKGEAI GNYYINWYRK TQGNTMTFIY REKDIYGPGF     60
KDNFQGDIDI AKNLAVLKIL APSERDEGSY YCACDT                              96

SEQ ID NO: 311           moltype = AA  length = 95
FEATURE                  Location/Qualifiers
REGION                   1..95
                         note = Human variable delta 3 (V delta 3) chain of a gamma
                          delta T cell receptor (TCR) - aka TRDV3 (minus leader)
source                   1..95
                         mol_type = protein
                         organism = Homo sapiens
SEQUENCE: 311
DKVTQSSPDQ TVASGSEVVL LCTYDTVYSN PDLFWYRIRP DYSFQFVFYG DNSRSEGADF     60
TQGRFSVKHI LTQKAFHLVI SPVRTEDSAT YYCAF                               95

SEQ ID NO: 312           moltype = AA  length = 119
FEATURE                  Location/Qualifiers
REGION                   1..119
                         note = E01 Variable Heavy
source                   1..119
                         mol_type = protein
                         organism = Homo sapiens
SEQUENCE: 312
```

```
QVQLVQSGAE VKKPGESLKI SCKGSGYSFT SYWIGWVRQM PGKGLEWMGI IYPGDSDTRY   60
SPSFQGQVTI SADKSISTAY LQWSSLKASD TAMYYCARHQ VDTRTADYWG QGTLVTVSS   119

SEQ ID NO: 313          moltype = AA   length = 112
FEATURE                 Location/Qualifiers
REGION                  1..112
                        note = E01 Variable Light
source                  1..112
                        mol_type = protein
                        organism = Homo sapiens
SEQUENCE: 313
ASQSALTQPA SVSGSPGQSV TISCTGTRSD VGGYNYVSWY QHHPGKAPKL MIYEVSNRPS   60
GVSNRFSGSK SGNTASLTIS GLQAEDEADY YCSSYTSTST LVFGGGTKLT VL          112

SEQ ID NO: 314          moltype =    length =
SEQUENCE: 314
000

SEQ ID NO: 315          moltype =    length =
SEQUENCE: 315
000

SEQ ID NO: 316          moltype =    length =
SEQUENCE: 316
000

SEQ ID NO: 317          moltype = AA   length = 8
FEATURE                 Location/Qualifiers
REGION                  1..8
                        note = C08 HCDR1
source                  1..8
                        mol_type = protein
                        organism = Homo sapiens
SEQUENCE: 317
GFTVSSNY                                                            8

SEQ ID NO: 318          moltype = AA   length = 7
FEATURE                 Location/Qualifiers
REGION                  1..7
                        note = C08 HCDR2
source                  1..7
                        mol_type = protein
                        organism = Homo sapiens
SEQUENCE: 318
IYSGGST                                                             7

SEQ ID NO: 319          moltype = AA   length = 9
FEATURE                 Location/Qualifiers
REGION                  1..9
                        note = C08 HCDR3
source                  1..9
                        mol_type = protein
                        organism = Homo sapiens
SEQUENCE: 319
PIELGAFDI                                                           9

SEQ ID NO: 320          moltype = AA   length = 8
FEATURE                 Location/Qualifiers
REGION                  1..8
                        note = B07 HCDR1
source                  1..8
                        mol_type = protein
                        organism = Homo sapiens
SEQUENCE: 320
GFTFSDYY                                                            8

SEQ ID NO: 321          moltype = AA   length = 8
FEATURE                 Location/Qualifiers
REGION                  1..8
                        note = B07 HCDR2
source                  1..8
                        mol_type = protein
                        organism = Homo sapiens
SEQUENCE: 321
ISSSGSTI                                                            8

SEQ ID NO: 322          moltype = AA   length = 9
FEATURE                 Location/Qualifiers
REGION                  1..9
```

```
                              note = B07 HCDR3
source                        1..9
                              mol_type = protein
                              organism = Homo sapiens
SEQUENCE: 322
ENYLNAFDI                                                              9

SEQ ID NO: 323                moltype = AA  length = 8
FEATURE                       Location/Qualifiers
REGION                        1..8
                              note = C05 HCDR1
source                        1..8
                              mol_type = protein
                              organism = Homo sapiens
SEQUENCE: 323
GFTFSSYA                                                               8

SEQ ID NO: 324                moltype = AA  length = 8
FEATURE                       Location/Qualifiers
REGION                        1..8
                              note = C05 HCDR2
source                        1..8
                              mol_type = protein
                              organism = Homo sapiens
SEQUENCE: 324
ISGGGGTT                                                               8

SEQ ID NO: 325                moltype = AA  length = 8
FEATURE                       Location/Qualifiers
REGION                        1..8
                              note = C05 HCDR3
source                        1..8
                              mol_type = protein
                              organism = Homo sapiens
SEQUENCE: 325
DSGVAFDI                                                               8

SEQ ID NO: 326                moltype = AA  length = 10
FEATURE                       Location/Qualifiers
REGION                        1..10
                              note = E04 HCDR1
source                        1..10
                              mol_type = protein
                              organism = Homo sapiens
SEQUENCE: 326
GDSVSSNSAA                                                            10

SEQ ID NO: 327                moltype = AA  length = 9
FEATURE                       Location/Qualifiers
REGION                        1..9
                              note = E04 HCDR2
source                        1..9
                              mol_type = protein
                              organism = Homo sapiens
SEQUENCE: 327
TYYRSKWYN                                                              9

SEQ ID NO: 328                moltype = AA  length = 8
FEATURE                       Location/Qualifiers
REGION                        1..8
                              note = E04 HCDR3
source                        1..8
                              mol_type = protein
                              organism = Homo sapiens
SEQUENCE: 328
SWNDAFDI                                                               8

SEQ ID NO: 329                moltype = AA  length = 10
FEATURE                       Location/Qualifiers
REGION                        1..10
                              note = F07 HCDR1
source                        1..10
                              mol_type = protein
                              organism = Homo sapiens
SEQUENCE: 329
GDSVSSNSAA                                                            10

SEQ ID NO: 330                moltype = AA  length = 9
FEATURE                       Location/Qualifiers
```

```
                                      -continued

REGION                  1..9
                        note = F07 HCDR2
source                  1..9
                        mol_type = protein
                        organism = Homo sapiens
SEQUENCE: 330
TYYRSKWYN                                                                  9

SEQ ID NO: 331          moltype = AA   length = 8
FEATURE                 Location/Qualifiers
REGION                  1..8
                        note = F07 HCDR3
source                  1..8
                        mol_type = protein
                        organism = Homo sapiens
SEQUENCE: 331
DYYYSMDV                                                                   8

SEQ ID NO: 332          moltype = AA   length = 8
FEATURE                 Location/Qualifiers
REGION                  1..8
                        note = G06 HCDR1
source                  1..8
                        mol_type = protein
                        organism = Homo sapiens
SEQUENCE: 332
GFTFSDYY                                                                   8

SEQ ID NO: 333          moltype = AA   length = 8
FEATURE                 Location/Qualifiers
REGION                  1..8
                        note = G06 HCDR2
source                  1..8
                        mol_type = protein
                        organism = Homo sapiens
SEQUENCE: 333
ISSSGSTI                                                                   8

SEQ ID NO: 334          moltype = AA   length = 9
FEATURE                 Location/Qualifiers
REGION                  1..9
                        note = G06 HCDR3
source                  1..9
                        mol_type = protein
                        organism = Homo sapiens
SEQUENCE: 334
HSWNDAFDV                                                                  9

SEQ ID NO: 335          moltype = AA   length = 10
FEATURE                 Location/Qualifiers
REGION                  1..10
                        note = G09 HCDR1
source                  1..10
                        mol_type = protein
                        organism = Homo sapiens
SEQUENCE: 335
GDSVSSNSAA                                                                10

SEQ ID NO: 336          moltype = AA   length = 9
FEATURE                 Location/Qualifiers
REGION                  1..9
                        note = G09 HCDR2
source                  1..9
                        mol_type = protein
                        organism = Homo sapiens
SEQUENCE: 336
TYYGSKWYN                                                                  9

SEQ ID NO: 337          moltype = AA   length = 8
FEATURE                 Location/Qualifiers
REGION                  1..8
                        note = G09 HCDR3
source                  1..8
                        mol_type = protein
                        organism = Homo sapiens
SEQUENCE: 337
DYYYSMDV                                                                   8

SEQ ID NO: 338          moltype = AA   length = 8
```

```
FEATURE                 Location/Qualifiers
REGION                  1..8
                        note = B09 HCDR1
source                  1..8
                        mol_type = protein
                        organism = Homo sapiens
SEQUENCE: 338
GFTFSDYY                                                                    8

SEQ ID NO: 339          moltype = AA  length = 8
FEATURE                 Location/Qualifiers
REGION                  1..8
                        note = B09 HCDR2
source                  1..8
                        mol_type = protein
                        organism = Homo sapiens
SEQUENCE: 339
ISSSGSTI                                                                    8

SEQ ID NO: 340          moltype = AA  length = 9
FEATURE                 Location/Qualifiers
REGION                  1..9
                        note = B09 HCDR3
source                  1..9
                        mol_type = protein
                        organism = Homo sapiens
SEQUENCE: 340
HSWSDAFDI                                                                   9

SEQ ID NO: 341          moltype = AA  length = 8
FEATURE                 Location/Qualifiers
REGION                  1..8
                        note = G10 HCDR1
source                  1..8
                        mol_type = protein
                        organism = Homo sapiens
SEQUENCE: 341
GFTFSDYY                                                                    8

SEQ ID NO: 342          moltype = AA  length = 8
FEATURE                 Location/Qualifiers
REGION                  1..8
                        note = G10 HCDR2
source                  1..8
                        mol_type = protein
                        organism = Homo sapiens
SEQUENCE: 342
ISSSGSTI                                                                    8

SEQ ID NO: 343          moltype = AA  length = 9
FEATURE                 Location/Qualifiers
REGION                  1..9
                        note = G10 HCDR3
source                  1..9
                        mol_type = protein
                        organism = Homo sapiens
SEQUENCE: 343
HSWNDAFDI                                                                   9

SEQ ID NO: 344          moltype = AA  length = 8
FEATURE                 Location/Qualifiers
REGION                  1..8
                        note = E01 HCDR1
source                  1..8
                        mol_type = protein
                        organism = Homo sapiens
SEQUENCE: 344
GYSFTSYW                                                                    8

SEQ ID NO: 345          moltype = AA  length = 8
FEATURE                 Location/Qualifiers
REGION                  1..8
                        note = E02 HCDR2
source                  1..8
                        mol_type = protein
                        organism = Homo sapiens
SEQUENCE: 345
IYPGDSDT                                                                    8
```

| | | |
|---|---|---|
| SEQ ID NO: 346 | moltype = AA length = 10 | |
| FEATURE | Location/Qualifiers | |
| REGION | 1..10 | |
| | note = E02 HCDR3 | |
| source | 1..10 | |
| | mol_type = protein | |
| | organism = Homo sapiens | |
| SEQUENCE: 346 | | |
| HQVDTRTADY | | 10 |
| | | |
| SEQ ID NO: 347 | moltype = AA length = 6 | |
| FEATURE | Location/Qualifiers | |
| REGION | 1..6 | |
| | note = C08 LCDR1 | |
| source | 1..6 | |
| | mol_type = protein | |
| | organism = Homo sapiens | |
| SEQUENCE: 347 | | |
| NIGSQS | | 6 |
| | | |
| SEQ ID NO: 348 | moltype = length = | |
| SEQUENCE: 348 | | |
| 000 | | |
| | | |
| SEQ ID NO: 349 | moltype = AA length = 11 | |
| FEATURE | Location/Qualifiers | |
| REGION | 1..11 | |
| | note = C08 LCDR3 | |
| source | 1..11 | |
| | mol_type = protein | |
| | organism = Homo sapiens | |
| SEQUENCE: 349 | | |
| QVWDSSSDHV V | | 11 |
| | | |
| SEQ ID NO: 350 | moltype = AA length = 6 | |
| FEATURE | Location/Qualifiers | |
| REGION | 1..6 | |
| | note = B07 LCDR1 | |
| source | 1..6 | |
| | mol_type = protein | |
| | organism = Homo sapiens | |
| SEQUENCE: 350 | | |
| QSLSNY | | 6 |
| | | |
| SEQ ID NO: 351 | moltype = length = | |
| SEQUENCE: 351 | | |
| 000 | | |
| | | |
| SEQ ID NO: 352 | moltype = AA length = 9 | |
| FEATURE | Location/Qualifiers | |
| REGION | 1..9 | |
| | note = B07 LCDR3 | |
| source | 1..9 | |
| | mol_type = protein | |
| | organism = Homo sapiens | |
| SEQUENCE: 352 | | |
| QQSYSTPLT | | 9 |
| | | |
| SEQ ID NO: 353 | moltype = AA length = 6 | |
| FEATURE | Location/Qualifiers | |
| REGION | 1..6 | |
| | note = C05 LCDR1 | |
| source | 1..6 | |
| | mol_type = protein | |
| | organism = Homo sapiens | |
| SEQUENCE: 353 | | |
| QNIRTW | | 6 |
| | | |
| SEQ ID NO: 354 | moltype = length = | |
| SEQUENCE: 354 | | |
| 000 | | |
| | | |
| SEQ ID NO: 355 | moltype = AA length = 9 | |
| FEATURE | Location/Qualifiers | |
| REGION | 1..9 | |
| | note = C05 LCDR3 | |
| source | 1..9 | |
| | mol_type = protein | |
| | organism = Homo sapiens | |

```
SEQUENCE: 355
QQFKRYPPT                                                                          9

SEQ ID NO: 356           moltype = AA  length = 6
FEATURE                  Location/Qualifiers
REGION                   1..6
                         note = E04 LCDR1
source                   1..6
                         mol_type = protein
                         organism = Homo sapiens
SEQUENCE: 356
QSISTW                                                                             6

SEQ ID NO: 357           moltype =    length =
SEQUENCE: 357
000

SEQ ID NO: 358           moltype = AA  length = 9
FEATURE                  Location/Qualifiers
REGION                   1..9
                         note = E04 LCDR3
source                   1..9
                         mol_type = protein
                         organism = Homo sapiens
SEQUENCE: 358
QQSYSTPLT                                                                          9

SEQ ID NO: 359           moltype = AA  length = 6
FEATURE                  Location/Qualifiers
REGION                   1..6
                         note = F07 LCDR1
source                   1..6
                         mol_type = protein
                         organism = Homo sapiens
SEQUENCE: 359
QSISSW                                                                             6

SEQ ID NO: 360           moltype =    length =
SEQUENCE: 360
000

SEQ ID NO: 361           moltype = AA  length = 9
FEATURE                  Location/Qualifiers
REGION                   1..9
                         note = F07 LCDR3
source                   1..9
                         mol_type = protein
                         organism = Homo sapiens
SEQUENCE: 361
QQSHSHPPT                                                                          9

SEQ ID NO: 362           moltype = AA  length = 6
FEATURE                  Location/Qualifiers
REGION                   1..6
                         note = G06 LCDR1
source                   1..6
                         mol_type = protein
                         organism = Homo sapiens
SEQUENCE: 362
QSISSY                                                                             6

SEQ ID NO: 363           moltype =    length =
SEQUENCE: 363
000

SEQ ID NO: 364           moltype = AA  length = 9
FEATURE                  Location/Qualifiers
REGION                   1..9
                         note = G06 LCDR3
source                   1..9
                         mol_type = protein
                         organism = Homo sapiens
SEQUENCE: 364
QQSYSTPDT                                                                          9

SEQ ID NO: 365           moltype = AA  length = 6
FEATURE                  Location/Qualifiers
REGION                   1..6
                         note = G09 LCDR1
```

-continued

| | | |
|---|---|---|
| source | 1..6<br>mol_type = protein<br>organism = Homo sapiens | |
| SEQUENCE: 365<br>QSISTW | | 6 |
| SEQ ID NO: 366<br>SEQUENCE: 366<br>000 | moltype =   length = | |
| SEQ ID NO: 367<br>FEATURE<br>REGION<br>source | moltype = AA  length = 9<br>Location/Qualifiers<br>1..9<br>note = G09 LCDR3<br>1..9<br>mol_type = protein<br>organism = Homo sapiens | |
| SEQUENCE: 367<br>QQSYSTPVT | | 9 |
| SEQ ID NO: 368<br>FEATURE<br>REGION<br>source | moltype = AA  length = 6<br>Location/Qualifiers<br>1..6<br>note = B09 LCDR1<br>1..6<br>mol_type = protein<br>organism = Homo sapiens | |
| SEQUENCE: 368<br>QDISNY | | 6 |
| SEQ ID NO: 369<br>SEQUENCE: 369<br>000 | moltype =   length = | |
| SEQ ID NO: 370<br>FEATURE<br>REGION<br>source | moltype = AA  length = 9<br>Location/Qualifiers<br>1..9<br>note = B09 LCDR3<br>1..9<br>mol_type = protein<br>organism = Homo sapiens | |
| SEQUENCE: 370<br>QQSYSTPLT | | 9 |
| SEQ ID NO: 371<br>FEATURE<br>REGION<br>source | moltype = AA  length = 6<br>Location/Qualifiers<br>1..6<br>note = G10 LCDR1<br>1..6<br>mol_type = protein<br>organism = Homo sapiens | |
| SEQUENCE: 371<br>QSISSH | | 6 |
| SEQ ID NO: 372<br>SEQUENCE: 372<br>000 | moltype =   length = | |
| SEQ ID NO: 373<br>FEATURE<br>REGION<br>source | moltype = AA  length = 9<br>Location/Qualifiers<br>1..9<br>note = G10 LCDR3<br>1..9<br>mol_type = protein<br>organism = Homo sapiens | |
| SEQUENCE: 373<br>QQSYSTLLT | | 9 |
| SEQ ID NO: 374<br>FEATURE<br>REGION<br>source | moltype = AA  length = 9<br>Location/Qualifiers<br>1..9<br>note = E01 LCDR1<br>1..9<br>mol_type = protein<br>organism = Homo sapiens | |
| SEQUENCE: 374<br>RSDVGGYNY | | 9 |
| SEQ ID NO: 375 | moltype =   length = | |

```
SEQUENCE: 375
000

SEQ ID NO: 376          moltype = AA  length = 10
FEATURE                 Location/Qualifiers
REGION                  1..10
                        note = E02 LCDR3
source                  1..10
                        mol_type = protein
                        organism = Homo sapiens
SEQUENCE: 376
SSYTSTSTLV                                                              10

SEQ ID NO: 377          moltype = AA  length = 661
FEATURE                 Location/Qualifiers
REGION                  1..661
                        note = Anti-Chick Lysozyme x FS1-67 Fcab (EGFR binding
                         domain)
source                  1..661
                        mol_type = protein
                        organism = synthetic construct
SEQUENCE: 377
ASDIQMTQSP SSLSASVGDR VTITCRASGN IHNYLAWYQQ KPGKAPKLLI YYTTTLADGV        60
PSRFSGSGSG TDYTFTISSL QPEDIATYYC QHFWSTPRTF GQGTKVEIKR TAAAPSVFIF       120
PPSDEQLKSG TASVVCLLNN FYPREAKVQW KVDNALQSGN SQESVTEQDS KDSTYSLSST       180
LTLSKADYEK HKLYACEVTH QGLSSPVTKS FNRGECQVQL QESGPGLVRP SQTLSLTCTV       240
SGSTFSGYGV NWVRQPPGRG LEWIGMIWGD GNTDYNSALK SRVTMLVDTS KNQFSLRLSS       300
VTAADTAVYY CAREDYRLD YWGQGSLVTV SSASTKGPSV FPLAPSSKST SGGTAALGCL        360
VKDYFPEPVT VSWNSGALTS GVHTFPAVLQ SSGLYSLSSV VTVPSSSLGT QTYICNVNHK       420
PSNTKVDKKV EPKSCDKTHT CPPCPAPELA GAPSVFLFPP KPKDTLMISR TPEVTCVVVD       480
VSHEDPEVKF NWYVDGVEVH NAKTKPREEQ YNSTYRVVSV LTVLHQDWLN GKEYKCKVSN       540
KALPAPIEKT ISKAKGQPRE PQVYTLPPSR DETDDGPVSL TCLVKGFYPS DIAVEWESTY       600
GPENNYKTTP PVLDSDGSFF LYSKLTVSYW RWYKGNVFSC SVMHEALHNH YTQKSLSLSP       660
G                                                                     661

SEQ ID NO: 378          moltype = AA  length = 662
FEATURE                 Location/Qualifiers
REGION                  1..662
                        note = Parent C08 x FS1-67 (LAGA)
source                  1..662
                        mol_type = protein
                        organism = Homo sapiens
SEQUENCE: 378
ASSYELTQPP SVSVAPGKTA RITCGGNNIG SQSVHWYQQK PGQAPMLVIY YDSDRPSGIP        60
ERFSGSNSGN TATLTISRVE AGDEADYYCQ VWDSSSDHVV FGGGTKLTVL GQPAAAPSVT       120
LFPPSSEELQ ANKATLVCLI SDFYPGAVTV AWKADSSPVK AGVETTTPSK QSNNKYAASS       180
YLSLTPEQWK SHRSYSCQVT HEGSTVEKTV APTECSEVQL LESGGGLVQP GRSLRLSCAA       240
SGFTVSSNYM SWVRQAPGKG LEWVSVIYSG GSTYYADSVK GRFTISRDNS KNTLYLQMNS       300
LRAEDTAVYY CASPIELGAF DIWGQGTLVT VSSASTKGPS VFPLAPSSKS TSGGTAALGC       360
LVKDYFPEPV TVSWNSGALT SGVHTFPAVL QSSGLYSLSS VVTVPSSSLG TQTYICNVNH       420
KPSNTKVDKK VEPKSCDKTH TCPPCPAPEL AGAPSVFLFP PKPKDTLMIS RTPEVTCVVV       480
DVSHEDPEVK FNWYVDGVEV HNAKTKPREE QYNSTYRVVS VLTVLHQDWL NGKEYKCKVS       540
NKALPAPIEK TISKAKGQPR EPQVYTLPPS RDETDDGPVS LTCLVKGFYP SDIAVEWEST       600
YGPENNYKTT PPVLDSDGSF FLYSKLTVSY WRWYKGNVFS CSVMHEALHN HYTQKSLSLS       660
PG                                                                    662

SEQ ID NO: 379          moltype = AA  length = 666
FEATURE                 Location/Qualifiers
REGION                  1..666
                        note = Parent G04 x FS1-67 (LAGA)
source                  1..666
                        mol_type = protein
                        organism = Homo sapiens
SEQUENCE: 379
ASDIQMTQSP PALSASVGDR VTITCRASQD INDWLAWYQH KPGKAPKLLI YDASSLESGV        60
PSRFSGSGSG TEFTLTISSL QPDDFATYYC QQSYSTPQVT FGQGTRLEIK RTAAAPSVFI       120
FPPSDEQLKS GTASVVCLLN NFYPREAKVQ WKVDNALQSG NSQESVTEQD SKDSTYSLSS       180
TLTLSKADYE KHKLYACEVT HQGLSSPVTK SFNRGECQVQ LQQSGPGLVK PSQTLSLTCA       240
ISGDSVSSKS AAWNWIRQSP SRGLEWLGRT YYRSKWSTDY AASVKSRITI NPDTSKNQLS       300
LQLNSVTPED TAVYYCARTW SGYVDVWGQG TLVTVSSAST KGPSVFPLAP SSKSTSGGTA       360
ALGCLVKDYF PEPVTVSWNS GALTSGVHTF PAVLQSSGLY SLSSVVTVPS SSLGTQTYIC       420
NVNHKPSNTK VDKKVEPKSC DKTHTCPPCP APELAGAPSV FLFPPKPKDT LMISRTPEVT       480
CVVVDVSHED PEVKFNWYVD GVEVHNAKTK PREEQYNSTY RVVSVLTVLH QDWLNGKEYK       540
CKVSNKALPA PIEKTISKAK GQPREPQVYT LPPSRDETDD GPVSLTCLVK GFYPSDIAVE       600
WESTYGPENN YKTTPPVLDS DGSFFLYSKL TVSYWRWYKG NVFSCSVMHE ALHNHYTQKS       660
LSLSPG                                                                666

SEQ ID NO: 380          moltype = AA  length = 663
FEATURE                 Location/Qualifiers
```

```
REGION                  1..663
                        note = Parent E07 x FS1-67 (LAGA)
source                  1..663
                        mol_type = protein
                        organism = Homo sapiens
SEQUENCE: 380
ASDIQMTQSP SSLSASVGDR VTIACRAGQS IGTYLNWYQQ KPGKAPKLLI YVASSLQSGV    60
PSRFSGSGSG TEFTLTISSL QPEDFATYYC QQSYSTLLTF GRGTKVEIKR TAAAPSVFIF   120
PPSDEQLKSG TASVVCLLNN FYPREAKVQW KVDNALQSGN SQESVTEQDS KDSTYSLSST   180
LTLSKADYEK HKLYACEVTH QGLSSPVTKS FNRGECQVQL VESGGGLVKP GGSLRLSCAA   240
SGFTFSDYYM SWIRQAPGKG LEWVSYISSS GSTIYYADSV KGRFTISRDN AKNSLYLQMN   300
SLRAEDTAVY YCARVDYADA FDIWGQGTLV TVSSASTKGP SVFPLAPSSK STSGGTAALG   360
CLVKDYFPEP VTVSWNSGAL TSGVHTFPAV LQSSGLYSLS SVVTVPSSSL GTQTYICNVN   420
HKPSNTKVDK KVEPKSCDKT HTCPPCPAPE LAGAPSVFLF PPKPKDTLMI SRTPEVTCVV   480
VDVSHEDPEV KFNWYVDGVE VHNAKTKPRE EQYNSTYRVV SVLTVLHQDW LNGKEYKCKV   540
SNKALPAPIE KTISKAKGQP REPQVYTLPP SRDETDDGPV SLTCLVKGFY PSDIAVEWES   600
TYGPENNYKT TPPVLDSDGS FFLYSKLTVS YWRWYKGNVF SCSVMHEALH NHYTQKSLSL   660
SPG                                                                 663

SEQ ID NO: 381          moltype =     length =
SEQUENCE: 381
000

SEQ ID NO: 382          moltype =     length =
SEQUENCE: 382
000

SEQ ID NO: 383          moltype =     length =
SEQUENCE: 383
000

SEQ ID NO: 384          moltype =     length =
SEQUENCE: 384
000

SEQ ID NO: 385          moltype = AA  length = 329
FEATURE                 Location/Qualifiers
REGION                  1..329
                        note = IgG1 CH1-CH2-CH3 FS-167 Fcab
source                  1..329
                        mol_type = protein
                        organism = Homo sapiens
SEQUENCE: 385
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
TDDGPVSLTC LVKGFYPSDI AVEWESTYGP ENNYKTTPPV LDSDGSFFLY SKLTVSYWRW   300
YKGNVFSCSV MHEALHNHYT QKSLSLSPG                                    329

SEQ ID NO: 386          moltype = AA  length = 329
FEATURE                 Location/Qualifiers
REGION                  1..329
                        note = IgG1 CH1-CH2-CH3 FS-167 Fcab (LAGA)
source                  1..329
                        mol_type = protein
                        organism = Homo sapiens
SEQUENCE: 386
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELAGA   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
TDDGPVSLTC LVKGFYPSDI AVEWESTYGP ENNYKTTPPV LDSDGSFFLY SKLTVSYWRW   300
YKGNVFSCSV MHEALHNHYT QKSLSLSPG                                    329

SEQ ID NO: 387          moltype =     length =
SEQUENCE: 387
000

SEQ ID NO: 388          moltype = AA  length = 664
FEATURE                 Location/Qualifiers
REGION                  1..664
                        note = ADT1-4-2 x FS1-67 EGFR (LAGA)
source                  1..664
                        mol_type = protein
                        organism = Homo sapiens
SEQUENCE: 388
DIQMTQSPPA LSASVGDRVT ITCRASQDIN DWLAWYQHKP GKAPKLLIYD ASSLESGVPL    60
RFSGSGSGTE FTLTISSLQP DDFATYYCQQ KYSAPQVTFG QGTRLEIKRT VAAPSVFIFP   120
```

```
PSDEQLKSGT ASVVCLLNNF YPREAKVQWK VDNALQSGNS QESVTEQDSK DSTYSLSSTL    180
TLSKADYEKH KVYACEVTHQ GLSSPVTKSF NRGECEVQLQ QSGPGLVKPS QTLSLTCAIS    240
GDSVSSKSAA WNWIRQSPSR GLEWLGRTYY RSKWSTDYAA SVKSRITINP DTSKNQLSLQ    300
LNSVTPEDTA VYYCARTWVG YVDRWGQGTL VTVSSASTKG PSVFPLAPSS KSTSGGTAAL    360
GCLVKDYFPE PVTVSWNSGA LTSGVHTFPA VLQSSGLYSL SSVVTVPSSS LGTQTYICNV    420
NHKPSNTKVD KKVEPKSCDK THTCPPCPAP ELAGAPSVFL FPPKPKDTLM ISRTPEVTCV    480
VVDVSHEDPE VKFNWYVDGV EVHNAKTKPR EEQYNSTYRV VSVLTVLHQD WLNGKEYKCK    540
VSNKALPAPI EKTISKAKGQ PREPQVYTLP PSRDETDDGP VSLTCLVKGF YPSDIAVEWE    600
STYGPENNYK TTPPVLDSDG SFFLYSKLTV SYWRWYKGNV FSCSVMHEAL HNHYTQKSLS    660
LSPG                                                                664

SEQ ID NO: 389          moltype = AA  length = 664
FEATURE                 Location/Qualifiers
REGION                  1..664
                        note = ADT1-4-2 x LEE (LAGA)
source                  1..664
                        mol_type = protein
                        organism = Homo sapiens
SEQUENCE: 389
DIQMTQSPPA LSASVGDRVT ITCRASQDIN DWLAWYQHKP GKAPKLLIYD ASSLESGVPL     60
RFSGSGSGTE FTLTISSLQP DDFATYYCQQ KYSAPQVTFG QGTRLEIKRT VAAPSVFIFP    120
PSDEQLKSGT ASVVCLLNNF YPREAKVQWK VDNALQSGNS QESVTEQDSK DSTYSLSSTL    180
TLSKADYEKH KVYACEVTHQ GLSSPVTKSF NRGECEVQLQ QSGPGLVKPS QTLSLTCAIS    240
GDSVSSKSAA WNWIRQSPSR GLEWLGRTYY RSKWSTDYAA SVKSRITINP DTSKNQLSLQ    300
LNSVTPEDTA VYYCARTWVG YVDRWGQGTL VTVSSASTKG PSVFPLAPSS KSTSGGTAAL    360
GCLVKDYFPE PVTVSWNSGA LTSGVHTFPA VLQSSGLYSL SSVVTVPSSS LGTQTYICNV    420
NHKPSNTKVD KKVEPKSCDK THTCPPCPAP ELAGAPSVFL FPPKPKDTLM ISRTPEVTCV    480
VVDVSHEDPE VKFNWYVDGV EVHNAKTKPR EEQYNSTYRV VSVLTVLHQD WLNGKEYKCK    540
VSNKALPAPI EKTISKAKGQ PREPQVYTLP PSRDELEEGP VSLTCLVKGF YPSDIAVEWE    600
STYGPENNYK TTPPVLDSDG SFFLYSKLTV SYWRWYKGNV FSCSVMHEAL HNHYTQKSLS    660
LSPG                                                                664

SEQ ID NO: 390          moltype =    length =
SEQUENCE: 390
000

SEQ ID NO: 391          moltype = AA  length = 329
FEATURE                 Location/Qualifiers
REGION                  1..329
                        note = EGFR (LEE) Binding Module (LAGA)
source                  1..329
                        mol_type = protein
                        organism = Homo sapiens
SEQUENCE: 391
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPELAGA    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LEEGPVSLTC LVKGFYPSDI AVEWESTYGP ENNYKTTPPV LDSDGSFFLY SKLTVSYWRW    300
YKGNVFSCSV MHEALHNHYT QKSLSLSPG                                     329

SEQ ID NO: 392          moltype = AA  length = 329
FEATURE                 Location/Qualifiers
REGION                  1..329
                        note = EGFR (LEE) Binding Module (IgG1 wt)
source                  1..329
                        mol_type = protein
                        organism = Homo sapiens
SEQUENCE: 392
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPELLGG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LEEGPVSLTC LVKGFYPSDI AVEWESTYGP ENNYKTTPPV LDSDGSFFLY SKLTVSYWRW    300
YKGNVFSCSV MHEALHNHYT QKSLSLSPG                                     329

SEQ ID NO: 393          moltype =    length =
SEQUENCE: 393
000

SEQ ID NO: 394          moltype =    length =
SEQUENCE: 394
000

SEQ ID NO: 395          moltype =    length =
SEQUENCE: 395
000

SEQ ID NO: 396          moltype =    length =
```

```
SEQUENCE: 396
000

SEQ ID NO: 397          moltype =    length =
SEQUENCE: 397
000

SEQ ID NO: 398          moltype =    length =
SEQUENCE: 398
000

SEQ ID NO: 399          moltype = AA   length = 664
FEATURE                 Location/Qualifiers
REGION                  1..664
                        note = ADT1-4-2 x FS1-67 EGFR (wt)
source                  1..664
                        mol_type = protein
                        organism = Homo sapiens
SEQUENCE: 399
DIQMTQSPPA LSASVGDRVT ITCRASQDIN DWLAWYQHKP GKAPKLLIYD ASSLESGVPL    60
RFSGSGSGTE FTLTISSLQP DDFATYYCQQ KYSAPQVTFG QGTRLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGECEVQLQ QSGPGLVKPS QTLSLTCAIS   240
GDSVSSKSAA WNWIRQSPSR GLEWLGRTYY RSKWSTDYAA SVKSRITINP DTSKNQLSLQ   300
LNSVTPEDTA VYYCARTWVG YVDRWGQGTL VTVSSASTKG PSVFPLAPSS KSTSGGTAAL   360
GCLVKDYFPE PVTVSWNSGA LTSGVHTFPA VLQSSGLYSL SSVVTVPSSS LGTQTYICNV   420
NHKPSNTKVD KKVEPKSCDK THTCPPCPAP ELLGGPSVFL FPPKPKDTLM ISRTPEVTCV   480
VVDVSHEDPE VKFNWYVDGV EVHNAKTKPR EEQYNSTYRV VSVLTVLHQD WLNGKEYKCK   540
VSNKALPAPI EKTISKAKGQ PREPQVYTLP PSRDETDDGP VSLTCLVKGF YPSDIAVEWE   600
STYGPENNYK TTPPVLDSDG SFFLYSKLTV SYWRWYKGNV FSCSVMHEAL HNHYTQKSLS   660
LSPG                                                                664

SEQ ID NO: 400          moltype = AA   length = 664
FEATURE                 Location/Qualifiers
REGION                  1..664
                        note = ADT1-4-2 x LEE (wt)
source                  1..664
                        mol_type = protein
                        organism = Homo sapiens
SEQUENCE: 400
DIQMTQSPPA LSASVGDRVT ITCRASQDIN DWLAWYQHKP GKAPKLLIYD ASSLESGVPL    60
RFSGSGSGTE FTLTISSLQP DDFATYYCQQ KYSAPQVTFG QGTRLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGECEVQLQ QSGPGLVKPS QTLSLTCAIS   240
GDSVSSKSAA WNWIRQSPSR GLEWLGRTYY RSKWSTDYAA SVKSRITINP DTSKNQLSLQ   300
LNSVTPEDTA VYYCARTWVG YVDRWGQGTL VTVSSASTKG PSVFPLAPSS KSTSGGTAAL   360
GCLVKDYFPE PVTVSWNSGA LTSGVHTFPA VLQSSGLYSL SSVVTVPSSS LGTQTYICNV   420
NHKPSNTKVD KKVEPKSCDK THTCPPCPAP ELLGGPSVFL FPPKPKDTLM ISRTPEVTCV   480
VVDVSHEDPE VKFNWYVDGV EVHNAKTKPR EEQYNSTYRV VSVLTVLHQD WLNGKEYKCK   540
VSNKALPAPI EKTISKAKGQ PREPQVYTLP PSRDELEEGP VSLTCLVKGF YPSDIAVEWE   600
STYGPENNYK TTPPVLDSDG SFFLYSKLTV SYWRWYKGNV FSCSVMHEAL HNHYTQKSLS   660
LSPG                                                                664

SEQ ID NO: 401          moltype =    length =
SEQUENCE: 401
000

SEQ ID NO: 402          moltype =    length =
SEQUENCE: 402
000

SEQ ID NO: 403          moltype =    length =
SEQUENCE: 403
000

SEQ ID NO: 404          moltype =    length =
SEQUENCE: 404
000

SEQ ID NO: 405          moltype =    length =
SEQUENCE: 405
000

SEQ ID NO: 406          moltype =    length =
SEQUENCE: 406
000

SEQ ID NO: 407          moltype =    length =
SEQUENCE: 407
```

```
SEQ ID NO: 408          moltype =    length =
SEQUENCE: 408
000

SEQ ID NO: 409          moltype =    length =
SEQUENCE: 409
000

SEQ ID NO: 410          moltype =    length =
SEQUENCE: 410
000

SEQ ID NO: 411          moltype =    length =
SEQUENCE: 411
000

SEQ ID NO: 412          moltype =    length =
SEQUENCE: 412
000

SEQ ID NO: 413          moltype =    length =
SEQUENCE: 413
000

SEQ ID NO: 414          moltype = AA  length = 215
FEATURE                 Location/Qualifiers
REGION                  1..215
                        note = ADT1-4-2 LC
source                  1..215
                        mol_type = protein
                        organism = Homo sapiens
SEQUENCE: 414
DIQMTQSPPA LSASVGDRVT ITCRASQDIN DWLAWYQHKP GKAPKLLIYD ASSLESGVPL   60
RFSGSGSGTE FTLTISSLQP DDFATYYCQQ KYSAPQVTFG QGTRLEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                            215

SEQ ID NO: 415          moltype =    length =
SEQUENCE: 415
000

SEQ ID NO: 416          moltype =    length =
SEQUENCE: 416
000

SEQ ID NO: 417          moltype =    length =
SEQUENCE: 417
000

SEQ ID NO: 418          moltype =    length =
SEQUENCE: 418
000

SEQ ID NO: 419          moltype =    length =
SEQUENCE: 419
000

SEQ ID NO: 420          moltype =    length =
SEQUENCE: 420
000

SEQ ID NO: 421          moltype = AA  length = 217
FEATURE                 Location/Qualifiers
REGION                  1..217
                        note = G04 LC
source                  1..217
                        mol_type = protein
                        organism = Homo sapiens
SEQUENCE: 421
ASDIQMTQSP PALSASVGDR VTITCRASQD INDWLAWYQH KPGKAPKLLI YDASSLESGV   60
PSRFSGSGSG TEFTLTISSL QPDDFATYYC QQSYSTPQVT FGQGTRLEIK RTAAAPSVFI  120
FPPSDEQLKS GTASVVCLLN NFYPREAKVQ WKVDNALQSG NSQESVTEQD SKDSTYSLSS  180
TLTLSKADYE KHKLYACEVT HQGLSSPVTK SFNRGEC                          217

SEQ ID NO: 422          moltype =    length =
SEQUENCE: 422
000
```

```
SEQ ID NO: 423          moltype = AA   length = 216
FEATURE                 Location/Qualifiers
REGION                  1..216
                        note = E07 LC
source                  1..216
                        mol_type = protein
                        organism = Homo sapiens
SEQUENCE: 423
ASDIQMTQSP SSLSASVGDR VTIACRAGQS IGTYLNWYQQ KPGKAPKLLI YVASSLQSGV    60
PSRFSGSGSG TEFTLTISSL QPEDFATYYC QQSYSTLLTF GRGTKVEIKR TAAAPSVFIF   120
PPSDEQLKSG TASVVCLLNN FYPREAKVQW KVDNALQSGN SQESVTEQDS KDSTYSLSST   180
LTLSKADYEK HKLYACEVTH QGLSSPVTKS FNRGEC                             216

SEQ ID NO: 424          moltype =    length =
SEQUENCE: 424
000

SEQ ID NO: 425          moltype = AA   length = 216
FEATURE                 Location/Qualifiers
REGION                  1..216
                        note = C08 LC
source                  1..216
                        mol_type = protein
                        organism = Homo sapiens
SEQUENCE: 425
ASSYELTQPP SVSVAPGKTA RITCGGNNIG SQSVHWYQQK PGQAPMLVIY YDSDRPSGIP    60
ERFSGSNSGN TATLTISRVE AGDEADYYCQ VWDSSSDHVV FGGGTKLTVL GQPAAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                             216

SEQ ID NO: 426          moltype = AA   length = 446
FEATURE                 Location/Qualifiers
REGION                  1..446
                        note = C08 HC (LAGA) EGFR FS1-67
source                  1..446
                        mol_type = protein
                        organism = Homo sapiens
SEQUENCE: 426
EVQLLESGGG LVQPGRSLRL SCAASGFTVS SNYMSWVRQA PGKGLEWVSV IYSGGSTYYA    60
DSVKGRFTIS RDNSKNTLYL QMNSLRAEDT AVYYCASPIE LGAFDIWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELAGAPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDETDD   360
GPVSLTCLVK GFYPSDIAVE WESTYGPENN YKTTPPVLDS DGSFFLYSKL TVSYWRWYKG   420
NVFSCSVMHE ALHNHYTQKS LSLSPG                                        446

SEQ ID NO: 427          moltype = AA   length = 447
FEATURE                 Location/Qualifiers
REGION                  1..447
                        note = E07 HC (LAGA) EGFR FS1-67
source                  1..447
                        mol_type = protein
                        organism = Homo sapiens
SEQUENCE: 427
QVQLVESGGG LVKPGGSLRL SCAASGFTFS DYYMSWIRQA PGKGLEWVSY ISSSGSTIYY    60
ADSVKGRFTI SRDNAKNSLY LQMNSLRAED TAVYYCARVD YADAFDIWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELAGAPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP APIEKTISKA KGQPREPQVY TLPPSRDETD   360
DGPVSLTCLV KGFYPSDIAV EWESTYGPEN NYKTTPPVLD SDGSFFLYSK LTVSYWRWYK   420
GNVFSCSVMH EALHNHYTQK SLSLSPG                                       447

SEQ ID NO: 428          moltype =    length =
SEQUENCE: 428
000

SEQ ID NO: 429          moltype =    length =
SEQUENCE: 429
000

SEQ ID NO: 430          moltype =    length =
SEQUENCE: 430
000

SEQ ID NO: 431          moltype = AA   length = 449
FEATURE                 Location/Qualifiers
```

| | | |
|---|---|---|
| REGION | 1..449 | |
| | note = ADT1-4-2 HC (LAGA) EGFR FS1-67 | |
| source | 1..449 | |
| | mol_type = protein | |
| | organism = Homo sapiens | |

SEQUENCE: 431
```
EVQLQQSGPG LVKPSQTLSL TCAISGDSVS SKSAAWNWIR QSPSRGLEWL GRTYYRSKWS   60
TDYAASVKSR ITINPDTSKN QLSLQLNSVT PEDTAVYYCA RTWVGYVDRW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELAGA  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
TDDGPVSLTC LVKGFYPSDI AVEWESTYGP ENNYKTTPPV LDSDGSFFLY SKLTVSYWRW  420
YKGNVFSCSV MHEALHNHYT QKSLSLSPG                                   449
```

| | | |
|---|---|---|
| SEQ ID NO: 432 | moltype = AA length = 449 | |
| FEATURE | Location/Qualifiers | |
| REGION | 1..449 | |
| | note = ADT1-4-2 HC (LAGA) EGFR LEE | |
| source | 1..449 | |
| | mol_type = protein | |
| | organism = Homo sapiens | |

SEQUENCE: 432
```
EVQLQQSGPG LVKPSQTLSL TCAISGDSVS SKSAAWNWIR QSPSRGLEWL GRTYYRSKWS   60
TDYAASVKSR ITINPDTSKN QLSLQLNSVT PEDTAVYYCA RTWVGYVDRW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELAGA  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LEEGPVSLTC LVKGFYPSDI AVEWESTYGP ENNYKTTPPV LDSDGSFFLY SKLTVSYWRW  420
YKGNVFSCSV MHEALHNHYT QKSLSLSPG                                   449
```

| | | |
|---|---|---|
| SEQ ID NO: 433 | moltype = length = | |
| SEQUENCE: 433 | | |
| 000 | | |

| | | |
|---|---|---|
| SEQ ID NO: 434 | moltype = length = | |
| SEQUENCE: 434 | | |
| 000 | | |

| | | |
|---|---|---|
| SEQ ID NO: 435 | moltype = AA length = 449 | |
| FEATURE | Location/Qualifiers | |
| REGION | 1..449 | |
| | note = ADT1-4-2 HC (wt) EGFR FS1-67 | |
| source | 1..449 | |
| | mol_type = protein | |
| | organism = Homo sapiens | |

SEQUENCE: 435
```
EVQLQQSGPG LVKPSQTLSL TCAISGDSVS SKSAAWNWIR QSPSRGLEWL GRTYYRSKWS   60
TDYAASVKSR ITINPDTSKN QLSLQLNSVT PEDTAVYYCA RTWVGYVDRW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
TDDGPVSLTC LVKGFYPSDI AVEWESTYGP ENNYKTTPPV LDSDGSFFLY SKLTVSYWRW  420
YKGNVFSCSV MHEALHNHYT QKSLSLSPG                                   449
```

| | | |
|---|---|---|
| SEQ ID NO: 436 | moltype = AA length = 449 | |
| FEATURE | Location/Qualifiers | |
| REGION | 1..449 | |
| | note = ADT1-4-2 HC (wt) EGFR LEE | |
| source | 1..449 | |
| | mol_type = protein | |
| | organism = Homo sapiens | |

SEQUENCE: 436
```
EVQLQQSGPG LVKPSQTLSL TCAISGDSVS SKSAAWNWIR QSPSRGLEWL GRTYYRSKWS   60
TDYAASVKSR ITINPDTSKN QLSLQLNSVT PEDTAVYYCA RTWVGYVDRW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LEEGPVSLTC LVKGFYPSDI AVEWESTYGP ENNYKTTPPV LDSDGSFFLY SKLTVSYWRW  420
YKGNVFSCSV MHEALHNHYT QKSLSLSPG                                   449
```

| | | |
|---|---|---|
| SEQ ID NO: 437 | moltype = AA length = 449 | |
| FEATURE | Location/Qualifiers | |
| REGION | 1..449 | |
| | note = G04 HC (LAGA) EGFR FS1-67 | |
| source | 1..449 | |

```
                        mol_type = protein
                        organism = Homo sapiens
SEQUENCE: 437
QVQLQQSGPG LVKPSQTLSL TCAISGDSVS SKSAAWNWIR QSPSRGLEWL GRTYYRSKWS    60
TDYAASVKSR ITINPDTSKN QLSLQLNSVT PEDTAVYYCA RTWSGYVDVW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELAGA   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
TDDGPVSLTC LVKGFYPSDI AVEWESTYGP ENNYKTTPPV LDSDGSFFLY SKLTVSYWRW   420
YKGNVFSCSV MHEALHNHYT QKSLSLSPG                                    449

SEQ ID NO: 438          moltype =    length =
SEQUENCE: 438
000

SEQ ID NO: 439          moltype =    length =
SEQUENCE: 439
000

SEQ ID NO: 440          moltype =    length =
SEQUENCE: 440
000

SEQ ID NO: 441          moltype =    length =
SEQUENCE: 441
000

SEQ ID NO: 442          moltype =    length =
SEQUENCE: 442
000

SEQ ID NO: 443          moltype =    length =
SEQUENCE: 443
000

SEQ ID NO: 444          moltype =    length =
SEQUENCE: 444
000

SEQ ID NO: 445          moltype =    length =
SEQUENCE: 445
000

SEQ ID NO: 446          moltype =    length =
SEQUENCE: 446
000

SEQ ID NO: 447          moltype =    length =
SEQUENCE: 447
000

SEQ ID NO: 448          moltype = AA  length = 118
FEATURE                 Location/Qualifiers
REGION                  1..118
                        note = EGFR VH
source                  1..118
                        mol_type = protein
                        organism = Homo sapiens
SEQUENCE: 448
QVQLKQSGPG LVQPSQSLSI TCTVSGFSLT NYGVHWVRQS PGKGLEWLGV IWSGGNTDYN    60
TPFTSRLSIN KDNSKSQVFF KMNSLQSNDT AIYYCARALT YYDYEFAYWG QGTLVTVS    118

SEQ ID NO: 449          moltype = AA  length = 107
FEATURE                 Location/Qualifiers
REGION                  1..107
                        note = EGFR VL
source                  1..107
                        mol_type = protein
                        organism = Homo sapiens
SEQUENCE: 449
DILLTQSPVI LSVSPGERVS FSCRASQSIG TNIHWYQQRT NGSPRLLIKY ASESISGIPS    60
RFSGSGSGTD FTLSINSVES EDIADYYCQQ NNNWPTTFGA GTKLELK                107

SEQ ID NO: 450          moltype = AA  length = 8
FEATURE                 Location/Qualifiers
REGION                  1..8
                        note = EGFR HCDR1
source                  1..8
```

-continued

```
                          mol_type = protein
                          organism = Homo sapiens
SEQUENCE: 450
GFSLTNYG                                                                  8

SEQ ID NO: 451            moltype = AA   length = 7
FEATURE                   Location/Qualifiers
REGION                    1..7
                          note = EGFR HCDR2
source                    1..7
                          mol_type = protein
                          organism = Homo sapiens
SEQUENCE: 451
IWSGGNT                                                                   7

SEQ ID NO: 452            moltype = AA   length = 13
FEATURE                   Location/Qualifiers
REGION                    1..13
                          note = EGFR HCDR3
source                    1..13
                          mol_type = protein
                          organism = Homo sapiens
SEQUENCE: 452
ARALTYYDYE FAY                                                           13

SEQ ID NO: 453            moltype = AA   length = 11
FEATURE                   Location/Qualifiers
REGION                    1..11
                          note = EGFR LCDR1
source                    1..11
                          mol_type = protein
                          organism = Homo sapiens
SEQUENCE: 453
RASQSIGTNI H                                                             11

SEQ ID NO: 454            moltype = AA   length = 7
FEATURE                   Location/Qualifiers
REGION                    1..7
                          note = EGFR LCDR2
source                    1..7
                          mol_type = protein
                          organism = Homo sapiens
SEQUENCE: 454
YASESIS                                                                   7

SEQ ID NO: 455            moltype = AA   length = 9
FEATURE                   Location/Qualifiers
REGION                    1..9
                          note = EGFR LCDR3
source                    1..9
                          mol_type = protein
                          organism = Homo sapiens
SEQUENCE: 455
QQNNNWPTT                                                                 9

SEQ ID NO: 456            moltype =    length =
SEQUENCE: 456
000

SEQ ID NO: 457            moltype =    length =
SEQUENCE: 457
000

SEQ ID NO: 458            moltype =    length =
SEQUENCE: 458
000

SEQ ID NO: 459            moltype =    length =
SEQUENCE: 459
000

SEQ ID NO: 460            moltype =    length =
SEQUENCE: 460
000

SEQ ID NO: 461            moltype =    length =
SEQUENCE: 461
000
```

| | | |
|---|---|---|
| SEQ ID NO: 462<br>SEQUENCE: 462<br>000 | moltype = | length = |
| SEQ ID NO: 463<br>SEQUENCE: 463<br>000 | moltype = | length = |
| SEQ ID NO: 464<br>SEQUENCE: 464<br>000 | moltype = | length = |
| SEQ ID NO: 465<br>SEQUENCE: 465<br>000 | moltype = | length = |
| SEQ ID NO: 466<br>SEQUENCE: 466<br>000 | moltype = | length = |
| SEQ ID NO: 467<br>SEQUENCE: 467<br>000 | moltype = | length = |
| SEQ ID NO: 468<br>SEQUENCE: 468<br>000 | moltype = | length = |
| SEQ ID NO: 469<br>SEQUENCE: 469<br>000 | moltype = | length = |
| SEQ ID NO: 470<br>SEQUENCE: 470<br>000 | moltype = | length = |
| SEQ ID NO: 471<br>SEQUENCE: 471<br>000 | moltype = | length = |
| SEQ ID NO: 472<br>SEQUENCE: 472<br>000 | moltype = | length = |
| SEQ ID NO: 473<br>SEQUENCE: 473<br>000 | moltype = | length = |
| SEQ ID NO: 474<br>SEQUENCE: 474<br>000 | moltype = | length = |
| SEQ ID NO: 475<br>SEQUENCE: 475<br>000 | moltype = | length = |
| SEQ ID NO: 476<br>SEQUENCE: 476<br>000 | moltype = | length = |
| SEQ ID NO: 477<br>SEQUENCE: 477<br>000 | moltype = | length = |
| SEQ ID NO: 478<br>SEQUENCE: 478<br>000 | moltype = | length = |
| SEQ ID NO: 479<br>SEQUENCE: 479<br>000 | moltype = | length = |
| SEQ ID NO: 480<br>SEQUENCE: 480<br>000 | moltype = | length = |
| SEQ ID NO: 481<br>SEQUENCE: 481<br>000 | moltype = | length = |

| | | |
|---|---|---|
| SEQ ID NO: 482<br>SEQUENCE: 482<br>000 | moltype = | length = |
| SEQ ID NO: 483<br>SEQUENCE: 483<br>000 | moltype = | length = |
| SEQ ID NO: 484<br>SEQUENCE: 484<br>000 | moltype = | length = |
| SEQ ID NO: 485<br>SEQUENCE: 485<br>000 | moltype = | length = |
| SEQ ID NO: 486<br>SEQUENCE: 486<br>000 | moltype = | length = |
| SEQ ID NO: 487<br>SEQUENCE: 487<br>000 | moltype = | length = |
| SEQ ID NO: 488<br>SEQUENCE: 488<br>000 | moltype = | length = |
| SEQ ID NO: 489<br>SEQUENCE: 489<br>000 | moltype = | length = |
| SEQ ID NO: 490<br>SEQUENCE: 490<br>000 | moltype = | length = |
| SEQ ID NO: 491<br>SEQUENCE: 491<br>000 | moltype = | length = |
| SEQ ID NO: 492<br>SEQUENCE: 492<br>000 | moltype = | length = |
| SEQ ID NO: 493<br>SEQUENCE: 493<br>000 | moltype = | length = |
| SEQ ID NO: 494<br>SEQUENCE: 494<br>000 | moltype = | length = |
| SEQ ID NO: 495<br>SEQUENCE: 495<br>000 | moltype = | length = |
| SEQ ID NO: 496<br>SEQUENCE: 496<br>000 | moltype = | length = |
| SEQ ID NO: 497<br>SEQUENCE: 497<br>000 | moltype = | length = |
| SEQ ID NO: 498<br>SEQUENCE: 498<br>000 | moltype = | length = |
| SEQ ID NO: 499<br>SEQUENCE: 499<br>000 | moltype = | length = |
| SEQ ID NO: 500<br>SEQUENCE: 500<br>000 | moltype = | length = |
| SEQ ID NO: 501<br>SEQUENCE: 501 | moltype = | length = |

```
000

SEQ ID NO: 502          moltype =    length =
SEQUENCE: 502
000

SEQ ID NO: 503          moltype =    length =
SEQUENCE: 503
000

SEQ ID NO: 504          moltype = AA  length = 664
FEATURE                 Location/Qualifiers
REGION                  1..664
                        note = ADT1-4-2 x LEE1 (LAGA)
source                  1..664
                        mol_type = protein
                        organism = Homo sapiens
SEQUENCE: 504
DIQMTQSPPA LSASVGDRVT ITCRASQDIN DWLAWYQHKP GKAPKLLIYD ASSLESGVPL    60
RFSGSGSGTE FTLTISSLQP DDFATYYCQQ KYSAPQVTFG QGTRLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGECEVQLQ QSGPGLVKPS QTLSLTCAIS   240
GDSVSSKSAA WNWIRQSPSR GLEWLGRTYY RSKWSTDYAA SVKSRITINP DTSKNQLSLQ   300
LNSVTPEDTA VYYCARTWVG YVDRWGQGTL VTVSSASTKG PSVFPLAPSS KSTSGGTAAL   360
GCLVKDYFPE PVTVSWNSGA LTSGVHTFPA VLQSSGLYSL SSVVTVPSSS LGTQTYICNV   420
NHKPSNTKVD KKVEPKSCDK THTCPPCPAP ELAGAPSVFL FPPKPKDTLM ISRTPEVTCV   480
VVDVSHEDPE VKFNWYVDGV EVHNAKTKPR EEQYNSTYRV VSVLTVLHQD WLNGKEYKCK   540
VSNKALPAPI EKTISKAKGQ PREPQVYTLP PSRDELTKNQ VSLTCLVKGF YPSDIAVEWE   600
STYGPENNYK TTPPVLDSDG SFFLYSKLTV SYWRWYKGNV FSCSVMHEAL HNHYTQKSLS   660
LSPG                                                                664

SEQ ID NO: 505          moltype = AA  length = 664
FEATURE                 Location/Qualifiers
REGION                  1..664
                        note = ADT1-4-2 x LEE1 (wt)
source                  1..664
                        mol_type = protein
                        organism = Homo sapiens
SEQUENCE: 505
DIQMTQSPPA LSASVGDRVT ITCRASQDIN DWLAWYQHKP GKAPKLLIYD ASSLESGVPL    60
RFSGSGSGTE FTLTISSLQP DDFATYYCQQ KYSAPQVTFG QGTRLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGECEVQLQ QSGPGLVKPS QTLSLTCAIS   240
GDSVSSKSAA WNWIRQSPSR GLEWLGRTYY RSKWSTDYAA SVKSRITINP DTSKNQLSLQ   300
LNSVTPEDTA VYYCARTWVG YVDRWGQGTL VTVSSASTKG PSVFPLAPSS KSTSGGTAAL   360
GCLVKDYFPE PVTVSWNSGA LTSGVHTFPA VLQSSGLYSL SSVVTVPSSS LGTQTYICNV   420
NHKPSNTKVD KKVEPKSCDK THTCPPCPAP ELLGGPSVFL FPPKPKDTLM ISRTPEVTCV   480
VVDVSHEDPE VKFNWYVDGV EVHNAKTKPR EEQYNSTYRV VSVLTVLHQD WLNGKEYKCK   540
VSNKALPAPI EKTISKAKGQ PREPQVYTLP PSRDELTKNQ VSLTCLVKGF YPSDIAVEWE   600
STYGPENNYK TTPPVLDSDG SFFLYSKLTV SYWRWYKGNV FSCSVMHEAL HNHYTQKSLS   660
LSPG                                                                664

SEQ ID NO: 506          moltype = AA  length = 449
FEATURE                 Location/Qualifiers
REGION                  1..449
                        note = ADT1-4-2 HC EGFR LEE1 (LAGA)
source                  1..449
                        mol_type = protein
                        organism = Homo sapiens
SEQUENCE: 506
EVQLQQSGPG LVKPSQTLSL TCAISGDSVS SKSAAWNWIR QSPSRGLEWL GRTYYRSKWS    60
TDYAASVKSR ITINPDTSKN QLSLQLNSVT PEDTAVYYCA RTWVGYVDRW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELAGA   240
PSVFLFPPKP KDTLMISRTP EVTCVVVDVS HEDPEVKFNW YVDGVEVHNA KTKPREEQYN   300
STYRVVSVLT VLHQDWLNGK EYCKVSNKA LPAPIEKTIS KAKGQPREPQ VYTLPPSRDE   360
LTKNQVSLTC LVKGFYPSDI AVEWESTYGP ENNYKTTPPV LDSDGSFFLY SKLTVSYWRW   420
YKGNVFSCSV MHEALHNHYT QKSLSLSPG                                     449

SEQ ID NO: 507          moltype = AA  length = 449
FEATURE                 Location/Qualifiers
REGION                  1..449
                        note = ADT1-4-2 HC EGFR LEE1 (wt)
source                  1..449
                        mol_type = protein
                        organism = Homo sapiens
SEQUENCE: 507
EVQLQQSGPG LVKPSQTLSL TCAISGDSVS SKSAAWNWIR QSPSRGLEWL GRTYYRSKWS    60
TDYAASVKSR ITINPDTSKN QLSLQLNSVT PEDTAVYYCA RTWVGYVDRW GQGTLVTVSS   120
```

```
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKVEP KSCDKTHTCP PCPAPELLGG    240
PSVFLFPPKP KDTLMISRTP EVTCVVVDVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSRDE    360
LTKNQVSLTC LVKGFYPSDI AVEWESTYGP ENNYKTTPPV LDSDGSFFLY SKLTVSYWRW    420
YKGNVFSCSV MHEALHNHYT QKSLSLSPG                                     449

SEQ ID NO: 508          moltype = AA  length = 329
FEATURE                 Location/Qualifiers
REGION                  1..329
                        note = EGFR LEE1 Binding Module CH1-CH2-CH3 (LAGA)
source                  1..329
                        mol_type = protein
                        organism = Homo sapiens
SEQUENCE: 508
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELAGA    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESTYGP ENNYKTTPPV LDSDGSFFLY SKLTVSYWRW    300
YKGNVFSCSV MHEALHNHYT QKSLSLSPG                                     329

SEQ ID NO: 509          moltype = AA  length = 329
FEATURE                 Location/Qualifiers
REGION                  1..329
                        note = EGFR LEE1 Binding Module CH1-CH2-CH3 (wt)
source                  1..329
                        mol_type = protein
                        organism = Homo sapiens
SEQUENCE: 509
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESTYGP ENNYKTTPPV LDSDGSFFLY SKLTVSYWRW    300
YKGNVFSCSV MHEALHNHYT QKSLSLSPG                                     329

SEQ ID NO: 510          moltype = AA  length = 106
FEATURE                 Location/Qualifiers
REGION                  1..106
                        note = EGFR LEE1 CH3 Binding Module
source                  1..106
                        mol_type = protein
                        organism = Homo sapiens
SEQUENCE: 510
GQPREPQVYT LPPSRDELTK NQVSLTCLVK GFYPSDIAVE WESTYGPENN YKTTPPVLDS    60
DGSFFLYSKL TVSYWRWYKG NVFSCSVMHE ALHNHYTQKS LSLSPG                  106

SEQ ID NO: 511          moltype =   length =
SEQUENCE: 511
000

SEQ ID NO: 512          moltype = AA  length = 7
FEATURE                 Location/Qualifiers
REGION                  1..7
                        note = EGFR LEE1 EF substitutions
source                  1..7
                        mol_type = protein
                        organism = Homo sapiens
SEQUENCE: 512
SYWRWYK                                                             7

SEQ ID NO: 513          moltype = AA  length = 8
FEATURE                 Location/Qualifiers
REGION                  1..8
                        note = EGFR LEE1 AB Loop (WT)
source                  1..8
                        mol_type = protein
                        organism = Homo sapiens
SEQUENCE: 513
RDELTKNQ                                                            8

SEQ ID NO: 514          moltype = AA  length = 9
FEATURE                 Location/Qualifiers
REGION                  1..9
                        note = EGFR LEE1 CD Loop
source                  1..9
                        mol_type = protein
                        organism = Homo sapiens
```

```
SEQUENCE: 514
STYGPENNY                                                                                    9

SEQ ID NO: 515              moltype = AA  length = 10
FEATURE                     Location/Qualifiers
REGION                      1..10
                            note = EGFR LEE1 EF Loop
source                      1..10
                            mol_type = protein
                            organism = Homo sapiens
SEQUENCE: 515
SYWRWYKGNV                                                                                  10

SEQ ID NO: 516              moltype = AA  length = 664
FEATURE                     Location/Qualifiers
REGION                      1..664
                            note = ADT1-4-2 x LEE2 (LAGA)
source                      1..664
                            mol_type = protein
                            organism = Homo sapiens
SEQUENCE: 516
DIQMTQSPPA LSASVGDRVT ITCRASQDIN DWLAWYQHKP GKAPKLLIYD ASSLESGVPL      60
RFSGSGSGTE FTLTISSLQP DDFATYYCQQ KYSAPQVTFG QGTRLEIKRT VAAPSVFIFP     120
PSDEQLKSGT ASVVCLLNNF YPREAKVQWK VDNALQSGNS QESVTEQDSK DSTYSLSSTL     180
TLSKADYEKH KVYACEVTHQ GLSSPVTKSF NRGECEVQLQ QSGPGLVKPS QTLSLTCAIS     240
GDSVSSKSAA WNWIRQSPSR GLEWLGRTYY RSKWSTDYAA SVKSRITINP DTSKNQLSLQ     300
LNSVTPEDTA VYYCARTWVG YVDRWGQGTL VTVSSASTKG PSVFPLAPSS KSTSGGTAAL     360
GCLVKDYFPE PVTVSWNSGA LTSGVHTFPA VLQSSGLYSL SSVVTVPSSS LGTQTYICNV     420
NHKPSNTKVD KKVEPKSCDK THTCPPCPAP ELAGAPSVFL FPPKPKDTLM ISRTPEVTCV     480
VVDVSHEDPE VKFNWYVDGV EVHNAKTKPR EEQYNSTYRV VSVLTVLHQD WLNGKEYKCK     540
VSNKALPAPI EKTISKAKGQ PREPQVYTLP PSRDELEEGP VSLTCLVKGF YPSDIAVEWE     600
SNGQPENNYK TTPPVLDSDG SFFLYSKLTV SYWRWYKGNV FSCSVMHEAL HNHYTQKSLS     660
LSPG                                                                 664

SEQ ID NO: 517              moltype = AA  length = 664
FEATURE                     Location/Qualifiers
REGION                      1..664
                            note = ADT1-4-2 x LEE2 (wt)
source                      1..664
                            mol_type = protein
                            organism = Homo sapiens
SEQUENCE: 517
DIQMTQSPPA LSASVGDRVT ITCRASQDIN DWLAWYQHKP GKAPKLLIYD ASSLESGVPL      60
RFSGSGSGTE FTLTISSLQP DDFATYYCQQ KYSAPQVTFG QGTRLEIKRT VAAPSVFIFP     120
PSDEQLKSGT ASVVCLLNNF YPREAKVQWK VDNALQSGNS QESVTEQDSK DSTYSLSSTL     180
TLSKADYEKH KVYACEVTHQ GLSSPVTKSF NRGECEVQLQ QSGPGLVKPS QTLSLTCAIS     240
GDSVSSKSAA WNWIRQSPSR GLEWLGRTYY RSKWSTDYAA SVKSRITINP DTSKNQLSLQ     300
LNSVTPEDTA VYYCARTWVG YVDRWGQGTL VTVSSASTKG PSVFPLAPSS KSTSGGTAAL     360
GCLVKDYFPE PVTVSWNSGA LTSGVHTFPA VLQSSGLYSL SSVVTVPSSS LGTQTYICNV     420
NHKPSNTKVD KKVEPKSCDK THTCPPCPAP ELLGGPSVFL FPPKPKDTLM ISRTPEVTCV     480
VVDVSHEDPE VKFNWYVDGV EVHNAKTKPR EEQYNSTYRV VSVLTVLHQD WLNGKEYKCK     540
VSNKALPAPI EKTISKAKGQ PREPQVYTLP PSRDELEEGP VSLTCLVKGF YPSDIAVEWE     600
SNGQPENNYK TTPPVLDSDG SFFLYSKLTV SYWRWYKGNV FSCSVMHEAL HNHYTQKSLS     660
LSPG                                                                 664

SEQ ID NO: 518              moltype = AA  length = 449
FEATURE                     Location/Qualifiers
REGION                      1..449
                            note = ADT1-4-2 HC EGFR LEE2 (LAGA)
source                      1..449
                            mol_type = protein
                            organism = Homo sapiens
SEQUENCE: 518
EVQLQQSGPG LVKPSQTLSL TCAISGDSVS SKSAAWNWIR QSPSRGLEWL GRTYYRSKWS      60
TDYAASVKSR ITINPDTSKN QLSLQLNSVT PEDTAVYYCA RTWVGYVDRW GQGTLVTVSS     120
ASTKGPSVFP LAPSSKSTSG GTAALGCLVK DYFPEPVTVS WNSGALTSGV HTFPAVLQSS     180
GLYSLSSVVT VPSSSLGTQT YICNVNHKPS NTKVDKKVEP KSCDKTHTCP PCPAPELAGA     240
PSVFLFPPKP KDTLMISRTP EVTCVVVDVS HEDPEVKFNW YVDGVEVHNA KTKPREEQYN     300
STYRVVSVLT VLHQDWLNGK EYKCKVSNKA LPAPIEKTIS KAKGQPREPQ VYTLPPSRDE     360
LEEGPVSLTC LVKGFYPSDI AVEWESNGQP ENNYKTTPPV LDSDGSFFLY SKLTVSYWRW     420
YKGNVFSCSV MHEALHNHYT QKSLSLSPG                                      449

SEQ ID NO: 519              moltype = AA  length = 449
FEATURE                     Location/Qualifiers
REGION                      1..449
                            note = ADT1-4-2 HC EGFR LEE2 (wt)
source                      1..449
                            mol_type = protein
                            organism = Homo sapiens
```

```
SEQUENCE: 519
EVQLQQSGPG LVKPSQTLSL TCAISGDSVS SKSAAWNWIR QSPSRGLEWL GRTYYRSKWS    60
TDYAASVKSR ITINPDTSKN QLSLQLNSVT PEDTAVYYCA RTWVGYVDRW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LEEGPVSLTC LVKGFYPSDI AVEWESNGQP ENNYKTTPPV LDSDGSFFLY SKLTVSYWRW   420
YKGNVFSCSV MHEALHNHYT QKSLSLSPG                                    449

SEQ ID NO: 520            moltype = AA   length = 329
FEATURE                   Location/Qualifiers
REGION                    1..329
                          note = EGFR LEE2 Binding Module CH1-CH2-CH3 (LAGA)
source                    1..329
                          mol_type = protein
                          organism = Homo sapiens
SEQUENCE: 520
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELAGA   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LEEGPVSLTC LVKGFYPSDI AVEWESNGQP ENNYKTTPPV LDSDGSFFLY SKLTVSYWRW   300
YKGNVFSCSV MHEALHNHYT QKSLSLSPG                                    329

SEQ ID NO: 521            moltype = AA   length = 329
FEATURE                   Location/Qualifiers
REGION                    1..329
                          note = EGFR LEE2 Binding Module CH1-CH2-CH3 (wt)
source                    1..329
                          mol_type = protein
                          organism = Homo sapiens
SEQUENCE: 521
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LEEGPVSLTC LVKGFYPSDI AVEWESNGQP ENNYKTTPPV LDSDGSFFLY SKLTVSYWRW   300
YKGNVFSCSV MHEALHNHYT QKSLSLSPG                                    329

SEQ ID NO: 522            moltype = AA   length = 106
FEATURE                   Location/Qualifiers
REGION                    1..106
                          note = EGFR LEE2 CH3 Binding Module
source                    1..106
                          mol_type = protein
                          organism = Homo sapiens
SEQUENCE: 522
GQPREPQVYT LPPSRDELEE GPVSLTCLVK GFYPSDIAVE WESNGQPENN YKTTPPVLDS    60
DGSFFLYSKL TVSYWRWYKG NVFSCSVMHE ALHNHYTQKS LSLSPG                  106

SEQ ID NO: 523            moltype = AA   length = 4
FEATURE                   Location/Qualifiers
REGION                    1..4
                          note = EGFR LEE2 AB substitutions
source                    1..4
                          mol_type = protein
                          organism = Homo sapiens
SEQUENCE: 523
EEGP                                                                 4

SEQ ID NO: 524            moltype = AA   length = 8
FEATURE                   Location/Qualifiers
REGION                    1..8
                          note = EGFR LEE2 AB Loop
source                    1..8
                          mol_type = protein
                          organism = Homo sapiens
SEQUENCE: 524
RDELEEGP                                                             8

SEQ ID NO: 525            moltype = AA   length = 9
FEATURE                   Location/Qualifiers
REGION                    1..9
                          note = EGFR LEE2 CD Loop (WT)
source                    1..9
                          mol_type = protein
                          organism = Homo sapiens
SEQUENCE: 525
```

```
SNGQPENNY                                                                      9

SEQ ID NO: 526          moltype = AA  length = 664
FEATURE                 Location/Qualifiers
REGION                  1..664
                        note = ADT1-4-2 x LEE3 (LAGA)
source                  1..664
                        mol_type = protein
                        organism = Homo sapiens
SEQUENCE: 526
DIQMTQSPPA LSASVGDRVT ITCRASQDIN DWLAWYQHKP GKAPKLLIYD ASSLESGVPL    60
RFSGSGSGTE FTLTISSLQP DDFATYYCQQ KYSAPQVTFG QGTRLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGECEVQLQ QSGPGLVKPS QTLSLTCAIS   240
GDSVSSKSAA WNWIRQSPSR GLEWLGRTYY RSKWSTDYAA SVKSRITINP DTSKNQLSLQ   300
LNSVTPEDTA VYYCARTWVG YVDRWGQGTL VTVSSASTKG PSVFPLAPSS KSTSGGTAAL   360
GCLVKDYFPE PVTVSWNSGA LTSGVHTFPA VLQSSGLYSL SSVVTVPSSS LGTQTYICNV   420
NHKPSNTKVD KKVEPKSCDK THTCPPCPAP ELAGAPSVFL FPPKPKDTLM ISRTPEVTCV   480
VVDVSHEDPE VKFNWYVDGV EVHNAKTKPR EEQYNSTYRV VSVLTVLHQD WLNGKEYKCK   540
VSNKALPAPI EKTISKAKGQ PREPQVYTLP PSRDELEEGP VSLTCLVKGF YPSDIAVEWE   600
STYGPENNYK TTPPVLDSDG SFFLYSKLTV SYWRWQQGNV FSCSVMHEAL HNHYTQKSLS   660
LSPG                                                              664

SEQ ID NO: 527          moltype = AA  length = 664
FEATURE                 Location/Qualifiers
REGION                  1..664
                        note = ADT1-4-2 x LEE3 (wt)
source                  1..664
                        mol_type = protein
                        organism = Homo sapiens
SEQUENCE: 527
DIQMTQSPPA LSASVGDRVT ITCRASQDIN DWLAWYQHKP GKAPKLLIYD ASSLESGVPL    60
RFSGSGSGTE FTLTISSLQP DDFATYYCQQ KYSAPQVTFG QGTRLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGECEVQLQ QSGPGLVKPS QTLSLTCAIS   240
GDSVSSKSAA WNWIRQSPSR GLEWLGRTYY RSKWSTDYAA SVKSRITINP DTSKNQLSLQ   300
LNSVTPEDTA VYYCARTWVG YVDRWGQGTL VTVSSASTKG PSVFPLAPSS KSTSGGTAAL   360
GCLVKDYFPE PVTVSWNSGA LTSGVHTFPA VLQSSGLYSL SSVVTVPSSS LGTQTYICNV   420
NHKPSNTKVD KKVEPKSCDK THTCPPCPAP ELLGGPSVFL FPPKPKDTLM ISRTPEVTCV   480
VVDVSHEDPE VKFNWYVDGV EVHNAKTKPR EEQYNSTYRV VSVLTVLHQD WLNGKEYKCK   540
VSNKALPAPI EKTISKAKGQ PREPQVYTLP PSRDELEEGP VSLTCLVKGF YPSDIAVEWE   600
STYGPENNYK TTPPVLDSDG SFFLYSKLTV SYWRWQQGNV FSCSVMHEAL HNHYTQKSLS   660
LSPG                                                              664

SEQ ID NO: 528          moltype = AA  length = 449
FEATURE                 Location/Qualifiers
REGION                  1..449
                        note = ADT1-4-2 HC EGFR LEE3 (LAGA)
source                  1..449
                        mol_type = protein
                        organism = Homo sapiens
SEQUENCE: 528
EVQLQQSGPG LVKPSQTLSL TCAISGDSVS SKSAAWNWIR QSPSRGLEWL GRTYYRSKWS    60
TDYAASVKSR ITINPDTSKN QLSLQLNSVT PEDTAVYYCA RTWVGYVDRW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELAGA   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LEEGPVSLTC LVKGFYPSDI AVEWESTYGP ENNYKTTPPV LDSDGSFFLY SKLTVSYWRW   420
QQGNVFSCSV MHEALHNHYT QKSLSLSPG                                   449

SEQ ID NO: 529          moltype = AA  length = 449
FEATURE                 Location/Qualifiers
REGION                  1..449
                        note = ADT1-4-2 HC EGFR LEE3 (wt)
source                  1..449
                        mol_type = protein
                        organism = Homo sapiens
SEQUENCE: 529
EVQLQQSGPG LVKPSQTLSL TCAISGDSVS SKSAAWNWIR QSPSRGLEWL GRTYYRSKWS    60
TDYAASVKSR ITINPDTSKN QLSLQLNSVT PEDTAVYYCA RTWVGYVDRW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LEEGPVSLTC LVKGFYPSDI AVEWESTYGP ENNYKTTPPV LDSDGSFFLY SKLTVSYWRW   420
QQGNVFSCSV MHEALHNHYT QKSLSLSPG                                   449

SEQ ID NO: 530          moltype = AA  length = 329
```

| FEATURE | Location/Qualifiers |
|---|---|
| REGION | 1..329 |
| | note = EGFR LEE3 Binding Module CH1-CH2-CH3 (LAGA) |
| source | 1..329 |
| | mol_type = protein |
| | organism = Homo sapiens |

SEQUENCE: 530

```
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELAGA   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LEEGPVSLTC LVKGFYPSDI AVEWESTYGP ENNYKTTPPV LDSDGSFFLY SKLTVSYWRW   300
QQGNVFSCSV MHEALHNHYT QKSLSLSPG                                    329
```

| SEQ ID NO: 531 | moltype = AA length = 329 |
|---|---|
| FEATURE | Location/Qualifiers |
| REGION | 1..329 |
| | note = EGFR LEE3 Binding Module CH1-CH2-CH3 (wt) |
| source | 1..329 |
| | mol_type = protein |
| | organism = Homo sapiens |

SEQUENCE: 531

```
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LEEGPVSLTC LVKGFYPSDI AVEWESTYGP ENNYKTTPPV LDSDGSFFLY SKLTVSYWRW   300
QQGNVFSCSV MHEALHNHYT QKSLSLSPG                                    329
```

| SEQ ID NO: 532 | moltype = AA length = 106 |
|---|---|
| FEATURE | Location/Qualifiers |
| REGION | 1..106 |
| | note = EGFR LEE3 CH3 Binding Module |
| source | 1..106 |
| | mol_type = protein |
| | organism = Homo sapiens |

SEQUENCE: 532

```
GQPREPQVYT LPPSRDELEE GPVSLTCLVK GFYPSDIAVE WESTYGPENN YKTTPPVLDS    60
DGSFFLYSKL TVSYWRWQQG NVFSCSVMHE ALHNHYTQKS LSLSPG                 106
```

| SEQ ID NO: 533 | moltype = length = |
|---|---|

SEQUENCE: 533
000

| SEQ ID NO: 534 | moltype = AA length = 10 |
|---|---|
| FEATURE | Location/Qualifiers |
| REGION | 1..10 |
| | note = EGFR LEE3 EF Loop |
| source | 1..10 |
| | mol_type = protein |
| | organism = Homo sapiens |

SEQUENCE: 534

```
SYWRWQQGNV                                                          10
```

| SEQ ID NO: 535 | moltype = AA length = 665 |
|---|---|
| FEATURE | Location/Qualifiers |
| REGION | 1..665 |
| | note = ADT1-4-2 x FS1-65 (LAGA) |
| source | 1..665 |
| | mol_type = protein |
| | organism = Homo sapiens |

SEQUENCE: 535

```
DIQMTQSPPA LSASVGDRVT ITCRASQDIN DWLAWYQHKP GKAPKLLIYD ASSLESGVPL    60
RFSGSGSGTE FTLTISSLQP DDFATYYCQQ KYSAPQVTFG QGTRLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGECEVQLQ QSGPGLVKPS QTLSLTCAIS   240
GDSVSSKSAA WNWIRQSPSR GLEWLGRTYY RSKWSTDYAA SVKSRITINP DTSKNQLSLQ   300
LNSVTPEDTA VYYCARTWVG YVDRWGQGTL VTVSSASTKG PSVFPLAPSS KSTSGGTAAL   360
GCLVKDYFPE PVTVSWNSGA LTSGVHTFPA VLQSSGLYSL SSVVTVPSSS LGTQTYICNV   420
NHKPSNTKVD KKVEPKSCDK THTCPPCPAP ELAGAPSVFL FPPKPKDTLM ISRTPEVTCV   480
VVDVSHEDPE VKFNWYVDGV EVHNAKTKPR EEQYNSTYRV VSVLTVLHQD WLNGKEYKCK   540
VSNKALPAPI EKTISKAKGQ PREPQVYTLP PSRDELDEGG PVSLTCLVKG FYPSDIAVEW   600
ESTYGPENNY KTTPPVLDSD GSFFLYSKLT VSYWRWVKGN VFSCSVMHEA LHNHYTQKSL   660
SLSPG                                                              665
```

| SEQ ID NO: 536 | moltype = AA length = 665 |
|---|---|
| FEATURE | Location/Qualifiers |
| REGION | 1..665 |
| | note = ADT1-4-2 x FS1-65 (wt) |

```
source                      1..665
                            mol_type = protein
                            organism = Homo sapiens
SEQUENCE: 536
DIQMTQSPPA LSASVGDRVT ITCRASQDIN DWLAWYQHKP GKAPKLLIYD ASSLESGVPL    60
RFSGSGSGTE FTLTISSLQP DDFATYYCQQ KYSAPQVTFG QGTRLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGECEVQLQ QSGPGLVKPS QTLSLTCAIS   240
GDSVSSKSAA WNWIRQSPSR GLEWLGRTYY RSKWSTDYAA SVKSRITINP DTSKNQLSLQ   300
LNSVTPEDTA VYYCARTWVG YVDRWGQGTL VTVSSASTKG PSVFPLAPSS KSTSGGTAAL   360
GCLVKDYFPE PVTVSWNSGA LTSGVHTFPA VLQSSGLYSL SSVVTVPSSS LGTQTYICNV   420
NHKPSNTKVD KKVEPKSCDK THTCPPCPAP ELLGGPSVFL FPPKPKDTLM ISRTPEVTCV   480
VVDVSHEDPE VKFNWYVDGV EVHNAKTKPR EEQYNSTYRV VSVLTVLHQD WLNGKEYKCK   540
VSNKALPAPI EKTISKAKGQ PREPQVYTLP PSRDELDEGG PVSLTCLVKG FYPSDIAVEW   600
ESTYGPENNY KTTPPVLDSD GSFFLYSKLT VSYWRWVKGN VFSCSVMHEA LHNHYTQKSL   660
SLSPG                                                              665

SEQ ID NO: 537              moltype = AA   length = 450
FEATURE                     Location/Qualifiers
REGION                      1..450
                            note = ADT1-4-2 HC EGFR FS1-65 (LAGA)
source                      1..450
                            mol_type = protein
                            organism = Homo sapiens
SEQUENCE: 537
EVQLQQSGPG LVKPSQTLSL TCAISGDSVS SKSAAWNWIR QSPSRGLEWL GRTYYRSKWS    60
TDYAASVKSR ITINPDTSKN QLSLQLNSVT PEDTAVYYCA RTWVGYVDRW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCAPELAGA   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LDEGGPVSLT CLVKGFYPSD IAVEWESTYG PENNYKTTPP VLDSDGSFFL YSKLTVSYWR   420
WVKGNVFSCS VMHEALHNHY TQKSLSLSPG                                   450

SEQ ID NO: 538              moltype = AA   length = 330
FEATURE                     Location/Qualifiers
REGION                      1..330
                            note = ADT1-4-2 HC EGFR FS1-65 (wt)
source                      1..330
                            mol_type = protein
                            organism = Homo sapiens
SEQUENCE: 538
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LDEGGPVSLT CLVKGFYPSD IAVEWESTYG PENNYKTTPP VLDSDGSFFL YSKLTVSYWR   300
WVKGNVFSCS VMHEALHNHY TQKSLSLSPG                                   330

SEQ ID NO: 539              moltype = AA   length = 330
FEATURE                     Location/Qualifiers
REGION                      1..330
                            note = EGFR FS1-65 Binding Module CH1-CH2-CH3 (LAGA)
source                      1..330
                            mol_type = protein
                            organism = Homo sapiens
SEQUENCE: 539
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCAPELAGA   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LDEGGPVSLT CLVKGFYPSD IAVEWESTYG PENNYKTTPP VLDSDGSFFL YSKLTVSYWR   300
WVKGNVFSCS VMHEALHNHY TQKSLSLSPG                                   330

SEQ ID NO: 540              moltype = AA   length = 450
FEATURE                     Location/Qualifiers
REGION                      1..450
                            note = EGFR FS1-65 Binding Module CH1-CH2-CH3 (wt)
source                      1..450
                            mol_type = protein
                            organism = Homo sapiens
SEQUENCE: 540
EVQLQQSGPG LVKPSQTLSL TCAISGDSVS SKSAAWNWIR QSPSRGLEWL GRTYYRSKWS    60
TDYAASVKSR ITINPDTSKN QLSLQLNSVT PEDTAVYYCA RTWVGYVDRW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LDEGGPVSLT CLVKGFYPSD IAVEWESTYG PENNYKTTPP VLDSDGSFFL YSKLTVSYWR   420
```

```
WVKGNVFSCS VMHEALHNHY TQKSLSLSPG                                         450

SEQ ID NO: 541          moltype = AA  length = 107
FEATURE                 Location/Qualifiers
REGION                  1..107
                        note = EGFR FS1-65 CH3 binding module
source                  1..107
                        mol_type = protein
                        organism = Homo sapiens
SEQUENCE: 541
GQPREPQVYT LPPSRDELDE GGPVSLTCLV KGFYPSDIAV EWESTYGPEN NYKTTPPVLD          60
SDGSFFLYSK LTVSYWRWVK GNVFSCSVMH EALHNHYTQK SLSLSPG                       107

SEQ ID NO: 542          moltype = AA  length = 6
FEATURE                 Location/Qualifiers
REGION                  1..6
                        note = EGFR FS1-65 AB substitutions
source                  1..6
                        mol_type = protein
                        organism = Homo sapiens
SEQUENCE: 542
LDEGGP                                                                      6

SEQ ID NO: 543          moltype = AA  length = 7
FEATURE                 Location/Qualifiers
REGION                  1..7
                        note = EGFR FS1-65 EF substitutions
source                  1..7
                        mol_type = protein
                        organism = Homo sapiens
SEQUENCE: 543
SYWRWVK                                                                     7

SEQ ID NO: 544          moltype = AA  length = 9
FEATURE                 Location/Qualifiers
REGION                  1..9
                        note = EGFR FS1-65 AB Loop
source                  1..9
                        mol_type = protein
                        organism = Homo sapiens
SEQUENCE: 544
RDELDEGGP                                                                   9

SEQ ID NO: 545          moltype = AA  length = 10
FEATURE                 Location/Qualifiers
REGION                  1..10
                        note = EGFR FS1-65 EF Loop
source                  1..10
                        mol_type = protein
                        organism = Homo sapiens
SEQUENCE: 545
SYWRWVKGNV                                                                 10

SEQ ID NO: 546          moltype = AA  length = 664
FEATURE                 Location/Qualifiers
REGION                  1..664
                        note = ADT1-4-2 x 747 (LAGA)
source                  1..664
                        mol_type = protein
                        organism = Homo sapiens
SEQUENCE: 546
DIQMTQSPPA LSASVGDRVT ITCRASQDIN DWLAWYQHKP GKAPKLLIYD ASSLESGVPL          60
RFSGSGSGTE FTLTISSLQP DDFATYYCQQ KYSAPQVTFG QGTRLEIKRT VAAPSVFIFP         120
PSDEQLKSGT ASVVCLLNNF YPREAKVQWK VDNALQSGNS QESVTEQDSK DSTYSLSSTL         180
TLSKADYEKH KVYACEVTHQ GLSSPVTKSF NRGECEVQLQ QSGPGLVKPS QTLSLTCAIS         240
GDSVSSKSAA WNWIRQSPSR GLEWLGRTYY RSKWSTDYAA SVKSRITINP DTSKNQLSLQ         300
LNSVTPEDTA VYYCARTWVG YVDRWGQGTL VTVSSASTKG PSVFPLAPSS KSTSGGTAAL         360
GCLVKDYFPE PVTVSWNSGA LTSGVHTFPA VLQSSGLYSL SSVVTVPSSS LGTQTYICNV         420
NHKPSNTKVD KKVEPKSCDK THTCPPCPAP ELAGAPSVFL FPPKPKDTLM ISRTPEVTCV         480
VVDVSHEDPE VKFNWYVDGV EVHNAKTKPR EEQYNSTYRV VSVLTVLHQD WLNGKEYKCK         540
VSNKALPAPI EKTISKAKGQ PREPQVYTLP PSRDETESGP VSLTCLVKGF YPSDIVVEWE         600
SKFGPENNYK TTPPVLDSDG SFFLYSKLTV SNLRWTKGHV FSCSVMHEAL HNHYTQKSLS         660
LSPG                                                                     664

SEQ ID NO: 547          moltype = AA  length = 664
FEATURE                 Location/Qualifiers
REGION                  1..664
                        note = ADT1-4-2 x 747 (wt)
source                  1..664
```

```
                        mol_type = protein
                        organism = Homo sapiens
SEQUENCE: 547
DIQMTQSPPA LSASVGDRVT ITCRASQDIN DWLAWYQHKP GKAPKLLIYD ASSLESGVPL    60
RFSGSGSGTE FTLTISSLQP DDFATYYCQQ KYSAPQVTFG QGTRLEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGECEVQLQ QSGPGLVKPS QTLSLTCAIS   240
GDSVSSKSAA WNWIRQSPSR GLEWLGRTYY RSKWSTDYAA SVKSRITINP DTSKNQLSLQ   300
LNSVTPEDTA VYYCARTWVG YVDRWGQGTL VTVSSASTKG PSVFPLAPSS KSTSGGTAAL   360
GCLVKDYFPE PVTVSWNSGA LTSGVHTFPA VLQSSGLYSL SSVVTVPSSS LGTQTYICNV   420
NHKPSNTKVD KKVEPKSCDK THTCPPCPAP ELLGGPSVFL FPPKPKDTLM ISRTPEVTCV   480
VVDVSHEDPE VKFNWYVDGV EVHNAKTKPR EEQYNSTYRV VSVLTVLHQD WLNGKEYKCK   540
VSNKALPAPI EKTISKAKGQ PREPQVYTLP PSRDETESGP VSLTCLVKGF YPSDIVVEWE   600
SKFGPENNYK TTPPVLDSDG SFFLYSKLTV SNLRWTKGHV FSCSVMHEAL HNHYTQKSLS   660
LSPG                                                                664

SEQ ID NO: 548          moltype = AA  length = 449
FEATURE                 Location/Qualifiers
REGION                  1..449
                        note = ADT1-4-2 HC EGFR 747 (LAGA)
source                  1..449
                        mol_type = protein
                        organism = Homo sapiens
SEQUENCE: 548
EVQLQQSGPG LVKPSQTLSL TCAISGDSVS SKSAAWNWIR QSPSRGLEWL GRTYYRSKWS    60
TDYAASVKSR ITINPDTSKN QLSLQLNSVT PEDTAVYYCA RTWVGYVDRW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELAGA   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
TESGPVSLTC LVKGFYPSDI VVEWESKFGP ENNYKTTPPV LDSDGSFFLY SKLTVSNLRW   420
TKGHVFSCSV MHEALHNHYT QKSLSLSPG                                     449

SEQ ID NO: 549          moltype = AA  length = 449
FEATURE                 Location/Qualifiers
REGION                  1..449
                        note = ADT1-4-2 HC EGFR 747 (wt)
source                  1..449
                        mol_type = protein
                        organism = Homo sapiens
SEQUENCE: 549
EVQLQQSGPG LVKPSQTLSL TCAISGDSVS SKSAAWNWIR QSPSRGLEWL GRTYYRSKWS    60
TDYAASVKSR ITINPDTSKN QLSLQLNSVT PEDTAVYYCA RTWVGYVDRW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
TESGPVSLTC LVKGFYPSDI VVEWESKFGP ENNYKTTPPV LDSDGSFFLY SKLTVSNLRW   420
TKGHVFSCSV MHEALHNHYT QKSLSLSPG                                     449

SEQ ID NO: 550          moltype = AA  length = 329
FEATURE                 Location/Qualifiers
REGION                  1..329
                        note = EGFR 747 Binding Module CH1-CH2-CH3 (LAGA)
source                  1..329
                        mol_type = protein
                        organism = Homo sapiens
SEQUENCE: 550
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELAGA   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
TESGPVSLTC LVKGFYPSDI VVEWESKFGP ENNYKTTPPV LDSDGSFFLY SKLTVSNLRW   300
TKGHVFSCSV MHEALHNHYT QKSLSLSPG                                     329

SEQ ID NO: 551          moltype = AA  length = 329
FEATURE                 Location/Qualifiers
REGION                  1..329
                        note = EGFR 747 Binding Module CH1-CH2-CH3 (wt)
source                  1..329
                        mol_type = protein
                        organism = Homo sapiens
SEQUENCE: 551
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
TESGPVSLTC LVKGFYPSDI VVEWESKFGP ENNYKTTPPV LDSDGSFFLY SKLTVSNLRW   300
TKGHVFSCSV MHEALHNHYT QKSLSLSPG                                     329
```

```
SEQ ID NO: 552          moltype = AA   length = 106
FEATURE                 Location/Qualifiers
REGION                  1..106
                        note = 747 CH3 Binding Module
source                  1..106
                        mol_type = protein
                        organism = Homo sapiens
SEQUENCE: 552
GQPREPQVYT LPPSRDETES GPVSLTCLVK GFYPSDIVVE WESKFGPENN YKTTPPVLDS    60
DGSFFLYSKL TVSNLRWTKG HVFSCSVMHE ALHNHYTQKS LSLSPG                  106

SEQ ID NO: 553          moltype = AA   length = 5
FEATURE                 Location/Qualifiers
REGION                  1..5
                        note = EGFR 747 AB substitutions
source                  1..5
                        mol_type = protein
                        organism = Homo sapiens
SEQUENCE: 553
TESGP                                                               5

SEQ ID NO: 554          moltype =   length =
SEQUENCE: 554
000

SEQ ID NO: 555          moltype = AA   length = 9
FEATURE                 Location/Qualifiers
REGION                  1..9
                        note = EGFR 747 EF substitutions
source                  1..9
                        mol_type = protein
                        organism = Homo sapiens
SEQUENCE: 555
SNLRWTKGH                                                           9

SEQ ID NO: 556          moltype = AA   length = 8
FEATURE                 Location/Qualifiers
REGION                  1..8
                        note = EGFR 747 AB Loop
source                  1..8
                        mol_type = protein
                        organism = Homo sapiens
SEQUENCE: 556
RDETESGP                                                            8

SEQ ID NO: 557          moltype = AA   length = 9
FEATURE                 Location/Qualifiers
REGION                  1..9
                        note = EGFR 747 CD Loop
source                  1..9
                        mol_type = protein
                        organism = Homo sapiens
SEQUENCE: 557
SKFGPENNY                                                           9

SEQ ID NO: 558          moltype = AA   length = 10
FEATURE                 Location/Qualifiers
REGION                  1..10
                        note = EGFR 747 EF Loop
source                  1..10
                        mol_type = protein
                        organism = Homo sapiens
SEQUENCE: 558
SNLRWTKGHV                                                          10

SEQ ID NO: 559          moltype = AA   length = 106
FEATURE                 Location/Qualifiers
REGION                  1..106
                        note = EGFR FS1-67 CH3 Binding Module
source                  1..106
                        mol_type = protein
                        organism = Homo sapiens
SEQUENCE: 559
GQPREPQVYT LPPSRDETDD GPVSLTCLVK GFYPSDIAVE WESTYGPENN YKTTPPVLDS    60
DGSFFLYSKL TVSYWRWYKG NVFSCSVMHE ALHNHYTQKS LSLSPG                  106

SEQ ID NO: 560          moltype = AA   length = 5
FEATURE                 Location/Qualifiers
```

```
REGION                  1..5
                        note = EGFR FS1-67 AB substitutions
source                  1..5
                        mol_type = protein
                        organism = Homo sapiens
SEQUENCE: 560
TDDGP                                                                         5

SEQ ID NO: 561          moltype = AA  length = 8
FEATURE                 Location/Qualifiers
REGION                  1..8
                        note = EGFR FS1-67 AB Loop
source                  1..8
                        mol_type = protein
                        organism = Homo sapiens
SEQUENCE: 561
RDETDDGP                                                                      8

SEQ ID NO: 562          moltype = AA  length = 106
FEATURE                 Location/Qualifiers
REGION                  1..106
                        note = EGFR LEE CH3 Binding Module
source                  1..106
                        mol_type = protein
                        organism = Homo sapiens
SEQUENCE: 562
GQPREPQVYT LPPSRDELEE GPVSLTCLVK GFYPSDIAVE WESTYGPENN YKTTPPVLDS            60
DGSFFLYSKL TVSYWRWYKG NVFSCSVMHE ALHNHYTQKS LSLSPG                          106

SEQ ID NO: 563          moltype = AA  length = 106
FEATURE                 Location/Qualifiers
REGION                  1..106
                        note = IgG1 wt CH3
source                  1..106
                        mol_type = protein
                        organism = Homo sapiens
SEQUENCE: 563
GQPREPQVYT LPPSRDELTK NQVSLTCLVK GFYPSDIAVE WESNGQPENN YKTTPPVLDS            60
DGSFFLYSKL TVDKSRWQQG NVFSCSVMHE ALHNHYTQKS LSLSPG                          106
```

MULTISPECIFIC ANTI-TCR DELTA VARIABLE 1 ANTIBODIES

RELATED APPLICATIONS

This application claims the benefit under 35 U.S.C. § 365(c) and § 120 and is a continuation of International Patent Application Number PCT/EP2022/054011, filed Feb. 17, 2022, which claims the benefit of Great Britain application number GB 2111685.0, filed Aug. 14, 2021, and Great Britain application number GB 2102224.9, filed Feb. 17, 2021, each of which is herein incorporated by reference in its entirety.

REFERENCE TO AN ELECTRONIC SEQUENCE LISTING

The contents of the electronic sequence listing (T083370049US00-SEQ-ARM.xml; Size: 660,846 bytes; and Date of Creation: Aug. 15, 2023) is herein incorporated by reference in its entirety.

FIELD OF THE INVENTION

The present invention relates to multispecific antibodies and fragments and variants thereof that specifically bind the T cell receptor of gamma delta T cells, and specifically bind to EGFR.

BACKGROUND

The growing interest in T cell immunotherapy for cancer has focused on the evident capacity of subsets of CD8+ and CD4+ alpha beta ($\alpha\beta$) T cells to recognize cancer cells and to mediate host-protective functional potentials, particularly when de-repressed by clinically mediated antagonism of inhibitory pathways exerted by PD-1, CTLA-4, and other receptors. However, $\alpha\beta$ T cells are MHC-restricted which can lead to graft versus host disease.

Gamma delta T cells ($\gamma\delta$ T cells) represent a subset of T cells that express on their surface a distinct, defining $\gamma\delta$ T-cell receptor (TCR). This TCR is made up of one gamma ($\gamma$) and one delta ($\delta$) chain, each of which undergoes chain rearrangement but have a limited number of V genes as compared to $\alpha\beta$ T cells. The main TRGV gene segments encoding V$\gamma$ are TRGV2, TRGV3, TRGV4, TRGV5, TRGV8, TRGV9 and TRGV11 and non-functional genes TRGV10, TRGV11, TRGVA and TRGVB. The most frequent TRDV gene segments encode V$\delta$1, V$\delta$2, and V$\delta$3, plus several V segments that have both V$\delta$ and V$\alpha$ designation (Adams et al., 296:30-40 (2015) *Cell Immunol.*). Human $\gamma\delta$ T cells can be broadly classified based on their TCR chains, as certain $\gamma$ and $\delta$ types are found on cells more prevalently, though not exclusively, in one or more tissue types. For example, most blood-resident $\gamma\delta$ T cells express a V$\delta$2 TCR, commonly V$\gamma$9V$\delta$2, whereas this is less common among tissue-resident $\gamma\delta$ T cells such as those in the skin, which more frequently use the V$\delta$1 TCR paired with gamma chains, for example often paired with V$\gamma$4 in the gut.

$\gamma\delta$ T cells play a critical role in immune surveillance, recognising malignant or transformed cells (such as cancer cells) through a pattern of stress markers and then exerting potent and selective cytotoxicity. $\gamma\delta$ T cells can therefore act as orchestrators of an immune response. Modulation of these cells in situ provides the potential to increase immunogenicity even in tumours with low mutational load which have proven challenging with other immunotherapies. Recognition of tumours by $\gamma\delta$ T cells is not dependent on any single tumour antigen and modulators of $\gamma\delta$ T cells therefore have potential in a range of disease indications, including both haematological and solid malignancies. The recognition mechanism of $\gamma\delta$ T cells is not MHC restricted.

The authors of WO2019147735 hypothesise that some $\gamma\delta$ cells have pro-tumour activity or inhibit the anti-cancer immune response mediated by $\alpha\beta$ T cells. The authors postulate that $\gamma\delta$ T cells are immunosuppressants and therefore suggest they should be depleted, inhibited or blocked in a cancer setting with the aid of antibodies.

However, despite the prevailing view that that anti-$\gamma\delta$ antibodies will negatively modulate $\gamma\delta$ cell function by blocking or killing such cells, it has been found that a positive correlation between $\gamma\delta$ T cell infiltration and prognosis and/or survival in patients exists.

Compared to $\alpha\beta$ TCR receptor/ligand interactions, understanding of v$\delta$1 TCR receptor/ligand interactions are limited. In the absence of such understanding, antibodies which recognize v$\delta$1 TCRs to date are mainly exploratory tools to probe this interaction. Such tools are typically crude, blocking antibodies which suggest TCR receptor/ligand interactions results in blocking, suppression or ablation of v$\delta$1+ cells. For example, tool antibodies TS8.2 and TS-1 are employed as anti-$\gamma\delta$ blocking antibodies in studies which suggest said antibodies reduce the cytotoxicity of v$\delta$1 cells. These studies, combined with others, suggest use of such anti-v$\delta$1 antibodies to favourably modulate the cytotoxicity of v$\delta$1 cells in an in situ disease setting is inconceivable and there is therefore the need for antibodies which increase, not reduce, v$\delta$1 cytotoxicity.

To exploit $\gamma\delta$ T cells for immunotherapy requires either a means to expand the cells in situ or to harvest them and expand them ex vivo prior to re-infusion. The latter approach has previously been described using the addition of exogenous cytokines, for example see WO2017/072367 and WO2018/212808. Methods for expanding a patients' own $\gamma\delta$ T cells has been described using pharmacologically modified forms of hydroxy-methyl but-2-enyl pyrophosphate (HMBPP) or clinically-approved aminobisphosphonates. By these approaches, over 250 cancer patients have been treated, seemingly safely, but with only rare incidences of complete remission. However, there is still a need for activating agents that have the proven capacity to expand large numbers of $\gamma\delta$ T cells.

Further, a binding or activating agent capable of preferentially targeting or binding or recognizing or specifically modulating or increasing the numbers of V$\delta$1+ cells in-situ may be highly desirable as a medicament.

However, whilst medicaments exist that do potentially modulate V$\delta$2+ cells inclusive of the aminobisphosphonates such as ZOMETA® (zoledronic acid), said medicines are primarily designed to slow bone reabsorption. And regardless of said V$\delta$2+ modulation, there is a need to develop medicines specifically designed to bind, target, modulate, activate, or increase the numbers of V$\delta$1+ cells. This is because, for example, repeat V$\delta$2+ modulation can result in long-lasting and a progressively exhausted phenotype.

Further, and given the predominate tissue-resident nature of V$\delta$1+ cells, an ideal medicament capable of modulating V$\delta$1+ would also exhibit fewer 'off-target' undesirable effects and rapid renal clearance. Typically, said undesirable effects can manifest when employing small-molecule chemicals. For example, the aforementioned aminobisphosphonates shown capable of modulating the separate class of V$\delta$2+ cells (as a secondary effect versus primary modulating effect on bone) are associated with renal toxicity which manifests as deterioration of renal function and potential renal failure (e.g. Markowitz et al. (2003) Kidney Int. 64(1):281-289). Additional undesirable effects as listed by the European Medicine Agency for ZOMETA® include anemia, hypersensitivity reactions, hypertension, arterial fibrillation, myalgia, general pain, malaise, blood urea increase, vomiting, joint swelling, chest pain, etc.

Further consideration must also be given to the in situ milieu in which vδ1+ cells find themselves. For example, it has previously been shown that non-haematopoietic, tissue-resident γδ T cells showed a strong proliferative response when first separated from tissue but only if they were not in direct cellular contact with autologous fibroblasts. It is found that the non-haematopoietic tissue-resident T cells (γδ T cells) must be separated from the non-haematopoietic cells, (e.g. stromal cells, particularly fibroblasts) in order to function. This is because direct contact of the lymphocytes with stromal or epithelial cells appears to inhibit expansion of tissue-resident γδ T cells. The observation that the pre-activated cells in situ exist in a further suppressed state is another reason vδ1 cells have not been considered a promising therapeutic target to date, Indeed, until the discoveries described herein it has not been conceived how one could favourably and selectively modulate these cells in situ, where blood and tissue vδ1+ cells are typically considered 'resting', 'pre-activated' or 'non-activated'.

Hence there is a need for improved medicaments specifically designed to target Vδ1+ cells and for the treatment of infections, autoimmune conditions, and cancer. Specifically, there is a need for medicaments that can be administered to ameliorate signs and symptoms of disease by specifically binding Vδ1+ cells, targeting Vδ1+ cells, specifically activating Vδ1+ cells, specifically enhancing proliferation and/or cytotoxicity activity Vδ1+ cells, or specifically blocking activation of Vδ1+ cells.

Various formats of bispecific and multispecific antibodies have been developed for a variety of therapeutic uses. Bi- and multispecific antibodies can be divided into separate, although overlapping, classes based on the types of biological targets and modes of action. For example, such multispecific antibodies can be divided into classes such as cytotoxic effector cell redirectors (also known as bispecific, T-cell-recruiting antibodies, bispecific T-cell engagers, TCEs, or BiTEs) and dual immunomodulators (DIs).

TCEs (T-cell engagers) are intended to enhance the patient's immune response to tumours by targeting T cells to tumour cells or vice versa, and work by targeting a first epitope of a T-cell receptor complex of a T-cell (usually CD3) and a second epitope, which is a cancer antigen or a cancer-associated antigen, such as a tumour associated antigen (TAA). Such antibodies colocalize tumour cells and T-cells to promote tumour cell killing. Examples of BiTEs include the CD3×CD19 bispecific antibody blinatumomab, the CD3×EpCAM bispecific antibody catumaxomab, and the CD3×HER2 bispecific antibody ertumaxomab. TCEs such as BiTEs are generally provided in an scFv format, although other formats have been provided. For example, BiKEs are similar to BiTEs, but they target CD16 on NK cells, rather than CD3.

The T-cell receptor has been described as the most intricate receptor structure of the mammalian immune system. It comprises a transmembrane multi-protein receptor complex comprises a T-cell receptor in close proximity to a number of CD3 chains. For example, in mammals, a typical such complex comprises a T-cell receptor, a CD3γ chain, a, CD3δ chain, and two CD3ε chains. These chains associate with the T-cell receptor (TCR) alongside a ζ-chain (zeta-chain) which combined then generate typical activation signals in T lymphocytes. However alternative complexes have also been reported. For example, T-cell receptor complexes comprising a T-cell receptor and a zeta chain homodimer have been described. Additional co-receptors such as CD4 and CD8 can also aid TCR function.

Regardless of receptor complex composition, it is well established that said complexes translate cell surface binding events to intracellular phosphorylation signaling cascade. These phosphorylation events culminate in the activation of transcription factors such as NFAT and NFkB that lead to increased expression of cytokines and effector proteins such as granzymes and perforin.

However, whilst the use of such TCEs to treat cancer remain a compelling concept, to date and even after 30 years of concerted efforts to advance TCEs in early clinical development, many of such bispecific antibodies have exhibited lackluster safety, efficacy and manufacturability profiles. Indeed, as of January 2020, blinatumomab remains the only approved TCE not then withdrawn. This TCE multispecific antibody fragment binds the T-cell receptor complex on a first binding arm and a CD19 target on a second binding arm.

Bispecific, T-cell-recruiting antibodies are discussed in Lejeune et al., 2020, Front Immunol., 11:762. However, the existing bispecific antibodies in this category, in particular those that recruit T-cells via CD3 binding, have significant off-target effects that result in severe adverse effects, given the potency of the CD3 antigen as signal transducer and its ubiquity in a patient's T-cell population. Hence for CD3 targeting bispecific examples such as Catumaxomab (now withdrawn), systemic delivery (e.g. intravenous) is not a realistic possibility. Instead, more contained delivery such as intra-operative, intra-peritoneal, intra-abdominal etc. is more often contemplated. This thereby limits optionality and use of said bispecifics as medicaments. Indeed, even for effector-attenuated anti-CD3 antibodies (i.e. a CD3 targeting T-cell complex engager but not a bispecific), the associated toxicity makes I.V. delivery challenging. For example, to limit exposure and reduce toxicity, the anti-CD3 antibody Foralumab is now most often being contemplated for oral delivery (e.g. in treatment of gut disease).

It is often stated that many of the current setbacks observed with such TCEs in early clinical trials are due to the high-affinity T-cell complex binding domains employed. Further, it has been proposed that this is because those designing these TCEs had not given due consideration to the low affinity of natural TCR-complex binding events they were hampered by severe dose-limiting toxicities resulting in prohibitively narrow therapeutic windows. Related to this it has been highlighted that many early TCE drug developers relied on three anti-CD3 T-cell complex binding domains derived from OKT3, SP34, and UCHT1. And these original binding domains all bind with a relatively high affinity in the single to low double-digit nM range equating to roughly to 1,000-fold higher affinity than a natural binding event. In turn it has been proposed that this can result in profoundly different (and often unfavourable) effects on the activation of T-cells compared to natural binding of the T-cell receptor complex. For example, TCE developers using platforms based on the higher affinity OKT3 may be confounded by the fact the OKT3 is apoptotic to T-cells in the presence of IL-2.

For these reasons it has become apparent that lower affinity T-cell complex binding is an important consideration for determining the design parameters of T-cell engaging bispecific antibody therapeutics.

Another issue when designing said TCEs, is the need to attenuate Fc function. Indeed, typically TCEs require the complete suppression of the Fc-mediated effector functions in order to maximize therapeutic efficacy and to minimize off-target toxicity because binding of Fc to Fc gamma receptor (FcγR) leads to activation of immune effector cells. In reality, the majority of the CD3-targeting bispecific antibodies currently in clinical practice have Fc domains with reduced binding activity to FcγR or are bispecific fragments intentionally without the Fc region. It would generally be expected that a TCE with unattenuated Fc function would induce an antibody-dependent cell-mediated cytotoxicity (ADCC) effect and thereby deplete the population of γδ T-cells recognized by the antibody. However, and again, by attenuating such functionality to avoid toxicity/safety complexities, one may also attenuate a potentially important efficacy angles too e.g. by engaging CD16+ or CD32+ or CD64+ immune cells, or by reducing half-life of the bispecific (e.g. if employing smaller bispecific antibody fragments such as BiTEs). Methods of reducing the interaction of the FcγR and the TCE (such as using an IgG format designed to reduce said interaction) would be expected to reduce Fc-mediated immobilization of the TCE and reduce TCR clustering by cross-linking with the immobilized TCE.

To address some but not all of these complications, many companies such as Xencor (Pasadena, CA), Macrogenics (Gaithersburg, MD) and Genentech (San Francisco, CA) have more recently reported reducing the binding affinity of the T-cell receptor complex binding arms in their respective TCE platforms. However, reducing the affinities of said binding may result in less effective efficacy and less optionality in terms of TCE design and functionality. For example, it is now demonstrated that affinity of the binding domains in such TCEs drives distribution profile in vivo. Specifically, it is typically observed that TCE distribution is biased towards its highest affinity target. Hence, by reducing the affinity of a TCE binding domain to the T-cell complex, it is typical to then bias distribution away from T-cells; the very cells needed to drive efficacy of such TCEs. It is partly for such reasons that TCE therapeutic windows have been termed 'prohibitively narrow'.

Further, and in particular for solid-tumours, significant extra hurdles still exist for immunomodulatory therapeutics. For example, current state-of-the-art approaches include CD3-targeting bispecifics wherein a first domain binds CD3 and a second domain targets a TAA. However often these prove problematic. For example, Middelburg J, et al. Overcoming Challenges for CD3-Bispecific Antibody Therapy in Solid Tumors. *Cancers.* 2021; 13(2):287 summarize some of these hurdles in solid tumour space for such multispecific, T-cell engaging, immunomodulatory moieties inclusive of;
  i. on-target, off-tumor toxicity issues—for example the authors highlight that solid tumor TAAs are often also expressed on tissues of healthy organs, which can in turn lead to immune pathology and organ failure with potential fatality, as shown in a preclinical mouse study using a CD3-bispecific.
  ii. the availability of effector cells in the tumor microenvironment (TME)—for example, conventional CD3+ 'naïve' T-cells exist primarily in the blood and lymph system without any additional dendritic cell mediated activation.
  iii. the quality of the tumour infiltrating lymphocytes (TILs) given these can include CD3+ Tregs and/or exhausted CD3+ cells—for example, CD3-targetting bispecifics may induce TIL apoptosis via activation-induced cell death, which hampers a strong anti-tumor response.

Hence there is need for improved multispecific immunomodulatory medicaments wherein at least one binding domain binds a T-cell and at least one second binding domain targets a TAA.

There is also a need for improved medicaments specifically designed to target Vδ1+ cells and for the treatment of infections, autoimmune conditions, and cancer. Specifically, there is a need for medicaments that can be administered to ameliorate signs and symptoms of disease by specifically binding Vδ1+ cells, targeting Vδ1+ cells, specifically activating Vδ1+ cells, specifically enhancing proliferation and/or cytotoxicity activity Vδ1+ cells, or specifically blocking activation of Vδ1+ cells.

SUMMARY OF THE INVENTION

The present invention relates to high-affinity antibodies that comprise multiple antigen-binding sites ("multispecific antibodies"), including an antigen-binding site for TCR delta variable 1 (Vδ1) and an antigen-binding site for EGFR. More specifically, the present invention relates to multispecific antibodies comprising a Fab region and an Fc region, wherein the Fab region comprises a binding site specific for an epitope of the variable delta 1 (Vδ1) chain of a γδ T cell receptor (TCR); and the Fc region comprises an binding site specific for EGFR.

The multispecific antibodies of the present invention are in the format known as "mAb$^2$ antibodies or "mAb squared antibodies", which are antibodies comprising an Fc region that has been engineered to contain antigen-binding loops in its CH3 domain—this modified Fc region is termed an "Fcab" (Fc with antigen binding). The resulting Fcabs can be rapidly inserted into a natural IgG antibody format to create tetravalent mAb$^2$ bispecific antibodies that bind to two different antigens. The mAb$^2$ antibody therefore further comprises a Fab region, comprising a VH-VL domain pair providing an antigen-binding site. mAb$^2$ molecules of the present invention comprise a EGFR binding Fcab and an vδ1-binding Fab.

The antibodies of the present invention have an advantageous functional profile. In particular, unlike anti-Vδ1 antibodies of the prior art which focus on depletion of Vδ1 T-cells, the antibodies of the present invention are useful for the activation of Vδ1 T-cells. Although they may cause downregulation of the TCRs on T-cells to which they bind, they do not cause Vδ1 T-cell depletion, but rather they stimulate the T-cells and hence may be useful in therapeutic settings that would benefit from the activation of this compartment of T-cells. Activation of Vδ1 T-cells is evident through TCR downregulation, changes in activation markers such as CD25, Ki67, degranulation marker CD107a, NCRs (natural cytotoxicity receptors) and/or 4-1BB. Activation of Vδ1 T-cell in turn triggers release of inflammatory cytokines such as INFγ and TNFα to promote immune licensing. Surprisingly, antibodies having suitably high affinity for TRDV1 elicit increased Vδ1 T-cell killing and, unlike (for example) antibodies that target CD3, the provision of high affinity antibodies is possible without adverse effects associated with large-scale activation via CD3. In turn, the high affinity antibodies are able to induce strong immunostimulatory effects via tumour-infiltrating lymphocytes (TILs). This can be achieved with minimal exhaustion or killing of the Vδ1 cells. Therefore, the multispecific antibodies of the invention may be considered agonistic antibodies.

The Fcab regions comprised within the multispecific antibodies of the present invention have a smaller binding interface than typical monoclonal antibody binding sites. Where the Fab arms of a typical mAb are separated by a flexible hinge region, the binding sites of Fcabs form a compact antibody fragment with two binding sites situated close together. The two antigen binding sites of an Fcab are also spatially close to each other, as compared with those of a typical mAb. Based on this smaller binding interface and reduced flexibility of the two binding sites it is surprising that the multispecific antibodies of the invention (comprising Fcab regions) are able to bind to and inhibit EGFR with similar affinity and potency as a monoclonal antibody benchmark.

According to a first aspect of the invention, there is provided a multispecific antibody comprising a Fab region and an Fc region, wherein the Fab region comprises a binding site specific for an epitope of the variable delta 1 (Vδ1) chain of a γδ T cell receptor (TCR); and the Fc region comprises an EGFR binding site.

In a second aspect of the invention, there is provided a polynucleotide sequence encoding a multispecific antibody of the invention. For example, there is provided a polynucleotide sequence encoding the anti-Vδ1 first binding domain comprising a sequence having at least 70% sequence identity with SEQ ID NO: 199 to 222, 224 to 247, 249 to 259 or 261 to 271.

In an third aspect of the invention, there is provided an expression vector comprising the polynucleotide sequence of the invention. There is also provided a host cell comprising a polynucleotide sequence of the invention or an expression vector of the invention. There is also provided a method for producing any multispecific antibody or antigen-binding fragment thereof of the invention, comprising culturing a host cell of the invention in a cell culture medium.

In a further aspect of the invention, there is provided a composition comprising a multispecific antibody of the invention. There is also provided a pharmaceutical composition comprising a multispecific antibody of the invention and a pharmaceutically acceptable diluent or carrier. Compositions and pharmaceutical compositions may optionally further comprise one or more additional therapeutically active agents.

In a further aspect of the invention, there is provided a kit comprising a multispecific antibody of the invention or a pharmaceutical composition of the invention, optionally comprising instructions for use and/or an additional therapeutically active agent.

In a further aspect of the invention there is provided a method of treating a disease or disorder in a subject, comprising administering to the subject a multispecific antibody of the invention, or a pharmaceutical composition of the invention. There is also provided a method of modulating an immune response in a subject, comprising administering to the subject a multispecific antibody of the invention, or a pharmaceutical composition of the invention. Administration of antibodies to a subject may be administration in a therapeutically effective amount.

In a still further aspect of the invention, there is provided a multispecific antibody of the invention, or a pharmaceutical composition of the invention, or a kit of the invention, for use in medicine. There is also provided the use of an a multispecific antibody of the invention in the manufacture of a medicament.

BRIEF DESCRIPTION OF THE FIGURES

(FIG. 1A) Phage selections round 1 to 3 for the ADT1-7 library. (FIG. 1B) Phage selections Round 1 to 3 for the ADT1-4 library. (FIG. 1C) Phage selections Round 1 to 3 for the ADT1-4 library with a selection strategy for isolating cyno cross-reactive binders.

(FIG. 2A) Schematics of the flow sorting of ADT1-7 library. (FIG. 2B) Schematics of the flow sorting of ADT1-4 library 1 (human). (FIG. 2C) Schematics of the flow sorting of ADT1-4 library 2 (cyno).

(FIG. 3A) ADT1-4 Lineage Mammalian Display Outputs: Human Dissociation off-rate (SPR) vs Human Antigen binding (Delfia ELISA, 0.4 nM Human Antigen) with LC 74S (open circle) or 74L (filled circle) usage indicated. Results highlight good fit between improved affinity by SPR and by antigen binding by Delfia ELISA. These results also highlight the improved binding conferred by variable domain S74L modification. (FIG. 3B) ADT1-4 Lineage Mammalian Display Outputs: Cyno Dissociation Off-Rate (SPR) vs Cyno Antigen Binding (Delfia ELISA, 10 nM Cyno Antigen) with LC 74S (open circle) or 74L (filled circle) usage indicated. (FIG. 3C) ADT1-4 Lineage Mammalian Display Outputs: Correlation between Human Antigen Dissociation Off-Rate (SPR) improvements vs Cyno Antigen Dissociation Off-Rates (SPR) plus LC 74S (open circle) or 74L (filled circle) usage indicated.

(FIG. 4A) Example heavy chain and light chain cross-sharing between affinity matured antibodies in ADT1-4 (G04) lineage (0.4 nM Human TRDV1 ELISA results heat-map graded). This "heat map" demonstrates the cross-sharing of CDR3 sequences between different affinity matured antibodies in the ADT1-4 lineage, showing the affinity maturation process provided antibody sequences that do not have to be provided as specific heavy and light chain pairs. The results highlight the affinity matured antibodies can cross-share light chains and heavy chains and that differing LC/HC combinations generate equivalent or improved outcomes in a high-stringency antigen binding study. Also included in the FIG. 4A is the ADT1-4 (G04) parent clone, (bottom left). Sequences shown on the x-axis correspond (left-right) to SEQ ID NOs: 54, 58, 67, 61, 74, 55, 56, 57, 60, and 70. Sequences shown on the y-axis correspond (top-bottom) to SEQ ID NOs: 83, 100, 84, 89, 87, 94, 103, 92, 98, 93, 99, 82, 88, 86, 90, 85, 104, and 81. (FIG. 4B) ADT1-4 Lineage Final Selection: CDR3 usage and cross-sharing+Cyno Antigen Binding 'Heat Map' versus starting parent ADT1-4 parent G04 mAb (bottom left). Sequences shown on the x-axis correspond (left-right) to SEQ ID NOs: 54, 57, 74, 55, 70, 58, 67, 61, 60, and 56. Sequences shown on the y-axis correspond (top-bottom) to SEQ ID NOs: 87, 93, 94, 103, 89, 92, 83, 100, 85, 98, 86, 88, 82, 84, 99, 90, 104, and 81. (FIG. 4C) ADT1-7 Lineage Final Selection: CDR3 usage and cross-sharing+Human Antigen Binding 'Heat Map' versus starting ADT1-7 parent E07 mAb (bottom left). Sequences shown on the x-axis correspond (left-right) to SEQ ID NOs: 132, 133, 138, 135, 143, 140, 136, 142, and 141. Sequences shown on the y-axis correspond (top-bottom) to SEQ ID NOs: 155, 152, 150, 147, 148, 149, and 146.

FIGS. 5A-5D: Fold enhancement in binding and for ADT1-4 linage compared to ADT1-4 parental G04. (FIG. 5A) Fold enhancement in recombinant human Vδ1 antigen binding. (FIG. 5B) Fold enhancement in recombinant cyno Vδ1 antigen binding. (FIG. 5C) Fold enhancement in primary Vδ1 MFI. (FIG. 5D) Fold enhancement in PEER Vδ1 cell line MFI.

(FIG. 6A). Fold enhancement in recombinant human Vδ1 antigen binding. (FIG. 6B). Fold enhancement in primary Vδ1 MFI. (FIG. 6C). Fold enhancement in PEER Vδ1 cell line MFI.

(FIG. 7A) Fold improvement in binding to human antigen. DELFIA ELISA signal of affinity matured clones vs parent ADT1-4 (G04), 0.4 nM of recombinant human L1 antigen (containing human Vδ1 TCR antigen). (FIG. 7B) Fold improvement in binding to cyno antigen (DV1/GV77 containing Cyno SEQ ID NO: 308 (mature, minus leader)). DELFIA ELISA signal of affinity matured clones vs parent ADT1-4 (G04), 0.4 nM of recombinant human L1 antigen. (FIG. 7C) Fold improvement in binding to human antigen. DELFIA ELISA signal of affinity matured clones vs parent ADT1-7 (E07), 0.4 nM of recombinant human L1 antigen.

(FIG. 8A) Fold improvement in human antigen KD for ADT1-4 (G04) lineage. (FIG. 8B) Fold improvement in cyno antigen KD for ADT1-4 (G04) lineage. (FIG. 8C) Fold improvement in human antigen KD for ADT1-7 (E07) lineage.

FIGS. 9A-9F. Binding affinity analysis (KD by SPR) to human Vδ1 antigen. (FIG. 9A) Surface plasmon resonance for ADT1-4 lineage. (FIG. 9B) Surface plasmon resonance for ADT1-7 lineage. (FIG. 9C) KD values and fold change against parental clone for ADT1-4 lineage. (FIG. 9D) KD values and fold change against parental clone for ADT1-7 lineage. (FIG. 9E) Fold change of KD against parental clone for ADT1-4 lineage. (FIG. 9F) Fold change of KD against parental clone for ADT1-7 lineage.

FIGS. 10A-10D. Binding affinity analysis (KD by SPR) to cyno antigen. (FIGS. 10A-10C) Surface plasmon resonance for ADT1-4 lineage for cyno antigen. (FIG. 10D) KD values for ADT1-4 lineage for cyno antigen.

FIGS. 11A-11D. Binding Affinity to cell surface Vδ1 TCR (EC50 for binding to cell surface Vδ1). (FIGS. 11A-11B) The level of binding by the Vδ1 mAbs to two γδ T cell donors, ATS006 (FIG. 11A) and TS164 (FIG. 11B). (FIG. 11C) Bar chart representing the average 50% binding values from the ADT1-4 and ADT1-7 clones binding to Vδ1-positive γδ T cell, represented as the mean two donors, with these values provided in tables with % improvement. (FIG. 11D) Table summarizing the IC50s plotted in (FIG. 11A) & (FIG. 11B), and Vδ1-negative cell types including HEK293A, Raji cells and various leukocyte subsets with primary blood mononuclear cells. For Vδ1-positive γδ T cell, data is represented as the mean two donors.

FIGS. 12A-12G. TCR downregulation. (FIGS. 12A-12B) ADT1-4 lineage FIG. 12A and ADT1-7 lineage (FIG. 12B). (FIG. 12C) Average TCR downregulation-IC50 results from two GD cell donors. (FIGS. 12D-12E) Fold TCR downregulation improved from the parental ADT1-4 clone (FIG. 12D) and the ADT1-7 clone (FIG. 12E). (FIG. 12F) 50% effect values from (FIG. 12C), with the percentage improvement calculated from the respective parents of ADT1-4 (upper) and ADT1-7 (lower). (FIG. 12G) 50% effect values from (FIG. 12C) with the fold improvement calculated from the respective parents of ADT1-4 (upper) and ADT1-7 (lower).

FIGS. 13A-13F. Vδ1 monoclonal antibodies on γδ activation measured by CD107a expression. (FIGS. 13A-13B) ADT1-4-2 clone in cells GD cells alone (FIG. 13A) or with THP-1 cells (FIG. 13B). (FIGS. 13C-13D) ADT1-7-3 clone in cells GD cells alone (FIG. 13C) or with THP-1 cells (FIG. 13D). (FIG. 13E) Table representing the percentage increase in γδ CD107a expression from cocultured cells treated with the highest concentration of Vδ1 mAb compared to untreated non-cocultured γδ cells. (FIG. 13F) Table representing the percentage increase in γδ CD107a expression from cocultured cells treated with the highest concentration of Vδ1 mAb compared to untreated, co- and non-cocultured γδ cells.

FIGS. 14A-14F. Vδ1 monoclonal antibodies on γδ activation measured by CD25 expression. (FIGS. 14A-14B) ADT1-4-2 clone in cells GD cells alone (FIG. 14A) or with THP-1 cells (FIG. 14B). (FIGS. 14C-14D) ADT1-7-3 clone in cells GD cells alone (FIG. 14C) or with THP-1 cells (FIG. 14D). (FIG. 14E) Table representing the percentage increase in γδ CD25 expression from cocultured cells treated with the highest concentration of Vδ1 mAb compared to untreated non-cocultured γδ cells. (FIG. 14F) Table representing the percentage increase in γδ CD25 expression from cocultured cells treated with the highest concentration of Vδ1 mAb compared to untreated, co- and non-cocultured γδ cells.

(FIG. 15A) Comparison of ADT1-4-2 and ADT1-4 capability to engage and reduce the expression of VD1 on cynomolgus γδ-T cells. (FIG. 15B) Percentage of cell surface expression of VD1 upon treatment with ADT1-4-2. (FIG. 15C) individual EC50 value for the different donors combined with the mean and standard deviation.

FIGS. 16A-16D. Quantification of live THP-1 cell numbers after 24 hours co-culture with γδ T-cells in the presence of Vδ1 mAbs or controls. (FIG. 16A) THP-1 cell killing assay for ADT1-4 clones. (FIG. 16B) THP-1 cell killing assay for ADT1-7 clones. (FIG. 16C) Mean EC50s in THP-1 killing assay for ADT1-4 and ADT1-7 clones. (FIG. 16D) Table summarizing the EC50s plotted in (FIG. 16C).

FIGS. 20A-20J. Effect of anti-Vδ1 antibodies on TIL populations from primary tumour biopsies. (FIGS. 20A-20B) Show % decrease in Vδ1 TCR expression on total tumour infiltrating-γδ T cells following 48 (FIG. 20A) or 72 (FIG. 20B) hours mAb stimulation in two separate donors, confirming target engagement in each case. (FIG. 20C) Shows enhanced expression of both CD25 and Ki67 on Vδ1+ T cells following 48 hour stimulation with ADT1-4-2 compared with stimulation with IgG1 isotype control or ADT1-4. (FIG. 20D) Shows substantial fold increases in IFN-γ production by TILs stimulated with ADT1-4-2 or ADT1-7-3 for 72 hours in the presence of 50 ng/ml IL-15. (FIG. 20E) Shows that stimulation of TILs with ADT-1-4-2 or ADT1-7-3 did not enhance secretion of type 17-associated cytokines IL-6 or IL-17 at this timepoint. (FIGS. 20F-20G) Show the % decrease in Vδ1 TCR expression on total tumour infiltrating-γδ T cells following mAb stimulation at 24 (FIG. 20F) or 72 (FIG. 20G) hours in two individual donors, confirming target engagement in TILs isolated by enzymatic digestion. (FIG. 20 H) Shows dose-dependent enhanced expression of Ki67 on γδ T cells following 72 hours stimulation with ADT1-4-2. (FIGS. 20I-20J) Show the fold increase in IFN-γ produced by TILs isolated from two individual donors by enzymatic digestion and stimulated with ADT1-4-2 at a concentration of 6.66 nM in the presence of 2 ng/ml IL-15 at 24 (FIG. 20I) or 72 (FIG. 20J) hours. In all cases, the concentration of the control anti-RSV and parent ADT1-4 are matched to highest concentration used in study (i.e. a conc. of 6.66 nM for FIG.

20A, FIG. 20C, FIGS. 20F-20J and a concentration of 66.6 nM for FIG. 20B and FIG. 20E).

FIGS. 21A-21E. Effect of anti-Vδ1 antibodies on TIL populations from primary tumour biopsies. (FIG. 21A) Shows enhanced expression of CD25 and Ki67 in γδ T cells stimulated for 10 days with ADT1-4-2. (FIG. 21B) Shows a substantial increase in Perforin+ Granzyme B+ γδ T cells following 10 days stimulation with ADT1-4-2. (FIG. 21C) Shows considerably enhanced expression of Granzyme B and Perforin by both CD8+ and CD8− αβ T cells following 10 days stimulation of tumour-infiltrating Vδ1+ T cells with ADT1-4-2. (FIG. 21D) Shows markedly increased production of IFN-γ, and moderately increased production of IL-17 and IL-6 by lung tumour-derived TILs following stimulation with ADT1-4-2. FIG. 21E Demonstrates enhanced production of the chemokines CCL2, CCL4 and CXCL10 by TILs following 10 days stimulation with ADT1-4-2. In all cases, control anti-RSV and parent ADT1-4 matched to same concentration as affinity matured ADT1-4-2.

FIGS. 22A-22B: Sequences of ADT1-4 lineage clones (light chains). In FIG. 22A, sequences shown correspond (top-bottom) to SEQ ID NOs: 27-38. In FIG. 22B, sequences shown correspond (top-bottom) to SEQ ID NOs: 39-40 and 42-50.

FIGS. 23A-23B: Sequences of ADT1-4 linage clones (heavy chains). In FIG. 23A, sequences shown correspond (top-bottom) to SEQ ID NOs: 2-13. In FIG. 23B, sequences shown correspond (top-bottom) to SEQ ID NOs: 14-15, 3, and 17-25.

FIG. 24: Sequences of ADT1-7 lineage clones (light chains). Sequences shown correspond (top-bottom) to SEQ ID NOs: 119-129.

FIG. 25: Sequences of ADT1-7 lineage clones (heavy chains). Sequences shown correspond (top-bottom) to SEQ ID NOs: 107-117.

Figure 26A:
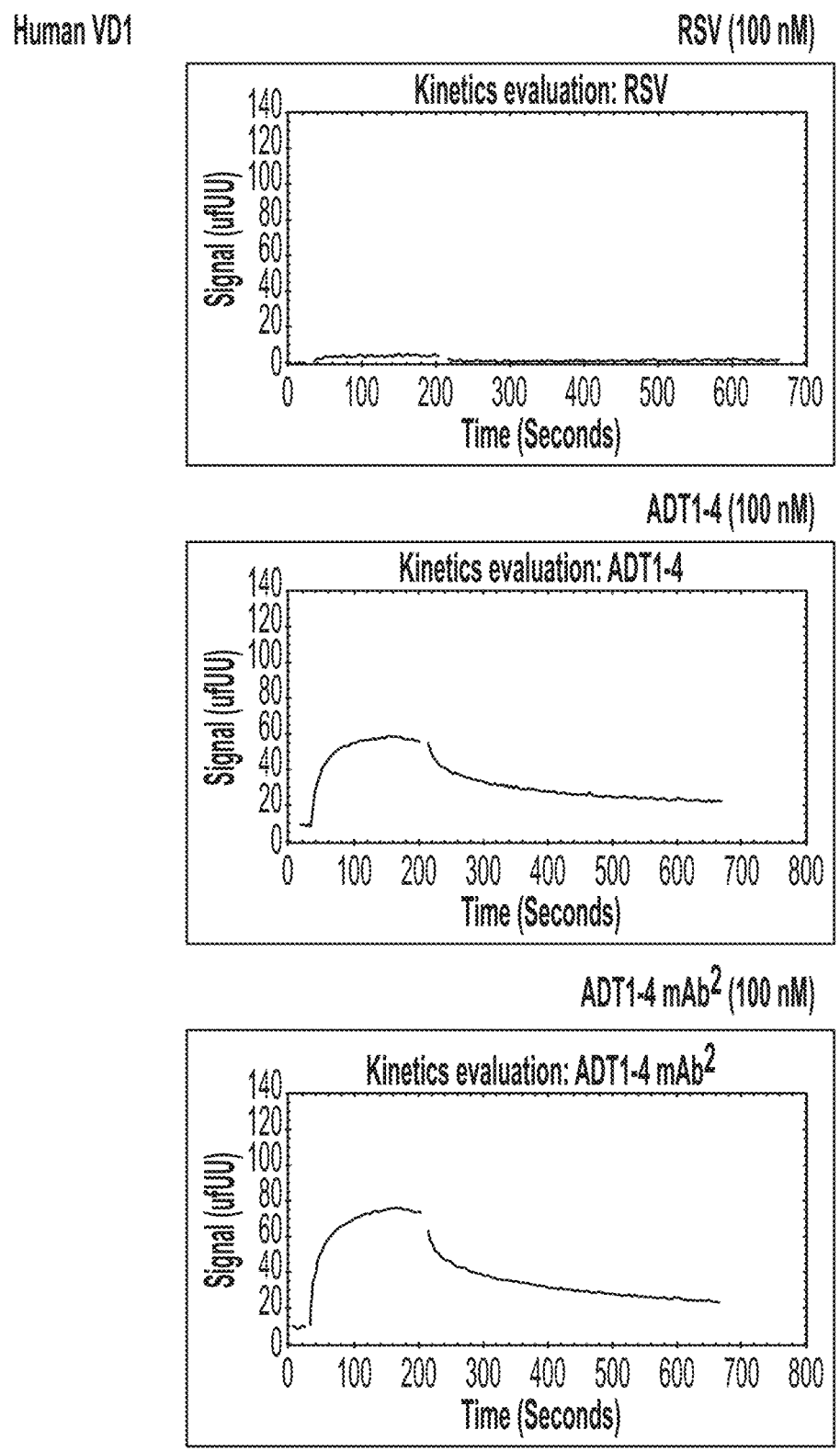
Figure 26B:
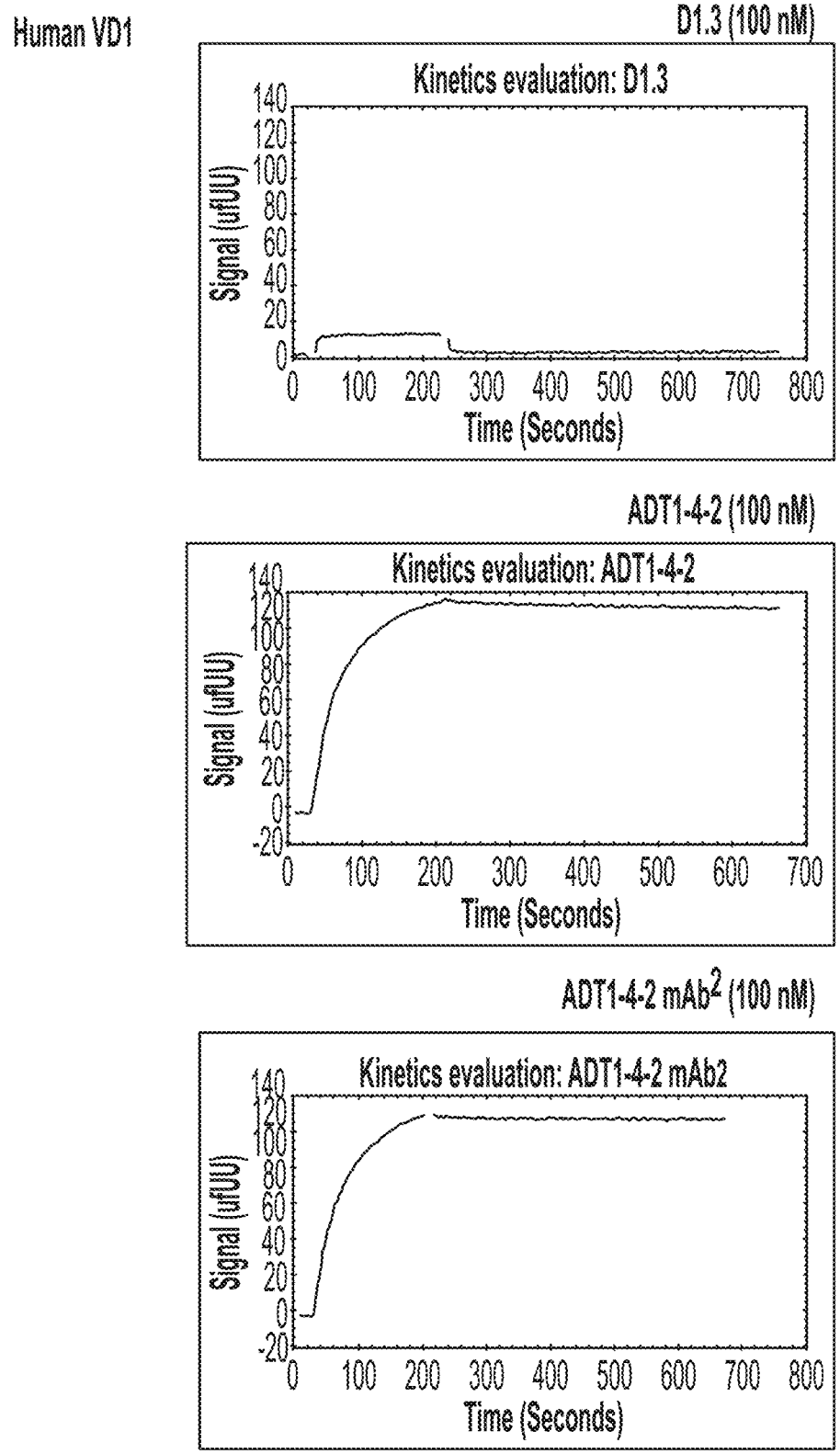
Figure 26D:
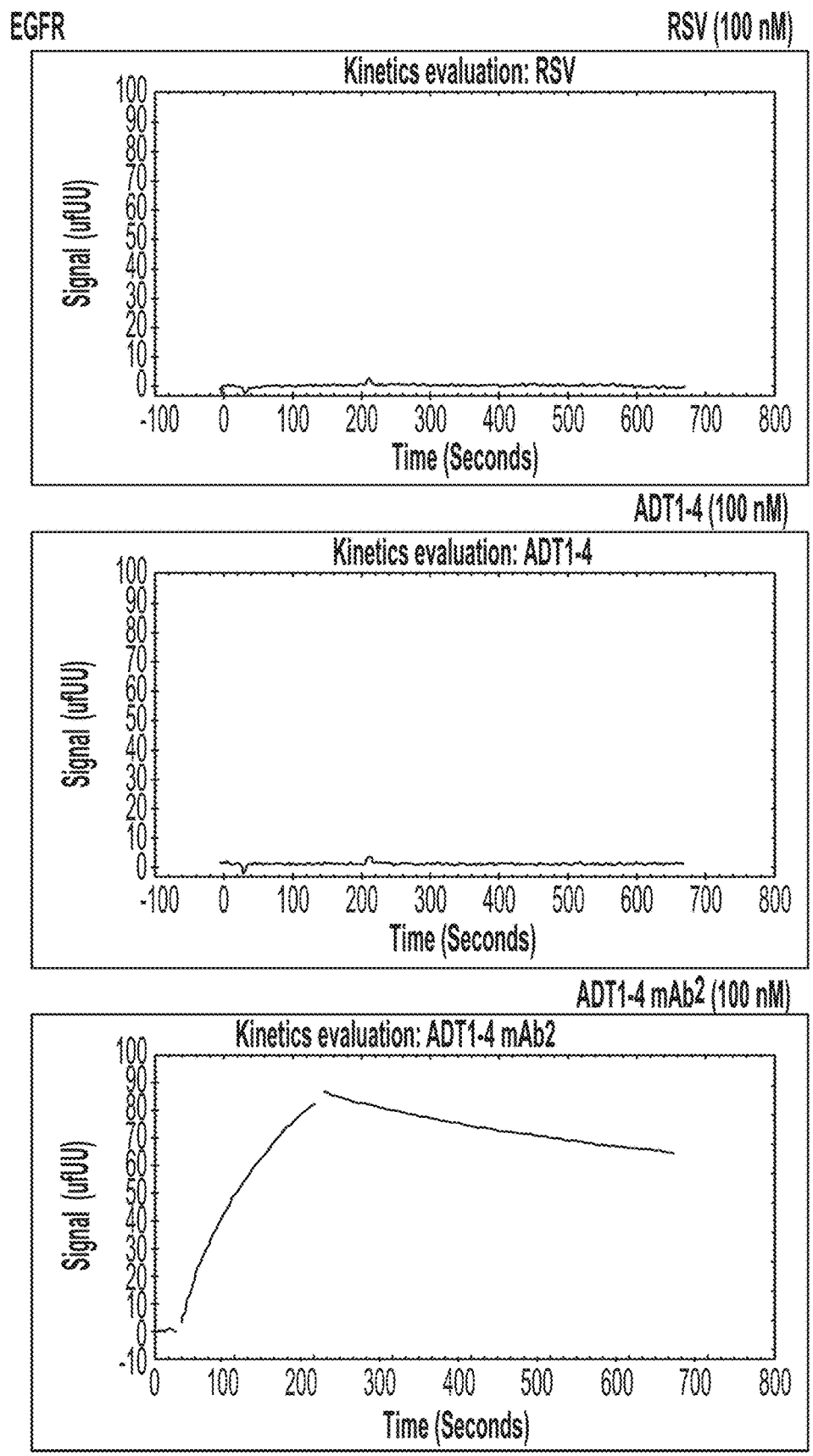

FIGS. 26A-26F: Vδ1/EGFR bispecific antibodies exhibit high affinity binding to human EGFR and a human Vδ1-binding affinity comparable to their parental mAbs. (FIGS. 26A-26F) Surface Plasmon Resonance (SPR) analysis was performed with Vδ1/EGFR bispecific variants to assess binding to human Vδ1 (FIGS. 26A-26C) and human EGFR antigen (FIGS. 26D-26F). The parental mAbs, CETUX-IMAB and negative control mAbs were included for comparison purposes.

Figure 27B:
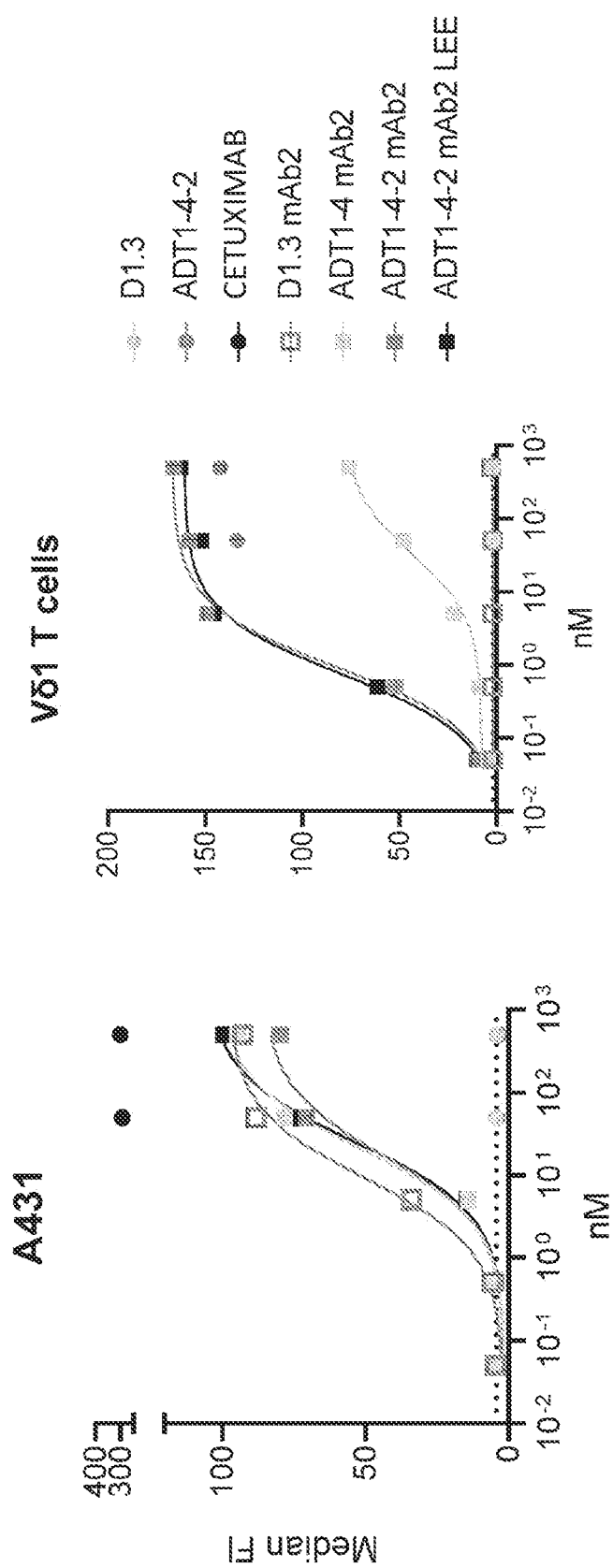
Figure 28A:
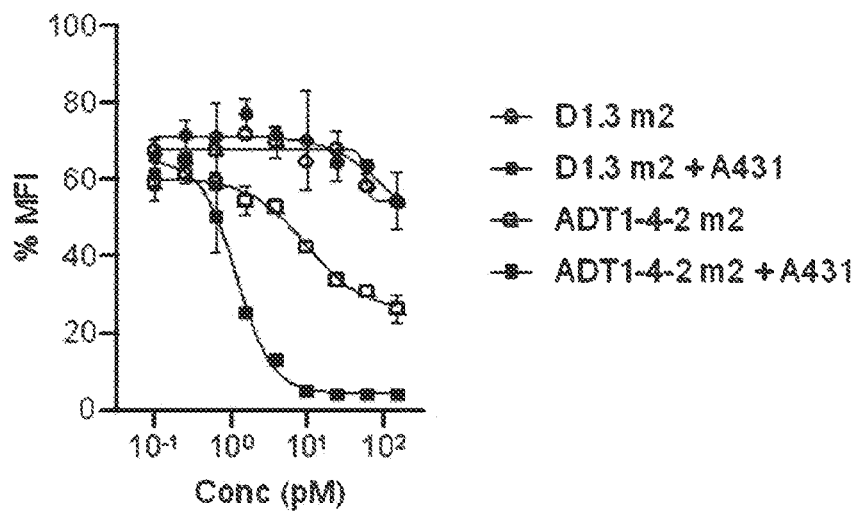
Figure 28B:
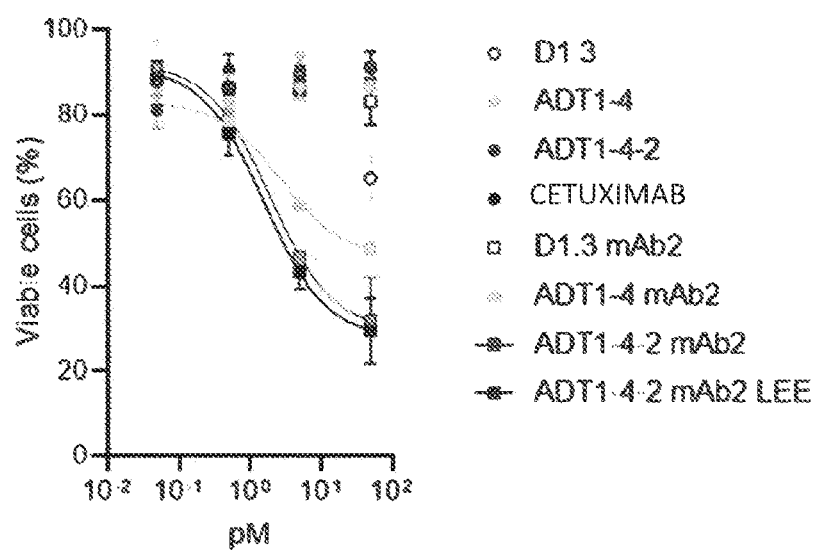
Figure 28C:
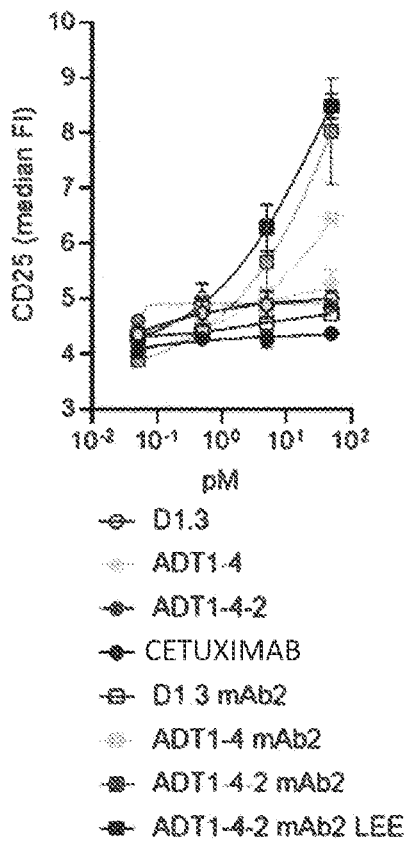
Figure 28D:
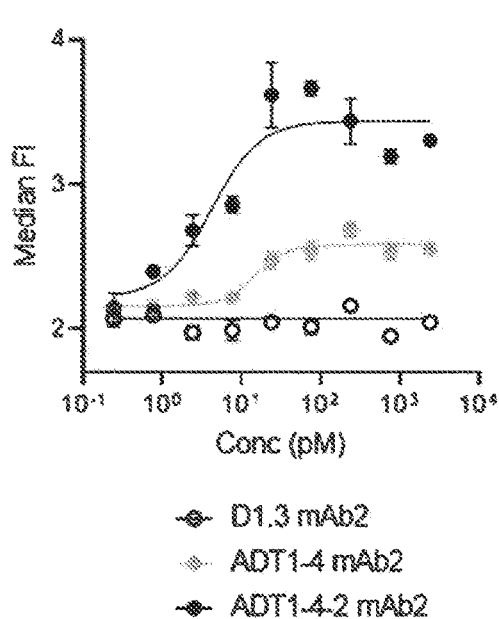
Figure 28E:
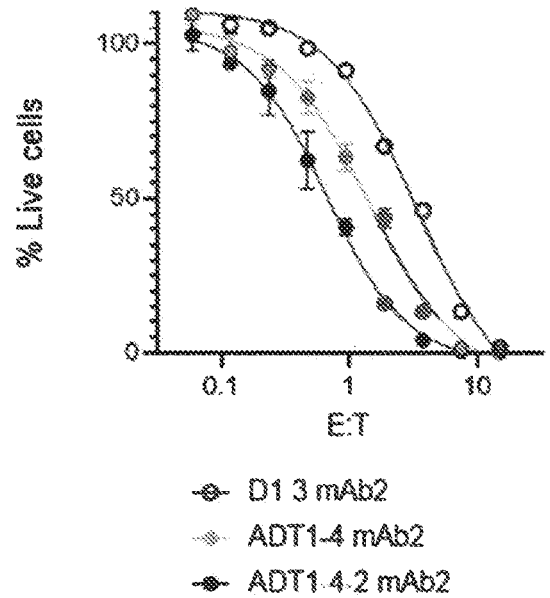

FIGS. 27A-27B: Vδ1/EGFR bispecific antibody binds to EGFR+ A431 target cells and Vδ1 γδ T-cells (FIG. 27A) Cell surface expression of EGFR and Vδ1 on A431 cell line and primary Vδ1 γδT-cells. (FIG. 27B) The level of binding by the Vδ1/EGFR bispecific antibodies to A431 cell line or primary Vδ1 γδ T-cells. Target cells were stained with varying concentrations of antibody, followed by a fluorescent anti-human IgG detection antibody. All incubation steps were performed at 4° C. and mAb binding was determined using flow cytometry to measure the median level of fluorescence. Logarithmic four parameter dose-response curves were fitted using GraphPad Prism 9.

FIGS. 28A-28E: Vδ1/EGFR bispecific antibodies induces EGFR-specific T cell activation and degranulation leading to increased γδ T cell-mediated cytotoxicity of A431 target cells. (FIG. 28A) Cell surface expression of γδTCR on primary Vδ1 γδ T-cells following culture with bispecific antibodies for 24 hours in the presence or absence of A431 cells. (FIGS. 28B-28C) The number of viable A431 cells (FIG. 28B) and activation status of primary Vδ1 γδ T-cells following co-culturing at 1:1 ratio alongside varying concentrations of antibody for 24 hours. Viability was measured by viability dye and activation status using a CD25 antibody. (FIG. 28D) Degranulation of primary Vδ1 γδ T-cells following co-culture with A431 cells at 1:1 ratio alongside varying concentrations of antibody for four hours. Degranulation was determined by adding fluorophore-conjugated anti-CD107α antibody directly into the cell-antibody mix at the start of the co-culture. (FIG. 28E) The number of viable A431 cells following 24-hours co-culture with 10 pM of antibody and varying quantity of primary Vδ1 γδ T-cells. (FIGS. 28A-28E) In all cases, fluorescence was determined using flow cytometry to measure the median level of fluorescence. Logarithmic four parameter dose-response curves were fitted using GraphPad Prism 9. Data is represented as mean±SD of two biological replicates.

Figures 29A, 29B:
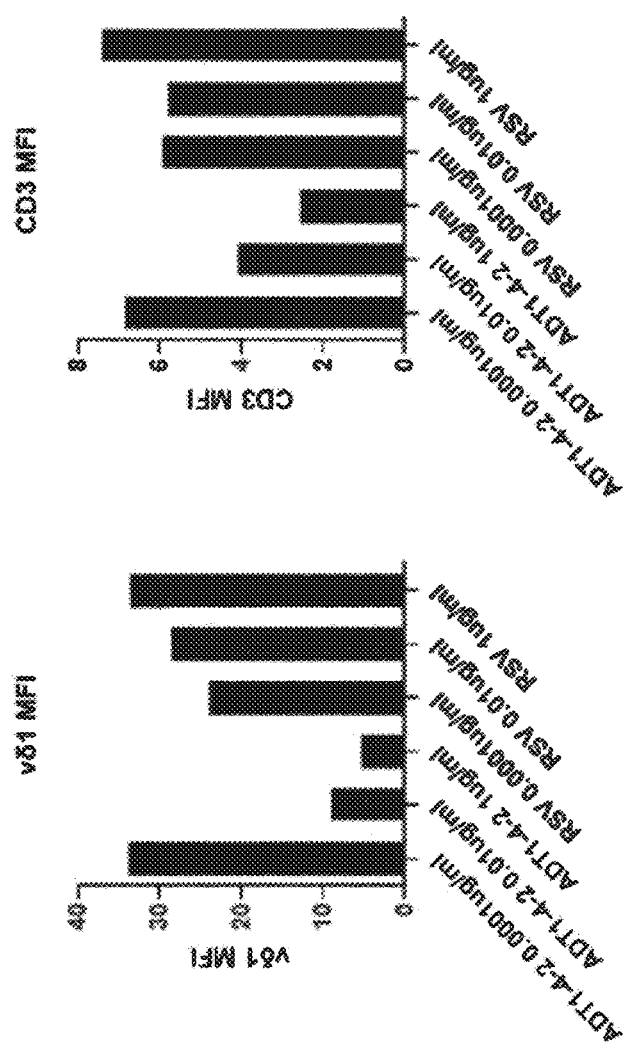

FIGS. 29A-29B: Further evidence of non-depletion and CD3 downregulation in both blood-derived and tumour-associated Vδ1 T cells. (FIG. 29A) shows the vδ1 TCR MFI upon antibody stimulation as an indication of mAb target engagement on blood derived Vδ1 T cells. (FIG. 29B) shows the MFI of CD3 expression on positively gated blood derived vδ1 cells. Stimulation with the vδ1 antibody engaged vδ1 cells and resulted in down-regulation of both vδ1 and CD3 on vδ1 cells.

Figure 30:
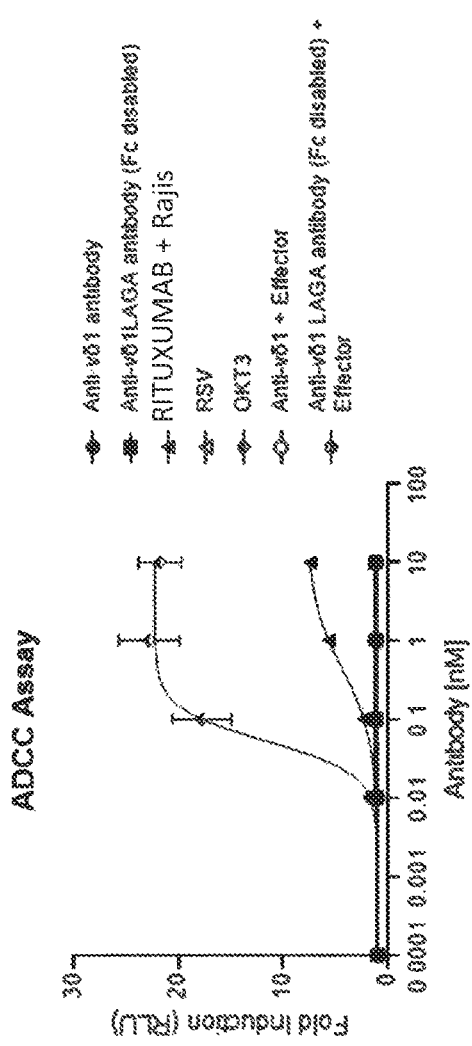

FIG. 30: ADCC reporter bioassay shows no ADCC as a result of the anti-vδ1 antibodies. Target cells, ie. γδ cells, were incubated with the ADCC bioassay effector cells in presence of anti-vδ1 antibodies, anti-vδ1 LAGA antibodies (Fc disabled), and RSV Isotype control. Luminescence signal was recorded as relative light units (RLU) and fold induction was calculated as described in the methods. N=2 γδ donors (performed in technical duplicates) for "anti-vδ1 antibody", "anti-vδ1 LAGA antibody", "RSV", "OKT3". N=1 Raji cell lines for the "RITUXIMAB+Rajis" condition (in technical duplicates) and n=1 γδ donors for the "anti-vδ1 antibody+Effector" and "anti-vδ1 LAGA antibody+Effector" conditions (performed in technical duplicate and singlicate, respectively). Effector:target ratio at 3:1.

FIGS. 31A-31H: Multispecific antibody conferred enhancement of Vδ1+ effector cell mediated cytotoxicity. The targeting of a tissue-centric disease associated antigen: (FIGS. 31A-31D) Example co-culture of Vδ1+ effector cells with A-431 cancer cells+/−multispecific antibodies comprising anti-Vδ1× anti-TAA (EGFR) bispecific binding moieties wherein the anti-Vδ1 VL+VH binding domain (to the first target) is paired with the CH1-CH2-CH3 domain of an anti-EGFR binding moiety (to the second target). (FIGS. 31E-31H) Example co-culture of Vδ1+ effector cells with A-431 cancer cells+/−multispecific antibodies comprising anti-Vδ1×anti-TAA (EGFR) bispecific binding moieties wherein the anti-Vδ1 binding domain (to the first target) comprises a full-length antibody (VH-CH1-CH2-CH3/VL-CL) then combined with an anti-EGFR CETUXIMAB-derived scFv binding moiety (to the second target).

FIGS. 32A-32B: Sequences of EGFR binding domains (IgG1 CH1-CH2-CH3) showing the sequence alignments and changes to IgG1 CH3 (EU numbering). In FIG. 32B, sequences shown correspond (top-bottom) to SEQ ID NOs: 563, 559, 562, 510, 522, 532, 552, and 541.

FIGS. 33A-33C: A table showing cross referenced CH3 residue numbering. The table is adapted from IMGT.org. The positions of the modified amino acids as per IMGT (standard), IMGT (exon), EU, and Kabat numbering referred to elsewhere herein are highlighted by shading. Please note a necessary but unconventional position nomenclature to describe the additional amino acid insert found in one example EGFR binding construct is also indicated—see below position 21.1 (IMGT exon column)/361.1 (EU column)/384.1 (Kabat column)/17.1 (IMGT standard column).

FIGS. 34A-34F: Manufacturability/Stability Assessment of Vδ1×EGFR multispecific antibodies: Expression and Analytical Studies on six molecules. (FIG. 34A) Yields in CHO. (FIG. 34B) Stability under accelerated storage conditions. (FIG. 34C) Aggregation Propensity. (FIG. 34D) Decay profile under accelerated conditions (non-reduced analysis). (FIG. 34E) Decay Profile under accelerated conditions (reduced analysis). (FIG. 34F) Overall Summary/Conclusion FIGS. 35A-35M: An extended study on VD1×EGFR multispecific antibodies and the differing effects conferred by dialing up/down affinity on the VD1 binding arm. (FIG. 35A) Affinity Summary. (FIGS. 35B-35C) Impact on multispecific binding to tissue-resident Vδ1+ cells. (FIGS. 35D-35E) Impact on Vδ1 TCR internalization of tissue-resident Vδ1+ cells. (FIGS. 35F-35G) Impact on degranulation of tissue-resident Vδ1+ cells. (FIGS. 35H-35I) Impact on multispecific cytolytic function towards EGFR+ cancer cells. (FIGS. 35J-35K) Impact on proliferation of tissue-resident Vδ1+ cells. (FIG. 35L) Overall Summary of this Study. (FIG. 35M) Impact of TAA copy number.

Figures 36A, 36B:
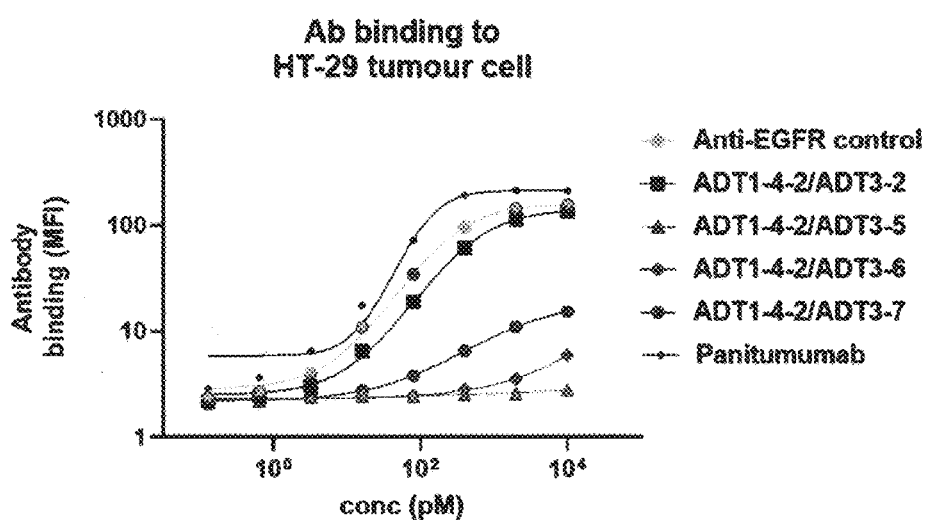
Figure 36N:
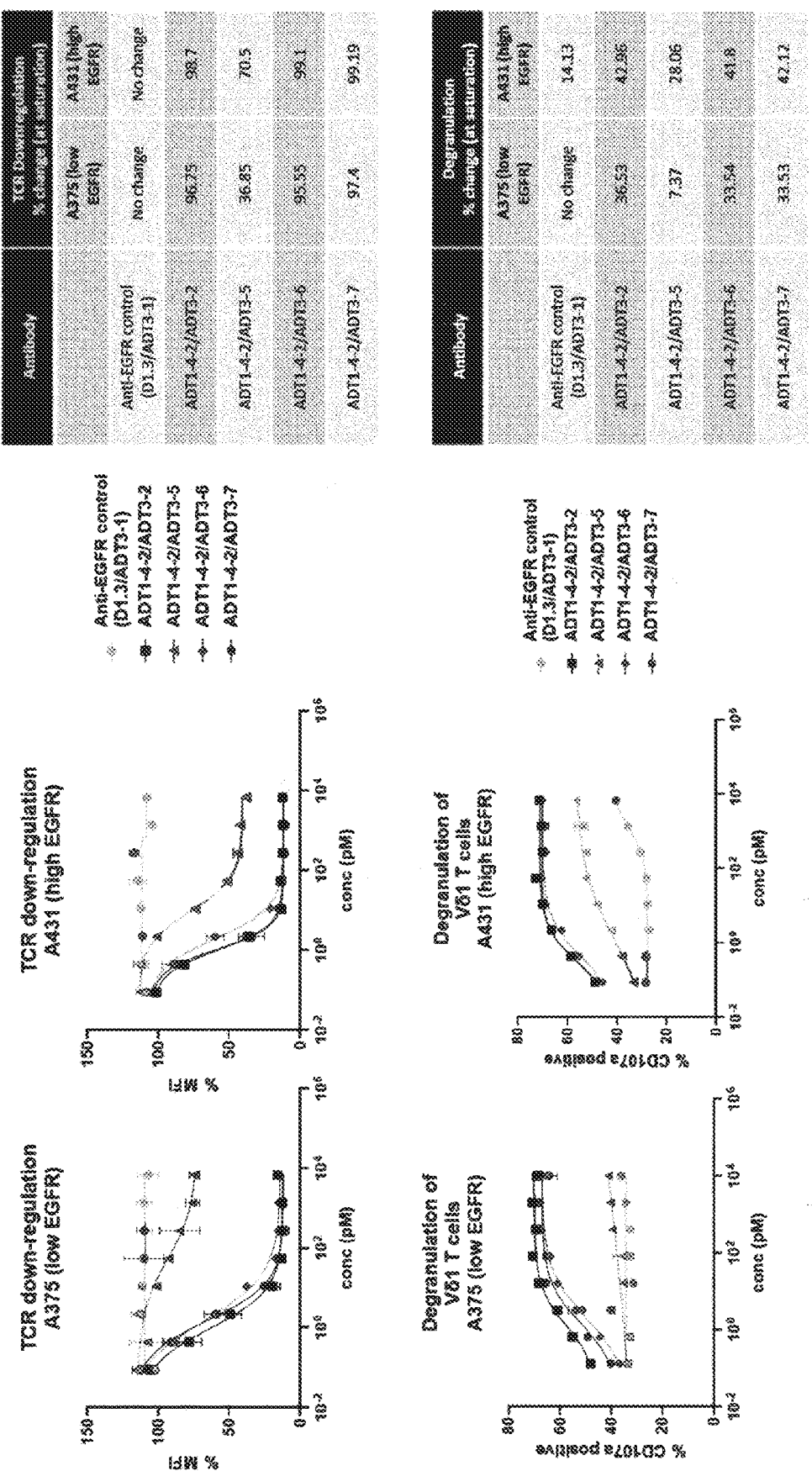

FIGS. 36A-36N: An extended study on VD1×EGFR multispecific antibodies and the differing effects conferred by dialing up/down affinity on the EGFR binding arm. (FIG. 36A) Affinity Summary. (FIGS. 36B-36C) Impact on multispecific binding to EGFR+ colon cancer cell line HT-29. (FIGS. 36D-36E) Impact on Vδ1 TCR downregulation of tissue-resident Vδ1+ cells. (FIGS. 36F-36G) Impact on degranulation of tissue-resident Vδ1+ cells. (FIGS. 36H-36I) Impact on 41BB activation status of tissue-resident Vδ1+ cells. (FIGS. 36J-36K) Impact on multispecific cytolytic function towards EGFR+ cancer cells. (FIGS. 36L-36M) Impact on proliferation of tissue-resident Vδ1+ cells. (FIG. 36N) Affinity to EGFR and impact of cancer cell TAA copy number.

Figures 37A, 37B, 37C:
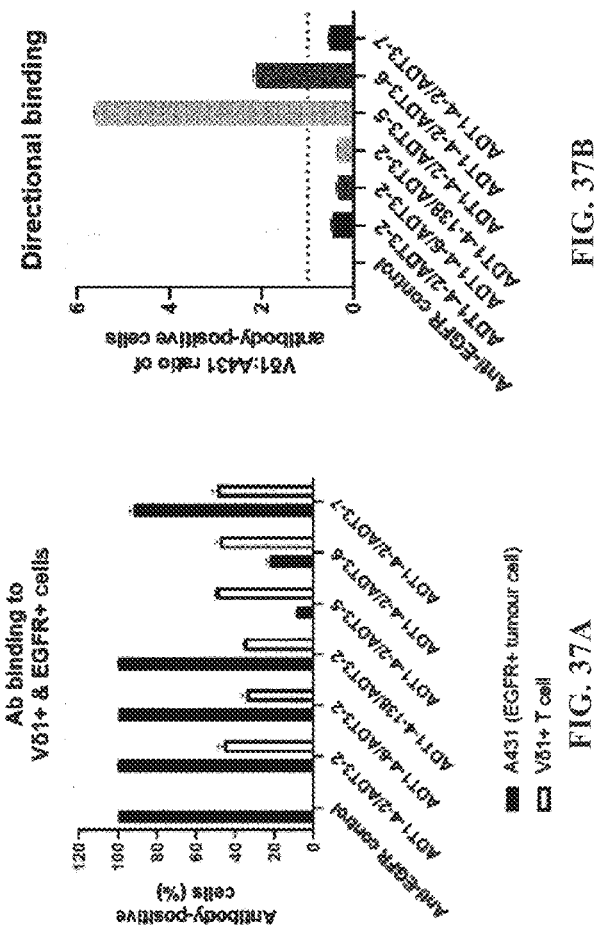

FIGS. 37A-37C: Impact of affinity on preferential binding to Vδ1 versus EGFR cells. Impact of affinity on preferential binding to Vδ1 versus EGFR cells as a bar chart (FIG. 37A), table (FIG. 37B) and ratio (FIG. 37C).

FIGS. 38A-38D: Impact of affinity to EGFR on multispecific antibody internalization by A431 tumour cells. (FIGS. 38A-38B) Affinity to EGFR; impact on multispecific antibody internalization by A431 tumour cells. (FIGS. 38C-38D) Impact on multispecific clearance by A431 tumour cells.

FIGS. 39A-39D: Impact of affinity to EGFR on multispecific antibody inhibition of EGF ligand binding and tumour cell proliferation. (FIGS. 39A-39B) Impact of affinity to EGFR on multispecific antibody inhibition of EGF ligand binding and tumour cell proliferation. (FIGS. 39C-39D) Impact of affinity to EGFR on multispecific inhibition of EGFR+ tumour cell proliferation.

FIGS. 40A-40C: VD1×EGFR multispecific antibodies: Sparing of healthy EGFR+ cells. (FIG. 40A and FIG. 40C) Dose titration effects presented. (FIG. 40B) Representative microscopy images from the experiment described in (FIG. 40A).

Figure 41A:
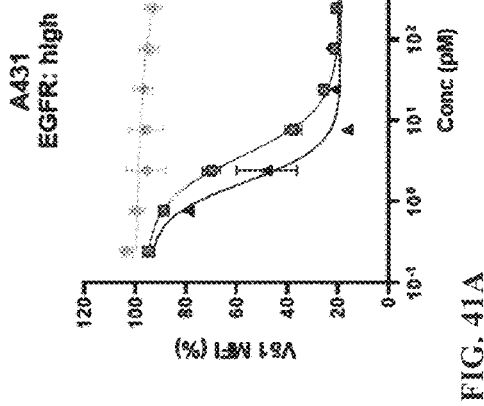
Figure 41B:
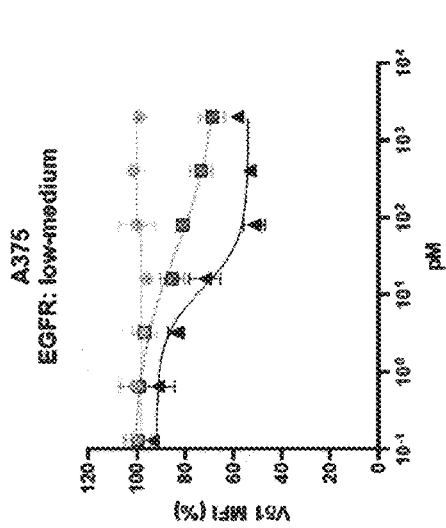

FIGS. 41A-41B: VD1×EGFR multispecific antibodies: ADT1-4-2×FS1-67 comparison to lower affinity 'parent' ADT1-4×FS1-67 (alias G04 FS1-67). (FIG. 41A) TCR downregulation-Dose response comparison of ADT1-4-2× FS1-67 with ADT1-4×FS1-67. (FIG. 41B) TCR downregulation Comparison-Result Summary.

FIGS. 42A-42I: VD1×EGFR multispecific antibodies: Comparison to a CD3×EGFR multispecific antibody. (FIGS. 42A-42C) Impact of T cell target receptor on Vδ1 TCR and CD3ε downregulation. (FIGS. 42D-42E) Impact on multispecific cytolytic function towards EGFR+ cancer cells. (FIGS. 42F-42G) Impact on induced cytokine secretion by activated T cells. (FIGS. 42H-42I) Impact on proliferation of tissue-resident Vδ1+ cells.

DETAILED DESCRIPTION OF THE INVENTION

The present invention provides multispecific antibodies and fragments and variants thereof that specifically bind the T cell receptor of gamma delta T cells, and specifically bind to EGFR.

More specifically, the present invention relates to high-affinity antibodies that comprise multiple antigen-binding sites, including an antigen-binding site for TCR delta variable 1 (Vδ1) and an antigen-binding site for EGFR ("multispecific antibodies").

The multispecific antibodies of the present invention are in mAb$^2$ format and comprise a Fc region that has been engineered to contain antigen-binding loops in its CH3 domain—this modified Fc region is termed an "Fcab". The mAb$^2$ antibody further comprises a Fab region, comprising a VH-VL domain pair providing an antigen-binding site. mAb$^2$ molecules of the present invention comprise a EGFR binding Fcab and an vδ1-binding Fab.

More specifically, the present invention relates to the provision and characterisation of optimised multispecific antibodies, for example antibodies prepared according to an optimised selection procedure beginning from parental anti-Vδ1 antibodies, such as the parental antibodies referred to herein as G04, E07, C08, B07, C05, E04, F07, G06, G09, B09, G10 and E01. The present invention relates in particular to optimised multispecific antibodies derived from G04 and E07.

Definitions

Unless defined otherwise, all technical and scientific terms used herein have the meaning commonly understood by a person skilled in the art to which this invention belongs. As used herein, the following terms have the meanings ascribed to them below.

Gamma delta (γδ) T cells represent a small subset of T cells that express on their surface a distinct, defining T Cell Receptor (TCR). This TCR is made up of one gamma (γ) and one delta (δ) chain. Each chain contains a variable (V) region, a constant (C) region, a transmembrane region and a cytoplasmic tail. The V region contains an antigen-binding site. There are two major sub-types of human γδ T cells: one that is dominant in the peripheral blood and one that is dominant in non-haematopoietic tissues. The two sub-types may be defined by the type of δ and/or γ present on the cells. For example, γδ T cells that are dominant in peripheral blood primarily express the delta variable 2 chain (Vδ2). γδ T cells that are dominant in non-haematopoietic tissues (i.e. are tissue-resident) primarily express the delta variable 1 chain. References to "Vδ1 T cells" or "Vδ1$^+$ T cells" refer to γδ T cells with a Vδ1 chain, i.e. Vδ1$^+$ cells.

References to "delta variable 1" may also referred to as Vδ1 or Vd1, while a nucleotide encoding a TCR chain containing this region or the TCR protein complex comprising this region may be referred to as "TRDV1". Antibodies or antigen-binding fragments thereof which interact with the Vδ1 chain of a γδ TCR, and also interact with EGFR are all effectively antibodies or antigen-binding fragments thereof which bind to Vδ1 and may referred to as "anti-TCR delta variable 1 antibodies or antigen-binding fragments thereof" or "anti-Vδ1 antibodies or antigen-binding fragments thereof" or "anti-TRDV1 antibodies or antigen-binding fragments thereof" or "anti-Vδ1×EGFR antibodies or antigen-binding fragments thereof".

Additional references are made herein to other delta chains such as the "delta variable 2" chain. These can be referred to in a similar manner. For example, delta variable 2 chains can be referred to as Vδ2, while a nucleotide encoding a TCR chain containing this region or the TCR protein complex comprising this region may be referred to as "TRDV2". In preferred embodiments multispecific antibodies or antigen-binding fragments thereof which interact with the Vδ1 chain of a γδ TCR, do not interact with other delta chains such as Vδ2. In the invention, the antibodies are specific to TRDV1 and do not bind to TRDV2 (SEQ ID NO: 310) or other antigens present on a gamma delta T-cell receptor, such as TRDV3 (SEQ ID NO: 311).

References to "gamma variable chains" are also made herein. These may be referred to as γ-chains or Vγ, while a nucleotide encoding a TCR chain containing this region or the TCR protein complex comprising this region may be referred to as TRGV. For example, TRGV4 refers to Vγ4 chain. In a preferred embodiment, multispecific antibodies or antigen-binding fragments thereof which interact with the Vδ1 chain of a γδ TCR, do not interact with gamma chains such as Vγ4 (e.g. SEQ ID NO: 309). The antibodies also do not bind or interact with other domains found within a γδ TCR, such as TRDJ, TRDC, TRGJ or TRGC.

The term "T-cell receptor complex" is the complex of proteins comprising the "T-cell receptor" (or "TCR") found on the surface of T-cells responsible for recognising a variety of antigens. The T-cell receptor complex comprises either the alpha and beta chains of the T-cell receptor, or in the case of gamma delta T cells, the gamma and delta chains of the T-cell receptor, and up to 6 additional chains or more, such as CD3δ, CD3γ, CD3ε and CD3ζ, although the precise makeup of T-cell receptor complexes can vary. The T-cell receptor complex mediates intracellular signalling in the T-cell, which may lead to T-cell activation.

The term "antibody" includes any antibody protein construct comprising at least one antibody variable domain comprising at least one antigen-binding site (ABS). Antibodies include, but are not limited to, immunoglobulins of types IgA, IgG, IgE, IgD, IgM (as well as subtypes thereof). The overall structure of Immunoglobulin G (IgG) antibodies assembled from two identical heavy (H)-chain and two identical light (L)-chain polypeptides is well established and highly conserved in mammals (Padlan (1994) *Mol. Immunol.* 31:169-217).

A conventional antibody or immunoglobulin (Ig) is a protein comprising four polypeptide chains: two heavy (H) chains and two light (L) chains. Each chain is divided into a constant region and a variable domain. The heavy (H) chain variable domains are abbreviated herein as VH, and the light (L) chain variable domains are abbreviated herein as VL. These domains, domains related thereto and domains derived therefrom, may be referred to herein as immunoglobulin chain variable domains. The VH and VL domains (also referred to as VH and VL regions) can be further subdivided into regions, termed "complementarity determining regions" ("CDRs"), interspersed with regions that are more conserved, termed "framework regions" ("FRs"). The framework and complementarity determining regions have been precisely defined (Kabat et al. Sequences of Proteins of Immunological Interest, *Fifth Edition U.S. Department of Health and Human Services*, (1991) NIH Publication Number 91-3242). There are also alternative numbering conventions for CDR sequences, for example those set out in Chothia et al. (1989) Nature 342:877-883 or as summarized by IMGT.org. In a conventional antibody, each VH and VL is composed of three CDRs and four FRs, arranged from amino-terminus to carboxy-terminus in the following order: FR1, CDR1, FR2, CDR2, FR3, CDR3, FR4. The conventional antibody tetramer of two heavy immunoglobulin chains and two light immunoglobulin chains is formed with the heavy and the light immunoglobulin chains inter-connected by e.g. disulphide bonds, and the heavy chains similarly connected. The whole antibody thus comprises two Fabs, each Fab comprising a VH-VL domain pair. The heavy chain constant region includes three domains, CH1, CH2 and CH3. The light chain constant region is comprised of one domain, CL. The variable domain of the heavy chains and the variable domain of the light chains are binding domains that interact with an antigen. The constant regions of the antibodies typically mediate the binding of the antibody to host tissues or factors, including various cells of the immune system (e.g. effector cells) and the first component (C1q) of the classical complement system.

"EU numbering" refers to a numbering convention used for the numbering of amino acid residues in antibodies. Each residue of the antibody is assigned a number to allow comparison of antibodies. Where a variant antibody contains a residue that was not present in the wildtype antibody (e.g. an insertion mutation) decimals are used to indicate the insertion. For example, if a residue was inserted between the residues designated numbers 361 and 362, the new residue would be given the EU number 361.1. EU numbering is an alternative numbering scheme to others such as Kabat, (Kabat et al. Sequences of Proteins of Immunological Interest, *Fifth Edition U.S. Department of Health and Human Services*, (1991) NIH Publication Number 91-3242). Chothia (Chothia et al. (1989) Nature 342:877-883) or as summarized by IMGT.org, wherein EU numbering is presented with further cross reference to Edelman, G. M. et al., Proc. Natl. Acad. USA, 63, 78-85 (1969). (10.1073/pnas.63.1.78). FIGS. 33A-33C show the correspondence between EU numbering, IMGT numbering and Kabat numbering for the CH3 domain residues. FIGS. 32A-32B show how the residues of the multispecific antibodies of the invention are numbered according to the EU numbering scheme.

A "Fab region" as used herein refers to a portion of an antibody (or constructs that contain said portion) comprising a VH-VL domain pair providing an antigen-binding site (also known as a CDR based antigen binding site). The Fab region may further comprise the CL and CH1 domains. A conventional antibody with two heavy and two light chains thus comprises two Fabs, each Fab comprising a VH-VL domain pair.

A "Fc region" (fragment crystallizable region), as used herein refers to a portion of an antibody (or constructs that contain said portion) comprising the CH2 and CH3 domains. The Fc region is the C-terminal region of an immunoglobulin heavy chain, including wild-type-sequence Fc regions and modified Fc regions. An Fc region is dimeric and thus comprises paired heavy chain constant regions each comprising a CH2 and CH3 domain.

A "fragment" of the antibody (which may also referred to as "antibody fragment", "immunoglobulin fragment", "antigen-binding fragment" or "antigen-binding polypeptide") as used herein refers to a portion of an antibody (or constructs that contain said portion) that specifically binds to the first target, the delta variable 1 (Vδ1) chain of a γδ T cell receptor or the second target, EGFR (e.g. a molecule in which one or more immunoglobulin chains is not full length, but which specifically binds to the target). Examples of binding fragments encompassed within the term antibody fragment include:
  (i) a Fab fragment (a monovalent fragment consisting of the VL, VH, CL and CH1 domains);
  (ii) a F(ab')2 fragment (a bivalent fragment consisting of two Fab fragments linked by a disulphide bridge at the hinge region);
  (iii) a Fd fragment (consisting of the VH and CH1 domains);
  (iv) a Fv fragment (consisting of the VL and VH domains of a single arm of an antibody);
  (v) a single chain variable fragment, scFv (consisting of VL and VH domains joined, using recombinant methods, by a synthetic linker that enables them to be made as a single protein chain in which the VL and VH regions pair to form monovalent molecules);
  (vi) a VH (an immunoglobulin chain variable domain consisting of a VH domain);
  (vii) a VL (an immunoglobulin chain variable domain consisting of a VL domain);
  (viii) a domain antibody (dAb, consisting of either the VH or VL domain);
  (ix) a minibody (consisting of a pair of scFv fragments which are linked via CH3 domains); and
  (x) a diabody (consisting of a noncovalent dimer of scFv fragments that consist of a VH domain from one antibody connected by a small peptide linker a VL domain from another antibody)
  (xi) a Fc fragment (consisting of the CH2 and CH3 domains)
  (xii) a Fcab fragment (consisting of an Fc fragment that has been engineered to contain antigen-binding loops in its CH3 domain)
  (xiii) an antigen-binding CH3 domain of an Fcab.

"Human antibody" refers to antibodies having variable and constant regions derived from human germline immunoglobulin sequences. Human subjects administered with said human antibodies do not generate cross-species antibody responses (for example termed HAMA responses-human-anti-mouse antibody) to the primary amino acids contained within said antibodies. Said human antibodies may include amino acid residues not encoded by human germline immunoglobulin sequences (e.g. mutations introduced by random or site-specific mutagenesis or by somatic mutation), for example in the CDRs and in particular CDR3. However, the term is not intended to include antibodies in which CDR sequences derived from the germline of another mammalian species, such as a mouse, have been grafted onto human framework sequences. Human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g. a mouse) that is transgenic for human immunoglobulin genes or antibodies prepared, expressed, created or isolated by any other means that involves splicing of human immunoglobulin gene sequences to other DNA sequences, may also be referred to as "recombinant human antibodies".

Substituting at least one amino acid residue in the framework region of a non-human immunoglobulin variable domain with the corresponding residue from a human variable domain is referred to as "humanisation". Humanisation of a variable domain may reduce immunogenicity in humans.

"Specificity" refers to the number of different types of antigens or antigenic determinants to which a particular antibody or antigen-binding fragment thereof can bind. The specificity of an antibody is the ability of the antibody to recognise a particular antigen as a unique molecular entity and distinguish it from another. An antibody that "specifically binds" to an antigen or an epitope (or is "specific" for an antigen or epitope) is a term well understood in the art. A molecule is said to exhibit "specific binding" if it reacts more frequently, more rapidly, with greater duration and/or with greater affinity with a particular target antigen or epitope, than it does with alternative targets. An antibody "specifically binds" to a target antigen or epitope if it binds with greater affinity, avidity, more readily, and/or with greater duration than it binds to other substances.

The antibodies of the present invention are multispecific antibodies. A "multispecific antibody" is an antibody that is capable of binding a plurality of different epitopes simultaneously or sequentially. Generally, the epitopes will not be on the same antigen. Hence a multispecific antibody has the capability to selectively bind to epitopes present on different antigens via a plurality of different binding domains. This contrasts with conventional mono-specific antibodies which do not have this capability. Rather, a "monospecific antibody" only has binding specificity for one antigen, although they may have multiple binding sites for that one antigen (e.g. the valency of a full human IgG antibody is 2, and the valency of other antibodies may be higher, but if the antibody only recognises one antigen, it is still classed as a monospecific antibody). Hence, the multispecific antibodies of the invention bind multiple different antigens simultaneously and/or sequentially.

In some embodiments of the invention, the antibodies are bispecific antibodies. A "bispecific antibody" is an antibody that is capable of binding two different epitopes simultaneously and/or sequentially. Generally, the epitopes will not be on the same antigen. Hence bispecific antibodies have the capability to selectively bind to two different epitopes present on two different antigens via two different binding domains. This contrasts with conventional monospecific antibodies which do not have this capability. Hence, the bispecific antibodies of the invention bind two different antigens simultaneously and/or sequentially.

"mAb$^2$" antibody or "mAb squared antibody" as used herein, refers to a bispecific antibody format according to which the bispecific antibodies comprise an Fc region that has been engineered to contain antigen-binding loops in its CH3 domain. This modified Fc region is termed an "Fcab". The mAb$^2$ antibody further comprises a Fab region, comprising a VH-VL domain pair providing an antigen-binding site.

The CH3 domain of human IgG1 starts at residue number 341 and ends at residue number 447 (EU numbering). Residue number 447 (EU numbering) is sometimes cleaved during manufacture so it does not always appear in the final molecule. The CH3 domain of human IgG1 (SEQ ID NO:563) is comprised of two β-sheets formed by three and four β strands, respectively. Three structural loops connect these β-strands at the C-terminus of the CH3 domain. In antibodies of this invention, these loops have been modified to form the EGFR binding site. Residues 355 to 362 were defined as the loop connecting strands A and B of the CH3 domain "AB loop", residues 383 to 391 as the loop connecting strands C and D of the CH3 domain "CD loop" and residues 413 to 422 as the loop connecting strands E and F of the CH3 domain "EF loop". EU numbering is used (see FIGS. 32A-32B).

"Affinity", represented by the equilibrium constant for the dissociation of an antigen with an antigen-binding polypeptide (KD), is a measure of the binding strength between an antigenic determinant and an antigen-binding site on the antibody (or antigen-binding fragment thereof): the lesser the value of the KD, the stronger the binding strength between an antigenic determinant and the antigen-binding polypeptide. Alternatively, the affinity can also be expressed as the affinity constant (KA), which is 1/KD. Affinity can be determined by known methods, depending on the specific antigen of interest. For example. KD may be determined by surface plasmon resonance.

Any KD value less than $10^{-6}$ is considered to indicate binding. Specific binding of an antibody, or antigen-binding fragment thereof, to an antigen or antigenic determinant can be determined in any suitable known manner, including, for example, Scatchard analysis and/or competitive binding assays, such as radioimmunoassays (RIA), enzyme immunoassays (EIA) and sandwich competition assays, equilibrium dialysis, equilibrium binding, gel filtration, ELISA, surface plasmon resonance, or spectroscopy (e.g. using a fluorescence assay) and the different variants thereof known in the art.

"Avidity" is the measure of the strength of binding between an antibody, or antigen-binding fragment thereof, and the pertinent antigen. Avidity is related to both the affinity between an antigenic determinant and its antigen-binding site on the antibody and the number of pertinent binding sites present on the antibody.

"In situ" means in the natural or original place, instead of being moved to another place. For example, an in situ Vδ1+ cell in a patient refers to a vδ1 cell in vivo, as opposed to an in vitro or ex vivo cell.

"Human tissue Vδ1+ cells," and "haemopoietic and blood Vδ1+ cells" and "tumour infiltrating lymphocyte (TIL) Vδ1+ cells," are defined as Vδ1+ cells contained in or derived from either human tissue or the haemopoietic blood system or human tumours respectively. All said cell types can be identified by their (i) location or from where they are derived and (ii) their expression of the Vδ1+ TCR.

"Modulating antibodies" are antibodies that confer a measurable change including, but not limited to, a measurable change in cell cycle, and/or in cell number, and/or cell viability, and/or in one or more cell surface markers, and/or in the secretion of one or more secretory molecules (e.g., cytokines, chemokines, leukotrienes, etc.), and/or a function (such as cytotoxicity towards a target cell or diseased cell), upon contacting or binding to a cell expressing the target to which the antibody binds. A method of "modulating" a cell, or population thereof, refers to a method wherein in at least one measurable change in said cell or cells, or secretion therefrom, is triggered to generate one or more "modulated cells".

An "immune response" is a measurable change in at least one cell, or one cell-type, or one endocrine pathway, or one exocrine pathway, of the immune system (including but not limited to a cell-mediated response, a humoral response, a cytokine response, a chemokine response) upon addition of a modulating antibody.

An "immune cell" is defined as a cell of the immune system including, but not limited to, CD34+ cells, B-Cells, CD45+ (lymphocyte common antigen) cells, Alpha-Beta T-cells, Cytotoxic T-cells, Helper T-cells, Plasma Cells, Neutrophils, Monocytes, Macrophages, Red Blood Cells, Platelets, Dendritic Cells, Phagocytes, Granulocytes, Innate lymphoid cells, Natural Killer (NK) cells and Gamma Delta T-cells. Typically, immune cells are classified with the aid of combinatorial cell surface molecule analysis (e.g., via flow cytometry) to identify or group or cluster to differentiate immune cells into sub-populations. These can be then still further sub-divided with additional analysis. For example, CD45+ lymphocytes can further sub-divided into vδ positive populations and vδ negative populations.

"Model systems" are biological models or biological representations designed to aid in the understanding of how a medicine such as an antibody or antigen-binding fragment thereof may function as a medicament in the amelioration of a sign or symptom of disease. Such models typically include the use of in vitro, ex vivo, and in vivo diseased cells, non-diseased cells, healthy cells, effector cells, and tissues etc., and in which the performance of said medicaments are studied and compared.

"Diseased cells" exhibit a phenotype associated with the progression of a disease such as a cancer, an infection such as a viral infection, or an inflammatory condition or inflammatory disease. For example, a diseased cell may be a tumour cell, an autoimmune tissue cell or a virally infected cell. Accordingly said diseased cells may be defined as tumorous, or virally infected, or inflammatory.

"Healthy cells" refers to normal cells that are not diseased. They may also be referred to as "normal" or "non-diseased" cells. Non-diseased cells include non-cancerous, or non-infected, or non-inflammatory cells. Said cells are often employed alongside relevant diseased cells to determine the diseased cell specificity conferred by a medicament and/or better understand the therapeutic index of a medicament.

"Diseased-cell-specificity" is a measure of how effective an effector cell or population thereof, (such as, for example, a population of Vδ1+ cells) is at distinguishing and killing diseased cells, such as cancer cells, whilst sparing non-diseased or healthy cells. This potential can be measured in model systems and may involve comparing the propensity of an effector cell, or a population of effector cells, to selectively kill or lyse diseased cells versus the potential of said effector cell/s to kill or lyse non-diseased or healthy cells. Said diseased-cell-specificity can inform the potential therapeutic index of a medicament.

"Enhanced diseased-cell specificity" describes a phenotype of an effector cell such as, for example, a Vδ1+ cell, or population thereof, which has been modulated to further increase its capacity to specifically kill diseased cells. This enhancement can be measured in a variety of ways inclusive of fold-change, or percentage increase, in diseased-cell killing specificity or selectivity.

"ADCC" or "antibody-dependent cell-mediated cytotoxicity" describes an immune response to cells coated with antibodies bound to the surface antigens of the cell. It is a cell-mediated process, whereby an immune effector cell (such as a NK cell, for example) recognise cell bound antibodies, triggering degranulation and lysis of the target cell. Typically, this is mediated via Fc-Fcγ interactions. The Fc region of the cell-bound antibody recruits effector cells expressing Fcγ receptors (eg. NK cells), leading to effector cell degranulation and death of the target cell.

"Fc enabled" refers to an antibody that comprises a functional Fc region (fragment crystallizable region), i.e. a Fc region that has not been disabled by mutation or otherwise. Fc enabled antibodies demonstrate unattenuated Fc function. The Fc enabled antibody may comprise human IGHC heavy chain sequence as listed by IMGT that has not been modified or engineered or constructed to reduce binding to one or more Fc gamma receptors. For example, via IGHC hinge mutation or by construction of an antibody comprising heavy chain constant domains which are chimeric or hybrid for IgG1/IgG2A or IgG1/IgG4 IGHC sequences.

Suitably, the antibody or antigen-binding fragment thereof (i.e. polypeptide) of the invention is isolated. An "Isolated" polypeptide is one that is removed from its original environment. The term "isolated" may be used to refer to an antibody that is substantially free of other antibodies having different antigenic specificities (e.g. an isolated antibody that specifically binds Vδ1, or a fragment thereof, is substantially free of antibodies that specifically bind antigens other than Vδ1). The term "isolated" may also be used to refer to preparations where the isolated antibody is sufficiently pure to be administered therapeutically when formulated as an active ingredient of a pharmaceutical composition, or at least 70-80% (w/w) pure, more preferably, at least 80-90% (w/w) pure, even more preferably, 90-95% pure; and, most preferably, at least 95%, 96%, 97%, 98%, 99%, or 100% (w/w) pure.

Suitably, the polynucleotides used in the present invention are isolated. An "isolated" polynucleotide is one that is removed from its original environment. For example, a naturally-occurring polynucleotide is isolated if it is separated from some or all of the coexisting materials in the natural system. A polynucleotide is considered to be isolated if, for example, it is cloned into a vector that is not a part of its natural environment or if it is comprised within cDNA.

The antibody or antigen-binding fragment thereof may be a "functionally active variant" which also includes naturally occurring allelic variants, as well as mutants or any other non-naturally occurring variants. As is known in the art, an allelic variant is an alternate form of a (poly) peptide that is characterized as having a substitution, deletion, or addition of one or more amino acids that does essentially not alter the biological function of the polypeptide. By way of non-limiting example, said functionally active variants may still function when the frameworks containing the CDRs are modified, when the CDRs themselves are modified, when said CDRs are grafted to alternate frameworks, or when N- or C-terminal extensions are incorporated. Further, CDR containing binding domains may be paired with differing partner chains such as those shared with another antibody. Upon sharing with so called 'common' light or 'common' heavy chains, said binding domains may still function. Further, said binding domains may function when multimerized. Further, 'antibodies or antigen-binding fragments thereof' may also comprise functional variants wherein the VH or VL or constant domains have been modified away or towards a different canonical sequence (for example as listed at IMGT.org) and which still function.

For the purposes of comparing two closely-related polypeptide sequences, the "% sequence identity" between a first polypeptide sequence and a second polypeptide sequence may be calculated using NCBI BLAST v2.0, using standard settings for polypeptide sequences (BLASTP). For the purposes of comparing two closely-related polynucleotide sequences, the "% sequence identity" between a first nucleotide sequence and a second nucleotide sequence may be calculated using NCBI BLAST v2.0, using standard settings for nucleotide sequences (BLASTN).

Polypeptide or polynucleotide sequences are said to be the same as or "identical" to other polypeptide or polynucleotide sequences, if they share 100% sequence identity over their entire length. Residues in sequences are numbered from left to right, i.e. from N- to C-terminus for polypeptides; from 5' to 3' terminus for polynucleotides.

In some embodiments, any specified % sequence identity of a sequence is calculated without the sequences of all 6 CDRs of the antibody. For example, the anti-Vδ1 antibody or antigen-binding fragment thereof may comprise a variable heavy chain region sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% to a specified variable heavy chain region sequence and/or a variable light chain region sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a specified variable light chain region sequence, wherein any amino acid variations occur only in the framework regions of the variable heavy and light chain region sequences. In such embodiments, the anti-Vδ1 antibody or antigen-binding fragment thereof having certain sequence identities retain the complete heavy and light chain CDR1, CDR2 and CDR3 sequences of the corresponding anti-Vδ1 antibody or antigen-binding fragment thereof. In a more specific example, although in no way limiting and only to further illustrate these embodiments of the invention, there is provided an anti-Vδ1 antibody or antigen-binding fragment thereof comprising a VH comprising or consisting of an amino acid sequence that is at least 90% identical to the amino acid sequence of SEQ ID NO: 15 and a VL comprising or consisting of an amino acid sequence that is at least 90% identical to the amino acid sequence of SEQ ID NO: 40, wherein any amino acid variations occur only in the framework regions of the variable heavy and light chain region sequences. The antibody of this specific example therefore further comprises a VHCDR1 comprising the amino acid sequence of SEQ ID NO: 51, a VHCDR2 comprising the amino acid sequence of SEQ ID NO: 53, a VHCDR3 comprising the amino acid sequence of SEQ ID NO: 68, a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 95.

Furthermore, multispecific antibodies provided herein may comprise a kappa light chain variable sequence and retain an amino acid residue at position 74 according to the IMGT numbering system that is not serine, for example a non-polar and/or non-human-germline residue, for example they may comprise a leucine residue at this position. For example, although in no way limiting and only to further illustrate these embodiments of the invention, there is provided an anti-Vδ1 antibody or antigen-binding fragment thereof comprising a VH comprising or consisting of an amino acid sequence that is at least 90% identical to the amino acid sequence of SEQ ID NO: 15 and a VL comprising or consisting of an amino acid sequence that is at least 90% identical to the amino acid sequence of SEQ ID NO: 40, wherein any amino acid variations occur only in the framework regions of the variable heavy and light chain region sequences, and wherein the antibody comprises a kappa light chain variable sequence comprising an amino acid residue at position 74 according to the IMGT numbering system that is non-human-germline and/or non-polar (for example a leucine residue at this position). The antibody of this specific example further comprises a VHCDR1 comprising the amino acid sequence of SEQ ID NO: 51, a VHCDR2 comprising the amino acid sequence of SEQ ID NO: 53, a VHCDR3 comprising the amino acid sequence of SEQ ID NO: 68, a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 95.

A "difference" between sequences refers to an insertion, deletion or substitution of a single amino acid residue in a position of the second sequence, compared to the first sequence. Two polypeptide sequences can contain one, two or more such amino acid differences. Insertions, deletions or substitutions in a second sequence which is otherwise identical (100% sequence identity) to a first sequence result in reduced % sequence identity. For example, if the identical sequences are 9 amino acid residues long, one substitution in the second sequence results in a sequence identity of 88.9%. If first and second polypeptide sequences are 9 amino acid residues long and share 6 identical residues, the first and second polypeptide sequences share greater than 66% identity (the first and second polypeptide sequences share 66.7% identity).

Alternatively, for the purposes of comparing a first, reference polypeptide sequence to a second, comparison polypeptide sequence, the number of additions, substitutions and/or deletions made to the first sequence to produce the second sequence may be ascertained. An "addition" is the addition of one amino acid residue into the sequence of the first polypeptide (including addition at either terminus of the first polypeptide). A "substitution" is the substitution of one amino acid residue in the sequence of the first polypeptide with one different amino acid residue. Said substitution may be conservative or non-conservative. A "deletion" is the deletion of one amino acid residue from the sequence of the first polypeptide (including deletion at either terminus of the first polypeptide).

Using the three letter and one letter codes the naturally occurring amino acids may be referred to as follows: glycine (G or Gly), alanine (A or Ala), valine (V or Val), leucine (L or Leu), isoleucine (I or Ile), proline (P or Pro), phenylalanine (F or Phe), tyrosine (Y or Tyr), tryptophan (W or Trp), lysine (K or Lys), arginine (R or Arg), histidine (H or His), aspartic acid (D or Asp), glutamic acid (E or Glu), asparagine (N or Asn), glutamine (Q or Gln), cysteine (C or Cys), methionine (M or Met), serine (S or Ser) and Threonine (T or Thr). Where a residue may be aspartic acid or asparagine, the symbols Asx or B may be used. Where a residue may be any amino acid the symbol Xaa or X may be used. Where a residue may be glutamic acid or glutamine, the symbols Glx or Z may be used. References to aspartic acid include aspartate, and glutamic acid include glutamate, unless the context specifies otherwise.

As used herein, numbering of polypeptide sequences and definitions of CDRs and FRs are as defined according to the EU and/or IMGT numbering system, as indicated in context. A "corresponding" amino acid residue between a first and second polypeptide sequence is an amino acid residue in a first sequence affinity which shares the same position according to the EU and/or IMGT numbering system, as indicated in context, with an amino acid residue in a second sequence, whilst the amino acid residue in the second sequence may differ in identity from the first. Suitably corresponding residues will share the same number (and letter) if the framework and CDRs are the same length according to EU or IMGT definition. Alignment can be achieved manually or by using, for example, a known computer algorithm for sequence alignment such as NCBI BLAST v2.0 (BLASTP or BLASTN) using standard settings.

References herein to an "epitope" refer to the portion of the target which is specifically bound by the antibody or antigen-binding fragment thereof. Epitopes may also be referred to as "antigenic determinants". An antibody binds "essentially the same epitope" as another antibody when they both recognize identical or sterically overlapping epitopes. Commonly used methods to determine whether two antibodies bind to identical or overlapping epitopes are competition assays, which can be configured in a number of different formats (e.g. well plates using radioactive or enzyme labels, or flow cytometry on antigen-expressing cells) using either labelled antigen or labelled antibody. An antibody binds "the same epitope" as another antibody when they both recognize identical epitopes (i.e. all contact points between the antigen and the antibody are the same).

Epitopes found on protein targets may be defined as "linear epitopes" or "conformational epitopes". Linear epitopes are formed by a continuous sequence of amino acids in a protein antigen. Conformational epitopes are formed of amino acids that are discontinuous in the protein sequence, but which are brought together upon folding of the protein into its three-dimensional structure.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g. bacterial vectors having a bacterial origin of replication and episomal mammalian and yeast vectors). Other vectors (e.g. non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g. replication defective retroviruses, adenoviruses and adeno-associated viruses), which serve equivalent functions, and also bacteriophage and phagemid systems. The term "recombinant host cell" (or simply "host cell"), as used herein, is intended to refer to a cell into which a recombinant expression vector has been introduced. Such terms are intended to refer not only to the particular subject cell but to the progeny of such a cell, for example, when said progeny are employed to make a cell line or cell bank which is then optionally stored, provided, sold, transferred, or employed to manufacture an antibody or antigen-binding fragment thereof as described herein.

References to "subject", "patient" or "individual" refer to a subject, in particular a mammalian subject, to be treated. Mammalian subjects include humans, non-human primates, farm animals (such as cows), sports animals, or pet animals, such as dogs, cats, guinea pigs, rabbits, rats or mice. In some embodiment, the subject is a human. In alternative embodiments, the subject is a non-human mammal, such as a mouse.

The term "sufficient amount" means an amount sufficient to produce a desired effect. The term "therapeutically effective amount" is an amount that is effective to ameliorate a symptom of a disease or disorder. A therapeutically effective amount can be a "prophylactically effective amount" as prophylaxis can be considered therapy.

A disease or disorder is "ameliorated" if the severity of a sign or symptom of the disease or disorder, the frequency with which such a sign or symptom is experienced by a subject, or both, is reduced (compared to an earlier point in time, for example, prior to administration of any antibody).

As used herein, "treating a disease or disorder" means reducing the frequency and/or severity of at least one sign or symptom of the disease or disorder experienced by a subject (compared to an earlier point in time, for example, prior to administration of any antibody).

"Cancer," as used herein, refers to the abnormal growth or division of cells. Generally, the growth and/or life span of a cancer cell exceeds, and is not coordinated with, that of the normal cells and tissues around it. Cancers may be benign, pre-malignant or malignant. Cancer occurs in a variety of cells and tissues, including the oral cavity (e.g., mouth, tongue, pharynx, etc.), digestive system (e.g., esophagus, stomach, small intestine, colon, rectum, liver, bile duct, gall bladder, pancreas, etc.), respiratory system (e.g., larynx, lung, bronchus, etc.), bones, joints, skin (e.g., basal cell, squamous cell, meningioma, etc.), breast, genital system, (e.g., uterus, ovary, prostate, testis, etc.), urinary system (e.g., bladder, kidney, ureter, etc.), eye, nervous system (e.g., brain, etc.), endocrine system (e.g., thyroid, etc.), and hematopoietic system (e.g., lymphoma, myeloma, leukemia, acute lymphocytic leukemia, chronic lymphocytic leukemia, acute myeloid leukemia, chronic myeloid leukemia, etc.).

As used herein, the term "about" when used herein includes up to and including 10% greater and up to and including 10% lower than the value specified, suitably up to and including 5% greater and up to and including 5% lower than the value specified, especially the value specified. The term "between", includes the values of the specified boundaries.

Multispecific Antibodies and Antigen-Binding Fragments Thereof

Provided herein are multispecific antibodies capable of specifically binding to the delta variable 1 chain (Vδ1) of a γδ T Cell Receptor (TCR), and also capable of specifically binding to EGFR. The invention relates to the use of said antibodies as medicaments for administration to a subject to be treated.

In one embodiment, the antibody or antigen-binding fragment thereof is an scFv, Fab, Fab', F(ab')2, Fv, variable domain (e.g. VH or VL), diabody, minibody or monoclonal antibody. In a further embodiment, the antibody or antigen-binding fragment thereof is an scFv.

Multispecific antibodies of the invention can be of any class, e.g. IgG, IgA, IgM, IgE, IgD, or isotypes thereof, and can comprise a kappa or lambda light chain. In one embodiment, the antibody is an IgG antibody, for example, at least one of isotypes, IgG1, IgG2, IgG3 or IgG4. In a further embodiment, the antibody may be in a format, such as an IgG format, that has been modified to confer desired properties, such as having the Fc mutated to reduce effector function, extend half-life, alter ADCC, or improve hinge stability. Such modifications are well known in the art.

In one embodiment, the antibody or antigen-binding fragment thereof is human. Thus, the antibody or antigen-binding fragment thereof may be derived from a human immunoglobulin (Ig) sequence. The CDR, framework and/or constant region of the antibody (or antigen-binding fragment thereof) may be derived from a human Ig sequence, in particular a human IgG sequence. The CDR, framework and/or constant region may be substantially identical for a human Ig sequence, in particular a human IgG sequence. An advantage of using human antibodies is that they are low or non-immunogenic in humans.

An antibody or antigen-binding fragment thereof can also be chimeric, for example a mouse-human antibody chimera.

Alternatively, the antibody or antigen-binding fragment thereof is derived from a non-human species, such as a mouse. Such non-human antibodies can be modified to increase their similarity to antibody variants produced naturally in humans, thus the antibody or antigen-binding fragment thereof can be partially or fully humanised. Therefore, in one embodiment, the antibody or antigen-binding fragment thereof is humanised.

Summary of Specific Fab Regions Provided Herein

A summary of some of the specific antigen-binding molecules (i.e. antibodies) used in the present invention is provided below, with identification of the assigned SEQ ID NO. in the accompanying sequence listing. Antigen-binding variants, derivatives and fragments thereof are also provided as part of the present invention. Sequences are provided in the attached sequence listing and the accompanying Figures. In the case of any discrepancy between the sequences in the sequence listing and those in FIG. 22A-FIG. 25, the sequences in the Figures should prevail.

TABLE 1

Summary of Fab regions derived from ADT1-4 (heavy chain) and the related SEQ ID NOs

| Antibody | VH | HFR1 | VHCDR1 | HFR2 | VHCDR2 | HFR3 | VHCDR3 | HFR4 |
| --- | --- | --- | --- | --- | --- | --- | --- | --- |
| Parental ADT1-4 | 1 | 170 | 51 | 172 | 53 | 173 | 54 | 174 |
| ADT1-4-105 | 2 | 170 | 51 | 172 | 53 | 173 | 55 | 174 |
| ADT1-4-107 | 3 | 170 | 51 | 172 | 53 | 173 | 56 | 174 |
| ADT1-4-110 | 4 | 170 | 51 | 172 | 53 | 173 | 57 | 174 |
| ADT1-4-112 | 5 | 170 | 51 | 172 | 53 | 173 | 58 | 174 |
| ADT1-4-117 | 6 | 170 | 51 | 172 | 53 | 173 | 59 | 174 |
| ADT1-4-19 | 7 | 170 | 51 | 172 | 53 | 173 | 60 | 174 |
| ADT1-4-21 | 8 | 170 | 52 | 172 | 53 | 173 | 61 | 174 |
| ADT1-4-31 | 9 | 170 | 51 | 172 | 53 | 173 | 62 | 174 |
| ADT1-4-139 | 10 | 170 | 51 | 172 | 53 | 173 | 63 | 174 |
| ADT1-4-4 | 11 | 170 | 51 | 172 | 53 | 173 | 64 | 174 |
| ADT1-4-143 | 12 | 171 | 51 | 172 | 53 | 173 | 65 | 174 |
| ADT1-4-53 | 13 | 170 | 52 | 172 | 53 | 173 | 66 | 174 |
| ADT1-4-173 | 14 | 170 | 51 | 172 | 53 | 173 | 67 | 174 |
| ADT1-4-2 | 15 | 170 | 51 | 172 | 53 | 173 | 68 | 174 |
| ADT1-4-8 | 16 | 170 | 51 | 172 | 53 | 173 | 69 | 174 |
| ADT1-4-82 | 17 | 170 | 51 | 172 | 53 | 173 | 70 | 174 |

TABLE 1-continued

Summary of Fab regions derived from ADT1-4 (heavy chain) and the related SEQ ID NOs

| Antibody | VH | HFR1 | VHCDR1 | HFR2 | VHCDR2 | HFR3 | VHCDR3 | HFR4 |
|---|---|---|---|---|---|---|---|---|
| ADT1-4-83 | 18 | 170 | 51 | 172 | 53 | 173 | 71 | 174 |
| ADT1-4-3 | 19 | 170 | 51 | 172 | 53 | 173 | 72 | 174 |
| ADT1-4-84 | 20 | 170 | 51 | 172 | 53 | 173 | 73 | 174 |
| ADT1-4-86 | 21 | 170 | 52 | 172 | 53 | 173 | 74 | 174 |
| ADT1-4-95 | 22 | 170 | 51 | 172 | 53 | 173 | 75 | 174 |
| ADT1-4-1 | 23 | 170 | 51 | 172 | 53 | 173 | 76 | 174 |
| ADT1-4-6 | 24 | 170 | 51 | 172 | 53 | 173 | 77 | 174 |
| ADT1-4-138 | 25 | 170 | 51 | 172 | 53 | 173 | 78 | 174 |

TABLE 2

Summary of Fab regions derived from ADT1-4 (light chain) and the related SEQ ID NOs

| Antibody | VL | LFR1 | VLCDR1 | LFR2 | VLCDR2 | LFR3 | VLCDR3 | LFR4 |
|---|---|---|---|---|---|---|---|---|
| Parental ADT1-4 | 26 | 175 | 79 | 176 | 80 | 178 | 81 | 179 |
| ADT1-4-105 | 27 | 175 | 79 | 176 | 80 | 177 | 82 | 179 |
| ADT1-4-107 | 28 | 175 | 79 | 176 | 80 | 177 | 83 | 179 |
| ADT1-4-110 | 29 | 175 | 79 | 176 | 80 | 177 | 84 | 180 |
| ADT1-4-112 | 30 | 175 | 79 | 176 | 80 | 177 | 85 | 179 |
| ADT1-4-117 | 31 | 175 | 79 | 176 | 80 | 177 | 86 | 179 |
| ADT1-4-19 | 32 | 175 | 79 | 176 | 80 | 177 | 87 | 179 |
| ADT1-4-21 | 33 | 175 | 79 | 176 | 80 | 177 | 88 | 179 |
| ADT1-4-31 | 34 | 175 | 79 | 176 | 80 | 177 | 89 | 179 |
| ADT1-4-139 | 35 | 175 | 79 | 176 | 80 | 177 | 90 | 179 |
| ADT1-4-4 | 36 | 175 | 79 | 176 | 80 | 177 | 91 | 179 |
| ADT1-4-143 | 37 | 175 | 79 | 176 | 80 | 177 | 92 | 181 |
| ADT1-4-53 | 38 | 175 | 79 | 176 | 80 | 177 | 93 | 179 |
| ADT1-4-173 | 39 | 175 | 79 | 176 | 80 | 177 | 94 | 179 |
| ADT1-4-2 | 40 | 175 | 79 | 176 | 80 | 177 | 95 | 179 |
| ADT1-4-8 | 41 | 175 | 79 | 176 | 80 | 177 | 96 | 179 |
| ADT1-4-82 | 42 | 175 | 79 | 176 | 80 | 177 | 97 | 179 |
| ADT1-4-83 | 43 | 175 | 79 | 176 | 80 | 177 | 98 | 179 |
| ADT1-4-3 | 44 | 175 | 79 | 176 | 80 | 177 | 99 | 179 |
| ADT1-4-84 | 45 | 175 | 79 | 176 | 80 | 177 | 100 | 179 |
| ADT1-4-86 | 46 | 175 | 79 | 176 | 80 | 177 | 101 | 179 |
| ADT1-4-95 | 47 | 175 | 79 | 176 | 80 | 177 | 102 | 182 |
| ADT1-4-1 | 48 | 175 | 79 | 176 | 80 | 177 | 103 | 179 |
| ADT1-4-6 | 49 | 175 | 79 | 176 | 80 | 177 | 104 | 179 |
| ADT1-4-138 | 50 | 175 | 79 | 176 | 80 | 178 | 105 | 179 |

TABLE 3

Summary of Fab regions derived from ADT1-7 (heavy chain) and the related SEQ ID NOs

| Antibody | VH | HFR1 | VHCDR1 | HFR2 | VHCDR2 | HFR3 | VHCDR3 | HFR4 |
|---|---|---|---|---|---|---|---|---|
| Parental ADT1-4 | 106 | 189 | 130 | 190 | 131 | 191 | 132 | 192 |
| ADT1-7-10 | 107 | 189 | 130 | 190 | 131 | 191 | 133 | 192 |
| ADT1-7-15 | 108 | 189 | 130 | 190 | 131 | 191 | 134 | 192 |
| ADT1-7-17 | 109 | 189 | 130 | 190 | 131 | 191 | 135 | 192 |
| ADT1-7-18 | 110 | 189 | 130 | 190 | 131 | 191 | 136 | 192 |
| ADT1-7-19 | 111 | 189 | 130 | 190 | 131 | 191 | 137 | 192 |
| ADT1-7-20 | 112 | 189 | 130 | 190 | 131 | 191 | 138 | 192 |
| ADT1-7-22 | 113 | 189 | 130 | 190 | 131 | 191 | 139 | 192 |
| ADT1-7-23 | 114 | 189 | 130 | 190 | 131 | 191 | 140 | 192 |
| ADT1-7-42 | 115 | 189 | 130 | 190 | 131 | 191 | 141 | 192 |
| ADT1-7-3 | 116 | 189 | 130 | 190 | 131 | 191 | 142 | 192 |
| ADT1-7-61 | 117 | 189 | 130 | 190 | 131 | 191 | 143 | 192 |

TABLE 4

Summary of Fab regions derived from ADT1-7 (light chain) and the related SEQ ID NOs

| Antibody | VL | LFR1 | VLCDR1 | LFR2 | VLCDR2 | LFR3 | VLCDR3 | LFR4 |
|---|---|---|---|---|---|---|---|---|
| Parental ADT1-7 | 118 | 193 | 144 | 195 | 145 | 196 | 146 | 197 |
| ADT1-7-10 | 119 | 193 | 144 | 195 | 145 | 196 | 147 | 197 |
| ADT1-7-15 | 120 | 193 | 144 | 195 | 145 | 196 | 148 | 197 |
| ADT1-7-17 | 121 | 193 | 144 | 195 | 145 | 196 | 149 | 197 |
| ADT1-7-18 | 122 | 194 | 144 | 195 | 145 | 196 | 150 | 197 |
| ADT1-7-19 | 123 | 193 | 144 | 195 | 145 | 196 | 151 | 197 |
| ADT1-7-20 | 124 | 193 | 144 | 195 | 145 | 196 | 152 | 197 |
| ADT1-7-22 | 125 | 193 | 144 | 195 | 145 | 196 | 153 | 197 |
| ADT1-7-23 | 126 | 193 | 144 | 195 | 145 | 196 | 154 | 197 |
| ADT1-7-42 | 127 | 193 | 144 | 195 | 145 | 196 | 155 | 197 |
| ADT1-7-3 | 128 | 193 | 144 | 195 | 145 | 196 | 156 | 197 |
| ADT1-7-61 | 129 | 193 | 144 | 195 | 145 | 196 | 157 | 197 |

TABLE 5

Summary of other parental Fab regions and the related SEQ ID NOs

| Parental Antibody | VH | VL |
|---|---|---|
| C08 | 273 | 282 |
| B07 | 274 | 283 |
| C05 | 275 | 284 |
| E04 | 276 | 285 |
| F07 | 277 | 286 |
| G06 | 278 | 287 |
| G09 | 279 | 288 |
| B09 | 280 | 289 |
| G10 | 281 | 290 |
| E01 | 312 | 313 |

ADT1-4- and ADT1-7-Derived Fab Regions

The present invention provides multispecific antibodies wherein the Fab regions are derived from parental antibody ADT1-4 (having a variable heavy region sequence according to SEQ ID NO: 1 and a variable light region sequence according to SEQ ID NO: 26), and antibodies derived from parental antibody ADT1-7 (having a variable heavy region sequence according to SEQ ID NO: 106 and a variable light region sequence according to SEQ ID No: 118). ADT1-4 is also referred to herein as G04, and ADT1-4 and G04 are used interchangeably. ADT1-7 is also referred to herein as E07, and ADT1-7 and E07 are used interchangeably.

In some embodiments, the invention provides multispecific antibodies, the anti-TCR delta variable 1 (anti-Vδ1) binding Fab region comprising:
a heavy chain variable region comprising or consisting of a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID NOs: 55 to 78 and 133 to 143; and/or a light chain variable region comprising a VLCDR3 comprising or consisting of an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID NOs: 82 to 105 and 147 to 157. Certain amino acid substitutions may be made to provide one or more variant antibodies as described herein.

In some embodiments, the invention provides multispecific antibodies, the anti-TCR delta variable 1 (anti-Vδ1) binding Fab region comprising:
a heavy chain variable region comprising:
a VHCDR1 comprising or consisting of an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of: SEQ ID NOs: 51, 52 and 130;
a VHCDR2 comprising or consisting of an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of: SEQ ID NO: 53 and 131; and
a VHCDR3 comprising or consisting of an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of: SEQ ID NOs: 55 to 78 and 133 to 143; and
a light chain variable region comprising:
a VLCDR1 comprising or consisting of an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of: SEQ ID NO: 79 and 144;
a VLCDR2 comprising or consisting of an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of: SEQ ID NO: 80 and 145; and
a VLCDR3 comprising or consisting of an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of: SEQ ID NOs: 82 to 105 and 147 to 157.

Certain amino acid substitutions may be made to provide one or more variant Fab regions as described herein.

In some embodiments, the invention provides multispecific antibodies, the anti-TCR delta variable 1 (anti-Vδ1) binding Fab region comprising:
- a heavy chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID NOs: 2 to 25 and 107 to 117; and/or
- a light chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID NOs: 27 to 50 and 119 to 129.

ADT1-4-Derived Fab Regions

The present invention provides multispecific antibodies comprising Fab regions derived from parental antibody ADT1-4 (having a variable heavy region sequence according to SEQ ID NO: 1 and a variable light region sequence according to SEQ ID NO: 26), for example as set out in the following. ADT1-4 is also referred to herein as G04, and ADT1-4 and G04 are used interchangeably.

Antibodies Comprising Particular CDR Sequences Derived from ADT1-4

The multispecific antibodies provided herein include the following Fab regions having particular sequences derived from ADT1-4.

For example, in some embodiments, there is provided multispecific antibodies, the anti-TCR delta variable 1 (anti-Vδ1) binding Fab region comprising a heavy chain variable region comprising a VHCDR3 comprising or consisting of an amino acid sequence selected from the group consisting of SEQ ID NOs: 55 to 78; and/or a light chain variable region comprising a VLCDR3 comprising or consisting of an amino acid sequence selected from the group consisting of SEQ ID NOs: 82 to 105. Certain amino acid substitutions may be made to provide one or more variant antibodies as described herein.

In some embodiments, there are provided multispecific antibodies, the anti-TCR delta variable 1 (anti-Vδ1) binding Fab region comprising a heavy chain variable region comprising a VHCDR3 comprising or consisting of an amino acid sequence selected from the group consisting of SEQ ID NOs: 55 to 77; and/or a light chain variable region comprising a VLCDR3 comprising or consisting of an amino acid sequence selected from the group consisting of SEQ ID NOs: 82 to 104. Certain amino acid substitutions may be made to provide one or more variant antibodies as described herein.

In some embodiments, there are multispecific antibodies, the anti-TCR delta variable 1 (anti-Vδ1) binding Fab region comprising a heavy chain variable region comprising a VHCDR3 comprising or consisting of an amino acid sequence selected from the group consisting of SEQ ID NOs: 58, 60, 61, 62, 65, 66, 68, 74, 76 and 77; and/or a light chain variable region comprising a VLCDR3 comprising or consisting of an amino acid sequence selected from the group consisting of SEQ ID NOs: 85, 87, 88, 89, 92, 93, 95, 101, 103 and 104. Certain amino acid substitutions may be made to provide one or more variant antibodies as described herein.

There are also provided multispecific antibodies, the anti-TCR delta variable 1 (anti-Vδ1) binding Fab region comprising:
- a heavy chain variable region comprising:
  - a VHCDR1 comprising or consisting of an amino acid sequence selected from the group consisting of: SEQ ID NOs: 51 and 52;
  - a VHCDR2 comprising or consisting of the amino acid sequence of SEQ ID NO: 53; and
  - a VHCDR3 comprising or consisting of an amino acid sequence selected from the group consisting of: SEQ ID NOs: 55 to 78; and
- a light chain variable region comprising:
  - a VLCDR1 comprising or consisting of the amino acid sequence of SEQ ID NO: 79;
  - a VLCDR2 comprising or consisting of the amino acid sequence of SEQ ID NO: 80; and
  - a VLCDR3 comprising or consisting of an amino acid sequence selected from the group consisting of: SEQ ID NOs: 82 to 105.

Certain amino acid substitutions may be made to provide one or more variant antibodies as described herein.

There are also provided multispecific antibodies, the anti-TCR delta variable 1 (anti-Vδ1) binding Fab region comprising:
- a heavy chain variable region comprising:
  - a VHCDR1 comprising or consisting of an amino acid sequence selected from the group consisting of: SEQ ID NOs: 51 and 52;
  - a VHCDR2 comprising or consisting of the amino acid sequence of SEQ ID NO: 53; and
  - a VHCDR3 comprising or consisting of an amino acid sequence selected from the group consisting of: SEQ ID NOs: 55 to 77; and
- a light chain variable region comprising:
  - a VLCDR1 comprising or consisting of the amino acid sequence of SEQ ID NO: 79;
  - a VLCDR2 comprising or consisting of the amino acid sequence of SEQ ID NO: 80; and
  - a VLCDR3 comprising or consisting of an amino acid sequence selected from the group consisting of: SEQ ID NOs: 82 to 104.

Certain amino acid substitutions may be made to provide one or more variant antibodies as described herein.

There are also provided multispecific antibodies, the anti-TCR delta variable 1 (anti-Vδ1) binding Fab region comprising:
- a heavy chain variable region comprising:
  - a VHCDR1 comprising or consisting of an amino acid sequence selected from the group consisting of: SEQ ID NOs: 51 and 52;
  - a VHCDR2 comprising or consisting of the amino acid sequence of SEQ ID NO: 53; and
  - a VHCDR3 comprising or consisting of an amino acid sequence selected from the group consisting of: SEQ ID NOs: 58, 60, 61, 62, 65, 66, 68, 74, 76 and 77; and
- a light chain variable region comprising:
  - a VLCDR1 comprising or consisting of the amino acid sequence of SEQ ID NO: 79;
  - a VLCDR2 comprising or consisting of the amino acid sequence of SEQ ID NO: 80; and
  - a VLCDR3 comprising or consisting of an amino acid sequence selected from the group consisting of: SEQ ID NOs: 85, 87, 88, 89, 92, 93, 95, 101, 103 and 104.

Certain amino acid substitutions may be made to provide one or more variant antibodies as described herein.

There are also provided multispecific antibodies, the anti-TCR delta variable 1 (anti-Vδ1) binding Fab region comprising a) a VHCDR1, a VHCDR2 and a VHCDR3 comprising or consisting of the amino acid sequences of SEQ ID NO: 51, 53 and 55, respectively, and a VLCDR1, a VLCDR2 and a VLCDR3 comprising or consisting of the amino acid sequences of SEQ ID NOs: 79, 80 and 82, respectively;

b) a VHCDR1, a VHCDR2 and a VHCDR3 comprising or consisting of the amino acid sequences of SEQ ID NO: 51, 53 and 56, respectively, and a VLCDR1, a VLCDR2 and a VLCDR3 comprising or consisting of the amino acid sequences of SEQ ID NOs: 79, 80 and 83, respectively;

c) a VHCDR1, a VHCDR2 and a VHCDR3 comprising or consisting of the amino acid sequences of SEQ ID NO: 51, 53 and 57, respectively, and a VLCDR1, a VLCDR2 and a VLCDR3 comprising or consisting of the amino acid sequences of SEQ ID NOs: 79, 80 and 84, respectively;

d) a VHCDR1, a VHCDR2 and a VHCDR3 comprising or consisting of the amino acid sequences of SEQ ID NO: 51, 53 and 58, respectively, and a VLCDR1, a VLCDR2 and a VLCDR3 comprising or consisting of the amino acid sequences of SEQ ID NOs: 79, 80 and 85, respectively;

e) a VHCDR1, a VHCDR2 and a VHCDR3 comprising or consisting of the amino acid sequences of SEQ ID NO: 51, 53 and 59, respectively, and a VLCDR1, a VLCDR2 and a VLCDR3 comprising or consisting of the amino acid sequences of SEQ ID NOs: 79, 80 and 86, respectively;

f) a VHCDR1, a VHCDR2 and a VHCDR3 comprising or consisting of the amino acid sequences of SEQ ID NO: 51, 53 and 60, respectively, and a VLCDR1, a VLCDR2 and a VLCDR3 comprising or consisting of the amino acid sequences of SEQ ID NOs: 79, 80 and 87, respectively;

g) a VHCDR1, a VHCDR2 and a VHCDR3 comprising or consisting of the amino acid sequences of SEQ ID NO: 52, 53 and 61, respectively, and a VLCDR1, a VLCDR2 and a VLCDR3 comprising or consisting of the amino acid sequences of SEQ ID NOs: 79, 80 and 88, respectively;

h) a VHCDR1, a VHCDR2 and a VHCDR3 comprising or consisting of the amino acid sequences of SEQ ID NO: 51, 53 and 62, respectively, and a VLCDR1, a VLCDR2 and a VLCDR3 comprising or consisting of the amino acid sequences of SEQ ID NOs: 79, 80 and 89, respectively;

i) a VHCDR1, a VHCDR2 and a VHCDR3 comprising or consisting of the amino acid sequences of SEQ ID NO: 51, 53 and 63, respectively, and a VLCDR1, a VLCDR2 and a VLCDR3 comprising or consisting of the amino acid sequences of SEQ ID NOs: 79, 80 and 90, respectively;

j) a VHCDR1, a VHCDR2 and a VHCDR3 comprising or consisting of the amino acid sequences of SEQ ID NO: 51, 53 and 64, respectively, and a VLCDR1, a VLCDR2 and a VLCDR3 comprising or consisting of the amino acid sequences of SEQ ID NOs: 79, 80 and 91, respectively;

k) a VHCDR1, a VHCDR2 and a VHCDR3 comprising or consisting of the amino acid sequences of SEQ ID NO: 51, 53 and 65, respectively, and a VLCDR1, a VLCDR2 and a VLCDR3 comprising or consisting of the amino acid sequences of SEQ ID NOs: 79, 80 and 92, respectively;

l) a VHCDR1, a VHCDR2 and a VHCDR3 comprising or consisting of the amino acid sequences of SEQ ID NO: 52, 53 and 66, respectively, and a VLCDR1, a VLCDR2 and a VLCDR3 comprising or consisting of the amino acid sequences of SEQ ID NOs: 79, 80 and 93, respectively;

m) a VHCDR1, a VHCDR2 and a VHCDR3 comprising or consisting of the amino acid sequences of SEQ ID NO: 51, 53 and 67, respectively, and a VLCDR1, a VLCDR2 and a VLCDR3 comprising or consisting of the amino acid sequences of SEQ ID NOs: 79, 80 and 94, respectively;

n) a VHCDR1, a VHCDR2 and a VHCDR3 comprising or consisting of the amino acid sequences of SEQ ID NO: 51, 53 and 68, respectively, and a VLCDR1, a VLCDR2 and a VLCDR3 comprising or consisting of the amino acid sequences of SEQ ID NOs: 79, 80 and 95, respectively;

o) a VHCDR1, a VHCDR2 and a VHCDR3 comprising or consisting of the amino acid sequences of SEQ ID NO: 51, 53 and 69, respectively, and a VLCDR1, a VLCDR2 and a VLCDR3 comprising or consisting of the amino acid sequences of SEQ ID NOs: 79, 80 and 96, respectively;

p) a VHCDR1, a VHCDR2 and a VHCDR3 comprising or consisting of the amino acid sequences of SEQ ID NO: 51, 53 and 70, respectively, and a VLCDR1, a VLCDR2 and a VLCDR3 comprising or consisting of the amino acid sequences of SEQ ID NOs: 79, 80 and 97, respectively;

q) a VHCDR1, a VHCDR2 and a VHCDR3 comprising or consisting of the amino acid sequences of SEQ ID NO: 51, 53 and 71, respectively, and a VLCDR1, a VLCDR2 and a VLCDR3 comprising or consisting of the amino acid sequences of SEQ ID NOs: 79, 80 and 98, respectively;

r) a VHCDR1, a VHCDR2 and a VHCDR3 comprising or consisting of the amino acid sequences of SEQ ID NO: 51, 53 and 72, respectively, and a VLCDR1, a VLCDR2 and a VLCDR3 comprising or consisting of the amino acid sequences of SEQ ID NOs: 79, 80 and 99, respectively;

s) a VHCDR1, a VHCDR2 and a VHCDR3 comprising or consisting of the amino acid sequences of SEQ ID NO: 51, 53 and 73, respectively, and a VLCDR1, a VLCDR2 and a VLCDR3 comprising or consisting of the amino acid sequences of SEQ ID NOs: 79, 80 and 100, respectively;

t) a VHCDR1, a VHCDR2 and a VHCDR3 comprising or consisting of the amino acid sequences of SEQ ID NO: 52, 53 and 74, respectively, and a VLCDR1, a VLCDR2 and a VLCDR3 comprising or consisting of the amino acid sequences of SEQ ID NOs: 79, 80 and 101, respectively;

u) a VHCDR1, a VHCDR2 and a VHCDR3 comprising or consisting of the amino acid sequences of SEQ ID NO: 51, 53 and 75, respectively, and a VLCDR1, a VLCDR2 and a VLCDR3 comprising or consisting of the amino acid sequences of SEQ ID NOs: 79, 80 and 102, respectively;

v) a VHCDR1, a VHCDR2 and a VHCDR3 comprising or consisting of the amino acid sequences of SEQ ID NO: 51, 53 and 76, respectively, and a VLCDR1, a VLCDR2 and a VLCDR3 comprising or consisting of the amino acid sequences of SEQ ID NOs: 79, 80 and 103, respectively;

w) a VHCDR1, a VHCDR2 and a VHCDR3 comprising or consisting of the amino acid sequences of SEQ ID NO: 51, 53 and 77, respectively, and a VLCDR1, a VLCDR2 and a VLCDR3 comprising or consisting of the amino acid sequences of SEQ ID NOs: 79, 80 and 104, respectively; or;

x) a VHCDR1, a VHCDR2 and a VHCDR3 comprising or consisting of the amino acid sequences of SEQ ID NO: 51, 53 and 78, respectively, and a VLCDR1, a VLCDR2 and a VLCDR3 comprising or consisting of the amino acid sequences of SEQ ID NOs: 79, 80 and 105, respectively.

The multispecific antibodies may comprise a kappa light chain variable sequence (or comprise a variable light chain that is derived from a kappa light chain variable sequence), wherein the residue at position 74 of the kappa light chain variable sequence according to the IMGT numbering system is not serine, for example a non-human-germline residue and/or a non-polar residue at position 74, for example the residue at position 74 is a leucine residue.

Further embodiments are provided below.

ADT1-4-105 and Fragments and Variants Thereof

Certain embodiments relate to the antibody ADT1-4-105 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 55 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 82. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 55 and/or a light chain variable region comprising a VLCDR3 comprising an amino acid sequence having at least 90% identity to the amino acid sequence of SEQ ID NO: 82. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 55 and/or a light chain variable region comprising a VLCDR3 comprising the amino acid sequence of SEQ ID NO: 82.

Amino acid substitutions may be made to provide variant antibodies with Fab regions derived from ADT1-4-105, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 55, optionally comprising 1 or 2 amino acid substitutions, and/or a light chain variable region comprising a VLCDR3 comprising the amino acid sequence of SEQ ID NO: 82, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 55; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 82.

In one embodiment, multispecific antibodies are provided, the anti-TCR delta variable 1 (anti-Vδ1) binding Fab region comprising:

a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 55; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 82.

In one embodiment, multispecific antibodies are provided, the anti-TCR delta variable 1 (anti-Vδ1) binding Fab region comprising:

a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 55; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 82.

Amino acid substitutions may be made to provide variant antibodies with Fab regions derived from ADT1-4-105, for example multispecific antibodies are provided, the anti-TCR delta variable 1 (anti-Vδ1) binding Fab region comprising:
- a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 55 optionally comprising 1 or 2 amino acid substitutions; and/or
- a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 82 optionally comprising 1 or 2 amino acid substitutions. The amino acid substitutions may be conservative amino acid substitutions.

The antibodies may alternatively consist of the specified sequences (with or without amino acid substitutions).

ADT1-4-107 and Fragments and Variants Thereof

Certain embodiments relate to the antibody ADT1-4-107 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 56 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 83. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 56 and/or a light chain variable region comprising a VLCDR3 comprising an amino acid sequence having at least 90% identity to the amino acid sequence of SEQ ID NO: 83. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 56 and/or a light chain variable region comprising a VLCDR3 comprising the amino acid sequence of SEQ ID NO: 83.

Amino acid substitutions may be made to provide variant antibodies comprising Fab regions derived from ADT1-4-107, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 56, optionally comprising 1 or 2 amino acid substitutions, and/or a light chain variable region comprising a VLCDR3 comprising the amino acid sequence of SEQ ID NO: 83, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:
- a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 56; and/or
- a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 83.

In one embodiment, multispecific antibodies are provided, the anti-TCR delta variable 1 (anti-Vδ1) binding Fab region comprising:
- a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 56; and/or
- a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 83.

In one embodiment, multispecific antibodies are provided, the anti-TCR delta variable 1 (anti-Vδ1) binding Fab region comprising:
- a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 56; and
- a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 83.

Amino acid substitutions may be made to provide variant antibodies comprising Fab regions derived from ADT1-4-107, for example multispecific antibodies are provided, the anti-TCR delta variable 1 (anti-Vδ1) binding Fab region comprising:

- a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 56 optionally comprising 1 or 2 amino acid substitutions; and/or
- a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 83 optionally comprising 1 or 2 amino acid substitutions. The amino acid substitutions may be conservative amino acid substitutions.

The antibodies may alternatively consist of the specified sequences (with or without amino acid substitutions).

ADT1-4-110 and Fragments and Variants Thereof

Certain embodiments relate to the antibody ADT1-4-110 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 57 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 84. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 57 and/or a light chain variable region comprising a VLCDR3 comprising an amino acid sequence having at least 90% identity to the amino acid sequence of SEQ ID NO: 84. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 57 and/or a light chain variable region comprising a VLCDR3 comprising the amino acid sequence of SEQ ID NO: 84.

Amino acid substitutions may be made to provide variant antibodies comprising Fab regions derived from ADT1-4-110, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 57, optionally comprising 1 or 2 amino acid substitutions, and/or a light chain variable region comprising a VLCDR3 comprising the amino acid sequence of SEQ ID NO: 84, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:

- a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 57; and/or
- a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 84.

In one embodiment, multispecific antibodies are provided, the anti-TCR delta variable 1 (anti-Vδ1) binding Fab region comprising:

- a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 57; and/or
- a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 84.

In one embodiment, multispecific antibodies are provided, the anti-TCR delta variable 1 (anti-Vδ1) binding Fab region comprising:

- a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 57; and
- a light chain variable region comprising a VLCDR1 comprising the amino acid sequence of SEQ ID NO:

79, a VLCDR2 comprising the amino acid sequence of SEQ ID NO: 80 and a VLCDR3 comprising the amino acid sequence of SEQ ID NO: 84.

Amino acid substitutions may be made to provide variant antibodies comprising Fab regions derived from ADT1-4-110, for example multispecific antibodies are provided, the anti-TCR delta variable 1 (anti-Vδ1) binding Fab region comprising:

- a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 57 optionally comprising 1 or 2 amino acid substitutions; and/or
- a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 84 optionally comprising 1 or 2 amino acid substitutions. The amino acid substitutions may be conservative amino acid substitutions.

The antibodies may alternatively consist of the specified sequences (with or without amino acid substitutions).

ADT1-4-112 and Fragments and Variants Thereof

Certain embodiments relate to the antibody ADT1-4-112 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 58 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 85. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 58 and/or a light chain variable region comprising a VLCDR3 comprising an amino acid sequence having at least 90% identity to the amino acid sequence of SEQ ID NO: 85. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 58 and/or a light chain variable region comprising a VLCDR3 comprising the amino acid sequence of SEQ ID NO: 85.

Amino acid substitutions may be made to provide variant antibodies having Fab regions derived from ADT1-4-112, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 58, optionally comprising 1 or 2 amino acid substitutions, and/or a light chain variable region comprising a VLCDR3 comprising the amino acid sequence of SEQ ID NO: 85, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:

- a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 58; and/or
- a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 85.

In one embodiment, multispecific antibodies are provided, the anti-TCR delta variable 1 (anti-Vδ1) binding Fab region comprising:

- a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 58; and/or
- a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 85.

In one embodiment, multispecific antibodies are provided, the anti-TCR delta variable 1 (anti-Vδ1) binding Fab region comprising:

- a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 58; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 85.

Amino acid substitutions may be made to provide variant antibodies with Fab regions derived from ADT1-4-112, for example multispecific antibodies are provided, the anti-TCR delta variable 1 (anti-Vδ1) binding Fab region comprising:
- a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 58 optionally comprising 1 or 2 amino acid substitutions; and/or
- a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 85 optionally comprising 1 or 2 amino acid substitutions. The amino acid substitutions may be conservative amino acid substitutions.

The antibodies may alternatively consist of the specified sequences (with or without amino acid substitutions).

ADT1-4-117 and Fragments and Variants Thereof

Certain embodiments relate to the antibody ADT1-4-117 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 59 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 86. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 59 and/or a light chain variable region comprising a VLCDR3 comprising an amino acid sequence having at least 90% identity to the amino acid sequence of SEQ ID NO: 86. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 59 and/or a light chain variable region comprising a VLCDR3 comprising the amino acid sequence of SEQ ID NO: 86.

Amino acid substitutions may be made to provide variant antibodies with Fab regions derived from ADT1-4-117, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 59, optionally comprising 1 or 2 amino acid substitutions, and/or a light chain variable region comprising a VLCDR3 comprising the amino acid sequence of SEQ ID NO: 86, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:
- a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 59; and/or
- a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 86.

In one embodiment, multispecific antibodies are provided, the anti-TCR delta variable 1 (anti-Vδ1) binding Fab region comprising:
- a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 59; and/or
- a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 86.

In one embodiment, multispecific antibodies are provided, the anti-TCR delta variable 1 (anti-Vδ1) binding Fab region comprising:
- a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 59; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 86.

Amino acid substitutions may be made to provide variant antibodies with Fab regions derived from ADT1-4-117, for example multispecific antibodies are provided, the anti-TCR delta variable 1 (anti-Vδ1) binding Fab region comprising:

- a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 59 optionally comprising 1 or 2 amino acid substitutions; and/or
- a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 86 optionally comprising 1 or 2 amino acid substitutions. The amino acid substitutions may be conservative amino acid substitutions.

The antibodies may alternatively consist of the specified sequences (with or without amino acid substitutions).

ADT1-4-19 and Fragments and Variants Thereof

Certain embodiments relate to the antibody ADT1-4-19 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 60 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 87. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 60 and/or a light chain variable region comprising a VLCDR3 comprising an amino acid sequence having at least 90% identity to the amino acid sequence of SEQ ID NO: 87. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 60 and/or a light chain variable region comprising a VLCDR3 comprising the amino acid sequence of SEQ ID NO: 87.

Amino acid substitutions may be made to provide variant antibodies comprising Fab regions derived from ADT1-4-19, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 60, optionally comprising 1 or 2 amino acid substitutions, and/or a light chain variable region comprising a VLCDR3 comprising the amino acid sequence of SEQ ID NO: 87, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:

- a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 60; and/or
- a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 87.

In one embodiment, multispecific antibodies are provided, the anti-TCR delta variable 1 (anti-Vδ1) binding Fab region comprising:

- a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 60; and/or
- a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 87.

In one embodiment, multispecific antibodies are provided, the anti-TCR delta variable 1 (anti-Vδ1) binding Fab region comprising:

- a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 60; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 87.

Amino acid substitutions may be made to provide variant antibodies with Fab regions derived from ADT1-4-19, for example multispecific antibodies are provided, the anti-TCR delta variable 1 (anti-Vδ1) binding Fab region comprising:
  a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 60 optionally comprising 1 or 2 amino acid substitutions; and/or
  a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 87 optionally comprising 1 or 2 amino acid substitutions. The amino acid substitutions may be conservative amino acid substitutions.

The antibodies may alternatively consist of the specified sequences (with or without amino acid substitutions).

ADT1-4-21 and Fragments and Variants Thereof

Certain embodiments relate to the antibody ADT1-4-21 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 61 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 88. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 61 and/or a light chain variable region comprising a VLCDR3 comprising an amino acid sequence having at least 90% identity to the amino acid sequence of SEQ ID NO: 88. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 61 and/or a light chain variable region comprising a VLCDR3 comprising the amino acid sequence of SEQ ID NO: 88.

Amino acid substitutions may be made to provide variant antibodies with Fab regions derived from ADT1-4-21, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 61, optionally comprising 1 or 2 amino acid substitutions, and/or a light chain variable region comprising a VLCDR3 comprising the amino acid sequence of SEQ ID NO: 88, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:
  a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 52, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 61; and/or
  a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 88.

In one embodiment, multispecific antibodies are provided, the anti-TCR delta variable 1 (anti-Vδ1) binding Fab region comprising:
  a heavy chain variable region comprising a VHCDR1 comprising at least 90% identity to the amino acid sequence of SEQ ID NO: 52, a VHCDR2 comprising at least 90% identity to the amino acid sequence of SEQ ID NO: 53 and a VHCDR3 comprising at least 90% identity to the amino acid sequence of SEQ ID NO: 61; and/or
  a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 88.

In one embodiment, multispecific antibodies are provided, the anti-TCR delta variable 1 (anti-Vδ1) binding Fab region comprising:
  a heavy chain variable region comprising a VHCDR1 comprising the amino acid sequence of SEQ ID NO: 52, a VHCDR2 comprising the amino acid sequence of SEQ ID NO: 53 and a VHCDR3 comprising the amino acid sequence of SEQ ID NO: 61; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 88.

Amino acid substitutions may be made to provide variant antibodies comprising Fab regions derived from ADT1-4-21, for example multispecific antibodies are provided, the anti-TCR delta variable 1 (anti-Vδ1) binding Fab region comprising:

- a heavy chain variable region comprising a VHCDR1 comprising the amino acid sequence of SEQ ID NO: 52 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 61 optionally comprising 1 or 2 amino acid substitutions; and/or
- a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 88 optionally comprising 1 or 2 amino acid substitutions. The amino acid substitutions may be conservative amino acid substitutions.

The antibodies may alternatively consist of the specified sequences (with or without amino acid substitutions).

ADT1-4-31 and Fragments and Variants Thereof

Certain embodiments relate to the antibody ADT1-4-31 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 62 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 89. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 62 and/or a light chain variable region comprising a VLCDR3 comprising an amino acid sequence having at least 90% identity to the amino acid sequence of SEQ ID NO: 89. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 62 and/or a light chain variable region comprising a VLCDR3 comprising the amino acid sequence of SEQ ID NO: 89.

Amino acid substitutions may be made to provide variant antibodies having Fab regions derived from ADT1-4-31, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 62, optionally comprising 1 or 2 amino acid substitutions, and/or a light chain variable region comprising a VLCDR3 comprising the amino acid sequence of SEQ ID NO: 89, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:

- a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 62; and/or
- a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 89.

In one embodiment, multispecific antibodies are provided, the anti-TCR delta variable 1 (anti-Vδ1) binding Fab region comprising:

- a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 62; and/or
- a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 89.

In one embodiment, multispecific antibodies are provided, the anti-TCR delta variable 1 (anti-Vδ1) binding Fab region comprising:

- a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 62; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 89.

Amino acid substitutions may be made to provide variant antibodies having Fab regions derived from ADT1-4-31, for example multispecific antibodies are provided, the anti-TCR delta variable 1 (anti-Vδ1) binding Fab region comprising:
- a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 62 optionally comprising 1 or 2 amino acid substitutions; and/or
- a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 89 optionally comprising 1 or 2 amino acid substitutions. The amino acid substitutions may be conservative amino acid substitutions.

The antibodies may alternatively consist of the specified sequences (with or without amino acid substitutions).

ADT1-4-139 and Fragments and Variants Thereof

Certain embodiments relate to the antibody ADT1-4-139 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 63 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 90. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 63 and/or a light chain variable region comprising a VLCDR3 comprising an amino acid sequence having at least 90% identity to the amino acid sequence of SEQ ID NO: 90. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 63 and/or a light chain variable region comprising a VLCDR3 comprising the amino acid sequence of SEQ ID NO: 90.

Amino acid substitutions may be made to provide variant antibodies having Fab regions derived from ADT1-4-139, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 63, optionally comprising 1 or 2 amino acid substitutions, and/or a light chain variable region comprising a VLCDR3 comprising the amino acid sequence of SEQ ID NO: 90, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:
- a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 63; and/or
- a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 90.

In one embodiment, multispecific antibodies are provided, the anti-TCR delta variable 1 (anti-Vδ1) binding Fab region comprising:
- a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 63; and/or
- a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 90.

In one embodiment, multispecific antibodies are provided, the anti-TCR delta variable 1 (anti-Vδ1) binding Fab region comprising:
- a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 63; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 90.

Amino acid substitutions may be made to provide variant antibodies having Fab regions derived from ADT1-4-139, for example multispecific antibodies are provided, the anti-TCR delta variable 1 (anti-Vδ1) binding Fab region comprising:

a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 63 optionally comprising 1 or 2 amino acid substitutions; and/or a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 90 optionally comprising 1 or 2 amino acid substitutions. The amino acid substitutions may be conservative amino acid substitutions.

The antibodies may alternatively consist of the specified sequences (with or without amino acid substitutions).

ADT1-4-4 and Fragments and Variants Thereof

Certain embodiments relate to the antibody ADT1-4-4 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 64 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 91. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 64 and/or a light chain variable region comprising a VLCDR3 comprising an amino acid sequence having at least 90% identity to the amino acid sequence of SEQ ID NO: 91. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 64 and/or a light chain variable region comprising a VLCDR3 comprising the amino acid sequence of SEQ ID NO: 91.

Amino acid substitutions may be made to provide variant antibodies having Fab regions derived from ADT1-4-4, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 64, optionally comprising 1 or 2 amino acid substitutions, and/or a light chain variable region comprising a VLCDR3 comprising the amino acid sequence of SEQ ID NO: 91, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 64; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 91.

In one embodiment, multispecific antibodies are provided, the anti-TCR delta variable 1 (anti-Vδ1) binding Fab region comprising:

a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 64; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 91.

In one embodiment, multispecific antibodies are provided, the anti-TCR delta variable 1 (anti-Vδ1) binding Fab region comprising:

a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 64; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 91.

Amino acid substitutions may be made to provide variant antibodies having Fab regions derived from ADT1-4-4, for example multispecific antibodies are provided, the anti-TCR delta variable 1 (anti-Vδ1) binding Fab region comprising:
  a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 64 optionally comprising 1 or 2 amino acid substitutions; and/or
  a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 91 optionally comprising 1 or 2 amino acid substitutions. The amino acid substitutions may be conservative amino acid substitutions.

The antibodies may alternatively consist of the specified sequences (with or without amino acid substitutions).

ADT1-4-143 and Fragments and Variants Thereof

Certain embodiments relate to the antibody ADT1-4-143 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 65 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 92. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 65 and/or a light chain variable region comprising a VLCDR3 comprising an amino acid sequence having at least 90% identity to the amino acid sequence of SEQ ID NO: 92. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 65 and/or a light chain variable region comprising a VLCDR3 comprising the amino acid sequence of SEQ ID NO: 92.

Amino acid substitutions may be made to provide variant antibodies having Fab regions derived from ADT1-4-143, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 65, optionally comprising 1 or 2 amino acid substitutions, and/or a light chain variable region comprising a VLCDR3 comprising the amino acid sequence of SEQ ID NO: 92, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:
  a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 65; and/or
  a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 92.

In one embodiment, multispecific antibodies are provided, the anti-TCR delta variable 1 (anti-Vδ1) binding Fab region comprising:
  a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 65; and/or
  a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 92.

In one embodiment, multispecific antibodies are provided, the anti-TCR delta variable 1 (anti-Vδ1) binding Fab region comprising:
  a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 65; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 92.

Amino acid substitutions may be made to provide variant antibodies having Fab regions derived from ADT1-4-143, for example multispecific antibodies are provided, the anti-TCR delta variable 1 (anti-Vδ1) binding Fab region comprising:
- a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 65 optionally comprising 1 or 2 amino acid substitutions; and/or
- a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 92 optionally comprising 1 or 2 amino acid substitutions. The amino acid substitutions may be conservative amino acid substitutions.

The antibodies may alternatively consist of the specified sequences (with or without amino acid substitutions).

ADT1-4-53 and Fragments and Variants Thereof

Certain embodiments relate to the antibody ADT1-4-53 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 66 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 93. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 66 and/or a light chain variable region comprising a VLCDR3 comprising an amino acid sequence having at least 90% identity to the amino acid sequence of SEQ ID NO: 93. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 66 and/or a light chain variable region comprising a VLCDR3 comprising the amino acid sequence of SEQ ID NO: 93.

Amino acid substitutions may be made to provide variant antibodies having Fab regions derived from ADT1-4-53, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 66, optionally comprising 1 or 2 amino acid substitutions, and/or a light chain variable region comprising a VLCDR3 comprising the amino acid sequence of SEQ ID NO: 93, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:
- a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 52, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 66; and/or
- a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 93.

In one embodiment, multispecific antibodies are provided, the anti-TCR delta variable 1 (anti-Vδ1) binding Fab region comprising:
- a heavy chain variable region comprising a VHCDR1 comprising at least 90% identity to the amino acid sequence of SEQ ID NO: 52, a VHCDR2 comprising at least 90% identity to the amino acid sequence of SEQ ID NO: 53 and a VHCDR3 comprising at least 90% identity to the amino acid sequence of SEQ ID NO: 66; and/or
- a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 93.

In one embodiment, multispecific antibodies are provided, the anti-TCR delta variable 1 (anti-Vδ1) binding Fab region comprising:
- a heavy chain variable region comprising a VHCDR1 comprising the amino acid sequence of SEQ ID NO: 52, a VHCDR2 comprising the amino acid sequence of SEQ ID NO: 53 and a VHCDR3 comprising the amino acid sequence of SEQ ID NO: 66; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 93.

Amino acid substitutions may be made to provide variant antibodies having Fab regions derived from ADT1-4-53, for example multispecific antibodies are provided, the anti-TCR delta variable 1 (anti-Vδ1) binding Fab region comprising:
- a heavy chain variable region comprising a VHCDR1 comprising the amino acid sequence of SEQ ID NO: 52 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 66 optionally comprising 1 or 2 amino acid substitutions; and/or
- a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 93 optionally comprising 1 or 2 amino acid substitutions. The amino acid substitutions may be conservative amino acid substitutions.

The antibodies may alternatively consist of the specified sequences (with or without amino acid substitutions).

ADT1-4-173 and Fragments and Variants Thereof

Certain embodiments relate to the antibody ADT1-4-173 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 67 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 94. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 67 and/or a light chain variable region comprising a VLCDR3 comprising an amino acid sequence having at least 90% identity to the amino acid sequence of SEQ ID NO: 94. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 67 and/or a light chain variable region comprising a VLCDR3 comprising the amino acid sequence of SEQ ID NO: 94.

Amino acid substitutions may be made to provide variant antibodies having Fab regions derived from ADT1-4-173, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 67, optionally comprising 1 or 2 amino acid substitutions, and/or a light chain variable region comprising a VLCDR3 comprising the amino acid sequence of SEQ ID NO: 94, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:
- a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 67; and/or
- a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 94.

In one embodiment, multispecific antibodies are provided, the anti-TCR delta variable 1 (anti-Vδ1) binding Fab region comprising:
- a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 67; and/or
- a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 94.

In one embodiment, multispecific antibodies are provided, the anti-TCR delta variable 1 (anti-Vδ1) binding Fab region comprising:
- a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 67; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 94.

Amino acid substitutions may be made to provide variant antibodies having Fab regions derived from ADT1-4-173, for example multispecific antibodies are provided, the anti-TCR delta variable 1 (anti-Vδ1) binding Fab region comprising:

- a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 67 optionally comprising 1 or 2 amino acid substitutions; and/or
- a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 94 optionally comprising 1 or 2 amino acid substitutions. The amino acid substitutions may be conservative amino acid substitutions.

The antibodies may alternatively consist of the specified sequences (with or without amino acid substitutions).

ADT1-4-2 and Fragments and Variants Thereof

Certain embodiments relate to the antibody ADT1-4-2 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 68 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 95. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 68 and/or a light chain variable region comprising a VLCDR3 comprising an amino acid sequence having at least 90% identity to the amino acid sequence of SEQ ID NO: 95. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 68 and/or a light chain variable region comprising a VLCDR3 comprising the amino acid sequence of SEQ ID NO: 95.

Amino acid substitutions may be made to provide variant antibodies having Fab regions derived from ADT1-4-2, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 68, optionally comprising 1 or 2 amino acid substitutions, and/or a light chain variable region comprising a VLCDR3 comprising the amino acid sequence of SEQ ID NO: 95, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:

- a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 68; and/or
- a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 95.

In one embodiment, multispecific antibodies are provided, the anti-TCR delta variable 1 (anti-Vδ1) binding Fab region comprising:

- a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 68; and/or
- a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 95.

In one embodiment, multispecific antibodies are provided, the anti-TCR delta variable 1 (anti-Vδ1) binding Fab region comprising:

- a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 68; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 95.

Amino acid substitutions may be made to provide variant antibodies having Fab regions derived from ADT1-4-2, for example multispecific antibodies are provided, the anti-TCR delta variable 1 (anti-Vδ1) binding Fab region comprising:

a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 68 optionally comprising 1 or 2 amino acid substitutions; and/or a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 95 optionally comprising 1 or 2 amino acid substitutions. The amino acid substitutions may be conservative amino acid substitutions.

The antibodies may alternatively consist of the specified sequences (with or without amino acid substitutions).

ADT1-4-8 and Fragments and Variants Thereof

Certain embodiments relate to the antibody ADT1-4-8 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 69 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 96. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 69 and/or a light chain variable region comprising a VLCDR3 comprising an amino acid sequence having at least 90% identity to the amino acid sequence of SEQ ID NO: 96. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 69 and/or a light chain variable region comprising a VLCDR3 comprising the amino acid sequence of SEQ ID NO: 96.

Amino acid substitutions may be made to provide variant antibodies having Fab regions derived from ADT1-4-8, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 69, optionally comprising 1 or 2 amino acid substitutions, and/or a light chain variable region comprising a VLCDR3 comprising the amino acid sequence of SEQ ID NO: 96, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 69; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 96.

In one embodiment, multispecific antibodies are provided, the anti-TCR delta variable 1 (anti-Vδ1) binding Fab region comprising:

a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 69; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 96.

In one embodiment, multispecific antibodies are provided, the anti-TCR delta variable 1 (anti-Vδ1) binding Fab region comprising:

a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 69; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 96.

Amino acid substitutions may be made to provide variant antibodies having Fab regions derived from ADT1-4-8, for example multispecific antibodies are provided, the anti-TCR delta variable 1 (anti-Vδ1) binding Fab region comprising:

- a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 69 optionally comprising 1 or 2 amino acid substitutions; and/or
- a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 96 optionally comprising 1 or 2 amino acid substitutions. The amino acid substitutions may be conservative amino acid substitutions.

The antibodies may alternatively consist of the specified sequences (with or without amino acid substitutions).

ADT1-4-82 and Fragments and Variants Thereof

Certain embodiments relate to the antibody ADT1-4-82 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 70 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 97. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 70 and/or a light chain variable region comprising a VLCDR3 comprising an amino acid sequence having at least 90% identity to the amino acid sequence of SEQ ID NO: 97. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 70 and/or a light chain variable region comprising a VLCDR3 comprising the amino acid sequence of SEQ ID NO: 97.

Amino acid substitutions may be made to provide variant antibodies having Fab regions derived from ADT1-4-82, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 70, optionally comprising 1 or 2 amino acid substitutions, and/or a light chain variable region comprising a VLCDR3 comprising the amino acid sequence of SEQ ID NO: 97, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:

- a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 70; and/or
- a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 97.

In one embodiment, multispecific antibodies are provided, the anti-TCR delta variable 1 (anti-Vδ1) binding Fab region comprising:

- a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 70; and/or
- a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 97.

In one embodiment, multispecific antibodies are provided, the anti-TCR delta variable 1 (anti-Vδ1) binding Fab region comprising:

- a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 70; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 97.

Amino acid substitutions may be made to provide variant antibodies having Fab regions derived from ADT1-4-82, for example multispecific antibodies are provided, the anti-TCR delta variable 1 (anti-Vδ1) binding Fab region comprising:

a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 70 optionally comprising 1 or 2 amino acid substitutions; and/or a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 97 optionally comprising 1 or 2 amino acid substitutions. The amino acid substitutions may be conservative amino acid substitutions.

The antibodies may alternatively consist of the specified sequences (with or without amino acid substitutions).

ADT1-4-83 and Fragments and Variants Thereof

Certain embodiments relate to the antibody ADT1-4-83 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 71 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 98. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 71 and/or a light chain variable region comprising a VLCDR3 comprising an amino acid sequence having at least 90% identity to the amino acid sequence of SEQ ID NO: 98. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 71 and/or a light chain variable region comprising a VLCDR3 comprising the amino acid sequence of SEQ ID NO: 98.

Amino acid substitutions may be made to provide variant antibodies having Fab regions derived from ADT1-4-83, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 71, optionally comprising 1 or 2 amino acid substitutions, and/or a light chain variable region comprising a VLCDR3 comprising the amino acid sequence of SEQ ID NO: 98, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 71; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 98.

In one embodiment, multispecific antibodies are provided, the anti-TCR delta variable 1 (anti-Vδ1) binding Fab region comprising:

a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 71; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 98.

In one embodiment, multispecific antibodies are provided, the anti-TCR delta variable 1 (anti-Vδ1) binding Fab region comprising:

a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 71; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 98.

Amino acid substitutions may be made to provide variant antibodies having Fab regions derived from ADT1-4-83, for example multispecific antibodies are provided, the anti-TCR delta variable 1 (anti-Vδ1) binding Fab region comprising:

a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 71 optionally comprising 1 or 2 amino acid substitutions; and/or a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 98 optionally comprising 1 or 2 amino acid substitutions. The amino acid substitutions may be conservative amino acid substitutions.

The antibodies may alternatively consist of the specified sequences (with or without amino acid substitutions).

ADT1-4-3 and Fragments and Variants Thereof

Certain embodiments relate to the antibody ADT1-4-3 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 72 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 99. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 72 and/or a light chain variable region comprising a VLCDR3 comprising an amino acid sequence having at least 90% identity to the amino acid sequence of SEQ ID NO: 99. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 72 and/or a light chain variable region comprising a VLCDR3 comprising the amino acid sequence of SEQ ID NO: 99.

Amino acid substitutions may be made to provide variant antibodies having Fab regions derived from ADT1-4-3, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 72, optionally comprising 1 or 2 amino acid substitutions, and/or a light chain variable region comprising a VLCDR3 comprising the amino acid sequence of SEQ ID NO: 99, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 72; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 99.

In one embodiment, multispecific antibodies are provided, the anti-TCR delta variable 1 (anti-Vδ1) binding Fab region comprising:

a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 72; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 99.

In one embodiment, multispecific antibodies are provided, the anti-TCR delta variable 1 (anti-Vδ1) binding Fab region comprising:

a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 72; and
a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 99.

Amino acid substitutions may be made to provide variant antibodies having Fab regions derived from ADT1-4-3, for example multispecific antibodies are provided, the anti-TCR delta variable 1 (anti-Vδ1) binding Fab region comprising:
- a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 72 optionally comprising 1 or 2 amino acid substitutions; and/or
- a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 99 optionally comprising 1 or 2 amino acid substitutions. The amino acid substitutions may be conservative amino acid substitutions.

The antibodies may alternatively consist of the specified sequences (with or without amino acid substitutions).

ADT1-4-84 and Fragments and Variants Thereof

Certain embodiments relate to the antibody ADT1-4-84 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 73 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 100. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 73 and/or a light chain variable region comprising a VLCDR3 comprising an amino acid sequence having at least 90% identity to the amino acid sequence of SEQ ID NO: 100. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 73 and/or a light chain variable region comprising a VLCDR3 comprising the amino acid sequence of SEQ ID NO: 100.

Amino acid substitutions may be made to provide variant antibodies having Fab regions derived from ADT1-4-84, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 73, optionally comprising 1 or 2 amino acid substitutions, and/or a light chain variable region comprising a VLCDR3 comprising the amino acid sequence of SEQ ID NO: 100, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:
- a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 73; and/or
- a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 100.

In one embodiment, multispecific antibodies are provided, the anti-TCR delta variable 1 (anti-Vδ1) binding Fab region comprising:
- a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 73; and/or
- a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 100.

In one embodiment, multispecific antibodies are provided, the anti-TCR delta variable 1 (anti-Vδ1) binding Fab region comprising:
- a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 73; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 100.

Amino acid substitutions may be made to provide variant antibodies having Fab regions derived from ADT1-4-84, for example multispecific antibodies are provided, the anti-TCR delta variable 1 (anti-Vδ1) binding Fab region comprising:

a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 73 optionally comprising 1 or 2 amino acid substitutions; and/or a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 100 optionally comprising 1 or 2 amino acid substitutions. The amino acid substitutions may be conservative amino acid substitutions.

The antibodies may alternatively consist of the specified sequences (with or without amino acid substitutions).

ADT1-4-86 and Fragments and Variants Thereof

Certain embodiments relate to the antibody ADT1-4-86 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 74 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 101. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 74 and/or a light chain variable region comprising a VLCDR3 comprising an amino acid sequence having at least 90% identity to the amino acid sequence of SEQ ID NO: 101. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 74 and/or a light chain variable region comprising a VLCDR3 comprising the amino acid sequence of SEQ ID NO: 101.

Amino acid substitutions may be made to provide variant antibodies having Fab regions derived from ADT1-4-86, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 74, optionally comprising 1 or 2 amino acid substitutions, and/or a light chain variable region comprising a VLCDR3 comprising the amino acid sequence of SEQ ID NO: 101, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 52, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 74; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 101.

In one embodiment, multispecific antibodies are provided, the anti-TCR delta variable 1 (anti-Vδ1) binding Fab region comprising:

a heavy chain variable region comprising a VHCDR1 comprising at least 90% identity to the amino acid sequence of SEQ ID NO: 52, a VHCDR2 comprising at least 90% identity to the amino acid sequence of SEQ ID NO: 53 and a VHCDR3 comprising at least 90% identity to the amino acid sequence of SEQ ID NO: 74; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 101.

In one embodiment, multispecific antibodies are provided, the anti-TCR delta variable 1 (anti-Vδ1) binding Fab region comprising:

a heavy chain variable region comprising a VHCDR1 comprising the amino acid sequence of SEQ ID NO: 52, a VHCDR2 comprising the amino acid sequence of SEQ ID NO: 53 and a VHCDR3 comprising the amino acid sequence of SEQ ID NO: 74; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 101.

Amino acid substitutions may be made to provide variant antibodies having Fab regions derived from ADT1-4-86, for example multispecific antibodies are provided, the anti-TCR delta variable 1 (anti-Vδ1) binding Fab region comprising:

a heavy chain variable region comprising a VHCDR1 comprising the amino acid sequence of SEQ ID NO: 52 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 74 optionally comprising 1 or 2 amino acid substitutions; and/or a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 101 optionally comprising 1 or 2 amino acid substitutions. The amino acid substitutions may be conservative amino acid substitutions.

The antibodies may alternatively consist of the specified sequences (with or without amino acid substitutions).

ADT1-4-95 and Fragments and Variants Thereof

Certain embodiments relate to the antibody ADT1-4-95 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 75 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 102. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 75 and/or a light chain variable region comprising a VLCDR3 comprising an amino acid sequence having at least 90% identity to the amino acid sequence of SEQ ID NO: 102. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 75 and/or a light chain variable region comprising a VLCDR3 comprising the amino acid sequence of SEQ ID NO: 102.

Amino acid substitutions may be made to provide variant antibodies having Fab regions derived from ADT1-4-95, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 75, optionally comprising 1 or 2 amino acid substitutions, and/or a light chain variable region comprising a VLCDR3 comprising the amino acid sequence of SEQ ID NO: 102, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 75; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 102.

In one embodiment, multispecific antibodies are provided, the anti-TCR delta variable 1 (anti-Vδ1) binding Fab region comprising:

a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 75; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 102.

In one embodiment, multispecific antibodies are provided, the anti-TCR delta variable 1 (anti-Vδ1) binding Fab region comprising:

a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 75; and
a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 102.

Amino acid substitutions may be made to provide variant antibodies having Fab regions derived from ADT1-4-95, for example multispecific antibodies are provided, the anti-TCR delta variable 1 (anti-Vδ1) binding Fab region comprising:
a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 75 optionally comprising 1 or 2 amino acid substitutions; and/or
a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 102 optionally comprising 1 or 2 amino acid substitutions. The amino acid substitutions may be conservative amino acid substitutions.

The antibodies may alternatively consist of the specified sequences (with or without amino acid substitutions).

ADT1-4-1 and Fragments and Variants Thereof

Certain embodiments relate to the antibody ADT1-4-1 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 76 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 103. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 76 and/or a light chain variable region comprising a VLCDR3 comprising an amino acid sequence having at least 90% identity to the amino acid sequence of SEQ ID NO: 103. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 76 and/or a light chain variable region comprising a VLCDR3 comprising the amino acid sequence of SEQ ID NO: 103.

Amino acid substitutions may be made to provide variant antibodies having Fab regions derived from ADT1-4-1, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 76, optionally comprising 1 or 2 amino acid substitutions, and/or a light chain variable region comprising a VLCDR3 comprising the amino acid sequence of SEQ ID NO: 103, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:
a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 76; and/or
a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 103.

In one embodiment, multispecific antibodies are provided, the anti-TCR delta variable 1 (anti-Vδ1) binding Fab region comprising:
a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 76; and/or
a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 103.

In one embodiment, multispecific antibodies are provided, the anti-TCR delta variable 1 (anti-Vδ1) binding Fab region comprising:
a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 76; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 103.

Amino acid substitutions may be made to provide variant antibodies having Fab regions derived from ADT1-4-1, for example multispecific antibodies are provided, the anti-TCR delta variable 1 (anti-Vδ1) binding Fab region comprising:

a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 76 optionally comprising 1 or 2 amino acid substitutions; and/or a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 103 optionally comprising 1 or 2 amino acid substitutions. The amino acid substitutions may be conservative amino acid substitutions.

The antibodies may alternatively consist of the specified sequences (with or without amino acid substitutions).

ADT1-4-6 and Fragments and Variants Thereof

Certain embodiments relate to the antibody ADT1-4-6 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 77 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 104. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 77 and/or a light chain variable region comprising a VLCDR3 comprising an amino acid sequence having at least 90% identity to the amino acid sequence of SEQ ID NO: 104. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 77 and/or a light chain variable region comprising a VLCDR3 comprising the amino acid sequence of SEQ ID NO: 104.

Amino acid substitutions may be made to provide variant antibodies having Fab regions derived from ADT1-4-6, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 77, optionally comprising 1 or 2 amino acid substitutions, and/or a light chain variable region comprising a VLCDR3 comprising the amino acid sequence of SEQ ID NO: 104, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 77; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 104.

In one embodiment, multispecific antibodies are provided, the anti-TCR delta variable 1 (anti-Vδ1) binding Fab region comprising:

a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 77; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 104.

In one embodiment, multispecific antibodies are provided, the anti-TCR delta variable 1 (anti-Vδ1) binding Fab region comprising:

a heavy chain variable region comprising a VHCDR1 comprising the amino acid sequence of SEQ ID NO: 51, a VHCDR2 comprising the amino acid sequence of SEQ ID NO: 53 and a VHCDR3 comprising the amino acid sequence of SEQ ID NO: 77; and a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 104.

Amino acid substitutions may be made to provide variant antibodies having Fab regions derived from ADT1-4-6, for example multispecific antibodies are provided, the anti-TCR delta variable 1 (anti-Vδ1) binding Fab region comprising:

a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 77 optionally comprising 1 or 2 amino acid substitutions; and/or a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 104 optionally comprising 1 or 2 amino acid substitutions. The amino acid substitutions may be conservative amino acid substitutions.

The antibodies may alternatively consist of the specified sequences (with or without amino acid substitutions).

ADT1-4-138 and Fragments and Variants Thereof

Certain embodiments relate to the antibody ADT1-4-138 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 78 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 105. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 78 and/or a light chain variable region comprising a VLCDR3 comprising an amino acid sequence having at least 90% identity to the amino acid sequence of SEQ ID NO: 105. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 78 and/or a light chain variable region comprising a VLCDR3 comprising the amino acid sequence of SEQ ID NO: 105.

Amino acid substitutions may be made to provide variant antibodies having Fab regions derived from ADT1-4-138, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 78, optionally comprising 1 or 2 amino acid substitutions, and/or a light chain variable region comprising a VLCDR3 comprising the amino acid sequence of SEQ ID NO: 105, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 51, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 53 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 78; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 79, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 80 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 105.

In one embodiment, multispecific antibodies are provided, the anti-TCR delta variable 1 (anti-Vδ1) binding Fab region comprising:

a heavy chain variable region comprising a VHCDR1 comprising at least 90% identity to the amino acid sequence of SEQ ID NO: 51, a VHCDR2 comprising at least 90% identity to the amino acid sequence of SEQ ID NO: 53 and a VHCDR3 comprising at least 90% identity to the amino acid sequence of SEQ ID NO: 78; and/or a light chain variable region comprising a VLCDR1 comprising the at least 90% identity to the amino acid sequence of SEQ ID NO: 79, a VLCDR2 comprising at least 90% identity to the amino acid sequence of SEQ ID NO: 80 and a VLCDR3 comprising at least 90% identity to the amino acid sequence of SEQ ID NO: 105.

In one embodiment, multispecific antibodies are provided, the anti-TCR delta variable 1 (anti-Vδ1) binding Fab region comprising:

a heavy chain variable region comprising a VHCDR1 comprising the amino acid sequence of SEQ ID NO:

51, a VHCDR2 comprising the amino acid sequence of SEQ ID NO: 53 and a VHCDR3 comprising the amino acid sequence of SEQ ID NO: 78; and
a light chain variable region comprising a VLCDR1 comprising the amino acid sequence of SEQ ID NO: 79, a VLCDR2 comprising the amino acid sequence of SEQ ID NO: 80 and a VLCDR3 comprising the amino acid sequence of SEQ ID NO: 105.

Amino acid substitutions may be made to provide variant antibodies having Fab regions derived from ADT1-4-138, for example multispecific antibodies are provided, the anti-TCR delta variable 1 (anti-Vδ1) binding Fab region comprising:
a heavy chain variable region comprising a VHCDR1 comprising the amino acid sequence of SEQ ID NO: 51 optionally comprising 1 or 2 amino acid substitutions, a VHCDR2 comprising the amino acid sequence of SEQ ID NO: 53 optionally comprising 1 or 2 amino acid substitutions, and a VHCDR3 comprising the amino acid sequence of SEQ ID NO: 78 optionally comprising 1 or 2 amino acid substitutions; and/or
a light chain variable region comprising a VLCDR1 comprising the amino acid sequence of SEQ ID NO: 79 optionally comprising 1 or 2 amino acid substitutions, a VLCDR2 comprising the amino acid sequence of SEQ ID NO: 80 optionally comprising 1 or 2 amino acid substitutions and a VLCDR3 comprising the amino acid sequence of SEQ ID NO: 105 optionally comprising 1 or 2 amino acid substitutions. The amino acid substitutions may be conservative amino acid substitutions.

The antibodies may alternatively consist of the specified sequences (with or without amino acid substitutions).

Antibodies Comprising Heavy and/or Light Chain Variable Regions Derived from ADT1-4

Multispecific antibodies are provided herein, the anti-TCR delta variable 1 (anti-Vδ1) binding Fab region comprising:
a heavy chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID NOs: 2 to 25; and/or
a light chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID NOs: 27 to 50.

Also provided are multispecific antibodies, the anti-TCR delta variable 1 (anti-Vδ1) binding Fab region comprising:
a heavy chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID NOs: 2 to 24; and/or
a light chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID NOs: 27 to 49.

Also provided are multispecific antibodies, the anti-TCR delta variable 1 (anti-Vδ1) binding Fab region comprising:
a heavy chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID NOs: 5, 7, 8, 9, 12, 13, 15, 21, 23 and 24; and/or
a light chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID NOs: 30, 32, 33, 34, 37, 38, 40, 46, 48 and 49.

Also provided are multispecific antibodies, the anti-TCR delta variable 1 (anti-Vδ1) binding Fab region comprising:
a heavy chain variable region comprising or consisting of a sequence having at least 90% identity to a sequence selected from the group consisting of SEQ ID NOs: 2 to 25; and/or
a light chain variable region comprising or consisting of a sequence having at least 90% identity to a sequence selected from the group consisting of SEQ ID NOs: 27 to 50.

Also provided are multispecific antibodies, the anti-TCR delta variable 1 (anti-Vδ1) binding Fab region comprising:
a heavy chain variable region comprising or consisting of a sequence having at least 90% identity to a sequence selected from the group consisting of SEQ ID NOs: 2 to 24; and/or
a light chain variable region comprising or consisting of a sequence having at least 90% identity to a sequence selected from the group consisting of SEQ ID NOs: 27 to 49.

Also provided are multispecific antibodies, the anti-TCR delta variable 1 (anti-Vδ1) binding Fab region comprising:
a heavy chain variable region comprising or consisting of a sequence having at least 90% identity to a sequence selected from the group consisting of SEQ ID NOs: 5, 7, 8, 9, 12, 13, 15, 21, 23 and 24; and/or
a light chain variable region comprising or consisting of a sequence having at least 90% identity to a sequence selected from the group consisting of SEQ ID NOs: 30, 32, 33, 34, 37, 38, 40, 46, 48 and 49.

Optionally the antibodies above retain the corresponding CDR sequences such that any variability in the VH and VL sequences occurs in the framework regions.

Also provided are multispecific antibodies, the anti-TCR delta variable 1 (anti-Vδ1) binding Fab region comprising:
a heavy chain variable region comprising or consisting of a sequence selected from the group consisting of SEQ ID NOs: 2 to 25; and/or
a light chain variable region comprising or consisting of a sequence selected from the group consisting of SEQ ID NOs: 27 to 50.

Also provided are multispecific antibodies, the anti-TCR delta variable 1 (anti-Vδ1) binding Fab region comprising:
a heavy chain variable region comprising or consisting of a sequence selected from the group consisting of SEQ ID NOs: 2 to 24; and/or a light chain variable region comprising or consisting of a sequence selected from the group consisting of SEQ ID NOs: 27 to 49.

Also provided are multispecific antibodies, the anti-TCR delta variable 1 (anti-Vδ1) binding Fab region comprising:
a heavy chain variable region comprising or consisting of a sequence selected from the group consisting of SEQ ID NOs: 5, 7, 8, 9, 12, 13, 15, 21, 23 and 24; and/or
a light chain variable region comprising or consisting of a sequence selected from the group consisting of SEQ ID NOs: 30, 32, 33, 34, 37, 38, 40, 46, 48 and 49.

In some embodiments, multispecific antibodies are provided, the anti-TCR delta variable 1 (anti-Vδ1) binding Fab region comprising:

a) a VH comprising or consisting of an amino acid sequence that is at least 90% identical to the amino acid sequence of SEQ ID NO: 2 and a VL comprising or consisting of an amino acid sequence that is at least 90% identical to the amino acid sequence of SEQ ID NO: 27;
b) a VH comprising or consisting of an amino acid sequence that is at least 90% identical to the amino acid sequence of SEQ ID NO: 3 and a VL comprising or consisting of an amino acid sequence that is at least 90% identical to the amino acid sequence of SEQ ID NO: 28;
c) a VH comprising or consisting of an amino acid sequence that is at least 90% identical to the amino acid sequence of SEQ ID NO: 4 and a VL comprising or consisting of an amino acid sequence that is at least 90% identical to the amino acid sequence of SEQ ID NO: 29;
d) a VH comprising or consisting of an amino acid sequence that is at least 90% identical to the amino acid sequence of SEQ ID NO: 5 and a VL comprising or consisting of an amino acid sequence that is at least 90% identical to the amino acid sequence of SEQ ID NO: 30;
e) a VH comprising or consisting of an amino acid sequence that is at least 90% identical to the amino acid sequence of SEQ ID NO: 6 and a VL comprising or consisting of an amino acid sequence that is at least 90% identical to the amino acid sequence of SEQ ID NO: 31;
f) a VH comprising or consisting of an amino acid sequence that is at least 90% identical to the amino acid sequence of SEQ ID NO: 7 and a VL comprising or consisting of an amino acid sequence that is at least 90% identical to the amino acid sequence of SEQ ID NO: 32;
g) a VH comprising or consisting of an amino acid sequence that is at least 90% identical to the amino acid sequence of SEQ ID NO: 8 and a VL comprising or consisting of an amino acid sequence that is at least 90% identical to the amino acid sequence of SEQ ID NO: 33;
h) a VH comprising or consisting of an amino acid sequence that is at least 90% identical to the amino acid sequence of SEQ ID NO: 9 and a VL comprising or consisting of an amino acid sequence that is at least 90% identical to the amino acid sequence of SEQ ID NO: 34;
i) a VH comprising or consisting of an amino acid sequence that is at least 90% identical to the amino acid sequence of SEQ ID NO: 10 and a VL comprising or consisting of an amino acid sequence that is at least 90% identical to the amino acid sequence of SEQ ID NO: 35;
j) a VH comprising or consisting of an amino acid sequence that is at least 90% identical to the amino acid sequence of SEQ ID NO: 11 and a VL comprising or consisting of an amino acid sequence that is at least 90% identical to the amino acid sequence of SEQ ID NO: 36;
k) a VH comprising or consisting of an amino acid sequence that is at least 90% identical to the amino acid sequence of SEQ ID NO: 12 and a VL comprising or consisting of an amino acid sequence that is at least 90% identical to the amino acid sequence of SEQ ID NO: 37;
l) a VH comprising or consisting of an amino acid sequence that is at least 90% identical to the amino acid sequence of SEQ ID NO: 13 and a VL comprising or consisting of an amino acid sequence that is at least 90% identical to the amino acid sequence of SEQ ID NO: 38;
m) a VH comprising or consisting of an amino acid sequence that is at least 90% identical to the amino acid sequence of SEQ ID NO: 14 and a VL comprising or consisting of an amino acid sequence that is at least 90% identical to the amino acid sequence of SEQ ID NO: 39;
n) a VH comprising or consisting of an amino acid sequence that is at least 90% identical to the amino acid sequence of SEQ ID NO: 15 and a VL comprising or consisting of an amino acid sequence that is at least 90% identical to the amino acid sequence of SEQ ID NO: 40;
o) a VH comprising or consisting of an amino acid sequence that is at least 90% identical to the amino acid sequence of SEQ ID NO: 16 and a VL comprising or consisting of an amino acid sequence that is at least 90% identical to the amino acid sequence of SEQ ID NO: 41;
p) a VH comprising or consisting of an amino acid sequence that is at least 90% identical to the amino acid sequence of SEQ ID NO: 17 and a VL comprising or consisting of an amino acid sequence that is at least 90% identical to the amino acid sequence of SEQ ID NO: 42;
q) a VH comprising or consisting of an amino acid sequence that is at least 90% identical to the amino acid sequence of SEQ ID NO: 18 and a VL comprising or consisting of an amino acid sequence that is at least 90% identical to the amino acid sequence of SEQ ID NO: 43;
r) a VH comprising or consisting of an amino acid sequence that is at least 90% identical to the amino acid sequence of SEQ ID NO: 19 and a VL comprising or consisting of an amino acid sequence that is at least 90% identical to the amino acid sequence of SEQ ID NO: 44;
s) a VH comprising or consisting of an amino acid sequence that is at least 90% identical to the amino acid sequence of SEQ ID NO: 20 and a VL comprising or consisting of an amino acid sequence that is at least 90% identical to the amino acid sequence of SEQ ID NO: 45;
t) a VH comprising or consisting of an amino acid sequence that is at least 90% identical to the amino acid sequence of SEQ ID NO: 21 and a VL comprising or consisting of an amino acid sequence that is at least 90% identical to the amino acid sequence of SEQ ID NO: 46;
u) a VH comprising or consisting of an amino acid sequence that is at least 90% identical to the amino acid sequence of SEQ ID NO: 22 and a VL comprising or consisting of an amino acid sequence that is at least 90% identical to the amino acid sequence of SEQ ID NO: 47;
v) a VH comprising or consisting of an amino acid sequence that is at least 90% identical to the amino acid sequence of SEQ ID NO: 23 and a VL comprising or consisting of an amino acid sequence that is at least 90% identical to the amino acid sequence of SEQ ID NO: 48;
w) a VH comprising or consisting of an amino acid sequence that is at least 90% identical to the amino acid sequence of SEQ ID NO: 24 and a VL comprising or consisting of an amino acid sequence that is at least 90% identical to the amino acid sequence of SEQ ID NO: 49; or
x) a VH comprising or consisting of an amino acid sequence that is at least 90% identical to the amino acid sequence of SEQ ID NO: 25 and a VL comprising or consisting of an amino acid sequence that is at least 90% identical to the amino acid sequence of SEQ ID NO: 50.

Optionally the antibodies above retain the corresponding CDR sequences such that any variability in the VH and VL sequences occurs in the framework regions.

In some embodiments, multispecific antibodies are provided, the anti-TCR delta variable 1 (anti-Vδ1) binding Fab region comprising:
a) a VH comprising or consisting of an amino acid sequence that is at least 96% identical to the amino acid sequence of SEQ ID NO: 2 and a VL comprising or consisting of an amino acid sequence that is at least 96% identical to the amino acid sequence of SEQ ID NO: 27;
b) a VH comprising or consisting of an amino acid sequence that is at least 96% identical to the amino acid sequence of SEQ ID NO: 3 and a VL comprising or consisting of an amino acid sequence that is at least 96% identical to the amino acid sequence of SEQ ID NO: 28;
c) a VH comprising or consisting of an amino acid sequence that is at least 96% identical to the amino acid sequence of SEQ ID NO: 4 and a VL comprising or consisting of an amino acid sequence that is at least 96% identical to the amino acid sequence of SEQ ID NO: 29;
d) a VH comprising or consisting of an amino acid sequence that is at least 96% identical to the amino acid sequence of SEQ ID NO: 5 and a VL comprising or consisting of an amino acid sequence that is at least 96% identical to the amino acid sequence of SEQ ID NO: 30;
e) a VH comprising or consisting of an amino acid sequence that is at least 96% identical to the amino acid sequence of SEQ ID NO: 6 and a VL comprising or consisting of an amino acid sequence that is at least 96% identical to the amino acid sequence of SEQ ID NO: 31;
f) a VH comprising or consisting of an amino acid sequence that is at least 96% identical to the amino acid sequence of SEQ ID NO: 7 and a VL comprising or consisting of an amino acid sequence that is at least 96% identical to the amino acid sequence of SEQ ID NO: 32;
g) a VH comprising or consisting of an amino acid sequence that is at least 96% identical to the amino acid sequence of SEQ ID NO: 8 and a VL comprising or consisting of an amino acid sequence that is at least 96% identical to the amino acid sequence of SEQ ID NO: 33;
h) a VH comprising or consisting of an amino acid sequence that is at least 96% identical to the amino acid sequence of SEQ ID NO: 9 and a VL comprising or consisting of an amino acid sequence that is at least 96% identical to the amino acid sequence of SEQ ID NO: 34;
i) a VH comprising or consisting of an amino acid sequence that is at least 96% identical to the amino acid sequence of SEQ ID NO: 10 and a VL comprising or consisting of an amino acid sequence that is at least 96% identical to the amino acid sequence of SEQ ID NO: 35;
j) a VH comprising or consisting of an amino acid sequence that is at least 96% identical to the amino acid sequence of SEQ ID NO: 11 and a VL comprising or consisting of an amino acid sequence that is at least 96% identical to the amino acid sequence of SEQ ID NO: 36;
k) a VH comprising or consisting of an amino acid sequence that is at least 96% identical to the amino acid sequence of SEQ ID NO: 12 and a VL comprising or consisting of an amino acid sequence that is at least 96% identical to the amino acid sequence of SEQ ID NO: 37;
l) a VH comprising or consisting of an amino acid sequence that is at least 96% identical to the amino acid sequence of SEQ ID NO: 13 and a VL comprising or consisting of an amino acid sequence that is at least 96% identical to the amino acid sequence of SEQ ID NO: 38;
m) a VH comprising or consisting of an amino acid sequence that is at least 96% identical to the amino acid sequence of SEQ ID NO: 14 and a VL comprising or consisting of an amino acid sequence that is at least 96% identical to the amino acid sequence of SEQ ID NO: 39;
n) a VH comprising or consisting of an amino acid sequence that is at least 96% identical to the amino acid sequence of SEQ ID NO: 15 and a VL comprising or consisting of an amino acid sequence that is at least 96% identical to the amino acid sequence of SEQ ID NO: 40;
o) a VH comprising or consisting of an amino acid sequence that is at least 96% identical to the amino acid sequence of SEQ ID NO: 16 and a VL comprising or consisting of an amino acid sequence that is at least 96% identical to the amino acid sequence of SEQ ID NO: 41;
p) a VH comprising or consisting of an amino acid sequence that is at least 96% identical to the amino acid sequence of SEQ ID NO: 17 and a VL comprising or consisting of an amino acid sequence that is at least 96% identical to the amino acid sequence of SEQ ID NO: 42;
q) a VH comprising or consisting of an amino acid sequence that is at least 96% identical to the amino acid sequence of SEQ ID NO: 18 and a VL comprising or consisting of an amino acid sequence that is at least 96% identical to the amino acid sequence of SEQ ID NO: 43;
r) a VH comprising or consisting of an amino acid sequence that is at least 96% identical to the amino acid sequence of SEQ ID NO: 19 and a VL comprising or consisting of an amino acid sequence that is at least 96% identical to the amino acid sequence of SEQ ID NO: 44;
s) a VH comprising or consisting of an amino acid sequence that is at least 96% identical to the amino acid sequence of SEQ ID NO: 20 and a VL comprising or consisting of an amino acid sequence that is at least 96% identical to the amino acid sequence of SEQ ID NO: 45;
t) a VH comprising or consisting of an amino acid sequence that is at least 96% identical to the amino acid sequence of SEQ ID NO: 21 and a VL comprising or consisting of an amino acid sequence that is at least 96% identical to the amino acid sequence of SEQ ID NO: 46;
u) a VH comprising or consisting of an amino acid sequence that is at least 96% identical to the amino acid sequence of SEQ ID NO: 22 and a VL comprising or consisting of an amino acid sequence that is at least 96% identical to the amino acid sequence of SEQ ID NO: 47;
v) a VH comprising or consisting of an amino acid sequence that is at least 96% identical to the amino acid sequence of SEQ ID NO: 23 and a VL comprising or consisting of an amino acid sequence that is at least 96% identical to the amino acid sequence of SEQ ID NO: 48;
w) a VH comprising or consisting of an amino acid sequence that is at least 96% identical to the amino acid sequence of SEQ ID NO: 24 and a VL comprising or consisting of an amino acid sequence that is at least 96% identical to the amino acid sequence of SEQ ID NO: 49; or
x) a VH comprising or consisting of an amino acid sequence that is at least 96% identical to the amino acid sequence of SEQ ID NO: 25 and a VL comprising or consisting of an amino acid sequence that is at least 96% identical to the amino acid sequence of SEQ ID NO: 50.

Optionally the antibodies above retain the corresponding CDR sequences such that any variability in the VH and VL sequences occurs in the framework regions.

Optionally the antibodies above retain the corresponding CDR sequences such that any variability in the VH and VL sequences occurs in the framework regions.

In some embodiments, multispecific antibodies are provided, the anti-TCR delta variable 1 (anti-Vδ1) binding Fab region comprising:
a) a VH comprising or consisting of the amino acid sequence of SEQ ID NO: 2 and a VL comprising or consisting of the amino acid sequence of SEQ ID NO: 27 optionally comprising up to 5, up to 4, up to 3, up to 2 or 1 amino acid substitutions across both variable regions;
b) a VH comprising or consisting of the amino acid sequence of SEQ ID NO: 3 and a VL comprising or consisting of the amino acid sequence of SEQ ID NO: 28 optionally comprising up to 5, up to 4, up to 3, up to 2 or 1 amino acid substitutions across both variable regions;
c) a VH comprising or consisting of the amino acid sequence of SEQ ID NO: 4 and a VL comprising or consisting of the amino acid sequence of SEQ ID NO: 29 optionally comprising up to 5, up to 4, up to 3, up to 2 or 1 amino acid substitutions across both variable regions;
d) a VH comprising or consisting of the amino acid sequence of SEQ ID NO: 5 and a VL comprising or consisting of the amino acid sequence of SEQ ID NO: 30 optionally comprising up to 5, up to 4, up to 3, up to 2 or 1 amino acid substitutions across both variable regions;
e) a VH comprising or consisting of the amino acid sequence of SEQ ID NO: 6 and a VL comprising or consisting of the amino acid sequence of SEQ ID NO: 31 optionally comprising up to 5, up to 4, up to 3, up to 2 or 1 amino acid substitutions across both variable regions;
f) a VH comprising or consisting of the amino acid sequence of SEQ ID NO: 7 and a VL comprising or consisting of the amino acid sequence of SEQ ID NO: 32 optionally comprising up to 5, up to 4, up to 3, up to 2 or 1 amino acid substitutions across both variable regions;
g) a VH comprising or consisting of the amino acid sequence of SEQ ID NO: 8 and a VL comprising or consisting of the amino acid sequence of SEQ ID NO: 33 optionally comprising up to 5, up to 4, up to 3, up to 2 or 1 amino acid substitutions across both variable regions;
h) a VH comprising or consisting of the amino acid sequence of SEQ ID NO: 9 and a VL comprising or consisting of the amino acid sequence of SEQ ID NO: 34 optionally comprising up to 5, up to 4, up to 3, up to 2 or 1 amino acid substitutions across both variable regions;
i) a VH comprising or consisting of the amino acid sequence of SEQ ID NO: 10 and a VL comprising or consisting of the amino acid sequence of SEQ ID NO: 35 optionally comprising up to 5, up to 4, up to 3, up to 2 or 1 amino acid substitutions across both variable regions;
j) a VH comprising or consisting of the amino acid sequence of SEQ ID NO: 11 and a VL comprising or consisting of the amino acid sequence of SEQ ID NO: 36 optionally comprising up to 5, up to 4, up to 3, up to 2 or 1 amino acid substitutions across both variable regions;
k) a VH comprising or consisting of the amino acid sequence of SEQ ID NO: 12 and a VL comprising or consisting of the amino acid sequence of SEQ ID NO: 37 optionally comprising up to 5, up to 4, up to 3, up to 2 or 1 amino acid substitutions across both variable regions;
l) a VH comprising or consisting of the amino acid sequence of SEQ ID NO: 13 and a VL comprising or consisting of the amino acid sequence of SEQ ID NO: 38 optionally comprising up to 5, up to 4, up to 3, up to 2 or 1 amino acid substitutions across both variable regions;
m) a VH comprising or consisting of the amino acid sequence of SEQ ID NO: 14 and a VL comprising or consisting of the amino acid sequence of SEQ ID NO: 39 optionally comprising up to 5, up to 4, up to 3, up to 2 or 1 amino acid substitutions across both variable regions;

n) a VH comprising or consisting of the amino acid sequence of SEQ ID NO: 15 and a VL comprising or consisting of the amino acid sequence of SEQ ID NO: 40 optionally comprising up to 5, up to 4, up to 3, up to 2 or 1 amino acid substitutions across both variable regions;

o) a VH comprising or consisting of the amino acid sequence of SEQ ID NO: 16 and a VL comprising or consisting of the amino acid sequence of SEQ ID NO: 41 optionally comprising up to 5, up to 4, up to 3, up to 2 or 1 amino acid substitutions across both variable regions;

p) a VH comprising or consisting of the amino acid sequence of SEQ ID NO: 17 and a VL comprising or consisting of the amino acid sequence of SEQ ID NO: 42 optionally comprising up to 5, up to 4, up to 3, up to 2 or 1 amino acid substitutions across both variable regions;

q) a VH comprising or consisting of the amino acid sequence of SEQ ID NO: 18 and a VL comprising or consisting of the amino acid sequence of SEQ ID NO: 43 optionally comprising up to 5, up to 4, up to 3, up to 2 or 1 amino acid substitutions across both variable regions;

r) a VH comprising or consisting of the amino acid sequence of SEQ ID NO: 19 and a VL comprising or consisting of the amino acid sequence of SEQ ID NO: 44 optionally comprising up to 5, up to 4, up to 3, up to 2 or 1 amino acid substitutions across both variable regions;

s) a VH comprising or consisting of the amino acid sequence of SEQ ID NO: 20 and a VL comprising or consisting of the amino acid sequence of SEQ ID NO: 45 optionally comprising up to 5, up to 4, up to 3, up to 2 or 1 amino acid substitutions across both variable regions;

t) a VH comprising or consisting of the amino acid sequence of SEQ ID NO: 21 and a VL comprising or consisting of the amino acid sequence of SEQ ID NO: 46 optionally comprising up to 5, up to 4, up to 3, up to 2 or 1 amino acid substitutions across both variable regions;

u) a VH comprising or consisting of the amino acid sequence of SEQ ID NO: 22 and a VL comprising or consisting of the amino acid sequence of SEQ ID NO: 47 optionally comprising up to 5, up to 4, up to 3, up to 2 or 1 amino acid substitutions across both variable regions;

v) a VH comprising or consisting of the amino acid sequence of SEQ ID NO: 23 and a VL comprising or consisting of the amino acid sequence of SEQ ID NO: 48 optionally comprising up to 5, up to 4, up to 3, up to 2 or 1 amino acid substitutions across both variable regions;

w) a VH comprising or consisting of the amino acid sequence of SEQ ID NO: 24 and a VL comprising or consisting of the amino acid sequence of SEQ ID NO: 49 optionally comprising up to 5, up to 4, up to 3, up to 2 or 1 amino acid substitutions across both variable regions; or x) a VH comprising or consisting of the amino acid sequence of SEQ ID NO: 25 and a VL comprising or consisting of the amino acid sequence of SEQ ID NO: 50 optionally comprising up to 5, up to 4, up to 3, up to 2 or 1 amino acid substitutions across both variable regions.

"Across both variable regions" means collectively, the antibody may comprise up to the specified number of substitutions in total when considering both the heavy and light chain variable regions. The amino acid substitutions may be conservative amino acid substitutions. In some embodiments, the substitutions (if present) may occur anywhere in the variable region sequences. In preferred embodiments, the substitutions (if present) may be limited to the framework regions. Accordingly, in some embodiments, the amino acid substitutions do not occur in a CDR sequence.

Optionally the antibodies above retain the corresponding CDR sequences such that any variability in the VH and VL sequences occurs in the framework regions.

In some embodiments, multispecific antibodies are provided, the anti-TCR delta variable 1 (anti-Vδ1) binding Fab region comprising:

a) a VH comprising or consisting of the amino acid sequence of SEQ ID NO: 2 and a VL comprising or consisting of the amino acid sequence of SEQ ID NO: 27;

b) a VH comprising or consisting of the amino acid sequence of SEQ ID NO: 3 and a VL comprising or consisting of the amino acid sequence of SEQ ID NO: 28;

c) a VH comprising or consisting of the amino acid sequence of SEQ ID NO: 4 and a VL comprising or consisting of the amino acid sequence of SEQ ID NO: 29;

d) a VH comprising or consisting of the amino acid sequence of SEQ ID NO: 5 and a VL comprising or consisting of the amino acid sequence of SEQ ID NO: 30;

e) a VH comprising or consisting of the amino acid sequence of SEQ ID NO: 6 and a VL comprising or consisting of the amino acid sequence of SEQ ID NO: 31;

f) a VH comprising or consisting of the amino acid sequence of SEQ ID NO: 7 and a VL comprising or consisting of the amino acid sequence of SEQ ID NO: 32;

g) a VH comprising or consisting of the amino acid sequence of SEQ ID NO: 8 and a VL comprising or consisting of the amino acid sequence of SEQ ID NO: 33;

h) a VH comprising or consisting of the amino acid sequence of SEQ ID NO: 9 and a VL comprising or consisting of the amino acid sequence of SEQ ID NO: 34;

i) a VH comprising or consisting of the amino acid sequence of SEQ ID NO: 10 and a VL comprising or consisting of the amino acid sequence of SEQ ID NO: 35;

j) a VH comprising or consisting of the amino acid sequence of SEQ ID NO: 11 and a VL comprising or consisting of the amino acid sequence of SEQ ID NO: 36;

k) a VH comprising or consisting of the amino acid sequence of SEQ ID NO: 12 and a VL comprising or consisting of the amino acid sequence of SEQ ID NO: 37;

l) a VH comprising or consisting of the amino acid sequence of SEQ ID NO: 13 and a VL comprising or consisting of the amino acid sequence of SEQ ID NO: 38;

m) a VH comprising or consisting of the amino acid sequence of SEQ ID NO: 14 and a VL comprising or consisting of the amino acid sequence of SEQ ID NO: 39;

n) a VH comprising or consisting of the amino acid sequence of SEQ ID NO: 15 and a VL comprising or consisting of the amino acid sequence of SEQ ID NO: 40;

o) a VH comprising or consisting of the amino acid sequence of SEQ ID NO: 16 and a VL comprising or consisting of the amino acid sequence of SEQ ID NO: 41;

p) a VH comprising or consisting of the amino acid sequence of SEQ ID NO: 17 and a VL comprising or consisting of the amino acid sequence of SEQ ID NO: 42;

q) a VH comprising or consisting of the amino acid sequence of SEQ ID NO: 18 and a VL comprising or consisting of the amino acid sequence of SEQ ID NO: 43;

r) a VH comprising or consisting of the amino acid sequence of SEQ ID NO: 19 and a VL comprising or consisting of the amino acid sequence of SEQ ID NO: 44;

s) a VH comprising or consisting of the amino acid sequence of SEQ ID NO: 20 and a VL comprising or consisting of the amino acid sequence of SEQ ID NO: 45;

t) a VH comprising or consisting of the amino acid sequence of SEQ ID NO: 21 and a VL comprising or consisting of the amino acid sequence of SEQ ID NO: 46;

u) a VH comprising or consisting of the amino acid sequence of SEQ ID NO: 22 and a VL comprising or consisting of the amino acid sequence of SEQ ID NO: 47;

v) a VH comprising or consisting of the amino acid sequence of SEQ ID NO: 23 and a VL comprising or consisting of the amino acid sequence of SEQ ID NO: 48;

w) a VH comprising or consisting of the amino acid sequence of SEQ ID NO: 24 and a VL comprising or consisting of the amino acid sequence of SEQ ID NO: 49; or x) a VH comprising or consisting of the amino acid sequence of SEQ ID NO: 25 and a VL comprising or consisting of the amino acid sequence of SEQ ID NO: 50.

Certain amino acid substitutions may be made to provide one or more variant antibodies as described herein.

In any embodiments relating to Fab regions having defined VH and/or VL sequences (for example any VH and/or VL sequences defined as having certain percent identities and/or substitutions), preferably the VH sequence is not SEQ ID NO: 1 and the VL sequence is not SEQ ID NO: 26.

Other Antibodies Comprising Fab Regions Derived from ADT1-4

In one embodiment multispecific antibodies are provided, the anti-TCR delta variable 1 (anti-Vδ1) binding Fab region comprising:

a) an HCDR1 sequence comprising or consisting of the sequence of GDSVSSKSX$_1$A (SEQ ID NO: 158);

b) an HCDR2 sequence comprising or consisting of the sequence of SEQ ID NO: 53 c) an HCDR3 sequence comprising or consisting of the sequence of X$_2$WX$_3$X$_4$X$_5$X$_6$DX$_7$ (SEQ ID NO: 162), wherein the HCDR3 sequence is not SEQ ID NO: 54;

d) an LCDR1 sequence comprising or consisting of the sequence of SEQ ID NO: 79;

e) an LCDR2 sequence comprising or consisting of the sequence of SEQ ID NO: 80; and f) an LCDR3 sequence comprising or consisting of the sequence of QQX$_8$YX$_9$X$_{10}$X$_{11}$X$_{12}$X$_{13}$T (SEQ ID NO: 166), wherein the LCDR3 sequence is not SEQ ID NO: 81;

and wherein each of X$_1$ to X$_{13}$ is a naturally occurring amino acid.

In one embodiment multispecific antibodies are provided, the anti-TCR delta variable 1 (anti-Vδ1) binding Fab region comprising:

a) an HCDR1 sequence comprising or consisting of the sequence of GDSVSSKSX$_1$A (SEQ ID NO: 159);

b) an HCDR2 sequence comprising or consisting of the sequence of SEQ ID NO: 53 c) an HCDR3 sequence comprising or consisting of the sequence of X$_2$WX$_3$X$_4$X$_5$X$_6$DX$_7$ (SEQ ID NO: 163), wherein the HCDR3 sequence is not SEQ ID NO: 54;

d) an LCDR1 sequence comprising or consisting of the sequence of SEQ ID NO: 79;

e) an LCDR2 sequence comprising or consisting of the sequence of SEQ ID NO: 80; and f) an LCDR3 sequence comprising or consisting of the sequence of QQX$_8$YX$_9$X$_{10}$X$_{11}$X$_{12}$X$_{13}$T (SEQ ID NO: 167), wherein the LCDR3 sequence is not SEQ ID NO: 81;

and wherein: X$_1$ is selected from the group consisting of A and V; X$_2$ is selected from the group consisting of S and T; X$_3$ is selected from the group consisting of V, A and L; X$_4$ is selected from the group consisting of G, E, and D; X$_5$ is selected from the group consisting of Y and N; X$_6$ is selected from the group consisting of V, A and P; X$_7$ is selected from the group consisting of V, Y and R; X$_8$ is selected from the group consisting of K, R and G; X$_9$ is selected from the group consisting of S and K; X$_{10}$ is selected from the group consisting of T, Q, A, E and D; X$_{11}$ is selected from the group consisting of P, H and D; X$_{12}$ is selected from the group consisting of Q, R, K, W, P, E and I; and X$_{13}$ is selected from the group consisting of I, V and L. The antibody may further comprise an HFR1 sequence comprising the sequence of SEQ ID NO: 170 or 171; an HFR2 sequence comprising the sequence of SEQ ID NO: 172; an HFR3 sequence comprising the sequence of SEQ ID NO: 173; an HFR4 sequence comprising the sequence of SEQ ID NO: 174; an LFR1 sequence comprising the sequence of SEQ ID NO: 175; an LFR2 sequence comprising the sequence of SEQ ID NO: 176; an LFR3 sequence comprising the sequence of SEQ ID NO: 177 or 178; and an LFR4 sequence comprising the sequence of SEQ ID NO: 179, 180, 181 or 182.

In one embodiment multispecific antibodies are provided, the anti-TCR delta variable 1 (anti-Vδ1) binding Fab region comprising:

a) an HCDR1 sequence comprising or consisting of the sequence of GDSVSSKSX$_1$A (SEQ ID NO: 160);

b) an HCDR2 sequence comprising or consisting of the sequence of SEQ ID NO: 53 c) an HCDR3 sequence comprising or consisting of the sequence of X$_2$WX$_3$X$_4$X$_5$X$_6$DX$_7$ (SEQ ID NO: 164), wherein the HCDR3 sequence is not SEQ ID NO: 54;

d) an LCDR1 sequence comprising or consisting of the sequence of SEQ ID NO: 79;
e) an LCDR2 sequence comprising or consisting of the sequence of SEQ ID NO: 80; and
f) an LCDR3 sequence comprising or consisting of the sequence of QQX$_8$YX$_9$X$_{10}$X$_{11}$X$_{12}$X$_{13}$T (SEQ ID NO: 168), wherein the LCDR3 sequence is not SEQ ID NO: 81;

and wherein X$_1$ is selected from the group consisting of A and V; X$_2$ is selected from the group consisting of S and T; X$_3$ is selected from the group consisting of V, A and L; X$_4$ is selected from the group consisting of G, E, and D; X$_5$ is selected from the group consisting of Y and N; X$_6$ is selected from the group consisting of V, A and P; X$_7$ is selected from the group consisting of V, Y and R; X$_8$ is selected from the group consisting of K, R and G; X$_9$ is selected from the group consisting of S and K; X$_{10}$ is selected from the group consisting of T, Q, A, E and D; X$_{11}$ is selected from the group consisting of P and H; X$_{12}$ is selected from the group consisting of Q, R, K, W, P, E and I; and X$_{13}$ is selected from the group consisting of I, V and L. The antibody may further comprise an HFR1 sequence comprising the sequence of SEQ ID NO: 170 or 171, an HFR2 sequence comprising the sequence of SEQ ID NO: 172, an HFR3 sequence comprising the sequence of SEQ ID NO: 173, an HFR4 sequence comprising the sequence of SEQ ID NO: 174, an LFR1 sequence comprising the sequence of SEQ ID NO: 175, an LFR2 sequence comprising the sequence of SEQ ID NO: 176, an LFR3 sequence comprising the sequence of SEQ ID NO: 177 and an LFR4 sequence comprising the sequence of SEQ ID NO: 179, 180, 181 or 182.

In one embodiment multispecific antibodies are provided, the anti-TCR delta variable 1 (anti-Vδ1) binding Fab region comprising:
a) an HCDR1 sequence comprising or consisting of the sequence of GDSVSSKSX$_1$A (SEQ ID NO: 161);
b) an HCDR2 sequence comprising or consisting of the sequence of SEQ ID NO: 53
c) an HCDR3 sequence comprising or consisting of the sequence of X$_2$WX$_3$X$_4$X$_5$X$_6$DX$_7$ (SEQ ID NO: 165), wherein the HCDR3 sequence is not SEQ ID NO: 54;
d) an LCDR1 sequence comprising or consisting of the sequence of SEQ ID NO: 79;
e) an LCDR2 sequence comprising or consisting of the sequence of SEQ ID NO: 80; and
f) an LCDR3 sequence comprising or consisting of the sequence of QQX$_8$YX$_9$X$_{10}$X$_{11}$X$_{12}$X$_{13}$T (SEQ ID NO: 169), wherein the LCDR3 sequence is not SEQ ID NO: 81;

and wherein X$_1$ is selected from the group consisting of A and V; X$_2$ is selected from the group consisting of S and T; X$_3$ is selected from the group consisting of V, A and L; X$_4$ is selected from the group consisting of G and D; X$_5$ is selected from the group consisting of Y and N; X$_6$ is selected from the group consisting of V, A and P; X$_7$ is selected from the group consisting of V, Y and R; X$_8$ is selected from the group consisting of K and R; X$_9$ is selected from the group consisting of S and K; X$_{10}$ is selected from the group consisting of T, Q, A and E; X$_{11}$ is selected from the group consisting of P and H; X$_{12}$ is selected from the group consisting of Q, K, W, P and I; and X$_{13}$ is selected from the group consisting of V and L. The antibody may further comprise an HFR1 sequence comprising the sequence of SEQ ID NO: 170 or 171; an HFR2 sequence comprising the sequence of SEQ ID NO: 172; an HFR3 sequence comprising the sequence of SEQ ID NO: 173; an HFR4 sequence comprising the sequence of SEQ ID NO: 174; an LFR1 sequence comprising the sequence of SEQ ID NO: 175; an LFR2 sequence comprising the sequence of SEQ ID NO: 176; an LFR3 sequence comprising the sequence of SEQ ID NO: 177; and an LFR4 sequence comprising the sequence of SEQ ID NO: 179 or 181.

ADT1-7-Derived Fab Regions

The present invention provides multispecific antibodies comprising Fab regions derived from parental antibody ADT1-7 (having a variable heavy region sequence according to SEQ ID NO: 106 and a variable light region sequence according to SEQ ID No: 118), for example as set out in the following. ADT1-7 is also referred to herein as E07, and ADT1-7 and E07 are used interchangeably.

Antibodies Comprising Particular CDR Sequences Derived from ADT1-7

The multispecific antibodies provided herein include the following Fab regions having particular sequences derived from ADT1-7.

For example, in some embodiments, multispecific antibodies are provided, the anti-TCR delta variable 1 (anti-Vδ1) binding Fab region comprising a heavy chain variable region comprising a VHCDR3 comprising or consisting of an amino acid sequence selected from the group consisting of SEQ ID NOs: 133 to 143; and/or a light chain variable region comprising a VLCDR3 comprising or consisting of an amino acid sequence selected from the group consisting of SEQ ID NOs: 147 to 157. Certain amino acid substitutions may be made to provide one or more variant antibodies as described herein.

In some embodiments multispecific antibodies are provided, the anti-TCR delta variable 1 (anti-Vδ1) binding Fab region comprising a heavy chain variable region comprising a VHCDR3 comprising or consisting of an amino acid sequence selected from the group consisting of SEQ ID NOs: 138, 142 and 143 and/or a light chain variable region comprising a VLCDR3 comprising or consisting of an amino acid sequence selected from the group consisting of SEQ ID NOs: 152, 156 and 157, Certain amino acid substitutions may be made to provide one or more variant antibodies as described herein.

There is also provided multispecific antibodies, the anti-TCR delta variable 1 (anti-Vδ1) binding Fab region comprising:
a heavy chain variable region comprising:
a VHCDR1 comprising or consisting of the amino acid sequence of SEQ ID NO: 130;
a VHCDR2 comprising or consisting of the amino acid sequence of SEQ ID NO: 131; and
a VHCDR3 comprising or consisting of an amino acid sequence selected from the group consisting of: SEQ ID NOs: 133 to 143; and
a light chain variable region comprising:
a VLCDR1 comprising or consisting of the amino acid sequence of SEQ ID NO: 144;
a VLCDR2 comprising or consisting of the amino acid sequence of SEQ ID NO: 145; and
a VLCDR3 comprising or consisting of an amino acid sequence selected from the group consisting of: SEQ ID NOs: 147 to 157.

Certain amino acid substitutions may be made to provide one or more variant antibodies as described herein.

Also provided are multispecific antibodies, the anti-TCR delta variable 1 (anti-Vδ1) binding Fab region comprising:
- a heavy chain variable region comprising:
  - a VHCDR1 comprising or consisting of the amino acid sequence of SEQ ID NO: 130;
  - a VHCDR2 comprising or consisting of the amino acid sequence of SEQ ID NO: 131; and
  - a VHCDR3 comprising or consisting of an amino acid sequence selected from the group consisting of: SEQ ID NOs: 138, 142 and 143; and
- a light chain variable region comprising:
  - a VLCDR1 comprising or consisting of the amino acid sequence of SEQ ID NO: 144;
  - a VLCDR2 comprising or consisting of the amino acid sequence of SEQ ID NO: 145; and
  - a VLCDR3 comprising or consisting of an amino acid sequence selected from the group consisting of: SEQ ID NOs: 152, 156 and 157.

Certain amino acid substitutions may be made to provide one or more variant antibodies as described herein.

Further embodiments are provided below.

ADT1-7-10 and Fragments and Variants Thereof

Certain embodiments relate to the antibody ADT1-7-10 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 133 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 147. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 133 and/or a light chain variable region comprising a VLCDR3 comprising an amino acid sequence having at least 90% identity to the amino acid sequence of SEQ ID NO: 147. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 133 and/or a light chain variable region comprising a VLCDR3 comprising the amino acid sequence of SEQ ID NO: 147.

Amino acid substitutions may be made to provide variant antibodies having Fab regions derived from ADT1-7-10, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 133, optionally comprising 1 or 2 amino acid substitutions, and/or a light chain variable region comprising a VLCDR3 comprising the amino acid sequence of SEQ ID NO: 147, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:
- a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 130, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 131 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 133; and/or
- a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 144, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 145 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 147.

In one embodiment, multispecific antibodies are provided, the anti-TCR delta variable 1 (anti-Vδ1) binding Fab region comprising:
- a heavy chain variable region comprising a VHCDR1 comprising at least 90% identity to the amino acid sequence of SEQ ID NO: 130, a VHCDR2 comprising at least 90% identity to the amino acid sequence of SEQ ID NO: 131 and a VHCDR3 comprising at least 90% identity to the amino acid sequence of SEQ ID NO: 133; and/or
- a light chain variable region comprising a VLCDR1 comprising the at least 90% identity to the amino acid sequence of SEQ ID NO: 144, a VLCDR2 comprising at least 90% identity to the amino acid sequence of SEQ ID NO: 145 and a VLCDR3 comprising at least 90% identity to the amino acid sequence of SEQ ID NO: 147.

In one embodiment, multispecific antibodies are provided, the anti-TCR delta variable 1 (anti-Vδ1) binding Fab region comprising:
- a heavy chain variable region comprising a VHCDR1 comprising the amino acid sequence of SEQ ID NO: 130, a VHCDR2 comprising the amino acid sequence of SEQ ID NO: 131 and a VHCDR3 comprising the amino acid sequence of SEQ ID NO: 133; and
- a light chain variable region comprising a VLCDR1 comprising the amino acid sequence of SEQ ID NO: 144, a VLCDR2 comprising the amino acid sequence of SEQ ID NO: 145 and a VLCDR3 comprising the amino acid sequence of SEQ ID NO: 147.

Amino acid substitutions may be made to provide variant antibodies having Fab regions derived from ADT1-7-10, for example multispecific antibodies are provided, the anti-TCR delta variable 1 (anti-Vδ1) binding Fab region comprising:
- a heavy chain variable region comprising a VHCDR1 comprising the amino acid sequence of SEQ ID NO: 130 optionally comprising 1 or 2 amino acid substitutions, a VHCDR2 comprising the amino acid sequence of SEQ ID NO: 131 optionally comprising 1 or 2 amino acid substitutions, and a VHCDR3 comprising the amino acid sequence of SEQ ID NO: 133 optionally comprising 1 or 2 amino acid substitutions; and/or
- a light chain variable region comprising a VLCDR1 comprising the amino acid sequence of SEQ ID NO: 144 optionally comprising 1 or 2 amino acid substitutions, a VLCDR2 comprising the amino acid sequence of SEQ ID NO: 145 optionally comprising 1 or 2 amino acid substitutions and a VLCDR3 comprising the amino acid sequence of SEQ ID NO: 147 optionally comprising 1 or 2 amino acid substitutions. The amino acid substitutions may be conservative amino acid substitutions.

The antibodies may alternatively consist of the specified sequences (with or without amino acid substitutions).

ADT1-7-15 and Fragments and Variants Thereof

Certain embodiments relate to the antibody ADT1-7-15 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 134 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 148. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 134 and/or a light chain variable region comprising a VLCDR3 comprising an amino acid sequence having at least 90% identity to the amino acid sequence of SEQ ID NO: 148. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 134 and/or a light chain variable region comprising a VLCDR3 comprising the amino acid sequence of SEQ ID NO: 148.

Amino acid substitutions may be made to provide variant antibodies having Fab regions derived from ADT1-7-15, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 134, optionally comprising 1 or 2 amino acid substitutions, and/or a light chain variable region comprising a VLCDR3 comprising the amino acid sequence of SEQ ID NO: 148, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:
- a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 130, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 131 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 134; and/or
- a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 144, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 145 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 148.

In one embodiment, multispecific antibodies are provided, the anti-TCR delta variable 1 (anti-Vδ1) binding Fab region comprising:
- a heavy chain variable region comprising a VHCDR1 comprising at least 90% identity to the amino acid sequence of SEQ ID NO: 130, a VHCDR2 comprising at least 90% identity to the amino acid sequence of SEQ ID NO: 131 and a VHCDR3 comprising at least 90% identity to the amino acid sequence of SEQ ID NO: 134; and/or
- a light chain variable region comprising a VLCDR1 comprising the at least 90% identity to the amino acid sequence of SEQ ID NO: 144, a VLCDR2 comprising at least 90% identity to the amino acid sequence of SEQ ID NO: 145 and a VLCDR3 comprising at least 90% identity to the amino acid sequence of SEQ ID NO: 148.

In one embodiment, multispecific antibodies are provided, the anti-TCR delta variable 1 (anti-Vδ1) binding Fab region comprising:
- a heavy chain variable region comprising a VHCDR1 comprising the amino acid sequence of SEQ ID NO: 130, a VHCDR2 comprising the amino acid sequence of SEQ ID NO: 131 and a VHCDR3 comprising the amino acid sequence of SEQ ID NO: 134; and
- a light chain variable region comprising a VLCDR1 comprising the amino acid sequence of SEQ ID NO:

144, a VLCDR2 comprising the amino acid sequence of SEQ ID NO: 145 and a VLCDR3 comprising the amino acid sequence of SEQ ID NO: 148.

Amino acid substitutions may be made to provide variant antibodies having Fab regions derived from ADT1-7-15, for example multispecific antibodies are provided, the anti-TCR delta variable 1 (anti-Vδ1) binding Fab region comprising:
- a heavy chain variable region comprising a VHCDR1 comprising the amino acid sequence of SEQ ID NO: 130 optionally comprising 1 or 2 amino acid substitutions, a VHCDR2 comprising the amino acid sequence of SEQ ID NO: 131 optionally comprising 1 or 2 amino acid substitutions, and a VHCDR3 comprising the amino acid sequence of SEQ ID NO: 134 optionally comprising 1 or 2 amino acid substitutions; and/or
- a light chain variable region comprising a VLCDR1 comprising the amino acid sequence of SEQ ID NO: 144 optionally comprising 1 or 2 amino acid substitutions, a VLCDR2 comprising the amino acid sequence of SEQ ID NO: 145 optionally comprising 1 or 2 amino acid substitutions and a VLCDR3 comprising the amino acid sequence of SEQ ID NO: 148 optionally comprising 1 or 2 amino acid substitutions. The amino acid substitutions may be conservative amino acid substitutions.

The antibodies may alternatively consist of the specified sequences (with or without amino acid substitutions).

ADT1-7-17 and Fragments and Variants Thereof

Certain embodiments relate to the antibody ADT1-7-17 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 135 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 149. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 135 and/or a light chain variable region comprising a VLCDR3 comprising an amino acid sequence having at least 90% identity to the amino acid sequence of SEQ ID NO: 149. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 135 and/or a light chain variable region comprising a VLCDR3 comprising the amino acid sequence of SEQ ID NO: 149.

Amino acid substitutions may be made to provide variant antibodies having Fab regions derived from ADT1-7-17, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 135, optionally comprising 1 or 2 amino acid substitutions, and/or a light chain variable region comprising a VLCDR3 comprising the amino acid sequence of SEQ ID NO: 149, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:
- a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 130, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 131 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 135; and/or
- a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 144, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 145 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 149.

In one embodiment, multispecific antibodies are provided, the anti-TCR delta variable 1 (anti-Vδ1) binding Fab region comprising:
- a heavy chain variable region comprising a VHCDR1 comprising at least 90% identity to the amino acid sequence of SEQ ID NO: 130, a VHCDR2 comprising at least 90% identity to the amino acid sequence of SEQ ID NO: 131 and a VHCDR3 comprising at least 90% identity to the amino acid sequence of SEQ ID NO: 135; and/or
- a light chain variable region comprising a VLCDR1 comprising the at least 90% identity to the amino acid sequence of SEQ ID NO: 144, a VLCDR2 comprising at least 90% identity to the amino acid sequence of SEQ ID NO: 145 and a VLCDR3 comprising at least 90% identity to the amino acid sequence of SEQ ID NO: 149.

In one embodiment, multispecific antibodies are provided, the anti-TCR delta variable 1 (anti-Vδ1) binding Fab region comprising:
- a heavy chain variable region comprising a VHCDR1 comprising the amino acid sequence of SEQ ID NO: 130, a VHCDR2 comprising the amino acid sequence of SEQ ID NO: 131 and a VHCDR3 comprising the amino acid sequence of SEQ ID NO: 135; and a light chain variable region comprising a VLCDR1 comprising the amino acid sequence of SEQ ID NO: 144, a VLCDR2 comprising the amino acid sequence of SEQ ID NO: 145 and a VLCDR3 comprising the amino acid sequence of SEQ ID NO: 149.

Amino acid substitutions may be made to provide variant antibodies having Fab regions derived from ADT1-7-17, for example multispecific antibodies are provided, the anti-TCR delta variable 1 (anti-Vδ1) binding Fab region comprising:

- a heavy chain variable region comprising a VHCDR1 comprising the amino acid sequence of SEQ ID NO: 130 optionally comprising 1 or 2 amino acid substitutions, a VHCDR2 comprising the amino acid sequence of SEQ ID NO: 131 optionally comprising 1 or 2 amino acid substitutions, and a VHCDR3 comprising the amino acid sequence of SEQ ID NO: 135 optionally comprising 1 or 2 amino acid substitutions; and/or
- a light chain variable region comprising a VLCDR1 comprising the amino acid sequence of SEQ ID NO: 144 optionally comprising 1 or 2 amino acid substitutions, a VLCDR2 comprising the amino acid sequence of SEQ ID NO: 145 optionally comprising 1 or 2 amino acid substitutions and a VLCDR3 comprising the amino acid sequence of SEQ ID NO: 149 optionally comprising 1 or 2 amino acid substitutions. The amino acid substitutions may be conservative amino acid substitutions.

The antibodies may alternatively consist of the specified sequences (with or without amino acid substitutions).

ADT1-7-18 and Fragments and Variants Thereof

Certain embodiments relate to the antibody ADT1-7-18 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 136 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 150. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 136 and/or a light chain variable region comprising a VLCDR3 comprising an amino acid sequence having at least 90% identity to the amino acid sequence of SEQ ID NO: 150. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 136 and/or a light chain variable region comprising a VLCDR3 comprising the amino acid sequence of SEQ ID NO: 150.

Amino acid substitutions may be made to provide variant antibodies having Fab regions derived from ADT1-7-18, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 136, optionally comprising 1 or 2 amino acid substitutions, and/or a light chain variable region comprising a VLCDR3 comprising the amino acid sequence of SEQ ID NO: 150, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:

- a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 130, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 131 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 136; and/or
- a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 144, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 145 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 150.

In one embodiment, multispecific antibodies are provided, the anti-TCR delta variable 1 (anti-Vδ1) binding Fab region comprising:

- a heavy chain variable region comprising a VHCDR1 comprising at least 90% identity to the amino acid sequence of SEQ ID NO: 130, a VHCDR2 comprising at least 90% identity to the amino acid sequence of SEQ ID NO: 131 and a VHCDR3 comprising at least 90% identity to the amino acid sequence of SEQ ID NO: 136; and/or
- a light chain variable region comprising a VLCDR1 comprising the at least 90% identity to the amino acid sequence of SEQ ID NO: 144, a VLCDR2 comprising at least 90% identity to the amino acid sequence of SEQ ID NO: 145 and a VLCDR3 comprising at least 90% identity to the amino acid sequence of SEQ ID NO: 150.

In one embodiment, multispecific antibodies are provided, the anti-TCR delta variable 1 (anti-Vδ1) binding Fab region comprising:

- a heavy chain variable region comprising a VHCDR1 comprising the amino acid sequence of SEQ ID NO: 130, a VHCDR2 comprising the amino acid sequence of SEQ ID NO: 131 and a VHCDR3 comprising the amino acid sequence of SEQ ID NO: 136; and a light chain variable region comprising a VLCDR1 comprising the amino acid sequence of SEQ ID NO: 144, a VLCDR2 comprising the amino acid sequence of SEQ ID NO: 145 and a VLCDR3 comprising the amino acid sequence of SEQ ID NO: 150.

Amino acid substitutions may be made to provide variant antibodies having Fab regions derived from ADT1-7-18, for example multispecific antibodies are provided, the anti-TCR delta variable 1 (anti-Vδ1) binding Fab region comprising:

a heavy chain variable region comprising a VHCDR1 comprising the amino acid sequence of SEQ ID NO: 130 optionally comprising 1 or 2 amino acid substitutions, a VHCDR2 comprising the amino acid sequence of SEQ ID NO: 131 optionally comprising 1 or 2 amino acid substitutions, and a VHCDR3 comprising the amino acid sequence of SEQ ID NO: 136 optionally comprising 1 or 2 amino acid substitutions; and/or a light chain variable region comprising a VLCDR1 comprising the amino acid sequence of SEQ ID NO: 144 optionally comprising 1 or 2 amino acid substitutions, a VLCDR2 comprising the amino acid sequence of SEQ ID NO: 145 optionally comprising 1 or 2 amino acid substitutions and a VLCDR3 comprising the amino acid sequence of SEQ ID NO: 150 optionally comprising 1 or 2 amino acid substitutions. The amino acid substitutions may be conservative amino acid substitutions.

The antibodies may alternatively consist of the specified sequences (with or without amino acid substitutions).

ADT1-7-19 and Fragments and Variants Thereof

Certain embodiments relate to the antibody ADT1-7-19 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 137 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 151. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 137 and/or a light chain variable region comprising a VLCDR3 comprising an amino acid sequence having at least 90% identity to the amino acid sequence of SEQ ID NO: 151. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 137 and/or a light chain variable region comprising a VLCDR3 comprising the amino acid sequence of SEQ ID NO: 151.

Amino acid substitutions may be made to provide variant antibodies having Fab regions derived from ADT1-7-19, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 137, optionally comprising 1 or 2 amino acid substitutions, and/or a light chain variable region comprising a VLCDR3 comprising the amino acid sequence of SEQ ID NO: 151, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 130, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 131 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 137; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 144, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 145 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 151.

In one embodiment, multispecific antibodies are provided, the anti-TCR delta variable 1 (anti-Vδ1) binding Fab region comprising:

a heavy chain variable region comprising a VHCDR1 comprising at least 90% identity to the amino acid sequence of SEQ ID NO: 130, a VHCDR2 comprising at least 90% identity to the amino acid sequence of SEQ ID NO: 131 and a VHCDR3 comprising at least 90% identity to the amino acid sequence of SEQ ID NO: 137; and/or a light chain variable region comprising a VLCDR1 comprising the at least 90% identity to the amino acid sequence of SEQ ID NO: 144, a VLCDR2 comprising at least 90% identity to the amino acid sequence of SEQ ID NO: 145 and a VLCDR3 comprising at least 90% identity to the amino acid sequence of SEQ ID NO: 151.

In one embodiment, multispecific antibodies are provided, the anti-TCR delta variable 1 (anti-Vδ1) binding Fab region comprising:

a heavy chain variable region comprising a VHCDR1 comprising the amino acid sequence of SEQ ID NO:

130, a VHCDR2 comprising the amino acid sequence of SEQ ID NO: 131 and a VHCDR3 comprising the amino acid sequence of SEQ ID NO: 137; and
a light chain variable region comprising a VLCDR1 comprising the amino acid sequence of SEQ ID NO: 144, a VLCDR2 comprising the amino acid sequence of SEQ ID NO: 145 and a VLCDR3 comprising the amino acid sequence of SEQ ID NO: 151.

Amino acid substitutions may be made to provide variant antibodies having Fab regions derived from ADT1-7-19, for example multispecific antibodies are provided, the anti-TCR delta variable 1 (anti-Vδ1) binding Fab region comprising:
a heavy chain variable region comprising a VHCDR1 comprising the amino acid sequence of SEQ ID NO: 130 optionally comprising 1 or 2 amino acid substitutions, a VHCDR2 comprising the amino acid sequence of SEQ ID NO: 131 optionally comprising 1 or 2 amino acid substitutions, and a VHCDR3 comprising the amino acid sequence of SEQ ID NO: 137 optionally comprising 1 or 2 amino acid substitutions; and/or
a light chain variable region comprising a VLCDR1 comprising the amino acid sequence of SEQ ID NO: 144 optionally comprising 1 or 2 amino acid substitutions, a VLCDR2 comprising the amino acid sequence of SEQ ID NO: 145 optionally comprising 1 or 2 amino acid substitutions and a VLCDR3 comprising the amino acid sequence of SEQ ID NO: 151 optionally comprising 1 or 2 amino acid substitutions. The amino acid substitutions may be conservative amino acid substitutions.

The antibodies may alternatively consist of the specified sequences (with or without amino acid substitutions).

ADT1-7-20 and Fragments and Variants Thereof

Certain embodiments relate to the antibody ADT1-7-20 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 138 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 152. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 138 and/or a light chain variable region comprising a VLCDR3 comprising an amino acid sequence having at least 90% identity to the amino acid sequence of SEQ ID NO: 152. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 138 and/or a light chain variable region comprising a VLCDR3 comprising the amino acid sequence of SEQ ID NO: 152.

Amino acid substitutions may be made to provide variant antibodies having Fab regions derived from ADT1-7-20, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 138, optionally comprising 1 or 2 amino acid substitutions, and/or a light chain variable region comprising a VLCDR3 comprising the amino acid sequence of SEQ ID NO: 152, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:
a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 130, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 131 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 138; and/or
a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 144, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 145 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 152.

In one embodiment, multispecific antibodies are provided, the anti-TCR delta variable 1 (anti-Vδ1) binding Fab region comprising:
a heavy chain variable region comprising a VHCDR1 comprising at least 90% identity to the amino acid sequence of SEQ ID NO: 130, a VHCDR2 comprising at least 90% identity to the amino acid sequence of SEQ ID NO: 131 and a VHCDR3 comprising at least 90% identity to the amino acid sequence of SEQ ID NO: 138; and/or
a light chain variable region comprising a VLCDR1 comprising the at least 90% identity to the amino acid sequence of SEQ ID NO: 144, a VLCDR2 comprising at least 90% identity to the amino acid sequence of SEQ ID NO: 145 and a VLCDR3 comprising at least 90% identity to the amino acid sequence of SEQ ID NO: 152.

In one embodiment, multispecific antibodies are provided, the anti-TCR delta variable 1 (anti-Vδ1) binding Fab region comprising:

a heavy chain variable region comprising a VHCDR1 comprising the amino acid sequence of SEQ ID NO: 130, a VHCDR2 comprising the amino acid sequence of SEQ ID NO: 131 and a VHCDR3 comprising the amino acid sequence of SEQ ID NO: 138; and a light chain variable region comprising a VLCDR1 comprising the amino acid sequence of SEQ ID NO: 144, a VLCDR2 comprising the amino acid sequence of SEQ ID NO: 145 and a VLCDR3 comprising the amino acid sequence of SEQ ID NO: 152.

Amino acid substitutions may be made to provide variant antibodies having Fab regions derived from ADT1-7-20, for example multispecific antibodies are provided, the anti-TCR delta variable 1 (anti-Vδ1) binding Fab region comprising:

a heavy chain variable region comprising a VHCDR1 comprising the amino acid sequence of SEQ ID NO: 130 optionally comprising 1 or 2 amino acid substitutions, a VHCDR2 comprising the amino acid sequence of SEQ ID NO: 131 optionally comprising 1 or 2 amino acid substitutions, and a VHCDR3 comprising the amino acid sequence of SEQ ID NO: 138 optionally comprising 1 or 2 amino acid substitutions; and/or a light chain variable region comprising a VLCDR1 comprising the amino acid sequence of SEQ ID NO: 144 optionally comprising 1 or 2 amino acid substitutions, a VLCDR2 comprising the amino acid sequence of SEQ ID NO: 145 optionally comprising 1 or 2 amino acid substitutions and a VLCDR3 comprising the amino acid sequence of SEQ ID NO: 152 optionally comprising 1 or 2 amino acid substitutions. The amino acid substitutions may be conservative amino acid substitutions.

The antibodies may alternatively consist of the specified sequences (with or without amino acid substitutions).

ADT1-7-22 and Fragments and Variants Thereof

Certain embodiments relate to the antibody ADT1-7-22 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 139 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 153. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 139 and/or a light chain variable region comprising a VLCDR3 comprising an amino acid sequence having at least 90% identity to the amino acid sequence of SEQ ID NO: 153. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 139 and/or a light chain variable region comprising a VLCDR3 comprising the amino acid sequence of SEQ ID NO: 153.

Amino acid substitutions may be made to provide variant antibodies having Fab regions derived from ADT1-7-22, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 139, optionally comprising 1 or 2 amino acid substitutions, and/or a light chain variable region comprising a VLCDR3 comprising the amino acid sequence of SEQ ID NO: 153, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:

a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 130, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 131 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 139; and/or a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 144, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 145 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 153.

In one embodiment, multispecific antibodies are provided, the anti-TCR delta variable 1 (anti-Vδ1) binding Fab region comprising:

a heavy chain variable region comprising a VHCDR1 comprising at least 90% identity to the amino acid sequence of SEQ ID NO: 130, a VHCDR2 comprising at least 90% identity to the amino acid sequence of SEQ ID NO: 131 and a VHCDR3 comprising at least 90% identity to the amino acid sequence of SEQ ID NO: 139; and/or a light chain variable region comprising a VLCDR1 comprising the at least 90% identity to the amino acid sequence of SEQ ID NO: 144, a VLCDR2 comprising at least 90% identity to the amino acid sequence of SEQ ID NO: 145 and a VLCDR3 comprising at least 90% identity to the amino acid sequence of SEQ ID NO: 153.

In one embodiment, multispecific antibodies are provided, the anti-TCR delta variable 1 (anti-Vδ1) binding Fab region comprising:
- a heavy chain variable region comprising a VHCDR1 comprising the amino acid sequence of SEQ ID NO: 130, a VHCDR2 comprising the amino acid sequence of SEQ ID NO: 131 and a VHCDR3 comprising the amino acid sequence of SEQ ID NO: 139; and
- a light chain variable region comprising a VLCDR1 comprising the amino acid sequence of SEQ ID NO: 144, a VLCDR2 comprising the amino acid sequence of SEQ ID NO: 145 and a VLCDR3 comprising the amino acid sequence of SEQ ID NO: 153.

Amino acid substitutions may be made to provide variant antibodies having Fab regions derived from ADT1-7-22, for example multispecific antibodies are provided, the anti-TCR delta variable 1 (anti-Vδ1) binding Fab region comprising:
- a heavy chain variable region comprising a VHCDR1 comprising the amino acid sequence of SEQ ID NO: 130 optionally comprising 1 or 2 amino acid substitutions, a VHCDR2 comprising the amino acid sequence of SEQ ID NO: 131 optionally comprising 1 or 2 amino acid substitutions, and a VHCDR3 comprising the amino acid sequence of SEQ ID NO: 139 optionally comprising 1 or 2 amino acid substitutions; and/or
- a light chain variable region comprising a VLCDR1 comprising the amino acid sequence of SEQ ID NO: 144 optionally comprising 1 or 2 amino acid substitutions, a VLCDR2 comprising the amino acid sequence of SEQ ID NO: 145 optionally comprising 1 or 2 amino acid substitutions and a VLCDR3 comprising the amino acid sequence of SEQ ID NO: 153 optionally comprising 1 or 2 amino acid substitutions. The amino acid substitutions may be conservative amino acid substitutions.

The antibodies may alternatively consist of the specified sequences (with or without amino acid substitutions).

ADT1-7-23 and Fragments and Variants Thereof

Certain embodiments relate to the antibody ADT1-7-23 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 140 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 154. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 140 and/or a light chain variable region comprising a VLCDR3 comprising an amino acid sequence having at least 90% identity to the amino acid sequence of SEQ ID NO: 154. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 140 and/or a light chain variable region comprising a VLCDR3 comprising the amino acid sequence of SEQ ID NO: 154.

Amino acid substitutions may be made to provide variant antibodies having Fab regions derived from ADT1-7-23, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 140, optionally comprising 1 or 2 amino acid substitutions, and/or a light chain variable region comprising a VLCDR3 comprising the amino acid sequence of SEQ ID NO: 154, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:
- a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 130, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 131 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 140; and/or
- a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 144, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 145 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 154.

In one embodiment, multispecific antibodies are provided, the anti-TCR delta variable 1 (anti-Vδ1) binding Fab region comprising:
- a heavy chain variable region comprising a VHCDR1 comprising at least 90% identity to the amino acid sequence of SEQ ID NO: 130, a VHCDR2 comprising at least 90% identity to the amino acid sequence of SEQ ID NO: 131 and a VHCDR3 comprising at least 90% identity to the amino acid sequence of SEQ ID NO: 140; and/or
- a light chain variable region comprising a VLCDR1 comprising the at least 90% identity to the amino acid sequence of SEQ ID NO: 144, a VLCDR2 comprising at least 90% identity to the amino acid sequence of SEQ ID NO: 145 and a VLCDR3 comprising at least 90% identity to the amino acid sequence of SEQ ID NO: 154.

In one embodiment, multispecific antibodies are provided, the anti-TCR delta variable 1 (anti-Vδ1) binding Fab region comprising:
a heavy chain variable region comprising a VHCDR1 comprising the amino acid sequence of SEQ ID NO: 130, a VHCDR2 comprising the amino acid sequence of SEQ ID NO: 131 and a VHCDR3 comprising the amino acid sequence of SEQ ID NO: 140; and
a light chain variable region comprising a VLCDR1 comprising the amino acid sequence of SEQ ID NO: 144, a VLCDR2 comprising the amino acid sequence of SEQ ID NO: 145 and a VLCDR3 comprising the amino acid sequence of SEQ ID NO: 154.

Amino acid substitutions may be made to provide variant antibodies having Fab regions derived from ADT1-7-23, for example multispecific antibodies are provided, the anti-TCR delta variable 1 (anti-Vδ1) binding Fab region comprising:
a heavy chain variable region comprising a VHCDR1 comprising the amino acid sequence of SEQ ID NO: 130 optionally comprising 1 or 2 amino acid substitutions, a VHCDR2 comprising the amino acid sequence of SEQ ID NO: 131 optionally comprising 1 or 2 amino acid substitutions, and a VHCDR3 comprising the amino acid sequence of SEQ ID NO: 140 optionally comprising 1 or 2 amino acid substitutions; and/or
a light chain variable region comprising a VLCDR1 comprising the amino acid sequence of SEQ ID NO: 144 optionally comprising 1 or 2 amino acid substitutions, a VLCDR2 comprising the amino acid sequence of SEQ ID NO: 145 optionally comprising 1 or 2 amino acid substitutions and a VLCDR3 comprising the amino acid sequence of SEQ ID NO: 154 optionally comprising 1 or 2 amino acid substitutions. The amino acid substitutions may be conservative amino acid substitutions.

The antibodies may alternatively consist of the specified sequences (with or without amino acid substitutions).

ADT1-7-42 and Fragments and Variants Thereof

Certain embodiments relate to the antibody ADT1-7-42 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 141 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 155. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 141 and/or a light chain variable region comprising a VLCDR3 comprising an amino acid sequence having at least 90% identity to the amino acid sequence of SEQ ID NO: 155. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 141 and/or a light chain variable region comprising a VLCDR3 comprising the amino acid sequence of SEQ ID NO: 155.

Amino acid substitutions may be made to provide variant antibodies having Fab regions derived from ADT1-7-42, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 141, optionally comprising 1 or 2 amino acid substitutions, and/or a light chain variable region comprising a VLCDR3 comprising the amino acid sequence of SEQ ID NO: 155, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:
a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 130, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 131 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 141; and/or
a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 144, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 145 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 155.

In one embodiment, multispecific antibodies are provided, the anti-TCR delta variable 1 (anti-Vδ1) binding Fab region comprising:
a heavy chain variable region comprising a VHCDR1 comprising at least 90% identity to the amino acid sequence of SEQ ID NO: 130, a VHCDR2 comprising at least 90% identity to the amino acid sequence of SEQ ID NO: 131 and a VHCDR3 comprising at least 90% identity to the amino acid sequence of SEQ ID NO: 141; and/or
a light chain variable region comprising a VLCDR1 comprising the at least 90% identity to the amino acid sequence of SEQ ID NO: 144, a VLCDR2 comprising at least 90% identity to the amino acid sequence of SEQ ID NO: 145 and a VLCDR3 comprising at least 90% identity to the amino acid sequence of SEQ ID NO: 155.

In one embodiment, multispecific antibodies are provided, the anti-TCR delta variable 1 (anti-Vδ1) binding Fab region comprising:
- a heavy chain variable region comprising a VHCDR1 comprising the amino acid sequence of SEQ ID NO: 130, a VHCDR2 comprising the amino acid sequence of SEQ ID NO: 131 and a VHCDR3 comprising the amino acid sequence of SEQ ID NO: 141; and
- a light chain variable region comprising a VLCDR1 comprising the amino acid sequence of SEQ ID NO: 144, a VLCDR2 comprising the amino acid sequence of SEQ ID NO: 145 and a VLCDR3 comprising the amino acid sequence of SEQ ID NO: 155.

Amino acid substitutions may be made to provide variant antibodies having Fab regions derived from ADT1-7-42, for example multispecific antibodies are provided, the anti-TCR delta variable 1 (anti-Vδ1) binding Fab region comprising:
- a heavy chain variable region comprising a VHCDR1 comprising the amino acid sequence of SEQ ID NO: 130 optionally comprising 1 or 2 amino acid substitutions, a VHCDR2 comprising the amino acid sequence of SEQ ID NO: 131 optionally comprising 1 or 2 amino acid substitutions, and a VHCDR3 comprising the amino acid sequence of SEQ ID NO: 141 optionally comprising 1 or 2 amino acid substitutions; and/or
- a light chain variable region comprising a VLCDR1 comprising the amino acid sequence of SEQ ID NO: 144 optionally comprising 1 or 2 amino acid substitutions, a VLCDR2 comprising the amino acid sequence of SEQ ID NO: 145 optionally comprising 1 or 2 amino acid substitutions and a VLCDR3 comprising the amino acid sequence of SEQ ID NO: 155 optionally comprising 1 or 2 amino acid substitutions. The amino acid substitutions may be conservative amino acid substitutions.

The antibodies may alternatively consist of the specified sequences (with or without amino acid substitutions).

ADT1-7-3 and Fragments and Variants Thereof

Certain embodiments relate to the antibody ADT1-7-3 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 142 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 156. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 142 and/or a light chain variable region comprising a VLCDR3 comprising an amino acid sequence having at least 90% identity to the amino acid sequence of SEQ ID NO: 156. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 142 and/or a light chain variable region comprising a VLCDR3 comprising the amino acid sequence of SEQ ID NO: 156.

Amino acid substitutions may be made to provide variant antibodies having Fab regions derived from ADT1-7-3, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 142, optionally comprising 1 or 2 amino acid substitutions, and/or a light chain variable region comprising a VLCDR3 comprising the amino acid sequence of SEQ ID NO: 156, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:
- a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 130, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 131 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 142; and/or
- a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 144, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 145 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 156.

In one embodiment, multispecific antibodies are provided, the anti-TCR delta variable 1 (anti-Vδ1) binding Fab region comprising:
- a heavy chain variable region comprising a VHCDR1 comprising at least 90% identity to the amino acid sequence of SEQ ID NO: 130, a VHCDR2 comprising at least 90% identity to the amino acid sequence of SEQ ID NO: 131 and a VHCDR3 comprising at least 90% identity to the amino acid sequence of SEQ ID NO: 142; and/or
- a light chain variable region comprising a VLCDR1 comprising the at least 90% identity to the amino acid sequence of SEQ ID NO: 144, a VLCDR2 comprising at least 90% identity to the amino acid sequence of SEQ ID NO: 145 and a VLCDR3 comprising at least 90% identity to the amino acid sequence of SEQ ID NO: 156.

In one embodiment, multispecific antibodies are provided, the anti-TCR delta variable 1 (anti-Vδ1) binding Fab region comprising:
- a heavy chain variable region comprising a VHCDR1 comprising the amino acid sequence of SEQ ID NO: 130, a VHCDR2 comprising the amino acid sequence of SEQ ID NO: 131 and a VHCDR3 comprising the amino acid sequence of SEQ ID NO: 142; and
- a light chain variable region comprising a VLCDR1 comprising the amino acid sequence of SEQ ID NO: 144, a VLCDR2 comprising the amino acid sequence of SEQ ID NO: 145 and a VLCDR3 comprising the amino acid sequence of SEQ ID NO: 156.

Amino acid substitutions may be made to provide variant antibodies having Fab regions derived from ADT1-7-3, for example multispecific antibodies are provided, the anti-TCR delta variable 1 (anti-Vδ1) binding Fab region comprising:
- a heavy chain variable region comprising a VHCDR1 comprising the amino acid sequence of SEQ ID NO: 130 optionally comprising 1 or 2 amino acid substitutions, a VHCDR2 comprising the amino acid sequence of SEQ ID NO: 131 optionally comprising 1 or 2 amino acid substitutions, and a VHCDR3 comprising the amino acid sequence of SEQ ID NO: 142 optionally comprising 1 or 2 amino acid substitutions; and/or
- a light chain variable region comprising a VLCDR1 comprising the amino acid sequence of SEQ ID NO: 144 optionally comprising 1 or 2 amino acid substitutions, a VLCDR2 comprising the amino acid sequence of SEQ ID NO: 145 optionally comprising 1 or 2 amino acid substitutions and a VLCDR3 comprising the amino acid sequence of SEQ ID NO: 156 optionally comprising 1 or 2 amino acid substitutions. The amino acid substitutions may be conservative amino acid substitutions.

The antibodies may alternatively consist of the specified sequences (with or without amino acid substitutions).

ADT1-7-61 and Fragments and Variants Thereof

Certain embodiments relate to the antibody ADT1-7-61 and fragments and variants thereof.

For example, in some embodiments, multispecific antibodies are provided, the anti-TCR delta variable 1 (anti-Vδ1) binding Fab region comprising a heavy chain variable region comprising a VHCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 143 and/or a light chain variable region comprising a VLCDR3 comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 157. In one embodiment, an antibody or antigen-binding-fragment or variant thereof is provided comprising a heavy chain variable region comprising a VHCDR3 comprising an amino acid sequence having at least 90% identity to the amino acid sequence of SEQ ID NO: 143 and/or a light chain variable region comprising a VLCDR3 comprising an amino acid sequence having at least 90% identity to the amino acid sequence of SEQ ID NO: 157. In one embodiment, multispecific antibodies are provided, the anti-TCR delta variable 1 (anti-Vδ1) binding Fab region comprising a heavy chain variable region comprising a VHCDR3 comprising the amino acid sequence of SEQ ID NO: 143 and/or a light chain variable region comprising a VLCDR3 comprising the amino acid sequence of SEQ ID NO: 157.

Amino acid substitutions may be made to provide variant antibodies having Fab regions derived from ADT1-7-61, for example multispecific antibodies are provided, the anti-TCR delta variable 1 (anti-Vδ1) binding Fab region comprising a heavy chain variable region comprising a VHCDR3 comprising the amino acid sequence of SEQ ID NO: 143, optionally comprising 1 or 2 amino acid substitutions, and/or a light chain variable region comprising a VLCDR3 comprising the amino acid sequence of SEQ ID NO: 157, optionally comprising 1 or 2 amino acid substitutions. The amino acid substitutions may be conservative amino acid substitutions.

In some embodiments, multispecific antibodies are provided, the anti-TCR delta variable 1 (anti-Vδ1) binding Fab region comprising:
- a heavy chain variable region comprising a VHCDR1 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 130, a VHCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 131 and a VHCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 143; and/or
- a light chain variable region comprising a VLCDR1 comprising the at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to amino acid sequence of SEQ ID NO: 144, a VLCDR2 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 145 and a VLCDR3 comprising at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to the amino acid sequence of SEQ ID NO: 157.

In one embodiment, multispecific antibodies are provided, the anti-TCR delta variable 1 (anti-Vδ1) binding Fab region comprising:
- a heavy chain variable region comprising a VHCDR1 comprising at least 90% identity to the amino acid sequence of SEQ ID NO: 130, a VHCDR2 comprising at least 90% identity to the amino acid sequence of SEQ ID NO: 131 and a VHCDR3 comprising at least 90% identity to the amino acid sequence of SEQ ID NO: 143; and/or a light chain variable region comprising a VLCDR1 comprising the at least 90% identity to the amino acid sequence of SEQ ID NO: 144, a VLCDR2 comprising at least 90% identity to the amino acid sequence of SEQ ID NO: 145 and a VLCDR3 comprising at least 90% identity to the amino acid sequence of SEQ ID NO: 157.

In one embodiment, multispecific antibodies are provided, the anti-TCR delta variable 1 (anti-Vδ1) binding Fab region comprising:
- a heavy chain variable region comprising a VHCDR1 comprising the amino acid sequence of SEQ ID NO: 130, a VHCDR2 comprising the amino acid sequence of SEQ ID NO: 131 and a VHCDR3 comprising the amino acid sequence of SEQ ID NO: 143; and
- a light chain variable region comprising a VLCDR1 comprising the amino acid sequence of SEQ ID NO: 144, a VLCDR2 comprising the amino acid sequence of SEQ ID NO: 145 and a VLCDR3 comprising the amino acid sequence of SEQ ID NO: 157.

Amino acid substitutions may be made to provide variant antibodies having Fab regions derived from ADT1-7-61, for example multispecific antibodies are provided, the anti-TCR delta variable 1 (anti-Vδ1) binding Fab region comprising:
- a heavy chain variable region comprising a VHCDR1 comprising the amino acid sequence of SEQ ID NO: 130 optionally comprising 1 or 2 amino acid substitutions, a VHCDR2 comprising the amino acid sequence of SEQ ID NO: 131 optionally comprising 1 or 2 amino acid substitutions, and a VHCDR3 comprising the amino acid sequence of SEQ ID NO: 143 optionally comprising 1 or 2 amino acid substitutions; and/or
- a light chain variable region comprising a VLCDR1 comprising the amino acid sequence of SEQ ID NO: 144 optionally comprising 1 or 2 amino acid substitutions, a VLCDR2 comprising the amino acid sequence of SEQ ID NO: 145 optionally comprising 1 or 2 amino acid substitutions and a VLCDR3 comprising the amino acid sequence of SEQ ID NO: 157 optionally comprising 1 or 2 amino acid substitutions. The amino acid substitutions may be conservative amino acid substitutions.

The antibodies may alternatively consist of the specified sequences (with or without amino acid substitutions).

Antibodies Comprising Heavy and/or Light Chain Variable Regions Derived from ADT1-7

Provided herein are multispecific antibodies, the anti-TCR delta variable 1 (anti-Vδ1) binding Fab region comprising:
- a heavy chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID NOs: 107 to 117; and/or
- a light chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID NOs: 119 to 129.

Also provided are multispecific antibodies, the anti-TCR delta variable 1 (anti-Vδ1) binding Fab region comprising:
- a heavy chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID NOs: 112, 116 and 117; and/or
- a light chain variable region comprising or consisting of a sequence having at least 70%, at least 75%, at least 80%, at least 85%, at least 90%, at least 91%, at least 92%, at least 93%, at least 94%, at least 95%, at least 96%, at least 97%, at least 98%, at least 99% or 100% identity to a sequence selected from the group consisting of SEQ ID NOs: 124, 128 and 129.

Also provided are multispecific antibodies, the anti-TCR delta variable 1 (anti-Vδ1) binding Fab region comprising:
- a heavy chain variable region comprising or consisting of a sequence having at least 90% identity to a sequence selected from the group consisting of SEQ ID NOs: 107 to 117; and/or
- a light chain variable region comprising or consisting of a sequence having at least 90% identity to a sequence selected from the group consisting of SEQ ID NOs: 119 to 129.

Also provided are multispecific antibodies, the anti-TCR delta variable 1 (anti-Vδ1) binding Fab region comprising:
- a heavy chain variable region comprising or consisting of a sequence having at least 90% identity to a sequence selected from the group consisting of SEQ ID NOs: 112, 116 and 117; and/or
- a light chain variable region comprising or consisting of a sequence having at least 90% identity to a sequence selected from the group consisting of SEQ ID NOs: 124, 128 and 129.

Optionally the antibodies above retain the corresponding CDR sequences such that any variability in the VH and VL sequences occurs in the framework regions.

Provided herein are multispecific antibodies, the anti-TCR delta variable 1 (anti-Vδ1) binding Fab region comprising:
- a heavy chain variable region comprising or consisting of a sequence selected from the group consisting of SEQ ID NOs: 107 to 117; and/or
- a light chain variable region comprising or consisting of a sequence selected from the group consisting of SEQ ID NOs: 119 to 129.

Also provided herein are multispecific antibodies, the anti-TCR delta variable 1 (anti-Vδ1) binding Fab region comprising:
- a heavy chain variable region comprising or consisting of a sequence selected from the group consisting of SEQ ID NOs: 112, 116 and 117; and/or
- a light chain variable region comprising or consisting of a sequence selected from the group consisting of SEQ ID NOs: 124, 128 and 129.

In some embodiments, multispecific antibodies are provided, the anti-TCR delta variable 1 (anti-Vδ1) binding Fab region comprising:
a) a VH comprising or consisting of an amino acid sequence that is at least 90% identical to the amino acid sequence of SEQ ID NO: 107 and a VL comprising or consisting of an amino acid sequence that is at least 90% identical to the amino acid sequence of SEQ ID NO: 119;
b) a VH comprising or consisting of an amino acid sequence that is at least 90% identical to the amino acid sequence of SEQ ID NO: 108 and a VL comprising or consisting of an amino acid sequence that is at least 90% identical to the amino acid sequence of SEQ ID NO: 120;
c) a VH comprising or consisting of an amino acid sequence that is at least 90% identical to the amino acid sequence of SEQ ID NO: 109 and a VL comprising or consisting of an amino acid sequence that is at least 90% identical to the amino acid sequence of SEQ ID NO: 121;
d) a VH comprising or consisting of an amino acid sequence that is at least 90% identical to the amino acid sequence of SEQ ID NO: 110 and a VL comprising or consisting of an amino acid sequence that is at least 90% identical to the amino acid sequence of SEQ ID NO: 122;
e) a VH comprising or consisting of an amino acid sequence that is at least 90% identical to the amino acid sequence of SEQ ID NO: 111 and a VL comprising or consisting of an amino acid sequence that is at least 90% identical to the amino acid sequence of SEQ ID NO: 123;
f) a VH comprising or consisting of an amino acid sequence that is at least 90% identical to the amino acid sequence of SEQ ID NO: 112 and a VL comprising or consisting of an amino acid sequence that is at least 90% identical to the amino acid sequence of SEQ ID NO: 124;
g) a VH comprising or consisting of an amino acid sequence that is at least 90% identical to the amino acid sequence of SEQ ID NO: 113 and a VL comprising or consisting of an amino acid sequence that is at least 90% identical to the amino acid sequence of SEQ ID NO: 125;
h) a VH comprising or consisting of an amino acid sequence that is at least 90% identical to the amino acid sequence of SEQ ID NO: 114 and a VL comprising or consisting of an amino acid sequence that is at least 90% identical to the amino acid sequence of SEQ ID NO: 126;
i) a VH comprising or consisting of an amino acid sequence that is at least 90% identical to the amino acid sequence of SEQ ID NO: 115 and a VL comprising or consisting of an amino acid sequence that is at least 90% identical to the amino acid sequence of SEQ ID NO: 127;
j) a VH comprising or consisting of an amino acid sequence that is at least 90% identical to the amino acid sequence of SEQ ID NO: 116 and a VL comprising or consisting of an amino acid sequence that is at least 90% identical to the amino acid sequence of SEQ ID NO: 128; or
k) a VH comprising or consisting of an amino acid sequence that is at least 90% identical to the amino acid sequence of SEQ ID NO: 117 and a VL comprising or consisting of an amino acid sequence that is at least 90% identical to the amino acid sequence of SEQ ID NO: 129.

Optionally the antibodies above retain the corresponding CDR sequences such that any variability in the VH and VL sequences occurs in the framework regions.

In some embodiments, multispecific antibodies are provided, the anti-TCR delta variable 1 (anti-Vδ1) binding Fab region comprising:
a) a VH comprising or consisting of the amino acid sequence of SEQ ID NO: 107 and a VL comprising or consisting of the amino acid sequence of SEQ ID NO: 119 optionally comprising up to 5, up to 4, up to 3, up to 2 or 1 amino acid substitutions across both variable regions;
b) a VH comprising or consisting of the amino acid sequence of SEQ ID NO: 108 and a VL comprising or consisting of the amino acid sequence of SEQ ID NO: 120 optionally comprising up to 5, up to 4, up to 3, up to 2 or 1 amino acid substitutions across both variable regions;
c) a VH comprising or consisting of the amino acid sequence of SEQ ID NO: 109 and a VL comprising or consisting of the amino acid sequence of SEQ ID NO: 121 optionally comprising up to 5, up to 4, up to 3, up to 2 or 1 amino acid substitutions across both variable regions;
d) a VH comprising or consisting of the amino acid sequence of SEQ ID NO: 110 and a VL comprising or consisting of the amino acid sequence of SEQ ID NO: 122 optionally comprising up to 5, up to 4, up to 3, up to 2 or 1 amino acid substitutions across both variable regions;
e) a VH comprising or consisting of the amino acid sequence of SEQ ID NO: 111 and a VL comprising or consisting of the amino acid sequence of SEQ ID NO: 123 optionally comprising up to 5, up to 4, up to 3, up to 2 or 1 amino acid substitutions across both variable regions;
f) a VH comprising or consisting of the amino acid sequence of SEQ ID NO: 112 and a VL comprising or consisting of the amino acid sequence of SEQ ID NO: 124 optionally comprising up to 5, up to 4, up to 3, up to 2 or 1 amino acid substitutions across both variable regions;
g) a VH comprising or consisting of the amino acid sequence of SEQ ID NO: 113 and a VL comprising or consisting of the amino acid sequence of SEQ ID NO: 125 optionally comprising up to 5, up to 4, up to 3, up to 2 or 1 amino acid substitutions across both variable regions;
h) a VH comprising or consisting of the amino acid sequence of SEQ ID NO: 114 and a VL comprising or consisting of the amino acid sequence of SEQ ID NO: 126 optionally comprising up to 5, up to 4, up to 3, up to 2 or 1 amino acid substitutions across both variable regions;
i) a VH comprising or consisting of the amino acid sequence of SEQ ID NO: 115 and a VL comprising or consisting of the amino acid sequence of SEQ ID NO: 127 optionally comprising up to 5, up to 4, up to 3, up to 2 or 1 amino acid substitutions across both variable regions;
j) a VH comprising or consisting of the amino acid sequence of SEQ ID NO: 116 and a VL comprising or consisting of the amino acid sequence of SEQ ID NO: 128 optionally comprising up to 5, up to 4, up to 3, up to 2 or 1 amino acid substitutions across both variable regions; or
k) a VH comprising or consisting of the amino acid sequence of SEQ ID NO: 117 and a VL comprising or consisting of the amino acid sequence of SEQ ID NO: 129 optionally comprising up to 5, up to 4, up to 3, up to 2 or 1 amino acid substitutions across both variable regions.

"Across both variable regions" means collectively, the antibody may comprise up to the specified number of substitutions in total when considering both the heavy and light chain variable regions. The amino acid substitutions may be conservative amino acid substitutions. In some embodiments, the substitutions (if present) may occur anywhere in the variable region sequences. In preferred embodiments, the substitutions (if present) may be limited to the framework regions. Accordingly in some embodiments, the amino acid substitutions do not occur in a CDR sequence.

Optionally the antibodies above retain the corresponding CDR sequences such that any variability in the VH and VL sequences occurs in the framework regions.

In some embodiments, multispecific antibodies are provided, the anti-TCR delta variable 1 (anti-Vδ1) binding Fab region comprising:
- a) a VH comprising or consisting of the amino acid sequence of SEQ ID NO: 107 and a VL comprising or consisting of the amino acid sequence of SEQ ID NO: 119;
- b) a VH comprising or consisting of the amino acid sequence of SEQ ID NO: 108 and a VL comprising or consisting of the amino acid sequence of SEQ ID NO: 120;
- c) a VH comprising or consisting of the amino acid sequence of SEQ ID NO: 109 and a VL comprising or consisting of the amino acid sequence of SEQ ID NO: 121;
- d) a VH comprising or consisting of the amino acid sequence of SEQ ID NO: 110 and a VL comprising or consisting of the amino acid sequence of SEQ ID NO: 122;
- e) a VH comprising or consisting of the amino acid sequence of SEQ ID NO: 111 and a VL comprising or consisting of the amino acid sequence of SEQ ID NO: 123;
- f) a VH comprising or consisting of the amino acid sequence of SEQ ID NO: 112 and a VL comprising or consisting of the amino acid sequence of SEQ ID NO: 124;
- g) a VH comprising or consisting of the amino acid sequence of SEQ ID NO: 113 and a VL comprising or consisting of the amino acid sequence of SEQ ID NO: 125;
- h) a VH comprising or consisting of the amino acid sequence of SEQ ID NO: 114 and a VL comprising or consisting of the amino acid sequence of SEQ ID NO: 126;
- i) a VH comprising or consisting of the amino acid sequence of SEQ ID NO: 115 and a VL comprising or consisting of the amino acid sequence of SEQ ID NO: 127;
- j) a VH comprising or consisting of the amino acid sequence of SEQ ID NO: 116 and a VL comprising or consisting of the amino acid sequence of SEQ ID NO: 128; or
- k) a VH comprising or consisting of the amino acid sequence of SEQ ID NO: 117 and a VL comprising or consisting of the amino acid sequence of SEQ ID NO: 129.

Certain amino acid substitutions may be made to provide one or more variant antibodies as described herein.

In any embodiments relating to Fab regions having defined VH and/or VL sequences (for example any VH and/or VL sequences defined as having certain percent identities and/or substitutions), preferably the VH sequence is not SEQ ID NO: 106 and the VL sequence is not SEQ ID NO: 118.

Other Antibodies Comprising Fab Regions Derived from ADT1-7

In one embodiment multispecific antibodies are provided, the anti-TCR delta variable 1 (anti-Vδ1) binding Fab region comprising:
- a) an HCDR1 sequence comprising or consisting of the sequence of SEQ ID NO: 130;
- b) an HCDR2 sequence comprising or consisting of the sequence of SEQ ID NO: 131;
- c) an HCDR3 sequence comprising or consisting of the sequence of $X_1X_2YX_3X_4AFDI$ (SEQ ID NO: 183), wherein the HCDR3 sequence is not SEQ ID NO: 132;
- d) an LCDR1 sequence comprising or consisting of the sequence of SEQ ID NO: 144;
- e) an LCDR2 sequence comprising or consisting of the sequence of SEQ ID NO: 145; and
- f) an LCDR3 sequence comprising or consisting of the sequence of $QQX_5X_6X_7X_8LX_9T$ (SEQ ID NO: 186), wherein the LCDR3 sequence is no SEQ ID NO: 146;

wherein each of $X_1$ to $X_9$ is a naturally occurring amino acid.

In one embodiment multispecific antibodies are provided, the anti-TCR delta variable 1 (anti-Vδ1) binding Fab region comprising:
- a) an HCDR1 sequence comprising or consisting of the sequence of SEQ ID NO: 130;
- b) an HCDR2 sequence comprising or consisting of the sequence of SEQ ID NO: 131;
- c) an HCDR3 sequence comprising or consisting of the sequence of $X_1X_2YX_3X_4AFDI$ (SEQ ID NO: 184), wherein the HCDR3 sequence is not SEQ ID NO: 132;
- d) an LCDR1 sequence comprising or consisting of the sequence of SEQ ID NO: 144;
- e) an LCDR2 sequence comprising or consisting of the sequence of SEQ ID NO: 145; and
- f) an LCDR3 sequence comprising or consisting of the sequence of $QQX_5X_6X_7X_8LX_9T$ (SEQ ID NO: 187), wherein the LCDR3 sequence is no SEQ ID NO: 146;

wherein $X_1$ is selected from the group consisting of D, I and V; $X_2$ is selected from the group consisting of D and S; $X_3$ is selected from the group consisting of N, E, D, Q and A; $X_4$ is selected from the group consisting of D and E; $X_5$ is selected from the group consisting of T and S; $X_6$ is selected from the group consisting of A, G, Y and S; $X_7$ is selected from the group consisting of S and D; $X_8$ is selected from the group consisting of T, E and G; and $X_9$ is selected from the group consisting of L and D. The antibody may further comprise an HFR1 sequence comprising the sequence of SEQ ID NO: 189; an HFR2 sequence comprising the sequence of SEQ ID NO: 190; an HFR3 sequence comprising the sequence of SEQ ID NO: 191; an HFR4 sequence comprising the sequence of SEQ ID NO: 192; an LFR1 sequence comprising the sequence of SEQ ID NO: 193 and 194; an LFR2 sequence comprising the sequence of SEQ ID NO: 195; an LFR3 sequence comprising the sequence of SEQ ID NO: 196; and an LFR4 sequence comprising the sequence of SEQ ID NO: 197.

In one embodiment multispecific antibodies are provided, the anti-TCR delta variable 1 (anti-Vδ1) binding Fab region comprising:
- a) an HCDR1 sequence comprising or consisting of the sequence of SEQ ID NO: 130
- b) an HCDR2 sequence comprising or consisting of the sequence of SEQ ID NO: 131
- c) an HCDR3 sequence comprising or consisting of the sequence of $X_1X_2YX_3X_4AFDI$ (SEQ ID NO: 185), wherein the HCDR3 sequence is not SEQ ID NO: 132;

d) an LCDR1 sequence comprising or consisting of the sequence of SEQ ID NO: 144;
e) an LCDR2 sequence comprising or consisting of the sequence of SEQ ID NO: 145; and
f) an LCDR3 sequence comprising or consisting of the sequence of QQX$_5$X$_6$X$_7$X$_8$LX$_9$T (SEQ ID NO: 188), wherein the LCDR3 sequence is no SEQ ID NO: 146;

wherein X$_1$ is selected from the group consisting of D and V; X$_2$ is selected from the group consisting of D and S; X$_3$ is selected from the group consisting of D, Q and A; X$_4$ is selected from the group consisting of D and E; X$_5$ is S; X$_6$ is selected from the group consisting of A and Y; X$_7$ is S; X$_8$ is selected from the group consisting of E and G; and X$_9$ is selected from the group consisting of L and D. The antibody may further comprise an HFR1 sequence comprising the sequence of SEQ ID NO: 189; an HFR2 sequence comprising the sequence of SEQ ID NO: 190; an HFR3 sequence comprising the sequence of SEQ ID NO: 191; an HFR4 sequence comprising the sequence of SEQ ID NO: 192; an LFR1 sequence comprising the sequence of SEQ ID NO: 193; an LFR2 sequence comprising the sequence of SEQ ID NO: 195; an LFR3 sequence comprising the sequence of SEQ ID NO: 196; and an LFR4 sequence comprising the sequence of SEQ ID NO: 197.

Antibodies Having Sequence Substitutions

The skilled person is aware that various amino acids have similar properties. One or more such amino acids of a substance can often be substituted by one or more other such amino acids without eliminating a desired activity of that substance.

Thus, the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains).

A "conservative" amino acid substitution is an amino acid substitution in which an amino acid residue is replaced with another amino acid residue of similar chemical structure and which is expected to have little influence on the function, activity or other biological properties of the polypeptide. Such conservative substitutions suitably are substitutions in which one amino acid within the following groups is substituted by another amino acid residue from within the same group:

| Group | Amino acid residue |
|---|---|
| Non-polar aliphatic | Glycine |
| | Alanine |
| | Valine |
| | Methionine |
| | Leucine |
| | Isoleucine |
| Aromatic | Phenylalanine |
| | Tyrosine |
| | Tryptophan |
| Polar uncharged | Serine |
| | Threonine |
| | Cysteine |
| | Proline |
| | Asparagine |
| | Glutamine |
| Negatively charged | Aspartate |
| | Glutamate |
| Positively charged | Lysine |
| | Arginine |
| | Histidine |

Suitably, a hydrophobic amino acid residue is a non-polar amino acid. More suitably, a hydrophobic amino acid residue is selected from V, I, L, M, F, W or C. In some embodiments, a hydrophobic amino acid residue is selected from glycine, alanine, valine, methionine, leucine, isoleucine, phenylalanine, tyrosine, or tryptophan.

Therefore, references to "conservative" amino acid substitutions refer to amino acid substitutions in which one or more of the amino acids in the sequence of the antibody (e.g. in the CDRs or in the VH or VL sequences) is substituted with another amino acid in the same class as indicated above. Conservative amino acid substitutions may be preferred in the CDR regions to minimise adverse effects on the function of the antibody. However, conservative amino acid substitutions may also occur in the framework regions. Therefore, in some embodiments, any substitutions in the CDRs may be conservative substitutions, whereas substitutions in the framework regions may by substitutions of naturally occurring amino acids with another other naturally occurring amino acids.

Amino acid deletions or insertions can also be made relative to the amino acid sequences provided for the antibodies described herein. Thus, for example, amino acids which do not have a substantial effect on the activity of the polypeptide, or at least which do not eliminate such activity, can be deleted. Such deletions can be advantageous since the overall length and the molecular weight of a polypeptide can be reduced whilst still retaining activity. This can enable the amount of polypeptide required for a particular purpose to be reduced—for example, dosage levels can be reduced.

Amino acid changes relative to the sequences provided herein can be made using any suitable technique e.g. by using site-directed mutagenesis or solid-state synthesis.

It should be appreciated that amino acid substitutions or insertions within the scope of the present invention can be made using naturally occurring or non-naturally occurring amino acids, although naturally occurring amino acids may be preferred. Whether or not natural or synthetic amino acids are used, it may be preferred that only L-amino acids are present.

Various embodiments comprising optional amino acid substitutions the provided sequences are provided herein. In addition, in one embodiment of the invention there is provided antibodies, or antigen-binding fragment thereof, of the invention comprising up to 10, suitably up to 5, or suitably up to 2 amino acid substitutions in the antibody binding domain or antigen-binding domains. For example, in one embodiment of the invention, there is provided an Vδ1 antibody or antigen-binding fragment thereof, wherein the antibody or antigen-binding fragment thereof comprises the 6 CDR regions of an antibody selected from the group consisting of ADT1-4-105, ADT1-4-107, ADT1-4-110, ADT1-4-112, ADT1-4-117, ADT1-4-19, ADT1-4-21, ADT1-4-31, ADT1-4-139, ADT1-4-4, ADT1-4-143, ADT1-4-53, ADT1-4-173, ADT1-4-2, ADT1-4-8, ADT1-4-82, ADT1-4-83, ADT1-4-3, ADT1-4-84, ADT1-4-86, ADT1-4-95, ADT1-4-1, ADT1-4-6, ADT1-4-138, ADT1-7-10, ADT1-7-15, ADT1-7-17, ADT1-7-18, ADT1-7-19, ADT1-7-20, ADT1-7-22, ADT1-7-23, ADT1-7-42, ADT1-7-3 and ADT1-7-61, wherein the antibody or antigen-binding fragment thereof has up to 10 amino acid substitutions across all of its CDR regions, suitably up to 5 amino acid substitutions or up to 2 amino acid substitutions. In a further embodiment of the invention, there is provided an anti-Vδ1 antibody or antigen-binding fragment thereof, wherein the antibody or antigen-binding fragment thereof comprises the VH and VL sequences of an antibody selected from the group consisting of ADT1-4-105, ADT1-4-107, ADT1-4-110, ADT1-4-112, ADT1-4-117, ADT1-4-19, ADT1-4-21, ADT1-4-31, ADT1-4-139, ADT1-4-4, ADT1-4-143, ADT1-4-53, ADT1-4-173, ADT1-4-2, ADT1-4-8, ADT1-4-82, ADT1-4-83, ADT1-4-3, ADT1-4-84, ADT1-4-86, ADT1-4-95, ADT1-4-1, ADT1-4-6, ADT1-4-138, ADT1-7-10, ADT1-7-15, ADT1-7-17, ADT1-7-18, ADT1-7-19, ADT1-7-20, ADT1-7-22, ADT1-7-23, ADT1-7-42, ADT1-7-3 and ADT1-7-61, wherein the antibody has up to 10 amino acid substitutions across its VH and VL sequences, suitably up to 5 amino acid substitutions or up to 2 amino acid substitutions. In a still further embodiment of the invention, there is provided an anti-Vδ1 antibody or antigen-binding fragment thereof, wherein the antibody or antigen-binding fragment thereof is an antibody selected from the group consisting of ADT1-4-105, ADT1-4-107, ADT1-4-110, ADT1-4-112, ADT1-4-117, ADT1-4-19, ADT1-4-21, ADT1-4-31, ADT1-4-139, ADT1-4-4, ADT1-4-143, ADT1-4-53, ADT1-4-173, ADT1-4-2, ADT1-4-8, ADT1-4-82, ADT1-4-83, ADT1-4-3, ADT1-4-84, ADT1-4-86, ADT1-4-95, ADT1-4-1, ADT1-4-6, ADT1-4-138, ADT1-7-10, ADT1-7-15, ADT1-7-17, ADT1-7-18, ADT1-7-19, ADT1-7-20, ADT1-7-22, ADT1-7-23, ADT1-7-42, ADT1-7-3 and ADT1-7-61, wherein the antibody has up to amino acid substitutions, suitably up to 5 amino acid substitutions or up to 2 amino acid substitutions. Substitutions are of course substitutions with reference to the original CDR or variable chain sequences of the starting antibody.

In some embodiments, the one or more amino acid substitutions are in the CDR region or regions. In other embodiments, the one or more amino acid substitutions are in the framework regions, i.e. in the variable heavy and light chains but not in the CDR region or regions. In other embodiments, the one or more amino acid substitutions may be at any position in the variable heavy and/or variable light regions. In some embodiments, the amino acid substitutions do not occur in a CDR sequence.

In some embodiments, the amino acid substitutions do not adversely affect the binding specificity and/or affinity of the antibody. Accordingly, the variant antibody may have the same (or substantially the same) or a superior functional profile as the antibody from which is it derived.

In some embodiments, amino acid substitutions may be made to increase the binding affinity of the antibody to a particular antigen. For example, in embodiments of the invention relating to the mutagenesis of the serine at position 74 of the (variable region of the) light chain, a substitution may be made to increase the cross reactivity of the antibody for a the cyno homolog of the human antigen against which the antibody was prepared. Unlike other substitutions described above, this substitution may preferably be non-conservative. In some embodiments, the substitution may be a substitution of the serine at position 74 to a non-polar amino acid (for example to an amino acid selected from the group consisting of glycine, alanine, valine, methionine, leucine and isoleucine). Alternatively, the serine may be substituted with a non-human-germline amino acid (for example to an amino acid selected from the group consisting of arginine, cysteine, glutamine, glutamic acid, glycine, histidine, isoleucine, leucine, lysine, methionine, phenylalanine, threonine, tryptophan, tyrosine and valine). In some embodiments, the serine may be substituted with an amino acid that is both non-human-germline and non-polar, i.e. an amino acid selected from the group consisting of glycine, valine, methionine, leucine and isoleucine. In some embodiments, the serine may be substituted with a leucine.

Epitopes

Provided herein are multispecific antibodies (or antigen-binding fragments thereof) which bind to an epitope of the Vδ1 chain of a γδ TCR. Such binding may optionally have an effect on γδ TCR activity, such as activation. The multispecific antibodies of the invention are specific for the Vδ1 chain of a γδ TCR, and do not bind epitopes of other antigens, such as the Vδ2 chain of a γδ TCR or the Vδ3 chain of a γδ TCR. The antibodies of the present invention may be considered agonistic antibodies, at least with respect to the agonistic effect conferred upon Vδ1 cells upon binding.

In one embodiment, the epitope may be an activating epitope of a γδ T cell. An "activating" epitope can include, for example, stimulating a TCR function, such as cell degranulation, TCR downregulation, cytotoxicity, proliferation, mobilisation, increased survival or resistance to exhaustion, intracellular signalling, cytokine or growth factor secretion, phenotypic change, or a change in gene expression. For example, the binding of the activating epitope may stimulate expansion (i.e. proliferation) of the γδ T cell population, preferably the Vδ1+ T cell population. Accordingly, these antibodies can be used to modulate γδ T cell activation, and, thereby, to modulate the immune response. Therefore, in one embodiment, binding of the activating epitope downregulates the γδ TCR. In an additional or alternative embodiment, binding of the activating epitope activates degranulation of the γδ T cell. In a further additional or alternative embodiment, binding of the activating epitope promotes γδ T cell mediated killing.

In some embodiments, an activating epitope of TRDV1 is one that, upon being bound by an antibody, results in down-regulation of the receptor and optionally activates the Vδ1 cell. In some embodiments, the activating epitope is one that upregulates expression of activatory markers on the Vδ1 cell, for example CD107a, CD25, CD69 and/or Ki67. In some embodiments, the activating epitope is one that upregulates expression of activatory markers on the Vδ1 cell, for example CD107 and CD25, and optionally CD69 and/or Ki67. In some embodiments, upregulation of the one or more activatory markers (such as CD107a) may be upregulation in the presence of cancer cells. In preferred embodiments of the invention, the antibodies bind activating epitopes of TRDV1, in particular via the TRDV1-binding domain.

As T-cell receptors are often complexed with other proteins, downregulation of the T-cell receptor via Vδ1 antibody binding may cause downregulation of other proteins associated with the T-cell receptor (i.e. the binding of the Vδ1 antibody causes down regulation of the T-cell receptor complex). For example, in some embodiments, an activating epitope of TRDV1 is one that upon binding, down-regulates the TCR/CD3 receptor complex. In this way, the antibodies of the invention may cause indirect downregulation of cell surface proteins that are not bound by the antibody, but are complexed to the T-cell receptor. Given T-cells expressing gamma delta 1 chains (i.e. Vδ1 cells) represent only a small number of the total T-cell population, the multispecific antibodies of the invention can be used to selectively (and indirectly) downregulate proteins in the TCR complex, such as CD3, by only downregulating them in Vδ1 cells.

In some embodiments, a T-cell receptor complex activating epitope is one that upon activation, downregulates the T-cell receptor complex, whilst not downregulating CD3 molecules not associated with said TRDV1 TCR complex.

The epitope is preferably comprised of or consists of at least one extracellular, soluble, hydrophilic or external portion of the Vδ1 chain of a γδ TCR.

In particular, the epitope does not comprise or consist of an epitope found in a hypervariable region of the Vδ1 chain of the γδ TCR, in particular CDR3 of the Vδ1 chain. In a preferred embodiment, the epitope is within the non-variable region of the Vδ1 chain of the γδ TCR. It will be appreciated that such binding allows for the unique recognition of the Vδ1 chain without the restriction to the sequences of the TCR which are highly variable (in particular CDR3). Various γδ TCR complexes which recognise antigen may be recognised in this way, solely by presence of the Vδ1 chain. As such, it will be appreciated that any Vδ1 chain-comprising γδ TCR may be recognised using the multispecific antibodies as defined herein, irrespective of the specificity of the γδ TCR. In one embodiment, the epitope comprises or consists of one or more amino acid residues within amino acid regions 1-24 and/or 35-90 of SEQ ID NO: 272, e.g. the portions of the Vδ1 chain which are not part of the CDR1 and/or CDR3 sequences. In one embodiment, the epitope does not comprise or consist of amino acid residues within amino acid region 91-105 (CDR3) of SEQ ID NO: 272.

In some embodiments the epitope comprises or consists of amino acids in the TRDV-1 CDR2 sequence.

In a similar manner to the well characterised αβ T cells, γδ T cells utilize a distinct set of somatically rearranged variable (V), diversity (D), joining (J), and constant (C) genes, although γδ T cells contain fewer V, D, and J segments than αβ T cells. In one embodiment, the epitope of Vδ1 bound by the multispecific antibodies (or antigen-binding fragments thereof) does not comprise or consist of an epitope found in the J region of the Vδ1 chain (e.g. one of the four J regions encoded in the human delta one chain germline: SEQ ID NO: 301 (J1*0) or 302 (J2*0) or 303 (J3*0) or 304 (J4*0)) or in the C-region of the Vδ1 chain (e.g. SEQ ID NO: 305 (C1*0) which contains the C-terminal juxtamembrane/transmembrane regions). In one embodiment, the epitope of Vδ1 bound by the multispecific antibodies (or antigen-binding fragments thereof) does not comprise or consist of an epitope found in the N-terminal leader sequence of the Vδ1 chain (e.g. SEQ ID NO: 299). The antibody or fragment may therefore only bind in the V region of the Vδ1 chain (e.g. SEQ ID NO: 300). Thus, in one embodiment, the epitope consists of an epitope in the V region of the γδ TCR (e.g. amino acid residues 1-90 of SEQ ID NO: 272).

Reference to the epitope are made in relation to the Vδ1 sequence derived from the sequence described in Luoma et al. (2013) *Immunity* 39:1032-1042, and RCSB Protein Data Bank entries: 3OMZ, shown as SEQ ID NO: 272:

(SEQ ID NO: 272)

```
AQKVTQAQSSVSMPVRKAVTLNCLYETSWWSYYIFWYKQLPSKEMIFLI

RQGSDEQNAKSGRYSVNFKKAAKSVALTISALQLEDSAKYFCALGESLT
```

-continued

```
RADKLIFGKGTRVTVEPNIQNPDPAVYQLRDSKSSDKSVCLFTDFDSQT

NVSQSKDSDVYITDKTVLDMRSMDFKSNSAVAWSNKSDFACANAFNNSI

IPEDTFFPSPESS
```

SEQ ID NO: 272 represents a soluble TCR comprising or consisting of a V region (also referred to as the variable domain), a D region, a J region and a TCR constant region. The V region comprises or consists of amino acid residues 1-90, the D region comprises or consists of amino acid residues 91-104, the J region comprises or consists of amino acid residues 105-115 and the constant region (derived from T-cell receptor alpha) comprises or consists of amino acid residues 116-209. Within the V region, CDR1 is defined as amino acid residues 25-34 of SEQ ID NO: 272, CDR2 is defined as amino acid residues 50-54 of SEQ ID NO: 272, and CDR3 is defined as amino acid residues 93-104 of SEQ ID NO: 272 (Xu et al., PNAS USA 108(6):2414-2419 (2011)).

Therefore, according to an aspect of the invention, there is provided an isolated antibody or antigen-binding fragment thereof, which binds to an epitope of a variable delta 1 (Vδ1) chain of a γδ T cell receptor (TCR) comprising or consisting of one or more amino acid residues within amino acid regions:

(i) 3-20 of SEQ ID NO: 272; and/or (ii) 37-77 of SEQ ID NO: 272.

In a further embodiment, the multispecific antibodies additionally recognize the polymorphic V region comprising or consisting of amino acid residues 1-90 epitope of SEQ ID NO: 306. Hence, amino acids 1-90 of SEQ ID NO: 272 and the polymorphic germline variant sequence (amino acids 1-90 SEQ ID NO: 306) may be considered interchangeable when defining epitopes described herein. Studies presented herein have demonstrated multispecific antibodies of the invention can recognize both variants of this germline sequence. By way of example, where it is stated that multispecific antibodies or antigen-binding fragments thereof as defined herein recognize epitopes comprising or consisting of one or more amino acid residues within amino acid regions 1-24 and/or 35-90 of SEQ ID NO: 272, they additionally recognise equivalent epitopes (i.e. at the same position) in SEQ ID NO: 306.

In one embodiment, multispecific antibodies or antigen-binding fragments thereof recognize one or more amino acid residues within amino acid regions 1-90 of SEQ ID NO: 272. More specifically, in one embodiment multispecific antibodies or antigen-binding fragments thereof as defined herein recognize a human germline epitope wherein said germline encodes either an alanine (A) or valine (V) at position 71 of SEQ ID NO: 272.

In one embodiment, the epitope comprises or consists of one or more, such as two, three, four, five, six, seven, eight, nine, ten or more amino acid residues within the described regions.

In a further embodiment, the epitope comprises or consists of one or more (such as 5 or more, such as 10 or more) amino acid residues within amino acid region 3-20 of SEQ ID NO: 272. In an alternative embodiment, the epitope comprises or consists of one or more (such as 5 or more, such as 10 or more) amino acid residues within amino acid region 37-77 of SEQ ID NO: 272 (such as amino acid region 50-54). In a yet further embodiment, the epitope comprises or consists of one or more (such as 5 or more, such as 10 or more) amino acid residues within amino acid region 3-20 (such as 5-20 or 3-17) and one or more (such as 5 or more, such as 10 or more) amino acid residues within amino acid region 37-77 (such as 62-77 or 62-69) of SEQ ID NO: 272.

It will be further understood that said antibody (or antigen-binding fragment thereof) does not need to bind to all amino acids within the defined range. Such epitopes may be referred to as linear epitopes. For example, an antibody which binds to an epitope comprising or consisting of amino acid residues within amino acid region 5-20 of SEQ ID NO: 272 may only bind with one or more of the amino acid residues in said range, e.g. the amino acid residues at each end of the range (i.e. amino acids 5 and 20), optionally including amino acids within the range (i.e. amino acids 5, 9, 16 and 20).

In one embodiment, the epitope comprises or consists of at least one of amino acid residues 3, 5, 9, 10, 12, 16, 17, 20, 37, 42, 50, 53, 59, 62, 64, 68, 69, 72 or 77 of SEQ ID NO: 272. In further embodiments, the epitope comprises or consists of one, two, three, four, five, six, seven, eight, nine, ten, eleven or twelve amino acids selected from amino acid residues 3, 5, 9, 10, 12, 16, 17, 20, 37, 42, 50, 53, 59, 62, 64, 68, 69, 72 or 77 of SEQ ID NO: 272.

In one embodiment, the epitope comprises or consists of one or more amino acid residues within the following amino acid regions of SEQ ID NO: 272:
(i) 3-17;
(ii) 5-20;
(iii) 37-53;
(iv) 50-64;
(v) 59-72;
(vi) 59-77;
(vii) 62-69; and/or
(viii) 62-77.

In further embodiments, the epitope comprises or consists of one or more amino acid residues within amino acid regions: 5-20 and 62-77 (for example, although not limited to, embodiments relating to antibodies derived from the parental clone E07, such as affinity matured variants thereof); 50-64 (for example, although not limited to, embodiments relating to antibodies derived from the parental clone C08, such as affinity matured variants thereof); 37-53 and 59-72 (for example, although not limited to, embodiments relating to antibodies derived from the parental clone G04, such as affinity matured variants thereof); 59-77 (for example, although not limited to, embodiments relating to antibodies derived from the parental clone C05, such as affinity matured variants thereof); or 3-17 and 62-69 (for example, although not limited to, embodiments relating to antibodies derived from the parental clone E01, such as affinity matured variants thereof), of SEQ ID NO: 272. In a further embodiment, the epitope consists of one or more amino acid residues within amino acid regions: 5-20 and 62-77; 50-64; 37-53 and 59-72; 59-77; or 3-17 and 62-69, of SEQ ID NO: 272.

In a further embodiment, the epitope comprises or consists of amino acid residues: 3, 5, 9, 10, 12, 16, 17, 62, 64, 68 and 69 of SEQ ID NO: 272, or suitably consists of amino acid residues: 3, 5, 9, 10, 12, 16, 17, 62, 64, 68 and 69 of SEQ ID NO: 272 (for example, although not limited to, embodiments relating to antibodies derived from the parental clone E01, such as affinity matured variants thereof). In a further embodiment, the epitope comprises or consists of amino acid residues: 5, 9, 16, 20, 62, 64, 72 and 77 of SEQ ID NO: 272, or suitably consists of amino acid residues: 5, 9, 16, 20, 62, 64, 72 and 77 of SEQ ID NO: 272 (for example, although not limited to, embodiments relating to antibodies derived from the parental clone E07, such as affinity matured variants thereof). In yet further embodiment, the epitope comprises or consists of the amino acid residues: 37, 42, 50, 53, 59, 64, 68, 69, 72, 73 and 77 of SEQ ID NO: 272, or suitably consists of amino acid residues: 37, 42, 50, 53, 59, 64, 68, 69, 72, 73 and 77 of SEQ ID NO: 272 (for example, although not limited to, embodiments relating to antibodies derived from the parental clone G04, such as affinity matured variants thereof). In a further embodiment, the epitope comprises or consists of the amino acid residues: 50, 53, 59, 62 and 64 of SEQ ID NO: 272, or suitably consists of amino acid residues: 50, 53, 59, 62 and 64 of SEQ ID NO: 272 (for example, although not limited to, embodiments relating to antibodies derived from the parental clone C08, such as affinity matured variants thereof). In a further embodiment, the epitope comprises or consists of amino acid residues: 59, 60, 68 and 72 of SEQ ID NO: 272, or suitably consists of amino acid residues: 59, 60, 68 and 72 of SEQ ID NO: 272 (for example, although not limited to, embodiments relating to antibodies derived from the parental clone C05, such as affinity matured variants thereof).

In one embodiment, the epitope comprises or consists of one or more amino acid residues within amino acid regions 37-53 and/or 59-77 of SEQ ID NO: 272. In a further embodiment, the epitope consists of one or more amino acid residues within amino acid regions 37-53 and 59-77 of SEQ ID NO: 272. In an alternative further embodiment, the epitope comprises or consists of one or more amino acid residues within amino acid regions 37-53 or 59-77 of SEQ ID NO: 272. Multispecific antibodies or antigen-binding fragments thereof having such epitopes may have some or all of the sequences of G04, or such antibodies or antigen-binding fragments thereof may be derived from G04. For example, multispecific antibodies or antigen-binding fragments thereof having one or more CDR sequences of G04 or one or both of the VH and VL sequences of G04 may bind such epitopes.

In one embodiment, the epitope comprises or consists of one or more amino acid residues within amino acid regions 5-20 and/or 62-77 of SEQ ID NO: 272. In a further embodiment, the epitope consists of one or more amino acid residues within amino acid regions 5-20 and 62-77 of SEQ ID NO: 272. In an alternative further embodiment, the epitope comprises or consists of one or more amino acid residues within amino acid regions 5-20 or 62-77 of SEQ ID NO: 272. Multispecific antibodies or antigen-binding fragments thereof having such epitopes may have some or all of the sequences of E07, or such antibodies or antigen-binding fragments thereof may be derived from E07. For example, multispecific antibodies or antigen-binding fragments thereof having one or more CDR sequences of E07 or one or both of the VH and VL sequences of E07 may bind such epitopes.

In one embodiment, the epitope comprises or consists of one or more amino acid residues within amino acid region 50-64 of SEQ ID NO: 272. In a further embodiment, the epitope consists of one or more amino acid residues within amino acid region 50-64 of SEQ ID NO: 272. Multispecific antibodies or antigen-binding fragments thereof having such epitopes may have some or all of the sequences of C08, or such antibodies or antigen-binding fragments thereof may be derived from C08. For example, multispecific antibodies or antigen-binding fragments thereof having one or more CDR sequences of C08 or one or both of the VH and VL sequences of C08 may bind such epitopes.

In one embodiment, the epitope comprises or consists of one or more amino acid residues within amino acid region 59-72 of SEQ ID NO: 272. In a further embodiment, the epitope consists of one or more amino acid residues within amino acid region 59-72 of SEQ ID NO: 272. Multispecific antibodies or antigen-binding fragments thereof having such epitopes may have some or all of the sequences of C05, or such antibodies or antigen-binding fragments thereof may be derived from C05. For example, multispecific antibodies or antigen-binding fragments thereof having one or more CDR sequences of C05 or one or both of the VH and VL sequences of C05 may bind such epitopes.

In one embodiment, the epitope does not comprise or consist of amino acid residues within amino acid region 11-21 of SEQ ID NO: 272. In one embodiment, the epitope does not comprise or consist of amino acid residues within amino acid region 21-28 of SEQ ID NO: 272. In one embodiment, the epitope does not comprise or consist of amino acid residues within amino acid region 59 and 60 of SEQ ID NO: 272. In one embodiment, the epitope does not comprise or consist of amino acid residues within amino acid region 67-82 of SEQ ID NO: 272.

The epitopes of affinity matured antibodies will generally be the same as the epitopes identified herein for the parental clone. For those epitopes on cyno TRDV1, the positions of the epitopes of the affinity matured antibodies will generally the same positions as the epitopes identified for the corresponding parental clone. The reference to "positions" is necessary since the skilled person would appreciate the identity of some of the amino acids in the epitopes differ from human TRDV1. Despite these variations between human and cyno TRDV1, such antibodies are still able to specifically bind to both antigens.

In one embodiment, the epitope is not the same epitope bound by a commercially available anti-Vδ1 antibody, such as TS-1 or TS8.2. As described in WO2017197347, binding of TS-1 and TS8.2 to soluble TCRs was detected when the δ1 chain included Vδ1 J1 and Vδ1 J2 sequences but not to the Vδ1 J3 chain, indicating that the binding of TS-1 and TS8.2 involved critical residues in the delta J1 and delta J2 region.

References to "within" herein include the extremities of the define range. For example, "within amino acid regions 5-20" refers to all of amino acid resides from and including residue 5 up to and including residue 20.

Various techniques are known in the art to establish which epitope is bound by an antibody. Exemplary techniques include, for example, routine cross-blocking assays, alanine scanning mutational analysis, peptide blot analysis, peptide cleavage analysis crystallographic studies and NMR analysis. In addition, methods such as epitope excision, epitope extraction and chemical modification of antigens can be employed. Another method that can be used to identify the amino acids within a polypeptide with which an antibody interacts is hydrogen/deuterium exchange detected by mass spectrometry (as described in Example 9). In general terms, the hydrogen/deuterium exchange method involves deuterium-labelling the protein of interest, followed by binding the antibody to the deuterium-labelled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labelled residues which correspond to the specific amino acids with which the antibody interacts.

The multispecific antibodies and antigen-binding fragments therefor suitably specifically bind to both human TRDV1 (SEQ ID NO: 272 and the polymorphic variant of SEQ ID NO: 306) as well as an ortholog in cynomolgus monkey, cyno TRDV1 (SEQ ID NO: 308 see also UniProtKB-G7P9S6 (G7P9S6_MACFA)). In some embodiments, the multispecific antibodies or antigen-binding fragments thereof are G04-derived antibodies that specifically bind to both human and cyno TRDV1. It is hypothesised the epitopes bound by the multispecific antibodies of the invention (for example although not limited to those binding in a region within amino acid resides 37 to 77 of any of SEQ ID NOs: 272, 306 or 308) may be particularly advantageous, since it allows the provision of anti-Vδ1 antibodies that are specific to Vδ1 (i.e. do not bind similar antigens, such as Vδ2 or Vδ3) but also provide cross-reactivity to polymorphic variants of Vδ1 (i.e. TRDV1 SEQ ID NO: 272 and TRDV1 SEQ ID NO: 306, despite the polymorphism at residue position 20 and this being identified as a possible contact residue or close to an identified contact residue for some antibodies) and provides cross-reactivity between human and cyno Vδ1 (despite all of residues 42, 50, 54, 59, 60, 68, 73, 75 and 76 occurring within the region of amino acid resides 37 to 77 of SEQ ID NOs: 272 and 308 being different between human and cyno TRDV1 sequences).

Epitopes of ADT1-4-Derived Antibodies

The ADT1-4-derived antibodies bind the same or substantially the same epitope as the ADT1-4 parental antibody. Accordingly, in some embodiments, in particular those relating to antibodies derived from or related to the ADT1-4 parental antibody, the anti-Vδ1 antibody or antigen-binding fragment binds an epitope comprising or consisting of one or more amino acid residues within amino acid region 37 to 77, for example within amino acid regions 37-53 and/or 59-77, of SEQ ID NO: 272 (or SEQ ID NO: 306). In some embodiments, the epitope comprises or consists of amino acid residues 37, 42, 50, 53, 59, 64, 68, 69, 72, 73 and 77 of SEQ ID NO: 272 (or SEQ ID NO: 306). In some embodiments, the epitope consists of amino acid residues 37, 42, 50, 53, 59, 64, 68, 69, 72, 73 and 77 of SEQ ID NO: 272 (or SEQ ID NO: 306).

The ADT1-4-derived antibodies also bind to epitope of the cyno variable delta 1 (Vδ1) chain of a γδ T cell receptor (TCR), aka cyno TRDV1 (SEQ ID NO: 308). Hence, in some embodiments, in particular those relating to antibodies derived from or related to the G04 parental antibody, the anti-Vδ1 antibody or antigen-binding fragment binds an epitope comprising or consisting of one or more amino acid residues within amino acid region 37 to 77, for example within amino acid regions 37-53 and/or 59-77, of SEQ ID NO: 308. In some embodiments, the epitope comprises or consists of amino acid residues 37, 42, 50, 53, 59, 64, 68, 69, 72, 73 and 77 of SEQ ID NO: 308. In some embodiments, the epitope consists of amino acid residues 37, 42, 50, 53, 59, 64, 68, 69, 72, 73 and 77 of SEQ ID NO: 308.

Given the cross-reactivity of the ADT1-4-derived antibodies in particular, and the ability of the antibodies disclosed herein to bind to the polymorphic variant of TRDV1, in some embodiments, in particular those relating to antibodies derived from or related to the G04 parental antibody, the anti-Vδ1 antibody or antigen-binding fragment binds an epitope comprising or consisting of one or more amino acid residues within amino acid region 37 to 77, for example within amino acid regions 37-53 and/or 59-77, of SEQ ID NOs: 272, 306 and 308. In some embodiments, the epitope comprises or consists of amino acid residues 37, 42, 50, 53, 59, 64, 68, 69, 72, 73 and 77 of SEQ ID NO: 272, 306 and 308. In some embodiments, the epitope consists of amino acid residues 37, 42, 50, 53, 59, 64, 68, 69, 72, 73 and 77 of SEQ ID NOs: 272, 306 and 308.

The provision of antibodies that comprise or consist of such epitopes as those described above yet providing cross-reactivity between human and cyno TRDV1 sequences is surprising, given the location of the amino acid variants between these sequences from the two species.

Epitopes of ADT1-7-Derived Antibodies

The ADT1-7-derived antibodies bind the same or substantially the same epitope as the ADT1-7 parental antibody. Accordingly, in some embodiments, in particular those relating to antibodies derived from or related to the ADT1-7 parental antibody, the anti-Vδ1 antibody or antigen-binding fragment binds an epitope comprising or consisting of one or more amino acid residues within amino acid regions 5-20 and/or 62-77 of SEQ ID NO: 272 (or SEQ ID NO: 306). In some embodiment, the epitope comprises or consists of amino acid residues 5, 9, 16, 20, 62, 64, 72 and 77 of SEQ ID NO: 272 (or SEQ ID NO: 306). In some embodiments, the epitope consists of amino acid residues 5, 9, 16, 20, 62, 64, 72 and 77 of SEQ ID NO: 272 (or SEQ ID NO: 306).

Framework and Other Sequences

Suitably the VH and VL regions of the multispecific antibodies or antigen-binding fragments of the invention each comprise four framework regions (FR1-FR4). In one embodiment, the antibody or antigen-binding fragment thereof comprises a framework region (e.g. FR1, FR2, FR3 and/or FR4) comprising a sequence having at least 80% sequence identity with the framework region in any one of SEQ ID NOs: 2 to 25 (for example in the case of light chain variable sequences derived from G04), SEQ ID NOs: 27 to 50 (for example in the case of heavy chain variable sequences derived from G04), SEQ ID NOs: 107 to 117 (for example in the case of light chain variable sequence derived from E07) or SEQ ID NOs: 119 to 129 (for example in the case of light chain variable sequence derived from E07). In one embodiment, the antibody or antigen-binding fragment thereof comprises a framework region (e.g. FR1, FR2, FR3 and/or FR4) comprising a sequence having at least 90%, such as at least 95%, 97% or 99% sequence identity with the framework region in any one of SEQ ID NOs: 2 to 25 (for example in the case of light chain variable sequences derived from G04), SEQ ID NOs: 27 to 50 (for example in the case of heavy chain variable sequences derived from G04), SEQ ID NOs: 107 to 117 (for example in the case of light chain variable sequence derived from E07) or SEQ ID NOs: 119 to 129 (for example in the case of light chain variable sequence derived from E07). In one embodiment, the antibody or antigen-binding fragment thereof comprises a framework region (e.g. FR1, FR2, FR3 and/or FR4) comprising a sequence in any one of SEQ ID NOs: 2 to 25 (for example in the case of light chain variable sequences derived from G04), SEQ ID NOs: 27 to 50 (for example in the case of heavy chain variable sequences derived from G04), SEQ ID NOs: 107 to 117 (for example in the case of light chain variable sequence derived from E07) or SEQ ID NOs: 119 to 129 (for example in the case of light chain variable sequence derived from E07). In one embodiment, the antibody or antigen-binding fragment thereof comprises a framework region (e.g. FR1, FR2, FR3 and/or FR4) consisting of a sequence in any one of SEQ ID NOs: 2 to 25 (for example in the case of light chain variable sequences derived from G04), SEQ ID NOs: 27 to 50 (for example in the case of heavy chain variable sequences derived from G04), SEQ ID NOs: 107 to 117 (for example in the case of light chain variable sequence derived from E07) or SEQ ID NOs: 119 to 129 (for example in the case of light chain variable sequence derived from E07).

In some embodiments, the anti-Vδ1 antibody or antigen-binding fragment thereof may comprise an HFR1 (i.e. heavy framework 1 region) sequence comprising or consisting of the sequence of SEQ ID NO: 170 or 171; an HFR2 sequence comprising or consisting of the sequence of SEQ ID NO: 172; an HFR3 sequence comprising or consisting of the sequence of SEQ ID NO: 173; an HFR4 sequence comprising or consisting of the sequence of SEQ ID NO: 174; an LFR1 sequence comprising or consisting of the sequence of SEQ ID NO: 175; an LFR2 sequence comprising or consisting of the sequence of SEQ ID NO: 176; an LFR3 sequence comprising or consisting of the sequence of SEQ ID NO: 177 or 178; and/or an LFR4 sequence comprising or consisting of the sequence of SEQ ID NO: 179, 180, 181 or 182.

In some embodiments, the anti-Vδ1 antibody or antigen-binding fragment thereof may comprise an HFR1 (i.e. heavy framework 1 region) sequence comprising or consisting of the sequence of SEQ ID NO: 170 or 171; an HFR2 sequence comprising or consisting of the sequence of SEQ ID NO: 172; an HFR3 sequence comprising or consisting of the sequence of SEQ ID NO: 173; an HFR4 sequence comprising or consisting of the sequence of SEQ ID NO: 174; an LFR1 sequence comprising or consisting of the sequence of SEQ ID NO: 175; an LFR2 sequence comprising or consisting of the sequence of SEQ ID NO: 176; an LFR3 sequence comprising or consisting of the sequence of SEQ ID NO: 177; and/or an LFR4 sequence comprising or consisting of the sequence of SEQ ID NO: 179, 180, 181 or 182.

In some embodiments, the anti-Vδ1 antibody or antigen-binding fragment thereof may comprise an HFR1 (i.e. heavy framework 1 region) sequence comprising or consisting of the sequence of SEQ ID NO: 170 or 171; an HFR2 sequence comprising or consisting of the sequence of SEQ ID NO: 172; an HFR3 sequence comprising or consisting of the sequence of SEQ ID NO: 173; an HFR4 sequence comprising or consisting of the sequence of SEQ ID NO: 174; an LFR1 sequence comprising or consisting of the sequence of SEQ ID NO: 175; an LFR2 sequence comprising or consisting of the sequence of SEQ ID NO: 176; an LFR3 sequence comprising or consisting of the sequence of SEQ ID NO: 177; and/or an LFR4 sequence comprising or consisting of the sequence of SEQ ID NO: 179 or 181.

In some embodiments, the anti-Vδ1 antibody or antigen-binding fragment thereof may comprise an HFR1 sequence comprising or consisting of the sequence of SEQ ID NO: 189; an HFR2 sequence comprising or consisting of the sequence of SEQ ID NO: 190; an HFR3 sequence comprising or consisting of the sequence of SEQ ID NO: 191; an HFR4 sequence comprising or consisting of the sequence of SEQ ID NO: 192; an LFR1 sequence comprising or consisting of the sequence of SEQ ID NO: 193 and 194; an LFR2 sequence comprising or consisting of the sequence of SEQ ID NO: 195; an LFR3 sequence comprising or consisting of the sequence of SEQ ID NO: 196; and an LFR4 sequence comprising or consisting of the sequence of SEQ ID NO: 197.

In some embodiments, the anti-Vδ1 antibody or antigen-binding fragment thereof may comprise an HFR1 sequence comprising or consisting of the sequence of SEQ ID NO: 189; an HFR2 sequence comprising or consisting of the sequence of SEQ ID NO: 190; an HFR3 sequence comprising or consisting of the sequence of SEQ ID NO: 191; an HFR4 sequence comprising or consisting of the sequence of SEQ ID NO: 192; an LFR1 sequence comprising or consisting of the sequence of SEQ ID NO: 193; an LFR2 sequence comprising or consisting of the sequence of SEQ ID NO: 195; an LFR3 sequence comprising or consisting of the sequence of SEQ ID NO: 196; and an LFR4 sequence comprising or consisting of the sequence of SEQ ID NO: 197.

For fragments comprising both the VH and VL regions, these may be associated either covalently (e.g. via disulphide bonds or a linker) or non-covalently. The antibody fragment described herein may comprise an scFv, i.e. a fragment comprising a VH region and a VL region joined by a linker. In one embodiment, the VH and VL region are joined by a (e.g. synthetic) polypeptide linker. The polypeptide linker may comprise a $(Gly_4Ser)_n$ linker, where n=from 1 to 8, e.g. 2, 3, 4, 5 or 7. The polypeptide linker may comprise a $[(Gly_4Ser)_n(Gly_3AlaSer)_m]_p$ linker, where n=from 1 to 8, e.g. 2, 3, 4, 5 or 7, m=from 1 to 8, e.g. 0, 1, 2 or 3, and p=from 1 to 8, e.g. 1, 2 or 3. In a further embodiment, the linker comprises SEQ ID NO: 291. In a further embodiment, the linker consists of SEQ ID NO: 291.

It will be understood by a person skilled in the art that scFv constructs may be designed and made inclusive of N-terminal and C-terminal modifications to aid with translation, purification and detection. For example, at the N-terminus of an scFv sequence, an additional methionine and/or alanine amino acid residue may be included ahead of the canonical VH sequences (e.g. starting QVQ or EVQ). At the C-terminus (i.e. C-terminal to the canonical mature VL domain sequence ending as per the IMGT definition), additional sequences may be included such as (i) a partial sequence of the constant domain and/or (ii) additional synthetic sequences inclusive of tags, such as His-tags and Flag-tags, to aid with purification and detection (for example the tags of any of SEQ ID NOs: 292 to 295).

As described herein, the antibodies may be in any format. In a preferred embodiment, the antibody is in an IgG1 (e.g. human IgG1) format (ie. the antibody is a human IgG1 antibody).

In some embodiments, the antibody or antigen-binding fragment thereof comprises a light chain constant region comprising the sequence of SEQ ID NO: 296 or SEQ ID NO: 307 (or a sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity with SEQ ID NO: 296 or SEQ ID NO: 307) and/or a heavy chain constant region comprising the sequence of SEQ ID NO: 297 or SEQ ID NO: 298 (or a sequence having at least 70%, at least 75%, at least 80%, at least 85%, at least 90%, at least 91%, at least 92%, at least 93%, at least 94%, at least 95%, at least 96%, at least 97%, at least 98%, or at least 99% sequence identity with SEQ ID NO: 297 or SEQ ID NO: 298). In some embodiments, effector function of the heavy chain constant region may be reduced or disabled (effector function disabling mutations). Suitable mutations to attenuate the effector functions are known to the skilled person. For example, the L235A and/or G237A mutations ("LAGA") or the L234A and/or L235A mutations ("LALA") according to the EU numbering. For example, in one embodiment, the antibody or antigen-binding fragment thereof comprises a light chain constant region comprising the sequence of SEQ ID NO: 296 and/or a heavy chain constant region comprising the sequence of SEQ ID NO: 297 or SEQ ID NO: 298.

Competing Antibodies

In one embodiment, the antibody binds to the same, or essentially the same, epitope as, or competes with, an antibody or antigen-binding fragment thereof as defined herein. One can easily determine whether an antibody binds to the same epitope as, or competes for binding with, a reference anti-Vδ1 antibody by using routine methods known in the art. For example, to determine if a test antibody binds to the same epitope as a reference anti-Vδ1 antibody of the invention, the reference antibody is allowed to bind to a Vδ1 protein or peptide under saturating conditions. Next, the ability of a test antibody to bind to the Vδ1 chain is assessed. If the test antibody is able to bind to Vδ1 following saturation binding with the reference anti-Vδ1 antibody, it can be concluded that the test antibody binds to a different epitope than the reference anti-Vδ1 antibody. On the other hand, if the test antibody is not able to bind to the Vδ1 chain following saturation binding with the reference anti-Vδ1 antibody, then the test antibody may bind to the same epitope as the epitope bound by the reference anti-Vδ1 antibody of the invention.

The present invention also includes anti-Vδ1 antibodies that compete for binding to Vδ1 with an antibody or antigen-binding fragment thereof as defined herein, or an antibody having the CDR sequences of any of the exemplary antibodies described herein. For example, competitive assays can be performed with the antibody of the present invention in order to determine what proteins, antibodies, and other antagonists compete for binding to the Vδ1 chain with the antibody of the present invention and/or share the epitope. These assays are readily known to those of skill in the art; they evaluate competition between antagonists or ligands for a limited number of binding sites on a protein, e.g. Vδ1. The antibody (or antigen-binding fragment thereof) is immobilized or insolubilized before or after the competition and the sample bound to the Vδ1 chain is separated from the unbound sample, for example, by decanting (where the antibody was pre-insolubilized) or by centrifuging (where the antibody was precipitated after the competitive reaction). Also, the competitive binding may be determined by whether the function is altered by the binding or lack of binding of the antibody to the protein, e.g. whether the antibody molecule inhibits or potentiates the enzymatic activity of, for example, a label. ELISA and other functional assays may be used, as known in the art and described herein.

Two antibodies bind to the same or overlapping epitope if each competitively inhibits (blocks) binding of the other to the target antigen. That is, a 1-, 5-, 10-, 20- or 100-fold excess of one antibody inhibits binding of the other by at least 50% but preferably 75%, 90% or even 99% as measured in a competitive binding assay. Alternatively, two antibodies have the same epitope if essentially all amino acid mutations in the target antigen that reduce or eliminate binding of one antibody reduce or eliminate binding of the other.

Additional routine experimentation (e.g. peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Antibody Binding and Pharmacological Properties of the Antibodies

The multispecific antibodies of the invention may have favourable binding and/or pharmacological properties, for example as described below.

In some embodiments, the binding affinity of the antibody or antigen-binding fragment thereof is established by coating the antibody or antigen-binding fragment thereof directly or indirectly (e.g. by capture with an anti-human IgG Fc) onto the surface of a sensor (e.g. an amine high capacity chip or equivalent), wherein the target bound by the antibody or antigen-binding fragment thereof (i.e. the Vδ1 chain of a γδ TCR or EGFR) is flowed over the chip to detect binding. Suitably, a MASS-2 instrument (which may also be referred to as Sierra SPR-32) is used at 25° C. in PBS+ 0.02% Tween 20 running buffer at 30 µl/min.

Described herein are other assays which may be used to define antibody function. For example, the multispecific antibody or antigen-binding fragment thereof described herein may be assessed by γδ TCR engagement, e.g. measuring downregulation of the γδ TCR upon antibody binding. Surface expression of the γδ TCR following application of the antibody or antigen-binding fragment thereof (optionally presented on the surface of a cell) can be measured, e.g. by flow cytometry. The antibody or antigen-binding fragment thereof described herein may also be assessed by measuring γδ T cell degranulation. For example, expression of CD107a, a marker for cell degranulation, can be measured following application of the antibody or antigen-binding fragment thereof (optionally presented on the surface of a cell) to γδ T cells, e.g. by flow cytometry. The antibody or antigen-binding fragment thereof described herein may also be assessed by measuring γδ T cell mediated killing activity (to test if the antibody has an effect on the killing activity of the γδ T cell). For example, target cells may be incubated with γδ T cells in the presence of the antibody or antigen-binding fragment thereof (optionally presented on the surface of a cell). Following incubation, the culture may be stained with a cell viability dye to distinguish between live and dead target cells. The proportion of dead cells can then be measured, e.g. by flow cytometry.

Additionally, described herein are assays which may be used to define multispecific antibody function as assessed in assays comprising a mixture of at least two different cell types comprising seperate γδ TCR+ve cells and EGFR+ve cells. These assays help to further highlight some of the surprising technical effects of the multispecific antibodies described herein, whereby further enhanced effects are observed (eg. increased TCR downregulation) when multispecific antibody function is assessed and defined in assays comprising such cell mixtures.

Binding Affinity ($K_D$) for Human TRDV1

Generally speaking, the affinity matured clones (and multispecific antibodies derived or related to such clones) will have an affinity for their antigen(s) that is higher than the parental clones. For example, the affinity for human TRDV1 (SEQ ID NOs 272 or 306) will be at least 20%, at least 30%, at least 40%, at least 50%, at least 100% or at least 500% greater affinity than the parental antibody.

The multispecific antibodies or antigen-binding fragments thereof of the invention may bind to human TRDV1 (SEQ ID NOs 272 or 306) with a binding affinity ($K_D$, for example as measured by surface plasmon resonance) of less than about 100 nM, preferably less than about 50 nM.

The multispecific antibodies or antigen-binding fragments thereof may further be defined as binding to human TRDV1 (SEQ ID NOs 272 or 306) with a binding affinity ($K_D$, for example as measured by surface plasmon resonance) of less than about 10 nM, preferably less than about 5 nM.

In some embodiments, for example multispecific antibodies or antigen-binding fragments thereof relating to or derived from the ADT1-4 lineage (e.g. multispecific antibodies of the invention with a Fab region relating to or derived from the ADT1-4 lineage, for example a a result of affinity maturation or otherwise), the multispecific antibodies or antigen-binding fragments thereof of the invention may bind to human TRDV1 with $K_D$ of less than about 100 nM, preferably less than about 50 nM.

In some embodiments, for example multispecific antibodies or antigen-binding fragments thereof relating to or derived from the ADT1-4 lineage (but excluding ADT1-4-138), the multispecific antibodies or antigen-binding fragments thereof of the invention may bind to human TRDV1 with $K_D$ of less than about 10 nM, preferably less than about 5 nM.

In some embodiments, for example multispecific antibodies or antigen-binding fragments thereof relating to or derived from the ADT1-4 lineage members ADT1-4-19, ADT1-4-21, ADT1-4-31, ADT1-4-53, ADT1-4-2, ADT1-4-86, ADT1-4-112, ADT1-4-143 and/or ADT1-4-1, the multispecific antibodies or antigen-binding fragments thereof of the invention may bind to human TRDV1 with $K_D$ of less than about 10 nM, preferably less than about 1 nM.

The multispecific antibodies or antigen-binding fragments thereof of the invention may bind to cyno TRDV1 (SEQ ID NO 308) with a binding affinity ($K_D$, for example as measured by surface plasmon resonance) of less than about 100 nM, preferably less than about 50 nM.

In some embodiments, for example multispecific antibodies or antigen-binding fragments thereof relating to or derived from the ADT1-4 lineage, the multispecific antibodies or antigen-binding fragments thereof of the invention may bind to cyno TRDV1 with $K_D$ of less than about 100 nM, preferably less than about 50 nM.

In some embodiments, for example multispecific antibodies or antigen-binding fragments thereof relating to or derived from the ADT1-4 lineage members ADT1-4-19, ADT1-4-21, ADT1-4-31, ADT1-4-53, ADT1-4-2, ADT1-4-86, ADT1-4-112, ADT1-4-143 and/or ADT1-4-1, the multispecific antibodies or antigen-binding fragments thereof of the invention may bind to cyno TRDV1 with $K_D$ of less than about 50 nM.

In some embodiments, for example those relating to or derived from the ADT1-4 lineage, the multispecific antibodies or antigen-binding fragments thereof of the invention may bind to human TRDV1 with $K_D$ of less than about 100 nM, preferably less than about 50 nM and bind to cyno TRDV1 with a binding affinity ($K_D$, for example as measured by surface plasmon resonance) of less than about 100 nM, preferably less than about 50 nM.

In some embodiments, for example multispecific antibodies or antigen-binding fragments thereof relating to or derived from the ADT1-4 lineage (but excluding ADT1-4-138), the multispecific antibodies or antigen-binding fragments thereof of the invention may bind to human TRDV1 with $K_D$ of less than about 10 nM and bind to cyno TRDV1 with a binding affinity ($K_D$, for example as measured by surface plasmon resonance) of less than about 100 nM. Preferably in this embodiment, the multispecific antibodies or antigen-binding fragments thereof of the invention may bind to human TRDV1 with $K_D$ of less than about 5 nM and bind to cyno TRDV1 with a binding affinity ($K_D$, for example as measured by surface plasmon resonance) of less than about 50 nM.

In some embodiments, for example multispecific antibodies or antigen-binding fragments thereof relating to or derived from the ADT1-4 lineage members ADT1-4-19, ADT1-4-21, ADT1-4-31, ADT1-4-53, ADT1-4-2, ADT1-4-86, ADT1-4-112, ADT1-4-143 and/or ADT1-4-1, the multispecific antibodies or antigen-binding fragments thereof of the invention may bind to human TRDV1 with $K_D$ of less than about 10 nM and bind to human TRDV1 with $K_D$ of less than 50 nM. Preferably in this embodiment, the multispecific antibodies or antigen-binding fragments thereof of the invention may bind to human TRDV1 with $K_D$ of less than about 1 nM and bind to cyno TRDV1 with a binding affinity ($K_D$, for example as measured by surface plasmon resonance) of less than about 50 nM.

In some embodiments, for example multispecific antibodies or antigen-binding fragments thereof relating to or derived from the ADT1-7 lineage (e.g. multispecific antibodies of the invention with a Fab region relating to or derived from the ADT1-7 lineage, for example a a result of affinity maturation or otherwise), the multispecific antibodies or antigen-binding fragments thereof of the invention may bind to human TRDV1 with $K_D$ of less than about 10 nM, preferably less than about 5 nM.

TABLE 6

Summary of the human TRDV1 affinities of exemplar multispecific antibodies of the invention, as determined by SPR.

| Antibody | Affinity to Vδ1 (nM) |
|---|---|
| ADT1-4-2 × LEE | 0.416 |
| ADT1-4-6 × LEE | 3.24 |
| ADT1-4-138 × LEE | 55 |

Increasing the binding affinity for human TRDV1 to less than about 10 nM is shown to convey advantageous technical effects, such as increased binding (MFI), improved vδ1 TCR downregulation, improved CD107A upregulation, increased cytotoxicity and increased proliferation (see FIG. 35L).

Binding Affinity ($K_D$) for EGFR

In some embodiments, the multispecific antibodies of the invention may bind to EGFR with a $K_D$ of less than about 150 nM, for example ADT1-4-2×FS1-65, ADT1-4-2×FS1-67, ADT1-4-2×LEE, ADT1-4-2×747, ADT1-4-2×LEE3, ADT1-4-2×LEE2 and ADT1-4-2×LEE1.

In some embodiments, the multispecific antibodies of the invention may bind to EGFR with a $K_D$ of less than about 20 nM, for example ADT1-4-2×FS1-65, ADT1-4-2×FS1-67, ADT1-4-2×LEE, ADT1-4-2×747 and ADT1-4-2×LEE3.

In some embodiments, the multispecific antibodies of the invention may bind to EGFR with a $K_D$ of less than about 10 nM, for example ADT1-4-2×FS1-65, ADT1-4-2×FS1-67, ADT1-4-2×LEE and ADT1-4-2×747.

In some embodiments, the multispecific antibodies of the invention may bind to EGFR with a $K_D$ of less than about 5 nM, for example ADT1-4-2×FS1-65, ADT1-4-2×FS1-67, ADT1-4-2×LEE and ADT1-4-2×747.

In any embodiment, the EGFR may be human EGFR.

Table 7 provides a summary of the EGFR affinities of exemplar multispecific antibodies of the invention, as determined by SPR.

TABLE 7

Summary of TRDV1 and EGFR affinities
Example affinity results for molecules as indicated
(note; inter-assay variation typically <2-fold)

| Antibody | Alias | Affinity to human EGFR (nM) | Affinity to human TRDV1 (nM) |
|---|---|---|---|
| ADT1-4-2/ADT3-3 | ADT1-4-2 × FS1-65 | 1.35 | 0.464 |
| ADT1-4-2/ADT3-1 | ADT1-4-2 × FS1-67 | 1.37 | 0.378 |
| ADT1-4-2/ADT3-2 | ADT1-4-2 × LEE | 1.49 | 0.416 |
| ADT1-4-2/ADT3-4 | ADT1-4-2 × 747 | 2.35 | 0.511 |
| ADT1-4-2/ADT3-7 | ADT1-4-2 × LEE3 | 8.63 | 0.462 |
| ADT1-4-2/ADT3-6 | ADT1-4-2 × LEE2 | 19.2 | 0.818 |
| ADT1-4-2/ADT3-5 | ADT1-4-2 × LEE1 | 142 | 0.883 |
| ADT1-4/ADT3-1 | G04 × FS1-67 | 1.14 | 152 |
| ADT1-4-138/ADT3-2 | ADT1-4-138 × LEE | 2.78 | 55 |
| ADT1-4-6/ADT3-2 | ADT1-4-6 × LEE | 0.655 | 3.24 |
| ADT1-4 | G04 | — | 115 |
| ADT1-4-2 | — | — | 0.522 |

In some embodiments, the multispecific antibodies of the invention may bind to human TRDV1 with a $K_D$ of less than about 5 nM and may bind to EGFR with a $K_D$ of less than about 150 nM, for example ADT1-4-2×FS1-65, ADT1-4-2×FS1-67, ADT1-4-2×LEE, ADT1-4-2×747, ADT1-4-2×LEE3, ADT1-4-2×LEE2 and ADT1-4-2×LEE1.

In some embodiments, the multispecific antibodies of the invention may bind to human TRDV1 with a $K_D$ of less than about 5 nM and may bind to EGFR with a $K_D$ of less than about 20 nM, for example ADT1-4-2×FS1-65, ADT1-4-2×FS1-67, ADT1-4-2×LEE, ADT1-4-2×747 and ADT1-4-2×LEE3.

In some embodiments, the multispecific antibodies of the invention may bind to human TRDV1 with a $K_D$ of less than about 5 nM and may bind to EGFR with a $K_D$ of less than about 10 nM, for example ADT1-4-2×FS1-65, ADT1-4-2×FS1-67, ADT1-4-2×LEE and ADT1-4-2×747.

In some embodiments, the multispecific antibodies of the invention may bind to human TRDV1 with a $K_D$ of less than about 5 nM and may bind to EGFR with a $K_D$ of less than about 5 nM, for example ADT1-4-2×FS1-65, ADT1-4-2×FS1-67, ADT1-4-2×LEE and ADT1-4-2×747.

Increasing the binding affinity for EGFR is shown to convey advantageous technical effects, such as increased binding (MFI), improved vδ1 TCR downregulation, improved degranulation, increased cytotoxicity, increased 4-1BB upregulation and increased proliferation (see FIGS. 36A-36N). A clustering effect is observed wherein multispecific antibodies of this invention with mid-to-high affinities to EGFR in the range of about 1 nM to about 20 nM affinity (ADT1-4-2×LEE, ADT1-4-2×LEE3, ADT1-4-2LEE2) functionally cluster together whilst the lower affinity molecule with an affinity of about 142 nM (ADT1-4-2×LEE1) is significantly impaired and is equivalent to the non-binding (to TCR) control in this assay. Interestingly the highest affinity EGFR binding (less than about 2 nM) does not confer the highest saturation effects for improved vδ1 TCR downregulation, improved degranulation, increased cytotoxicity, increased 41BB upregulation and increased proliferation. Rather, the mid-range affinity molecules at about 9 nM-19 nM (ADT1-4-2×LEE3 and ADT1-4-2×LEE2 respectively) confer the highest effects at saturating concentrations of the antibodies. This more optimal effect conferred by mid-range affinity multispecific antibodies of this invention is discussed later herein. The results are shown in FIGS. 36A-36N.

Dialing Up and Down Affinity of Binding Domains

Multispecific antibodies as presented herein comprise at least one first binding domain which binds the TRDV1 domain of Vδ1 TCR and at least one second binding domain which binds EGFR. Each binding domain binds to its target with a different binding affinity (Kd). These binding affinities can be altered independently of each other. Fine-tuning affinities up or down to both the first binding domain and to the second binding domain impact functionality and conferred technical effects.

Affinity of the first binding domain (to the TRDV1 domain of Vδ1 TCR):
1) Increasing affinity to the first binding domain (to greater than about 10 nM) can further enhance effects of these multispecific antibodies in certain circumstances. This is surprising given all naturally occurring ligands to the human Vδ1 TCR reported to date exhibit much lower affinities ranging from 2.9 uM (MART1) through 900 uM (MICA)
2) Increasing the concentration of multispecific antibodies with lower affinities to TRDV1 (of lower than about 10 nM) can overcome some of the observed lower activities conferred by these molecules (e.g. proliferative effects) but interestingly, not all effects can be replicated by increased concentrations of the lower affinity variant.
3) Cancer cells with a higher TAA copy number can further enhance observed effects conferred by these multispecific antibodies; particularly of the lower affinity (to TRDV1) variant.

Affinity of the Second Binding Domain (to EGFR)
1) Multispecific antibodies of this invention with higher affinities to EGFR performed more optimally in a number of the exploratory studies undertaken (See Examples 13 to 17).
2) A threshold effect was observed wherein affinity to EGFR could range between 1 nM and 20 nM without a major impact on many functional effects (See Examples 13 to 17). This clustered or threshold effect observed for high-to-mid affinity multispecific antibodies was unexpected.
3) Higher TAA copy number on a cancer cell line can overcome some of the reduced effects observed by the lower affinity (to EGFR) multispecific antibodies-however, and again, in some circumstances only (See Examples 13 to 17).
4) Some multispecific antibodies of the invention with mid-range affinity for EGFR (9 nm to 20 nM) performed more favorably than the highest affinity variants (less than 2 nM) at saturating concentrations in some instances. For example, when operating at nM antibody concentrations it was observed multispecific antibodies with mid-range affinities to EGFR (of about 8 nM to 20 nM) conferred enhanced proliferative effects and 41BB activation status when compared to both the highest affinity variants (less than 2 nM, preferably less than 1.5 nM) and lowest affinity variants (of about 142 nM) in the assays described.

Dialing up and down affinity provides a "tool-box" of multispecific antibodies, some of which are optimal for lower copy number TAA scenarios, others more optimal at nM concentration/dose ranges in certain circumstances, and some more selective only for high-copy number TAA cancers.

| Affinity to TRDV1 | Affinity to EGFR | Example molecules | Potential Utility |
| --- | --- | --- | --- |
| Higher affinity | Higher affinity | ADT1-4-2 × FS1-65<br>ADT1-4-2 × LEE<br>ADT1-4-2 × FS1-67<br>ADT1-4-2 × 747 | Treatment of EGFR-positive cancers; most potent format by a variety of measures. Very effective against both lower and higher EGFR copy number cancer cells by many measures. |
| Higher affinity | Mid affinity | ADT1-4-2 × LEE2<br>ADT1-4-2 × LEE3 | Treatment of EGFR-positive cancers; shown to cluster with high affinity molecules (see above) by several measures, but potentially a more potent format at saturating concentrations (such as conferred proliferative effects on Vδ1+ cells) |
| Higher affinity | Lower affinity | ADT1-4-2 × LEE1 | Treatment of EGFR-positive cancers. Potentially more selective against higher EGFR copy number cancer cells. This format will likely bias distribution towards Vδ1+ cells. |
| Lower affinity | Higher affinity | ADT1-4-6 × LEE | Treatment of EGFR-positive cancers. Potentially more selective against higher EGFR copy number cancer cells. Equipotent with higher/higher molecules by certain measures at saturation (eg. conferred proliferative effects on Vδ1+ cells). This format will more likely bias distribution towards EGFR bearing cells. |

Inhibition Concentrations (IC50)

TCR Downregulation

TCR down regulation may be measured according to the assays described herein. For example, the antibody to be tested may be incubated at different concentration with a culture of γδ T cells and the downregulation measured. If measuring cell killing (for example THP-1 cell killing, or A375 cell killing), the γδ T cells are co-cultured with a suitable cell line, for example THP-1 cells or A375 cells. TCR down regulation may be measured flow cytometry. Cell killing may be achieved by any suitable means, for example by flow cytometry.

For the initial TCR downregulation studies with the parental antibodies (eg. ADT1-7 and ADT1-4), the TCR downregulation assay involved 'loading' the antibody onto Fc gamma receptor +ve THP-1 cells (see Example 1, Example 6 and Table 5 of WO2021/032963). As such, the antibodies in this instance are presented on a cell surface ahead of co-incubation with γδ T cells. Such loading thereby affords maximum opportunity to exploit cross-linking effects upon TCR engagement. Aside loading antibodies onto Fc receptor +ve cells, alternate similar approaches to presenting the antibody on sold-surfaces may include pre-incubating the antibody on a plate (so-called plate-bound), or the use of carrier beads to present the antibody. In all such assays, and once presented on a solid surface, it is then typical to investigate and measure the technical effect conferred by the antibody upon engagement of the target receptor (in this instance a γδ T cell receptor), Presenting antibodies in this way is commonplace, particularly when exploring the effects of antibody engagement of immune cell receptor targets and complexes such as antibody engagement of targets such as CD3, CD28 etc.

In contrast, for affinity matured antibodies of the invention as described herein, we wanted to dissect and compare the impact of affinity maturation to its fullest and hence we explored the capabilities of these antibodies in more 'soluble' TCR downregulation assay formats. Assessing the effect in solution may also be more physiologically relevant. For these reasons, and unless otherwise indicated, in all TCR downregulation cell-based experiments wherein the effects of affinity-matured antibodies, multispecific antibodies, or fragments thereof, are measured or characterized and compared to parent antibodies (e.g. see FIGS. 35A-35M), a soluble assay format is explored. The IC50 difference of employing this more stringent soluble assay is summarized below wherein the TCR downregulation of EC50 values for an example parent molecule (ADT1-4) is summarised via both approaches.

TCR Downregulation: 'Presented' versus 'Soluble' Assay Format:

ADT1-4 IC50(loaded on THP-1 cells):0.01-0.05 ug/ml=0.065 nM to 0.325 nM (See Example 1, Example 6, and Table 5 of WO2021/ 032963)

Vs.

ADT1-4 IC50(soluble assay,added in solution)=38.28 nM (See FIGS. 12A-12G)

The multispecific antibodies or antigen-binding fragments thereof of the invention may have an IC50 for TCR downregulation of less than about 50 nM, less than about 10 nM, or less than about 1 mM. Preferably the IC50 is less than about 1 nM.

In some embodiments, for example multispecific antibodies or antigen-binding fragments thereof relating to or derived from the ADT1-4 lineage (e.g. multispecific antibodies of the invention with a Fab region relating to or derived from the ADT1-4 lineage, for example a a result of affinity maturation or otherwise), the multispecific antibodies or antigen-binding fragments thereof of the invention may have an IC50 for TCR downregulation of less than about 50 nM, less than about 10 nM, or less than about 1 mM. Preferably the IC50 is less than about 1 nM.

In some embodiments, for example multispecific antibodies or antigen-binding fragments thereof relating to or derived from the ADT1-4 lineage (but excluding ADT1-4-138), the multispecific antibodies or antigen-binding fragments thereof of the invention may have an IC50 for TCR downregulation of less than about 1 nM. Preferably the IC50 is less than about 0.5 nM.

In some embodiments, for example multispecific antibodies or antigen-binding fragments thereof relating to or derived from the ADT1-4 lineage members ADT1-4-19, ADT1-4-21, ADT1-4-31, ADT1-4-53, ADT1-4-2, ADT1-4-86, ADT1-4-112, ADT1-4-143 and/or ADT1-4-1, the antibodies or multispecific antigen-binding fragments thereof of the invention may have an IC50 for TCR downregulation of less than about 1 nM. Preferably the IC50 is less than about 0.5 nM.

In some embodiments, for example multispecific antibodies or antigen-binding fragments thereof relating to or derived from the ADT1-7 lineage (e.g. multispecific antibodies of the invention with a Fab region relating to or derived from the ADT1-7 lineage, for example a a result of affinity maturation or otherwise), the multispecific antibodies or antigen-binding fragments thereof of the invention may have an IC50 for TCR downregulation of less than about 50 nM, less than about 10 nM, or less than about 1 mM. Preferably the IC50 is less than about 1 nM.

In some embodiments, for example multispecific antibodies or antigen-binding fragments thereof relating to or derived from the ADT1-7 lineage members ADT1-7-20 or ADT1-7-3, the multispecific antibodies or antigen-binding fragments thereof of the invention may have an IC50 for TCR downregulation of less than about 5 nM. Preferably the IC50 is less than about 10 nM.

Cell Killing

Cell killing may be measured according to the assays described herein. For example, the antibody to be tested may be incubated at different concentration with a co-culture of γδ T cells and tumour cells (for example THP-1 cells or A375 cells). Cell killing may be measured by any suitable means, for example by flow cytometry.

The multispecific antibodies or antigen-binding fragments thereof of the invention may have an IC50 for A375 cell killing of less than about 10 nM, less than about 5 nM, less than about 1 nM, less than about 0.1 nM or less than about 0.01 nM. Preferably the IC50 is less than about 1 nM.

In some embodiments, for example multispecific antibodies or antigen-binding fragments thereof relating to or derived from the ADT1-4 lineage (e.g. multispecific antibodies of the invention with a Fab region relating to or derived from the ADT1-4 lineage, for example as a result of affinity maturation or otherwise), the multispecific antibodies or antigen-binding fragments thereof of the invention may have an IC50 for A375 cell killing of less than about 10 nM, less than about 5 nM, less than about 1 nM, less than about 1 nM, less than about 0.1 nM or less than about 0.01 nM. Preferably the IC50 is less than about 1 nM.

In some embodiments, for example multispecific antibodies or antigen-binding fragments thereof relating to or derived from the ADT1-7 lineage (e.g. multispecific antibodies of the invention with a Fab region relating to or derived from the ADT1-7 lineage, for example as a result of affinity maturation or otherwise), the multispecific antibodies or antigen-binding fragments thereof of the invention may have an IC50 for A375 cell killing of less than about 5 nM, less than about 1 nM, or less than about 0.1 nM. Preferably the IC50 is less than about 1 nM.

In some embodiments, for example multispecific antibodies or antigen-binding fragments thereof relating to or derived from the ADT1-7 lineage members ADT1-7-20 or ADT1-7-3, the multispecific antibodies or antigen-binding fragments thereof of the invention may have an IC50 for A375 cell killing of less than about 10 nM, less than about 5 nM, less than about 1 nM or less than about 0.1 nM. Preferably the IC50 is less than about 1 nM.

Of course, the advantageous pharmacological profiles of the multispecific antibodies can be combined such that the antibodies exhibit an advantageous $K_D$ and advantageous IC50 values for the various tested properties.

For example, in some embodiments, the multispecific antibodies or antigen-binding fragments thereof of the invention may:
  bind to human TRDV1 (SEQ ID NOs 272 or 306) with a binding affinity ($K_D$, for example as measured by surface plasmon resonance) of less than about 100 nM (preferably less than about 50 nM);
  optionally bind to cyno TRDV1 (SEQ ID NO 308) with a binding affinity ($K_D$, for example as measured by surface plasmon resonance) of less than about 100 nM (preferably less than about 50 nM);
  have an IC50 for TCR downregulation of less than about 50 nM (preferably less than about 1 nM);
  have an IC50 for A375 cell killing of less than about 10 nM (preferably less than about 5 nM).

In some embodiments, in particular those relating to the ADT1-4 lineage, the multispecific antibodies or antigen-binding fragments thereof may:
  bind to human TRDV1 with a $K_D$ of less than about 100 nM (preferably less than about 50 nM);
  bind to cyno TRDV1 with a $K_D$ of less than about 100 nM (preferably less than about 50 nM);
  have an IC50 for TCR downregulation of less than about 50 nM (preferably less than about 1 nM);
  have an IC50 for A375 cell killing of less than about 10 nM (preferably less than about 5 nM).

In some embodiments, for example multispecific antibodies or antigen-binding fragments thereof relating to or derived from the ADT1-4 lineage (but excluding ADT1-4-138), the multispecific antibodies or antigen-binding fragments thereof of the invention may:
  bind to human TRDV1 with a $K_D$ of less than about 10 nM (preferably less than about 5 nM);
  bind to cyno TRDV1 with a $K_D$ of less than about 100 nM (preferably less than about 50 nM);
  have an IC50 for TCR downregulation of less than about 1 nM (preferably less than about 0.5 nM); have an IC50 for A375 cell killing of less than about 10 nM (preferably less than about 5 nM).

In some embodiments, for example multispecific antibodies or antigen-binding fragments thereof relating to or derived from the ADT1-4 lineage members ADT1-4-19, ADT1-4-21, ADT1-4-31, ADT1-4-53, ADT1-4-2, ADT1-4-86, ADT1-4-112, ADT1-4-143 and/or ADT1-4-1, the multispecific antibodies or antigen-binding fragments thereof of the invention may:
  bind to human TRDV1 with a $K_D$ of less than about 10 nM (preferably less than about 1 nM);
  bind to cyno TRDV1 with a $K_D$ of less than about 50 nM;
  have an IC50 for TCR downregulation of less than about 1 nM (preferably less than about 0.5 nM)
  have an IC50 for A375 cell killing of less than about 10 nM (preferably less than about 5 nM).

In some embodiments, in particular those relating to the ADT1-7 lineage, the multispecific antibodies or antigen-binding fragments thereof may:
  bind to human TRDV1 with a $K_D$ of less than about 10 nM (preferably less than about 5 nM);
  have an IC50 for TCR downregulation of less than about 50 nM (preferably less than about 10 nM);
  have an IC50 for A375 cell killing of less than about 5 nM (preferably less than about 1 nM).

In some embodiments, in particular those relating to the ADT1-7 lineages ADT1-7-20 or ADT1-7-3, the multispecific antibodies or antigen-binding fragments thereof may:
  bind to human TRDV1 with a $K_D$ of less than about 10 nM (preferably less than about 5 nM);
  have an IC50 for TCR downregulation of less than about 5 nM (preferably less than about 1 nM);
  have an IC50 for A375 cell killing of less than about 10 nM (preferably less than about 5 nM).

Pharmacological Properties of Antibodies Comprising Fab Regions of or Derived from the ADT1-4 Lineage The pharmacological properties of the antibodies with respect to their binding (via the Fab region) to TRDV1 may fall within certain parameters. For example, antibodies of or derived from ADT1-4-105 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM.

Antibodies of or derived from ADT1-4-107 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM.

Antibodies of or derived from ADT1-4-110 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM.

Antibodies of or derived from ADT1-4-112 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM. Such antibodies may alternatively or additionally have an IC50 for TCR down regulation of less than about 1 nM (preferably less than about 0.5 nM).

Antibodies of or derived from ADT1-4-117 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM.

Antibodies of or derived from ADT1-4-19 (for example fragments thereof, variants having one or more amino acid substitutions or having certain percent identity thereto) may have a $K_D$ for human TRDV1 of less than about 1 nM (preferably less than about 0.5 nM) and/or a $K_D$ for cyno TRDV1 of less than about 10 nM (preferably less than about 5 nM). Such antibodies may alternatively or additionally have an IC50 for TCR down regulation of less than about 1 nM (preferably less than about 0.5 nM).

Antibodies of or derived from ADT1-4-21 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM (preferably less than about 10 nM). Such antibodies may alternatively or additionally have an IC50 for TCR down regulation of less than about 1 nM (preferably less than about 0.5 nM).

Antibodies of or derived from ADT1-4-31 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM (preferably less than about 10 nM). Such antibodies may alternatively or additionally have an IC50 for TCR down regulation of less than about 1 nM (preferably less than about 0.5 nM).

Antibodies of or derived from ADT1-4-139 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM.

Antibodies of or derived from ADT1-4-4 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM.

Antibodies of or derived from ADT1-4-143 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM (preferably less than about 10 nM). Such antibodies may alternatively or additionally have an IC50 for TCR down regulation of less than about 1 nM (preferably less than about 0.5 nM).

Antibodies of or derived from ADT1-4-53 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM (preferably less than about 10 nM). Such antibodies may alternatively or additionally have an IC50 for TCR down regulation of less than about 1 nM (preferably less than about 0.5 nM).

Antibodies of or derived from ADT1-4-173 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM.

Antibodies of or derived from ADT1-4-2 (for example fragments thereof, variants having one or more amino acid substitutions or having certain percent identity thereto) may have a $K_D$ for human TRDV1 of less than about 1 nM (preferably less than about 0.5 nM) and/or a $K_D$ for cyno TRDV1 of less than about 10 nM (preferably less than about 5 nM). Such antibodies may alternatively or additionally have an IC50 for TCR down regulation of less than about 1 nM (preferably less than about 0.5 nM).

Antibodies of or derived from ADT1-4-8 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM.

Antibodies of or derived from ADT1-4-82 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM.

Antibodies of or derived from ADT1-4-83 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM.

Antibodies of or derived from ADT1-4-3 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM.

Antibodies of or derived from ADT1-4-84 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM.

Antibodies of or derived from ADT1-4-86 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM (preferably less than about 10 nM). Such antibodies may alternatively or additionally have an IC50 for TCR down regulation of less than about 1 nM (preferably less than about 0.5 nM).

Antibodies of or derived from ADT1-4-95 (for example fragments thereof, variants having one or more amino acid substitutions or having certain percent identity thereto) may have a $K_D$ for human TRDV1 of less than about 10 nM (preferably less than about 1 nM) and/or a $K_D$ for cyno TRDV1 of less than about 50 nM.

Antibodies of or derived from ADT1-4-1 (for example fragments thereof, variants having one or more amino acid substitutions or having certain percent identity thereto) may have a $K_D$ for human TRDV1 of less than about 1 nM (preferably less than about 0.5 nM) and/or a $K_D$ for cyno TRDV1 of less than about 10 nM (preferably less than about 1 nM). Such antibodies may alternatively or additionally have an IC50 for TCR down regulation of less than about 1 nM (preferably less than about 0.5 nM).

Antibodies of or derived from ADT1-4-6 (for example fragments thereof, variants having one or more amino acid substitutions or having certain percent identity thereto) may have a $K_D$ for human TRDV1 of less than about 10 nM (preferably less than about 5 nM) and/or a $K_D$ for cyno TRDV1 of less than about 10 nM (preferably less than about 1 nM). Such antibodies may alternatively or additionally have an IC50 for TCR down regulation of less than about 1 nM (preferably less than about 0.5 nM).

Antibodies of or derived from ADT1-4-138 (for example fragments thereof, variants having one or more amino acid substitutions or having certain percent identity thereto) may have a $K_D$ for human TRDV1 of less than about 100 nM (preferably less than about 50 nM) and/or a $K_D$ for cyno TRDV1 of less than about 100 nM (preferably less than about 50 nM). Such antibodies may alternatively or additionally have an IC50 for TCR down regulation of less than about 50 nM (preferably less than about 10 nM).

Pharmacological Properties of Antibodies Comprising Fab Regions of the ADT1-7 Lineage The pharmacological properties of the antibodies with respect to their binding (via the Fab region) to TRDV1 may fall within certain parameters. For example, antibodies of or derived from ADT1-7-10 (for example fragments thereof, variants having one or more amino acid substitutions or having certain percent identity thereto) may have a $K_D$ for human TRDV1 of less than about 10 nM (preferably less than about 5 nM).

Antibodies of or derived from ADT1-7-15 (for example fragments thereof, variants having one or more amino acid substitutions or having certain percent identity thereto) may have a $K_D$ for human TRDV1 of less than about 10 nM (preferably less than about 5 nM).

Antibodies of or derived from ADT1-7-17 (for example fragments thereof, variants having one or more amino acid substitutions or having certain percent identity thereto) may have a $K_D$ for human TRDV1 of less than about 10 nM (preferably less than about 5 nM).

Antibodies of or derived from ADT1-7-18 (for example fragments thereof, variants having one or more amino acid substitutions or having certain percent identity thereto) may have a $K_D$ for human TRDV1 of less than about 10 nM (preferably less than about 5 nM).

Antibodies of or derived from ADT1-7-19 (for example fragments thereof, variants having one or more amino acid substitutions or having certain percent identity thereto) may have a $K_D$ for human TRDV1 of less than about 10 nM (preferably less than about 5 nM).

Antibodies of or derived from ADT1-7-20 (for example fragments thereof, variants having one or more amino acid substitutions or having certain percent identity thereto) may have a $K_D$ for human TRDV1 of less than about 10 nM (preferably less than about 5 nM). Such antibodies may alternatively or additionally have an IC50 for TCR down regulation of less than about 5 nM (preferably less than about 1 nM).

Antibodies of or derived from ADT1-7-22 (for example fragments thereof, variants having one or more amino acid substitutions or having certain percent identity thereto) may have a $K_D$ for human TRDV1 of less than about 10 nM (preferably less than about 5 nM).

Antibodies of or derived from ADT1-7-23 (for example fragments thereof, variants having one or more amino acid substitutions or having certain percent identity thereto) may have a $K_D$ for human TRDV1 of less than about 10 nM (preferably less than about 5 nM).

Antibodies of or derived from ADT1-7-42 (for example fragments thereof, variants having one or more amino acid substitutions or having certain percent identity thereto) may have a $K_D$ for human TRDV1 of less than about 10 nM (preferably less than about 5 nM).

Antibodies of or derived from ADT1-7-3 (for example fragments thereof, variants having one or more amino acid substitutions or having certain percent identity thereto) may have a $K_D$ for human TRDV1 of less than about 10 nM (preferably less than about 1 nM). Such antibodies may alternatively or additionally have an IC50 for TCR down regulation of less than about 5 nM (preferably less than about 1 nM).

Antibodies of or derived from ADT1-7-61 (for example fragments thereof, variants having one or more amino acid substitutions or having certain percent identity thereto) may have a $K_D$ for human TRDV1 of less than about 10 nM (preferably less than about 1 nM). Such antibodies may alternatively or additionally have an IC50 for TCR down regulation of less than about 50 nM (preferably less than about 10 nM).

Other Functional Properties of the Antibodies

The antibodies of the present invention have an advantageous functional profile. In particular, unlike anti-Vδ1 antibodies of the prior art which focus on depletion of Vδ1 T-cells, the antibodies of the present invention are useful for the activation of Vδ1 T-cells. Although they may cause downregulation of the TCRs on T-cells to which they bind, they do not cause Vδ1 T-cell depletion, but rather they stimulate the T-cells and hence may be useful in therapeutic settings that would benefit from the activation of this compartment of T-cells. Activation of Vδ1 T-cells is evident through TCR downregulation, changes in activation markers such as CD25 and Ki67 and degranulation marker CD107a. Activation of Vδ1 T-cell in turn triggers release of inflammatory cytokines such as INFγ and TNFα to promote immune licensing. Surprisingly, antibodies having suitably high affinity for TRDV1 elicit increased Vδ1 T-cell killing and, unlike (for example) antibodies that target CD3, the provision of high affinity antibodies is possible without adverse effects associated with large-scale activation via CD3. In turn, the high affinity antibodies are able to induce strong immunostimulatory effects via tumour-infiltrating lymphocytes (TILs). This can be achieved with minimal exhaustion or killing of the Vδ1 cells. Therefore, the antibodies of the present invention may be considered agonistic antibodies.

In one embodiment of the invention, there is provided an anti-Vδ1 antibody or antigen-binding fragment thereof, characterised in that it:
  a) causes downregulation of TCRs on Vδ1 T-cells;
  b) does not exhibit CDC or ADCC; and
  c) does not deplete Vδ1 T-cells.

In some embodiments, the multispecific anti-Vδ1 antibody or antigen-binding fragments also stimulate Vδ1 T-cell proliferation.

In some embodiments, multispecific antibodies of this invention confer one or more of
  (a) enhanced TCR downregulation effects;
  (b) enhanced Vδ1 T-cell profileration effects; and/or
  (c) enhanced Vδ1 T-cell activation effects
  upon Vδ1 T-cells when said cells are in the presence of (mixed with, proximal to, or are adjacent to) EGFR+ve cells such as EGFR+ cancer cells.

The multispecific antibodies or antigen-binding fragments thereof may further be defined as binding to human TRDV1 (SEQ ID NOs 272 or 306) with a binding affinity ($K_D$, for example as measured by surface plasmon resonance) of less than about 10 nM, preferably less than about 5 nM.

The multispecific antibodies or antigen-binding fragments thereof may further be defined as having the advantageous $K_D$ and/or IC50 values as discussed above.

T-cell depletion is the process of T cell death removal or reduction. References to the antibodies or antigen binding fragments not depleting the Vδ1 T cells refers to a depletion of less than about 30% or less than about 20% (preferably less than about 10%) of the viable Vδ1 T+ cell population when incubated by one or more of the multispecific antibodies of the invention as described herein (for example when the antibodies is provided as an IgG1 antibody), and as measured by any via suitable means in a controlled study (for example via controlled flow cytometry methodology or via other established controlled assays such as described in FIG. 18 and FIGS. 29A-29B).

ADCC and CDC are mechanisms by which T-cell depletion may occur. Reference to the antibodies or antigen binding fragments herein not causing ADCC or CDC refers to a depletion of less than about 30% or less than about 20% (preferably less than about 10%) of the viable Vδ1 T+ cell population via ADCC and/or CDC when incubated by one or more of the multispecific antibodies of the invention as described herein (for example when the antibodies is provided as an IgG1 antibody), as measured by any via suitable means (for example via controlled flow cytometry methodology or via other established controlled assays such as described in FIG. 18).

In one embodiment, there is provided an anti-Vδ1 antibody or antigen-binding fragment thereof, characterised in that it does not induce secretion of IL-17A. IL-17A (Interleukin-17A) is a pro-tumorigenic cytokine which is produced by activated T-cells. IL-17A can enhance tumour growth and dampen the anti-cancer immune response. As shown in FIGS. 40A-40C, anti-vδ1 antibodies do not induce secretion of IL-17A when added to a population of cells comprising human lymphocytes that include Vδ1+ve cells, whereas comparator anti-CD3 antibodies (such as OKT 3) do induce IL17A in such circumstances. Hence, reference to the antibodies or antigen binding fragments herein not inducing secretion of IL-17A refers to inducing less than about 30%, or less than about 20%, or less than about 10% of the IL-17A secretion induced by comparator anti-CD3 antibodies in such circumstances (as typified by OKT 3; the anti-CD3 comparator employed in FIGS. 42G-42I).

Antibody Modifications

The antibodies and fragments thereof may be modified in other ways using known methods. Sequence modifications to antibody molecules described herein can be readily incorporate by those skilled in the art. The following examples are non-limiting.

During antibody discovery and sequence recovery from phage libraries, desired antibody variable domains may be re-formatted into full length IgG by sub-cloning. To accelerate the process, variable domains are often transferred using restriction enzymes. These unique restriction sites may introduce additional/alternate amino acids and away from the canonical sequence (such canonical sequences may be found, for example, in the international ImMunoGeneTics [IMGT] information system, see imgt.org). These may be introduced as kappa or lambda light chain sequence modifications.

Light Chain Modifications

The variable light chain variable sequences may be cloned using restriction sites (e.g. Nhe1-Not1) during re-formatting into full length IgG. More specifically, at the light chain N-terminus, an additional Ala-Ser sequence was introduced in the parental (non-affinity matured) antibodies to support cloning. Preferably, this additional AS sequence is then removed during further development such to generate the canonical N-terminal sequence. Hence, in some embodiments, light chain containing antibodies described herein do not contain an AS sequence at their N-termini, i.e. SEQ ID NOs: 26, 118, 282 to 290 or 313 do not comprise the initial AS sequence. The N-termini of the light chain sequences of the affinity-matured antibodies already do not comprise this AS motif.

Additional amino acid changes may be made to support cloning. For example, for the parental antibodies described herein having kappa light chains (i.e. B07, C05, E04, F07, G06, G09, 809, G10, G04 and E07), at the kappa light-chain variable-domain/constant domain border a valine-to-alanine change was introduced to support cloning when preparing full-length sequences. This resulted in a kappa constant domain modification. Specifically, this results in the constant domain beginning RTAAAPS (from a NotI restriction site). Preferably, such sequences can be modified during further development to generate the canonical kappa light-chain constant regions which start with RTVAAPS. Such modifications do not change the functional properties of the antibodies. Hence, in some embodiments, kappa light chain containing antibodies described herein contain a constant domain starting with the sequence RTV (for example as in SEQ ID NO: 296).

As another example, for the antibodies described herein (specifically E01 and C08) at the lambda light-chain variable-domain/constant domain border a lysine-to-alanine sequence change was introduced to support cloning. This resulted in a lambda constant domain modification. Specifically, this results in the constant domain beginning with GQPAAAPS (from a NotI restriction site). Preferably, this sequence can be modified during further development such to generate the canonical lambda light constant region which starts GQPKAAPS. Hence, in some embodiments, lambda light chain containing antibodies described herein contain a constant domain starting with the sequence GQPK.

Heavy Chain Modifications

Typically, human variable heavy chain sequences start with either the basic glutamine (Q) or acidic glutamate (E). However, both such sequences are then known to convert to the acidic amino acid residue, pyro-glutamate (pE). The Q to pE conversion results in a charge change to the antibody, whilst an E to pE conversion does not change the charge of the antibody. Hence to avoid a variable charge-change over time one option is to modify a starting heavy chain sequence from Q to E in the first instance. Hence, in one embodiment, the heavy chain of antibody described herein having a Q residue at the N-terminus of the heavy chain may contain a Q to E modification at the N-terminus. In particular, the initial residue of any of SEQ ID NOs: 1, 106, 276 to 279 or 312 may be modified from Q to E. It will be understood that this embodiment also applies to any embodiment incorporating these sequences, for example into full-length multi-specific antibodies or antigen-binding fragments thereof. In some embodiments, it may be advantageous to substitute an E residue at the N-terminus of the heavy chain to an E residue. Accordingly, in some embodiments, the E residue at the N-terminus of any one SEQ ID NOs: 2 to 25, 107 to 117, 273 to 275, 280 or 281 may be substituted with a Q residue.

Furthermore, the C-terminus of the IgG1 constant domain ends with PGK. However, the terminal basic lysine (K, EU position 447) is then often cleaved during expression (e.g. in CHO cells). This in turn results in charge change to the antibody through varied loss of the C-terminal lysine residue. Therefore, one option is to remove the lysine in the first instance resulting in a uniform and consistent heavy chain C-terminus sequence ending in PG. An alternative option is to also remove the terminal G (EU position 446). Hence, in one embodiment, the heavy chain of an antibody described herein has the terminal K, or the terminal GK, removed from its C-terminus.

In some embodiments, the antibody or antigen-binding fragment thereof contains a modified effector function through alteration to the sugars linked to Asn 297 (EU numbering scheme). In a further said modification, Asn 297 is not fucosylated or exhibits reduced fucosylation (i.e., a defucosylated antibody or a non-fucosylated antibody). Fucosylation includes the addition of the sugar fucose to a molecule, for example, the attachment of fucose to N-glycans, O-glycans and glycolipids. Accordingly, in a defucosylated antibody, fucose is not attached to the carbohydrate chains of the constant region. The antibody may be modified to prevent or inhibit fucosylation of the antibody. Typically, glycosylation modifications involve expressing said antibody or antigen-binding fragment thereof in a host cell containing alternate glycosylation processing capabilities either through targeted engineering or through targeted or serendipitous host or clone selection (e.g. see Example 13). These and other effector modifications are discussed further in recent reviews such as by Xinhua Wang et al. (2018) Protein & Cell 9:63-73 and by Pereira et al. (2018) mAbs 10(5):693-711 and which are hereby incorporated.

Optional Allotype Modifications

During antibody discovery, specific human allotypes may be employed. Optionally, the antibodies can be switched to differing human allotypes during development. By way of non-limiting example, for the kappa chain there are three human allotypes designated Km1, Km1,2 and Km3 which define three Km alleles (using allotype numbering): Km1 correlates with valine 153 (IMGT V45.1) and leucine 191 (IMGT L101); Km1,2 correlates with alanine 153 (IMGT A45.1) and leucine 191 (IMGT L101); and Km3 correlates with alanine 153 (IMGT A45.1) and valine 191 (IMGT V101). Optionally, one can therefore modify a sequence from one allotype to another by standard cloning approaches. For example, a L191V (IMGT L101V) change will convert a Km1,2 allotype to a Km3 allotype. For further reference on such allotypes see Jefferis and Lefranc (2009) *MAbs* 1 (4): 332-8, which is herein incorporated by reference.

Hence in one embodiment an antibody described herein contains amino acid substitutions derived from another human allotype of the same gene. In a further embodiment, the antibody contains a L191V (IMGT L101V) substitution to the kappa chain to convert the c-domain from a km1,2 to a km3 allotype.

Multispecific Antibodies

The antibodies of the present invention are multispecific. They may be bispecificmultispecific. Multispecific antibodies may be specific for different epitopes of one target polypeptide or may be specific for more than one target polypeptide. Therefore, in one embodiment, the antibody or antigen-binding fragment thereof comprises a first binding specificity for Vδ1 and a second binding specificity for EGFR.

In particular, the present invention provides a new class of high-affinity antibodies that comprise multiple antigen-binding sites ("multispecific antibodies"), including an antigen-binding site for TCR delta variable 1 (Vδ1) and an antigen-binding site for EGFR.

The multispecific antibodies of the present invention are in the format known as "mAb$^2$ antibodies" or "mAb squared antibodies", which are antibodies comprising an Fc region that has been engineered to contain antigen-binding loops in its CH3 domain—this modified Fc region is termed an "Fcab". The mAb$^2$ antibody further comprises a Fab region, comprising a VH-VL domain pair providing an antigen-binding site. mAb$^2$ molecules of the present invention comprise a EGFR binding Fcab and an vδ1-binding Fab.

The TCEs of the present invention provide several advantages over the TCEs of the prior art. In particular, the TCEs may overcome many of the challenges associated with TCEs of the prior art by targeting the T-cell receptor complex via an entirely novel and discrete mechanism. Indeed, by specifically targeting (and activating) the T-cell receptor complex solely via binding to an epitope on the TRDV1 domain, a number of advantages are realized including:

Engaging only a sub-set of T-cells rather than all T-cells (e.g. engagement of T-regs in a cancer setting may be undesirable);

Engaging only a sub-set of T-cells (TRDV1+ T-cells) that are predominantly 'tissue-resident' and whose presence often positively correlates with good prognosis in a cancer/tumour setting;

Activating the T-cell receptor complex via TRDV1 engagement thereby affording more optionality (e.g. increasing affinity of this binding domain, as in the antibodies of the present invention). For example, by developing recombinant TCEs which engage a T-Cell Receptor complex solely via the TRDV1 domain rather than via CD3, increased affinity may drive more favourable functionality. For example, high-affinity TRDV1-binding TCEs may activate but not exhaust T-cells; and/or Engaging the TCE complex via said novel means and via recombinant TRDV1 binding domains may result in less deleterious effects and so reduce the need to attenuate Fc functionality in said TCE moieties. It would generally be expected that a TCE with unattenuated Fc function would induce an antibody-dependent cell-mediated cytotoxicity (ADCC) effect and thereby deplete the population of γδ T-cells recognized by the antibody. However, and again, by attenuating such functionality to avoid toxicity/safety complexities, one may also attenuate a potentially important efficacy angles too e.g. by engaging CD16+ or CD32+ or CD64+ immune cells, or by reducing half-life of the bispecific (e.g. if employing smaller bispecific antibody fragments such as BiTEs). Methods of reducing the interaction of the FcγR and the TCE (such as using an IgG format designed to reduce said interaction) would be expected to reduce Fc-mediated immobilization of the TCE and reduce TCR clustering by cross-linking with the immobilized TCE. Reducing the need to attenuate Fc functionality in said TCE moieties then may afford additional optionality, for example by allowing TRDV1 TCEs to engage TRDV1+ cells via one binding domain, engaging a second cell type (such as a cancerous cell) by a second binding arm, and engaging other effector cells such as CD16+ or CD32+ or CD64+ immune cells via a functioning Fc domain.

Activate the vδ1 TCR without depleting v01+ T cells. The multispecific antibodies described herein can therefore engage and activate the CD3/γδ TCR complex and confer its downregulation and loss of surface expression, without unwanted depletion of vδ1 T cells (see FIGS. 29A-29B). This enables the multispecific antibodies described herein to be employed as medicaments to treat a disease or disorder such to ameliorate at least one sign or symptom of a disease or disorder through a mechanism involving the activation of blood, tissue and tumour resident Vδ1+ T cells.

Hence through the discoveries as described herein, the present inventors have generated a novel class of recombinant TCEs. Specifically, the present inventors have discovered a new class of TCEs which engage the T-cell receptor via a TRDV1 domain rather than other domains in said T-cell receptor signalling complexes. More specifically the present inventors have discovered a new class of TCEs which engage this complex via an activating epitope on TRDV1 and which may be bound at higher affinities without potentially conferring some of the previously reported deleterious effects high-affinity T-cell receptor complex engagement. Further this new class of TCEs may engage in such a way which may allow for wild-type Fc functionality too, thereby affording additional efficacy potential too.

The multispecific antibodies of the invention may also display improved properties compared to equivalent monospecific antibodies. For example, the multispecific antibodies of the invention may also display improved properties compared to monospecific antibodies having the same antigen binding domains as the component parts of the multispecific antibodies. In some embodiments, for example, the recombinant multispecific antibody confers increased gamma delta T-cell mediated cytotoxicity towards a diseased cell expressing the second epitope compared to the cytotoxicity conferred by an equivalent amount of said first monospecific antibody. The multispecific antibodies of the invention may also display improved cytotoxicity towards diseased cells whilst still sparing healthy cells.

In some embodiments the multispecific antibody is a human recombinant antibody encoded by a recombinant nucleic acid open reading frame or frames expressed from a recombinant host cell. In some embodiments the multispecific antibody is not a rodent or other non-human antibody derived from B-cell fusion hybridoma technologies. In some embodiments the multispecific antibody does not comprise non-human IgG constant domain sequence found only in non-human animal species, such as sequence found in rodent-derived hybridomas.

In preferred embodiments, the multispecific antibodies (suitably bispecific antibodies) of the invention, do not specifically bind (or directly interact with) CD3.

References herein to an antigen being "on" a cell refer to antigens that are expressed on the cell surface membrane or are associated with the (extracellular side of) the cell surface membrane of such cells.

The second target epitope is EGFR. EGFR (epidermal growth factor receptor) is a cancer-associated antigen and is an example of a receptor tyrosine kinase, in the ErbB subfamily. EGFR is expressed in multiple organs and plays an important role in initiating signaling that directs the behaviour of epithelial cells and tumours of epithelial origin. EGFR-mediated signaling is also involved in controlling cell proliferation, migration, survival, and metastasis by regulating diverse cellular pathways. As with other receptor tyrosine kinases, mutations affecting EGFR activity or leading to EGFR upregulation are associated with many cancers. In fact, genetic alterations in EGFR are observed in up to 30% of solid tumours and are typically associated with poor prognosis. Disruption of EGFR signalling, by inhibiting binding of EGF to the extracellular domain or by inhibiting the intracellular tyrosine kinase activity can limit EGFR-expressing tumour growth. EGFR inhibitors can therefore be anti-cancer agents. Indeed, certain tumour cells are dependent on EGFR signaling and thus possess an "Oncogene addiction", which makes this receptor an attractive target for therapy. Monoclonal antibodies that specifically bind to epitopes of EGFR are well known in the art. For example, CETUXIMAB is a monoclonal antibody which binds specifically to an epitope of EGFR.

Healthy Cell Sparing

While the mechanisms by which γδ T-cells recognize antigens and distinguish between healthy and diseased cells are not fully understood (Ming Heng and Madalene Heng, *Antigen Recognition by γδ T-Cells*. Madame Curie Bioscience Database [Internet], Austin (TX): Landes Bioscience; 2000-2013), the fact that γδ T-cells are able to distinguish between healthy cells and diseased cells and exhibit remarkable diseased cell polycytotoxicity (see non-limiting example cell types in Table 8) this means that they can be leveraged to provide improved medicaments with improved therapeutic windows. Further, by leveraging such γδ T-cell capabilities, there is provided an opportunity to treat disease while sparing healthy cells, by colocalizing γδ T-cells with diseased cells even when a particular cancer antigen, inflammatory antigen, or pathogen antigen is either not known, or is also present on healthy cells, in a particular patient.

TABLE 8

| Example cancer cells killed by polycytotoxic human Vδ1+ cells | |
|---|---|
| Breast Cancer | |
| M-CSF7, T47D, MDA-MB-231 | Mahvi et al (1993) Cancer Imm. Immunother. (1993) 37: 181-186 |
| | Dutta I et al (2017). Front. Immunol. 8: 776 |
| Lung Cancer | |
| GLC1, N592 | Ferrarini et al (1996) Jn of Nat. Cancer Inst., Volume 88 (7) pp 436-441 |
| Pancreas Cancer | |
| panc89, QGP-1, PANC-1 | Maeurer et al (1996) JEM 183 (4) 1681-1696 |
| | Kitayama 1993 Clin Exp Imm 93 (3) 442-7 |
| Gastrointestinal Cancer | |
| HT29, HCT116, Y, SKCO1, Caco2, HCT116, Lovo, DLD-1, SW480 | Wu, et al. (2015), OncoImmunology, 4: 3, e992749 |
| | Mikulak, et al (2019) JCI Insight. 4(24): e125884 |
| | Groh et al (1999) PNAS 96 (12) 6879-6884 |
| Neuroblastoma | |
| LAN1, KELLY | Fisher et al (2014) Clin Cancer Res; 20(22); 5720-32 |
| Melanoma | |
| A375 | Cordova (2012) Plos ONE 7 (11) e49878 |
| Ovarian Cancer | |
| OV-1063, SW626 | Groh et al (1999) PNAS 96 (12) 6879-6884 |
| Liver Cancer | |
| HepG2 | Groh et al (1999) PNAS 96 (12) 6879-6884 |
| Cervical Cancer | |
| HeLa | Groh et al (1999) PNAS 96 (12) 6879-6884 |
| Prostate Cancer | |
| DV145, PC-3 | Groh et al (1999) PNAS 96 (12) 6879-6884 |
| Multiple Myeloma | |
| ARH77, U266 | Knight et al (2012) Cytotherapy, 14: 9, 1110-1118, |

TABLE 8-continued

| Example cancer cells killed by polycytotoxic human Vδ1+ cells | |
|---|---|
| AML | |
| KG-1, KASUMI-1, OCI-AML3, U937, HL60, MV4 11, AML193, HEL, THP-1 | Lorenzo et al (2019) Canc Imm Res 7 (4) |
| CLL | |
| MEC-1 | Almeida et al (2016) Clin Can Res 22 (23) |

By way of one non-limiting example, recent studies with CD3×EGFR multispecifics highlight the challenges of current or conventional approaches. Specifically, use of such conventional approaches can result in less favorable toxicity profiles. This is because like many other tumour associated antigens (TAAs), the EGFR antigen is not only expressed in cancers such as breast cancer, colorectal cancer, and head and neck cancer, but is also expressed on healthy tissues such as epithelial cells. Hence use of CD3×EGFR medicaments which engage and co-localize all T-cells with EGFR positive cells can result in less favorable therapy windows or therapeutic indices. This is because such medicaments will engage all T-cells of which the vast majority in circulation will be αβ T-cells (CD4+ positive, CD8+ positive etc.). And once αβ T-cells are co-localized with EGFR positive cells, such conventional αβ T-cells exhibit limited capabilities to spare EGFR+ healthy cells and limited capabilities to kill only diseased EGFR+ diseased cells. These hurdles are further highlighted in example toxicology studies in (male only) cynomolgus monkeys. In studies by Lutterbuese et al 2010 (doi: 10.1073/pnas.1000976107), small BiTE® formatted CD3×EGFR bispecifics were employed. And because these molecules exhibit reduced half-lives/systemic exposure profiles relative to larger antibody-based molecules (which are >70 Kda)) one might anticipate such moieties to be relatively well tolerated. However even at modest "higher" doses by continuous i.v. infusion of 31 and 154 μg/kg/day, severe signs of toxicity were observed within 56 h after the start of infusion. This led to termination of animals for welfare reasons. Histopathological analysis of the dosed animals showed signs of liver and kidney toxicity, which may be a result of redirected lysis of cells expressing low levels of EGFR in these organs. Additionally, animals in both high-dose groups showed increased levels of inflammatory cytokines in serum (i.e., TNF-α, IFN-γ, IL-6, IL-5, and IL-2), as presumably released by T cells encountering EGFR-positive cells. Histopathological changes including lymphocyte infiltration and cell death were noted in all tissues known to express EGFR, i.e., salivary glands, liver, stomach, small intestine, colon, rectum, kidneys, adrenal glands, ureter, urinary bladder, prostate, and epididymides.

Hence instead of employing such conventional approaches, provided herein are multispecific antibodies wherein at least one first binding domain is able to specifically bind Vδ1+ cells and at least one second binding domain is able to specifically bind to EGFR, a target present on diseased tissues and cells. The use of such multispecific antibodies in this way may thereby result in the co-localization of Vδ1+ cells to diseased cells expressing the second target. Further, and given such disease associated targets are not often 100% disease specific, this approach of targeting and co-localizing Vδ1+ effector cells specifically, may be more preferred over conventional approaches. This is because Vδ1+ effector cells may be capable of recognizing stress patterns in diseased or infected cells and so able to selectively kill diseased cells whilst sparing healthy cells also expressing the same target.

The multispecific antibodies presented herein are therefore able to engage on the TCR of vδ1 cells but full activation does not occur unless tumour cells are also present. Full engagement of the presently presented antibodies on the TCR leads to partial downregulation and it is believed the vδ1 cells bound by the presently presented antibodies only become fully activated and become cytotoxic when in the presence of stressed cells such as tumour cells. This is shown, for example, in Example 18 and FIGS. 40A-40C). This represents another vital safety advantage for the approach presented herein, since off target cytotoxicity is reduced and the full potency of the multispecific antibodies to activate vδ1 cells is only unleashed in the presence of tumour cells, meaning healthy cells (even healthy cells expressing EGFR) are spared.

One mechanism behind γδ T cells being able to detect stress signals on tumour cells is believed to be due to the NCRs (natural cytotoxicity receptors) they express. The NCRs are able to engage NCR ligands on tumour cells. A dual mechanism of activation may therefore be employed, wherein the γδ T cells are activated via TCR stimulation, including via NCRs, which can sense the tumour cells to enable full activation and cytotoxicity.

This contrasts with stimulation of αβ T cells via CD3, for example, wherein all stimulation is via the TCR. Such cells are therefore almost indiscriminate between healthy or transformed cells because they do not have mechanisms such as antigen presentation independent sensing of tumour cells, for example via NCRs. Therefore, if CD3 antibodies are Fc enabled they will attract other immune cells which can trigger a cascade of unpredictable and desirable events such as cytokine storms, exhaustion and even overactivation of immune cells leading to, for example, NK cells killing T cells etc. In the present approach, stimulation of γδ T cells with the presently presented multispecific antibodies do not lead to such concerns because γδ T cells) are able to distinguish between healthy cells and tumour cells, including via their NCR sensing mechanism and therefore selectively kill stressed cells such as cancer cells or virally infected cells due to this diseased cell specificity.

The second target epitope may be on a different cell including a different T-cell, a B-cell, a tumour cell, an autoimmune tissue cell or a virally infected cell.

Various antibody-derived multispecific formats have been described previously and are typically built empirically from the component binding parts. Typically, once constructed, the performance of such multispecific or multi-target binding formats as described herein may be measured in one or more of the aforementioned model systems (cell killing, cell proliferation, healthy cell sparing/diseased cell specific models etc). Optionally they are also compared to said component parts and other comparator molecules.

Whilst not being limited by this approach, in general when constructing antibodies as multispecific antibodies of this invention, the binding domain modules to each target (first and second) are built from Fab and Fcab binding modules which are combined into full length antibodies. Modification and generation of multispecific antibodies and desired Fab and Fcab binding domains can be undertaken by routine molecular biology methodology well known in the art. By way of none-limiting examples, oligonucleotide-based approaches with or without aid of PCR amplification can be employed to build synthetic DNA sequences encoding a desired CH3 domain and/or other elements of the desired bispecific antibody. Optionally these can then be correctly cloned into an open reading frame (ORF) encoding the starting antibody heavy chain (such as one described herein) via restriction enzyme based sub-cloning methodologies such to replace the starting CH3 sequence with the desired modified CH3 sequence. Reciprocally, one can employ oligonucleotide-based approaches with or without aid of PCR amplification to generate DNA ORF elements designed to encode the desired VH region (such as one described herein) and then sub-clone or switch this into a pre-existing heavy chain ORF cassette already expressing the desired CH3 domain encoding region. Alternatively, larger elements or indeed the entire antibody heavy chain encoding ORF can be built de-novo from a starting in-silico sequence with oligonucleotide and/or PCR methodologies to generate the entire final ORF encoding a preferred full-length heavy chain comprising a VH binding arm and modified CH3 domain of the multispecific antibody such as described herein. This can then be expressed, recovered and purified in combination with a preferred cognate kappa light chain such as that described herein in order to generate a final purified, multispecific antibody which binds the TRDV1 domain of human Vδ1 TCR and is operatively linked to a modified CH3 binding domains which bind human EGFR.

Remarkably, multispecific antibodies comprising at least one (first) binding domain targeting the Vδ1 chain of a γδ TCR as described herein are further enhanced when said first binding domain is formatted with a multispecific antibody format comprising at least one second binding domain against EGFR.

Multispecific Antibodies-Non-Limiting Examples:

To outline the applicability of the approach a series of non-limiting example multispecific antibodies were constructed. These multispecific antibodies comprised at least one (first) binding domain targeting the Vδ1 chain of a γδ TCR and at least one (second) binding domain targeting EGFR:

Vδ1-EGFR Multispecific Antibody (LEE)

In this aspect of the invention, a multispecific antibody is provided comprising a Fab region and an Fc region, wherein the Fab region comprises a binding site specific for an epitope of the variable delta 1 (Vδ1) chain of a γδ T cell receptor (TCR); and the Fc region comprises an EGFR binding site. The Fab region specifically comprises a VH and cognate VL domain. The Fc region comprises a binding domain within a heavy chain constant domain (CH1-CH2-CH3), specifically a CH3 domain.

| SEQ ID NO: | Description |
|---|---|
| 389 | ADT1-4-2 × LEE (LAGA) |
| 391 | EGFR (LEE) Binding Module CH1-CH2-CH3 (LAGA) |
| 392 | EGFR (LEE) Binding Module CH1-CH2-CH3 (IgG1 wt) |
| 400 | ADT1-4-2 × LEE (wt) |
| 432 | ADT1-4-2 HC (LAGA) EGFR LEE |
| 436 | ADT1-4-2 HC (wt) EGFR LEE |
| 562 | EGFR LEE CH3 Binding Module |
| 523 | EGFR LEE AB substitutions residues 359 to 362 (EU numbering) |
| 511 | EGFR LEE CD substitutions residues 384 to 386 (EU numbering) |
| 512 | EGFR LEE EF substitutions residues 413 to 419 (EU numbering) |
| 524 | EGFR LEE AB Loop residues 355 to 362 (EU numbering) |
| 514 | EGFR LEE CD Loop residues 383 to 391 (EU numbering) |
| 515 | EGFR LEE EF Loop residues 413 to 422 (EU numbering) |
| 563 | IgG1 wt CH3 (residues 341 to 446 (EU numbering) |

In this aspect the EGFR binding site may be provided by an IgG1 CH3 domain in which residues 359 to 362 (EU numbering) comprise EEGP (SEQ ID NO: 523), residues 384 to 386 (EU numbering) comprise TYG (SEQ ID NO:511), and residues 413 to 419 (EU numbering) comprise SYWRWYK (SEQ ID NO: 512).

In this aspect residues 355 to 362 (EU numbering) form an AB loop comprising RDELEEGP (SEQ ID NO: 524), residues 383 to 391 (EU numbering) form an CD loop comprising STYGPENNYKT (SEQ ID NO: 514) and residues 413 to 422 (EU numbering) form an EF loop comprising SYWRWYKGNV (SEQ ID NO: 515).

In this aspect, the IgG1 CH3 domain may comprise the following mutations (EU numbering). In the AB loop the following mutations may be present: T359E.K360E.N361G.Q362P. In the CD loop the following mutations may be present: N384T.G385Y.Q386G. In the EF loop the following mutations may be present: D413S.K414Y.S415W.Q418Y.Q419K.

In this aspect the amino acid sequence of the CH3 domain may be at least 90% identical to, or at least 95% identical to, or 100% identical to SEQ ID NO: 562.

In this aspect, the heavy chain constant domain may comprise SEQ ID NO: 391 or SEQ ID NO: 392.

In this aspect, the multispecific antibody may comprise SEQ ID NO: 389; or SEQ ID NO: 414 and SEQ ID NO: 432. In this aspect, the multispecific antibody may comprise SEQ ID NO: 400; or SEQ ID NO: 414 and SEQ ID NO: 436.

In this aspect the Fab region may be any of the Fab regions described herein (see Table 9, for example). Specifically, the Fab region of this aspect may comprise a VHCDR1, a VHCDR2 and a VHCDR3 comprising the amino acid sequences of SEQ ID NO: 51, 53 and 68, respectively, and a VLCDR1, a VLCDR2 and a VLCDR3 comprising the amino acid sequences of SEQ ID NOs: 79, 80 and 95, respectively. The Fab region of this aspect may comprise a VH comprising SEQ ID NO: 15 and a VL comprising SEQ ID NO: 40.

In one embodiment of this aspect, the multispecific antibody comprises a Fab region comprising a VH comprising the amino acid sequence of SEQ ID NO: 15 and a VL sequence comprising the amino acid sequence of SEQ ID NO: 40; and an Fc region comprising a CH3 domain comprising the amino acid sequence of SEQ ID NO: 562. In some embodiments, the multispecific antibodies of the invention may comprise an additional lysine (K) residue at the immediate C-terminus of the CH3 domain sequence (K447, EU numbering). In some embodiments, the multispecific antibodies of the invention may have the terminal glycine (G) residue at the immediate C-terminus of the CH3 domain sequence removed (G446, EU antibodies. Therefore, the human IgG1 antibodies may comprise a CH3 domain comprising the sequence of SEQ ID NO: 562.

TABLE 9

LEE - Example multispecific vδ1-EGFR human IgG1 antibodies having the CDRs of antibodies derived from ADT1-4 and ADT1-7 and the related SEQ ID NOs

| Derived from | Fab Region | | | | | | Fc Region | | |
|---|---|---|---|---|---|---|---|---|---|
| | VH | | | VL | | | AB loop | CD loop | EF loop |
| Antibody | CDR1 | CDR2 | CDR3 | CDR1 | CDR2 | CDR3 | comprises | comprises | comprises |
| Parental ADT1-4 | 51 | 53 | 54 | 79 | 80 | 81 | Residues 359 to 362 (EU numbering) comprise EEGP SEQ ID NO: 523 | Residues 384 to 386 (EU numbering) comprise TYG SEQ ID NO: 511 | Residues 413 to 419 (EU numbering) comprise SYWRWYK SEQ ID NO: 512 |
| ADT1-4-105 | 51 | 53 | 55 | 79 | 80 | 82 | | | |
| ADT1-4-107 | 51 | 53 | 56 | 79 | 80 | 83 | | | |
| ADT1-4-110 | 51 | 53 | 57 | 79 | 80 | 84 | | | |
| ADT1-4-112 | 51 | 53 | 58 | 79 | 80 | 85 | | | |
| ADT1-4-117 | 51 | 53 | 59 | 79 | 80 | 86 | | | |
| ADT1-4-19 | 51 | 53 | 60 | 79 | 80 | 87 | | | |
| ADT1-4-21 | 52 | 53 | 61 | 79 | 80 | 88 | | | |
| ADT1-4-31 | 51 | 53 | 62 | 79 | 80 | 89 | | | |
| ADT1-4-139 | 51 | 53 | 63 | 79 | 80 | 90 | | | |
| ADT1-4-4 | 51 | 53 | 64 | 79 | 80 | 91 | | | |
| ADT1-4-143 | 51 | 53 | 65 | 79 | 80 | 92 | | | |
| ADT1-4-53 | 52 | 53 | 66 | 79 | 80 | 93 | | | |
| ADT1-4-173 | 51 | 53 | 67 | 79 | 80 | 94 | | | |
| ADT1-4-2 | 51 | 53 | 68 | 79 | 80 | 95 | | | |
| ADT1-4-8 | 51 | 53 | 69 | 79 | 80 | 96 | | | |
| ADT1-4-82 | 51 | 53 | 70 | 79 | 80 | 97 | | | |
| ADT1-4-83 | 51 | 53 | 71 | 79 | 80 | 98 | | | |
| ADT1-4-3 | 51 | 53 | 72 | 79 | 80 | 99 | | | |
| ADT1-4-84 | 51 | 53 | 73 | 79 | 80 | 100 | | | |
| ADT1-4-86 | 52 | 53 | 74 | 79 | 80 | 101 | | | |
| ADT1-4-95 | 51 | 53 | 75 | 79 | 80 | 102 | | | |
| ADT1-4-1 | 51 | 53 | 76 | 79 | 80 | 103 | | | |
| ADT1-4-6 | 51 | 53 | 77 | 79 | 80 | 104 | | | |
| ADT1-4-138 | 51 | 53 | 78 | 79 | 80 | 105 | | | |
| Parental ADT1-7 | 130 | 131 | 132 | 144 | 145 | 146 | | | |
| ADT1-7-10 | 130 | 131 | 133 | 144 | 145 | 147 | | | |
| ADT1-7-15 | 130 | 131 | 134 | 144 | 145 | 148 | | | |
| ADT1-7-17 | 130 | 131 | 135 | 144 | 145 | 149 | | | |
| ADT1-7-18 | 130 | 131 | 136 | 144 | 145 | 150 | | | |
| ADT1-7-19 | 130 | 131 | 137 | 144 | 145 | 151 | | | |
| ADT1-7-20 | 130 | 131 | 138 | 144 | 145 | 152 | | | |
| ADT1-7-22 | 130 | 131 | 139 | 144 | 145 | 153 | | | |
| ADT1-7-23 | 130 | 131 | 140 | 144 | 145 | 154 | | | |
| ADT1-7-42 | 130 | 131 | 141 | 144 | 145 | 155 | | | |
| ADT1-7-3 | 130 | 131 | 142 | 144 | 145 | 156 | | | |
| ADT1-7-61 | 130 | 131 | 143 | 144 | 145 | 157 | | | |

The present disclosure explicitly includes an antibody having the sequences of each row of the above table. For example, the present disclosure includes a multispecific antibody comprising a Fab region and an Fc region wherein the Fab region comprises a binding site specific for an epitope of the variable delta 1 (Vδ1) chain of a γδ T cell receptor (TCR), wherein the Fab region comprises a VHCDR1 comprising the sequence of SEQ ID NO: 51, a VHCDR2 comprising the sequence of SEQ ID NO: 53, a VHCDR3 comprising the sequence of SEQ ID NO: 68, a VLCDR1 comprising the sequence of SEQ ID NO: 79, a VLCDR2 comprising the sequence of SEQ ID NO: 80 and a VLCDR3 comprising the sequence of SEQ ID NO: 95; and the Fc region comprises an EGFR binding site, wherein the EGFR binding site is provided by a CH3 domain in which residues 359 to 362 (EU numbering) comprise SEQ ID NO: 523, residues 384 to 386 (EU numbering) comprise SEQ ID NO:511 and residues 413 to 419 (EU numbering) comprise SEQ ID NO: 512. Every row of the above table is disclosed in the same manner. Such antibodies are human IgG1

TABLE 10

LEE - Example multispecific vδ1-EGFR human IgG1 antibodies having the variable regions of antibodies derived from ADT1-4 and ADT1-7 and the related SEQ ID NOs

| Derived from | Fab Region | | Fc Region | | |
|---|---|---|---|---|---|
| Antibody | VH | VL | AB loop comprises | CD loop comprises | EF loop comprises |
| Parental ADT1-4 | 1 | 26 | Residues 359 to 362 (EU numbering) comprise EEGP SEQ ID NO: 523 | Residues 384 to 386 (EU numbering) comprise TYG SEQ ID NO: 511 | Residues 413 to 419 (EU numbering) comprise SYWRWYK SEQ ID NO: 512 |
| ADT1-4-105 | 2 | 27 | | | |
| ADT1-4-107 | 3 | 28 | | | |
| ADT1-4-110 | 4 | 29 | | | |
| ADT1-4-112 | 5 | 30 | | | |
| ADT1-4-117 | 6 | 31 | | | |
| ADT1-4-19 | 7 | 32 | | | |
| ADT1-4-21 | 8 | 33 | | | |
| ADT1-4-31 | 9 | 34 | | | |
| ADT1-4-139 | 10 | 35 | | | |
| ADT1-4-4 | 11 | 36 | | | |
| ADT1-4-143 | 12 | 37 | | | |

TABLE 10-continued

LEE - Example multispecific vδ1-EGFR human IgG1 antibodies having the variable regions of antibodies derived from ADT1-4 and ADT1-7 and the related SEQ ID NOs

| Derived from Antibody | Fab Region | | Fc Region | | |
|---|---|---|---|---|---|
| | VH | VL | AB loop comprises | CD loop comprises | EF loop comprises |
| ADT1-4-53 | 13 | 38 | | | |
| ADT1-4-173 | 14 | 39 | | | |
| ADT1-4-2 | 15 | 40 | | | |
| ADT1-4-8 | 16 | 41 | | | |
| ADT1-4-82 | 17 | 42 | | | |
| ADT1-4-83 | 18 | 43 | | | |
| ADT1-4-3 | 19 | 44 | | | |
| ADT1-4-84 | 20 | 45 | | | |
| ADT1-4-86 | 21 | 46 | | | |
| ADT1-4-95 | 22 | 47 | | | |
| ADT1-4-1 | 23 | 48 | | | |
| ADT1-4-6 | 24 | 49 | | | |
| ADT1-4-138 | 25 | 50 | | | |
| Parental ADT1-7 | 106 | 118 | | | |
| ADT1-7-10 | 107 | 119 | | | |
| ADT1-7-15 | 108 | 120 | | | |
| ADT1-7-17 | 109 | 121 | | | |
| ADT1-7-18 | 110 | 122 | | | |
| ADT1-7-19 | 111 | 123 | | | |
| ADT1-7-20 | 112 | 124 | | | |
| ADT1-7-22 | 113 | 125 | | | |
| ADT1-7-23 | 114 | 126 | | | |
| ADT1-7-42 | 115 | 127 | | | |
| ADT1-7-3 | 116 | 128 | | | |
| ADT1-7-61 | 117 | 129 | | | |
| C08 | 273 | 282 | | | |
| B07 | 274 | 283 | | | |
| C05 | 275 | 284 | | | |
| E04 | 276 | 285 | | | |
| F07 | 277 | 286 | | | |
| G06 | 278 | 287 | | | |
| G09 | 279 | 288 | | | |
| B09 | 280 | 289 | | | |
| G10 | 281 | 290 | | | |
| E01 | 312 | 313 | | | |

The present disclosure explicitly includes an antibody having the sequences of each row of the above table. For example, the present disclosure includes a multispecific antibody comprising a Fab region and an Fc region wherein the Fab region comprises a binding site specific for an epitope of the variable delta 1 (Vδ1) chain of a γδ T cell receptor (TCR), wherein the Fab region comprises a VH region comprising the sequence of SEQ ID NO: 15 and a VL region comprising the SEQUENCE of SEQ ID NO: 40; and the Fc region comprises an EGFR binding site, wherein the EGFR binding site is provided by a CH3 domain in which residues 359 to 362 (EU numbering) comprise SEQ ID NO: 523, residues 384 to 386 (EU numbering) comprise SEQ ID NO:511 and residues 413 to 419 (EU numbering) comprise SEQ ID NO: 512. Every row of the above table is disclosed in the same manner. Such antibodies are human IgG1 antibodies. Therefore, the human IgG1 antibodies may comprise a CH3 domain comprising the sequence of SEQ ID NO: 562.

Vδ1-EGFR Multispecific Antibody (LEE1)

In this aspect of the invention, a multispecific antibody is provided comprising a Fab region and an Fc region, wherein the Fab region comprises a binding site specific for an epitope of the variable delta 1 (Vδ1) chain of a γδ T cell receptor (TCR); and the Fc region comprises an EGFR binding site. The Fab region specifically comprises a VH and cognate VL domain. The Fc region comprises a binding domain within a heavy chain constant domain (CH1-CH2-CH3), specifically a CH3 domain.

| SEQ ID NO: | Description |
|---|---|
| 504 | ADT1-4-2 × LEE1 (LAGA) |
| 505 | ADT1-4-2 × LEE1 (wt) |
| 506 | ADT1-4-2 HC EGFR LEE1 (LAGA) |
| 507 | ADT1-4-2 HC EGFR LEE1 (wt) |
| 508 | EGFR LEE1 Binding Module CH1-CH2-CH3 (LAGA) |
| 509 | EGFR LEE1 Binding Module CH1-CH2-CH3 (wt) |
| 510 | EGFR LEE1 CH3 Binding Module |
| 511 | EGFR LEE1 CD substitutions residues 384 to 386 (EU numbering) |
| 512 | EGFR LEE1 EF substitutions residues 413 to 419 (EU numbering) |
| 513 | EGFR LEE1 AB Loop (WT) residues 355 to 362 (EU numbering) |
| 514 | EGFR LEE1 CD Loop residues 383 to 391 (EU numbering) |
| 515 | EGFR LEE1 EF Loop residues 413 to 422 (EU numbering) |

In this aspect the EGFR binding site may be provided by an IgG1 CH3 domain in which residues 384 to 386 (EU numbering) comprise TYG (SEQ ID NO: 511, and residues 413 to 419 (EU numbering) comprise SYWRWYK (SEQ ID NO: 512).

In this aspect residues 355 to 362 (EU numbering) form an AB loop comprising RDELTKNQ (SEQ ID NO: 513, residues 383 to 391 (EU numbering) form an CD loop comprising STYGPENNYKT (SEQ ID NO: 514) and residues 413 to 422 (EU numbering) form an EF loop comprising SYWRWYKGNV (SEQ ID NO: 515).

In this aspect, the IgG1 CH3 domain may comprise the following mutations (EU numbering). The AB loop may be wildtype (no mutations present). In the CD loop the following mutations may be present: N384T.G385Y.Q386G. In the EF loop the following mutations may be present: D413S.K414Y.S415W.Q418Y.Q419K.

In this aspect the amino acid sequence of the CH3 domain may be at least 90% identical to, or at least 95% identical to, or 100% identical to SEQ ID NO: 510.

In this aspect, the heavy chain constant domain may comprise SEQ ID NO: 508 or SEQ ID NO: 509.

In this aspect, the multispecific antibody may comprise SEQ ID NO: 504; or SEQ ID NO: 414 and SEQ ID NO: 506. In this aspect, the multispecific antibody may comprise SEQ ID NO: 505; or SEQ ID NO: 414 and SEQ ID NO: 507.

In this aspect the Fab region may be any of the Fab regions described herein (see Table 11, for example). Specifically, the Fab region of this aspect may comprise a VHCDR1, a VHCDR2 and a VHCDR3 comprising the amino acid sequences of SEQ ID NO: 51, 53 and 68, respectively, and a VLCDR1, a VLCDR2 and a VLCDR3 comprising the amino acid sequences of SEQ ID NOs: 79, 80 and 95, respectively. The Fab region of this aspect may comprise a VH comprising SEQ ID NO: 15 and a VL comprising SEQ ID NO: 40.

In one embodiment of this aspect, the multispecific antibody comprises a Fab region comprising a VH comprising the amino acid sequence of SEQ ID NO: 15 and a VL sequence comprising the amino acid sequence of SEQ ID NO: 40; and an Fc region comprising a CH3 domain comprising the amino acid sequence of SEQ ID NO: 510. In some embodiments, the multispecific antibodies of the invention may comprise an additional lysine (K) residue at the immediate C-terminus of the CH3 domain sequence (K447, EU numbering). In some embodiments, the multispecific antibodies of the invention may have the terminal glycine (G) residue at the immediate C-terminus of the CH3 domain sequence removed (G446, EU

TABLE 11

LEE1 -- Example multispecific vδ1-EGFR human IgG1 antibodies having the
CDRs of antibodies derived from ADT1-4 and ADT1-7 and the related SEQ ID NOs

| Derived from | Fab Region | | | | | | Fc Region | | |
|---|---|---|---|---|---|---|---|---|---|
| | VH | | | VL | | | | | |
| Antibody | CDR1 | CDR2 | CDR3 | CDR1 | CDR2 | CDR3 | AB loop | CD loop | EF loop |
| Parental ADT1-4 | 51 | 53 | 54 | 79 | 80 | 81 | Residues 355 to 362 (EU numbering) comprise RDELTKNQ SEQ ID NO: 513 | Residues 384 to 386 (EU numbering) comprise TYG SEQ ID NO: 511 | Residues 413 to 419 (EU numbering) comprise SYWRWYK SEQ ID NO: 512 |
| ADT1-4-105 | 51 | 53 | 55 | 79 | 80 | 82 | | | |
| ADT1-4-107 | 51 | 53 | 56 | 79 | 80 | 83 | | | |
| ADT1-4-110 | 51 | 53 | 57 | 79 | 80 | 84 | | | |
| ADT1-4-112 | 51 | 53 | 58 | 79 | 80 | 85 | | | |
| ADT1-4-117 | 51 | 53 | 59 | 79 | 80 | 86 | | | |
| ADT1-4-19 | 51 | 53 | 60 | 79 | 80 | 87 | | | |
| ADT1-4-21 | 52 | 53 | 61 | 79 | 80 | 88 | | | |
| ADT1-4-31 | 51 | 53 | 62 | 79 | 80 | 89 | | | |
| ADT1-4-139 | 51 | 53 | 63 | 79 | 80 | 90 | | | |
| ADT1-4-4 | 51 | 53 | 64 | 79 | 80 | 91 | | | |
| ADT1-4-143 | 51 | 53 | 65 | 79 | 80 | 92 | | | |
| ADT1-4-53 | 52 | 53 | 66 | 79 | 80 | 93 | | | |
| ADT1-4-173 | 51 | 53 | 67 | 79 | 80 | 94 | | | |
| ADT1-4-2 | 51 | 53 | 68 | 79 | 80 | 95 | | | |
| ADT1-4-8 | 51 | 53 | 69 | 79 | 80 | 96 | | | |
| ADT1-4-82 | 51 | 53 | 70 | 79 | 80 | 97 | | | |
| ADT1-4-83 | 51 | 53 | 71 | 79 | 80 | 98 | | | |
| ADT1-4-3 | 51 | 53 | 72 | 79 | 80 | 99 | | | |
| ADT1-4-84 | 51 | 53 | 73 | 79 | 80 | 100 | | | |
| ADT1-4-86 | 52 | 53 | 74 | 79 | 80 | 101 | | | |
| ADT1-4-95 | 51 | 53 | 75 | 79 | 80 | 102 | | | |
| ADT1-4-1 | 51 | 53 | 76 | 79 | 80 | 103 | | | |
| ADT1-4-6 | 51 | 53 | 77 | 79 | 80 | 104 | | | |
| ADT1-4-138 | 51 | 53 | 78 | 79 | 80 | 105 | | | |
| Parental ADT1-7 | 130 | 131 | 132 | 144 | 145 | 146 | | | |
| ADT1-7-10 | 130 | 131 | 133 | 144 | 145 | 147 | | | |
| ADT1-7-15 | 130 | 131 | 134 | 144 | 145 | 148 | | | |
| ADT1-7-17 | 130 | 131 | 135 | 144 | 145 | 149 | | | |
| ADT1-7-18 | 130 | 131 | 136 | 144 | 145 | 150 | | | |
| ADT1-7-19 | 130 | 131 | 137 | 144 | 145 | 151 | | | |
| ADT1-7-20 | 130 | 131 | 138 | 144 | 145 | 152 | | | |
| ADT1-7-22 | 130 | 131 | 139 | 144 | 145 | 153 | | | |
| ADT1-7-23 | 130 | 131 | 140 | 144 | 145 | 154 | | | |
| ADT1-7-42 | 130 | 131 | 141 | 144 | 145 | 155 | | | |
| ADT1-7-3 | 130 | 131 | 142 | 144 | 145 | 156 | | | |
| ADT1-7-61 | 130 | 131 | 143 | 144 | 145 | 157 | | | |

TABLE 12

LEE1 - Example multispecific vδ1-EGFR human IgG1
antibodies having the CDRs of antibodies derived
from ADT1-4 and ADT1-7 and the related SEQ ID NOs

| Derived from | Fab Region | | Fc Region | | |
|---|---|---|---|---|---|
| Antibody | VH | VL | AB loop | CD loop | EF loop |
| Parental ADT1-4 | 1 | 26 | Residues 355 to 362 (EU numbering) comprise RDELTKNQ SEQ ID NO: 513 | Residues 384 to 386 (EU numbering) comprise TYG SEQ ID NO: 511 | Residues 413 to 419 (EU numbering) comprise SYWRWYK SEQ ID NO: 512 |
| ADT1-4-105 | 2 | 27 | | | |
| ADT1-4-107 | 3 | 28 | | | |
| ADT1-4-110 | 4 | 29 | | | |
| ADT1-4-112 | 5 | 30 | | | |
| ADT1-4-117 | 6 | 31 | | | |
| ADT1-4-19 | 7 | 32 | | | |
| ADT1-4-21 | 8 | 33 | | | |
| ADT1-4-31 | 9 | 34 | | | |
| ADT1-4-139 | 10 | 35 | | | |
| ADT1-4-4 | 11 | 36 | | | |
| ADT1-4-143 | 12 | 37 | | | |
| ADT1-4-53 | 13 | 38 | | | |
| ADT1-4-173 | 14 | 39 | | | |
| ADT1-4-2 | 15 | 40 | | | |
| ADT1-4-8 | 16 | 41 | | | |
| ADT1-4-82 | 17 | 42 | | | |
| ADT1-4-83 | 18 | 43 | | | |
| ADT1-4-3 | 19 | 44 | | | |
| ADT1-4-84 | 20 | 45 | | | |
| ADT1-4-86 | 21 | 46 | | | |
| ADT1-4-95 | 22 | 47 | | | |
| ADT1-4-1 | 23 | 48 | | | |
| ADT1-4-6 | 24 | 49 | | | |
| ADT1-4-138 | 25 | 50 | | | |
| Parental ADT1-7 | 106 | 118 | | | |
| ADT1-7-10 | 107 | 119 | | | |
| ADT1-7-15 | 108 | 120 | | | |
| ADT1-7-17 | 109 | 121 | | | |
| ADT1-7-18 | 110 | 122 | | | |

TABLE 12-continued

LEE1 - Example multispecific vδ1-EGFR human IgG1 antibodies having the CDRs of antibodies derived from ADT1-4 and ADT1-7 and the related SEQ ID NOs

| Derived from | Fab Region | | Fc Region | | |
|---|---|---|---|---|---|
| Antibody | VH | VL | AB loop | CD loop | EF loop |
| ADT1-7-19 | 111 | 123 | | | |
| ADT1-7-20 | 112 | 124 | | | |
| ADT1-7-22 | 113 | 125 | | | |
| ADT1-7-23 | 114 | 126 | | | |
| ADT1-7-42 | 115 | 127 | | | |
| ADT1-7-3 | 116 | 128 | | | |
| ADT1-7-61 | 117 | 129 | | | |
| C08 | 273 | 282 | | | |
| B07 | 274 | 283 | | | |
| C05 | 275 | 284 | | | |
| E04 | 276 | 285 | | | |
| F07 | 277 | 286 | | | |
| G06 | 278 | 287 | | | |
| G09 | 279 | 288 | | | |
| B09 | 280 | 289 | | | |
| G10 | 281 | 290 | | | |
| E01 | 312 | 313 | | | |

Vδ1-EGFR Multispecific Antibody (LEE2)

In this aspect of the invention, a multispecific antibody is provided comprising a Fab region and an Fc region, wherein the Fab region comprises a binding site specific for an epitope of the variable delta 1 (Vδ1) chain of a γδ T cell receptor (TCR); and the Fc region comprises an EGFR binding site. The Fab region specifically comprises a VH and cognate VL domain. The Fc region comprises a binding domain within a heavy chain constant domain (CH1-CH2-CH3), specifically a CH3 domain.

| SEQ ID NO: | Description |
|---|---|
| 516 | ADT1-4-2 × LEE2 (LAGA) |
| 517 | ADT1-4-2 × LEE2 (wt) |
| 518 | ADT1-4-2 HC EGFR LEE2 (LAGA) |
| 519 | ADT1-4-2 HC EGFR LEE2 (wt) |
| 520 | EGFR LEE2 Binding Module CH1-CH2-CH3 (LAGA) |
| 521 | EGFR LEE2 Binding Module CH1-CH2-CH3 (wt) |
| 522 | EGFR LEE2 CH3 Binding Module |
| 523 | EGFR LEE2 AB substitutions residues 359 to 362 (EU numbering) |
| 512 | EGFR LEE2 EF substitutions residues 413 to 419 (EU numbering) |
| 524 | EGFR LEE2 AB Loop residues 355 to 362 (EU numbering) |
| 525 | EGFR LEE2 CD Loop (WT) residues 383 to 391 (EU numbering) |
| 515 | EGFR LEE2 EF Loop residues 413 to 422 (EU numbering) |

In this aspect the EGFR binding site may be provided by an IgG1 CH3 domain in which residues 359 to 362 (EU numbering) comprise EEGP (SEQ ID NO: 523), and residues 413 to 419 (EU numbering) comprise SYWRWYK (SEQ ID NO: 512).

In this aspect residues 355 to 362 (EU numbering) form an AB loop comprising RDELEEGP (SEQ ID NO: 524), residues 383 to 391 (EU numbering) form an CD loop comprising SNGQPENNYKT (SEQ ID NO: 525) and residues 413 to 422 (EU numbering) form an EF loop comprising SYWRWYKGNV (SEQ ID NO: 515).

In this aspect, the IgG1 CH3 domain may comprise the following mutations (EU numbering). In the AB loop the following mutations may be present: T359E.K360E.N361G.Q362P. The CD loop may be wildtype (no mutations present). In the EF loop the following mutations may be present: D413S.K414Y.S415W.Q418Y.Q419K.

In this aspect the amino acid sequence of the CH3 domain may be at least 90% identical to, or at least 95% identical to, or 100% identical to SEQ ID NO: 522.

In this aspect, the heavy chain constant domain may comprise SEQ ID NO: 520 or SEQ ID NO: 521. In this aspect, the multispecific antibody may comprise SEQ ID NO: 516; or SEQ ID NO: 414 and SEQ ID NO: 518. In this aspect, the multispecific antibody may comprise SEQ ID NO: 517; or SEQ ID NO: 414 and SEQ ID NO: 519.

In this aspect the Fab region may be any of the Fab regions described herein (see Table 13, for example). Specifically, the Fab region of this aspect may comprise a VHCDR1, a VHCDR2 and a VHCDR3 comprising the amino acid sequences of SEQ ID NO: 51, 53 and 68, respectively, and a VLCDR1, a VLCDR2 and a VLCDR3 comprising the amino acid sequences of SEQ ID NOs: 79, 80 and 95, respectively. The Fab region of this aspect may comprise a VH comprising SEQ ID NO: 15 and a VL comprising SEQ ID NO: 40.

In one embodiment of this aspect, the multispecific antibody comprises a Fab region comprising a VH comprising the amino acid sequence of SEQ ID NO: 15 and a VL sequence comprising the amino acid sequence of SEQ ID NO: 40; and an Fc region comprising a CH3 domain comprising the amino acid sequence of SEQ ID NO: 522. In some embodiments, the multispecific antibodies of the invention may comprise an additional lysine (K) residue at the immediate C-terminus of the CH3 domain sequence (K447, EU numbering). In some embodiments, the multispecific antibodies of the invention may have the terminal glycine (G) residue at the immediate C-terminus of the CH3 domain sequence removed (G446, EU

TABLE 13

LEE2 - Example multispecific vδ1-EGFR human IgG1 antibodies having the CDRs of antibodies derived from ADT1-4 and ADT1-7 and the related SEQ ID NOs

| Derived from | Fab Region | | | | | | Fc Region | | |
|---|---|---|---|---|---|---|---|---|---|
| | VH | | | VL | | | | | |
| Antibody | CDR1 | CDR2 | CDR3 | CDR1 | CDR2 | CDR3 | AB loop | CD loop | EF loop |
| Parental ADT1-4 | 51 | 53 | 54 | 79 | 80 | 81 | Residues 359 to 362 EU numbering) | Wildtype residues 383 to 391 (EU | Residues 413 to 419 (EU numbering) |
| ADT1-4-105 | 51 | 53 | 55 | 79 | 80 | 82 | | numbering) | |

TABLE 13-continued

LEE2 - Example multispecific vδ1-EGFR human IgG1 antibodies having the
CDRs of antibodies derived from ADT1-4 and ADT1-7 and the related SEQ ID NOs

| Derived from | Fab Region | | | | | | Fc Region | | |
|---|---|---|---|---|---|---|---|---|---|
| | VH | | | VL | | | | | |
| Antibody | CDR1 | CDR2 | CDR3 | CDR1 | CDR2 | CDR3 | AB loop | CD loop | EF loop |
| ADT1-4-107 | 51 | 53 | 56 | 79 | 80 | 83 | comprise | numbering) | comprise |
| ADT1-4-110 | 51 | 53 | 57 | 79 | 80 | 84 | EEGP | form an CD | SYWRWYK |
| ADT1-4-112 | 51 | 53 | 58 | 79 | 80 | 85 | SEQ ID NO: | loop comprise | SEQ ID NO: |
| ADT1-4-117 | 51 | 53 | 59 | 79 | 80 | 86 | 523 | SNGQPENNYKT | 512 |
| ADT1-4-19 | 51 | 53 | 60 | 79 | 80 | 87 | | SEQ ID NO: | |
| ADT1-4-21 | 52 | 53 | 61 | 79 | 80 | 88 | | 525 | |
| ADT1-4-31 | 51 | 53 | 62 | 79 | 80 | 89 | | | |
| ADT1-4-139 | 51 | 53 | 63 | 79 | 80 | 90 | | | |
| ADT1-4-4 | 51 | 53 | 64 | 79 | 80 | 91 | | | |
| ADT1-4-143 | 51 | 53 | 65 | 79 | 80 | 92 | | | |
| ADT1-4-53 | 52 | 53 | 66 | 79 | 80 | 93 | | | |
| ADT1-4-173 | 51 | 53 | 67 | 79 | 80 | 94 | | | |
| ADT1-4-2 | 51 | 53 | 68 | 79 | 80 | 95 | | | |
| ADT1-4-8 | 51 | 53 | 69 | 79 | 80 | 96 | | | |
| ADT1-4-82 | 51 | 53 | 70 | 79 | 80 | 97 | | | |
| ADT1-4-83 | 51 | 53 | 71 | 79 | 80 | 98 | | | |
| ADT1-4-3 | 51 | 53 | 72 | 79 | 80 | 99 | | | |
| ADT1-4-84 | 51 | 53 | 73 | 79 | 80 | 100 | | | |
| ADT1-4-86 | 52 | 53 | 74 | 79 | 80 | 101 | | | |
| ADT1-4-95 | 51 | 53 | 75 | 79 | 80 | 102 | | | |
| ADT1-4-1 | 51 | 53 | 76 | 79 | 80 | 103 | | | |
| ADT1-4-6 | 51 | 53 | 77 | 79 | 80 | 104 | | | |
| ADT1-4-138 | 51 | 53 | 78 | 79 | 80 | 105 | | | |
| Parental ADT1-7 | 130 | 131 | 132 | 144 | 145 | 146 | | | |
| ADT1-7-10 | 130 | 131 | 133 | 144 | 145 | 147 | | | |
| ADT1-7-15 | 130 | 131 | 134 | 144 | 145 | 148 | | | |
| ADT1-7-17 | 130 | 131 | 135 | 144 | 145 | 149 | | | |
| ADT1-7-18 | 130 | 131 | 136 | 144 | 145 | 150 | | | |
| ADT1-7-19 | 130 | 131 | 137 | 144 | 145 | 151 | | | |
| ADT1-7-20 | 130 | 131 | 138 | 144 | 145 | 152 | | | |
| ADT1-7-22 | 130 | 131 | 139 | 144 | 145 | 153 | | | |
| ADT1-7-23 | 130 | 131 | 140 | 144 | 145 | 154 | | | |
| ADT1-7-42 | 130 | 131 | 141 | 144 | 145 | 155 | | | |
| ADT1-7-3 | 130 | 131 | 142 | 144 | 145 | 156 | | | |
| ADT1-7-61 | 130 | 131 | 143 | 144 | 145 | 157 | | | |

TABLE 14

LEE2 - Example multispecific vδ1-EGFR human IgG1 antibodies
having the variable regions of antibodies derived from
ADT1-4 and ADT1-7 and the related SEQ ID NOs

| Derived from | Fab Region | | Fc Region | | |
|---|---|---|---|---|---|
| Antibody | VH | VL | AB loop | CD loop | EF loop |
| Parental ADT1-4 | 1 | 26 | Residues 359 to 362 (EU numbering) comprise EEGP SEQ ID NO: 523 | Wildtype residues 383 to 391 (EU numbering) form an CD loop comprise SNGQPENNYKT SEQ ID NO: 525 | Residues 413 to 419 (EU numbering) comprise SYWRWYK SEQ ID NO: 512 |
| ADT1-4-105 | 2 | 27 | | | |
| ADT1-4-107 | 3 | 28 | | | |
| ADT1-4-110 | 4 | 29 | | | |
| ADT1-4-112 | 5 | 30 | | | |
| ADT1-4-117 | 6 | 31 | | | |
| ADT1-4-19 | 7 | 32 | | | |
| ADT1-4-21 | 8 | 33 | | | |
| ADT1-4-31 | 9 | 34 | | | |
| ADT1-4-139 | 10 | 35 | | | |
| ADT1-4-4 | 11 | 36 | | | |
| ADT1-4-143 | 12 | 37 | | | |
| ADT1-4-53 | 13 | 38 | | | |
| ADT1-4-173 | 14 | 39 | | | |
| ADT1-4-2 | 15 | 40 | | | |
| ADT1-4-8 | 16 | 41 | | | |
| ADT1-4-82 | 17 | 42 | | | |

TABLE 14-continued

LEE2 - Example multispecific vδ1-EGFR human IgG1 antibodies having the variable regions of antibodies derived from ADT1-4 and ADT1-7 and the related SEQ ID NOs

| | Fab Region | | Fc Region | | |
|---|---|---|---|---|---|
| Derived from Antibody | VH | VL | AB loop | CD loop | EF loop |
| ADT1-4-83 | 18 | 43 | | | |
| ADT1-4-3 | 19 | 44 | | | |
| ADT1-4-84 | 20 | 45 | | | |
| ADT1-4-86 | 21 | 46 | | | |
| ADT1-4-95 | 22 | 47 | | | |
| ADT1-4-1 | 23 | 48 | | | |
| ADT1-4-6 | 24 | 49 | | | |
| ADT1-4-138 | 25 | 50 | | | |
| Parental ADT1-7 | 106 | 118 | | | |
| ADT1-7-10 | 107 | 119 | | | |
| ADT1-7-15 | 108 | 120 | | | |
| ADT1-7-17 | 109 | 121 | | | |
| ADT1-7-18 | 110 | 122 | | | |
| ADT1-7-19 | 111 | 123 | | | |
| ADT1-7-20 | 112 | 124 | | | |
| ADT1-7-22 | 113 | 125 | | | |
| ADT1-7-23 | 114 | 126 | | | |
| ADT1-7-42 | 115 | 127 | | | |
| ADT1-7-3 | 116 | 128 | | | |
| ADT1-7-61 | 117 | 129 | | | |
| C08 | 273 | 282 | | | |
| B07 | 274 | 283 | | | |
| C05 | 275 | 284 | | | |
| E04 | 276 | 285 | | | |
| F07 | 277 | 286 | | | |
| G06 | 278 | 287 | | | |
| G09 | 279 | 288 | | | |
| B09 | 280 | 289 | | | |
| G10 | 281 | 290 | | | |
| E01 | 312 | 313 | | | |

Vδ1-EGFR Multispecific antibody (LEE3)

In this aspect of the invention, a multispecific antibody is provided comprising a Fab region and an Fc region, wherein the Fab region comprises a binding site specific for an epitope of the variable delta 1 (Vδ1) chain of a γδ T cell receptor (TCR); and the Fc region comprises an EGFR binding site. The Fab region specifically comprises a VH and cognate VL domain. The Fc region comprises a binding domain within a heavy chain constant domain (CH1-CH2-CH3), specifically a CH3 domain.

| SEQ ID NO: | Description |
|---|---|
| 526 | ADT1-4-2 × LEE3 (LAGA) |
| 527 | ADT1-4-2 × LEE3 (wt) |
| 528 | ADT1-4-2 HC EGFR LEE3 (LAGA) |
| 529 | ADT1-4-2 HC EGFR LEE3 (wt) |
| 530 | EGFR LEE3 Binding Module CH1-CH2-CH3 (LAGA) |
| 531 | EGFR LEE3 Binding Module CH1-CH2-CH3 (wt) |
| 532 | EGFR LEE3 CH3 binding Module |
| 523 | EGFR LEE3 AB substitutions residues 359 to 362 (EU numbering) |
| 511 | EGFR LEE3 CD substitutions residues 384 to 386 (EU numbering) |
| 533 | EGFR LEE3 EF substitutions residues 413 to 415 (EU numbering) |
| 524 | EGFR LEE3 AB Loop residues 355 to 362 (EU numbering) |
| 514 | EGFR LEE3 CD Loop residues 383 to 391 (EU numbering) |
| 534 | EGFR LEE3 EF Loop residues 413 to 422 (EU numbering) |

In this aspect the EGFR binding site may be provided by an IgG1 CH3 domain in which residues 359 to 362 (EU numbering) comprise EEGP (SEQ ID NO: 523), residues 384 to 386 (EU numbering) comprise TYG (SEQ ID NO: 511), and residues 413 to 415 (EU numbering) comprise SYW (SEQ ID NO: 533).

In this aspect residues 355 to 362 (EU numbering) form an AB loop comprising RDELEEGP (SEQ ID NO: 524), residues 383 to 391 (EU numbering) form an CD loop comprising STYGPENNYKT (SEQ ID NO: 514), and residues 413 to 422 (EU numbering) form an EF loop comprising SYWRWYKGNV (SEQ ID NO: 515).

In this aspect, the IgG1 CH3 domain may comprise the following mutations (EU numbering). In the AB loop the following mutations may be present: T359E.K360E.N361G.Q362P. In the CD loop the following mutations may be present: N384T.G385Y.Q386G. In the EF loop the following mutations may be present D413S.K414Y.S415W.

In this aspect the amino acid sequence of the CH3 domain may be at least 90% identical to, or at least 95% identical to, or 100% identical to SEQ ID NO: 532.

In this aspect, the heavy chain constant domain may comprise SEQ ID NO: 530 or SEQ ID NO: 531.

In this aspect, the multispecific antibody may comprise SEQ ID NO: 526; or SEQ ID NO: 414 and SEQ ID NO: 528. In this aspect, the multispecific antibody may comprise SEQ ID NO: 527; or SEQ ID NO: 414 and SEQ ID NO: 529.

In this aspect the Fab region may be any of the Fab regions described herein (see Table 15, for example). Specifically, the Fab region of this aspect may comprise a VHCDR1, a VHCDR2 and a VHCDR3 comprising the amino acid sequences of SEQ ID NO: 51, 53 and 68, respectively, and a VLCDR1, a VLCDR2 and a VLCDR3 comprising the amino acid sequences of SEQ ID NOs: 79, 80 and 95, respectively. The Fab region of this aspect may comprise a VH comprising SEQ ID NO: 15 and a VL comprising SEQ ID NO: 40.

In one embodiment of this aspect, the multispecific antibody comprises a Fab region comprising a VH comprising the amino acid sequence of SEQ ID NO: 15 and a VL sequence comprising the amino acid sequence of SEQ ID NO: 40; and an Fc region comprising a CH3 domain comprising the amino acid sequence of SEQ ID NO: 532. In some embodiments, the multispecific antibodies of the invention may comprise an additional lysine (K) residue at the immediate C-terminus of the CH3 domain sequence (K447, EU numbering). In some embodiments, the multispecific antibodies of the invention may have the terminal glycine (G) resiside at the immediate C-terminus of the CH3 domain sequence removed (G446, EU

TABLE 15

LEE3 - Example multispecific vδ1-EGFR human IgG1 antibodies having the CDRs of antibodies derived from ADT1-4 and ADT1-7 and the related SEQ ID NOs

| Derived from | Fab Region | | | | | | Fc Region | | |
|---|---|---|---|---|---|---|---|---|---|
| | VH | | | VL | | | | | |
| Antibody | CDR1 | CDR2 | CDR3 | CDR1 | CDR2 | CDR3 | AB loop | CD loop | EF loop |
| Parental ADT1-4 | 51 | 53 | 54 | 79 | 80 | 81 | Residues 359 to 362 (EU numbering) comprise EEGP SEQ ID NO: 523 | Residues 384 to 386 (EU numbering) comprise TYG SEQ ID NO: 511 | Residues 413 to 415 (EU numbering) comprise SYW SEQ ID NO: 533 |
| ADT1-4-105 | 51 | 53 | 55 | 79 | 80 | 82 | | | |
| ADT1-4-107 | 51 | 53 | 56 | 79 | 80 | 83 | | | |
| ADT1-4-110 | 51 | 53 | 57 | 79 | 80 | 84 | | | |
| ADT1-4-112 | 51 | 53 | 58 | 79 | 80 | 85 | | | |
| ADT1-4-117 | 51 | 53 | 59 | 79 | 80 | 86 | | | |
| ADT1-4-19 | 51 | 53 | 60 | 79 | 80 | 87 | | | |
| ADT1-4-21 | 52 | 53 | 61 | 79 | 80 | 88 | | | |
| ADT1-4-31 | 51 | 53 | 62 | 79 | 80 | 89 | | | |
| ADT1-4-139 | 51 | 53 | 63 | 79 | 80 | 90 | | | |
| ADT1-4-4 | 51 | 53 | 64 | 79 | 80 | 91 | | | |
| ADT1-4-143 | 51 | 53 | 65 | 79 | 80 | 92 | | | |
| ADT1-4-53 | 52 | 53 | 66 | 79 | 80 | 93 | | | |
| ADT1-4-173 | 51 | 53 | 67 | 79 | 80 | 94 | | | |
| ADT1-4-2 | 51 | 53 | 68 | 79 | 80 | 95 | | | |
| ADT1-4-8 | 51 | 53 | 69 | 79 | 80 | 96 | | | |
| ADT1-4-82 | 51 | 53 | 70 | 79 | 80 | 97 | | | |
| ADT1-4-83 | 51 | 53 | 71 | 79 | 80 | 98 | | | |
| ADT1-4-3 | 51 | 53 | 72 | 79 | 80 | 99 | | | |
| ADT1-4-84 | 51 | 53 | 73 | 79 | 80 | 100 | | | |
| ADT1-4-86 | 52 | 53 | 74 | 79 | 80 | 101 | | | |
| ADT1-4-95 | 51 | 53 | 75 | 79 | 80 | 102 | | | |
| ADT1-4-1 | 51 | 53 | 76 | 79 | 80 | 103 | | | |
| ADT1-4-6 | 51 | 53 | 77 | 79 | 80 | 104 | | | |
| ADT1-4-138 | 51 | 53 | 78 | 79 | 80 | 105 | | | |
| Parental ADT1-7 | 130 | 131 | 132 | 144 | 145 | 146 | | | |
| ADT1-7-10 | 130 | 131 | 133 | 144 | 145 | 147 | | | |
| ADT1-7-15 | 130 | 131 | 134 | 144 | 145 | 148 | | | |
| ADT1-7-17 | 130 | 131 | 135 | 144 | 145 | 149 | | | |
| ADT1-7-18 | 130 | 131 | 136 | 144 | 145 | 150 | | | |
| ADT1-7-19 | 130 | 131 | 137 | 144 | 145 | 151 | | | |
| ADT1-7-20 | 130 | 131 | 138 | 144 | 145 | 152 | | | |
| ADT1-7-22 | 130 | 131 | 139 | 144 | 145 | 153 | | | |
| ADT1-7-23 | 130 | 131 | 140 | 144 | 145 | 154 | | | |
| ADT1-7-42 | 130 | 131 | 141 | 144 | 145 | 155 | | | |
| ADT1-7-3 | 130 | 131 | 142 | 144 | 145 | 156 | | | |
| ADT1-7-61 | 130 | 131 | 143 | 144 | 145 | 157 | | | |

TABLE 16

LEE3-Example multispecific vδ1-EGFR human IgG1 antibodies having the variable regions of antibodies derived from ADT1-4 and ADT1-7 and the related SEQ ID NOs

| Derived from Antibody | Fab Region | | Fc Region | | |
|---|---|---|---|---|---|
| | VH | VL | AB loop | CD loop | EF loop |
| Parental ADT1-4 | 1 | 26 | Residues 359 to 362 (EU numbering) comprise EEGP SEQ ID NO: 523 | Residues 384 to 386 (EU numbering) comprise TYG SEQ ID NO: 511 | Residues 413 to 415 (EU numbering) comprise SYW SEQ ID NO: 533 |
| ADT1-4-105 | 2 | 27 | | | |
| ADT1-4-107 | 3 | 28 | | | |
| ADT1-4-110 | 4 | 29 | | | |
| ADT1-4-112 | 5 | 30 | | | |
| ADT1-4-117 | 6 | 31 | | | |
| ADT1-4-19 | 7 | 32 | | | |
| ADT1-4-21 | 8 | 33 | | | |
| ADT1-4-31 | 9 | 34 | | | |
| ADT1-4-139 | 10 | 35 | | | |
| ADT1-4-4 | 11 | 36 | | | |
| ADT1-4-143 | 12 | 37 | | | |
| ADT1-4-53 | 13 | 38 | | | |
| ADT1-4-173 | 14 | 39 | | | |
| ADT1-4-2 | 15 | 40 | | | |
| ADT1-4-8 | 16 | 41 | | | |
| ADT1-4-82 | 17 | 42 | | | |
| ADT1-4-83 | 18 | 43 | | | |
| ADT1-4-3 | 19 | 44 | | | |
| ADT1-4-84 | 20 | 45 | | | |
| ADT1-4-86 | 21 | 46 | | | |
| ADT1-4-95 | 22 | 47 | | | |
| ADT1-4-1 | 23 | 48 | | | |
| ADT1-4-6 | 24 | 49 | | | |
| ADT1-4-138 | 25 | 50 | | | |
| Parental ADT1-7 | 106 | 118 | | | |
| ADT1-7-10 | 107 | 119 | | | |
| ADT1-7-15 | 108 | 120 | | | |
| ADT1-7-17 | 109 | 121 | | | |
| ADT1-7-18 | 110 | 122 | | | |
| ADT1-7-19 | 111 | 123 | | | |
| ADT1-7-20 | 112 | 124 | | | |
| ADT1-7-22 | 113 | 125 | | | |
| ADT1-7-23 | 114 | 126 | | | |
| ADT1-7-42 | 115 | 127 | | | |
| ADT1-7-3 | 116 | 128 | | | |
| ADT1-7-61 | 117 | 129 | | | |
| C08 | 273 | 282 | | | |
| B07 | 274 | 283 | | | |
| C05 | 275 | 284 | | | |
| E04 | 276 | 285 | | | |
| F07 | 277 | 286 | | | |
| G06 | 278 | 287 | | | |
| G09 | 279 | 288 | | | |
| B09 | 280 | 289 | | | |
| G10 | 281 | 290 | | | |
| E01 | 312 | 313 | | | |

Vδ1-EGFR Multispecific Antibody (FS1-67)

In this aspect of the invention, a multispecific antibody is provided comprising a Fab region and an Fc region, wherein the Fab region comprises a binding site specific for an epitope of the variable delta 1 (Vδ1) chain of a γδ T cell receptor (TCR); and the Fc region comprises an EGFR binding site. The Fab region specifically comprises a VH and cognate VL domain. The Fc region comprises a binding domain within a heavy chain constant domain (CH1-CH2-CH3), specifically a CH3 domain.

| SEQ ID NO: | Description |
|---|---|
| 377 | Anti-Chick Lysozyme × FS1-67 (EGFR binding domain) |
| 378 | Parent C08 × FS1-67 (LAGA) |
| 379 | Parent G04 × FS1-67 (LAGA) |
| 380 | Parent E07 × FS1-67 (LAGA) |
| 385 | EGFR (FS-167) Binding Module CH1-CH2-CH3 (IgG1 wt) |
| 386 | EGFR (FS-167) Binding Module CH1-CH2-CH3 (LAGA) |
| 388 | ADT1-4-2 × FS1-67 EGFR (LAGA) |
| 399 | ADT1-4-2 × FS1-67 EGFR (wt) |
| 426 | C08 HC (LAGA) EGFR FS1-67 |
| 427 | E07 HC (LAGA) EGFR FS1-67 |
| 431 | ADT1-4-2 HC (LAGA) EGFR FS1-67 |
| 435 | ADT1-4-2 HC (wt) EGFR FS1-67 |
| 437 | G04 HC (LAGA) EGFR FS1-67 |
| 559 | EGFR FS1-67 CH3 Binding Module |
| 560 | EGFR FS1-67 AB substitutions residues 358 to 362 (EU numbering) |
| 511 | EGFR FS1-67 CD substitutions residues 384 to 386 (EU numbering) |
| 512 | EGFR FS1-67 EF substitutions residues 413 to 419 (EU numbering) |
| 561 | EGFR FS1-67 AB Loop residues 355 to 362 (EU numbering) |
| 514 | EGFR FS1-67 CD Loop residues 383 to 391 (EU numbering) |

| SEQ ID NO: | Description |
|---|---|
| 515 | EGFR FS1-67 EF Loop residues 413 to 422 (EU numbering) |

In this aspect the EGFR binding site may be provided by an IgG1 CH3 domain in which residues 358 to 362 (EU numbering) comprise TDDGP (SEQ ID NO: 560), residues 384 to 386 (EU numbering) comprise TYG (SEQ ID NO: 511), and residues 413 to 419 (EU numbering) comprise SYWRWYK (SEQ ID NO: 512).

In this aspect residues 355 to 362 (EU numbering) form an AB loop comprising RDETDDGP (SEQ ID NO: 561), residues 383 to 391 (EU numbering) form an CD loop comprising STYGPENNYKT (SEQ ID NO: 514), and residues 413 to 422 (EU numbering) form an EF loop comprising SYWRWYKGNV (SEQ ID NO: 515).

In this aspect, the IgG1 CH3 domain may comprise the following mutations (EU numbering). In the AB loop the following mutations may be present: L358T.T359D.K360D.N361G.Q362P. In the CD loop the following mutations may be present: N384T.G385Y.Q386G. In the EF loop the following mutations may be present: D413S.K414Y.S415W.Q418Y.Q419K.

In this aspect the amino acid sequence of the CH3 domain may be at least 90% identical to, or at least 95% identical to, or 100% identical to SEQ ID NO: 559.

In this aspect, the heavy chain constant domain may comprise SEQ ID NO: 385 or SEQ ID NO: 386.

In this aspect, the multispecific antibody may comprise SEQ ID NO: 388; or SEQ ID NO: 414 and SEQ ID NO: 431. In this aspect, the multispecific antibody may comprise SEQ ID NO: 399; or SEQ ID NO: 414 and SEQ ID NO: 435.

In this aspect the Fab region may be any of the Fab regions described herein (see Table 17, for example). Specifically, the Fab region of this aspect may comprise a VHCDR1, a VHCDR2 and a VHCDR3 comprising the amino acid sequences of SEQ ID NO: 51, 53 and 68, respectively, and a VLCDR1, a VLCDR2 and a VLCDR3 comprising the amino acid sequences of SEQ ID NOs: 79, 80 and 95, respectively. The Fab region of this aspect may comprise a VH comprising SEQ ID NO: 15 and a VL comprising SEQ ID NO: 40.

In one embodiment of this aspect, the multispecific antibody comprises a Fab region comprising a VH comprising the amino acid sequence of SEQ ID NO: 15 and a VL sequence comprising the amino acid sequence of SEQ ID NO: 40; and an Fc region comprising a CH3 domain comprising the amino acid sequence of SEQ ID NO: 559. In some embodiments, the multispecific antibodies of the invention may comprise an additional lysine (K) residue at the immediate C-terminus of the CH3 domain sequence (K447, EU numbering). In some embodiments, the multispecific antibodies of the invention may have the terminal glycine (G) residue at the immediate C-terminus of the CH3 domain sequence removed (G446, EU In one embodiment, the multispecific antibody of the invention is not ADT1-4×FS1-67.

TABLE 17

FS1-67 - Example multispecific vδ1-EGFR human IgG1 antibodies having the CDRs of antibodies derived from ADT1-4 and ADT1-7 and the related SEQ ID NOs

| Derived from | Fab region | | | | | | Fc region | | |
|---|---|---|---|---|---|---|---|---|---|
| | VH | | | VL | | | | | |
| Antibody | CDR1 | CDR2 | CDR3 | CDR1 | CDR2 | CDR3 | AB loop | CD loop | EF loop |
| Parental ADT1-4 | 51 | 53 | 54 | 79 | 80 | 81 | Residues 358 to 362 (EU numbering) comprise TDDGP SEQ ID NO: 560 | Residues 384 to 386 (EU numbering) comprise TYG SEQ ID NO: 511 | Residues 413 to 419 (EU numbering) comprise SYWRWYK SEQ ID NO: 512 |
| ADT1-4-105 | 51 | 53 | 55 | 79 | 80 | 82 | | | |
| ADT1-4-107 | 51 | 53 | 56 | 79 | 80 | 83 | | | |
| ADT1-4-110 | 51 | 53 | 57 | 79 | 80 | 84 | | | |
| ADT1-4-112 | 51 | 53 | 58 | 79 | 80 | 85 | | | |
| ADT1-4-117 | 51 | 53 | 59 | 79 | 80 | 86 | | | |
| ADT1-4-19 | 51 | 53 | 60 | 79 | 80 | 87 | | | |
| ADT1-4-21 | 52 | 53 | 61 | 79 | 80 | 88 | | | |
| ADT1-4-31 | 51 | 53 | 62 | 79 | 80 | 89 | | | |
| ADT1-4-139 | 51 | 53 | 63 | 79 | 80 | 90 | | | |
| ADT1-4-4 | 51 | 53 | 64 | 79 | 80 | 91 | | | |
| ADT1-4-143 | 51 | 53 | 65 | 79 | 80 | 92 | | | |
| ADT1-4-53 | 52 | 53 | 66 | 79 | 80 | 93 | | | |
| ADT1-4-173 | 51 | 53 | 67 | 79 | 80 | 94 | | | |
| ADT1-4-2 | 51 | 53 | 68 | 79 | 80 | 95 | | | |
| ADT1-4-8 | 51 | 53 | 69 | 79 | 80 | 96 | | | |
| ADT1-4-82 | 51 | 53 | 70 | 79 | 80 | 97 | | | |
| ADT1-4-83 | 51 | 53 | 71 | 79 | 80 | 98 | | | |
| ADT1-4-3 | 51 | 53 | 72 | 79 | 80 | 99 | | | |
| ADT1-4-84 | 51 | 53 | 73 | 79 | 80 | 100 | | | |
| ADT1-4-86 | 52 | 53 | 74 | 79 | 80 | 101 | | | |
| ADT1-4-95 | 51 | 53 | 75 | 79 | 80 | 102 | | | |
| ADT1-4-1 | 51 | 53 | 76 | 79 | 80 | 103 | | | |
| ADT1-4-6 | 51 | 53 | 77 | 79 | 80 | 104 | | | |
| ADT1-4-138 | 51 | 53 | 78 | 79 | 80 | 105 | | | |
| Parental ADT1-7 | 130 | 131 | 132 | 144 | 145 | 146 | | | |
| ADT1-7-10 | 130 | 131 | 133 | 144 | 145 | 147 | | | |
| ADT1-7-15 | 130 | 131 | 134 | 144 | 145 | 148 | | | |
| ADT1-7-17 | 130 | 131 | 135 | 144 | 145 | 149 | | | |
| ADT1-7-18 | 130 | 131 | 136 | 144 | 145 | 150 | | | |

TABLE 17-continued

FS1-67 - Example multispecific vδ1-EGFR human IgG1 antibodies having the
CDRs of antibodies derived from ADT1-4 and ADT1-7 and the related SEQ ID NOs

| Derived from | Fab region | | | | | | Fc region | | |
|---|---|---|---|---|---|---|---|---|---|
| | VH | | | VL | | | | | |
| Antibody | CDR1 | CDR2 | CDR3 | CDR1 | CDR2 | CDR3 | AB loop | CD loop | EF loop |
| ADT1-7-19 | 130 | 131 | 137 | 144 | 145 | 151 | | | |
| ADT1-7-20 | 130 | 131 | 138 | 144 | 145 | 152 | | | |
| ADT1-7-22 | 130 | 131 | 139 | 144 | 145 | 153 | | | |
| ADT1-7-23 | 130 | 131 | 140 | 144 | 145 | 154 | | | |
| ADT1-7-42 | 130 | 131 | 141 | 144 | 145 | 155 | | | |
| ADT1-7-3  | 130 | 131 | 142 | 144 | 145 | 156 | | | |
| ADT1-7-61 | 130 | 131 | 143 | 144 | 145 | 157 | | | |

TABLE 18

FS1-67-Example multispecific vδ1-EGFR human IgG1 antibodies having the variable
regions of antibodies derived from ADT1-4 and ADT1-7 and the related SEQ ID NOs

| Derived from Antibody | Fab region | | Fc region | | |
|---|---|---|---|---|---|
| | VH | VL | AB loop | CD loop | EF loop |
| Parental ADT1-4 | 1 | 26 | Residues 358 to 362 (EU numbering) comprise TDDGP SEQ ID NO: 560 | Residues 384 to 386 (EU numbering) comprise TYG SEQ ID NO: 511 | Residues 413 to 419 (EU numbering) comprise SYWRWYK SEQ ID NO: 512 |
| ADT1-4-105 | 2 | 27 | | | |
| ADT1-4-107 | 3 | 28 | | | |
| ADT1-4-110 | 4 | 29 | | | |
| ADT1-4-112 | 5 | 30 | | | |
| ADT1-4-117 | 6 | 31 | | | |
| ADT1-4-19 | 7 | 32 | | | |
| ADT1-4-21 | 8 | 33 | | | |
| ADT1-4-31 | 9 | 34 | | | |
| ADT1-4-139 | 10 | 35 | | | |
| ADT1-4-4 | 11 | 36 | | | |
| ADT1-4-143 | 12 | 37 | | | |
| ADT1-4-53 | 13 | 38 | | | |
| ADT1-4-173 | 14 | 39 | | | |
| ADT1-4-2 | 15 | 40 | | | |
| ADT1-4-8 | 16 | 41 | | | |
| ADT1-4-82 | 17 | 42 | | | |
| ADT1-4-83 | 18 | 43 | | | |
| ADT1-4-3 | 19 | 44 | | | |
| ADT1-4-84 | 20 | 45 | | | |
| ADT1-4-86 | 21 | 46 | | | |
| ADT1-4-95 | 22 | 47 | | | |
| ADT1-4-1 | 23 | 48 | | | |
| ADT1-4-6 | 24 | 49 | | | |
| ADT1-4-138 | 25 | 50 | | | |
| Parental ADT1-7 | 106 | 118 | | | |
| ADT1-7-10 | 107 | 119 | | | |
| ADT1-7-15 | 108 | 120 | | | |
| ADT1-7-17 | 109 | 121 | | | |
| ADT1-7-18 | 110 | 122 | | | |
| ADT1-7-19 | 111 | 123 | | | |
| ADT1-7-20 | 112 | 124 | | | |
| ADT1-7-22 | 113 | 125 | | | |
| ADT1-7-23 | 114 | 126 | | | |
| ADT1-7-42 | 115 | 127 | | | |
| ADT1-7-3 | 116 | 128 | | | |
| ADT1-7-61 | 117 | 129 | | | |
| C08 | 273 | 282 | | | |
| B07 | 274 | 283 | | | |
| C05 | 275 | 284 | | | |
| E04 | 276 | 285 | | | |
| F07 | 277 | 286 | | | |
| G06 | 278 | 287 | | | |
| G09 | 279 | 288 | | | |
| B09 | 280 | 289 | | | |
| G10 | 281 | 290 | | | |
| E01 | 312 | 313 | | | |

Vδ1-EGFR Multispecific Antibody (FS1-65)

In this aspect of the invention, a multispecific antibody is provided comprising a Fab region and an Fc region, wherein the Fab region comprises a binding site specific for an epitope of the variable delta 1 (Vδ1) chain of a γδ T cell receptor (TCR); and the Fc region comprises an EGFR binding site. The Fab region specifically comprises a VH and cognate VL domain. The Fc region comprises a binding domain within a heavy chain constant domain (CH1-CH2-CH3), specifically a CH3 domain.

| SEQ ID NO: | Description |
|---|---|
| 535 | ADT1-4-2 × FS1-65 (LAGA) |
| 536 | ADT1-4-2 × FS1-65 (wt) |
| 537 | ADT1-4-2 HC EGFR FS1-65 (LAGA) |
| 538 | ADT1-4-2 HC EGFR FS1-65 (wt) |
| 539 | EGFR FS1-65 Binding Module CH1-CH2-CH3 (LAGA) |
| 540 | EGFR FS1-65 Binding Module CH1-CH2-CH3 (wt) |
| 541 | EGFR FS1-65 CH3 binding module |
| 542 | EGFR FS1-65 AB substitutions residues 358 to 362 (INCLUDING 361.1) (EU numbering) |
| 511 | EGFR FS1-65 CD substitutions residues 384 to 386 (EU numbering) |
| 543 | EGFR FS1-65 EF substitutions residues 413 to 419 (EU numbering) |
| 544 | EGFR FS1-65 AB Loop residues 355 to 362 (INCLUDING 361.1) (EU numbering) |
| 514 | EGFR FS1-65 CD Loop residues 383 to 391 (EU numbering) |
| 545 | EGFR FS1-65 EF Loop residues 413 to 422 (EU numbering) |

In this aspect the EGFR binding site may be provided by an IgG1 CH3 domain in which residues 358 to 361, 361.1 and 362 (EU numbering) comprise LDEEGP (SEQ ID NO: 542), residues 384 to 386 (EU numbering) comprise TYG (SEQ ID NO: 511), and residues 413 to 419 (EU numbering) comprise SYWRWVK (SEQ ID NO: 543). Wherein residue 361.1 denotes an additional residue between residue 361 and 362 (EU numbering).

In this aspect residues 355 to 362, inclusive of residue 361.1 (EU numbering) form an AB loop comprising RDEL-DEGGP (SEQ ID NO: 544), residues 383 to 391 (EU numbering) form an CD loop comprising STYGPENNYKT (SEQ ID NO: 514), and residues 413 to 422 (EU numbering) form an EF loop comprising SYWRWVKGNV (SEQ ID NO: 545). Wherein residue 361.1 denotes an additional residue between residue 361 and 362 (EU numbering).

In this aspect, the IgG1 CH3 domain may comprise the following mutations (EU numbering). In the AB loop the following mutations may be present: T359D.K360E.N361G.361-1G.Q362P. In the CD loop the following mutations may be present: N384K.G385F.Q386G. In the EF loop the following mutations may be present: D413S.K414Y.S415W.Q418V.Q419K. Wherein residue 361-1 denotes an additional residue between residue 361 and 362 (EU numbering).

In this aspect the amino acid sequence of the CH3 domain may be at least 90% identical to, or at least 95% identical to, or 100% identical to SEQ ID NO: 541.

In this aspect, the heavy chain constant domain may comprise SEQ ID NO: 539 or SEQ ID NO: 540.

In this aspect, the multispecific antibody may comprise SEQ ID NO: 535; or SEQ ID NO: 414 and SEQ ID NO: 537. In this aspect, the multispecific antibody may comprise SEQ ID NO: 536; or SEQ ID NO: 414 and SEQ ID NO: 538.

In this aspect the Fab region may be any of the Fab regions described herein (see Table 19, for example). Specifically, the Fab region of this aspect may comprise a VHCDR1, a VHCDR2 and a VHCDR3 comprising the amino acid sequences of SEQ ID NO: 51, 53 and 68, respectively, and a VLCDR1, a VLCDR2 and a VLCDR3 comprising the amino acid sequences of SEQ ID NOs: 79, 80 and 95, respectively. The Fab region of this aspect may comprise a VH comprising SEQ ID NO: 15 and a VL comprising SEQ ID NO: 40.

In one embodiment of this aspect, the multispecific antibody comprises a Fab region comprising a VH comprising the amino acid sequence of SEQ ID NO: 15 and a VL sequence comprising the amino acid sequence of SEQ ID NO: 40; and an Fc region comprising a CH3 domain comprising the amino acid sequence of SEQ ID NO: 541. In some embodiments, the multispecific antibodies of the invention may comprise an additional lysine (K) residue at the immediate C-terminus of the CH3 domain sequence (K447, EU numbering). In some embodiments, the multispecific antibodies of the invention may have the terminal glycine (G) residue at the immediate C-terminus of the CH3 domain sequence removed (G446, EU

TABLE 19

FS1-65 - Example multispecific vδ1-EGFR human IgG1 antibodies having the CDRs of antibodies derived from ADT1-4 and ADT1-7 and the related SEQ ID NOs

| Derived from | Fab region | | | | | | Fc region | | |
|---|---|---|---|---|---|---|---|---|---|
| | VH | | | VL | | | | | |
| Antibody | CDR1 | CDR2 | CDR3 | CDR1 | CDR2 | CDR3 | AB loop | CD loop | EF loop |
| Parental ADT1-4 | 51 | 53 | 54 | 79 | 80 | 81 | Residues 358 to 361, 361.1 and 362 (EU numbering) comprise LDEEGP SEQ ID NO: 542 | Residues 384 to 386 (EU numbering) comprise TYG SEQ ID NO: 511 | Residues 413 to 419 (EU numbering) comprise SYWRWVK SEQ ID NO: 543 |
| ADT1-4-105 | 51 | 53 | 55 | 79 | 80 | 82 | | | |
| ADT1-4-107 | 51 | 53 | 56 | 79 | 80 | 83 | | | |
| ADT1-4-110 | 51 | 53 | 57 | 79 | 80 | 84 | | | |
| ADT1-4-112 | 51 | 53 | 58 | 79 | 80 | 85 | | | |
| ADT1-4-117 | 51 | 53 | 59 | 79 | 80 | 86 | | | |
| ADT1-4-19 | 51 | 53 | 60 | 79 | 80 | 87 | | | |
| ADT1-4-21 | 52 | 53 | 61 | 79 | 80 | 88 | | | |
| ADT1-4-31 | 51 | 53 | 62 | 79 | 80 | 89 | | | |
| ADT1-4-139 | 51 | 53 | 63 | 79 | 80 | 90 | | | |
| ADT1-4-4 | 51 | 53 | 64 | 79 | 80 | 91 | | | |
| ADT1-4-143 | 51 | 53 | 65 | 79 | 80 | 92 | | | |
| ADT1-4-53 | 52 | 53 | 66 | 79 | 80 | 93 | | | |
| ADT1-4-173 | 51 | 53 | 67 | 79 | 80 | 94 | | | |
| ADT1-4-2 | 51 | 53 | 68 | 79 | 80 | 95 | | | |

TABLE 19-continued

FS1-65 - Example multispecific vδ1-EGFR human IgG1 antibodies having the CDRs of antibodies derived from ADT1-4 and ADT1-7 and the related SEQ ID NOs

| Derived from Antibody | Fab region | | | | | | Fc region | | |
|---|---|---|---|---|---|---|---|---|---|
| | VH | | | VL | | | | | |
| | CDR1 | CDR2 | CDR3 | CDR1 | CDR2 | CDR3 | AB loop | CD loop | EF loop |
| ADT1-4-8 | 51 | 53 | 69 | 79 | 80 | 96 | | | |
| ADT1-4-82 | 51 | 53 | 70 | 79 | 80 | 97 | | | |
| ADT1-4-83 | 51 | 53 | 71 | 79 | 80 | 98 | | | |
| ADT1-4-3 | 51 | 53 | 72 | 79 | 80 | 99 | | | |
| ADT1-4-84 | 51 | 53 | 73 | 79 | 80 | 100 | | | |
| ADT1-4-86 | 52 | 53 | 74 | 79 | 80 | 101 | | | |
| ADT1-4-95 | 51 | 53 | 75 | 79 | 80 | 102 | | | |
| ADT1-4-1 | 51 | 53 | 76 | 79 | 80 | 103 | | | |
| ADT1-4-6 | 51 | 53 | 77 | 79 | 80 | 104 | | | |
| ADT1-4-138 | 51 | 53 | 78 | 79 | 80 | 105 | | | |
| Parental ADT1-7 | 130 | 131 | 132 | 144 | 145 | 146 | | | |
| ADT1-7-10 | 130 | 131 | 133 | 144 | 145 | 147 | | | |
| ADT1-7-15 | 130 | 131 | 134 | 144 | 145 | 148 | | | |
| ADT1-7-17 | 130 | 131 | 135 | 144 | 145 | 149 | | | |
| ADT1-7-18 | 130 | 131 | 136 | 144 | 145 | 150 | | | |
| ADT1-7-19 | 130 | 131 | 137 | 144 | 145 | 151 | | | |
| ADT1-7-20 | 130 | 131 | 138 | 144 | 145 | 152 | | | |
| ADT1-7-22 | 130 | 131 | 139 | 144 | 145 | 153 | | | |
| ADT1-7-23 | 130 | 131 | 140 | 144 | 145 | 154 | | | |
| ADT1-7-42 | 130 | 131 | 141 | 144 | 145 | 155 | | | |
| ADT1-7-3 | 130 | 131 | 142 | 144 | 145 | 156 | | | |
| ADT1-7-61 | 130 | 131 | 143 | 144 | 145 | 157 | | | |

TABLE 20

FS1-65-Example multispecific vδ1-EGFR human IgG1 antibodies having the variable regions of antibodies derived from ADT1-4 and ADT1-7 and the related SEQ ID NOs

| Derived from Antibody | Fab region | | Fc region | | |
|---|---|---|---|---|---|
| | VH | VL | AB loop | CD loop | EF loop |
| Parental ADT1-4 | 1 | 26 | Residues 358 to 361, 361.1 and 362 (EU numbering) comprise LDEEGP SEQ ID NO: 542 | Residues 384 to 386 (EU numbering) comprise TYG SEQ ID NO: 511 | Residues 413 to 419 (EU numbering) comprise SYWRWVK SEQ ID NO: 543 |
| ADT1-4-105 | 2 | 27 | | | |
| ADT1-4-107 | 3 | 28 | | | |
| ADT1-4-110 | 4 | 29 | | | |
| ADT1-4-112 | 5 | 30 | | | |
| ADT1-4-117 | 6 | 31 | | | |
| ADT1-4-19 | 7 | 32 | | | |
| ADT1-4-21 | 8 | 33 | | | |
| ADT1-4-31 | 9 | 34 | | | |
| ADT1-4-139 | 10 | 35 | | | |
| ADT1-4-4 | 11 | 36 | | | |
| ADT1-4-143 | 12 | 37 | | | |
| ADT1-4-53 | 13 | 38 | | | |
| ADT1-4-173 | 14 | 39 | | | |
| ADT1-4-2 | 15 | 40 | | | |
| ADT1-4-8 | 16 | 41 | | | |
| ADT1-4-82 | 17 | 42 | | | |
| ADT1-4-83 | 18 | 43 | | | |
| ADT1-4-3 | 19 | 44 | | | |
| ADT1-4-84 | 20 | 45 | | | |
| ADT1-4-86 | 21 | 46 | | | |
| ADT1-4-95 | 22 | 47 | | | |
| ADT1-4-1 | 23 | 48 | | | |
| ADT1-4-6 | 24 | 49 | | | |
| ADT1-4-138 | 25 | 50 | | | |
| Parental ADT1-7 | 106 | 118 | | | |
| ADT1-7-10 | 107 | 119 | | | |
| ADT1-7-15 | 108 | 120 | | | |
| ADT1-7-17 | 109 | 121 | | | |
| ADT1-7-18 | 110 | 122 | | | |

TABLE 20-continued

FS1-65-Example multispecific vδ1-EGFR human IgG1 antibodies having the variable regions of antibodies derived from ADT1-4 and ADT1-7 and the related SEQ ID NOs

| | Fab region | | Fc region | | |
|---|---|---|---|---|---|
| Derived from Antibody | VH | VL | AB loop | CD loop | EF loop |
| ADT1-7-19 | 111 | 123 | | | |
| ADT1-7-20 | 112 | 124 | | | |
| ADT1-7-22 | 113 | 125 | | | |
| ADT1-7-23 | 114 | 126 | | | |
| ADT1-7-42 | 115 | 127 | | | |
| ADT1-7-3 | 116 | 128 | | | |
| ADT1-7-61 | 117 | 129 | | | |
| C08 | 273 | 282 | | | |
| B07 | 274 | 283 | | | |
| C05 | 275 | 284 | | | |
| E04 | 276 | 285 | | | |
| F07 | 277 | 286 | | | |
| G06 | 278 | 287 | | | |
| G09 | 279 | 288 | | | |
| B09 | 280 | 289 | | | |
| G10 | 281 | 290 | | | |
| E01 | 312 | 313 | | | |

Vδ1-EGFR Multispecific Antibody (747)

In this aspect of the invention, a multispecific antibody is provided comprising a Fab region and an Fc region, wherein the Fab region comprises a binding site specific for an epitope of the variable delta 1 (Vδ1) chain of a γδ T cell receptor (TCR); and the Fc region comprises an EGFR binding site. The Fab region specifically comprises a VH and cognate VL domain. The Fc region comprises a binding domain within a heavy chain constant domain (CH1-CH2-CH3), specifically a CH3 domain.

| SEQ ID NO: | Description |
|---|---|
| 546 | ADT1-4-2 × 747 (LAGA) |
| 547 | ADT1-4-2 × 747 (wt) |
| 548 | ADT1-4-2 HC EGFR 747 (LAGA) |
| 549 | ADT1-4-2 HC EGFR 747 (wt) |
| 550 | EGFR 747 Binding Module CH1-CH2-CH3 (LAGA) |
| 551 | EGFR 747 Binding Module CH1-CH2-CH3 (wt) |
| 552 | 747 CH3 Binding Module–Plus additional framework mutation A378V |
| 553 | EGFR 747 AB substitutions residues 358 to 362 (EU numbering) |
| 554 | EGFR 747 CD substitutions residues 384 to 386 (EU numbering) |
| 555 | EGFR 747 EF substitutions residues 413 to 421 (EU numbering) |
| 556 | EGFR 747 AB Loop residues 355 to 362 (EU numbering) |
| 557 | EGFR 747 CD Loop residues 383 to 391 (EU numbering) |
| 558 | EGFR 747 EF Loop residues 413 to 422 (EU numbering) |

In this aspect the EGFR binding site may be provided by an IgG1 CH3 domain in which residues 358 to 362 (EU numbering) comprise TESGP (SEQ ID NO: 553), residues 384 to 386 (EU numbering) comprise KFG (SEQ ID NO: 554), residues 413 to 421 (EU numbering) comprise SNLRWTKGH (SEQ ID NO: 555), and residue 378 is valine.

In this aspect residues 355 to 362 (EU numbering) form an AB loop comprising RDETESGP (SEQ ID NO: 556), residues 383 to 391 (EU numbering) form an CD loop comprising SKFGPENNYKT (SEQ ID NO: 557), residues 413 to 422 (EU numbering) form an EF loop comprising SNLRWTKGHV (SEQ ID NO: 558) and residue 378 is valine.

In this aspect, the IgG1 CH3 domain may comprise the following mutations (EU numbering). In the AB loop the following mutations may be present: L358T.T359E.K360S.N361G.Q362P. In the CD loop the following mutations may be present: N384K.G385F.Q386G. In the EF loop the following mutations may be present: D413S.K414N.S415L.Q418T.Q419K.N421H. The following mutation is also present A378V.

In this aspect the amino acid sequence of the CH3 domain may be at least 90% identical to, or at least 95% identical to, or 100% identical to SEQ ID NO: 552.

In this aspect, the heavy chain constant domain may comprise SEQ ID NO: 550 or SEQ ID NO: 551.

In this aspect, the multispecific antibody may comprise SEQ ID NO: 546; or SEQ ID NO: 414 and SEQ ID NO: 548. In this aspect, the multispecific antibody may comprise SEQ ID NO: 547; or SEQ ID NO: 414 and SEQ ID NO: 549.

In this aspect the Fab region may be any of the Fab regions described herein (see Table 21, for example). Specifically, the Fab region of this aspect may comprise a VHCDR1, a VHCDR2 and a VHCDR3 comprising the amino acid sequences of SEQ ID NO: 51, 53 and 68, respectively, and a VLCDR1, a VLCDR2 and a VLCDR3 comprising the amino acid sequences of SEQ ID NOs: 79, 80 and 95, respectively. The Fab region of this aspect may comprise a VH comprising SEQ ID NO: 15 and a VL comprising SEQ ID NO: 40.

In one embodiment of this aspect, the multispecific antibody comprises a Fab region comprising a VH comprising the amino acid sequence of SEQ ID NO: 15 and a VL sequence comprising the amino acid sequence of SEQ ID NO: 40; and an Fc region comprising a CH3 domain comprising the amino acid sequence of SEQ ID NO: 552. In some embodiments, the multispecific antibodies of the invention may comprise an additional lysine (K) residue at the immediate C-terminus of the CH3 domain sequence (K447, EU numbering). In some embodiments, the multispecific antibodies of the invention may have the terminal glycine (G) resisdue at the immediate C-terminus of the CH3 domain sequence removed (G446, EU

TABLE 21

747 - Example multispecific vδ1-EGFR human IgG1 antibodies having the
CDRs of antibodies derived from ADT1-4 and ADT1-7 and the related SEQ ID NOs

| Derived from Antibody | Fab Region | | | | | | Fc Region | | |
|---|---|---|---|---|---|---|---|---|---|
| | VH | | | VL | | | | | |
| | CDR1 | CDR2 | CDR3 | CDR1 | CDR2 | CDR3 | AB loop | CD loop | EF loop |
| Parental ADT1-4 | 51 | 53 | 54 | 79 | 80 | 81 | Residues 358 to 362 (EU numbering) comprise TESGP SEQ ID NO: 553 and residue 378 is valine | Residues 384 to 386 (EU numbering) comprise KFG SEQ ID NO: 554 | Residues 413 to 421 (EU numbering) comprise SNLRWTKGH SEQ ID NO: 555 |
| ADT1-4-105 | 51 | 53 | 55 | 79 | 80 | 82 | | | |
| ADT1-4-107 | 51 | 53 | 56 | 79 | 80 | 83 | | | |
| ADT1-4-110 | 51 | 53 | 57 | 79 | 80 | 84 | | | |
| ADT1-4-112 | 51 | 53 | 58 | 79 | 80 | 85 | | | |
| ADT1-4-117 | 51 | 53 | 59 | 79 | 80 | 86 | | | |
| ADT1-4-19 | 51 | 53 | 60 | 79 | 80 | 87 | | | |
| ADT1-4-21 | 52 | 53 | 61 | 79 | 80 | 88 | | | |
| ADT1-4-31 | 51 | 53 | 62 | 79 | 80 | 89 | | | |
| ADT1-4-139 | 51 | 53 | 63 | 79 | 80 | 90 | | | |
| ADT1-4-4 | 51 | 53 | 64 | 79 | 80 | 91 | | | |
| ADT1-4-143 | 51 | 53 | 65 | 79 | 80 | 92 | | | |
| ADT1-4-53 | 52 | 53 | 66 | 79 | 80 | 93 | | | |
| ADT1-4-173 | 51 | 53 | 67 | 79 | 80 | 94 | | | |
| ADT1-4-2 | 51 | 53 | 68 | 79 | 80 | 95 | | | |
| ADT1-4-8 | 51 | 53 | 69 | 79 | 80 | 96 | | | |
| ADT1-4-82 | 51 | 53 | 70 | 79 | 80 | 97 | | | |
| ADT1-4-83 | 51 | 53 | 71 | 79 | 80 | 98 | | | |
| ADT1-4-3 | 51 | 53 | 72 | 79 | 80 | 99 | | | |
| ADT1-4-84 | 51 | 53 | 73 | 79 | 80 | 100 | | | |
| ADT1-4-86 | 52 | 53 | 74 | 79 | 80 | 101 | | | |
| ADT1-4-95 | 51 | 53 | 75 | 79 | 80 | 102 | | | |
| ADT1-4-1 | 51 | 53 | 76 | 79 | 80 | 103 | | | |
| ADT1-4-6 | 51 | 53 | 77 | 79 | 80 | 104 | | | |
| ADT1-4-138 | 51 | 53 | 78 | 79 | 80 | 105 | | | |
| Parental ADT1-7 | 130 | 131 | 132 | 144 | 145 | 146 | | | |
| ADT1-7-10 | 130 | 131 | 133 | 144 | 145 | 147 | | | |
| ADT1-7-15 | 130 | 131 | 134 | 144 | 145 | 148 | | | |
| ADT1-7-17 | 130 | 131 | 135 | 144 | 145 | 149 | | | |
| ADT1-7-18 | 130 | 131 | 136 | 144 | 145 | 150 | | | |
| ADT1-7-19 | 130 | 131 | 137 | 144 | 145 | 151 | | | |
| ADT1-7-20 | 130 | 131 | 138 | 144 | 145 | 152 | | | |
| ADT1-7-22 | 130 | 131 | 139 | 144 | 145 | 153 | | | |
| ADT1-7-23 | 130 | 131 | 140 | 144 | 145 | 154 | | | |
| ADT1-7-42 | 130 | 131 | 141 | 144 | 145 | 155 | | | |
| ADT1-7-3 | 130 | 131 | 142 | 144 | 145 | 156 | | | |
| ADT1-7-61 | 130 | 131 | 143 | 144 | 145 | 157 | | | |

TABLE 22

747-Example multispecific vδ1-EGFR human IgG1 antibodies having the CDRs
of antibodies derived from ADT1-4 and ADT1-7 and the related SEQ ID NOS

| Derived from Antibody | Fab Region | | Fc Region | | |
|---|---|---|---|---|---|
| | VH | VL | AB loop | CD loop | EF loop |
| Parental ADT1-4 | 1 | 26 | Residues 358 to 362 (EU numbering) comprise TESGP SEQ ID NO: 553 and residue 378 is valine | Residues 384 to 386 (EU numbering) comprise KFG SEQ ID NO: 554 | Residues 413 to 421 (EU numbering) comprise SNLRWTKGH SEQ ID NO: 555 |
| ADT1-4-105 | 2 | 27 | | | |
| ADT1-4-107 | 3 | 28 | | | |
| ADT1-4-110 | 4 | 29 | | | |
| ADT1-4-112 | 5 | 30 | | | |
| ADT1-4-117 | 6 | 31 | | | |
| ADT1-4-19 | 7 | 32 | | | |
| ADT1-4-21 | 8 | 33 | | | |
| ADT1-4-31 | 9 | 34 | | | |
| ADT1-4-139 | 10 | 35 | | | |
| ADT1-4-4 | 11 | 36 | | | |
| ADT1-4-143 | 12 | 37 | | | |
| ADT1-4-53 | 13 | 38 | | | |
| ADT1-4-173 | 14 | 39 | | | |
| ADT1-4-2 | 15 | 40 | | | |
| ADT1-4-8 | 16 | 41 | | | |
| ADT1-4-82 | 17 | 42 | | | |
| ADT1-4-83 | 18 | 43 | | | |
| ADT1-4-3 | 19 | 44 | | | |

TABLE 22-continued

747-Example multispecific vδ1-EGFR human IgG1 antibodies having the CDRs of antibodies derived from ADT1-4 and ADT1-7 and the related SEQ ID NOS

| Derived from Antibody | Fab Region | | Fc Region | | |
|---|---|---|---|---|---|
|  | VH | VL | AB loop | CD loop | EF loop |
| ADT1-4-84 | 20 | 45 | | | |
| ADT1-4-86 | 21 | 46 | | | |
| ADT1-4-95 | 22 | 47 | | | |
| ADT1-4-1 | 23 | 48 | | | |
| ADT1-4-6 | 24 | 49 | | | |
| ADT1-4-138 | 25 | 50 | | | |
| Parental ADT1-7 | 106 | 118 | | | |
| ADT1-7-10 | 107 | 119 | | | |
| ADT1-7-15 | 108 | 120 | | | |
| ADT1-7-17 | 109 | 121 | | | |
| ADT1-7-18 | 110 | 122 | | | |
| ADT1-7-19 | 111 | 123 | | | |
| ADT1-7-20 | 112 | 124 | | | |
| ADT1-7-22 | 113 | 125 | | | |
| ADT1-7-23 | 114 | 126 | | | |
| ADT1-7-42 | 115 | 127 | | | |
| ADT1-7-3 | 116 | 128 | | | |
| ADT1-7-61 | 117 | 129 | | | |
| C08 | 273 | 282 | | | |
| B07 | 274 | 283 | | | |
| C05 | 275 | 284 | | | |
| E04 | 276 | 285 | | | |
| F07 | 277 | 286 | | | |
| G06 | 278 | 287 | | | |
| G09 | 279 | 288 | | | |
| B09 | 280 | 289 | | | |
| G10 | 281 | 290 | | | |
| E01 | 312 | 313 | | | |

Remarkably in all said examples comprising at least one (first) binding domain targeting the Vδ1 chain of a γδ TCR, and at least one (second) binding domain targeting EGFR enhanced functionality was observed versus the controls and component parts (see Examples 2, and 6 to 10 herein).

Collectively, these non-limiting examples highlight the flexibility of the multispecific antibodies or antigen-binding fragments thereof as described herein. These non-limiting examples outline that multispecific antibody approach wherein antibodies of fragments thereof targeting the germline Vδ1 chain (amino acids 1-90 of e.g. SEQ ID NO: 272) may be further enhanced by combining with EGFR binding domains to form multispecific antibodies.

In one embodiment multispecific antibody binding domains which target Vδ1 chain of a γδ TCR (the first target) may comprise (i) one or two or more antibody binding domains each comprising a heavy chain (VH-CH1-CH2-CH3) and a cognate light chain partner (VL-CL) and/or (ii) one or two or more antibody binding domains each comprising a heavy chain variable domain (VH, or VH-CH1) and a cognate light chain variable domain partner (VL, or VL-VC) and/or (iii) one or two or more antibody binding domains each comprising a CDR-containing antibody fragment.

In one embodiment there is provided a multispecific antibody comprising at least one first antibody-derived binding domain targeting the Vδ1 chain of a γδ TCR and which is operatively linked to at least one second antibody binding domain targeting EGFR. Optionally, said binding domains comprise one or more VH and cognate VL binding domain, or one or more VH-CH1-CH2-CH3 and cognate VL-CL binding domain, or one or more antibody fragment binding domains. Said multispecific antibody comprising at least one first antibody-derived binding domain targeting the Vδ1 chain of a γδ TCR is operatively linked to a second binding domain binding the EGF receptor and comprising one or more of the following heavy chain modifications in accordance with EU numbering; L358T and/or (T359D or T359E) and/or (K360D or K360E ["LEE"] or K360S) and/or N361G and/or Q362P and/or 361.1G (wherein 361.1 is an additional residue between 361 and 362) and/or A378V and/or (N384T or N384K) and/or (G385Y or G385F) and/or Q386G and/or D413S and/or (K414Y or K414N) and/or (S415W or S415L) and/or (Q418Y or Q418T or Q418V) and/or Q419K and/or N421H.

Such heavy chain modifications are found to be advantageous. For example, a multispecific antibody comprising at least one first antibody-derived binding domain targeting the Vδ1 chain of a γδ TCR operatively linked to a second binding domain binding EGFR and which include wild-type L358 and T359E and K360E heavy chain modifications have a number of advantages. Firstly, such heavy chain modifications eliminate a double isomerisation risk present in the unmodified heavy chain sequence. Isomerisation motifs are liabilities which have the potential to reduce affinity, potency, stability, and homogeneity of an antibody, which may lead to complications in product development or manufacture. Additionally, a T358L change reverts a threonine back to a leucine in the AB Loop of molecules such as ADT1-4-2×FS1-67. Leucine corresponds to the canonical wild-type human sequence at that position and results in a more conserved AB modified loop sequence. An additional surprising finding is that multispecific antibody comprising at least one first antibody-derived binding domain targeting the Vδ1 chain of a γδ TCR operatively linked to a second binding domain binding the EGF receptor and comprising L358 and with T359E and K360E heavy chain modifications leads to improved expression in transient CHO cells relative to a highly related antibody comprising T358 and D359 and D360 and which is otherwise identical. This improved expression profile means the harvest titre of the CH3 modified multispecific antibodies of this invention from the CHO cells comprising heavy chain CH3 domains with L358 and E359 and E360 (such as incorporated into SEQ ID NO: 389) can be greatly increased when compared to antibodies with the T358, D359 and D360 heavy chain modifications such as incorporated into SEQ ID NO: 388 and which is otherwise identical. This is surprising since removal of isomerisation risks would not be expected to improve expression. See FIG. 34A. In any embodiment, the multispecific antibody of the invention may not comprise additional DD and DG higher-risk isomerisation dual amino acid motifs across position 359, 360 and 361 (EU numbering). Rather, and more specifically, in any embodiment, the multispecific antibody of the invention may comprise a modified AB loop which include modifications T359E, K360E, N361G. More specifically, in any embodiment, the multispecific antibody of the invention may comprise a CH3 modified AB loop comprising a double negative charge at positions 359 and 360 wherein this double negative charge is provided for by glutamic acid (E, Glu) instead of aspartic acid (D, Asp).

A multispecific antibody comprising at least one first antibody-derived binding domain targeting the Vδ1 chain of a γδ TCR is operatively linked to a second binding domain comprising SEQ ID NO: 385 or SEQ ID NO: 386 or SEQ ID NO: 391 or SEQ ID NO: 392 or SEQ ID NO: 520 or SEQ ID NO: 521 or SEQ ID NO: 530 or SEQ ID NO: 531, or SEQ ID NO: 539 or SEQ ID NO: 540, or SEQ ID NO: 508 or SEQ ID NO: 509, or SEQ ID NO: 550 or SEQ ID NO: 551, or functionally equivalent binding variants thereof and which target EGFR. Optionally, multispecific antibodies comprise SEQ ID NO: 389; or SEQ ID NO: 414 and SEQ ID NO: 432; or SEQ ID NO: 400; or SEQ ID NO: 414 and SEQ ID NO: 436; or SEQ ID NO: 516; or SEQ ID NO: 414 and SEQ ID NO: 518; or SEQ ID NO: 517; or SEQ ID NO: 414 and SEQ ID NO: 519; SEQ ID NO: 526; or SEQ ID NO: 414 and SEQ ID NO: 528; or SEQ ID NO: 527; or SEQ ID NO: 414 and SEQ ID NO: 529; or SEQ ID NO: 535; or SEQ ID NO: 414 and SEQ ID NO: 537; or SEQ ID NO: 536; or SEQ ID NO: 414 and SEQ ID NO: 538; or SEQ ID NO: 504; or SEQ ID NO: 414 and SEQ ID NO: 506; or SEQ ID NO: 505; or SEQ ID NO: 414 and SEQ ID NO: 507; or SEQ ID NO: 388; or SEQ ID NO: 414 and SEQ ID NO: 431; or SEQ ID NO: 399; or SEQ ID NO: 414 and SEQ ID NO: 435; or SEQ ID NO: 546; or SEQ ID NO: 414 and SEQ ID NO: 548; or SEQ ID NO: 547; or SEQ ID NO: 414 and SEQ ID NO: 549; or SEQ ID NO: 378; or SEQ ID NO: 425 and SEQ ID NO: 426; or SEQ ID NO: 379; or SEQ ID NO: 421 and SEQ ID NO: 437; or SEQ ID NO: 380; or SEQ ID NO: 423 and SEQ ID NO: 427.

In one aspect of the invention multispecific antibodies of the invention can be used in therapeutically effective amounts to treat a disease or disorder such to ameliorate at least one sign or symptom of a disease or disorder.

In one embodiment, there is provided a method of selecting or characterizing or comparing antibodies or antigen-binding fragment thereof as described herein which bind to the Vδ1 chain of a γδ TCR in a multispecific antibody format wherein said multispecific antibody is applied to Vδ1+ cells in order to measure the conferred effect by said multispecific entity Vδ1+ cells (e.g. upon said Vδ1+ phenotype and/or cytotoxicity and/or diseased-cell specificity and/or enhancement thereof).

Combinatorial Therapies

The multispecific antibodies of the invention may be used in certain combination therapies. In some embodiments, the multispecific antibodies may be combined with a modulator of a cancer antigen or a cancer-associated antigen, for example selected from the group consisting of AFP, AKAP-4, ALK, alpha-fetoprotein, Androgen receptor, B7H3, BAGE, BCA225, BCAA, Bcr-abl, beta-Catenin, beta-HCG, beta-human chorionic gonadotropin, BORIS, BTAA, CA 125, CA 15-3, CA 195, CA 19-9, CA 242, CA 27.29, CA 72-4, CA-50, CAM 17.1, CAM43, Carbonic anhydrase IX, carcinoembryonic antigen, CD22, CD33/IL3Ra, CD68\P1, CDK4, CEA, chondroitin sulfate proteoglycan 4 (CSPG4), c-Met, CO-029, CSPG4, Cyclin B1, cyclophilin C-associated protein, CYP1B1, E2A-PRL, EGFR, EGFRvIII, ELF2M, EpCAM, EphA2, EphrinB2, Epstein Barr virus antigens EBVA, ERG (TMPRSS2ETS fusion gene), ETV6-AML, FAP, FGF-5, Fos-related antigen 1, Fucosyl GM1, G250, Ga733\EpCAM, GAGE-1, GAGE-2, GD2, GD3, glioma-associated antigen, GloboH, Glycolipid F77, GM3, GP 100, GP 100 (Pmel 17), H4-RET, HER-2/neu, HER-2/Neu/ErbB-2, high-molecular-weight melanoma-associated antigen (HMW-MAA), HPV E6, HPV E7, hTERT, HTgp-175, human telomerase reverse transcriptase, Idiotype, IGF-I receptor, IGF-II, IGH-IGK, insulin growth factor (IGF)-I, intestinal carboxyl esterase, K-ras, LAGE-1a, LCK, lectin-reactive AFP, Legumain, LMP2, M344, MA-50, Mac-2 binding protein, MAD-CT-1, MAD-CT-2, MAGE, MAGE A1, MAGE A3, MAGE-1, MAGE-3, MAGE-4, MAGE-5, MAGE-6, MART-1, MART-1/MelanA, M-CSF, melanoma-associated chondroitin sulfate proteoglycan (MCSP), Mesothelin, MG7-Ag, ML-IAP, MN-CA IX, MOV18, MUC1, Mum-1, hsp70-2, MYCN, MYL-RAR, NA17, NB/70K, neuron-glial antigen 2 (NG2), neutrophil elastase, nm-23H1, NuMa, NY-BR-1, NY-CO-1, NY-ESO, NY-ESO-1, NY-ESO-1, OY-TES1, p15, p16, p180erbB3, p185erbB2, p53, p53 mutant, Page4, PAX3, PAX5, PDGFR-beta, PLAC1, Polysialic Acid, prostate-carcinoma tumor antigen-1 (PCTA-1), prostate-specific antigen, prostatic acid phosphatase (PAP), Proteinase3 (PR1), PSA, PSCA, PSMA, RAGE-1, Ras, Ras-mutant, RCAS1, RGS5, RhoC, ROR1, RU1, RU2 (AS), SART3, SDCCAG16, sLe(a), Sperm protein 17, SSX2, STn, Survivin, TA-90, TAAL6, a TAG-72, telomerase, thyroglobulin, Tie 2, TLP, Tn, TPS, TRP-1, TRP-2, TRP-2, TSP-180, Tyrosinase, VEGF, VEGFR2, VISTA, WT1, XAGE 1, 43-9F, 5T4, and 791Tgp72.

In some embodiments, the multispecific antibodies may be combined with a modulator of a immunomodulatory antigen, for example selected from the group consisting of B7-1 (CD80), B7-2 (CD86), B7-DC (CD273), B7-H1 (CD274), B7-H2 (CD275), B7-H3 (CD276), B7-H4 (VTCN1), B7-H5 (VISTA), BTLA (CD272), CD137, CD137L, CD24, CD27, CD28, CD38, CD40, CD40L (CD154), CD54, CD59, CD70, CTLA4 (CD152), CXCL9, GITR (CD357), HVEM (CD270), ICAM-1 (CD54), ICOS (CD278), LAG-3 (CD223), OX40 (CD134), OX40L (CD252), PD-1 (CD279), PD-L1 (CD274), TIGIT, CD314, CD334, CD335, CD337, and TIM-3 (CD366).

In some embodiments, the multispecific antibodies may be combined with a modulator of a CD antigen, for example selected from the group consisting of CD1a, CD1b, CD1c, CD1d, CD1e, CD2, CD3, CD3d, CD3e, CD3g, CD4, CD5, CD6, CD7, CD8, CD8a, CD8b, CD9, CD10, CD11a, CD11b, CD11c, CD11d, CD13, CD14, CD15, CD16, CD16a, CD16b, CD17, CD18, CD19, CD20, CD21, CD22, CD23, CD24, CD25, CD26, CD27, CD28, CD29, CD30, CD31, CD32A, CD32B, CD33, CD34, CD35, CD36, CD37, CD38, CD39, CD40, CD41, CD42, CD42a, CD42b, CD42c, CD42d, CD43, CD44, CD45, CD46, CD47, CD48, CD49a, CD49b, CD49c, CD49d, CD49e, CD49f, CD50, CD51, CD52, CD53, CD54, CD55, CD56, CD57, CD58, CD59, CD60a, CD60b, CD60c, CD61, CD62E, CD62L, CD62P, CD63, CD64a, CD65, CD65s, CD66a, CD66b, CD66c, CD66d, CD66e, CD66f, CD68, CD69, CD70, CD71, CD72, CD73, CD74, CD75, CD75s, CD77, CD79A, CD79B, CD80, CD81, CD82, CD83, CD84, CD85A, CD85B, CD85C, CD85D, CD85F, CD85G, CD85H, CD85I, CD85J, CD85K, CD85M, CD86, CD87, CD88, CD89, CD90, CD91, CD92, CD93, CD94, CD95, CD96, CD97, CD98, CD99, CD100, CD101, CD102, CD103, CD104, CD105, CD106, CD107, CD107a, CD107b, CD108, CD109, CD110, CD111, CD112, CD113, CD114, CD115, CD116, CD117, CD118, CD119, CD120, CD120a, CD120b, CD121a, CD121b, CD122, CD123, CD124, CD125, CD126, CD127, CD129, CD130, CD131, CD132, CD133, CD134, CD135, CD136, CD137, CD138, CD139, CD140A, CD140B, CD141, CD142, CD143, CD144, CDw145, CD146, CD147, CD148, CD150, CD151, CD152, CD153, CD154, CD155, CD156, CD156a, CD156b, CD156c, CD157, CD158, CD158A, CD158B1, CD158B2, CD158C, CD158D, CD158E1, CD158E2, CD158F1, CD158F2, CD158G, CD158H, CD158I, CD158J, CD158K, CD159a, CD159c, CD160, CD161, CD162, CD163, CD164, CD165, CD166, CD167a, CD167b, CD168, CD169, CD170, CD171, CD172a, CD172b, CD172g, CD173, CD174, CD175, CD175s, CD176, CD177, CD178, CD179a, CD179b, CD180, CD181, CD182, CD183, CD184, CD185, CD186, CD187, CD188, CD189, CD190, CD191, CD192, CD193, CD194, CD195, CD196, CD197, CDw198, CDw199, CD200, CD201, CD202b, CD203c, CD204, CD205, CD206, CD207, CD208, CD209, CD210, CDw210a, CDw210b, CD211, CD212, CD213a1, CD213a2, CD214, CD215, CD216, CD217, CD218a, CD218b, CD219, CD220, CD221, CD222, CD223, CD224, CD225, CD226, CD227, CD228, CD229, CD230, CD231, CD232, CD233, CD234, CD235a, CD235b, CD236, CD237, CD238, CD239, CD240CE, CD240D, CD241, CD242, CD243, CD244, CD245, CD246, CD247, CD248, CD249, CD250, CD251, CD252, CD253, CD254, CD255, CD256, CD257, CD258, CD259, CD260, CD261, CD262, CD263, CD264, CD265, CD266, CD267, CD268, CD269, CD270, CD271, CD272, CD273, CD274, CD275, CD276, CD277, CD278, CD279, CD280, CD281, CD282, CD283, CD284, CD285, CD286, CD287, CD288, CD289, CD290, CD291, CD292, CDw293, CD294, CD295, CD296, CD297, CD298, CD299, CD300A, CD300C, CD301, CD302, CD303, CD304, CD305, CD306, CD307, CD307a, CD307b, CD307c, CD307d, CD307e, CD308, CD309, CD310, CD311, CD312, CD313, CD314, CD315, CD316, CD317, CD318, CD319, CD320, CD321, CD322, CD323, CD324, CD325, CD326, CD327, CD328, CD329, CD330, CD331, CD332, CD333, CD334, CD335, CD336, CD337, CD338, CD339, CD340, CD344, CD349, CD351, CD352, CD353, CD354, CD355, CD357, CD358, CD360, CD361, CD362, CD363, CD364, CD365, CD366, CD367, CD368, CD369, CD370, and CD371.

In some embodiments, the modulators may be antagonistic or agonistic. Suitable modulators include antibodies, fusion proteins or small molecules.

Immunoconjugates

The multispecific antibodies of the present invention may be conjugated to a therapeutic moiety, such as a cytotoxin or a chemotherapeutic agent. Such conjugates may be referred to as immunoconjugates. As used herein, the term "immunoconjugate" refers to an antibody which is chemically or biologically linked to another moiety, such as a cytotoxin, a radioactive agent, a cytokine, an interferon, a target or reporter moiety, an enzyme, a toxin, a peptide or protein or a therapeutic agent. The antibody may be linked to the cytotoxin, radioactive agent, cytokine, interferon, target or reporter moiety, enzyme, toxin, peptide or therapeutic agent at any location along the molecule so long as it is able to bind its target. Examples of immunoconjugates include antibody drug conjugates and antibody-toxin fusion proteins. In one embodiment, the agent may be a second different antibody to Vδ1. In certain embodiments, the antibody may be conjugated to an agent specific for a tumor cell or a virally infected cell. The type of therapeutic moiety that may be conjugated to the anti-Vδ1 antibody and will take into account the condition to be treated and the desired therapeutic effect to be achieved. In one embodiment, the agent may be a second antibody, or antigen-binding fragment thereof, that binds to a molecule other than Vδ1.

Cyno-Cross Reactivity

Suitably, the multispecific antibodies exhibit cross-reactivity to both human TRDV1 SEQ ID NO: 272 (including the polymorphic variant i.e. SEQ ID NO: 306) and cyno TRDV1 (SEQ ID NO: 308). Cross reactivity is clearly useful in providing antibodies that can be used in in vivo animal studies during pre-clinical evaluation.

The present inventors have surprisingly identified a framework mutation that can confer increased binding of antibodies, for example anti-Vδ1×EGFR antibodies and antigen-binding fragments thereof, to cynomolgus antigens. The framework mutation does not adversely affect the affinity of the antibody or antigen-binding fragment thereof to the corresponding human version of the antigen. The mutation is the mutation of the serine residue to position 74 according to the IMGT numbering system of a kappa light chain variable sequence to a residue that is not serine (for example a non-human-germline and/or non-polar residue). Non-polar amino acids may be selected from the group consisting of glycine, alanine, valine, methionine, leucine and isoleucine. Non-germline amino acids may be selected from the group consisting of arginine, cysteine, glutamine, glutamic acid, glycine, histidine, isoleucine, leucine, lysine, methionine, phenylalanine, threonine, tryptophan, tyrosine and valine. Non-polar and non-germline amino acids (i.e. amino acids that are both non-polar and non-germline) may be selected from the group consisting of glycine, valine, methionine, leucine and isoleucine). In some embodiments, the mutation is the mutation of the serine residue to position 74 according to the IMGT numbering system of a kappa light chain variable sequence to a leucine residue. The mutation is a direct substitution such the overall length of the chain does not change. Therefore, the serine a position 74 according to the IMGT numbering system is removed and directly replaced with another amino acid (such as a non-human-germline and/or non-polar amino acid, such as a leucine). The substitution may be achieved according to any suitable method known to the skilled person.

References herein to antibodies comprising a kappa light chain variable sequence comprising a residue at position 74 according to the IMGT numbering that is not serine may alternatively be defined as antibodies comprising a light chain variable sequence comprising a LFR1 region, a LCDR1 region, a LFR2 region, a LCDR2 region, a LFR3 region, a LCDR3 region and a LFR4 region, wherein the LFR3 region comprises a residue at position 74 according to the IMGT numbering that is not serine (for example a non-human-germline and/or non-polar amino acid, such as a leucine residue). Such an alternative definition is applicable to all antibodies disclosed herein comprising a kappa light chain variable sequence comprising a residue at position 74 according to the IMGT numbering that is not serine (for example a non-human-germline and/or non-polar amino acid, such as a leucine residue).

Accordingly, the present invention provides anti-TCR delta variable 1 (anti-Vδ1)×EGFR multispecific antibodies or antigen-binding fragments thereof comprising a kappa light chain variable sequence, in which the residue at position 74 according to the IMGT numbering system of the light chain variable sequence is a not serine (for example a non-human-germline and/or non-polar amino acid, such as a leucine residue). In some embodiments, the residue at position 74 according to the IMGT numbering system of the light chain variable sequence is a leucine. Suitably, the antibody may be an IgG antibody. For example, the antibody may be IgG1 antibody.

The anti-Vδ1×EGFR multispecific antibodies and antigen-binding fragments thereof provided herein may be provided with the substitution at position 74 (according to the IMGT numbering system) of the light chain variable sequence. For example, the anti-Vδ1×EGFR multispecific antibodies and antigen-binding fragments and variants thereof described herein may comprise a kappa light chain variable sequence comprising a residue other than serine at position 74 according to the IMGT numbering system (for example a non-human-germline and/or non-polar amino acid, such as a leucine residue). In some embodiments, the anti-Vδ1×EGFR multispecific antibodies and antigen-binding fragments and variants thereof described herein may comprise a kappa light chain variable sequence comprising a leucine residue at position 74 according to the IMGT numbering system. Embodiments comprising a mutation at position 74 according to the IMGT numbering system of a kappa light chain may be particularly relevant to antibodies derived from ADT1-4, although the mutation is equally applicable to other antibodies. For example, it is observed that light chain position 74 is not highly conserved across the different kappa/lambda light chain germlines. Further it is noted that differing light chain germlines contain differently polarising and/or charged amino acids at this position ranging from non-polar (e.g. alanine) to polar neutral (e.g. serine) to negatively or positively charged (e.g. aspartate or asparagine respectively). It is well understood that amino acid polarity/charge at any given position may impact protein structure. For example, it is well understood that a change in polarity and charge can impact hydrophobicity and tendency for an amino acid to be more surface exposed or more buried. Regardless, this remarkable finding highlights that non-conservative amino acid changes at light chain position 74 can modify affinity to a selected target by greater than 10-fold. Hence aside improving affinity as outlined herein, use of this knowledge may offer a new approach to dialling up or down affinity more broadly. For example, a method comprising changing the residue at position 74 from more polar to non-polar, or for example non-polar to more charged, may be more preferable to complex/cumbersome mutagenesis methods such as saturation mutagenesis etc when one desires to dial up or dial down affinity for any given antibody.

In a further embodiment of the invention there is also provided a method of mutating an antibody or antigen-binding fragment thereof, comprising providing an antibody comprising a kappa light chain having a serine at position 74 of the light chain variable sequence according to the IMGT numbering system, and mutating the serine to a different residue, for example a non-human-germline and/or non-polar amino acid, such as a leucine. In some embodiments, the antibody is an anti-TCR delta variable 1 (anti-Vδ1) antibody or antigen-binding fragment thereof. In some embodiments, the antibody is an antibody having a VH comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 1 and a VL comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical identical to SEQ ID NO: 26 both before and after the mutation at position 74 of the light chain variable sequence is introduced. In some embodiments, the antibody is an antibody having a VH comprising an amino acid sequence that is 100% identical to SEQ ID NO: 1 with the exception of the mutation at position 74 and a VL comprising an amino acid sequence that is 100% identical to SEQ ID NO: 26 with the exception of the mutation at position 74.

In some embodiments, the antibody is an antibody having a VH comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 106 and a VL comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 118 both before and after the mutation at position 74 of the light chain variable sequence is introduced. In some embodiments, the antibody is an antibody having a VH comprising an amino acid sequence that is 100% identical to SEQ ID NO: 106 with the exception of the mutation at position 74 and a VL comprising an amino acid sequence that is 100% identical to SEQ ID NO: 118 with the exception of the mutation at position 74.

In some embodiments, the antibody is an antibody comprising:
   a VH comprising an amino acid sequence that is at least 70%, at least 75%, at least 80%, at least least 97%, at least 98%, or at least 99% identical to the amino acid sequence of SEQ ID NO: 273 and a VL comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 282 both before and after the mutation is introduced;
   a VH comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 274 and a VL comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 283 both before and after the mutation is introduced;
   a VH comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 275 and a VL comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 284 both before and after the mutation is introduced;
a VH comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 276 and a VL comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical identical to the amino acid sequence of SEQ ID NO: 285 both before and after the mutation is introduced;
a VH comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 277 and a VL comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 286 both before and after the mutation is introduced;
a VH comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 278 and a VL comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 287 both before and after the mutation is introduced;
a VH comprising an amino acid sequence that is at least 70%, at least 75%, at least 80%, at least least 97%, at least 98%, or at least 99% identical to the amino acid sequence of SEQ ID NO: 279 and a VL comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 288 both before and after the mutation is introduced;
a VH comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 280 and a VL comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 289 both before and after the mutation is introduced;
a VH comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 281 and a VL comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 290 both before and after the mutation is introduced; or
a VH comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 312 and a VL comprising an amino acid sequence that is at least 70%, at least 75%, at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 313 both before and after the mutation is introduced.

In some embodiments, the antibody is an antibody comprising:
a VH comprising the amino acid sequence of SEQ ID NO: 273 and a VL comprising the amino acid sequence of SEQ ID NO: 282;
a VH comprising the amino acid sequence of SEQ ID NO: 274 and a VL comprising the amino acid sequence of SEQ ID NO: 283;
a VH comprising the amino acid sequence of SEQ ID NO: 275 and a VL comprising the amino acid sequence of SEQ ID NO: 284;
a VH comprising the amino acid sequence of SEQ ID NO: 276 and a VL comprising the amino acid sequence of SEQ ID NO: 285;
a VH comprising the amino acid sequence of SEQ ID NO: 277 and a VL comprising the amino acid sequence of SEQ ID NO: 286;
a VH comprising the amino acid sequence of SEQ ID NO: 278 and a VL comprising the amino acid sequence of SEQ ID NO: 287;
a VH comprising the amino acid sequence of SEQ ID NO: 279 and a VL comprising the amino acid sequence of SEQ ID NO: 288;
a VH comprising the amino acid sequence of SEQ ID NO: 280 and a VL comprising the amino acid sequence of SEQ ID NO: 289;
a VH comprising the amino acid sequence of SEQ ID NO: 281 and a VL comprising the amino acid sequence of SEQ ID NO: 290; or
a VH comprising the amino acid sequence of SEQ ID NO: 312 and a VL comprising the amino acid sequence of SEQ ID NO: 313.

The antibody produced by such methods has 100% identity to the specified VH and VL sequences, with the exception of the mutation at position 74.

In some embodiments, the mutation at position 74 increases the affinity of the antibody or antigen-binding fragment thereof for a homologous cynomolgus (cyno) monkey antigen. The increase of the affinity of the antibody or antigen-binding fragment thereof is relative to the affinity of the antibody or antigen-binding fragment thereof before the mutation was introduced (when measured under the same or substantially the same conditions). In some embodiments, the antibody or antigen-binding fragment thereof is an anti-TCR delta variable 1 (anti-Vδ1) antibody or antigen-binding fragment thereof that binds to a human variable delta 1 (Vδ1) chain of a γδ T cell receptor (TCR) (for example SEQ ID NO: 272 and 306) before and after the mutation is introduced, and the antibody has increased affinity for a cynomolgus monkey variable delta 1 (Vδ1) chain of a γδ T cell receptor (TCR) (for example SEQ ID NO: 308) after the mutation is introduced.

Polynucleotide Sequences and Expression Vectors

In one aspect of the invention there is provided a polynucleotide encoding the multispecific antibody of the invention. In one embodiment, the polynucleotide comprises or consists of a sequence having at least 70%, such as at least 80%, such as at least 90%, such as at least 95%, such as at least 99% sequence identity with any one of SEQ ID NOs: 199 to 222, 224 to 247, 249 to 259 or 261 to 271. In a further embodiment the polynucleotide comprises or consists of any one of SEQ ID NOs: 199 to 222, 224 to 247, 249 to 259 or 261 to 271. In a further aspect there is provided a cDNA comprising said polynucleotide.

In one aspect of the invention there is provided a polynucleotide comprising or consisting of a sequence having at least 70%, such as at least 80%, such as at least 90%, such as at least 95%, such as at least 99% sequence identity with any one of the portions SEQ ID NOs: 199 to 222, 224 to 247, 249 to 259 or 261 to 271 which encodes CDR1, CDR2 and/or CDR3 of the encoded immunoglobulin chain variable domain.

In one aspect of the invention there is provided a polynucleotide comprising or consisting of a sequence having at least 70%, such as at least 80%, such as at least 90%, such as at least 95%, such as at least 99% sequence identity with any one of the portions of SEQ ID NOs: 199 to 222, 224 to 247, 249 to 259 or 261 to 271 which encodes FR1, FR2, FR3 and/or FR4 of the encoded immunoglobulin chain variable domain.

The present invention also provides expression vectors and plasmids comprising the polynucleotide sequences of the invention. In some embodiments, the expression vectors comprise a sequence having at least 70%, such as at least 80%, such as at least 90%, such as at least 95%, such as at least 99% sequence identity or 100% identity with any one of SEQ ID NOs: 199 to 222 or 249 to 259 (encoding variable heavy regions). In some embodiments, the expression vectors comprise a sequence having at least 70%, such as at least 80%, such as at least 90%, such as at least 95%, such as at least 99% sequence identity or 100% identity with any one of SEQ ID NOs: 224 to 247 or 261 to 271 (encoding variable light regions). Such expression vectors may be used in pairs, suitable pairing the heavy and light chain variable sequences according to the pairing of various amino acid sequences providing the multispecific antibodies of the invention disclosed herein. In some embodiments, the expression vectors comprise a sequence having at least 70%, such as at least 80%, such as at least 90%, such as at least 95%, such as at least 99% sequence identity or 100% identity with any one of SEQ ID NOs: 199 to 222 or 249 to 259 (encoding a variable heavy region) and further comprises a sequence having at least 70%, such as at least 80%, such as at least 90%, such as at least 95%, such as at least 99% sequence identity or 100% identity with any one of SEQ ID NOs: 224 to 247 or 261 to 271 (encoding a variable light region). Again, the sequences may be provided in specific pairs as described herein to encode the multispecific antibodies of the invention.

The present invention also provides polynucleotide sequences and expression vectors and plasmids encoding all of the antibody sequences disclosed herein, including any variant antibody sequences disclosed herein optionally comprising one or more amino acid substitutions.

The polynucleotides and expression vectors of the invention may also be described in reference to the amino acid sequence encoded. Therefore, in one embodiment, the polynucleotide comprises or consists of a sequence encoding the amino acid sequence of any one of SEQ ID NOs: 1 to 197.

To express the multispecific antibodies, or antigen-binding fragments thereof, polynucleotides encoding partial or full-length light and heavy chains, as described herein, are inserted into expression vectors such that the genes are operatively linked to transcriptional and translational control sequences. Therefore, in one aspect of the invention there is provided an expression vector comprising the polynucleotide sequence as defined herein. In one embodiment, the expression vector comprises the VH region of any one of SEQ ID NOs: 199 to 222 or 249 to 259. In another embodiment, the expression vector comprises the VL region of any one of SEQ ID NOs: 224 to 247 or 261 to 271.

It will be understood that the nucleotide sequences described herein may comprise additional sequences encoding amino acid residues to aid with translation, purification and detection, however alternative sequences may be used depending upon the expression system used. These optional sequences can be removed, modified or substituted if alternate design, translation, purification or detection strategies are adopted.

Mutations can be made to the DNA or cDNA that encode polypeptides which are silent as to the amino acid sequence of the polypeptide, but which provide preferred codons for translation in a particular host. The preferred codons for translation of a nucleic acid in, e.g. *E. coli* and *S. cerevisiae*, as well as mammalian, specifically human, are known.

Mutation of polypeptides can be achieved for example by substitutions, additions or deletions to a nucleic acid encoding the polypeptide. The substitutions, additions or deletions to a nucleic acid encoding the polypeptide can be introduced by many methods, including for example error-prone PCR, shuffling, oligonucleotide-directed mutagenesis, assembly PCR, PCR mutagenesis, in vivo mutagenesis, cassette mutagenesis, recursive ensemble mutagenesis, exponential ensemble mutagenesis, site-specific mutagenesis, gene reassembly, artificial gene synthesis, Gene Site Saturation Mutagenesis (GSSM), synthetic ligation reassembly (SLR) or a combination of these methods. The modifications, additions or deletions to a nucleic acid can also be introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, ensemble mutagenesis, chimeric nucleic acid multimer creation, or a combination thereof.

In particular, artificial gene synthesis may be used. A gene encoding a polypeptide of the invention can be synthetically produced by, for example, solid-phase DNA synthesis. Entire genes may be synthesized de novo, without the need for precursor template DNA. To obtain the desired oligonucleotide, the building blocks are sequentially coupled to the growing oligonucleotide chain in the order required by the sequence of the product. Upon the completion of the chain assembly, the product is released from the solid phase to solution, deprotected, and collected. Products can be isolated by high-performance liquid chromatography (HPLC) to obtain the desired oligonucleotides in high purity.

Expression vectors include, for example, plasmids, retroviruses, cosmids, yeast artificial chromosomes (YACs) and Epstein-Barr virus (EBV) derived episomes. The polynucleotide is ligated into a vector such that transcriptional and translational control sequences within the vector serve their intended function of regulating the transcription and translation of the polynucleotide. Expression and/or control sequences can include promoters, enhancers, transcription terminators, a start codon (i.e. ATG) 5' to the coding sequence, splicing signals for introns and stop codons. The expression vector and expression control sequences are chosen to be compatible with the expression host cell used. For example, the sequences may comprise nucleotide sequences encoding single chain variable fragments versions of the antibodies invention, comprising a VH region and a VL region joined by a synthetic linker (e.g. encoding SEQ ID NO: 291). It will be understood that polynucleotides or expression vectors of the invention may comprise the VH region, the VL region or both (optionally including the linker). Therefore, polynucleotides encoding the VH and VL regions can be inserted into separate vectors, alternatively sequences encoding both regions are inserted into the same expression vector. The polynucleotide(s) are inserted into the expression vector by standard methods (e.g. ligation of complementary restriction sites on the polynucleotide and vector, or blunt end ligation if no restriction sites are present).

A convenient vector is one that encodes a functionally complete human CH or CL immunoglobulin sequence, with appropriate restriction sites engineered so that any VH or VL sequence can be easily inserted and expressed, as described herein. The expression vector can also encode a signal peptide that facilitates secretion of the antibody (or antigen-binding fragment thereof) from a host cell. The polynucleotide may be cloned into the vector such that the signal peptide is linked in-frame to the amino terminus of the antibody. The signal peptide can be an immunoglobulin signal peptide or a heterologous signal peptide (i.e. a signal peptide from a non-immunoglobulin protein).

In one aspect of the invention there is provided a cell (e.g. a host cell, such as a recombinant host cell) comprising the polynucleotide or expression vector as defined herein. It will be understood that the cell may comprise a first vector encoding the light chain of the antibody or antigen-binding fragment thereof, and a second vector encoding the heavy chain of the antibody or antigen-binding fragment thereof. Alternatively, the heavy and light chains both encoded on the same expression vector introduced into the cell.

In one embodiment, the polynucleotide or expression vector encodes a membrane anchor or transmembrane domain fused to the antibody or antigen-binding fragment thereof, wherein the antibody or antigen-binding fragment thereof is presented on an extracellular surface of the cell.

Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors.

Mammalian cell lines available as hosts for expression are well known in the art and include many immortalized cell lines available from the AMERICAN TYPE CULTURE COLLECTION® (ATCC®). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g. Hep G2), A549 cells, 3T3 cells, and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. Antigen-binding fragments of antibodies such as the scFv and Fv fragments can be isolated and expressed in *E. coli* using methods known in the art.

The antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Antibodies (or fragments) of the invention can be obtained and manipulated using the techniques disclosed for example in Green and Sambrook, *Molecular Cloning: A Laboratory Manual* (2012) 4th Edition Cold Spring Harbour Laboratory Press.

Monoclonal antibodies can be produced using hybridoma technology, by fusing a specific antibody-producing B cell with a myeloma (B cell cancer) cell that is selected for its ability to grow in tissue culture and for an absence of antibody chain synthesis.

A monoclonal antibody directed against a determined antigen can, for example, be obtained by:
a) immortalizing lymphocytes obtained from the peripheral blood of an animal previously immunized with a determined antigen, with an immortal cell and preferably with myeloma cells, in order to form a hybridoma,
b) culturing the immortalized cells (hybridoma) formed and recovering the cells producing the antibodies having the desired specificity.

Alternatively, the use of a hybridoma cell is not required. Antibodies capable of binding to the target antigens as described herein may be isolated from a suitable antibody library via routine practice, for example, using the phage display, yeast display, ribosomal display, or mammalian display technology known in the art. Accordingly, monoclonal antibodies can be obtained, for example, by a process comprising the steps of:
a) cloning into vectors, especially into phages and more particularly filamentous bacteriophages, DNA or cDNA sequences obtained from lymphocytes especially peripheral blood lymphocytes of an animal (suitably previously immunized with determined antigens),
b) transforming prokaryotic cells with the above vectors in conditions allowing the production of the antibodies,
c) selecting the antibodies by subjecting them to antigen-affinity selection,
d) recovering the antibodies having the desired specificity.

Optionally, isolated polynucleotide encoding antibodies or antigen-binding fragment thereof as described herein and which bind to the Vδ1 chain of a γδ can also be readily manufactured to make sufficient quantities to be employed as a medicaments to ameliorate the signs or symptoms of disease. When employed as a medicament in this manner, typically the polynucleotides of interest are first operatively linked to an expression vector or expression cassette designed to express said antibodies or antigen-binding fragment thereof in a subject or patient. Such expression cassettes and methods of delivery of polynucleotides or what are sometime termed 'nucleic-based' medicaments are well known in the art. For recent review see Hollevoet and Declerck (2017) J. Transl. Med. 15(1): 131.

Also provided is a method for the production of an anti-Vδ1 antibody or antigen-binding fragment or variant thereof, comprising culturing a host cell of the invention in a cell culture medium under conditions to express the encoding nucleic acid sequence of the plasmid or vector inside the cell. The method may further comprise obtaining the anti-Vδ1 antibody or antigen-binding fragment or variant thereof from the cell culture supernatant. The obtained antibody may then be formulated into a pharmaceutical composition. Further, there is provided a method of producing cell that expresses an anti-Vδ1 antibody or antigen-binding fragment or variant thereof, comprising transfecting said cell with a plasmid or vector of the invention. Said cells can then be cultured for the production of the anti-Vδ1 antibody or antigen-binding fragment or variant thereof.

Pharmaceutical Compositions

According to a further aspect of the invention, there is provided a composition comprising the multispecific antibodies as defined herein. In such embodiments, the composition may comprise the antibody, optionally in combination with other excipients. Also included are compositions comprising one or more additional active agents (e.g. active agents suitable for treating the diseases mentioned herein).

According to a further aspect of the invention, there is provided a pharmaceutical composition comprising the antibody or antigen-binding fragment thereof as defined herein, together with a pharmaceutically acceptable diluent or carrier. The multispecific antibodies of the invention can be incorporated into pharmaceutical compositions suitable for administration to a subject. Typically, the pharmaceutical composition comprises an antibody of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, salts, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable substances such as wetting or minor amounts of auxiliary substances such as wetting or emulsifying agents, preservatives or buffers, which enhance the shelf life or effectiveness of the antibody or antigen-binding fragment thereof.

The compositions of this invention may be in a variety of forms. These include, for example, liquid, semi-solid and solid dosage forms, such as liquid solutions (e.g. injectable and infusible solutions), dispersions or suspensions, tablets, pills, powders, liposomes and suppositories. The preferred form depends on the intended mode of administration and therapeutic application. Typical preferred compositions are in the form of injectable or infusible solutions.

The preferred mode of administration is parenteral (e.g. intravenous, subcutaneous, intraperitoneal, intramuscular, intrathecal). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration.

It is within the scope of the invention to use the pharmaceutical composition of the invention in therapeutic methods for the treatment of diseases as described herein as an adjunct to, or in conjunction with, other established therapies normally used in the treatment of such diseases.

In a further aspect of the invention, the antibody, composition or pharmaceutical composition is administered sequentially, simultaneously or separately with at least one active agent.

Treatment Methods

According to a further aspect of the invention, there is provided an isolated multispecific antibody as defined herein for use as a medicament. References herein to an antibody "for use" as a medicament or in therapy are limited to administration of the antibody to a subject.

In one embodiment, the multispecific antibody is for use in the treatment of cancer. In one embodiment, the invention is a method of treating a disease or disorder in a subject in need thereof, comprising the step of administering an multispecific antibody to the subject. In various embodiments, the disease or disorder is cancer. In one embodiment, the multispecific antibody is for use in the treatment of cancer, leads to the death of diseased cells while sparing healthy cells. In a further embodiment, the antibody or antigen-binding fragment thereof is for use in the treatment of cancer.

In one embodiment, the antibody or antigen-binding fragment thereof is for use in the treatment of cancer. In a further embodiment, the antibody or antigen-binding fragment thereof is for use in the treatment of cancer.

According to a further aspect of the invention, there is provided the pharmaceutical composition as defined herein for use as a medicament. In one embodiment, the pharmaceutical composition is for use in the treatment of cancer. In a further embodiment, the pharmaceutical composition is for use in the treatment of cancer.

According to a further aspect of the invention, there is provided a method of modulating an immune response in a subject in need thereof comprising administering a therapeutically effective amount of the isolated multispecific antibody as defined herein. In various embodiments, modulating an immune response in a subject comprises binding or targeting γδ T cells, activating γδ T cells, causing or increasing proliferation of γδ T cells, causing or increasing expansion of γδ T cells, causing or increasing γδ T cell degranulation, causing or increasing γδ T cell mediated killing activity, causing or increasing γδ T cell mediated killing activity while sparing healthy cells, causing or increasing γδ T cytotoxicity, causing or increasing γδ T cytotoxicity while sparing healthy cells, causing or increasing γδ T cell mobilization, increasing survival of γδ T cells, or increasing resistance to exhaustion of γδ T cells. Modulating the immune response in a subject may further comprise binding or targeting the second antigen. For example, in some embodiments, binding of the second antigen, in particular when it is an immunomodulatory antigen, may stimulate immunomodulation via the second antigen in addition to immunomodulation via binding of the multispecific antibody to TRDV1. Hence the modulation of the immune response may comprise modulation via two different signalling pathways, a first signalling pathway modulated via TRDV1 antigen engagement and a second signalling pathway modulated via engagement of a second immunomodulatory antigen.

According to a further aspect of the invention, there is provided method of treating a cancer in a subject in need thereof, comprising administering a therapeutically effective amount of the multispecific antibody as defined herein. Alternatively, a therapeutically effective amount of the pharmaceutical composition is administered.

According to further aspects of the invention, there is provided the use of an antibody or antigen-binding fragment thereof as defined herein for the manufacture of a medicament, for example in the treatment of cancer.

In one embodiment, the antibody or antigen-binding fragment thereof is administered to a subject, wherein the subject has cancer.

According to a further aspect of the invention, there is provided the pharmaceutical composition as defined herein for use as a medicament. In one embodiment, the pharmaceutical composition is administered to a subject, wherein the subject has cancer.

According to a further aspect of the invention, there is provided a method of administering a therapeutically effective amount of the isolated multispecific antibody as defined herein to a subject, wherein the subject has cancer. Alternatively, a therapeutically effective amount of the pharmaceutical composition is administered.

According to further aspects of the invention, there is provided the use of an antibody or antigen-binding fragment thereof as defined herein for the manufacture of a medicament, for example for the administration to a subject, wherein the subject has cancer.

In various embodiments, the cancer that can be treated by the disclosed methods and compositions include, but are not limited to acute lymphoblastic, acute myeloid leukemia, adrenocortical carcinoma, appendix cancer, basal cell carcinoma, bile duct cancer, bladder cancer, bone cancer, osteosarcoma and malignant fibrous histiocytoma, brain stem glioma, brain tumor, brain tumor, brain stem glioma, central nervous system atypical teratoid/rhabdoid tumor, central nervous system embryonal tumors, cerebellar astrocytoma, cerebral astrocytoma/malignant glioma, craniopharyngioma, ependymoblastoma, ependymoma, medulloblastoma, medulloepithelioma, pineal parenchymal tumors of intermediate differentiation, supratentorial primitive neuroectodermal tumors and pineoblastoma, visual pathway and hypothalamic glioma, brain and spinal cord tumors, breast cancer, bronchial tumors, Burkitt lymphoma, carcinoid tumor, gastrointestinal carcinoid tumor, central nervous system atypical teratoid/rhabdoid tumor, central nervous system embryonal tumors, central nervous system lymphoma, cerebellar astrocytoma cerebral astrocytoma/malignant glioma, cervical cancer, chordoma, chronic lymphocytic leukemia, chronic myelogenous leukemia, chronic myeloproliferative disorders, colon cancer, colorectal cancer, craniopharyngioma, cutaneous T-cell lymphoma, esophageal cancer, Ewing family of tumors, extragonadal germ cell tumor, extrahepatic bile duct cancer, intraocular melanoma, retinoblastoma, gallbladder cancer, gastric (stomach) cancer, gastrointestinal carcinoid tumor, gastrointestinal stromal tumor (gist), germ cell tumor, gestational trophoblastic tumor, glioma, glioma brain stem, glioma cerebral astrocytoma, glioma visual pathway and hypothalamic, hairy cell leukemia, head and neck cancer, hepatocellular (liver) cancer, Langerhans cell histiocytosis, Hodgkin lymphoma, hypopharyngeal cancer, hypothalamic and visual pathway glioma, intraocular melanoma, islet cell tumors, kidney (renal cell) cancer, Langerhans cell histiocytosis, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, non-small cell lung cancer, small cell lung cancer, aids-related lymphoma, Burkitt lymphoma, cutaneous T-cell lymphoma, non-Hodgkin lymphoma, primary central nervous system lymphoma, Waldenstrom macroglobulinemia, malignant fibrous histiocvtoma of bone and osteosarcoma, medulloblastoma, melanoma, Merkel cell carcinoma, mesothelioma, metastatic squamous neck cancer with occult primary, mouth cancer, multiple endocrine neoplasia syndrome, multiple myeloma/plasma cell neoplasm, mycosis, fungoides, myelodysplastic syndromes, myelodysplastic/myeloproliferative diseases, myelogenous leukemia, myeloid leukemia, myeloid leukemia acute, multiple myeloma, myeloproliferative disorders, nasal cavity and paranasal sinus cancer, nasopharyngeal cancer, neuroblastoma, non-small cell lung cancer, oral cancer, oral cavity cancer, oropharyngeal cancer, osteosarcoma and malignant fibrous histiocytoma of bone, ovarian cancer, ovarian epithelial cancer, ovarian germ cell tumor, ovarian low malignant potential tumor, pancreatic cancer, pancreatic cancer, papillomatosis, parathyroid cancer, penile cancer, pharyngeal cancer, pheochromocytoma, pineal parenchymal tumors of intermediate differentiation, pineoblastoma and supratentorial primitive neuroectodermal tumors, pituitary tumor, plasma celt neoplasm/multiple myeloma, pleuropulmonary blastoma, primary central nervous system lymphoma, prostate cancer, rectal cancer, renal cell (kidney) cancer, renal pelvis and ureter, respiratory tract carcinoma involving the nut gene on chromosome 15, retinoblastoma, rhabdomyosarcoma, salivary gland cancer, sarcoma, Ewing family of tumors, Kaposi sarcoma, soft tissue sarcoma, uterine sarcoma, Sezary syndrome, skin cancer (nonmelanoma), skin cancer (melanoma), Merkel cell skin carcinoma, small cell lung cancer, small intestine cancer, soft tissue sarcoma, squamous cell carcinoma, squamous neck cancer, stomach (gastric) cancer, supratentorial primitive neuroectodermal tumors, T-cell lymphoma, testicular cancer, throat cancer, thymoma and thymic carcinoma, thyroid cancer, transitional cell cancer of the renal pelvis and ureter, gestational trophoblastic tumor, urethral cancer, uterine cancer, uterine sarcoma, vaginal cancer, vulvar cancer, Waldenstrom macroglobulinemia, and Wilms tumor. In various embodiments, the cancer that can be treated by the disclosed methods and compositions is treated while healthy cells are spared.

In various embodiments, the cancer that can be treated by the disclosed methods and compositions include EGFR positive (EGFR+) cancers.

In one embodiment, the invention is a method of activating at least one γδ T cell in a subject, comprising the step of administering a multispecific antibody as defined herein.

In one embodiment, the invention is a method of causing or increasing proliferation of γδ T cells in a subject, comprising the step of administering to the subject a multispecific antibody as defined herein.

In one embodiment, the invention is a method of causing or increasing γδ T cell degranulation in a subject, comprising the step of administering to the subject a multispecific antibody as defined herein.

In one embodiment, the invention is a method of causing or increasing γδ T cell killing activity (e.g. T cell mediated killing activity) in a subject, comprising the step of administering to the subject an anti-Vδ1 antibody or antigen-binding fragment thereof as defined herein. In one embodiment, the invention is a method of causing or increasing γδ T cell killing activity (e.g. T cell mediated killing activity) in a subject, while sparing healthy cells, comprising the step of administering to the subject an anti-Vδ1 antibody or antigen-binding fragment thereof as defined herein.

In one embodiment, the invention is a method of causing or increasing γδ T cytotoxicity in a subject, comprising the step of administering to the subject an anti-Vδ1 antibody or antigen-binding fragment thereof as defined herein. In one embodiment, the invention is a method of causing or increasing γδ T cytotoxicity in a subject, while sparing healthy cells, comprising the step of administering to the subject an anti-Vδ1 antibody or antigen-binding fragment thereof as defined herein.

In one embodiment, the invention is a method of causing or increasing γδ T cell mobilization in a subject, comprising the step of administering to the subject multispecific antibody as defined herein.

In one embodiment, the invention is a method of increasing survival of γδ T cells in a subject, comprising the step of administering to the subject a multispecific antibody as defined herein.

In one embodiment, the invention is a method of or increasing resistance to exhaustion of γδ T cells in a subject, comprising the step of administering to the subject a multispecific antibody as defined herein.

According to a further aspect of the invention, there is provided a method of stimulating an immune response in a subject, the method comprising administration to the subject multispecific antibody in an amount effective at stimulating an immune response.

Uses of Multispecific Antibodies or Antigen-Binding Fragments Thereof

According to a further aspect of the invention, there is provided the use of a multispecific antibody as described herein to study antigen recognition, activation, signal transduction or function of γδ T cells (in particular Vδ1 T cells). As described herein, the antibodies have been shown to be active in assays which can be used to investigate γδ T cell function. Such antibodies may also be useful for inducing the proliferation of γδ T cells, therefore may be used in methods of expanding γδ T cells (such as Vδ1 T cells).

Antibodies which bind to the Vδ1 chain can be used to detect γδ T cells. For example, the antibody may be labelled with a detectable label or reporter molecule or used as a capture ligand to selectively detect and/or isolate Vδ1 T cells in a sample. Labelled antibodies find use in many methods known in the art, for example immunohistochemistry and ELISA.

The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, β-galactosidase, horseradish peroxidase, or luciferase. Fluorescent labels applied to multispecific antibodies of the invention may then be used in fluorescence-activated cell sorting (FACS) methods.

Thus in various embodiments, the invention includes in vivo methods of modulating γδ T cells, methods of binding γδ T cells, methods of targeting γδ T cells, methods of activating γδ T cells, methods of proliferating γδ T cells, methods of expanding γδ T cells, methods of detecting γδ T cells, methods of causing γδ T cell degranulation, methods of causing γδ T cell mediated killing activity, methods of selecting antibodies or antigen-binding fragments thereof, the methods comprising the step of administering a multispecific antibody or antigen-binding fragment thereof to a subject as described herein.

Medicaments for Modulating Gamma Delta T Cells

The multispecific antibody as described herein may be used to modulate or useful for modulating delta variable 1 chain (Vδ1) T cells in a patient in situ (i.e. in vivo). The multispecific antibodies or antigen-binding fragments thereof may be comprised in medicaments for such purposes.

Modulation of Vδ1 T cells may include:
expansion of the Vδ1 T cells, e.g. by selectively increasing the number of Vδ1 T cells or promotion of survival of Vδ1 T cells;
stimulation of the Vδ1 T cells, e.g. by increasing Vδ1 T cell potency, i.e. increasing target cell killing;
prevention of Vδ1 T cell exhaustion, e.g. by increasing persistence of the Vδ1 T cells;
degranulation of Vδ1 T cells;
increase in NCR expression;
immunomodulation of the Vδ1 T cells, e.g. by downregulation of Vδ1 TCR cell surface expression, i.e. by causing Vδ1 TCR internalisation or reduced expression of Vδ1 TCR protein, or blocking the Vδ1 TCR from binding; and/or
downregulation of a TCR/CD3 complex.

Unlike anti-Vδ1 antibodies of the prior art which focus on depletion of Vδ1 T-cells, the antibodies of the present invention are useful for the activation of Vδ1 T-cells via the TRDV1-binding domain. Although they may cause downregulation of the TCRs on T-cells to which they bind, they do not cause Vδ1 T-cell depletion, but rather they stimulate the T-cells and hence may be useful in therapeutic settings that would benefit from the activation of this compartment of T-cells. Activation of Vδ1 T-cells is evident through TCR downregulation, CD3 downregulation, changes in activation markers such as CD25 and Ki67 and degranulation marker CD107a. Activation of Vδ1 T-cell in turn triggers release of inflammatory cytokines such as INFγ and TNFα to promote immune licensing.

Medicaments that Modulate Immune Cell Markers on Vδ1+ Cells

The antibody or antigen-binding fragment thereof may modulate immune cell markers of Vδ1+ cells upon administration to a patient.

An antibody or antigen-binding fragment thereof described herein may also be assessed for its suitability for its therapeutic use by measuring γδ T modulation. For example, by measuring a change in the levels of CD25 or CD69 or CD107α present on a Vδ1+ T-cell or cells in a model system. Such markers are often used as markers of lymphocyte modulation (e.g. proliferation or degranulation) and can be measured following application of an antibody or antigen-binding fragment thereof as described herein, e.g. by flow cytometry. Surprisingly, during such assessments (e.g. see e.g. Examples 7, 17, 18) it was observed that antibodies as described herein conferred measurably higher levels of CD25 or CD69 or CD107α levels on target Vδ1+ T-cells. Optionally, the change in phenotype of a Vδ1+ cell or population thereof tested in the model system can then be compared to the change in phenotype when an alternative comparator antibody is applied (e.g. OKT-3, TS8.2, etc.) to said equivalent γδ T cells.

Hence in one aspect of the invention, there is provided a method of assessing an antibody or antigen-binding fragment thereof which binds to the Vδ1 chain of a γδ TCR for therapeutic use comprising administering the antibody or antigen-binding fragment thereof to a cell population comprising Vδ1+ cells and determining the effect on the level of CD25 and/or CD69 and/or CD107α on the surface of the Vδ1+ cells. The effect on the level of CD25, CD69 and/or CD107α may be determined/measured over a period of time. It will be understood that the effect can be measured in comparison to the level of CD25 and/or CD69 and/or CD107α on the surface of the Vδ1+ cell when said antibody is not applied to said cell over the same period of time. In a further aspect of the invention there is provided a method of selecting or characterizing or comparing the multispecific antibodies or antigen-binding fragments thereof as described herein which bind to the Vδ1 chain of a γδ TCR by adding said antibodies to a cell population comprising Vδ1+ cells and then measuring the level (or expression) of CD25 or CD69 or CD107α on the surface of said Vδ1+ cells.

Medicaments that Modulate Growth Properties or Numbers of Vδ1+ Cells

The antibody or antigen-binding fragment thereof may modulate the growth properties of Vδ1+ cells upon administration to a patient. For example, the antibody or antigen-binding fragment thereof may expand Vδ1+ cells.

An alternate approach to measuring γδ T proliferation may include measuring the change in relative number of Vδ1+ cells over time when applying an antibody or antigen-binding fragment thereof as described herein to model systems containing said cells. Surprisingly, during such assessments it was observed that antibodies as described herein where able to measurably increase the number of said Vδ1+ T-cells (e.g. see e.g. Example 10, 17 and 18), Optionally this change in number can then be compared to the change in number observed when an alternative comparator antibody is applied (e.g. anti-OKT3) to said model systems.

Hence in another aspect of the invention, there is provided a method of assessing an antibody or antigen-binding fragment thereof which binds to the Vδ1 chain of a γδ TCR comprising administering the antibody or antigen-binding fragment thereof to a cell population comprising Vδ1+ cells and determining the effect on the number of Vδ1+ cells in the population. The effect on cell number can be determined/measured over a period of time. It will be understood that the effect can be measured in comparison to the effect on cell numbers observed when said antibody is not applied to the cell population for the same period of time. In a further aspect of the invention there is provided a method of selecting or characterizing or comparing antibodies or antigen-binding fragment thereof as described herein which bind to the Vδ1 chain of a γδ TCR by applying said antibodies to a cell population comprising Vδ1+ cells and then measuring the number of said cells over time.

Medicaments that Modulate the Proliferative Capacity and Numbers of Vδ1+ Cells

An ideal therapeutic antibody or antigen-binding fragment thereof as described herein which binds to the Vδ1 chain of a γδ TCR may be one that is capable of enhancing the proliferation of Vδ1+ cells in vivo. Such antibodies can then be employed as medicaments designed to specifically increase the Vδ1+ cell number in a subject or patient. For example:

Cancer:

Relative increases in the numbers of Vδ1+ cells have been reported as a positive prognostic indicator associated with improved outcomes for many cancer (for example see Gentles et al (2015) Nature Immunology 21:938-945; Wu et al. (2019) Sci. Trans. Med. 11(513): eaax9364; Catellani et al. (2007) Blood 109(5): 2078-2085). In one embodiment, presented herein is a medicament capable of increasing the relative or absolute numbers of Vδ1+ cells in situ within in a cancer patient.

Pathogenic/Parasitic/Viral Infections:

Vδ1+ cell enrichment is observed during host defense against numerous acquired pathogenic/parasitic/viral infections. For recent general review see Zhao et al. (2018) Immunol. Res. 2018:5081634. Furthermore, increased numbers Vδ1+ are also considered protective against a variety of DNA and RNA viral infections. For example, increased numbers are also considered protective during CMV infections associated with allogeneic transplants (see van Dorp et al. (2011) Biology of Blood and Marrow Transplantation 17(2): S217). Additionally, Vδ+ cell numbers increase in patients with coronavirus infection (Poccia et al. (2006) J. Infect. Dis. 193(9): 1244-1249).

In another embodiment, presented herein is a medicament capable of increasing the relative or absolute numbers of Vδ1+ cells in a subject or patient harboring a pathogenic infection.

Stem Cell Transplant:

Increased numbers of Vδ1+ cells have also been associated with less disease relapse, fewer viral infections, higher overall and disease-free survival and favorable clinical outcomes in general during hematopoietic stem cell transplant (for example see Aruda et al. (2019) Blood 3(21): 3436-3448 and see Godder et al. (2007) Bone Marrow Transplantation 39:751-757). Hence another embodiment, presented herein is a medicament capable of increasing the relative or absolute numbers of Vδ1+ cells in a subject as part of a treatment regimen supporting a stem cell transplant.

Consequently, a medicament capable of preferentially or specifically increasing the numbers of Vδ1+ cells in-situ is highly desirable.

Medicaments that Maintain or Induce or Increase Vδ1+ Cell Cytokine Secretion

Cytokines are a large group of proteins, peptides or glycoproteins that are secreted by specific cells of immune system. They are a category of signaling molecules that mediate and regulate immunity, inflammation, and hematopoiesis. A number of cytokines have been implicated in ameliorating signs and symptoms of disease through either direct or indirect modulation of the tumour and cellular microenvironment, autoimmune tissue and associated microenvironment, or virally infected tissue or cellular environment. Exemplar pro-inflammatory cytokines include tumour necrosis factor-alpha (TNFα) and Interferon-gamma (IFNγ).

However, many such cytokines exhibit unfavourable toxicity when dosed systemically. For example, whilst TNFα can induce the haemorrhagic necrosis of transplanted tumours, and has been reported to exert synergic anti-tumour effects when combined with other chemotherapeutic drugs, various clinical trials with systemic recombinant human TNFα (rhTNFα) have highlighted significant dose limiting side effects inclusive of hypotension, rigors, phlebitis, thrombocytopenia, leucopenia and hepatotoxicity, fever, fatigue, nausea/vomiting, malaise and weakness, headache, chest tightness, low back pain, diarrhoea and shortness of breath.

Use of recombinant IFNγ also faces similar systemic toxicity challenges. For example, whilst in a cancer setting IFNγ can exert favorable pleiotropic effects including MHC class I and II upregulation to stimulate anti-tumour immunity, increasing T-cell infiltration, conferring anti-angiogenesis effects, inducing chemokine/cytokine secretion, and exerting direct cancer cell anti-proliferative effects, adverse side-effects are also observed. These include fever, headache, chills, fatigue, diarrhoea, nausea, vomiting, anorexia, transient increases in hepatic transaminase, and transient decreases in granulocyte and leucocyte counts.

For a recent review on both the potential and limitation of systemic recombinant TNFα and IFNγ see Shen et al. (2018) Cell Prolif. 51(4):e12441.

Hence there is a need for more in situ controlled, more localized, more tissue or cell specific production of such cytokines. For example, more controlled expression or induction of pro-inflammatory cytokines is proposed as one approach whereby "cold" tumours can be turned "hot". Hot tumours are also sometimes termed "T-cell-inflamed" because of an increase in the number or density of CD45+ T-cells also observed. See Bonaventura et al. (2019) Front. Immunol. 10:168 for a recent review.

For such reasons, an ideal therapeutic antibody or antigen-binding fragment thereof as described herein which binds to the Vδ1 chain of a γδ TCR may be one that can maintain or enhance or induce the secretion of cytokines in Vδ1+ cells in vivo. Such antibodies can then be employed as medicaments designed to specifically increase or induce cytokines in a subject or patient and in a more localized, less systemic manner and one which better correlates with the distribution of Vδ1+ cells in said subject or patient.

Remarkably, when antibodies as described herein which bind to the the Vδ1 chain of a γδ TCR are applied to Vδ1+ cells, a significantly higher level of secreted cytokines are observed. More specifically, and as a non-limiting example, a significant higher level of TNFα and IFNγ is observed. See e.g. Example 15.

Hence in another aspect of the invention, there is provided a method of assessing an antibody or antigen-binding fragment thereof which binds to the Vδ1 chain of a γδ TCR comprising administering the antibody or antigen-binding fragment thereof to a cell population comprising Vδ1+ cells and determining the amount of at least one cytokine produced by the cell population. The amount of cytokine produced can be determined/measured over a period of time and optionally compared to the amount observed when said antibody is not applied to the cell population for the same period of time. In one embodiment, the observed level of cytokine produced when the antibody is administered to the cell population is more than about 10%, more than about 20%, more than about 30%, more than about 50%, more than about 100%, more than about 150%, more than about 200%, more than about 250%, more than about 300%, more than about 350%, more than about 400%, more than about 450%, more than about 500%, more than about 1000%, relative to the level of cytokine produced when the antibody is not applied. In a further aspect of the invention, the cytokine is a pro-Inflammatory cytokine. In a further aspect of the invention, the cytokine is the TNF-α cytokine. In a further aspect of the invention, is IFN-γ cytokine.

In a further aspect of the invention there is provided a method of selecting or characterizing or comparing antibodies or antigen-binding fragment thereof as described herein which bind to the Vδ1 chain of a γδ TCR by applying said antibodies to a cell population comprising Vδ1+ cells and then measuring the level of at least one cytokine generated. In a further aspect of the invention the cytokine measured is TNF-α cytokine and/or IFN-γ cytokine.

In a further aspect of the invention, there is provided a method of assessing an antibody or antigen-binding fragment thereof which binds to the Vδ1 chain of a γδ TCR by applying said antibody or antigen-binding fragment thereof to a cell population comprising Vδ1+ cells and measuring the effect of the antibody on modulating a colder or cold tumour to become a hotter or hot tumour by determining the quantity of proinflammatory cytokines produced and/or the number or density of CD45+ T-cells present in the tumour or tumour microenvironment.

Medicaments that Maintain or Induce or Increase Vδ1+ Cell Granzyme B Activity

Granzyme B is a serine protease commonly found in the granules of natural killer cells (NK cells) and cytotoxic T cells. It is secreted by these cells along with the pore forming protein perforin to mediate apoptosis in target cells, such as diseased cells.

When Vδ1+ cells are incubated in co-cultures with target diseased cells (such as cancer cells) in model systems, levels of Granzyme B levels and activity can be measured in the target diseased cells ahead of lysis. Remarkably when an antibody or antigen-binding fragment thereof as described herein which binds to the Vδ1 chain of a γδ TCR is then applied to such co-cultures of Vδ1+ cells and cancer cells in such model systems, higher Granzyme B levels and activity are then observed in the diseased cancer cells ahead of cell death (see e.g. Example 16).

Hence in another aspect of the invention, there is provided a method for assessing an antibody or antigen-binding fragment thereof which binds to the Vδ1 chain of a γδ TCR comprising administering the antibody or antigen-binding fragment thereof to a co-culture comprising Vδ1+ cells and diseased cells (such as cancer cells) and measuring the effect on the amount of Granzyme B produced by the diseased cells in the co-culture. The amount of cytokine produced can be determined/measured over a period of time and optionally compared to the amount observed when said antibody is not applied to said co-cultures for the same period of time. In one embodiment, the level of Granzyme B measured when said antibody is applied to said co-culture is more than about 10%, more than about 20%, more than about 30%, more than about 40%, more than about 50%, more than about 70%, more than about 80%, more than about 90%, more than about 100%, more than about 200%, relative to the Granzyme B level observed when said antibody is not applied.

In a further aspect of the invention there is provided a method of selecting or characterizing or comparing antibodies or antigen-binding fragment thereof as described herein which bind to the Vδ1 chain of a γδ TCR by applying said antibodies to a co-culture comprising Vδ1+ cells and diseased cells and then measuring the quantity or activity of Granzyme B in the diseased cell.

Medicaments that Expand Polyclonal Vδ1+ Cell Populations

An ideal antibody medicament may also be one designed to ensure the expanding Vδ1+ cells do not become too clonally focused at the hypervariable CDR3 sequence level. Hence an ideal antibody medicament may be designed such to avoid inducing proliferation Vδ1+ cells by binding to specific or 'private' δ1+ CDR3 sequence paratopes. Rather, the antibody may bind via conserved germline sequences present on all Vδ1+ T cell receptors and in a gamma-chain independent manner, rather than bind to sequences presented only a sub-set of Vδ1+ cells.

Hence an ideal antibody medicament may stimulate the expansion Vδ1+ cells to generate a plurality of Vδ1+ cells containing a mixture of CDR3 sequences. This in turn would result in an in vivo expanded heterogenous polyclonal population of Vδ1+ cells displaying different CDR3 sequences on delta variable 1 chains. Remarkably, during analysis of expanded Vδ1+ cell populations generated by a method of adding an antibody or antigen-binding fragment thereof as described herein to a starting population of immune cells containing Vδ1+ cells, extensive polyclonality is observed by RNAseq based methodologies designed to sequence through the CDR3 hypervariable regions of RNA extracted (see e.g. Example 10).

Accordingly in one aspect, there is provided a method of assessing an antibody or antigen-binding fragment thereof which binds to the Vδ1 chain of a γδ TCR comprising administering the antibody or antigen-binding fragment thereof to a cell population comprising Vδ1+ cells and determining the polyclonality of the expanded Vδ1+ cells. It is desirable for an antibody medicament to generate an expanded polyclonal population containing a plurality of Vδ1+ CDR3 sequences. Polyclonality can be determined using methods known in the art, such as by nucleic acid sequencing approaches capable of analysing the Vδ1 chain hypervariable CDR3 content of said Vδ1+ cells.

Medicaments that Expand Polyclonal Vδ1+ Cells for Extended Periods of Time

An ideal antibody medicament may be able to enhance or promote or stimulate the proliferation of primary Vδ1+ cells without exhausting such cells in vivo. For example, and by way of comparison, anti-CD3 medicaments such as OKT3 (e.g. Muronomab), whilst capable of expanding CD3 positive T-cells may also exhaust or induce anergy. To assess the capacity of antibodies as described herein and which bind to the Vδ1 chain of a γδ TCR to drive continued cell division of viable Vδ1+ cells, longer term proliferation studies were undertaken. Remarkably these studies revealed that antibodies as described herein and which bind to the Vδ1 chain of a γδ TCR are capable of driving cell division/proliferation of viable and still functionally cytotoxic Vδ1+ cells for over 40 days (see e.g. Example 10).

In one embodiment, there is provided a method of assessing an antibody or antigen-binding fragment thereof which binds to the Vδ1 chain of a γδ TCR comprising applying the antibody or antigen-binding fragment thereof to a cell population and monitoring the length of time Vδ1+ cell division occurs. Ideally, the antibody is capable of stimulating Vδ1+ cell division for a period of 5 to 60 days, such as at least 7 to 45 days, 7 to 21 days, or 7 to 18 days.

In a further embodiment, there provided an antibody or antigen-binding fragment thereof as described herein which binds to the Vδ1 chain of a γδ TCR and which when administered to a patient is capable of stimulating Vδ1+ cell division to increase the number by at least 2-fold in number, at least 5-fold in number, at least 10-fold in number, at least 25-fold in number, at least 50-fold in number, at least 60-fold in number, at least 70-fold in number, at least 80-fold in number, at least 90-fold in number, at least 100-fold in number, at least 200-fold in number, at least 300-fold in number, at least 400-fold in number, at least 500-fold in number, at 600-fold in number, or at least 1,000-fold in number.

In a further aspect of the invention there is provided a method of selecting or characterizing or comparing antibodies or antigen-binding fragment thereof as described herein which bind to the Vδ1 chain of a γδ TCR by applying said antibodies to Vδ1+ cells or mixed cell population containing Vδ1+ cells and then measuring Vδ1+ cell numbers over time.

Medicaments that Modulate Non-Vδ1+ Immune Cells Through Targeting Vδ1+ Immune Cells An antibody or antigen-binding fragment thereof as described herein may also be assessed by measuring Vδ1+ cell mediated modulation of other immune cells. For example, a change observed in a non-γδ T cell 'fraction' can be measured following application of an antibody or antigen-binding fragment thereof as described herein to a model system comprising mixed population of immune cells such as one comprising human tissue αβ cells and γδ T cells. Further, the effect on non-γδ cell types in said models can be measured by flow cytometry. For example, by measuring the relative change in numbers of CD8+αβ T cells upon addition of an antibody or antigen-binding fragment thereof as described herein to mixed cultures comprising γδ T cells and non-γδ T cells. Optionally, the observed change in number or phenotype of a non-γδ T-cell CD8+ lymphocyte population can then be compared to the change in number when an alternative comparator antibody is applied (e.g. OKT-3) to said mixed population.

Hence in another aspect of the invention, there is provided a method of assessing an antibody or antigen-binding fragment thereof which binds to the Vδ1 chain of a γδ TCR comprising administering the antibody or antigen-binding fragment thereof to a mixed population of immune cells or tissues comprising Vδ1+ cells and Vδ1-negative immune cells and measuring the effect on the Vδ1-negative immune cells. The effect can be determined/measured over a period of time and optionally compared to the effect observed in Vδ1-negative cells when said antibody is not applied for the same period of time. The effect may be measured as a change in the number of Vδ1-negative immune cells. For example, the antibody may increase the number Vδ1-negative immune cells by more than about 10%, more than about 20%, more than about 30%, more than about 40%, more than about 50%, more than about 70%, more than about 80%, more than about 90%, more than about 100%, more than about 500%, relative to the levels observed when said antibody is not applied.

In a further aspect of the invention the modulated Vδ1-negative cell is a CD45+ cell. In a further aspect of the invention the modulated cell is a αβ T-cell. In a further aspect of the invention the modulated αβ+ cell is CD8+ lymphocyte. In a further aspect of the invention the modulated αβ T-cell, or population thereof, exhibits evidence of enhanced cell division. In a further aspect of the invention there is provided a method of selecting or characterizing or comparing antibodies or antigen-binding fragment thereof as described herein which bind to the Vδ1 chain of a γδ TCR by administering said antibodies to a population of mixed immune cells comprising Vδ1+ cells and Vδ1-negative immune cells and then measuring an effect conferred on the Vδ1-negative cell population by Vδ1+ cells modulated by said multispecific antibodies or antigen-binding fragments thereof.

Optionally, and during "Vδ1+ cell mediated immune system modulation" as conferred by an antibody or antigen-binding fragment thereof as described herein, a concomitant increase in Vδ1+ cell number is also observed. And whilst not being bound by this theory, it is possible that said increase in Vδ1+ cell number may be causal in driving the concomitant expansion of co-present Vδ1-negative immune cells, such as αβ T-cells. An alternate hypothesis may be that antibody-induced cytokine secretions from the Vδ1+ T cells stimulate the expansion of Vδ1-negative immune cells.

In a further aspect of the invention the observed increase in αβ+CD8+ lymphocyte population is compared to a comparator antibody such as OKT3 antibody or alternate anti-Vδ1 antibody. In a further aspect of the invention there is provided a method of selecting or characterizing or comparing antibodies or antigen-binding fragment thereof as described herein which bind to the Vδ1 chain of a γδ TCR by applying said antibodies to a population of mixed immune cells comprising Vδ1+ T-cells and αβ T-cells and then measuring the numbers of CD8+αβ+ T-cells lymphocytes over time.

Medicaments that Modulate Tumour Infiltrating Lymphocytes (TILs)

An antibody or antigen-binding fragment thereof as described herein may also be assessed by measuring the effect conferred on tumour-infiltrating populations (TILs) in model systems. Surprisingly (see e.g. Example 18) during such assessments antibodies as described herein measurably modulated TIL populations in human tumours. For example, a change in either the number or phenotype of γδ+ lymphocyte TIL population or the non-γδ lymphocyte TIL population is measured following application of an antibody or antigen-binding fragment thereof as described herein to a human tumour such as a human renal cell carcinoma. Optionally, the observed change in number or phenotype of either the γδ+ lymphocyte TIL population or non-γδ lymphocyte TIL population can then be compared to the change observed when an alternative comparator antibody is applied (e.g. OKT-3) to said model system.

Hence in another aspect of the invention, there is provided a method of assessing an antibody or antigen-binding fragment thereof which binds to the Vδ1 chain of a γδ TCR comprising administering the antibody or antigen-binding fragment thereof to TILs located in, or derived from, a human tumour and determining the effect on the number of TILs. The effect can be determined/measured over a period of time and optionally compared to the TIL number observed when said antibody is not applied over the same period of time. The effect may be an increase in the number of TILs. For example, the antibody may increase the number of TILs more than about 10%, more than about 20%, more than about 30%, more than about 40%, more than about 50%, more than about 70%, more than about 80%, more than about 90%, more than about 100% relative to the number of TILs observed when said antibody is not applied. In a further aspect, the TILs in which the number observed are γδ+ lymphocyte TIL cells and/or non-γδ lymphocyte TIL cells.

In a further aspect of the invention there is provided a method of selecting or characterizing or comparing antibodies or antigen-binding fragment thereof as described herein which bind to the Vδ1 chain of a γδ TCR cells antibodies by applying said antibodies to TIL or TILs located in or derived from a human tumour and then measuring the change in number of TIL or TILs cells over a period of time.

Medicaments that Modulate Human Vδ1+ Cytotoxicity

An antibody or antigen-binding fragment thereof as described herein may also be assessed by measuring the conferred effect on Vδ1+ mediated cell cytotoxicity. Surprisingly, during such assessments of antibodies as described herein (e.g. see e.g. Examples 19 and 27) measurably enhanced Vδ1+ mediated cell cytotoxicity was observed. For example, a reduction in the number of cancer cells or an increase in the number of killed cancer cells is observed following application of an antibody or antigen-binding fragment thereof to a model system comprising a mixed culture comprising Vδ1+ cells and said cancer cells. Optionally, the reduction in the number of cancer cells or the increase in the number of killed cancer cells can then be compared to the outcome when an alternative comparator antibody is applied (e.g. OKT-3) to said model systems.

Hence in another aspect of the invention, there is provided a method of assessing an antibody or antigen-binding fragment thereof which binds to the Vδ1 chain of a γδ TCR comprising applying the antibody or antigen-binding fragment thereof to a mixed population of cells comprising Vδ1+ cells and cancer cells and measuring the cytotoxicity of the Vδ1+ cells towards the cancer cells. The cytotoxicity may be measured by an increase in the number of dead cancer cells over a period of time, optionally compared to the number of dead cancer cells observed when said antibody is not applied to the mixed population of cells over the same period of time. For example, the observed increase in dead cells when said antibody is applied may be more than about 10%, by more than about 20%, by more than about 30%, by more than about 40%, by more than about 50%, more than about 70%, more than about 80%, more than about 90%, more than about 100%, more than about 200%, more than about 500%, relative to the number of dead cells observed when said antibody is not applied.

In a further aspect of the invention there is provided a method of selecting or characterizing or comparing antibodies or antigen-binding fragment thereof as described herein which bind to the Vδ1 chain of a γδ TCR cells by adding said antibodies to said population of mixed immune cells comprising human Vδ1+ cells and cancer cells and then measuring an increase in dead cancer cells overtime.

Medicaments that Modulate Vδ1+ Cell Target-to-Effector Cell Ratios (T:E Ratios)

An antibody or antigen-binding fragment thereof as described herein may also be assessed by measuring how said antibodies enhance Vδ1+ mediated cancer cell cytotoxicity by determining the target cell to effector cell ratio wherein the 50% of the target cells (EC50) are killed in a model system to assess said antibodies as potential medicaments. For example, mixed cultures comprising target cancer cells with human Vδ1+ effector cells. Surprisingly, during such assessments (e.g. see e.g. Example 19) antibodies as described herein favourably modify the EC50 T:E ratio in model systems. Such modifications can be measured as numbers of Vδ1+ cells required to observe 50% killing of cancer cells over a set time. This can also be reported as change or as fold-improvements or as percent-improvements in cytotoxicity towards said cancer cells. Optionally, the T:E ratio conferred by antibodies of this invention can then be compared to the T:E ratios when an alternative comparator antibody is applied (e.g. OKT-3) to said model systems. In some scenarios, the multispecific antibodies of the invention present opportunities for improved cancer cell cytotoxicity even at lower E:T ratios, compared to monospecific antibodies.

Hence in another aspect of the invention, there is provided a method of assessing an antibody or antigen-binding fragment thereof which binds to the Vδ1 chain of a γδ TCR comprising applying the antibody or antigen-binding fragment thereof to a mixed population of cells comprising human Vδ1+ cells and cancer cells and measuring the number of Vδ1+ cells required to kill 50% of the cancer cells. This may be measured relative to the number Vδ1+ cells required to kill 50% of cancer cells without application of said antibody, optionally over the same period of time. For example, the reduction in the number of Vδ1+ cells required to kill 50% of the cancer cells when said antibody is applied may be greater than about 10%, greater than about 20%, greater than about 30%, greater than about 40%, greater than about 50%, greater than about 70%, greater than about 80%, greater than about 90%, greater than about 100%, greater about 200%, greater than about 500%, relative to the number of Vδ1+ cells required to kill 50% of the cancer cells when said antibody is not applied.

In a further aspect of the invention there is provided a method of selecting or characterizing or comparing antibodies or antigen-binding fragment thereof as described herein which bind to the Vδ1 chain by adding said antibodies to said population of cells comprising Vδ1+ cells plus cancer cells and then measuring the numbers of Vδ1+ cells required to kill 50% of the cancer cells.

Medicaments which Enhance Vδ1+ Cell EC50 Cytotoxicity

An alternate way to measure the observed enhanced cytotoxicity of human Vδ1+ cells or population thereof is to measure the number of cells required to kill 50% of the cancer cells over a set period of time in condition A (such as starting control) and compare this to the number of cells required to kill 50% of the cancer cells over a set period of time in condition B (such as upon application of antibody of the invention as described herein).

Whilst it is recognized that there are a variety of ways to measure such parameters, to aid in understanding, the following non-limiting hypothetical example will be outlined:

Hypothetically, effector cell cytotoxicity enhancement can be measured as follows:—In condition A (control treatment) it is observed that 1000 Vδ1+ cells are required to kill 50% of the cancer cells over a set period of time (e.g. 5 hours). In condition B (e.g. application of antibody of the invention described herein) it is observed that 500 Vδ1+ cells were required to kill 50% of the cancer cell over the same period of time. Hence in this example, the application of an antibody has enhanced the cytotoxicity of the Vδ1+ cell population by 200%:

$$(1000/500) \times 100 = 200\%$$

For example (see e.g. Examples 19 to 21), surprisingly such percentage enhancements have been observed for multispecific antibodies of the invention as described herein.

In a further aspect of the invention there is provided a method of selecting or characterizing or comparing antibodies or antigen-binding fragment thereof as described herein which bind to the Vδ1 chain of a γδ TCR by adding said antibodies to said population of mixed immune cells comprising Vδ1+ cells and cancer cells and determining the relative or percent-change in cytotoxicity versus an equivalent or control experiment wherein there is no application of said antibody to said mixture of cells.

Medicaments which Enhance Vδ1+ Cells Diseased-Cell Specificity Whilst Sparing Healthy Cells Another approach to assess multispecific antibodies or antigen-binding fragments thereof as described herein is to measure how said antibodies modulate diseased-cell specific cytotoxicity. Surprisingly during such studies, it was discovered such antibodies can specifically enhance the Vδ1+ cell specific killing of diseased-cells such as cancer cells (e.g. see e.g. Examples 19 and 27) whilst sparing healthy or non-diseased cells. Ideal antibody medicaments administered to a patient to ameliorate a symptom of cancer will confer enhanced cytotoxicity specifically towards diseased cells whilst sparing healthy cells. And medicaments which enhance effector cell cytotoxicity specifically towards diseased cells, such as cancer cells, can be said to exhibit an enhanced therapeutic index (TI) over medicaments which do not selectively enhance effector cell cytotoxicity specifically towards said diseased cells. The therapeutic index is also referred to as therapeutic ratio and is a quantitative measurement of the relative safety of a drug. It is a comparison of the amount of a therapeutic agent that causes the therapeutic effect to the amount that causes toxicity e.g. by conferring undesirable death in related or relevant healthy cell populations. An antibody or antigen-binding fragment thereof as described herein may be assessed by measuring its ability to change or to enhance or to fold-improve Vδ1+ cell capacity to selectivity kill diseased cells over and above healthy cells in model systems. For example, said model systems may comprise Vδ1+ effector cells, cancer cells, and control cells (such as healthy cells). Optionally, the fold-improvement in selective diseased-cell killing conferred by multispecific antibodies of the invention can then be compared to the fold-improvement observed when an alternative comparator antibody is applied (e.g. OKT-3) to said model systems.

The diseased-cell specificity and diseased-cell specificity-enhancement of Vδ1+ cells can be measured in cultures comprising Vδ1+ cells, diseased cells, and healthy cells. For example, Vδ1+ specificity towards diseased cells can be measured by observing the number of cancer cells killed by the Vδ1+ cells and then comparing the number of healthy cells killed by the Vδ1+ cells. Such comparisons can be controlled by including equivalent numbers of diseased cells and healthy cells in a model system also containing Vδ1+ cells e.g. "tricultures". Alternative comparison methodology can also be considered—for example when analytical or equipment limitations reduce the ability to distinguish and track all three cell types or more in parallel in a single assay (inclusive of Vδ1+ cells, diseased cells, and non-diseased cells). In said instances, comparing Vδ1+ cell cytotoxicity towards diseased cells in one experiment and then comparing Vδ1+ cell cytotoxicity towards healthy cells in a separate equivalent experiment offers an alternate approach to such studies.

In another aspect of the invention, there is provided a method of assessing an antibody or antigen-binding fragment thereof which binds to the Vδ1 chain of a γδ TCR comprising administering the antibody or antigen-binding fragment thereof to a cell population comprising Vδ1+ cells and target cells and measuring the cell cytotoxic specificity towards the target cells. In one embodiment, the cell cytotoxicity specificity to a first target cell type can be compared to the cytotoxicity observed towards a second target cell type, therefore the method may be repeated using different target cell types. In a further aspect of the invention the first target cell type is a diseased cell and the second target cell type is a control cell such as a healthy cell or a cell with a different disease to the first target cell type.

In a further aspect of the invention there is provided a method for selecting or characterizing or comparing antibodies or antigen-binding fragment thereof as described herein which bind to the Vδ1 chain of a γδ TCR wherein the effect conferred by said antibody on Vδ1+ cell cytotoxicity towards (i) a first cell type and (ii) a second cell type is measured and compared. In a further aspect of the invention an antibody is thereby selected which enhances the specific cytotoxicity towards the first cell type more so than towards the second cell type. In a further aspect of the invention the first cell type is a diseased-cell and the second cell type is a healthy cell.

As described herein, the multispecific antibodies or antigen-binding fragments thereof used in the assays may be presented on a surface, for example the surface of a cell, such as a cell comprising an Fc receptor. For example, the multispecific antibodies or antigen-binding fragments thereof may be presented on the surface of THP-1 cells, such as TIB-202™ cells (available from AMERICAN TYPE CULTURE COLLECTION® (ATCC®)). Alternatively, the multispecific antibodies or antigen-binding fragments thereof may be used directly in the assays.

In such functional assays, output may be measured by calculating the half maximal concentration, also referred to as "EC50" or "effective concentration at 50 percent". The term "IC50" refers to the inhibitory concentration. Both EC50 and IC50 may be measured using methods known in the art, such as flow cytometry methods. In some instances, EC50 and IC50 are the same value or can be considered equivalent. For example, the effective concentration (EC) of effector cells required to inhibit (e.g. kill) 50% of a certain cell type may also be considered the 50% inhibitory concentration (IC). For the avoidance of doubt, the values of EC50 in the present application are provided using IgG1 formatted antibody when referring to an antibody. Such values can be easily converted based on the molecular weight of the antibody format for equivalent values as follows:

(μg/ml)/(MW in kDa)=μM

The EC50 for downregulation of the γδ TCR upon antibody (or fragment) binding for the parental clones described herein may be less than 0.50 μg/ml, such as less than 0.40 μg/ml, 0.30 μg/ml, 0.20 μg/ml, 0.15 μg/ml, 0.10 μg/ml, 0.06 μg/ml or 0.05 μg/ml. In a preferred embodiment, the EC50 for downregulation of the γδ TCR upon antibody (or fragment) binding is less than 0.10 μg/ml. In particular, the EC50 for downregulation of the γδ TCR upon antibody (or fragment) binding may be less than 0.06 μg/ml, such as less than 0.05 μg/ml, 0.04 μg/ml or 0.03 g/ml. In particular, said EC50 values are when the antibody is measured in an IgG1 format. For example, the EC50 γδ TCR downregulation value can be measured using flow cytometry (e.g. as described in the assay of e.g. Examples 6 and 27).

The EC50 for γδ T cell degranulation upon antibody (or fragment) binding may be less than 0.050 μg/ml, such as less than 0.040 μg/ml, 0.030 μg/ml, 0.020 μg/ml, 0.015 μg/ml, 0.010 μg/ml or 0.008 μg/ml. In particular, the EC50 for γδ T cell degranulation upon antibody (or fragment) binding may be less than 0.005 μg/ml, such as less than 0.002 μg/ml. In a preferred embodiment, the EC50 for γδ T cell degranulation upon antibody (or fragment) binding is less than 0.007 μg/ml. In particular, said EC50 values are when the antibody is measured in an IgG1 format. For example, the γδ T cell degranulation EC50 value can be measured by detecting CD107α expression (i.e. a marker of cell degranulation) using flow cytometry (e.g. as described in the assay of Example 7). In one embodiment, CD107α expression is measured using an anti-CD107α antibody, such as anti-human CD107α BV421 (clone H4A3) (BD® Biosciences).

The EC50 for γδ T cell killing upon the antibody (or fragment) binding may be less than 0.50 μg/ml, such as less than 0.40 μg/ml, 0.30 μg/ml, 0.20 μg/ml, 0.15 μg/ml, 0.10 μg/ml or 0.07 μg/ml. In a preferred embodiment, the EC50 for γδ T cell killing upon the antibody (or fragment) binding is less than 0.10 μg/ml. In particular, the EC50 for γδ T cell killing upon the antibody (or fragment) binding may be less than 0.060 μg/ml, such as less than 0.055 μg/ml, in particular less than 0.020 μg/ml. In particular, said EC50 values are when the antibody is measured in an IgG1 format. For example, the EC50 γδ T cell killing value can be measured by detecting proportion of dead cells (i.e. using a cell viability dye) using flow cytometry following incubation of the antibody, γδ T cell and target cells (e.g. as described in the assay of Example 8). In one embodiment, death of the target cell is measured using a cell viability dye is Viability Dye eFluor™ 520 (THERMO FISHER™)).

In the assays described in these aspects, the antibody or antigen-binding fragment thereof may be presented on the surface of a cell, such as a THP-1 cell, for example TIB-202™ (ATCC®). The THP-1 cells are optionally labelled with a dye, such as CellTracker™ Orange CMTMR (THERMO FISHER™)).

Medicaments that Downregulate CD3 Molecules Associated with a Vδ1 TCR.

Presented herein are antibodies which engage the T-cell/CD3 complex differently. Specifically, these antibodies can engage via the TRDV1 domain of Vδ1 TCRs expressed only on Vδ1+ cells. In doing so such medicaments function differently. In turn this engagement event can downregulate TCR-associated CD3 molecule complexes. Such CD3 downregulation can be synonymous with T-cell activation. However, by engaging the T-cell/CD3 complex via the TRDV1 domain in this way, only CDR3 molecules associated with the Vδ1 TCR are then downregulated. This mechanism is clearly shown in FIGS. 29A-29B.

Hence in one embodiment there is provided a method of downregulating a TRDV1-containing Vδ1 TCR and the associated CD3 molecule complex on the surface of a cell with an antibody, and the use of such antibodies for this purpose.

In some embodiments, also presented herein are multispecific TCEs capable of engaging the T-cell/CD3 complex via the TRDV1 domain. Current multispecific TCE-formatted medicaments typically engage and activate a T-Cell via CD3 binding events. This can result in downregulation of CD3 molecule complexes from the surface of a T-cell. However, it also well understood that TCEs can also overstimulate T-cells via such engagement and downregulation. CD3 molecule complexes are not specific to one class of T-cell and are therefore not a precise target to aim for. Stimulating all T-cells (mainly αβ subtype) via CD3 can in turn can result in overproduction of cytokines, leading to acute cytokine flares (so-called cytokine storms). Additionally, in non-targeted approaches which engage and activate all T-cells via CD3, paradoxically the T-cells can become overactivated which leads to chronic T-cell exhaustion and/or T-cell death. Indeed, this non-specific pan T cell activation leads to activation of both effector and regulatory T cells whereas the presently presented approach interacts specifically with an effector population. This 'sledge-hammer' approach is therefore far from ideal when one may wish to upregulate selective T-cells only.

By contrast, presented herein are multispecific antibodies, in particular T-cell engagers, which engage the T-cell/CD3 complex differently. Specifically, these TCEs can engage via the TRDV1 domain of Vδ1 TCRs expressed only on Vδ1+ cells. In doing so such TCE-based medicaments function differently. First, these TCEs are able to down-regulate a TCR via engaging a TRDV-1 epitope. In turn this engagement event downregulates TCR-associated CD3 molecule complexes. Such CD3 downregulation can be synonymous with T-cell activation. However, by engaging the T-cell/CD3 complex via the TRDV1 domain in this way, only CDR3 molecules associated with the Vδ1 TCR are then downregulated. This approach of specifically targeting and activating Vδ1 cells allows many of the above issues (cytokine storms, T-cell exhaustion/depletion and ADCC, for example) to be avoided. Again, this mechanism is clearly shown in FIGS. 29A-29B.

Stimulation of T-cells via the CD3 'sledge-hammer' approach can also contribute to depletion of T-cells via Fc gamma receptor driven mechanisms, such as ADCC. Therefore, the majority of the CD3-targeting bispecific antibodies currently in clinical practice have Fc domains with reduced binding activity to FcγR or are bispecific fragments intentionally without the Fc region. CD3-targeting therapies may also have reduced binding affinity of the T-cell receptor complex binding arms.

This reduction in affinity may result in reduced efficacy and less optionality in terms of TCE design and functionality. For example, affinity of the binding domains in such TCEs is known to drive distribution profile in vivo. Specifically, it is typically observed that TCE distribution is biased towards its highest affinity target. Hence, by reducing the affinity of a TCE binding domain to the T-cell complex, it is typical to then bias distribution away from T-cells; the very cells needed to drive efficacy of such TCEs. It is partly for such reasons that TCE therapeutic windows have been termed 'prohibitively narrow'. The approach presented here specifically targets and activates vδ1 cells, avoiding the need to ablate Fc function or reduce affinity.

This is shown, for example, in FIGS. 37A-37C and Example 15, which demonstrates the potential to further reduce dose-limiting skin toxicities relative to higher affinity EGFR variants of this invention, for example.

Additionally, in the approach presented here, the antibodies engage on the TCR of vδ1 cells but full activation does not occur unless tumour cells are also present. Full engagement of the presently presented antibodies on the TCR leads to partial downregulation and the vδ1 cells bound by the presently presented antibodies only become fully activated and become cytotoxic in the tumour microenvironment. This represents another vital safety advantage for the present approach, since off target cytotoxicity is reduced and the full potency of the present antibodies to activate vδ1 cells is only unleashed in the presence of tumour cells.

One mechanism behind γδ T cells being able to detect stress signals on tumour cells is believed to be due to the NCRs (natural cytotoxicity receptors) they express. The NCRs are able to engage NCR ligands on tumour cells. A dual mechanism of activation is therefore employed, wherein the γδ T cells are activated via TCR stimulation and the NCRs sense the tumour cells to enable full activation and cytotoxicity.

This is in contrast to stimulation of αβ T cells via CD3, wherein all stimulation is via the TCR. Such cells are therefore almost indiscriminate between healthy or transformed cells because they don't have this antigen presentation independent sensing of tumour cells via NCRs. Therefore, if CD3 antibodies are Fc enabled they will attract other immune cells which can trigger a cascade of unpredictable and desirable events such as cytokine storms, exhaustion and even overactivation of immune cells leading to, for example, NK cells killing T cells etc. In the present approach, stimulation of γδ T cells with the presently presented antibodies does not lead to such concerns because both γδ T cells (and other immune cells such as NK cells) are able to distinguish between healthy cells and tumour cells including via their NCR sensing mechanism and therefore selectively kill stressed cells such as cancer cells or virally infected cells due to this diseased cell specificity.

For example, in initial cynomolgus studies with the anti-vδ1 Fc-enabled multispecific antibody presented herein, with specificity to both human and cyno vδ1 antigen (SEQ ID NO: 1 and SEQ ID NO: 172), was found to be safe and well tolerated, in dose-escalating, repeat dose in-vivo studies by all parameters measured. None of the side effects typically associated with T cell activation, such as cytokine release or weight loss were observed.

These findings also highlight another advantage of the approach described herein. Specifically, and unlike TCEs typified by CD3 engagers and the like, TCE bispecifics of the invention can optionally be designed as full-length antibody, for example comprising heavy chains with a VH-CH1-CH2-CH3 format with cognate light chains with a VL-CL format. Unlike smaller bispecific formats (e.g. less than 70 KDa), such full-length bispecific format can exhibit longer half-lives in-vivo and thereby require less frequent dosing regimens. The longer half-lives observed by such formats are for a variety of reasons inclusive of increased size (>70 KDa) which means such formats are not filtered by kidneys (glomerulus pore size cut-off 60-70 KDa). In one embodiment, the multispecific antibodies may be larger than about 70 KDa, and may comprise human IGHC sequence (e.g. IGHA, IGHD, IGHD, IGHM, IGHG sequence) as listed by IMGT. Such IgG1 formats can also be re-cycled by FcRn mechanism. The clear downside of such full-length antibody formats for TCE bispecifics in particular is that such format exhibit unfavorable safety profiles due to the reduce clearance rate, increased and more chronic exposures.

Therefore, the present approach allows the possibility of Fc functionality without any concern of off-target effects, such as NK cells killing γδ T cells or vice versa. The present approach is therefore superior to CD3 directed approaches which are stunted by the necessity of workarounds such as reducing CD3 affinity, eliminating Fc function etc. to limit collateral damage outside the tumour environment. The multispecific antibodies, in particular T-cell engagers, presented here are able to bind to vδ1 cells without any damage potential and the full activation and cytotoxicity enhancement is only engaged when the vδ1 cells are in close contact with tumour cells.

Hence in one embodiment there is provided a method of downregulating a TRDV1-containing Vδ1 TCR and the associated CD3 molecule complex on the surface of a cell with a TCE multispecific antibody, and the use of such multispecific antibodies for this purpose.

Other features and advantages of the present invention will be apparent from the description provided herein. It should be understood, however, that the description and the specific examples while indicating preferred embodiments of the invention are given by way of illustration only, since various changes and modifications will become apparent to those skilled in the art. The invention will now be described using the following, non-limiting examples:

EXAMPLES

Example 1: Tables

Parental antibody clones were prepared as set out in Examples 1 to 19 in WO2021/032963.

The sequences of the CDRs of the parental clones are shown below in Table 24.

TABLE 23

| DV1 binders for IgG conversion | | | | | | |
|---|---|---|---|---|---|---|
| Clone ID | Heavy CDR1 | SEQ ID NO. | Heavy CDR2 | SEQ ID NO. | Heavy CDR3 | SEQ ID NO. |
| 1245_P02_G04 | GDSVSSKSAA | 51 | TYYRSKWST | 53 | TWSGYVDV | 54 |
| 1245_P01_E07 | GFTFSDYY | 130 | ISSSGSTI | 131 | VDYADAFDI | 132 |

TABLE 23-continued

| | | | | | | | |
|---|---|---|---|---|---|---|---|
| \multicolumn{8}{c}{DV1 binders for IgG conversion} |
| 1252_P01_C08 | GFTVSSNY | 317 | IYSGGST | 318 | PIELGAFDI | 319 | |
| 1245_P01_B07 | GFTFSDYY | 320 | ISSSGSTI | 321 | ENYLNAFDI | 322 | |
| 1251_P02_C05 | GFTFSSYA | 323 | ISGGGGTT | 324 | DSGVAFDI | 325 | |
| 1139_P01_E04 | GDSVSSNSAA | 326 | TYYRSKWYN | 327 | SWNDAFDI | 328 | |
| 1245_P02_F07 | GDSVSSNSAA | 329 | TYYRSKWYN | 330 | DYYYSMDV | 331 | |
| 1245_P01_G06 | GFTFSDYY | 332 | ISSSGSTI | 333 | HSWNDAFDV | 334 | |
| 1245_P01_G09 | GDSVSSNSAA | 335 | TYYGSKWYN | 336 | DYYYSMDV | 337 | |
| 1138_P01_B09 | GFTFSDYY | 338 | ISSSGSTI | 339 | HSWSDAFDI | 340 | |
| 1251_P02_G10 | GFTFSDYY | 341 | ISSSGSTI | 342 | HSWNDAFDI | 343 | |
| 1141_P01_E01 | GYSFTSYW | 344 | IYPGDSDT | 345 | HQVDTRTADY | 346 | |

| Clone ID | Light CDR1 | SEQ ID NO. | Light CDR2 | SEQ | Light CDR3 | SEQ ID NO. | 100 nM L1 |
|---|---|---|---|---|---|---|---|
| 1245_P02_G04 | QDINDW | 79 | DAS | 80 | QQSYSTPQVT | 81 | 5896 |
| 1245_P01_E07 | QSIGTY | 144 | VAS | 145 | QQSYSTLLT | 146 | 162591 |
| 1252_P01_C08 | NIGSQS | 347 | YDS | 348 | QVWDSSSDHVV | 349 | 1977 |
| 1245_P01_B07 | QSLSNY | 350 | AAS | 351 | QQSYSTPLT | 352 | 64271 |
| 1251_P02_C05 | QNIRTW | 353 | DAS | 354 | QQFKRYPPT | 355 | 65269 |
| 1139_P01_E04 | QSISTW | 356 | DAS | 357 | QQSYSTPLT | 358 | 23786 |
| 1245_P02_F07 | QSISSW | 359 | DAS | 360 | QQSHSHPPT | 361 | 10450 |
| 1245_P01_G06 | QSISSY | 362 | AAS | 363 | QQSYSTPDT | 364 | 22474 |
| 1245_P01_G09 | QSISTW | 365 | DAS | 366 | QQSYSTPVT | 367 | 18430 |
| 1138_P01_B09 | QDISNY | 368 | DAS | 369 | QQSYSTPLT | 370 | 29193 |
| 1251_P02_G10 | QSISSH | 371 | AAS | 372 | QQSYSTLLT | 373 | 17053 |
| 1141_P01_E01 | RSDVGGYNY | 374 | EVS | 375 | SSYTSTSTLV | 376 | 136780 |

The $K_D$ values of the parental clones, as determined by SPR analysis, was as follows:

TABLE 24

Results of IgG capture

| Analyte | Clone ID | $K_D$ (nM) | $K_D$ (M) |
|---|---|---|---|
| L1 (DV1-GV4) | 1245_P01_E07 | 12.4 | 1.24e-08 |
| L1 (DV1-GV4) | 1252_P01_C08 | 100 | 1.00e-07 |
| L1 (DV1-GV4) | 1245_P02_G04 | 126 | 1.26e-07 |
| L1 (DV1-GV4) | 1245_P01_B07 | 341 | 3.41e-07 |
| L1 (DV1-GV4) | 1251_P02_C05 | 1967* | 1.97e-06 |
| L1 (DV1-GV4) | 1139_P01_E04 | 251 | 2.51e-07 |
| L1 (DV1-GV4) | 1245_P02_F07 | 193 | 1.93e-07 |
| L1 (DV1-GV4) | 1245_P01_G06 | 264 | 2.64e-07 |
| L1 (DV1-GV4) | 1245_P01_G09 | 208 | 2.08e-07 |
| L1 (DV1-GV4) | 1138_P01_B09 | 290 | 2.90e-07 |
| L1 (DV1-GV4) | 1251_P02_G10 | 829 | 8.29e-07 |
| L1 (DV1-GV4) | TS8.2 (commercial anti-vδ1 antibody) | 44 | 4.40e-08 |

*Binding of 1252_P02_C05 did not reach saturation, therefore data was extrapolated Epitope mapping was conducted for 5 of the parental clones, using hydrogen-deuterium exchange. A summary of the epitope mapping results is presented in Table 25.

TABLE 25

Results of epitope mapping for antigen/antibody complexes

| Clone ID | Epitope mapping, amino acid numbering of SEQ ID NO: 272 |
|---|---|
| 1245_P01_E07 | 5, 9, 16, 20, 62, 64, 72, 77 |
| 1252_P01_C08 | 50, 53, 59, 62, 64 |
| 1245_P02_G04 | 37, 42, 50, 53, 59, 64, 68, 69, 72, 73, 77 |
| 1251_P02_C05 | 59, 60, 68, 72 |
| 1141_P01_E01 | 3, 5, 9, 10, 12, 16, 17, 62, 64, 68, 69 |

Example 2: Multispecific Antibody Conferred Enhancement of Vδ1+ Effector Cell Mediated Cytotoxicity; Targeting a Tissue-Centric Disease Associated Antigen Cytotoxicity/potency-assay studies were undertaken to explore the effect of multispecific antibodies on co-cultures of Vδ1+ effector cells and A-431 cancer cells. A-431 (EGFR$^{++}$; ATCC®) target cells were seeded in a 384-well imaging plate (PERKINELMER®) at 1,000 cells/well and incubated at 37° C. overnight in DMEM (10% FCS). Antibodies and multispecific antibodies as indicated were diluted to 10 μg/ml and added assay plate (2 μg/ml final assay concentration). Expanded skin-derived Vδ1 γδ T-cells were detached from tissue culture flasks and serial diluted to give a range of E:T ratios (top E:T ratio of 60:1) before adding to assay plate. A-431 cells were incubated with Vδ1 γδ T-cells in the presence of antibodies or controls at 30° C., 5% $CO_2$. After 24 hours incubation, Hoechst 33342 (THERMO FISHER™) was added to stain cells (2 μM final). To determine the numbers of live A-431 cells, confocal images were acquired using an Opera Phenix high content platform capturing nine fields of view at 10× magnification. Live cell counts were quantified base on size, morphology, texture, and intensity of live cell stains. Effector/Target (E:T) time course studies to determine the ET ratio wherein 50% of target cells are killed in model systems +/− the controls, comparators, antibodies and multispecific antibodies as indicated. Results are presented in FIGS. 31A-31H.

First, (FIGS. 31A-31D) present example co-culture results wherein Vδ1+/A-431 co-cultures were studies+/− multispecific antibodies comprising anti-Vδ1×anti-TAA (EGFR) bispecific binding moieties wherein the anti-Vδ1 VL+VH binding domain (to the first target) is combined with the CH1-CH2-CH3 domain of an anti-EGFR binding moiety (to the second target). Controls and comparators employed as indicated; from left to right: No mAb=no antibody added; D1.3=D1.3 control; D1.3 IgG LAGA=D1.3+L235A,G237A; D1.3 FS1-67=D1.3 variable domain with EGFR binding constant domain plus L235A, G237A; CETUXIMAB (in-house generated). More specifically, (FIG. 31A) presents the results for five-hour co-cultures with aforementioned controls, comparators, and the following test articles: C08-LAGA=1252_P01_C08 with L235A,G237A; C08 FS1-67=1252_P01_C08 combined with EGFR binding domain containing a L235A,G237A. (FIG. 31B) presents equivalent data of five-hour co-cultures with aforementioned controls, comparators, and the following test articles: G04-LAGA=1245_P02_G04 with L235A, G237A; G04 FS1-67=1245_P02_G04 combined with EGFR binding domain containing L235A,G237A. (FIG. 31C) presents equivalent data of five-hour co-cultures with controls, comparators, and the following test articles: E07-LAGA=1245_P01_E07 with L235A,G237A; E07 FS1-67=1245_P01_E07 combined with EGFR binding domain containing L235A,G237A. (FIG. 31D) presents a Table summarizing the percent improvement in cytotoxicity of Vδ1 γδ T-cells in the presence of controls, comparators, and test articles over 5, 12 and 24 hours. A greater than 450% enhancement can be observed when antibodies or antigen-binding fragment thereof as described herein are presented in a multispecific format.

Second, (FIGS. 31E-31H) present example results wherein Vδ1+/A-431 co-cultures were studied+/−multispecific antibodies comprising anti-Vδ1×anti-TAA (EGFR) bispecific binding moieties wherein the anti-Vδ1 binding domain (to the first target) comprises a full-length antibody (VH-CH1-CH2-CH3/VL-CL) then combined with an anti-EGFR scFv binding moiety (to the second target). Controls and comparators employed as indicated; from left to right: No mAb=no antibody added; D1.3=Control; D1.3 IgG LAGA=D1.3+L235A,G237A; D1.3 LAGA CETUXIMAB=D1.3 with L235A, G237A plus a C-term CETUXIMAB-derived scFv; CETUXIMAB (in-house generated). More specifically, (FIG. 31E) presents five-hour co-cultures with aforementioned controls, comparators, and the following test articles: C08-LAGA=1252_P01_C08 with L235A, G237A; C08 LAGA CETUXIMAB=1252_P01_C08 with L235A,G237A and with C-term CETUXIMAB-derived scFv. (FIG. 31F) presents five-hour culture with aforementioned controls, comparators, and the following test articles: G04-LAGA=1245_P02_G04 with L235A, G237A; G04 LAGA CETUXIMAB=1245_P02_G04 with L235A, G237A and with C-term CETUXIMAB-derived scFv. (FIG. 31G) presents five-hour culture with controls, comparators, and the following test articles: E07-LAGA=1245_P01_E07 with L235A,G237A; E07 LAGA CETUXIMAB=1245_P01_E07 with L235A,G237A and with C-term CETUXIMAB-derived scFv. (FIG. 31H) presents a Table summarizing the percent improvement in potency of Vδ1 γδ T-cells in the presence of controls, comparators, and test articles over 5, 12 and 24 hours. A greater than 300% enhancement can be observed when antibodies or antigen-binding fragment thereof as described herein are presented in a multispecific format.

Example 3: Mammalian Display

Two clones were selected for affinity maturation. The above examples describe the preparation and characterisation of affinity matured clones derived from clone ADT1-4 (G04) and clone ADT1-7 (E07).

Affinity Maturation of Human Anti-Vδ1 Monoclonal Antibodies

Phage display employed to generate parental anti Vd1 monoclonal antibodies yielded antibodies with the affinity ranging from 10 nM-1 μM, as described above. Parental antibodies clone ADT1-4 (G04) and clone ADT1-7 (E07) were then affinity matured in vitro to surprisingly attain 100 fold improved affinity for superior target engagement. In vitro affinity maturation of parental antibodies was achieved via two-step process: diversification of the parental antibody sequence using targeted CDR3 mutagenesis and then selective enrichment of affinity improved antibodies using phage and mammalian display platforms. VH and VL CDR3 2-mer libraries for the clones ADT1-4 and ADT1-7 were created using Kunkel mutagenesis (Kunkel et al., 1987; Sidhu and Weiss, 2004) and RCA amplification. Combinations of all single and double amino acid substitutions at specified positions in the VH and VL CDR3s were incorporated using Agilent primer synthesis technology. The number of different amino acids to be incorporated at a particular position were specified. Cysteine and methionine were omitted. The changes made in the CDRs of the clones are summarised below in Table 26.

TABLE 26

| | | CDR3 positions and specified residue changes | | | |
|---|---|---|---|---|---|
| | POS | AMINO ACID(S) | POS | AMINO ACID(S) | |
| E07 (V3-11/Vκ1-39) | V | A,D,E,F,G,H,I,K,L,N,P,Q,R,S,T,W,Y | Q | A,D,E,F,G,H,I,K,L,N,P,R,S,T,V,W,Y | |
| | D | A,E,F,G,H,I,K,L,N,P,Q,R,S,T,V,W,Y | S | A,D,E,F,G,H,I,K,L,N,P,Q,R,T,V,W,Y | |
| | Y | A,D,E,F,G,H,I,K,L,N,P,Q,R,S,T,V,W | Y | A,D,E,F,G,H,I,K,L,N,P,Q,R,S,T,V,W | |
| | A | D,E,F,G,H,I,K,L,N,P,Q,R,S,T,V,W,Y | S | A,D,E,F,G,H,I,K,L,N,P,Q,R,T,V,W,Y | |
| | D | A,E,F,G,H,I,K,L,N,P,Q,R,S,T,V,W,Y | Y | A,D,E,F,G,H,I,K,L,N,P,Q,R,S,V,W,Y | |
| | A | D,E,F,G,H,I,K,L,N,P,Q,R,S,T,V,W,Y | L | A,D,E,F,G,H,I,K,N,P,Q,R,S,T,V,W,Y | |
| | F | A,G,H,I,L,N,P,S,T,V,Y | L | A,D,E,F,G,H,I,K,N,P,Q,R,S,T,V,W,Y | |
| | D | A,G,N,S,Y | K | A,G,Q,S,T,V | |
| | I | G,S,V,Y | | | |
| G04 (VH6-1/Vκ1-5) | T | A,D,E,F,G,H,I,K,L,N,P,Q,R,S,V,W,Y | S | A,D,E,F,G,H,I,K,L,N,P,Q,R,T,V,W,Y | |
| | W | A,D,E,F,G,H,I,K,L,N,P,Q,R,S,T,V,Y | V | A,D,E,F,G,H,I,K,L,N,P,Q,R,T,V,W,Y | |
| | S | A,D,E,F,G,H,I,K,L,N,P,Q,R,T,V,W,Y | S | A,D,E,F,G,H,I,K,L,N,P,Q,R,S,T,V,W | |
| | G | A,D,E,F,H,I,K,L,N,P,Q,R,S,T,V,W,Y | T | A,D,E,F,G,H,I,K,L,N,P,Q,R,T,V,W,Y | |
| | Y | A,D,E,F,G,H,I,K,L,N,P,Q,R,S,T,V,W | P | A,D,E,F,G,H,I,K,L,N,Q,R,S,T,V,W,Y | |
| | V | A,F,G,H,I,L,L,N,P,S,T,Y | Q | A,D,E,F,G,H,I,K,L,N,P,R,S,T,V,W,Y | |

TABLE 26-continued

CDR3 positions and specified residue changes

| POS | AMINO ACID(S) | POS | AMINO ACID(S) |
|---|---|---|---|
| D | A,G,N,S,Y | V | A,D,E,F,G,H,I,K,L,N,P,Q,R,S,T,W,Y |
| V | G,I,S,Y | Q | A,G,R,S,T,V |

The size of each library is shown in Table 27.

TABLE 27

| | Library Size |
|---|---|
| ADT1-7 | 5.4 × 10$^9$ |
| ADT1-4 | 5.5 × 10$^9$ |

Generation of Mutagenized VH and VL CDR3 Libraries

Figure 1A:
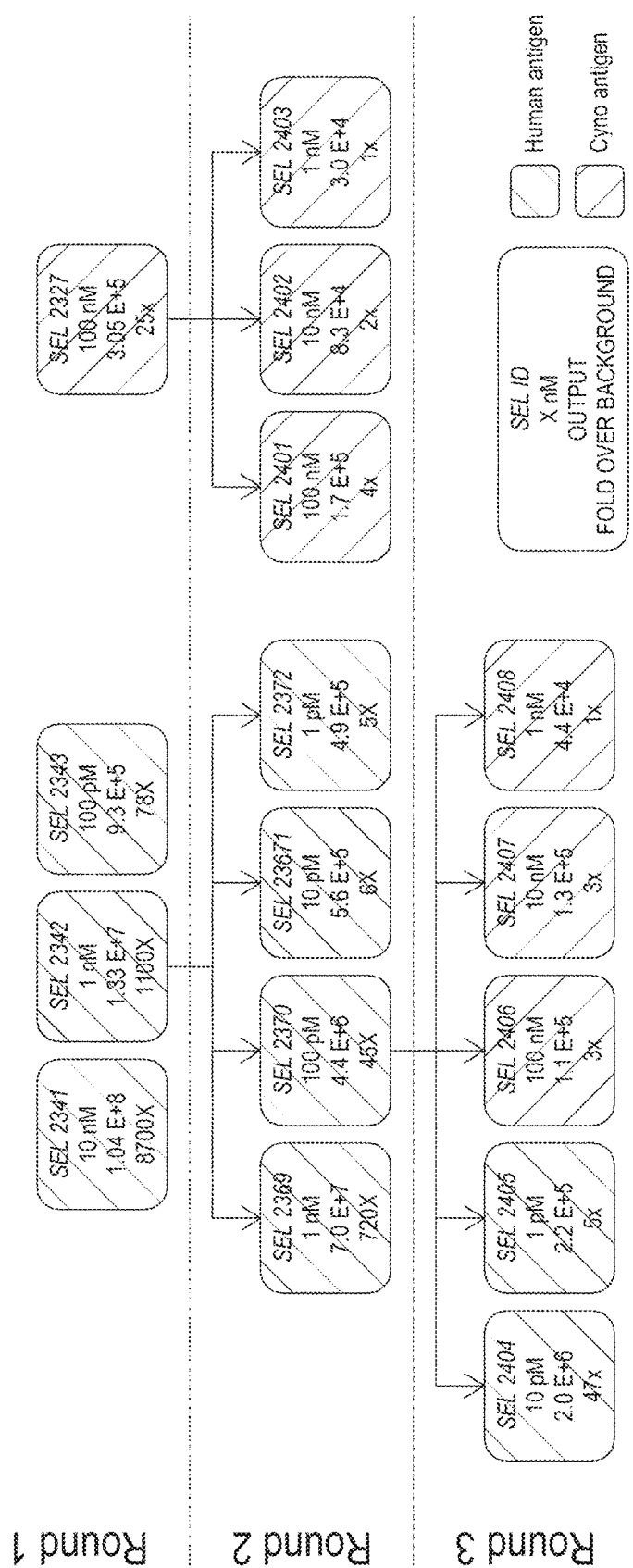
FIGS. 1A-1C: Phage selection rounds.
Figure 1B:
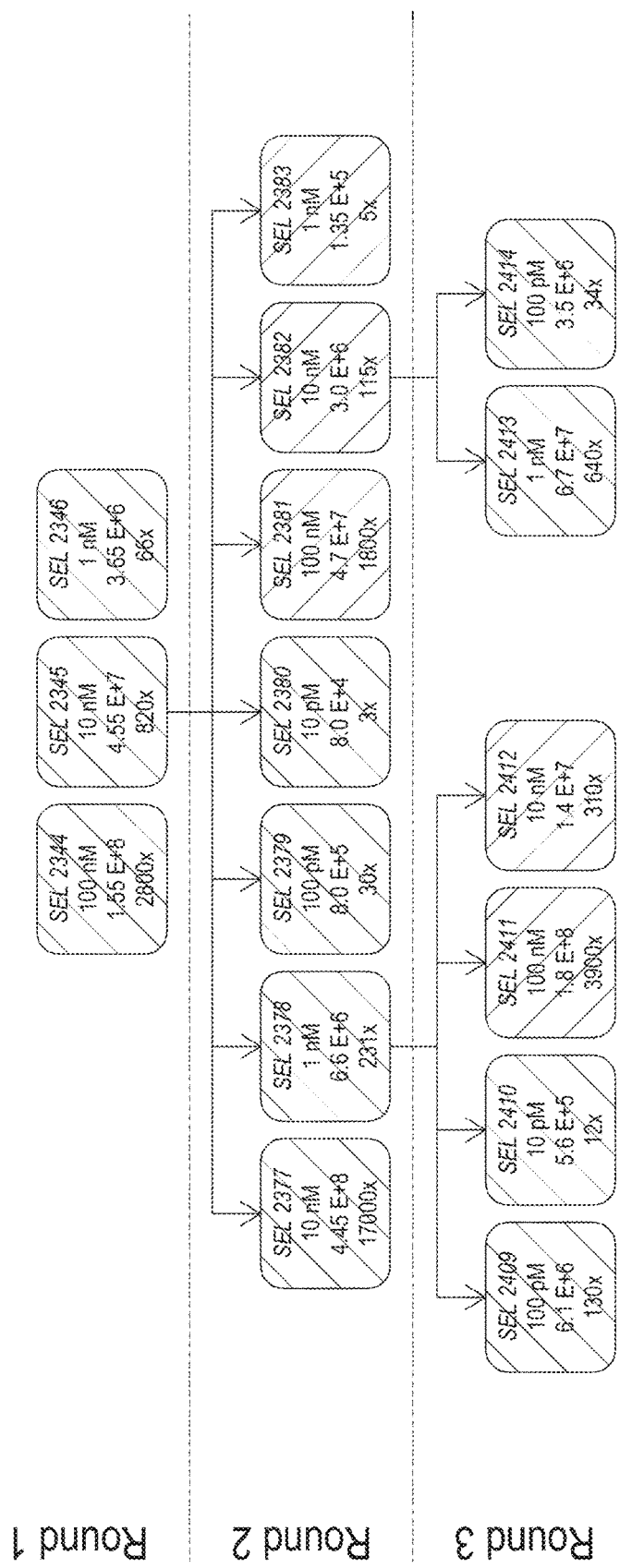
Figure 1C:
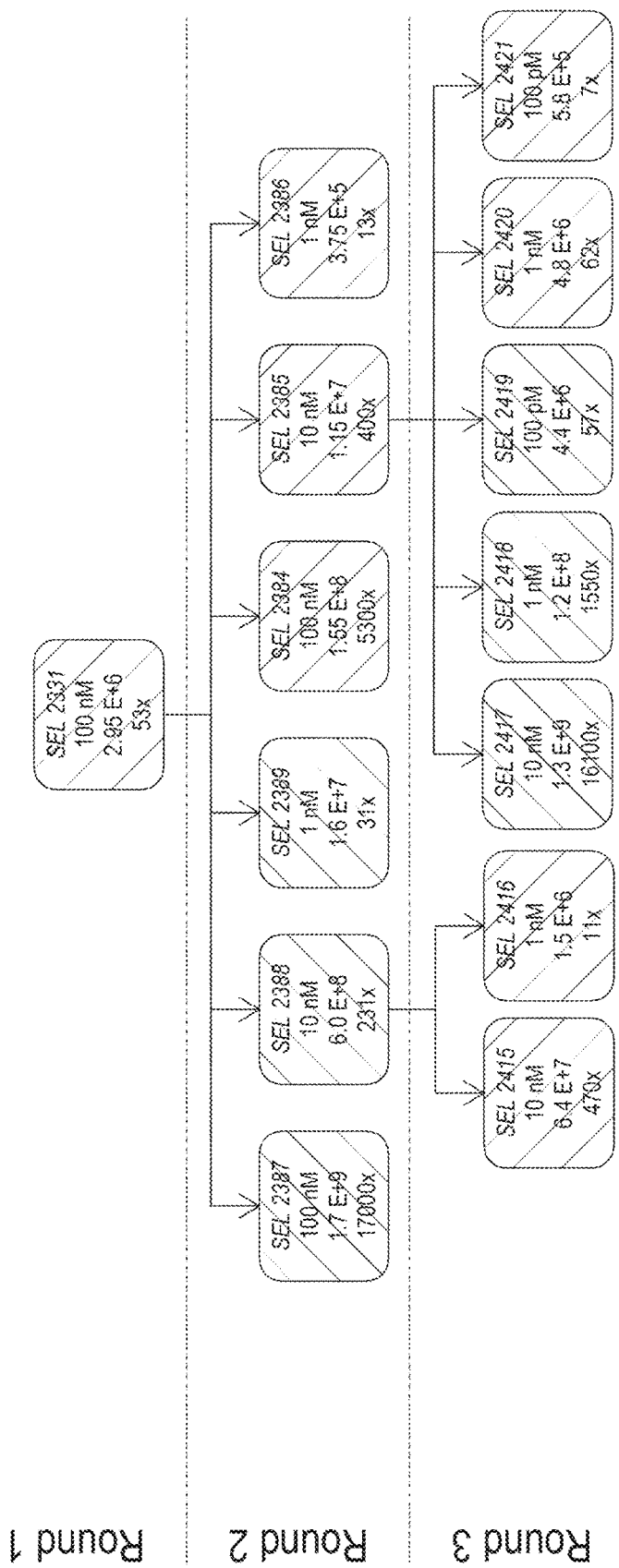

Mutagenised libraries were prepared from suitable culture volumes covering an appropriate excess of library members. Affinity maturation was performed using phage display technology as described in Schofield et al. (2007) using solution phase selection. Selections were performed in the solutions using human and cyno antigen. To isolate binders from a mutant library with higher affinities antigen concentration was controlled to give a series of increasingly stringent selections. Several rounds of phage display selections with human and with cyno antigen were performed for each clone as presented in FIGS. 1A-1C. For ADT1-4 lineage the antigen concentration used in the selection was ranging from 100 nm-10 pM for human and 100 nM and 10 nM for cyno antigen. For ADT1-7 lineage the human antigen was used at concentration from 10 nM to 1 pM and for cyno from 100 nM to 100 pM. FIGS. 1A-1C show the phage selection rounds for the ADT1-7 library (iA), the ADT1-4 library (iB) and the ADT1-7 library with a selection strategy for isolating cyno cross-reactive binders (iC).

Polyclonal phage ELISA was used to evaluate the progress of the selections. Human DV1/GV4 and Cyno DV1/GV76 were coated overnight at 150 ng/well, 50 µL/well. Cyno DV2/GV76 and HSA were used as controls. Only the outputs from the ADT4-1 library were both cross reactive to human and cyno DV1 antigen. The output from ADT1-7 were only reactive to human antigen. Selected outputs were characterised further by monoclonal phage ELISA and the summary is presented in Table 28. The italicized and bolded text indicates the selection was carried out with either human or cyno antigen, respectively. The arrows provide an indication as to the percentage of clones that are classified as binders to human or cyno VD1 (pointing up being high and pointing down being low).

TABLE 28

Monoclonal phage ELISA summary

| G04 | phage rounds | | | Binding | | | |
|---|---|---|---|---|---|---|---|
| selection | #1 | #2 | #3 | huDV1 | | cyDV1 | |
| 2378 | 10 nM | 1 nM | | ↑ | 79% | ↘ | 25% |
| 2409 | | 100 pM | | ↑ | 75% | ↑ | 100% |
| 2412 | | 10 nM | | ↗ | 72% | ↑ | 100% |
| 2413 | | 10 nM | 1 nM | ↑ | 84% | ↑ | 100% |
| 2385 | 100 nM | 10 nM | | ↗ | 71% | ↑ | 75% |
| 2418 | | | 1 nM | ↑ | 100% | ↑ | 94% |
| 2420 | | | 1 nM | ↑ | 94% | ↑ | 94% |
| 2415 | | 10 nM | 10 nM | | | ↑ | 100% | ↑ | 94% |

| E07 | phage rounds | | | | | |
|---|---|---|---|---|---|---|
| selection | #1 | #2 | #3 | huDV1 | | cyDV1 |
| 2370 | 1 nM | 100 pM | | ↑ | 96% | ↓ 0% |
| 2404 | | | 10 pM | ↑ | 83% | ↓ 0% |

The sequence diversity is summarised in Table 29. The italicized and bolded text indicates the selection was carried out with either human or cyno antigen, respectively. The arrows provide an indication as to the level of diversity (pointing up being high and pointing down being low.

TABLE 29

Monoclonal phage sequencing summary

| G04 | phage rounds | | | diversity | | |
|---|---|---|---|---|---|---|
| | | | | heavy | light | heavy-light |
| selection | #1 | #2 | #3 | CDR3 | CDR3 | CDR3 |
| 2378 | 10 nM | 1 nM | | ↑ 83% | ↑ 96% | ↑ 100% |
| 2409 | | 100 pM | | ↘ 50% | ↘ 53% | ↗ 72% |
| 2412 | | 10 nM | | ↘ 63% | ↑ 97% | ↑ 97% |
| 2413 | | 10 nM | 1 nM | ↗ 71% | ↑ 97% | ↑ 100% |
| 2385 | 100 nM | 10 nM | | ↑ 83% | ↑ 88% | ↑ 100% |
| 2418 | | | 1 nM | ↗ 66% | ↗ 81% | ↑ 88% |
| 2420 | | | 1 nM | ↘ 63% | ↗ 73% | ↗ 80% |
| 2415 | | 10 nM | 10 nM | ↘ 63% | ↗ 78% | ↑ 88% |

| EO7 | phage rounds | | | heavy | light | heavy-light |
|---|---|---|---|---|---|---|
| selection | #1 | #2 | #3 | CDR3 | CDR3 | CDR3 |
| 2370 | 1 nM | 100 pM | | ↑ 88% | ↑ 96% | ↑ 100% |
| 2404 | | | 10 pM | ↗ 75% | ↗ 67% | ↑ 96% |

Generation of IgG Mammalian Display Libraries

To form final libraries for mammalian display the following ADT1-4 selections were polled:
SEL2409, 2412 and 2413 to create ADT1-4 library 1 (human)
SEL 2418, 2420 and 2415 to create ADT1-4 library 2 (cyno)
SEL2370 and 2404 to create ADT1-7 library.

Pools were then advanced to mammalian display. Single chain variable fragment antibodies (scFvs) populations were converted en masse into the IgG format, maintaining the original variable heavy (VH) and variable light (VL) chain pairing. The IgG formatted antibodies were then cloned into a mammalian display donor vector which was co-transfected with plasmids encoding a TALE nuclease pair to enable nuclease directed antibody gene integration at a single chromosomal locus. A mammalian display antibody library covering the phage output diversity (>10$^6$ clones) was created in HEK293 cells. Stable populations of cells expressing antibodies on the cell surface were selected by blasticidin addition 2 days post transfection (dpt). Cells expressing antibodies on the cell surface were enriched by magnetic-activated cell sorting (MACS) sorting (7 dpt); the cells were labelled with anti-Fc-PE followed by anti-PE microbeads and sorted using Midi MACS magnet (MILTENYI BIOTEC®) and LS columns. These populations of cells were advanced to selections.

Selection of Matured Antibodies by Mammalian Display

Figures 2A, 2B:
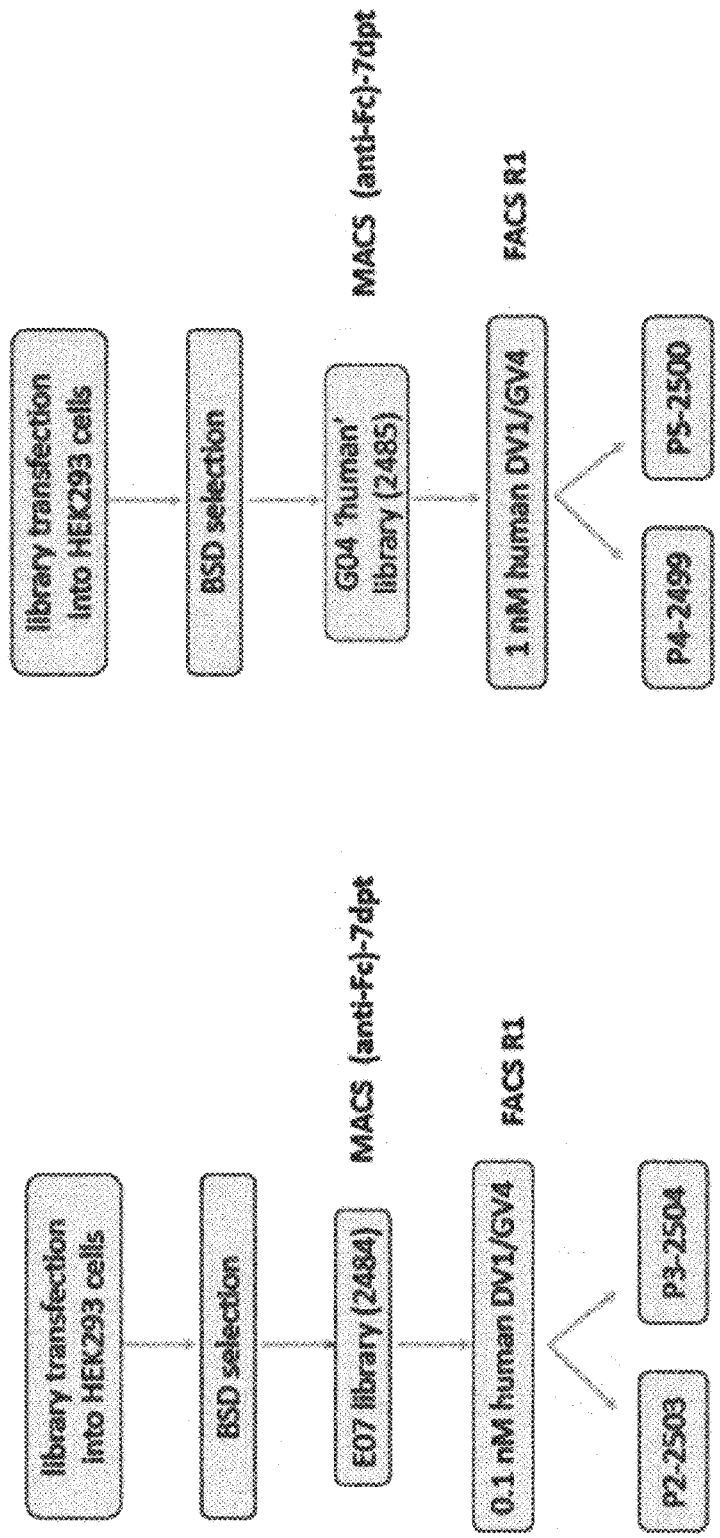
FIGS. 2A-2C: A schematic overview of selection of matured antibodies by mammalian display.
Figure 2C:
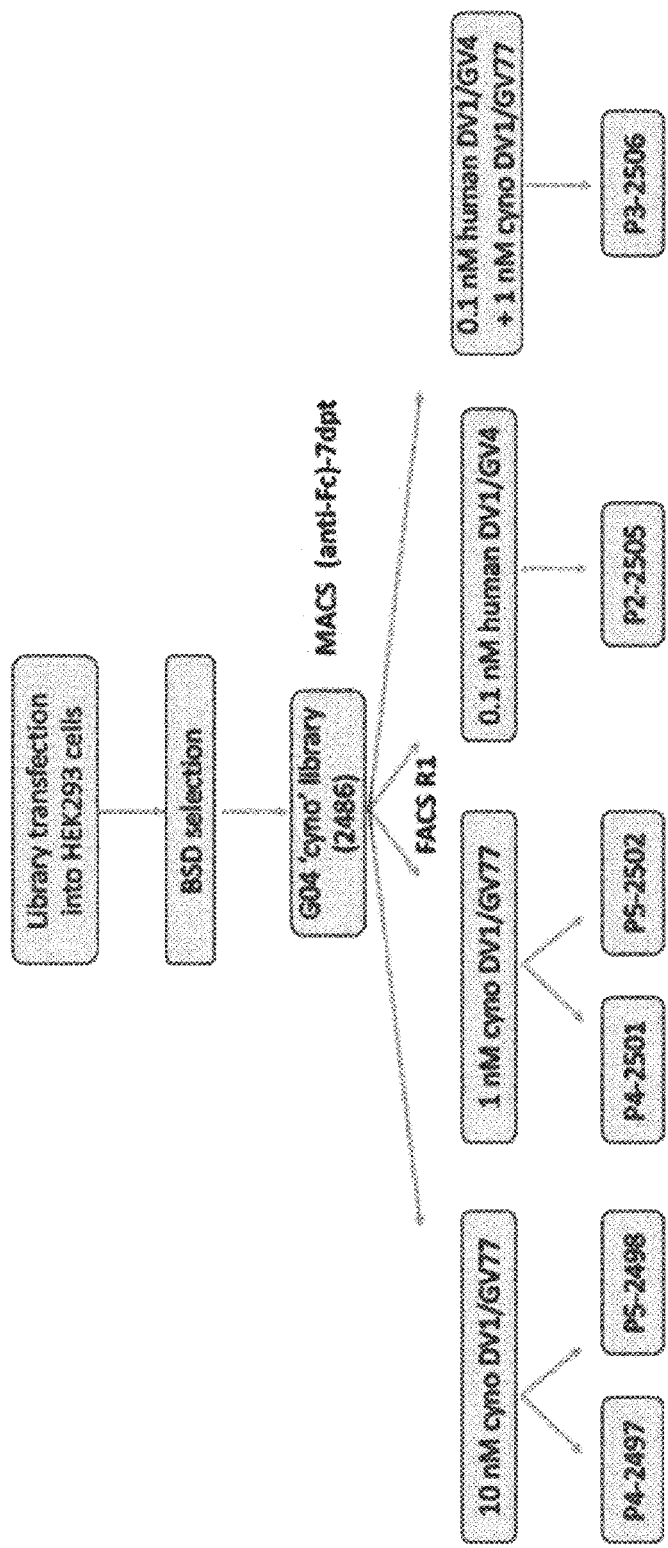
Figure 3A:
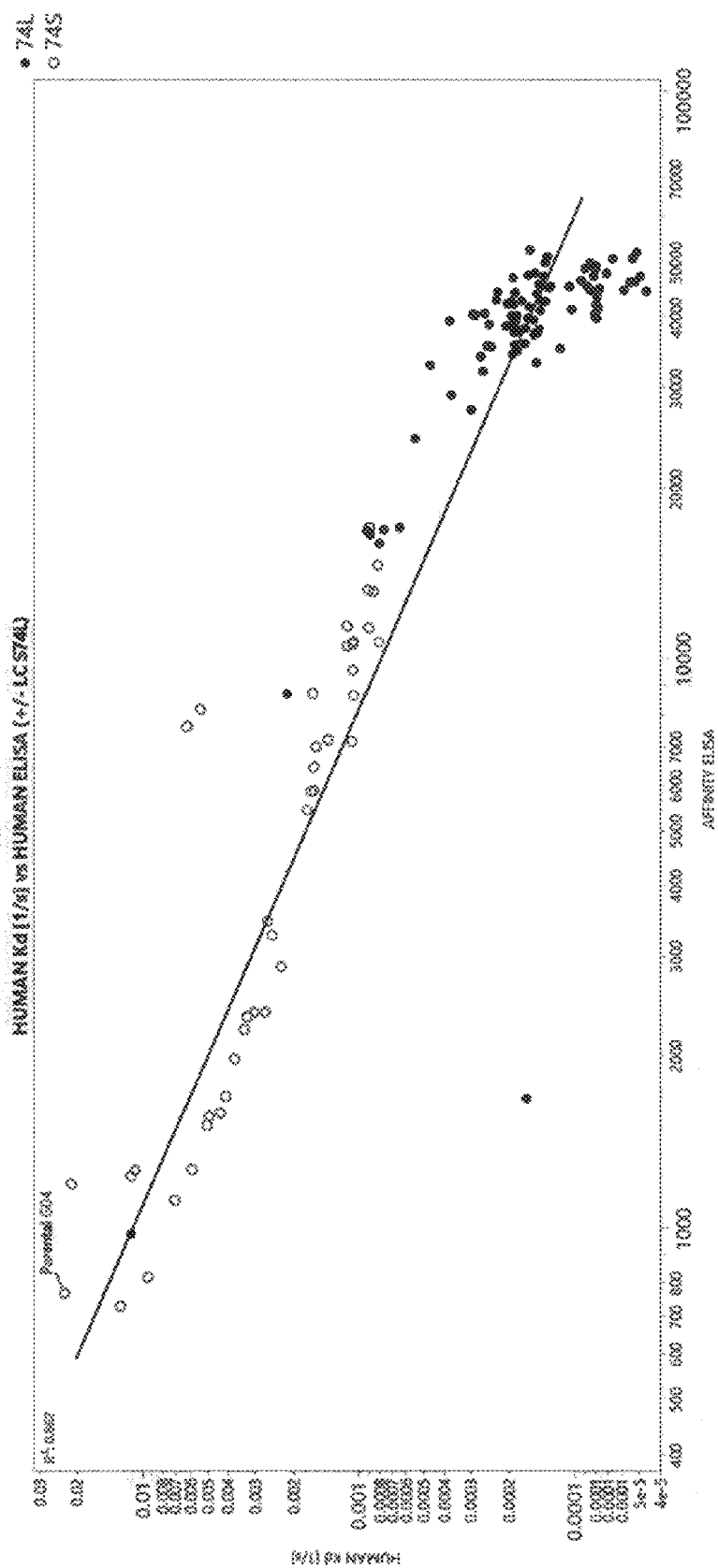
FIGS. 3A-3C: Impact of S74L change on affinity.
Figure 3B:
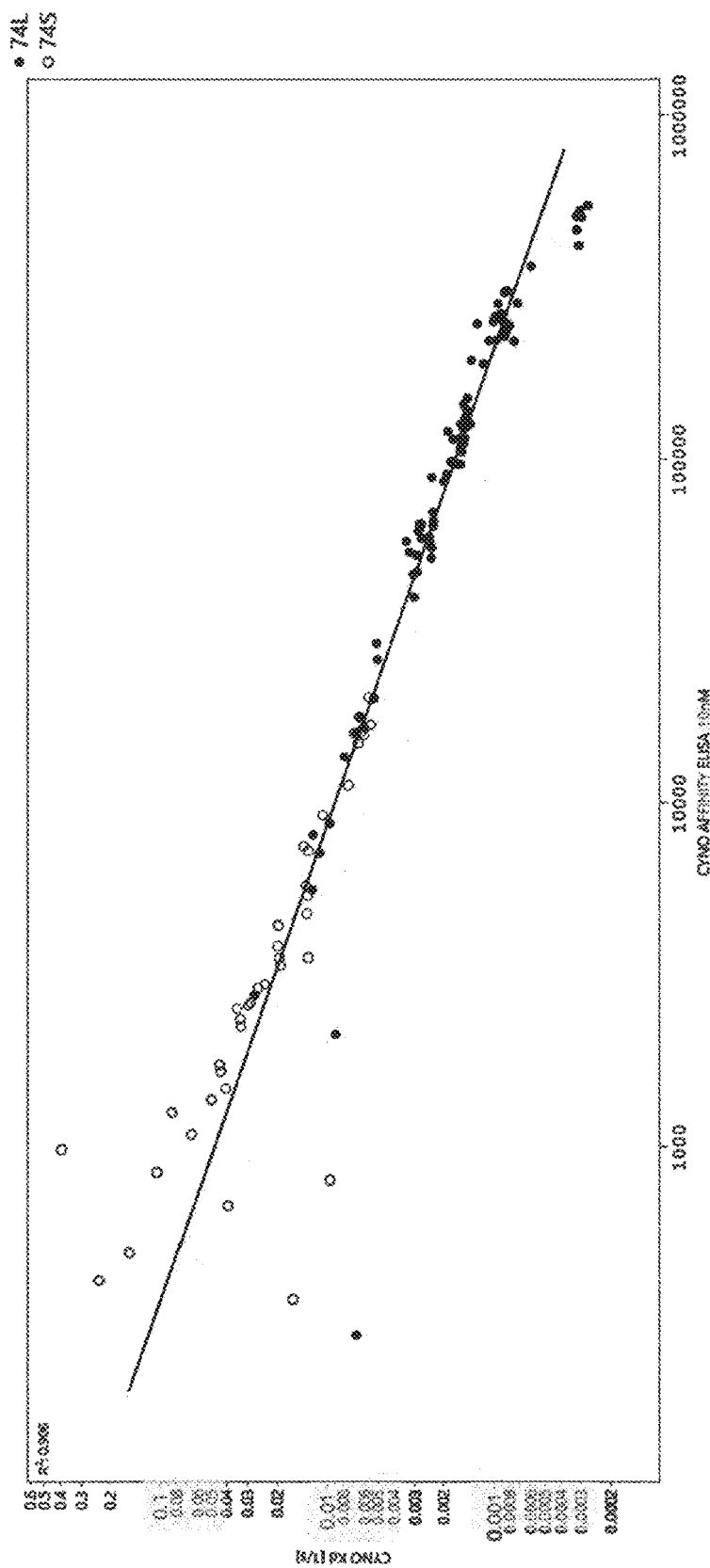
Figure 3C:
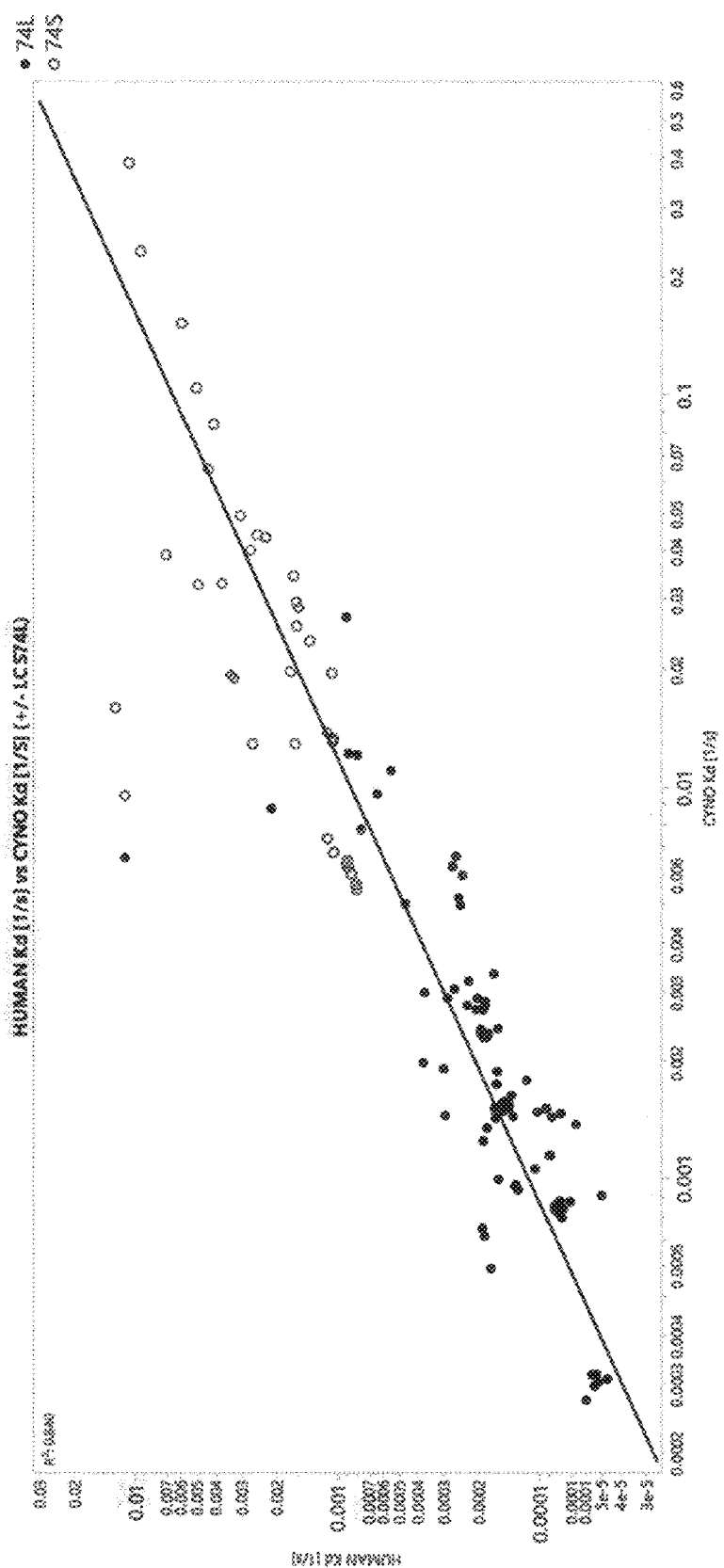
Figure 4A:
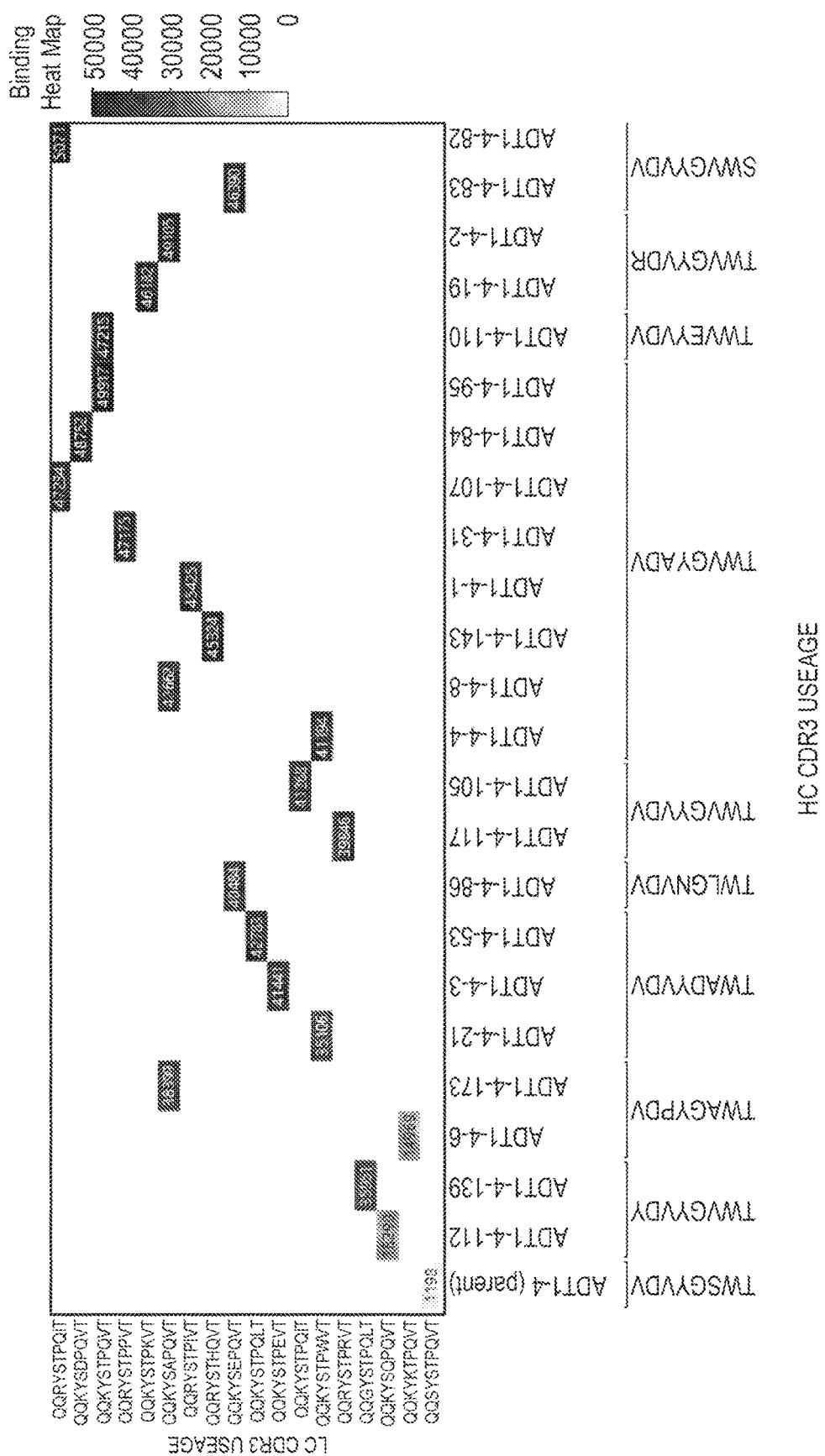
FIGS. 4A-4C: CDR3 usage and cross-sharing.
Figure 4B:
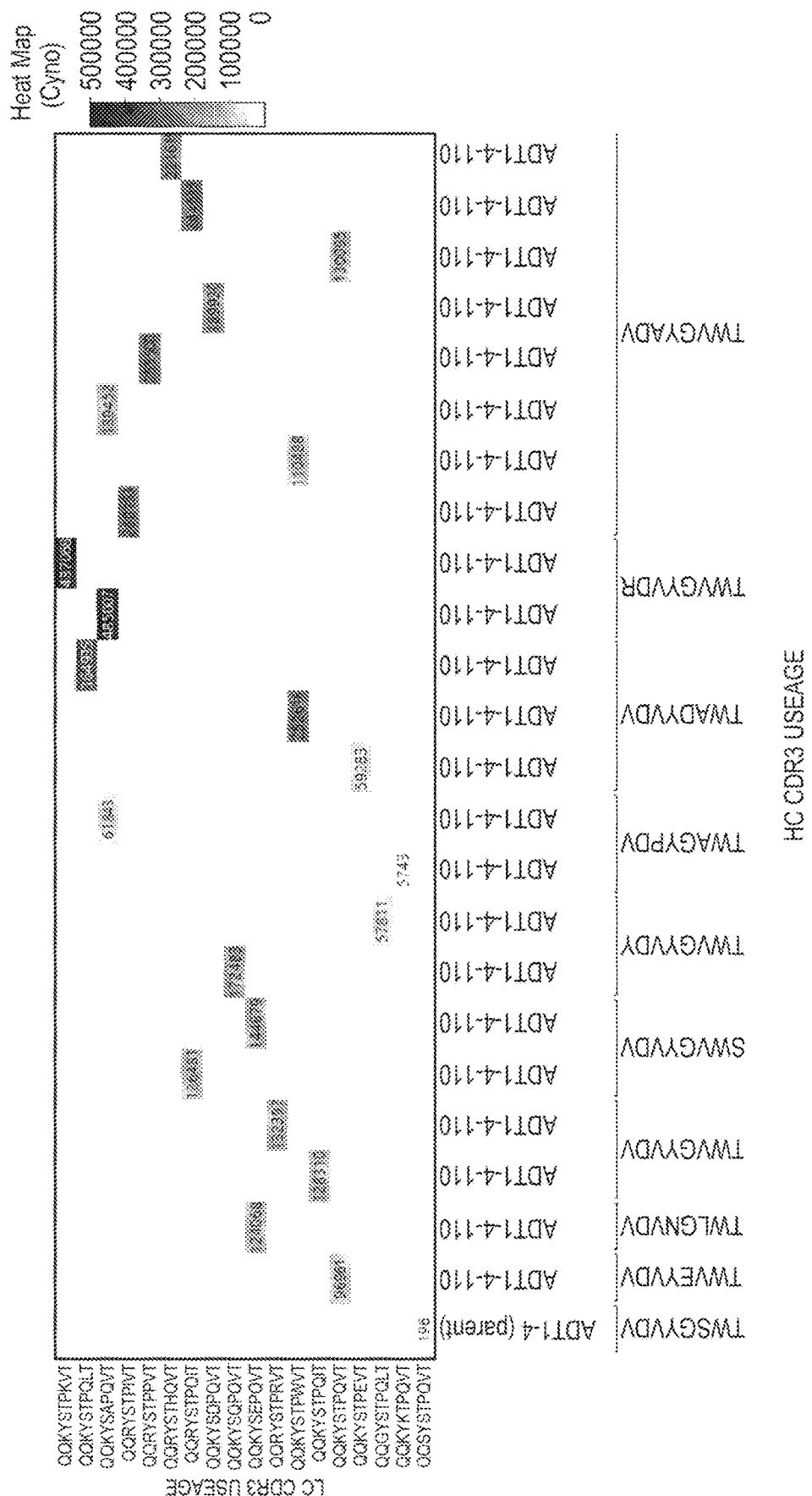
Figure 4C:
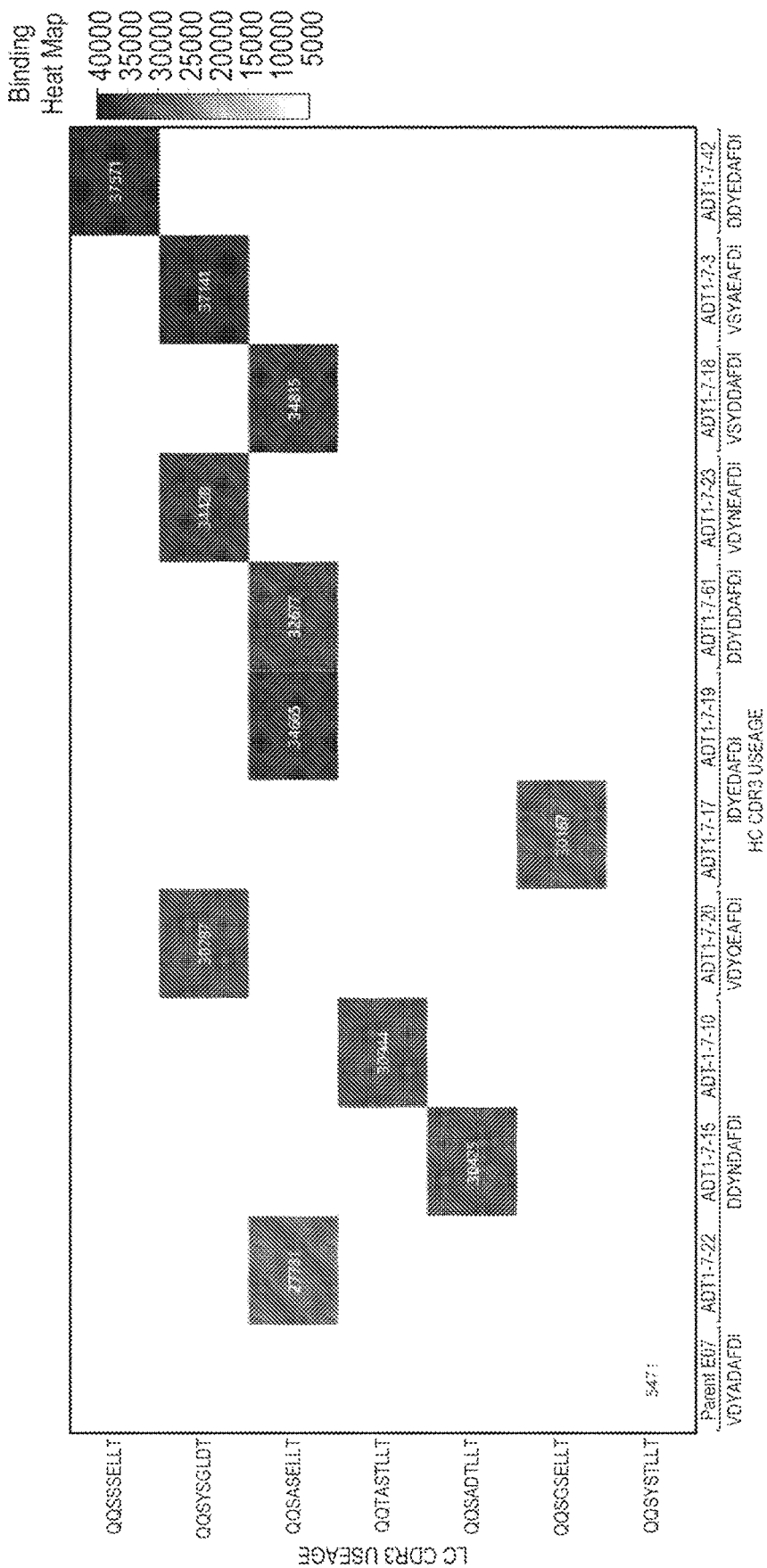

Following MACS to enrich antibody expressing cells, two strategies were adopted to identify TRDV1 binders. The main strategy involved dual colour fluorescence sorting based on Fc expression and antigen binding. The other involved dual colour fluorescence sorting based on the binding of both cyno and human antigens to maximise the chances of isolating high affinity cross-reactive binders. A schematic overview of the process is presented in FIGS. 2A-2C.

Sequence, Specificity, Affinity Ranking and Characterisation

Genomic DNA was extracted from eight different sorted populations. DNA encoding the selected IgGs were amplified and cloned into the soluble IgG1 expression vector. A total of 1472 clones from the 8 different selections were chosen. The pDNA was transfected into Expi293 cells. Supernatants were harvested 5 days after transfection and the expressed antibodies affinity ranked for human and cyno TRDV1 binding in a capture ELISA. A total of 93 anti-DV1 antibodies from each selections strand were chosen for sequence and SPR off-rate analysis. In addition, these clones were checked by direct ELISA for binding to: human TRDV1, human TRDV1 (A→V), human TRDV2, cyno TRDV1 and BSA.

Example 4: Binding Affinity to Human and Cyno Antigens

Binding to Recombinant Antigen and vδ1 TCR Expressed on Cells: ADT1-4 Lineage

Studies were undertaken to explore the binding of anti-vδ1 antibodies to their target antigens. The binding of vd1 mAbs to vd1 TCR antigen was tested by ELISA. 1 ug of human antigen or 1 ug of cynomolgus antigen was immobilized per well onto 96 well Immunoassay plates (SLS #475904) and then blocked with BSA to prevent non-specific binding. 1.3 pmol (20 ng) of each mAb were added and incubated for 1 hour at room temperature. mAb binding to antigen was detected using ProteinA-HRP (ABCAM® #Ab7456) along with TMB substrate (THERMO FISHER™) #12750000) and Stop solution (BIOLEGEND® #423001) by measuring absorbance at 450 nM. Parental controls were included as positive controls for both the assay and inter-plate variability. Hits were identified as those mAbs giving absorbance readings above those of the parental mAbs. FIG. 5A shows the fold increase in absorbance for matured ADT1-4 clones compared to parental ADT1-4 binding absorbance when 1.3 pmol of antibody was bound to human vδ1 antigen. FIG. 5B shows the fold increase in absorbance for matured ADT1-4 clones compared to parental ADT1-4 binding absorbance when 1.3 pmol of antibody was bound to cynomolgus vδ1 antigen.

mAb binding to endogenous vd1-TCR was tested using flow cytometry. Skin vd1 cells (donor ATS006; ADT expanded E0000113) or the PEER vδ1 cell line were seeded at 3×10^5 cells/well into 96 well round bottom plates and resuspended in 50 ul of FACS buffer (v/v: 2% FCS, 0.1% NaAzide and 1 mM EDTA in PBS) containing 3 ug/ml of test mAb for 15 min at 4° C. Cells were pelleted and secondary anti-hmIgG-APC antibody (MILTENYI® #130-119-772) was added at 1/100 in FACS buffer and incubated for a further 20 min at 4° C. Cells were washed and fixed in CELLFIX™ (BD® #340181) and analysed by flow cytometry. The % vd1 phenotype and Mean Fluorescence Intensity was calculated (INIVAI TECHNOLOGIES®, FLOW-LOGIC™ v7.2). As a positive control the parental antibody was included. FIG. 5C shows the fold increase in mean fluorescence intensity for matured ADT1-4 clones compared to parental ADT1-4 binding primary skin derived human vδ1 cells. FIG. 5D shows the fold increase in mean fluorescence intensity for matured ADT1-4 clones compared to parental ADT1-4 binding the transformed PEER vδ1 cell line.

Figure 6A:
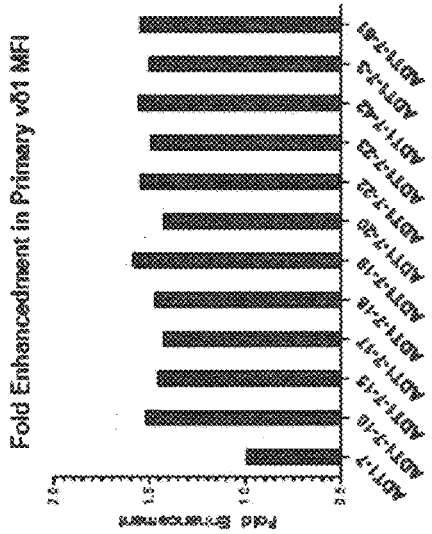
FIGS. 6A-6C: Fold enhancement in binding and for ADT1-1 linage compared to ADT1-4 parental E07.
Figure 6B:
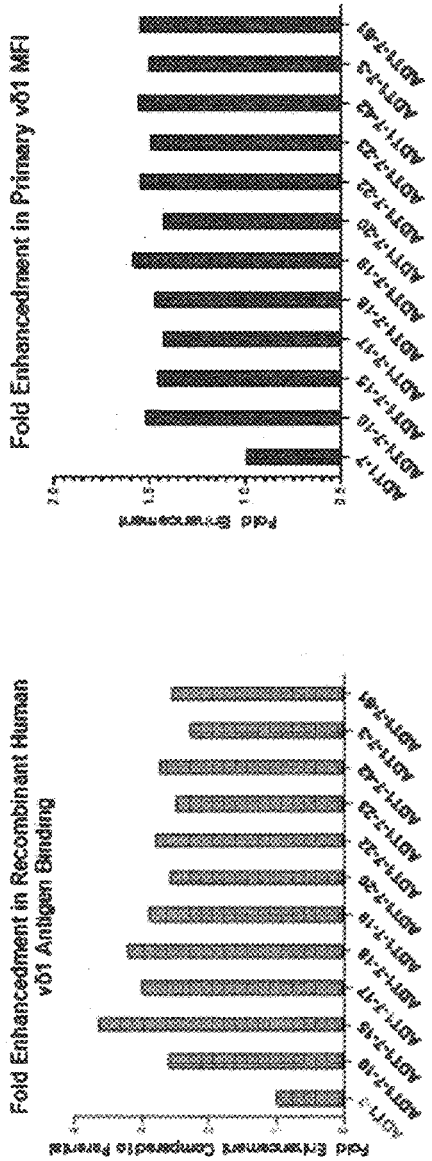
Figure 6C:
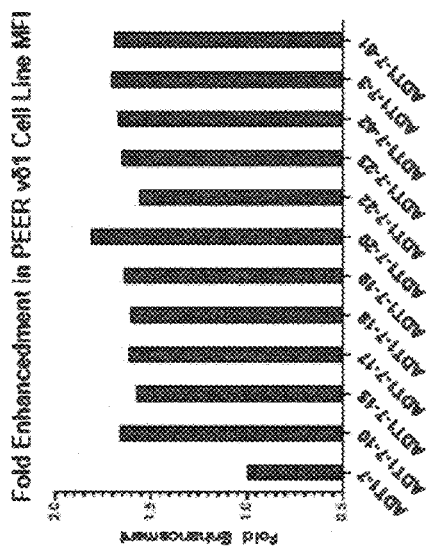

Binding to Recombinant Antigen and vδ1 TCR Expressed on Cells: ADT1-7 Lineage:

Studies were undertaken to explore the binding of ADT1-7 matured anti-vδ1 antibodies to their target antigens. The binding of vd1 mAbs to vδ1 TCR antigen was tested by ELISA. 1 ug of antigen was immobilized per well onto 96 well Immunoassay plates (SLS #475904) and then blocked with BSA to prevent non-specific binding. A titration of 6.7 pmol (100 ng), 1.3 pmol (20 ng) and 0.27 pmol (4 ng) of mAb were added and incubated for 1 hour at room temperature. mAb binding to antigen was detected using ProteinA-HRP (ABCAM® #Ab7456) along with TMB substrate (THERMO FISHER™) #12750000) and Stop solution (Biologend #423001) by measuring absorbance at 450 nM. Parental controls were included as positive controls for both the assay and inter-plate variability. Hits were identified as those mAbs giving absorbance readings above those of the parental mAbs. FIG. 6A shows the fold increase in absorbance for matured ADT1-4 clones compared to parental ADT1-4 binding absorbance when 1.3 pmol of antibody was bound to human vδ1 antigen.

mAb binding to endogenous vd1-TCR was tested using flow cytometry. Skin vδ1 cells (donor ATS006; ADT expanded E0000113) or the PEER vδ1 cell line were seeded at 3×10^5 cells/well into 96 well round bottom plates and resuspended in 50 ul of FACS buffer (v/v: 2% FCS, 0.1% NaAzide and 1 mM EDTA in PBS) containing 3 ug/ml of test mAb for 15 min at 4° C. Cells were pelleted and secondary anti-hmIgG-APC antibody (MILTENYI® #130-119-772) was added at 1/100 in FACS buffer and incubated for a further 20 min at 4° C. Cells were washed and fixed in CELLFIX™ (BD® #340181) and analysed by flow cytometry. The % vd1 phenotype and Mean Fluorescence Intensity was calculated (INIVAI TECHNOLOGIES®, FLOW-LOGIC™ v7.2). As a positive control the parental antibody was included. FIG. 6B shows the fold increase in mean fluorescence intensity for matured ADT1-4 clones compared to parental ADT1-4 binding primary skin derived human vδ1 cells. FIG. 6C shows the fold increase in mean fluorescence intensity for matured ADT1-7 clones compared to parental ADT1-7 binding the transformed PEER vδ1 cell line.

Fold Improvements Over Parental Clones

Dissociation-Enhanced Lanthanide Fluorescence Immunoassay (DELFIA)

For the confirmation of improvement in binding of affinity matures mAb to human and cyno antigen's, DELFIA immunoassay was performed with the antigen directly coated to the plate (3 µg/ml of antigen in 50 µL PBS at 4° C. overnight (Nunc #437111). For detection DELFIA Eu-N1 Anti-Human IgG (PERKINELMER® #1244-330) was used as secondary antibody at 1/500 dilution in 50 µL of 3% of MPBS (PBS+ skimmed 3% (w/V) milk powder). Development was with 50 µL of DELFIA enhancement solution (PERKINELMER® #4001-0010).

Figure 7A:
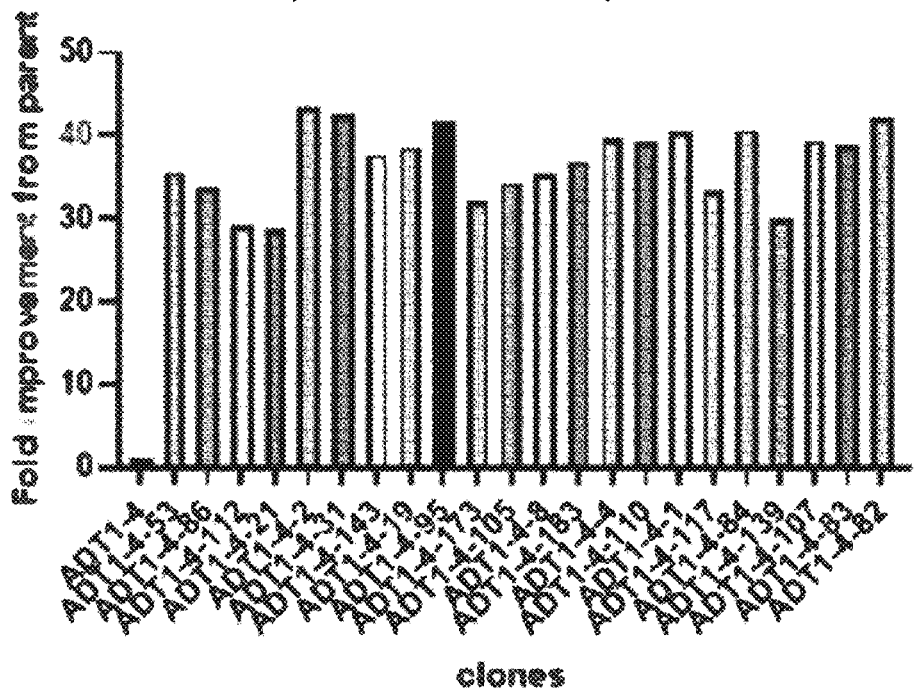
FIGS. 7A-7C. Fold improvements in human (and cyno) antigen binding over parental clones.
Figure 7B:
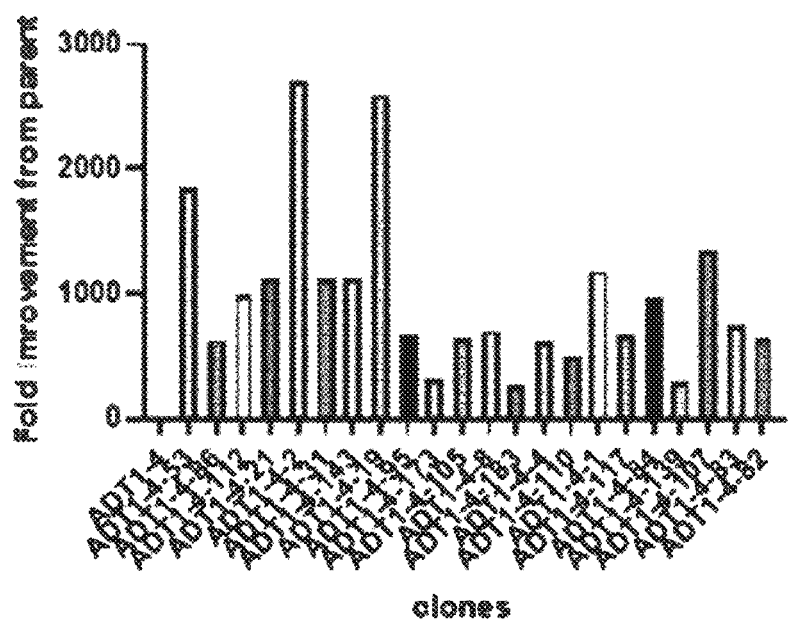
Figure 7C:
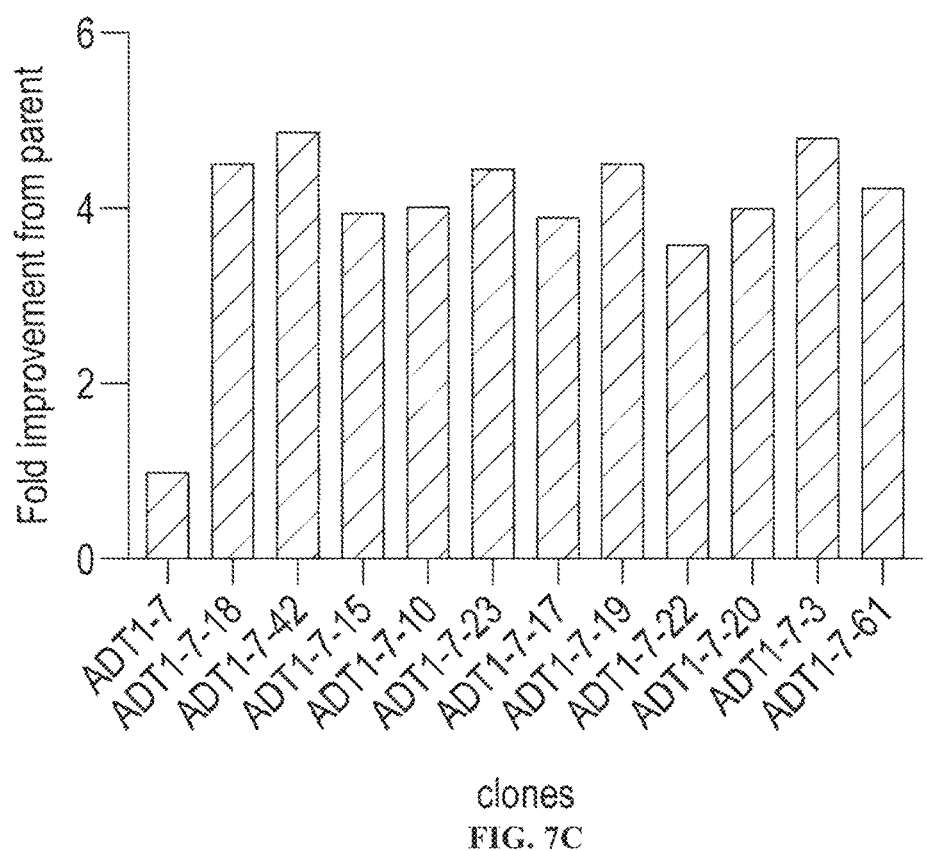

Affinity ranking of antibody of interest were performed using DELFIA immunoassay in which antibodies were captured via protein G coated on the plate and human soluble biotinylated L1 (DV1-GV4) antigen was added at 0.4 nM and cyno antigen DV1/GV77 at 10 nM (3 MPBS). For detection 50 µL of streptavidin-Eu (1:500 in assay buffer, PERKINELMER®) was used and signal was developed with DELFIA enhancement solution. D1.3 hIgG1 (described in England et al. (1999) *J. Immunol.* 162:2129-2136) was used as a negative control. The results are provided in FIGS. 7A-7C.

SPR Analysis-IgG Capture

Figure 8A:
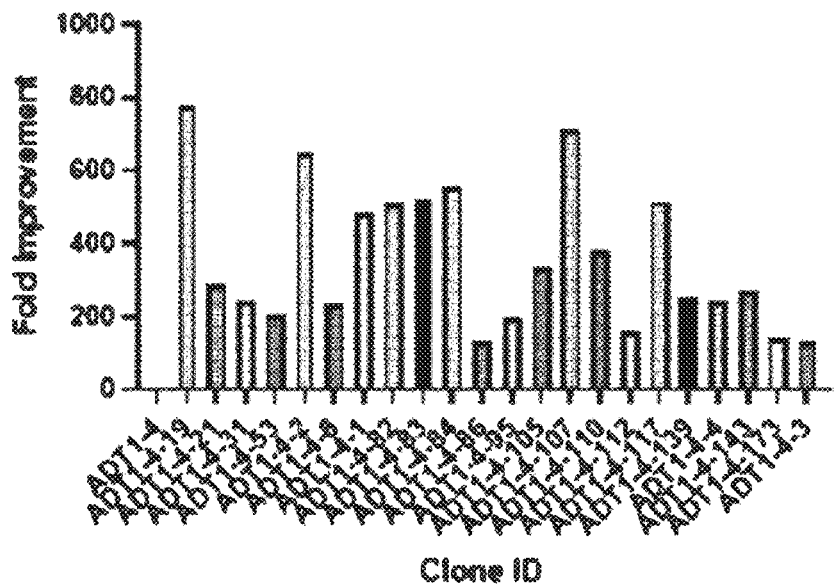
FIGS. 8A-8C. Fold improvements in KD for human (and cyno) antigen over parental clones.
Figure 8B:
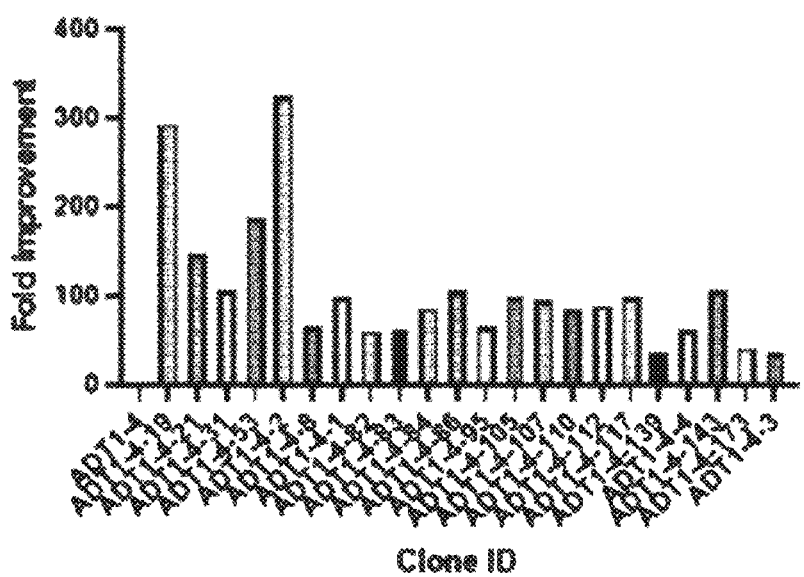
Figure 8C:
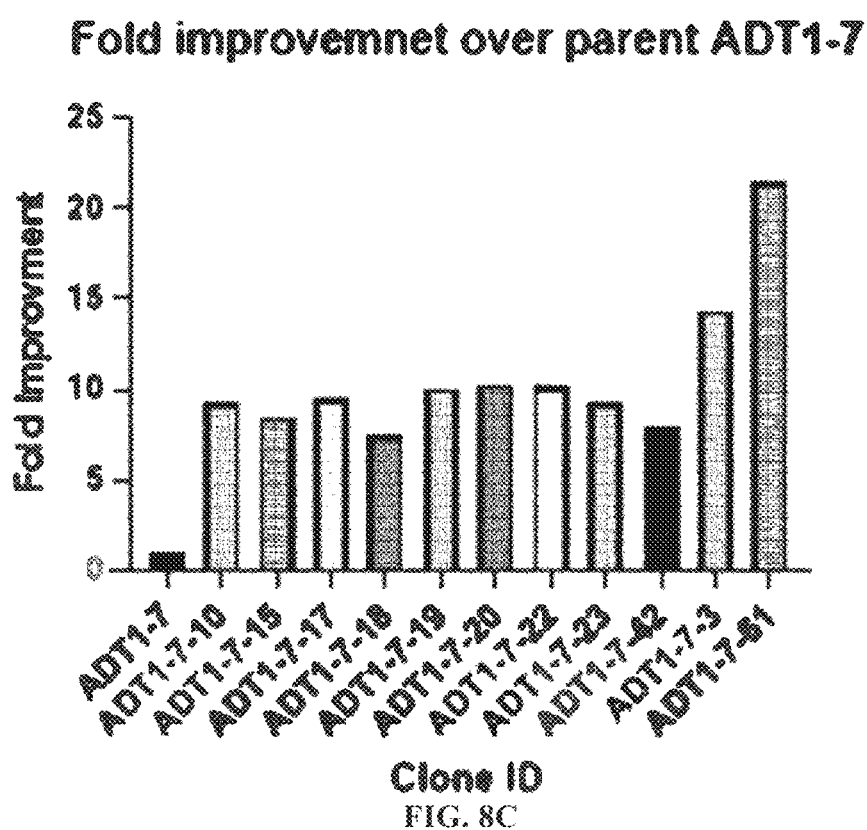

SPR analysis was used to compare KD values for the affinity matured clones compared to the parental clones. Instrument used: MASS-2 (Sierra Sensors); Chip: amine high capacity (Sierra Sensors); running buffer PBS+0.02% Tween 20. Experiments were performed at room temperature or 37° C., protein G was coupled to the chip. Antigen was flown over the cell in a dilution series ranging from 50 nM to 0.2 nM for human DV1-GV4 and from 100 nM to 1 nM for Cyno DV1-77. 120 sec association, 600 sec dissociation, 50 µL/min flowrate, regeneration with 10 mM glycine pH 1.5 kinetic fit according to Langmuir 1:1 binding using software Sierra Analyzer. The results are shown in FIGS. 8A-8C.

Binding Affinity Analysis (KD by SPR)

Vδ1 Monoclonal Antibody Binding Affinity to Vδ1 Antigen

The binding affinity of the antibodies to target (i.e. the Vδ1 chain of a γδ TCR) is established by SPR analysis using a REICHERT® 4SPR instrument (REICHERT TECHNOLOGIES®). Antibody (1.5 ug/mL) is coated onto a Planar Protein A Sensor Chip (REICHERT TECHNOLOGIES®) to give an increase on baseline of approximately 500 uRIU. Antigen (e.g. L1 (DV1-GV4) was flown over the cell at a 1:3 dilution series from 300 nM to 3.7 nM with the following parameters: 180 s association, 600 s dissociation, flowrate 25 µL/min, running buffer PBS+0.05% Tween 20. All experiments were performed at room temperature. Steady state fitting was determined according to Langmuir 1:1 binding using software TraceDrawer (REICHERT TECHNOLOGIES®).

Human Antigen

Figure 9A:
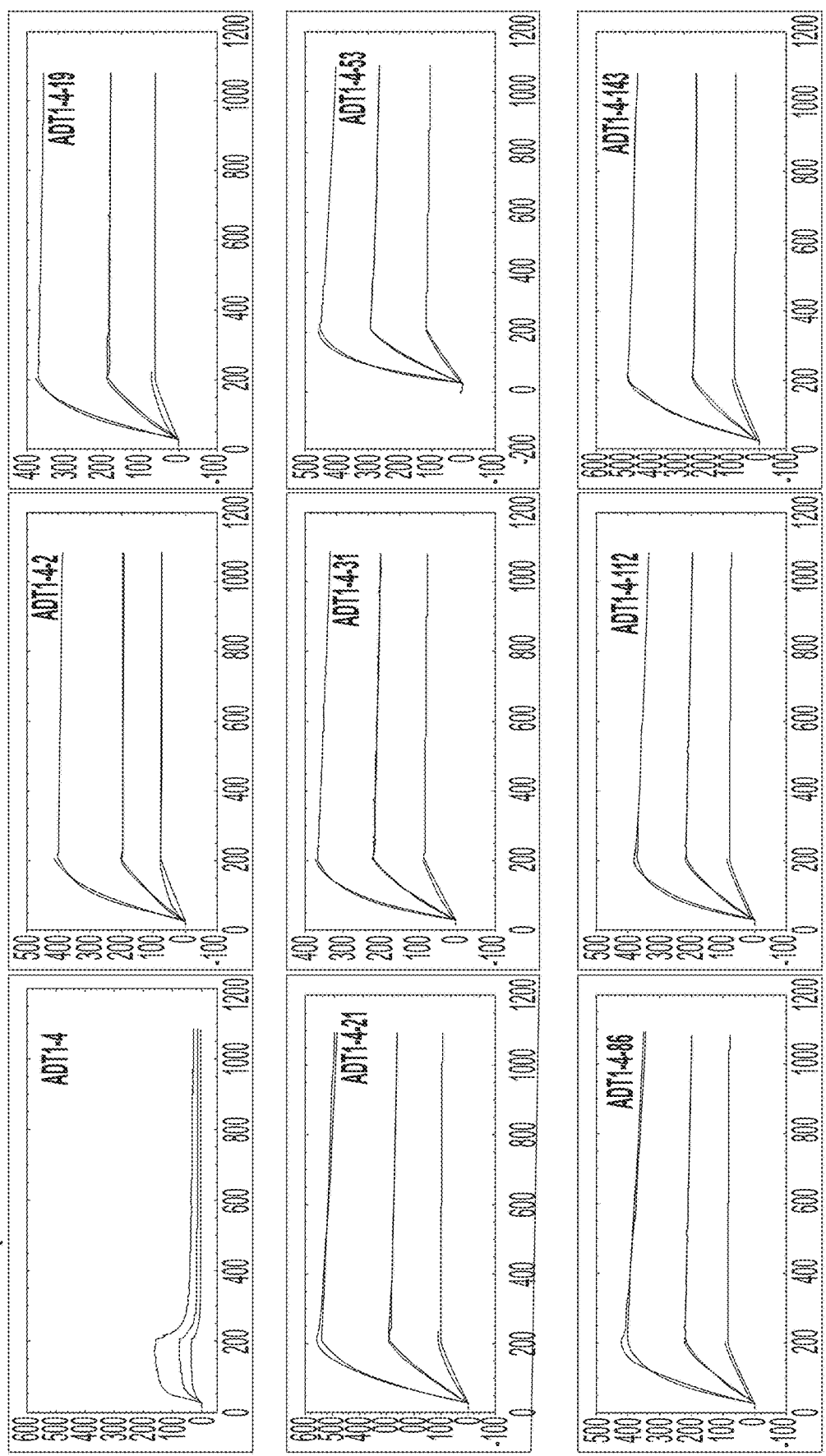
Figure 9B:
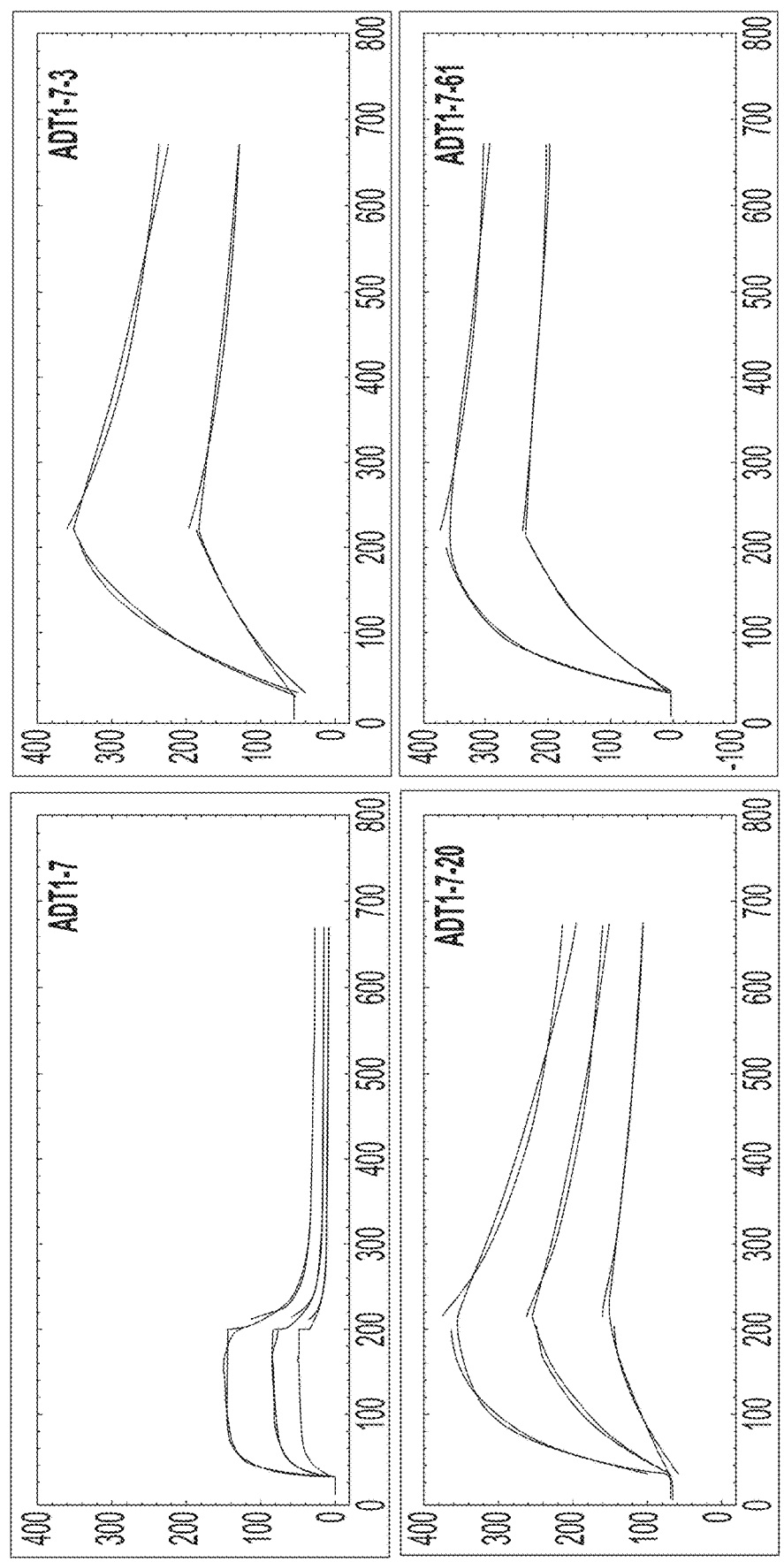

Affinity-matured Vδ1 mAbs exhibit greatly enhanced affinity to human Vδ1 antigen that either parent as determine by surface plasmon resonance (SPR) analysis (FIGS. 9A-9F). (FIGS. 9A-9B) Surface Plasmon Resonance (SPR) analysis was performed with ADT1-4 (FIG. 9A) or ADT1-7 (FIG. 9B) parent mAbs and their affinity-matured derivatives to determine the binding affinity to human Vδ1 antigen. The binding interaction of Vδ1 and the affinity-matured mAbs were modelled according to Langmuir 1:1 binding. (FIGS. 9C-9D) Tables summarizing the equilibrium dissociation constant (KD) of Vδ1-targeted antibodies, as derived from the sensograms illustrated in (FIG. 9A) and (FIG. 9B). The data is represented as the mean of two replicates performed on two different SPR instruments. (FIGS. 9E-9F) Bar charts representing the fold increase in equilibrium dissociation constant (KD) of the affinity-matured derivative to Vδ1 antigen, as compared to their parent, ADT1-4 or ADT1-7.

Conclusions: This data demonstrates that the affinity-matured derivatives of ADT1-4 and ADT1-7 demonstrate significantly higher affinity to human Vδ1 antigen than the parent antibodies.

Cyno Antigen

Figure 10B:
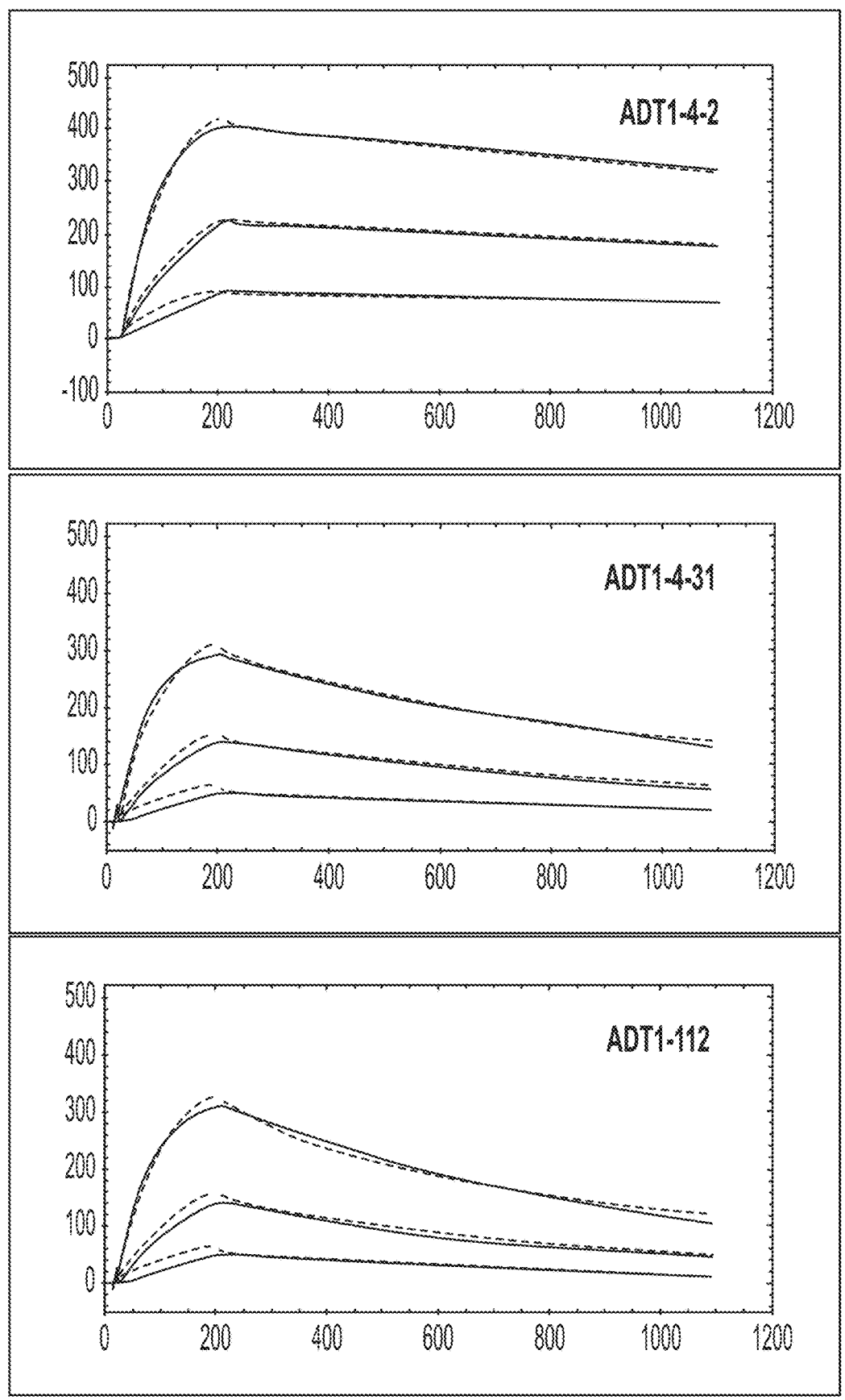
Figure 10C:
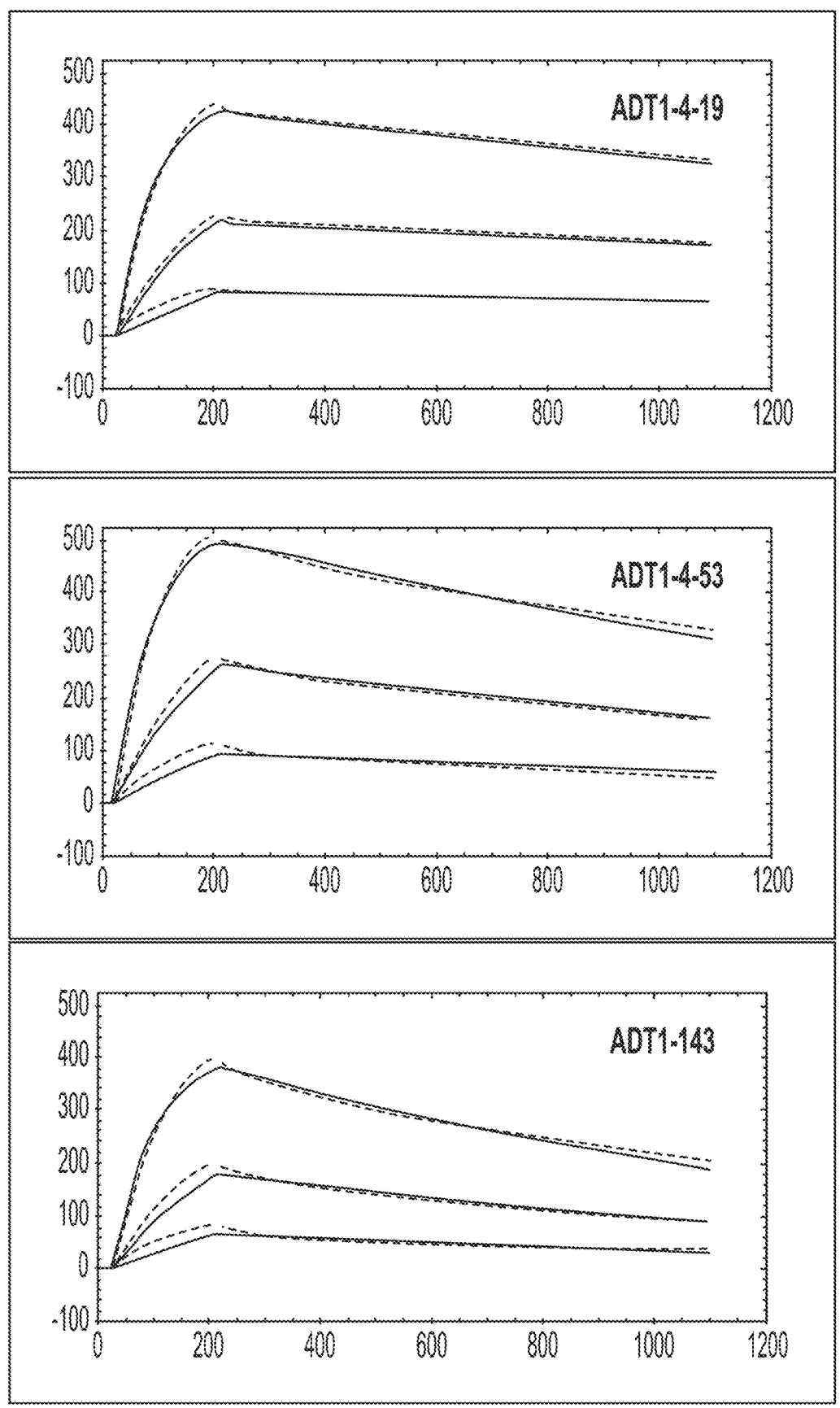
Figure 11A:
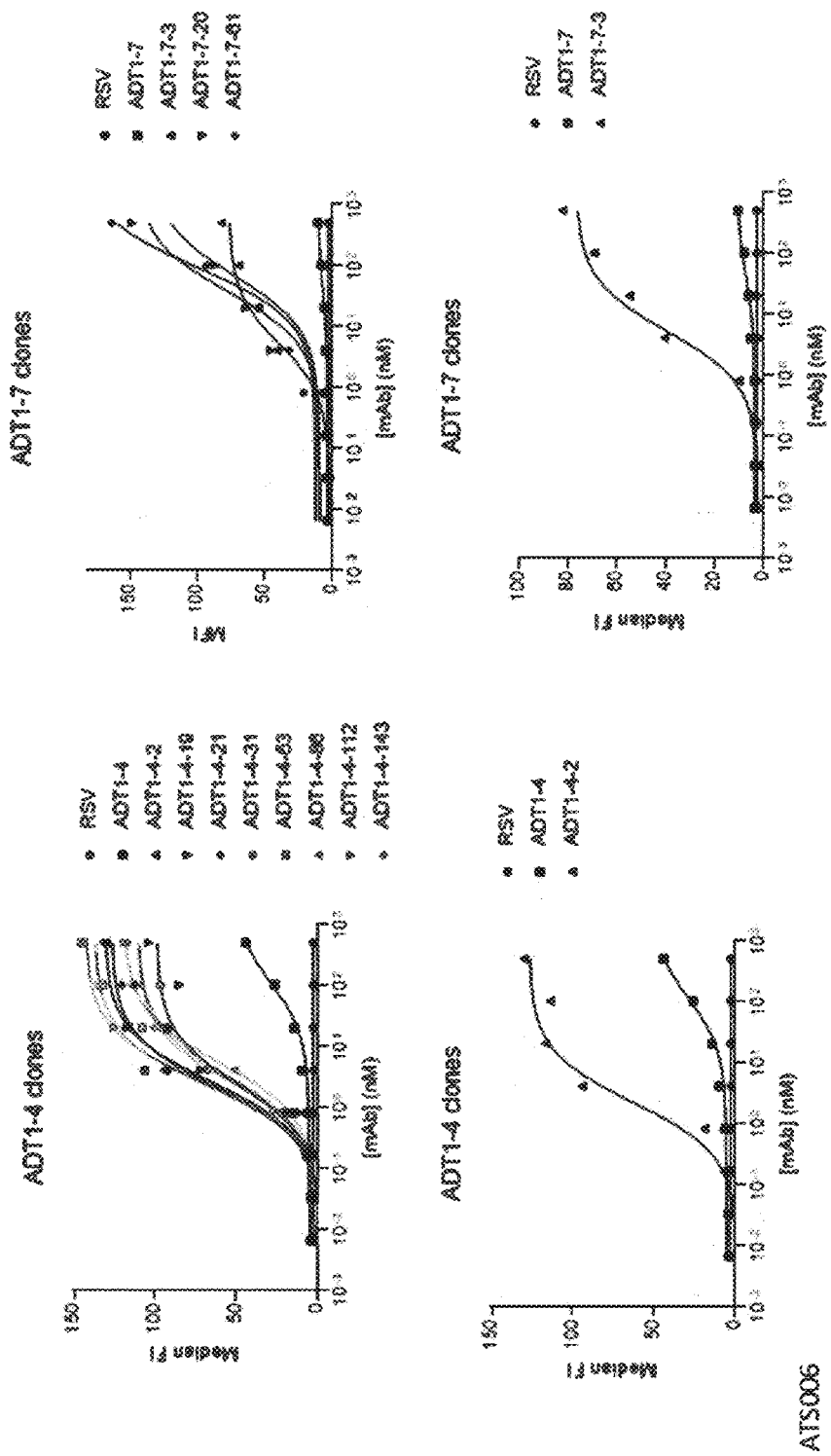
Figure 11B:
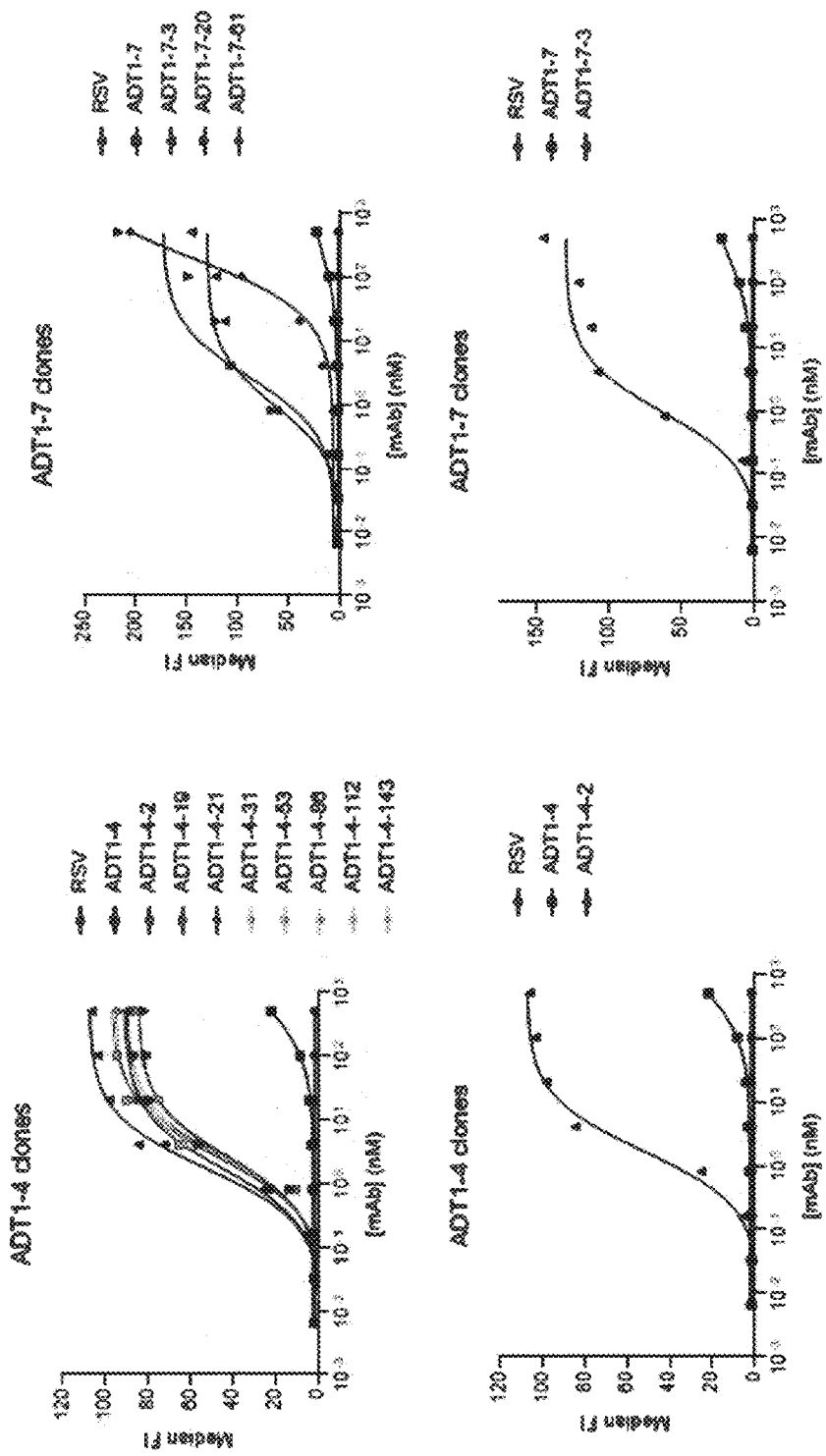
Figure 11C:
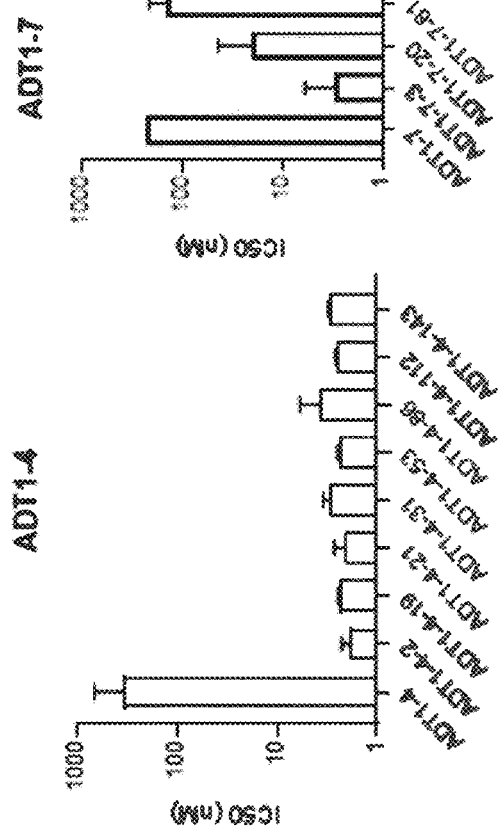

Surface plasmon resonance analysis demonstrates that the affinity-matured Vδ1 mAbs of the ADT1-4 lineage show a greatly enhanced affinity to cynomolgus Vδ1 antigen than the parent antibody (FIGS. 10A-10D). (FIGS. 10A-10C) Surface Plasmon Resonance (SPR) analysis was performed with ADT1-4 parent antibody and the affinity-matured derivatives to determine the binding affinity to cynomolgus Vδ1 antigen. The binding interaction of Vδ1 and the affinity-matured mAbs were modelled according to Langmuir 1:1 binding. (FIG. 10D) Table summarizing the equilibrium dissociation constant (KD) of Vδ1-targeted antibodies, as derived from the sensograms illustrated in (FIG. 10A-10C). The data is represented as the mean of two replicates performed on two different SPR instruments. The results are shown in FIGS. 10A-10D.

Conclusions: This data demonstrates that the affinity-matured derivatives of ADT1-4 demonstrate significantly higher affinity to cynomolgus Vδ1 antigen than the parent antibody.

Binding Affinity to Cell Surface Vδ1 TCR (EC50 for Binding to Cell Surface Vδ1)

Affinity matured Vδ1 mAbs exhibit greatly enhanced affinity to Vδ1-positive γδT cells, with no demonstrable binding to cells lacking Vδ1, as show in FIGS. 11A-11D. (FIGS. 11A-11B) The level of binding by the Vδ1 mAbs to two γδ T cell donors, ATS006 (FIG. 11A) and TS164 (FIG. 11B). γδ T cells were stained with varying concentrations of Vδ1 mAbs, followed by a fluorescent anti-human IgG detection antibody (xxx). All incubation steps were performed at 4° C. and mAb binding was determined using flow cytometry to measure the median level of fluorescence. Logarithmic four parameter dose-response curves were fitted using GraphPad Prism 9. (FIG. 11C) Bar chart representing the average EC50s from the ADT1-4 and ADT1-7 clones binding to Vδ1-positive γδ T cell, represented as the mean two donors. (FIG. 11D) Table summarizing the EC50s plotted in (FIG. 11A) & (FIG. 11B), and Vδ1-negative cell types including HEK293A, Raji cells and various leukocyte subsets with primary blood mononuclear cells. For Vδ1-positive γδ T cell, data is represented as the mean two donors.

Conclusions: This data demonstrates that the affinity-matured derivatives of ADT1-4 and ADT1-7 demonstrate significantly higher affinity to Vδ1-positive γδ T cells than their parent mAbs, whilst showing no binding to Vδ1-negative cells HEK293T, Raji, or CD8, CD4, NK, CD19 or monocytic cells within PBMCs.

Target Cell Binding of Vδ1 Monoclonal Antibodies

A range of target cells were assayed to determine the specificity and affinity of Vδ1 mAb binding. This included expanded skin-derived Vδ1 γδ T-cells, HEK293T cells, Raji cells, and multiple leukocyte subsets within human primary blood mononuclear cells. Adherent or semi-adherent cells (skin-derived Vδ1 γδ T-cells, HEK293T) were detached from tissue culture flask and resuspended in PBS. Similarly, non-adherent cell types (Raji, PBMC), were harvested and resuspended in PBS. Cells were seeded at a final density of 100,000 cells per well in v-bottom 96-well plates. Cells underwent centrifugation and the cell pellets were resuspended in FcR blocking reagent according to the manufacturer's instructions, and incubated for 20 minutes at 4 C prior to a further wash. Vδ1 mAbs, anti-RSV IgG control and anti-CD3 OKT3 were diluted to 500 nM in PBS and serially diluted 1:5 in PBS to 6.4 pM, and added to the cells, followed by a 20-minute incubation at 4 C. To determine the quantity of mAb bound to the cell surface, the cells were then stained with a murine anti-human IgG secondary antibody, conjugated to APC (product code . . . , dilution: 1:100). For Vδ1 γδ T-cells, HEK293T and Raji, the cells were also stained solely with a viability dye. For PBMC, conjugated antibodies against CD4, CD8, CD56, CD11b and CD19 (all at 1:100) were also included, allowing the discrimination of αβ subsets, NK cells, B cell and monocytic cells. Following 20-minute incubation at 4C, the cells were washed twice, and fluorescence measured using the MACSQUANT®. IC50s are shown in FIG. 11D.

Summary of KD Values for ADT1-4 lineage (Human and Cyno)

The table below provides the KD values for the 24 clones in the ADT1-4 lineage and the ADT1-4 parent clone (G04) (for binding to human TRDV1 and cyno TRDV1):

| Clone ID | HUMAN $K_D$ [M] | HUMAN $K_D$ (nM) | CYNO $K_D$ [M] | CYNO $K_D$ (nM) |
| --- | --- | --- | --- | --- |
| ADT1-4 | 1.26E−07 | 126 nM | N/A | N/A |
| ADT1-4-19 | 1.63E−10 | 0.163 nM | 3.40E−09 | 3.40 nM |
| ADT1-4-21 | 4.41E−10 | 0.441 nM | 6.79E−09 | 6.79 nM |
| ADT1-4-31 | 5.22E−10 | 0.522 nM | 9.43E−09 | 9.43 nM |
| ADT1-4-53 | 6.08E−10 | 0.608 nM | 5.34E−09 | 5.34 nM |
| ADT1-4-2 | 1.95E−10 | 0.195 nM | 3.08E−09 | 3.08 nM |
| ADT1-4-8 | 5.41E−10 | 0.541 nM | 1.51E−08 | 15.1 nM |
| ADT1-4-82 | 2.49E−10 | 0.249 nM | 1.67E−08 | 16.7 nM |
| ADT1-4-83 | 2.41E−10 | 0.241 nM | 1.58E−08 | 15.8 nM |
| ADT1-4-84 | 2.27E−10 | 0.227 nM | 1.16E−08 | 11.6 nM |
| ADT1-4-86 | 9.39E−10 | 0.939 nM | 9.49E−09 | 9.49 nM |
| ADT1-4-95 | 6.42E−10 | 0.642 nM | 1.50E−08 | 15.0 nM |
| ADT1-4-105 | 3.81E−10 | 0.381 nM | 1.01E−08 | 10.1 nM |
| ADT1-4-107 | 1.77E−10 | 0.177 nM | 1.05E−08 | 10.5 nM |
| ADT1-4-110 | 3.33E−10 | 0.333 nM | 1.19E−08 | 11.9 nM |
| ADT1-4-112 | 7.84E−10 | 0.784 nM | 1.11E−08 | 11.1 nM |
| ADT1-4-117 | 2.45E−10 | 0.245 nM | 1.01E−08 | 10.1 nM |
| ADT1-4-139 | 4.99E−10 | 0.499 nM | 2.69E−08 | 26.9 nM |
| ADT1-4-4 | 5.19E−10 | 0.519 nM | 1.62E−08 | 16.2 nM |
| ADT1-4-143 | 4.63E−10 | 0.463 nM | 9.39E−09 | 9.39 nM |
| ADT1-4-173 | 9.07E−10 | 0.907 nM | 2.40E−08 | 24.0 nM |
| ADT1-4-3 | 9.35E−10 | 0.935 nM | 2.85E−08 | 28.5 nM |
| ADT1-4-1 | 8.00E−11 | 0.08 nM | 4.1E−10 | 0.41 nM |
| ADT1-4-6 | 1.06E−9 | 1.06 nM | 1.01E−9 | 1.01 nM |
| ADT1-4-138 | 4.38E−8 | 43.8 nM | 3.47E−8 | 34.7 nM |

Summary of KD Values for ADT1-7 Lineage (Human Only)

The table below provides the KD values for the 11 clones in the ADT1-7 lineage and the ADT1-7 parental clone (E07) (for binding to human TRDV1 only):

| Clone ID | $K_D$ [M] | $K_D$ (nM) |
| --- | --- | --- |
| ADT1-7 | 1.24E−08 | 12.4 nM |
| ADT1-7-10 | 1.30E−09 | 1.30 nM |
| ADT1-7-15 | 1.42E−09 | 1.42 nM |
| ADT1-7-17 | 1.26E−09 | 1.26 nM |
| ADT1-7-18 | 1.61E−09 | 1.61 nM |
| ADT1-7-19 | 1.19E−09 | 1.19 nM |
| ADT1-7-20 | 1.17E−09 | 1.17 nM |
| ADT1-7-22 | 1.18E−09 | 1.18 nM |
| ADT1-7-23 | 1.29E−09 | 1.29 nM |
| ADT1-7-42 | 1.51E−09 | 1.51 nM |
| ADT1-7-3 | 8.31E−10 | 0.831 nM |
| ADT1-7-61 | 5.57E−10 | 0.557 nM |

Summary of Pharmacological Data for the Preferred Members of the ADT1-4 Lineage

| Clone ID | HUMAN K_D [M] | HUMAN K_D (nM) | CYNO K_D [M] | CYNO K_D (nM) | IC50 TCR DR (no THP-1) | IC90 TCR DR (noTHP-1) | IC50 Killing | IC90 Killing |
| --- | --- | --- | --- | --- | --- | --- | --- | --- |
| ADT1-4 | 1.26E−07 | 126 nM | N/A | N/A | N/A | N/A | 2.603E−08 (26.03 nM) | 7.048E−08 |
| ADT1-4-19 | 1.63E−10 | 0.163 nM | 3.40E−09 | 3.40 nM | 3.67E−10 (0.367 nM) | 1.583E−9 (1.583 nM) | 1.12E−09 (1.12 nM) | 8.38E−09 (8.38 nM) |
| ADT1-4-21 | 4.41E−10 | 0.441 nM | 6.79E−09 | 6.79 nM | 2.66E−10 (0.266 nM) | 8.92E−10 (0.892 nM) | 9.4E−10 (0.94 mM) | 5.88E−09 (5.88 nM) |
| ADT1-4-31 | 5.22E−10 | 0.522 nM | 9.43E−09 | 9.43 nM | 2.45E−10 (0.245 nM) | 1.091E−9 (1.091 nM) | 1.63E−09 (1.63 nM) | 1.658E−08 (16.58 nM) |
| ADT1-4-53 | 6.08E−10 | 0.608 nM | 5.34E−09 | 5.34 nM | 2.54E−10 (0.254 nM) | 6.98E−10 (0.698 nM) | 1.05E−09 (1.05 nM) | 4.23E−09 (4.23 nM) |
| ADT1-4-2 | 1.95E−10 | 0.195 nM | 3.08E−09 | 3.08 nM | 3.1E−10 (0.31 nM) | 8.34E−10 (0.834 nM) | 8.7E−10 (0.87 nM) | 3.12E−09 (3.12 nM) |
| ADT1-4-86 | 9.39E−10 | 0.939 nM | 9.49E−09 | 9.49 nM | 3.07E−10 (0.307 nM) | 1.001E−9 (1.001 nM) | 1.05E−09 (1.05 nM) | 4.3E−09 (4.3 nM) |
| ADT1-4-112 | 7.84E−10 | 0.784 nM | 1.11E−08 | 11.1 nM | 2.95E−10 (0.295 nM) | 1.093E−9 (1.093 nM) | 9E−10 (0.9 nM) | 3.8E−09 (3.8 nM) |
| ADT1-4-143 | 4.63E−10 | 0.463 nM | 9.39E−09 | 9.39 nM | 3.13E−10 (0.313 nM) | 8.53E−10 (0.853 nM) | 1.78E−09 (1.78 nM) | 1.42E−08 (14.2 nM) |
| ADT1-4-1 | 8.00E−11 | 0.08 | 4.1E−10 | 0.41 | 3.604E−10 (0.3604 nM) | 6.702E−10 (0.6702 nM) | 1.4E−10 (0.14 nM) | 2.8E−10 (0.28 nM) |
| ADT1-4-6 | 1.06E−9 | 1.06 | 1.01E−9 | 1.01 | 4.796E−10 (0.4796 nM) | 1.911E−9 (1.911 nM) | 1.4E−10 (0.14 nM) | 2E−10 (0.2 nM) |
| ADT1-4-138 | 4.38E−8 | 43.8 | 3.47E−8 | 34.7 | 8.384E−9 (8.384 nM) | 3.83E−8 (38.3 nM) | 3.8E−10 (0.38 nM) | 6.44E−09 (6.44 nM) |

Summary of Pharmacological Data for the Preferred Members of the ADT1-7 Lineage

| Clone ID | K_D [M] | K_D (nM) | IC50 TCR DR (no THP-1) | IC90 TCR DR (noTHP-1) | IC50 Killing | IC90 Killing |
| --- | --- | --- | --- | --- | --- | --- |
| ADT1-7 | 1.24E−08 | 12.4 nM | — | — | 5.53E−09 (5.53 nM) | 7.48E−08 (74.8 nM) |
| ADT1-7-20 | 1.17E−09 | 1.17 nM | 1.64E−10 (0.164 nM) | 1.036E−9 (1.036 nM) | 2.80E−10 (0.28 nM) | 2.47E−09 (2.47 nM) |
| ADT1-7-3 | 8.31E−10 | 0.831 nM | 1.61E−10 (0.161 nM) | 7.90E−10 (0.79 nM) | 1.60E−10 (0.16 nM) | 1.06E−09 (1.06 nM) |
| ADT1-7-61 | 5.57E−10 | 0.557 nM | 6.264E−9 (6.264 nM) | 1.704E−6* (1704.445 nM) | 4.20E−10 (0.42 nM) | 1.66E−08 (16.6 nM) |

*Artefact of data due to 100% inhibition not being reached for this clone

Example 5. Functional Characterisation

Vδ1 Monoclonal Antibodies on TCR Downregulation

The capacity of ADT mAb to engage with and resultantly downregulate γδ T-cell receptors is evaluated by measuring TCR expression. Skin γδ T-cells (from donor ATS006 and TS164) were seeded into a 96 well round bottom plate at $3 \times 10^5$ cells/ml in γδ media with increasing concentration of the test mAbs (range from 0.00067 to 67 nM) or the highest concentration (67 nM) of the corresponding isotype control (hIgG1, RSV), diluted in PBS. The cells were incubated for 2 hours in a humidified CO2 chamber at 37° C. The cells were washed and stained for dead cells (THERMO FISHER™) #15580607) and their VD1 TCRs (MILTENYI® #130-117-697) for 30 minutes at 4° C. The cells were washed in FACS buffer and resuspended in CELLFIX™ (BD® sciences #340181) before incubating overnight at 4° C. in the dark. The VD1 TCR expression level, determined by median fluorescence intensity (MFI), was measured by flow cytometry the following day using the MACSQUANT® Analyzer 16.

Figure 12A:
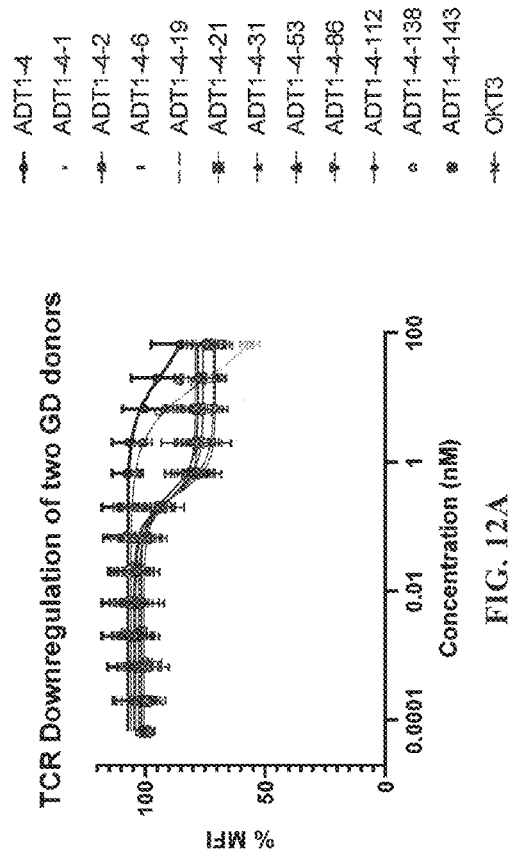
Figure 12B:
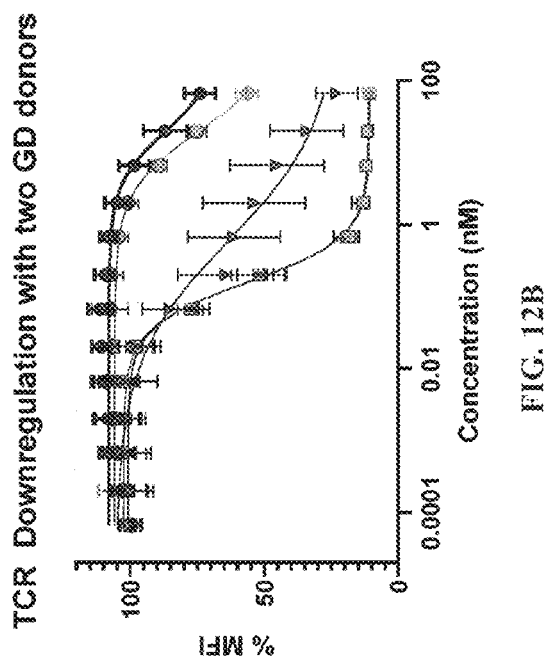
Figure 13A:
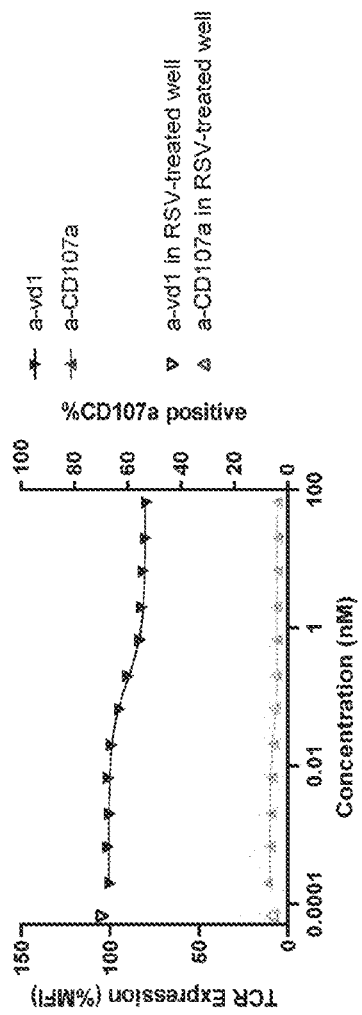
Figure 13B:
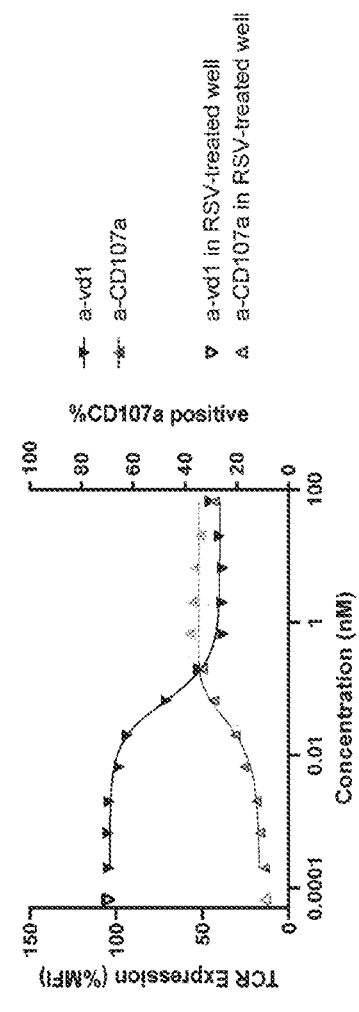

The results are shown in FIGS. 12A-12G, which show affinity matured Vδ1 mAbs bind and downregulate Vδ1 TCR more effectively than their parental clone and OKT3. (FIGS. 12A-12B). Quantification of γδ TCR expression after 2 hours incubation of γδ cells with Vδ1 mAbs and OKT3 before staining of the Vδ1 TCR with a-Vδ1 TCR-PE-Vio770. MFI of a-Vδ1 staining was acquired using flow cytometry and calculated from the TCR positive gate before calculating % MFI from the MFI of TCR positive, untreated γδ cells. The upper graph represents data from the ADT1-4 lineage and the lower graph represents data from the ADT1-7 lineage. (FIG. 12C) Bar chart representing the IC50 values calculated from (FIG. 12A). (FIGS. 12D-12E). Bar chart representing the IC50 values in (FIG. 12B) presented as fold improvement from the parent ADT1-4 (left) and ADT1-7 (right). (FIG. 12F) Table representing IC50 values from (FIG. 12B) with the percentage improvement calculated from the respective parents of ADT1-4 (upper) and ADT1-7 (lower). (FIG. 12G) Table representing IC50 values from (FIG. 12B) with the fold improvement calculated from the respective parents of ADT1-4 (upper) and ADT1-7 (lower).

Vδ1 Monoclonal Antibodies on γδ Activation Measured by CD107a Expression

The capacity of ADT mAb to engage with and activate VD1 γδ cells is evaluated by measuring CD107a expression. Skin γδ T-cells (from donor ATS006) were seeded into a 96 well round bottom plate at $6 \times 10^5$ cells/ml in γδ media with THP-1 cells (ATCC®-TIB-202) at $1.2 \times 10^6$ cells/ml and increasing concentration of the test mAbs (range from 0.00067 to 67 nM) or the highest concentration (67 nM) of the corresponding isotype control (hIgG1, RSV), diluted in PBS. The cells were incubated for 2 hours in a humidified CO2 chamber at 37° C. The cells were washed and stained for dead cells (THERMO FISHER™) #15580607), VD1 TCRs (MILTENYI® #130-117-697) and aCD107a (MILTENYI® #130-112-610) for 30 minutes at 4° C. The cells were washed in FACS buffer before incubating overnight at 4° C. in the dark. The VD1 TCR and CD107α expression level, determined by median fluorescence intensity (MFI), was measured by flow cytometry the following day using the MACSQUANT® Analyzer 16.

The results are shown in FIGS. 13A-13F, which show affinity matured Vδ1 mAbs induce activation only when in the presence of target cells. (FIGS. 13A-13B) Quantification of γδ TCR expression (black) and CD107a expression (grey) after 2 hours incubation of γδ cells with ADT1-4-2 alone (upper) and with THP-1 cells (lower) at a 1:2 target-to-effector ratio before staining of the Vδ1 TCR and CD107a with a-Vδ1 TCR-PE-Vio770 and a-CD107a-VioBlue respectively. MFI of Vδ1 staining was acquired using flow cytometry and calculated from the TCR positive gate before calculating % MFI from the MFI of TCR positive, untreated and non-cocultured γδ cells. MFI of CD107a staining was acquired using flow cytometry and calculated from the 'NOT THP-1' gate before calculating % MFI from the CD107a MFI of untreated non-cocultured γδ cells. (FIGS. 13C-13D) Quantification of γδ TCR expression (black) and CD107a expression (grey) after 2 hours incubation of γδ cells with ADT1-7-3 alone (upper) and with THP-1 cells (lower) at a 1:2 target-to-effector ratio before staining of the Vδ1 TCR and CD107a with a-Vδ1 TCR-PE-Vio770 and a-CD107a-VioBlue respectively. MFI of Vδ1 staining was acquired using flow cytometry and calculated from the TCR positive gate before calculating % MFI from the MFI of TCR positive, untreated and non-cocultured γδ cells. MFI of CD107a staining was acquired using flow cytometry and calculated from the 'NOT THP-1' gate before calculating % MFI from the CD107a MFI of untreated non-cocultured γδ cells. (FIG. 13E) Table representing the percentage increase in γδ CD107a expression from cocultured cells treated with the highest concentration of Vδ1 mAb compared to untreated non-cocultured γδ cells. (FIG. 13F) Table representing the percentage increase in γδ CD107a expression from cocultured cells treated with the highest concentration of Vδ1 mAb compared to untreated, co- and non-cocultured γδ cells.

Vδ1 Monoclonal Antibodies on γδ Activation Measured by CD25 Expression

The capacity of ADT mAb to engage with and activate VD1 γδ cells is evaluated by measuring CD25 expression. Skin γδ T-cells (from donor ATS006) were seeded into a 96 well round bottom plate at $6 \times 10^5$ cells/ml in γδ media with THP-1 cells (ATCC®-TIB-202) at 1.2×10^6 cells/ml and increasing concentration of the test mAbs (range from 0.00067 to 67 nM) or the highest concentration (67 nM) of the corresponding isotype control (higG1, RSV), diluted in PBS. The cells were incubated for 24 hours in a humidified CO2 chamber at 37° C. The cells were washed and stained for dead cells (THERMO FISHER™ #15580607), VD1 TCRs (MILTENYI® #130-117-697) and CD25 (MILTENYI® #130-113-280) for 30 minutes at 4° C. The cells were washed in FACS buffer before incubating overnight at 4° C. in the dark. The VD1 TCR and CD107a expression level, determined by median fluorescence intensity (MFI), was measured by flow cytometry the following day using the MACSQUANT® Analyzer 16.

The results are shown in FIGS. 14A-14F, which show affinity matured Vδ1 mAbs induce activation only when in the presence of target cells. (FIGS. 14A-14B) Quantification of γδ TCR expression (black) and CD25 expression (grey) after 24 hours incubation of γδ cells with RSV (added at 67 nM) and ADT1-4-2 alone (upper) and with THP-1 cells (lower) at a 1:2 target-to-effector ratio before staining of the Vδ1 TCR and CD25 with a-Vδ1 TCR-PE-Vio770 and a-CD25-VioBlue respectively. MFI of Vδ1 staining was acquired using flow cytometry and calculated from the TCR positive gate before calculating % MFI from the MFI of TCR positive, untreated and non-cocultured γδ cells. MFI of CD25 staining was acquired using flow cytometry and calculated from the 'NOT THP-1' gate before calculating % MFI from the CD25 MFI of untreated non-cocultured γδ cells. (FIGS. 14C-14D) Quantification of γδ TCR expression (black) and CD25 expression (grey) after 2 hours incubation of γδ cells with RSV (added at 67 nM) and ADT1-7-3 alone (upper) and with THP-1 cells (lower) at a 1:2 target-to-effector ratio before staining of the Vδ1 TCR and CD25 with a-Vδ1 TCR-PE-Vio770 and a-CD25-VioBlue respectively. MFI of Vδ1 staining was acquired using flow cytometry and calculated from the TCR positive gate before calculating % MFI from the MFI of TCR positive, untreated and non-cocultured γδ cells. MFI of CD25 staining was acquired using flow cytometry and calculated from the 'NOT THP-1' gate before calculating % MFI from the CD25 MFI of untreated non-cocultured γδ cells. (FIG. 14E) Table representing the percentage increase in γδ CD25 expression from cocultured cells treated with the highest concentration of Vδ1 mAb compared to untreated non-cocultured γδ cells. (FIG. 14F) Table representing the percentage increase in γδ CD25 expression from cocultured cells treated with the highest concentration of Vδ1 mAb compared to untreated, co- and non-cocultured γδ cells.

Cyno TCR Downregulation

Figure 15A:
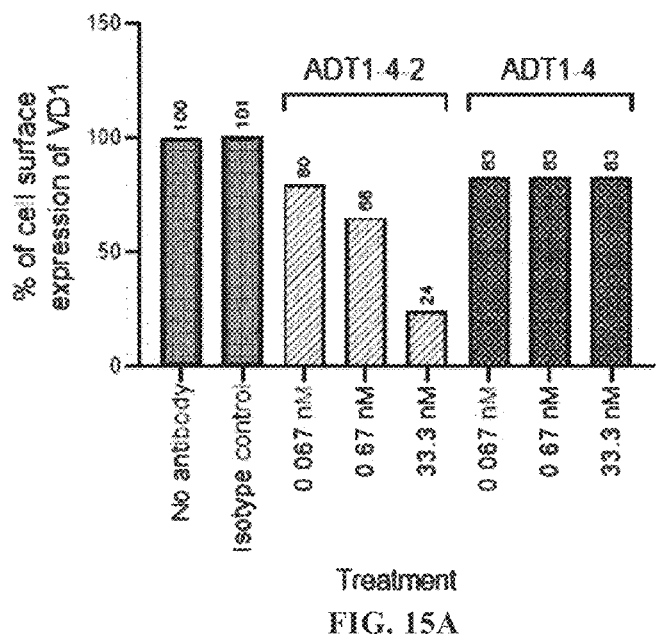
FIGS. 15A-15C. Cyno TCR Downregulation.
Figure 15B:
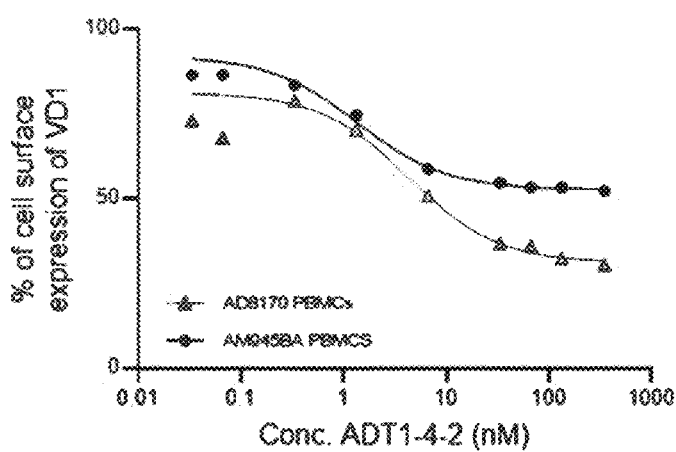
Figure 15C:
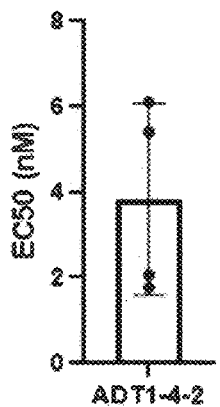

Studies were undertaken to explore the capability of ADT1-4-2 to bind to cynomolgus vδ1 gamma delta T cells and to induce its TCR down-regulation. For these studies, cynomolgus monkeys PBMCs were collected from fresh blood and put into culture for 14 days to expand γδ-T cells. Alternatively, αβ-T cells were depleted from the total PBMCs population using magnetic beads coated with an anti-αβ antibody (Clone R73) before to be expanded in vitro. Expansion was as followed, 250,000 cells were added per well of a U-bottom 96-well plate in RPMI-1640 media containing 10% of FCS, antibiotics (P/S) and a cocktail of cytokines (IFNγ, IL21, IL4, IL1β and IL15). Seven days later, cells were spiked with 10 μl of fresh media containing 10% of FCS, antibiotics (P/S) and the cytokines IL21 and IL15. It was followed by the replacement of 100 μl of media by fresh media containing 10% of FCS, antibiotics (P/S) and IL15 at day 11. At day 14, cells were collected and subjected to the TCR down-regulation assay. This assay consists of mixing the cells with various concentrations of antibodies for 2 hours. After the incubation time, cells were stained for flow cytometry analysis for the following markers: CD3, TCR-αβ, TCR-γδ and VD1. A live/death cell dye was also included to discriminate the live population of cells. Flow cytometry analysis was performed by gating on the CD3+, TCR-γδ+ and VD1+ cell population and VD1 mean florescence intensity was measured inside the VD1+ gate. Isotype control (anti-RSV) or no antibodies were use as negative control at the highest concentration only. Data were normalized to the control without any antibody. (FIG. 15A) shows the comparison of ADT1-4-2 and ADT1-4 capability to engage and reduce the expression of VD1 on cynomolgus γδ-T cells. Results shows a dose response reduction of VD1 expression upon treatment with ADT1-4-2 (up to 76% at 33.3 nM) but not ADT1-4 antibody. In that particular assay, γδ-T cells were expanded from an αβ-T cell depleted population. A 500 time fold range of concentration was used. (FIG. 15B) shows the percentage of cell surface expression of VD1 upon treatment with ADT1-4-2. In this assay, expansion of γδ-T cells was from the all PBMCs population. A 10,000 fold range of concentration was used. Data shows a dose response reduction of VD1 cellular expression in 2 different donors (AD8170 and AM945BA) as an example. A total of 4 donors was tested and EC50 was extracted individually using GraphPad Prism nonlinear fit curve function. (FIG. 15C) shows the individual EC50 value for the different donors combined with the mean and standard deviation. The mean is 3.83±2.23 nM.

Antibodies:
  CD3-AF700 (BD® Bioscience, clone SP34-2, ref: 557917)
  TCR-αβ-AF647 (BIOLEGEND®, clone R73, ref: 201116)
  TCR-γδ-BV421 (BIOLEGEND®, clone B1, ref: 331218
  VD1-PE (EBIOSCIENCE®, clone TS8.2, ref: 12-5679-42)

Enhanced Cytotoxicity of Affinity Matured Clones

Affinity maturation of both ADT1-4 and ADT1-7 Vδ1 clones significantly enhances the cytotoxic effect of Vδ1 γδ T-cells in the in vitro THP-1 killing assay THP-1 Cell Killing Assay Vδ1 mAbs and anti-RSV IgG control were diluted to 1 μg/ml in PBS and serially diluted 1:10 in PBS before adding to 384-well ultra imaging assay plates (PERKINELMER®). THP-1 cells (ATCC®) cultured in RPMI, 10% FCS (INVITROGEN®) were stained with [0.5 μM] CELLTRACE™ CFSE live cell dye for 20 minutes. Expanded skin derived Vδ1 γδ T-cells were detached from tissue culture flasks and re-suspended in basal growth media before mixing 1:1 with THP-1 cells in suspension. Cell suspensions were seeding into 384-well assay plates to give a final cell seeding density of 1,000 THP-1 cells per well and 2,000 Vδ1 γδ T-cells per well. mAbs were diluted in the final assay volumes to concentrations ranging from 200 ng/ml to 0.2 pg/ml. THP-1 and Vδ1 γδ T-cells were cultured in the presence of Vδ1 mAbs at 37° C., 5% $CO_2$ for 24 hours. To determine the numbers of live THP-1 cells after 24 hours, confocal images were acquired using an Opera Phenix high content platform capturing nine fields of view at 10× magnification. Live cell counts were quantified base on size, morphology, texture and intensity of live cell stains.

FIGS. 16A-16D show the affinity matured Vδ1 mAbs exhibit enhanced potency in a THP-1 high content cytotoxicity assay compared to parental clones. (FIGS. 16A-16B) Quantification of live THP-1 cell numbers after 24 hours co-culture with γδ T-cells in the presence of Vδ1 mAbs or controls [Effector: Target ratio 2:1]. Cell numbers were normalized as a percentage of the no γδ T-cell control (100%). OKT3 (anti-CD3 antibody) and an anti-RSV isotype control were included as assay controls. Cell numbers were calculated using high content confocal microscopy on live cells. Graphs are representative of parental ADT1-4 (FIG. 16A) and ADT1-7 (FIG. 16B) clones. (FIG. 16C) Bar chart representing the average EC50s from OKT3 control, and the ADT1-4 and ADT1-7 clones. Data is represented as Mean±standard deviation of n=3 biological replicates. (FIG. 16D) Table summarizing the EC50s plotted in (FIG. 16C). Data is represented as Mean, Standard deviation, fold change and percentage improvement compared to ADT1-4 and ADT1-7 parental clones.

Vδ1 Monoclonal Antibodies on Antibody-Dependent Cellular Cytotoxicity (ADCC)

Expanded skin-derived Vδ1 γδ T-cells from three donors were detached from tissue culture flasks and re-suspended in basal growth media and seeded at a final density of 20,000 cells per well in white 96-well plates. Raji cells were similarly seeded at 20,000 per well, to be used as a positive control for ADCC induced by the CD20-targeted antibody RITUXIMAB. mAbs were diluted and added to each well in final concentrations ranging from 1 to 100 nM. FcγRIIIa+ ADD Bioassay effector cells were thawed, and 62,500 cells were added to each well followed by incubation at 37° C., 5% $CO_2$ for 4.5 hours. Luciferin-containing BIO-GLO™ reagent was added to each well, followed by a further 10-minute incubation, and luminescence measured using a plate reader.

Figure 17:
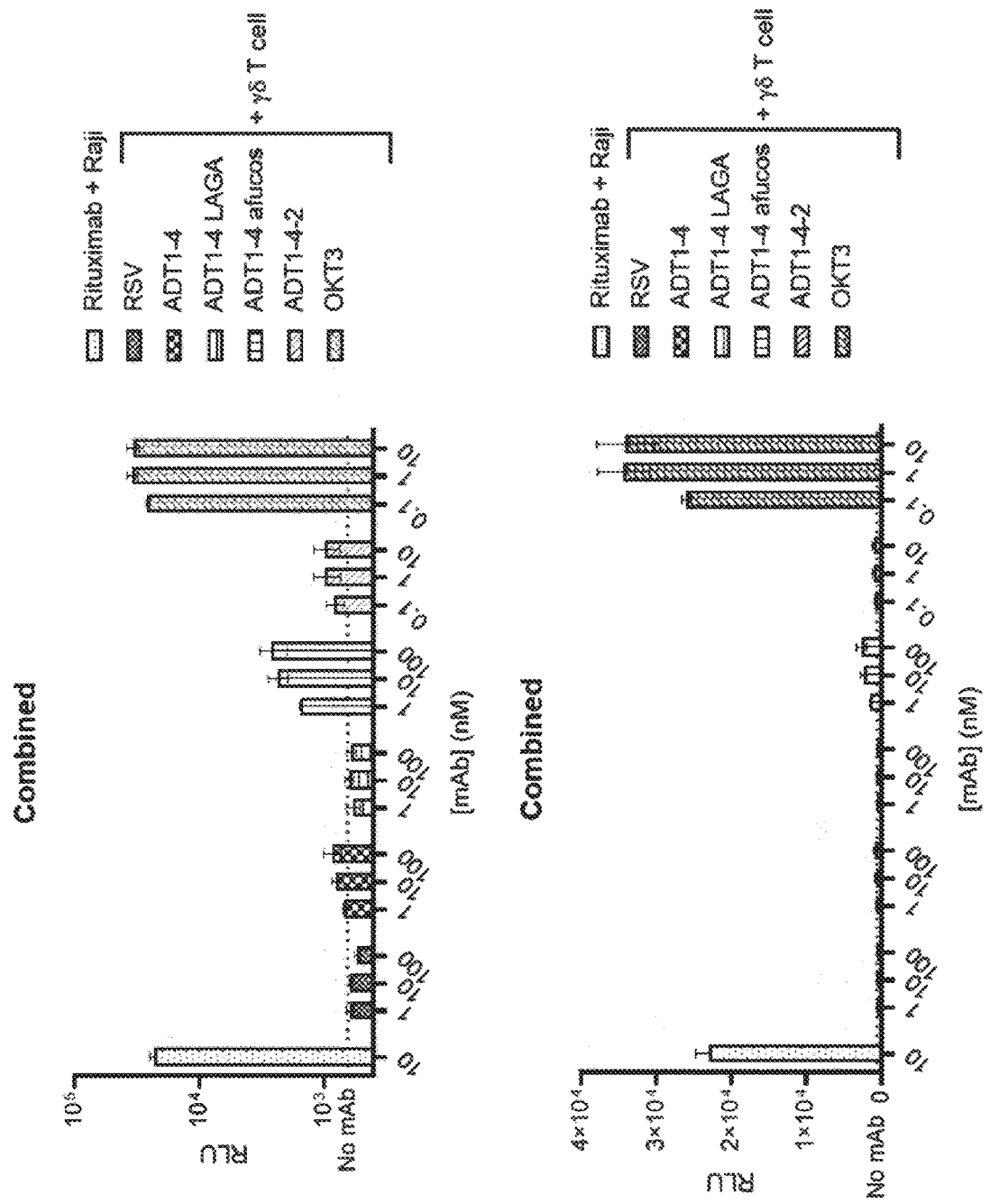
FIG. 17. Vδ1 monoclonal antibodies on antibody-dependent cellular cytotoxicity (ADCC).

FIG. 17 shows the Vδ1-targeted mAbs induce negligible antibody-dependent cellular cytotoxicity (ADCC). ADCC, as measured using a surrogate reporter assay in which downstream NFAT signalling is measured by induction of luciferase activity within FcγRIIIa+ effector cells. The effector cells were co-cultured with three γδ T-cell donors (Effector: Target ratio 3) and varying concentrations of monoclonal antibody. CD20+ Raji cells and RITUXIMAB were included as a positive control. Bioluminescence was measured after 4.5 hours of co-culture. Data is represented as mean±SD of three biological replicates (three γδ T-cell donors).

Conclusions: This data demonstrates that ADT1-4 parent and the affinity matured derivative ADT1-4-2 does not induce ADCC, demonstrated via a FcγRIIIa+ effector reporter cell line in which NFAT signalling induces luciferase activity. OKT3, however, appears to induce high levels of ADCC-specific signalling.

Vδ1 Monoclonal Antibodies on Complement-Dependent Cytotoxicity (CDC)

Expanded skin-derived Vδ1 γδ T-cells were detached from tissue culture flasks and re-suspended in basal growth media and seeded at a final density of 75,000 cells per well in white 96-well plates. Raji cells were similarly seeded at 75,000 per well, to be used as a positive control for CDC induced by the CD20-targeted antibody RITUXIMAB. mAbs were diluted and added to each well in final concentrations ranging from 1 to 100 nM. Human serum, either fresh or heat-inactivated, was added to a final concentration of 40%. Heat-inactivation was performed by warming the serum in a water-bath at 56C for 30 minutes, followed by cooling on ice. The cultures were then incubated at 37° C., 5% $CO_2$ for 24 hours. To determine the numbers of live cells after 24 hours, the cells were harvested and stained with xx viability dye at a 1:1000 dilution for 20 minutes. Fluorescence was measured using the MACSQUANT® and live cell counts were quantified based on negative staining for the viability dye.

Figure 18:
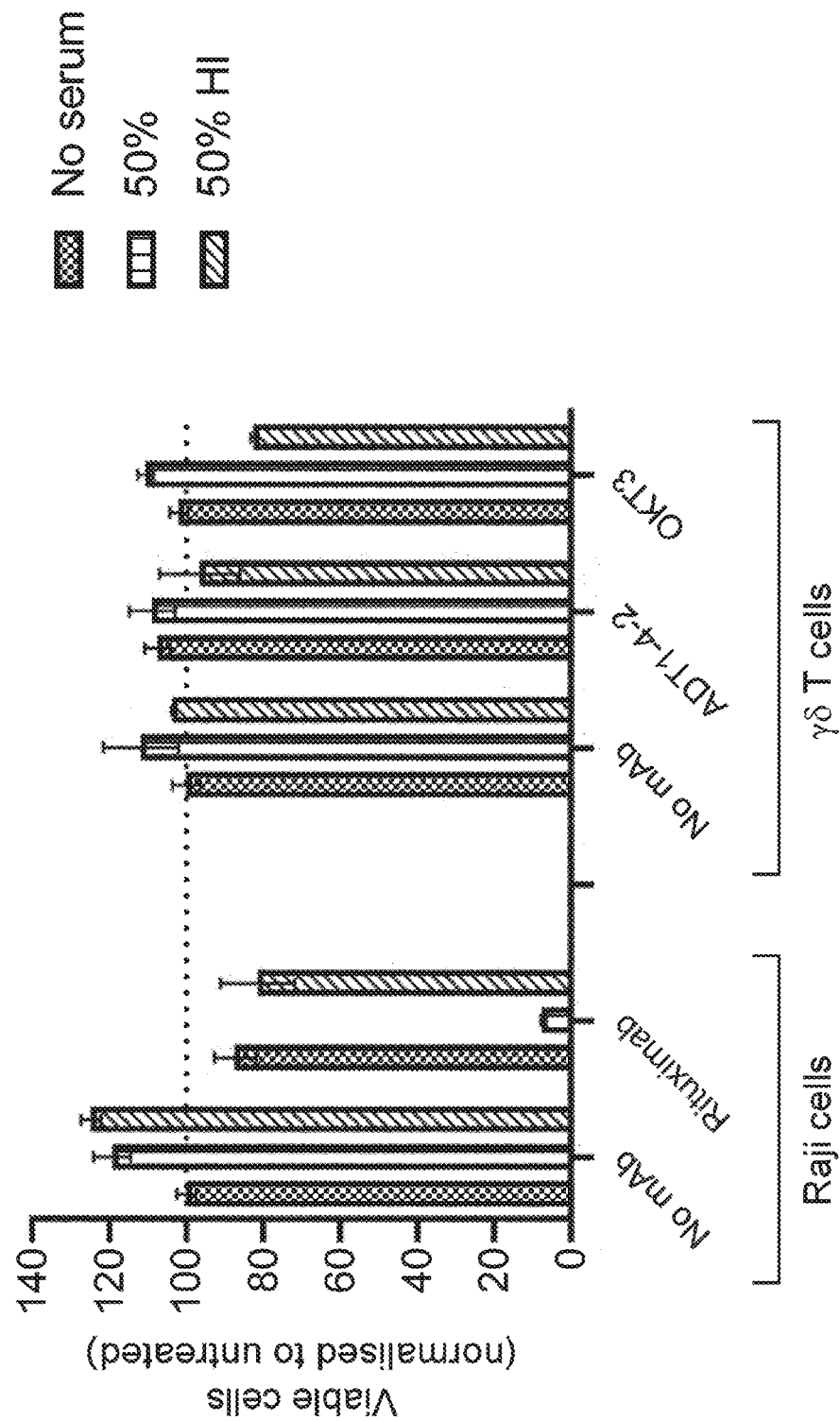
FIG. 18. Vδ1 monoclonal antibodies on complement-dependent cytotoxicity (CDC).

The results are shown in FIG. 18, which demonstrates Vδ1-targeted mAbs do not induce complement-dependent cytotoxicity (CDC). The number of viable γδ T cells following culture with 40% human serum and 50 nM anti-CD3 OKT3 or anti-Vδ1 ADT1-4-2. and varying concentrations of monoclonal antibody. Serum was used fresh or underwent prior heat-inactivation. CD20+ Raji cells and RITUXIMAB were included as a positive control. Viability was measured after 24 hours of co-culture via viability dye. Data is represented as mean±SD of three biological replicates.

Conclusions: This data demonstrates that ADT1-4-2 does not induce complement-dependent cytotoxicity (CDC), with no increase in cytotoxicity of Vδ1-positive cells in the presence of complement-containing serum. RITUXIMAB, however, shows strong CDC stimulation against CD20-positive Raji cells.

Healthy Cell Sparing

Studies were undertaken to explore the effect of stimulating/activating vδ1 cells with anti-vδ1 antibody with respect to cytotoxicity towards healthy cells. This was tested by incubating the anti-vδ1 clone ADT1-4-2 with PBMC and then assessing monocyte cytotoxicity and apoptosis.

Cryopreserved human peripheral blood mononuclear cells (PBMC) were commercially sourced from 3 healthy donors. PBMC were seeded into round bottom 96-well tissue culture plates at 250,000 cells/well in 250 ul of complete media (RPMI supplemented with 10% FCS, pen/strep, non-essential amino acids, sodium pyruvate and HEPES) with 10 ng/ml IL15. A titration vδ1 antibody ADT1-4-2 was added to a final concentration of 6.6 nM. RSV IgG, IgG2α and OKT3 antibodies were included as controls. Stimulations were performed for 20 hours. Flow cytometry analysis was performed at the end-point to determine the monocyte phenotype in each condition and apoptotic monocytes. on vδ1 cells. Cells were gated firstly on live singlets, followed by CD14 (MILTENYI® 130-110-523) to identify monocytes. Apoptotic monocytes were then identified through positive ApoTracker Green staining (BIOLEGEND® 427402).

Figure 19:
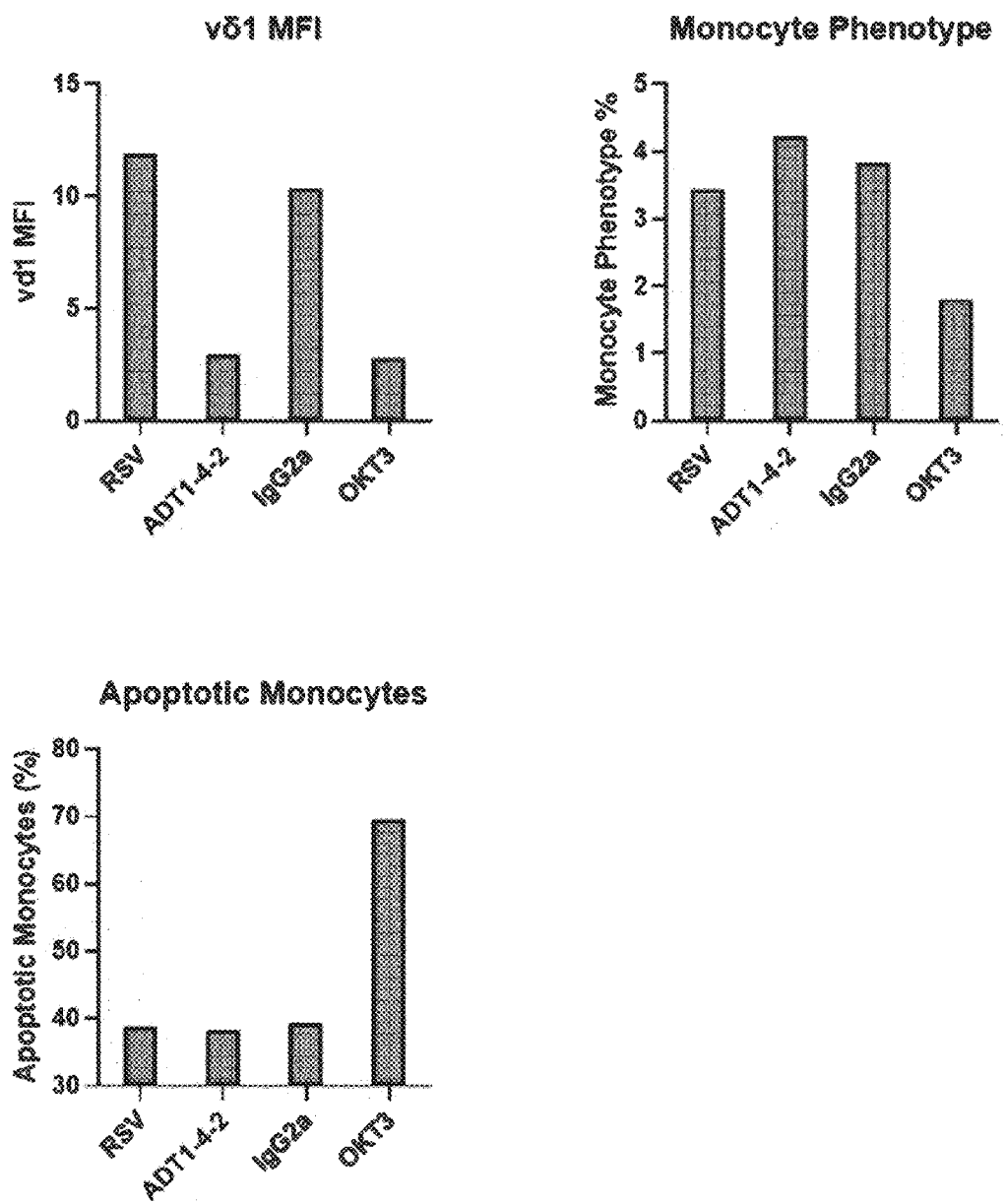
FIG. 19. Healthy cell sparing of clone ADT1-4-2.

FIG. 19 (upper left panel) shows the vδ1 TCR staining MFI upon antibody stimulation as an indication of target engagement. FIG. 19 (upper right panel and lower panel) shows the endpoint monocyte phenotype and apoptotic monocytes (respectively) following antibody stimulation. Stimulation with the vδ1 antibody clone ADT1-4-2 engaged Vδ1 cells but did not cause healthy monocyte cytotoxicity.

Example 6. Effect of Anti-Vδ1 Antibody on TIL Populations from Primary Tumour Biopsies Anti-Vδ1 Antibody Promoted Activation, Proliferation, and Cytotoxicity in Tumour-Infiltrating Lymphocytes.

Studies were undertaken to explore anti-Vδ1 antibody-conferred modulation of human tumour-infiltrating lymphocytes (TILs). For these studies, human renal cell carcinoma (RCC) tumour biopsies were shipped fresh and processed upon receipt. Biopsies were cut into pieces measuring ~2 $mm^2$ and TILs were obtained using an adaptation of the method originally described by Kupper and Clarke (Clarke et al, 2006). Specifically, up to four 2 $mm^2$ biopsies were placed on 9 mm×9 mm×1.5 mm Cellfoam matrices, and one matrix was placed per well on a 24-well plate. Biopsies were then cultured in 2 ml Iscove's Modified Dulbecco's Medium (IMDM) supplemented with 4% human plasma, β-mercaptoethanol (50 µM), penicillin (100 U/ml), streptomycin (100 µg/ml), amphotericin B (2.5 µg/ml), HEPES (10 mM), Na Pyruvate (1 mM), MEM Non-Essential Amino Acids Solution (1×) and IL-15 (2 ng/ml, MILTENYI BIOTEC®). 1 ml of medium was aspirated every 3-4 days and replaced with 1 ml complete medium containing 2× concentrated IL-15. TILs were harvested 10 or 11 days later, passed through a 70 µM nylon cell strainer, centrifuged at 300×g for 5 minutes and resuspended in complete medium for counting. 400,000 cells were then plated per well in 96-well plates prior to stimulation with anti-Vδ1 antibodies. TILs were stimulated with ADT1-4, ADT1-4-2, ADT1-7-3, or RSV IgG1 isotype control antibodies in the presence of IL-15 at a concentration of 2 or 50 ng/ml.

(FIGS. 20A-20B) show the % decrease in Vδ1 TCR expression on total tumour infiltrating-γδ T cells following 48 (FIG. 20A) or 72 (FIG. 20B) hours mAb stimulation in two separate donors, confirming target engagement in each case. Tumour-infiltrating Vδ1$^+$ cells were analysed for expression of CD25 and Ki67. (FIG. 20C) shows enhanced expression of both CD25 and Ki67 on Vδ1$^+$ T cells following 48 hour stimulation with ADT1-4-2 compared with stimulation with IgG1 isotype control or ADT1-4. Supernatants from cultures of mAb-stimulated TILs were analysed for cytokine production by MSD. (FIG. 20D) shows substantial fold increases in IFN-γ production by TILs stimulated with ADT1-4-2 or ADT1-7-3 for 72 hours in the presence of 50 ng/ml IL-15. (FIG. 20E) shows that stimulation of TILs with ADT-1-4-2 or ADT1-7-3 did not enhance secretion of type 17-associated cytokines IL-6 or IL-17 at this timepoint.

Alternatively, biopsies from different donors were digested enzymatically upon receipt to obtain a single cell suspension. Specifically, up to 1 g of tissue was placed into a MILTENYI® C tube along with 4.7 ml RPMI supplemented with enzymes from MILTENYI®'s Tumour Dissociation Kit at concentrations recommended by the manufacturer aside from Enzyme R which was used at 0.2× concentration to prevent cleavage of pertinent cell surface molecules. C-Tubes were placed on the gentleMACS™ Octo Dissociator with heating blocks attached. Program 37C_h_TDK_1 for the dissociation of small tumours was selected. After 1 hour the digest was filtered through a 70 µM filter and complete IMDM containing 4% human plasma was added to quench enzymatic activity. Cells were then washed twice and resuspended in complete IMDM for counting. Depending on cell numbers, 2×10$^6$ or 4×10$^6$ cells were plated per well in 48-well plates and were stimulated with ADT1-4, ADT1-4-2, or RSV IgG1 isotype control antibodies in the presence of IL-15 at a concentration of 2 ng/ml. TILs isolated by enzymatic digestion were analysed by flow cytometry 24-72 hours post mAb stimulation. (FIGS. 20F-20G) show the % decrease in Vδ1 TCR expression on total tumour infiltrating-γδ T cells following mAb stimulation at 24 (FIG. 20F) or 72 (FIG. 20G) hours in two individual donors, confirming target engagement in TILs isolated by enzymatic digestion. (FIG. 20H) shows dose-dependent enhanced expression of Ki67 on γδ T cells following 72 hours stimulation with ADT1-4-2. Supernatants from cultures of mAb-stimulated TILs were analysed for cytokine production by MSD. (FIGS. 20I-20J) show the fold increase in IFN-γ produced by TILs isolated from two individual donors by enzymatic digestion and stimulated with ADT1-4-2 at a concentration of 6.66 nM in the presence of 2 ng/ml IL-15 at two time points, 24 hours (FIG. 20I) and 72 hours (FIG. 20J). In summary, these combined results highlight the ability of affinity matured anti-Vδ1 antibody to drive activation, proliferation and anti-tumourigenic cytokine production by tumour-infiltrating γδ T cells within 72 hours of stimulation.

In another experiment, lung tumour-derived TILs were isolated on grid matrices and stimulated with ADT1-4, ADT1-4-2 or IgG1 isotype control for 10 days in the presence of 2 ng/ml IL-15. (FIG. 21A) shows enhanced expression of CD25 and Ki67 in γδ T cells stimulated for 10 days with ADT1-4-2. (FIG. 21B) shows a substantial increase in Perforin$^+$ Granzyme B$^+$ γδ T cells following 10 days stimulation with ADT1-4-2. Stimulation with mAbs over a longer time period allowed for the analysis of immune licensing of αβ T cells via anti-Vδ1 antibody-stimulated Vδ1$^+$ T cells. (FIG. 21C) shows considerably enhanced expression of Granzyme B and Perforin by both CD8$^+$ and CD8$^-$ αβ T cells following 10 days stimulation of tumour-infiltrating Vδ1$^+$ T cells with ADT1-4-2. Supernatants from TILs cultured for 10 days with mAbs were analysed by MSD. (FIG. 21D) shows markedly increased production of IFN-γ, and moderately increased production of IL-17 and IL-6 by lung tumour-derived TILs following stimulation with ADT1-4-2. (FIG. 21E) demonstrates enhanced production of the chemokines CCL2, CCL4 and CXCL10 by TILs following 10 days stimulation with ADT1-4-2. In summary, these results highlight the ability of anti-Vδ1 antibody to drive activation and cytotoxicity in tumour-infiltrating γδ T cells, which can then promote cytotoxicity in tumour-infiltrating αβ T cells.

Example 7. Vδ1-EGFR Bispecific Antibody Binding Affinity to Human Vδ1 and Human EGFR Antigen The binding affinity of the antibodies to target (i.e. the Vδ1 chain of a γδ TCR and EGFR) is established by SPR analysis using a REICHERT® 4SPR instrument (REICHERT TECHNOLOGIES®). Antibody (1.5 ug/mL) is coated onto a Planar Protein A Sensor Chip (REICHERT TECHNOLOGIES®) to give an increase on baseline of approximately 500 uRIU. Recombinant human Vδ1 heterodimer or human EGFR was flown over the cell at a concentration of 100 nM with the following parameters: 180 s association, 480 s dissociation, flowrate 25 µL/min, running buffer PBS+0.05% Tween 20. All experiments were performed at room temperature. The results are shown in FIGS. 26A-26F.

Conclusions: This data demonstrates that the Vδ1/EGFR bispecific antibodies demonstrate binding to human Vδ1 that is comparable to that of the monospecific anti-Vδ1 antibodies used in their preparation, notwithstanding the introduction of human EGFR binding capability.

Example 8. Target Cell Binding of Vδ1-EGFR Bispecific Antibodies

EGFR-positive A431 and Vδ1-positive primary γδT-cells were assayed to determine the specificity and affinity of EGFR/Vδ1 bispecific antibody binding. Target cells were detached from tissue culture flask, resuspended in PBS and seeded at a final density of 100,000 cells per well in v-bottom 96-well plates. Cells underwent centrifugation and the cell pellets were resuspended in FcR blocking reagent according to the manufacturer's instructions, and incubated for 20 minutes at 4 C prior to a further wash. Antibodies were diluted to 500 nM in PBS and serially diluted 1:10 in PBS to 50 pM, and added to the cells, followed by a 20-minute incubation at 4 C. To determine the quantity of mAb bound to the cell surface, the cells were then stained with a murine anti-human IgG secondary antibody, conjugated to APC (dilution: 1:100) in addition to a viability dye. Following 20-minute incubation at 4C, the cells were washed twice, and fluorescence measured using the MACSQUANT®. The results are shown in FIGS. 27A-27B.

Conclusions: This data demonstrates that the Vδ1/EGFR bispecific antibodies demonstrate binding to Vδ1-positive γδT-cells that is comparable to that of the monospecific anti-Vδ1 antibodies used in their preparation, notwithstanding the introduction of binding to the EGFR-positive A431 cell line.

Example 9. Assessing γδ T Cell Activation and Target Cell Cytotoxicity In Vitro

Expanded skin-derived Vδ1 γδ T-cells and A431 cells were detached from tissue culture flasks and re-suspended in basal growth media and seeded in 96-well plates at the relevant cell dilutions dependent on the desired effector: target ratio. mAbs were diluted and added to each well at the specified concentration. The cultures were then incubated at 37° C., 5% CO2 for 4 (D) or 24 hours (A-C, E). To determine the numbers of live cells, the cells were harvested and stained with viability dye at a 1:1000 dilution for 20 minutes. To determine CD25 status, cells were surface stained with an anti-CD25 antibody following cell harvest. To measure degranulation, a fluorophore-conjugated anti-CD107α antibody was added directly into the cell-antibody mix at the start of the co-culture. Following, two washes and cell fixation, fluorescence was measured using the MACSQUANT® and live cell counts and median fluorescence intensity determined. The results are shown in FIGS. 28A-28E.

Conclusions: This data demonstrates that the Vδ1/EGFR bispecific antibodies induce activation and degranulation of primary Vδ1-positive γδ T-cells leading to increased cell-mediated lysis of EGFR-positive A431 cell line.

Example 10. Further Assessing γδ T Cell Activation and Non-Depletion Effects Conferred by Antibodies of this Invention Studies were undertaken to explore the effect of stimulating/activating vδ1 cells with anti-vδ1 antibody with respect to down-regulation of CD3 on vδ1 cells. This was tested by incubating the anti-vδ1 clone ADT1-4-2 with PBMC and then analysing the TCR by phenotyping.

Cryopreserved human peripheral blood mononuclear cells (PBMC) were commercially sourced and seeded into round bottom 96-well tissue culture plates at 250,000 cells/well in 250 ul of complete media (RPMI supplemented with 10% FCS, pen/strep, non-essential amino acids, sodium pyruvate and HEPES) with 10 ng/ml IL15. A titration vδ1 antibody ADT1-4-2 was added to a final concentration of 1 ug/ml (6.67 nM), 0.01 ug/ml (0.067 nM) or 0.0001 ug/ml (0.00067 nM). RSV IgG antibody was included as a control at matched concentration. Cultures were incubated for 14 days, with media and antibody replenished every 3 days. Flow cytometry analysis was performed at the end-point to phenotype the vδ1 cells and TCR expression in each condition. Cells were gated firstly on live singlets, followed by panyδ (MILTENYI® REA592; 130-113-508), which was the parent gate for vδ1 (MILTENYI® REA173; 130-100-553), which was itself the parent gate for CD3 (MILTENYI® REA613; 130-113-142). Cell populations were identified through positive staining, and then the relative level of expression of each marker between samples through the MFI.

FIG. 29A shows the vδ1 TCR MFI upon antibody stimulation as an indication of mAb target engagement. FIG. 29B shows the MFI of CD3 expression on positively gated vδ1 cells. Stimulation with the vδ1 antibody clone ADT1-4-2 engaged vδ1 cells and resulted in down-regulation of both vδ1 and CD3 on v01 cells.

Example 11: Anti-vδ1 Antibodies do not Induce ADCC

An ADCC Reporter Bioassay (PROMEGA®) was used to assess the level of ADCC (antibody dependent cell-mediated cytotoxicity) induced by anti-vδ1 antibodies compared to control antibodies.

ADCC refers to the biological phenomenon whereby effector cells kill target cells that are tagged by antibodies. The effector cells bind to the antibodies through their Fcγ receptors and subsequently kill the target cell. The ADCC reporter bioassay presented here uncovers potential ADCC mechanisms of action of antibodies that are tested within the assay, by detecting the early initiation of ADCC via activation of gene transcription through the NFAT (nuclear factor of activated T-cells) pathway. The reporter assay is an engineered system that utilizes effector cells (Jurkats) that express high affinity FcγRIIIa receptor linked to the NFAT pathway which is further engineered in order to, upon its activation, induce further activation of the firefly luciferase enzyme. Luciferase activity is quantified with a luminescence readout which can correlate to levels of ADCC taking place.

This assay was utilized to understand whether anti-vδ1 antibodies, or suitably the anti-vδ1 arm of multispecific antibodies, would drive an ADCC reaction. The target cells utilized were γδ cells which bind to the anti-vδ1 antibody through the vδ1 γδ TCR. If an ADCC mechanism of action exists, the anti-vδ1 antibody would bind the Fcγ receptors on the assay effector cells and generate a luminescence signal; if no signal is generated, this would suggest that ADCC is not taking place.

The ADCC Reporter Bioassay Kit (PROMEGA®) was utilised for this assay. One bottle of BIO-GLO™ Luciferase Assay Buffer was thawed and transferred to the substrate bottle. The mixture was kept at room temperature for 4-6 hours. A dilution plate was prepared with antibody concentrations (at 3× concentration) ranging from 10 nM to 0.01 nM (final concentration) for the following antibodies: anti-vδ1 antibody (ADT1-4-2), same anti-vδ1 antibody but Fc disabled (L235A, G237A) (ADT1-4-2 LAGA), RITUXIMAB, RSV and OKT3. The target cells (γδ cells) were seeded into the 2 assay plates at 25 μl per well. Then 25 μl of the appropriate antibody solution from the antibody dilution plate were transferred to the appropriate well. The effector cells (engineered Jurkat cells) were thawed into warm assay buffer, resuspended into 4 ml of the assay buffer, and 25 μl of the effector cell solution was pipetted into each well. The plates were then incubated at 37° C. for 4.5 hours. Following the incubation period, the plates were allowed to equilibrate to room temperature, after which 75 μl BIO-GLO™ Luciferase Assay reagent was added to each well and the plates were incubated for 10 mins at room temperature. The plates were then read using a Biotek H4 plate reader which collected the luminescence signals (as relative light units RLU) from the plates. Fold induction was calculated using the following equation: Fold of Induction=RLU (induced-background)/RLU (no antibody control-background).

As a positive control, OKT3 (anti-CD3 antibody) was used. As an additional positive control, Raji cells were seeded instead of γδ cells in the control wells. Raji cells are a commonly accepted cell line used to demonstrate a strong ADCC reaction when utilised with the anti-CD20 antibody, RITUXIMAB. As an internal control and in order to understand whether anti-vδ1 antibodies drive ADCC in the absence of vδ1 binding on γδ cells, anti-vδ1 antibodies of this invention and the same anti-vδ1 antibodies but Fc-disabled, L235A, G237A) were also added with the effector cells alone.

The results are shown in FIG. 30.

Conclusions: A strong ADCC reaction was shown in the positive control using RITUXIMAB with Raji cells and an even stronger ADCC reaction was demonstrated with OKT3 against γδ cells. Contrastingly, no ADCC reaction was detected in either conditions using the anti-vδ1 antibodies of this invention, the same anti-vδ1 antibodies but also Fc disabled L235A, G237A, or RSV negative control. This demonstrates that in this system, antibodies of this invention that bind to vδ1 (such as anti-vδ1 mAbs or anti-vδ1 multispecific antibodies) do not show evidence of an ADCC mechanism of action. Remarkably, even Fc-enabled anti-Vδ1 antibodies do not deplete γδ T cells, which provides the option of maintaining Fc function in the anti-Vδ1 antibodies presented herein, adding functionality, for example in high Fcγ tumour environments. This further highlights the suitability of such anti-Vδ1 antibodies for inclusion in bispecific antibody formats as described herein.

Example 12: Manufacturability/Stability Assessment of Vδ1×EGFR Multispecific Antibodies To better understand the manufacturability/stability of the novel Vδ1×EGFR multispecific molecules as described herein the inventors assessed a panel of these molecules via a variety of methods. The studies revealed surprising differences which are now outlined.

(A) Yields in CHO

Method: Multispecific antibodies were first produced in a standard CHO expression platform ("CHO Platform 1"). This platform comprises standard expression vectors containing heavy and light chain cassettes. Suspension-adapted CHO K1 cells (originally from ATCC® and adapted to serum-free growth in suspension culture) were employed for manufacture. The seed cells were grown in a chemically defined, animal-component free, serum-free medium. Cells were then transfected with vectors and transfection reagent, and cells were grown further. Supernatant was harvested by centrifugation and the antibody was purified using MabSelect™ SuRe™ prior to formulation.

Figure 34A:
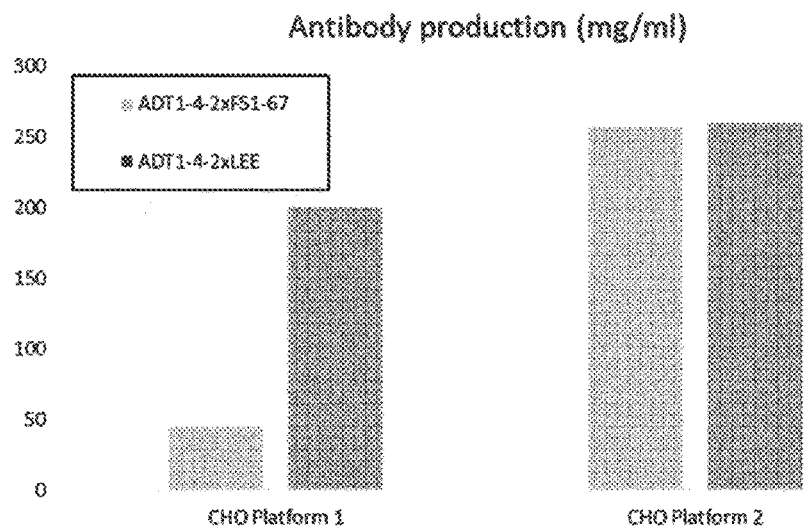

Conclusions: The comparative yields for the two molecules expressed in this platform are indicated in FIG. 34A and highlight the superior expression and recoveries observed for ADT1-4-2×LEE when compared to ADT1-4-2×FS1-67 (indicated by an arrow). A further comparison was then undertaken in an alternative CHO platform ("CHO Platform 2"). In this alternative platform, the yields for each molecule were more comparable.

(B) Stability Under Accelerated Storage Conditions

Method: The antibodies produced in 'CHO platform 2' above were then formulated in a typical antibody formulation buffer at 2 mg/ml and studied under accelerated stress conditions (37° C.). The molecules were then analyzed by standard icIEF methods using the Uncle platform and standard protocols (UNCHAINED LABS®, CA, USA).

Figure 34B:
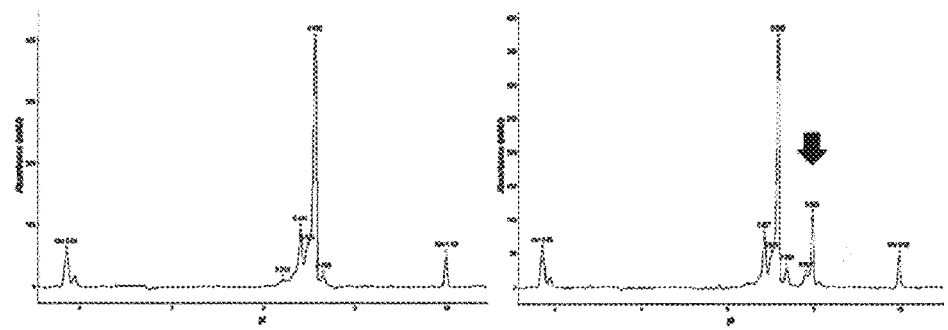

Conclusions: FIG. 34B shows that whilst most molecules appeared relatively stable, a marked increase in a basic species was noted after only 48 hours for the ADT1-4-2× FS1-67 molecule (indicated by arrow). No such increase was observed for the other molecules, as exemplified by ADT1-4-2×LEE molecule in this FIG. 34B. This finding demonstrates ADT1-4-2×LEE molecule is a more stable (e.g. more thermally stable) Vδ1×EGFR multispecific antibody. Given the only sequence differences between ADT1-4-2×FS1-67 and ADT1-4-2×LEE are at positions L358.T359.K360 this suggests that in some instances a Vδ1×EGFR multispecific antibody comprising at least one first antibody-derived binding domain targeting the Vδ1 chain of a γδ TCR and a second binding domain binding the EGF receptor and comprising L358.E359E.E360 is a more preferred variant relative to a Vδ1×EGFR bispecific which instead comprises T358.D359.D360 at these positions (all numbering in accordance with EU).

(C) Aggregation Propensity

Method: The melting profile of the multispecific antibodies were assessed using an Uncle and standard protocols (UNCHAINED LABS®, CA, USA).

Conclusions: FIG. 34C highlights that for the ADT1-4-2×FS1-65 molecule, the onset of aggregation occurred ahead of melting resulting in a significant delta (indicated by arrow). This contrasted with the other molecule wherein onset of aggregation was more concurrent with onset of melting. Concurrent melting/aggregation is typically indicative of a more stable molecule.

(D) Decay Profile at Higher Concentrations Under Accelerated Conditions (Non-Reduced Analysis)

Method: Whilst studies exploring aggregating propensity at 2 mg/ml did not reveal significant differences, studies at 5 mg/ml (under accelerated conditions, 18 days at 37° C.) revealed marked changes in the differing molecules when analyzed by non-reduced CE-SDS with the Maurice and standard protocols (UNCHAINED LABS®, CA, USA).

Conclusions: By such analysis significant increases were noted in the appearance of non-monomer impurities in a number (but not all) of the bispecific molecules analyzed. Exemplar results and tabulated summary results of this study are presented in FIG. 34D (marked changes indicated by arrows).

(E) Decay Profile at High Concentrations Under Accelerated Conditions (Reduced Analysis)

Whilst studies in (FIG. 34D) above highlight that ADT1-4-2×FS1-67 exhibited a more stable profile under accelerated conditions when analyzed under non-reducing conditions, when analyzed under reducing CE-SDS conditions (again using the Uncle and standard protocols, UNCHAINED LABS®, CA, USA), this same ADT1-4-2× FS1-67 molecule exhibited a uniquely atypical profile relative to the other multispecific molecules exemplified in the FIG. 34E by ADT1-4-2×LEE. ADT1-4-2×LEE does not display the increased 'shouldering' observed after 18-day at 37° C. (which is specific only to ADT1-4-2×FS1-67) which may be suggestive of more favorable properties for ADT1-4-2×LEE.

Example 13: Dialing Up/Down Affinity on the VD1 Binding Arm of VD1×EGFR Multispecific Antibodies In these studies, a series of multispecific antibodies were created wherein
(i) the affinity to Vδ1+ was dialled up/down between about 0.2 nM and 20 nM whilst
(ii) the affinity to EGFR was kept constant at about 1 nM.

The effects of these molecules were then studied in a series of experiments. A control D1.3×EGFR multispecific molecule was also included in this series of studies. This control comprised a first binding domain of mAb D1.3, which binds chicken lysozyme (instead of Vδ1 TCR), and a second binding domain, which binds EGFR with an affinity of around 1 nM.

(A) Affinity Summary.

The nomenclature and affinity of this panel of multispecific molecules is presented.

SPR method for example 13: The binding affinity of the antibodies to target (human Vδ1) was established by SPR analysis using a 4SPR instrument (REICHERT TECHNOLOGIES®). Antibodies (1.5 µg/mL) were coated onto a Planar Protein A Sensor Chip (REICHERT TECHNOLOGIES®) to give an increase on baseline of approximately 500 uRIU. Human Vδ1 antigen was flown over the cell at a 1:3 dilution series with top concentrations of 50 nM with the following parameters: 180s association, 900s dissociation, flow rate 25 µL/min, running buffer PBS+0.05% Tween-20. The chip surface was regenerated using 20 mM phosphoric acid following each injection. All experiments were performed at room temperature. Steady state fitting was determined according to Langmuir 1:1 binding using TraceDrawer software (REICHERT TECHNOLOGIES®).

(B)(C) Impact of vδ1 TCR Affinity on Multispecific Binding to Tissue-Resident Vδ1+ Cells.

In this first experiment with this panel of molecules, the role of affinity to the Vδ1 TCR was explored.

Method: Skin tissue-derived Vδ1+ effector cells were co-incubated with antibodies that were serially diluted in PBS to a range of concentrations from 10 nM to 0.13 pM. The cells were incubated for 20 minutes at 4° C. Cells were washed and stained with an anti-human Fc secondary antibody (Jackson Immunoresearch) and a viability dye for dead cells (EFLOUR® 780, INVITROGEN®) for 20 minutes at 4° C. The cells were washed in FACS buffer and resuspended in CELLFIX™ (BD® sciences) before analysis on a MACSQUANT® Analyser 10 flow cytometer (MILTENYI®).

Figures 35A, 35B, 35C:
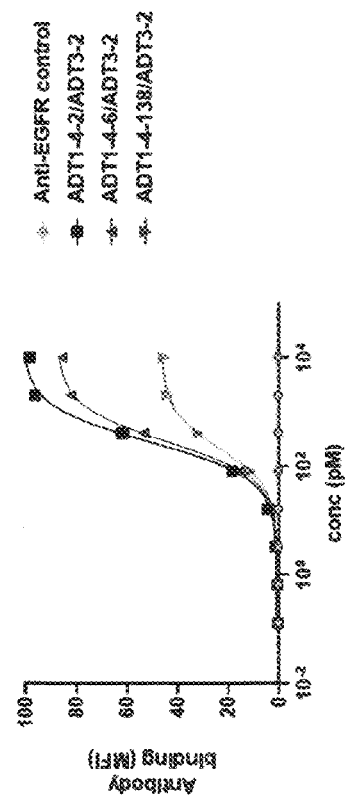
Figure 35I:
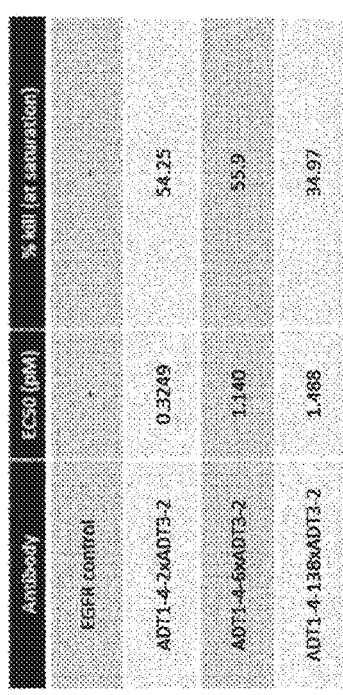
Figure 35K:
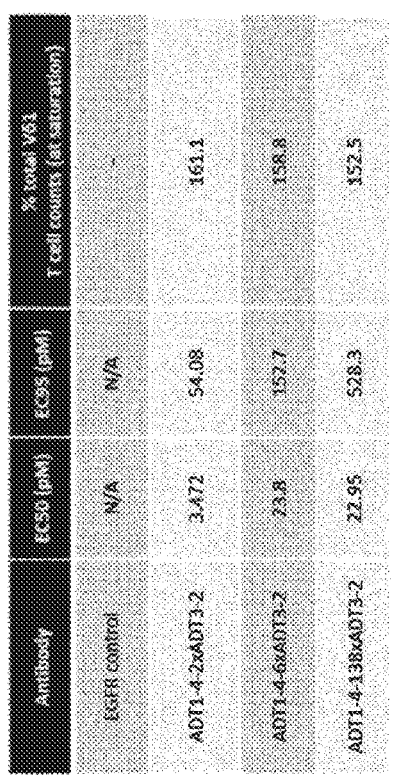

Conclusions: The binding data presented suggests a strong correlation between increased Vδ1 affinity and increased level of multispecific antibody binding to tissue-resident Vδ1+ cells. See FIG. 35B and FIG. 35C showing the tabulated results of FIG. 35B. This data highlights that higher affinity molecules confer enhanced effects at saturating concentrations. Remarkably the effects conferred by higher affinity variants cannot be mimicked or recapitulated with higher concentrations of lower affinity variants of the antibodies. This suggests molecules with (unnaturally) high affinity to the Vδ1 TCR confer differing effects which lower affinity molecules are incapable of mimicking, even at significantly higher concentrations (e.g. 100-fold). This discovery is also discussed further herein.

Further effects of these molecules were then studied in the following series of experiments. Skin tissue-derived Vδ1+ effector cells were co-incubated with EGFR+A375 melanoma cancer cell line as follows:

First, EGFR+ target cells were seeded into multi-well tissue-culture plates ~16 hours prior to assay setup.

The following day antibodies were serially diluted to a range of concentrations in basal growth before adding to EGFR+ target cells.

Skin derived Vδ1 γδ T-cells were detached from culture flasks and cell suspensions were seeded into assay plates and co-cultures incubated for the specified duration at 37° C., 5% CO2.

Cells were processed and analysed dependent on the chosen readout, as described in each case.

The results of these studies are presented as follows:

(D)(E) Impact of vδ1 TCR Affinity on Vδ1 TCR Internalization of Tissue-Resident Vδ1+ Cells.

In this first analysis wherein Vδ1+ effector cells are co-incubated with EGFR+ cancer cells, the focus is on the induction of Vδ1 TCR internalization following multispecific antibody engagement.

Method: Co-cultures were established as above with 2.5×10^4 Vδ1 γδ T-cells added to 2.5×10^4 EGFR+ target cells per well in U-bottomed 96-well plates. Prior to addition, Vδ1 γδ T-cells were stained with [0.5 µM] CELL-TRACE™ Violet live cell dye for 20 minutes. Final assay antibody concentrations ranged from 10 nM to 0.13 pM. Following incubation for 4 hours at 37° C., 5% CO2, cells were harvested and stained for dead cells (EFLOUR® 780, INVITROGEN®) and Vδ1 TCR (MILTENYI BIOTEC®) surface expression for 20 minutes at 4° C. The cells were washed in FACS buffer and resuspended in CELLFIX™ (BD® sciences) before analysis on a MACSQUANT® Analyser 10 flow cytometer (MILTENYI®).

Conclusion: The reduction in MFI is presented in FIG. 35D. These results are indicative of increased TCR downregulation upon antibody engagement. It was also discovered that the higher the affinity, the greater the reduction in MFI signal (and therefore TCR downregulation). Remarkably, even when 100-fold more of the lower affinity molecule (ADT1-4-138×ADT3-2) was added, no equivalent signal reduction could be induced. This suggests unnaturally high affinities to the TRDV1 target can further enhance TCR downregulation. It also suggests very high affinity binding confers differing effects on TCR function. It can only be speculated as to why such high affinities are required to achieve more optimal saturating downregulation effects. It is possible this is a stochastic effect on a homogenous Vδ1+ population wherein longer residence time (through reduced off-rate) of the higher affinity molecules confers higher saturating effects, possibly via higher levels of TCR cross-linking. A possible alternative is that a subset of Vδ1+ cells are refractory to TCR downregulation effects conferred by the lower affinity molecules. A summary of the findings in FIG. 35D is presented in tabulated form (See FIG. 35E). This further highlights the fact that high affinity delivers differing effects at saturating concentrations and that the reduced effect conferred by lower affinity molecules cannot be compensated for by dosing at higher concentrations.

(F)(G) Impact of vδ1 TCR Affinity on Degranulation of Tissue-Resident Vδ1+ Cells.

This next analysis is focused on the degranulation effects conferred by multispecific antibodies of this invention.

Method: Co-cultures were established as above with 2.5×10^4 Vδ1 γδ T-cells added to 2.5×10^4 EGFR+ target cells per well in U-bottomed 96-well plates. Prior to addition, Vδ1 γδ T-cells were stained with [0.5 µM] CELL-TRACE™ Violet live cell dye for 20 minutes. Final assay multispecific antibody concentrations ranged from 10 nM to 0.13 pM. Additionally, a fluorophore-conjugated antibody specific for CD107a (MILTENYI BIOTEC®) was added at the start of the co-incubation. Following incubation for 4 hours at 37° C., 5% CO2, cells were harvested and stained for dead cells (EFLOUR® 780, INVITROGEN®) for 20 minutes at 4° C. The cells were washed in FACS buffer and resuspended in CELLFIX™ (BD® sciences) before analysis on a MACSQUANT® Analyser 10 flow cytometer (MILTENYI®). See FIG. 35F.

Conclusions: These studies demonstrate once again that increased affinity confers optimal effects. A direct correlation between increased CD107a upregulation and increased affinity is observed. Once more this data suggests unnaturally high affinities to the Vδ1 TCR drive remarkably differing, more favorable effects which cannot be recapitulated with molecules with a lower affinity to Vδ1, even when dosed at much higher concentrations. Summary results of FIG. 35F are presented in tabulated form. (See FIG. 35G) Once again, this summary highlights the discovery that higher affinity molecules at saturating concentrations confer differing, more enhanced saturating effects relative to a lower affinity molecule, even when employed at much higher concentrations.

(H)(I) Impact of vδ1 TCR Affinity on Multispecific Cytolytic Function Towards EGFR+ Cancer Cells.

This next analysis is focused on the cytolytic effect conferred by multispecific antibodies of this invention.

Method: Co-cultures were established as above with $4 \times 10^{\wedge}3$ Vδ1 γδ T-cells added to $4 \times 10^{\wedge}3$ EGFR+ target cells per well in 384-well CellCarrier Ultra plates (PERKINELMER®). Final assay antibody concentrations ranged from 5 nM to 0.03 pM. Following incubation for 24 hours at 37° C., 5% CO2, cells were stained with Hoechst 33342 (INVITROGEN®) and for dead cells (DRAQ7, ABCAM®) for 1 hour at 37° C. The cells were imaged on an Opera Phenix system (PERKINELMER®) and quantity of viable target cells determined using a linear regression model (Harmony 4.9) based on size, morphology, texture and intensity of live cell stains and the absence of DRAQ7 staining.

Figure 35H:
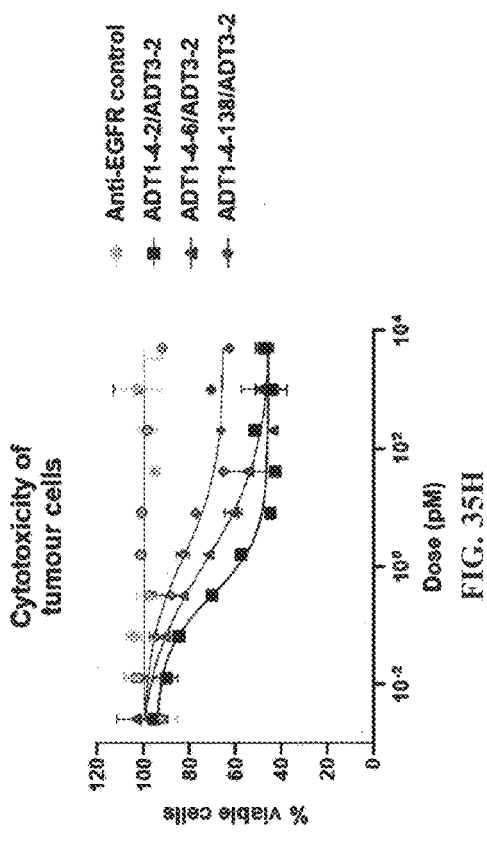
Figure 35J:
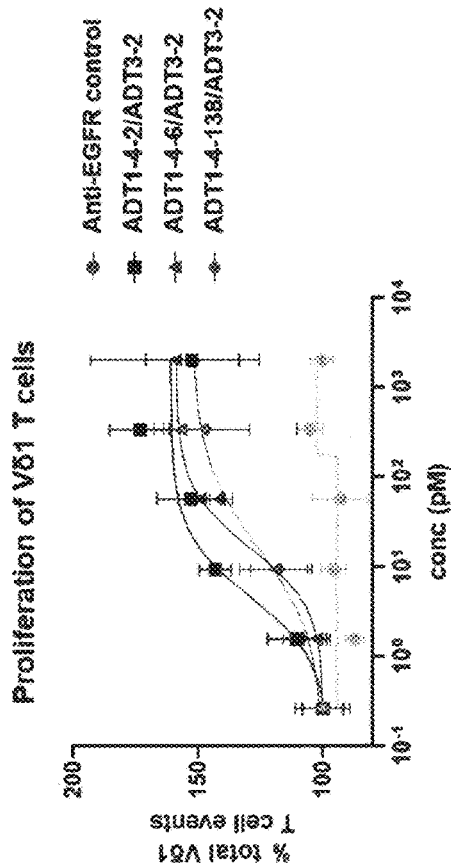
Figure 35M:
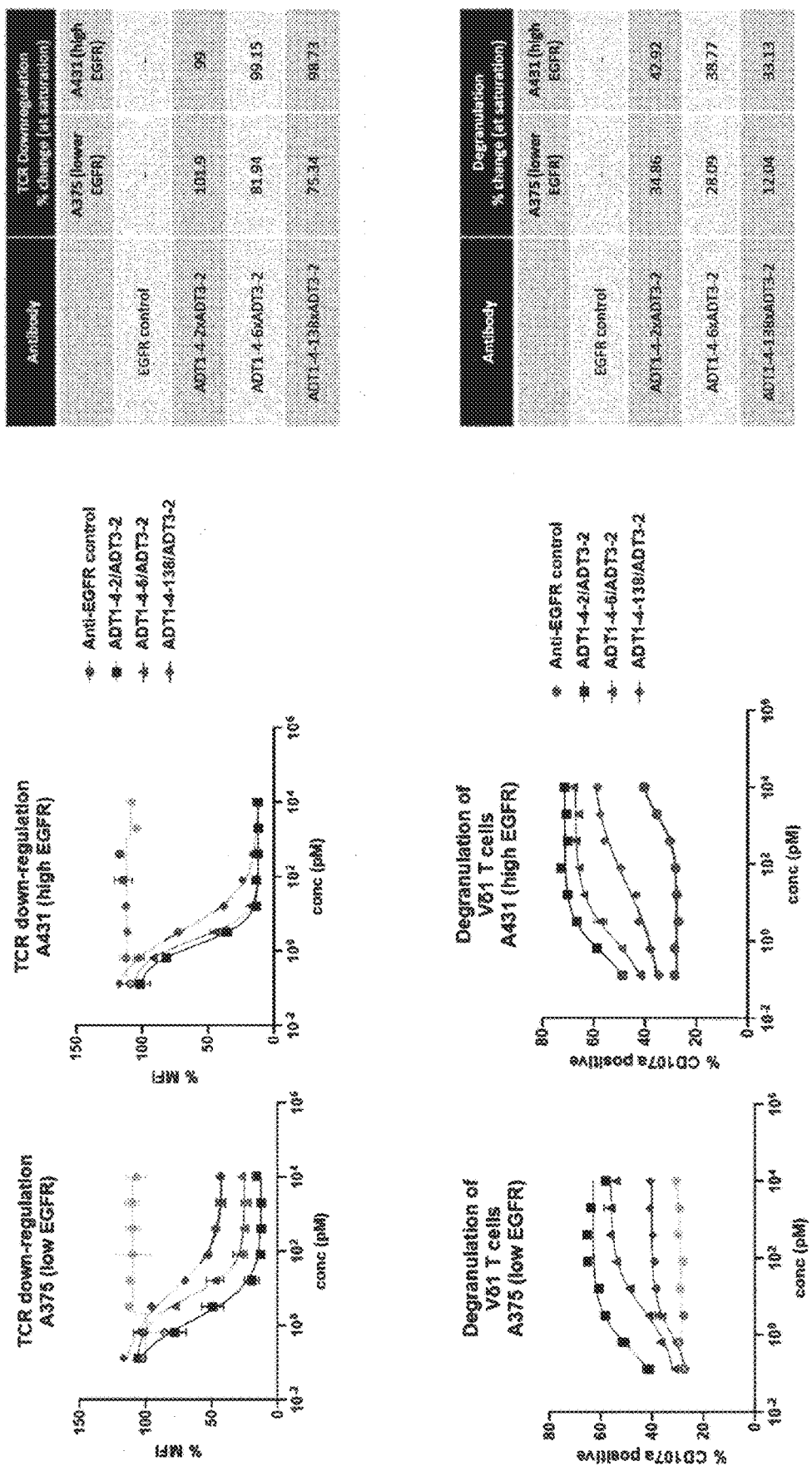

Conclusion: The data presented here demonstrates the highest Vδ1 affinity molecules to be the most potent and cytolytic towards EGFR+ cancer cells. See FIG. 35H. Further, qualitative differences were observed between the lowest Vδ1 affinity multispecific antibody (20 nM) and mid/high-Vδ1 affinity multispecific antibodies (1.2 nM and 0.2 nM respectively) wherein markedly differing saturating effects were observed. This suggests unnaturally high affinities confer remarkably different, enhanced effects. These effects cannot be mimicked using molecules with lower affinity to Vδ1 TCR, even when dosed at much higher (e.g. 100-fold) concentrations. Summary results from FIG. 35H are presented in tabulated form (see FIG. 35I). This highlights the discovery that higher affinity molecules at saturation concentrations confer differing more enhanced effects relative to a lower affinity molecule-even if delivered at much higher concentrations.

(J)(K) Impact of vδ1 TCR Affinity on Proliferation of Tissue-Resident Vδ1+ Cells.

This next analysis is focused on the induction of proliferation of Vδ1+ cells conferred by multispecific antibodies of this invention.

Method: Co-cultures were established as above with $3 \times 10^{\wedge}4$ Vδ1 γδ T-cells added to $1.5 \times 10^{\wedge}4$ EGFR+ target cells per well in U-bottomed 96-well plates. Prior to addition, target cells were stained with [0.5 µM] CELLTRACE™ Violet live cell dye for 20 minutes. Final assay multispecific antibody concentrations ranged from 2 nM to 0.25 pM. The cells were incubated for 5 or 7 days at 37° C., 5% CO2. Complete media with the addition of cytokines (IL-2, IL-15, IL-4 and IL-21; need units) were added at day 3 and day 5. Cells were washed and stained for dead cells (EFLOUR® 780, INVITROGEN®) for 20 minutes at 4° C. The cells were washed in FACS buffer and resuspended in CELLFIX™ (BD® sciences). The number of events was measured by flow cytometry the following day using the MACSQUANT® Analyzer 10.

Conclusion: These studies further reinforce the finding that increased affinity confers more enhanced effects wherein a direct correlate between increased induction of proliferation of Vδ1 T cells and increased affinity is observed. See FIG. 35J (and summarised in tabulated form in FIG. 35K). This is most evident in the highest affinity iteration demonstrating the lowest EC50 and EC95 and the highest maximum cell numbers. Higher affinity molecules are more potent at driving proliferation of Vδ1 T cells proliferation. Interestingly, and somewhat different to other technical effects conferred by higher affinity molecules, lower affinity molecules variant can confer similar effects when delivered at 100-fold higher concentrations in this instance.

(L) Overall Summary of this Study

See FIG. 35L.

This summary highlights
(i) the advantageous technical effects conferred by antibodies of this invention with a higher affinity (less than 10 nM) to the Vδ1+ TCR; and
(ii) which of the reduced effects conferred by lower affinity molecules (more than 10 nM) can then compensated for by increasing the concentration 100-fold or more.

(M) Impact of TAA Copy Number.

The above findings as summarized in FIG. 35L highlight some intriguing results. Specifically
(i) high-affinity molecules (to Vδ1 TCR) deliver enhanced effects relative to lower affinity molecule variants and
(ii) the reduced effects conferred by lower affinity variants can not always be compensated for by increasing concentration of these molecules.

However, the inventors next explored the impact of copy number against the second target (in this instance EGFR) in such assays. (See FIG. 35M). The studies employed the same methodologies as outlined above but replaced the lower copy number TAA cancer cell line (A375) with the cancer cell line (A431), which displays an extremely high copy number. Intriguingly, in this equivalent study which therefore involved co-incubation of primary Vδ1+ cells with a uniquely high copy number EGFR+ cancer cell line, a different finding was uncovered. Specifically, in some instances the inferior effects observed by lower affinity variants can be overcome by increasing the concentration of these variants in the assay if combined with a higher TAA copy number cancer cell line. Whilst high affinity molecules exhibit similar effects at similar concentrations irrespective of EGFR copy number of cancer cell line employed in the assay, for lower affinity molecules, a combination of increasing the concentration of the molecule, combined with use of a higher copy number cancer cell line resulted in compensatory effects. When using higher concentrations of the low affinity variants in such circumstances, saturated CD107a upregulation and saturated TCR downregulation conferred by the lower affinity molecules can—for the first time—mimic the saturating effects of higher affinity molecules.

This suggests that the reduced effects of lower affinity molecules can be 'recovered' if
(a) very high TAA target cell lines are employed in the assay and
(b) 100-fold (or more) increased concentrations of the molecule are employed.

Whilst the mechanism behind these findings can only be speculated upon, it does highlight once again the advantages of molecules of this invention with higher affinity to the Vδ1 TCR. For example, the efficacy of the lower affinity variants is significantly reduced if target cancer cell lines have normal EGFR TAA levels. This may not be overcome by higher dosing. Additionally, in the case for the EGFR TAA, it is well understood that extremely high copy number EGFR cancers are in a minority in most cancers e.g. see recent studies on certain breast cancer (eg. Kim et al 201310.1371/journal.pone.0079014) or head and neck cancers (eg. Licitra et al 2011 DOI: 10.1093/annonc/mdq588) or gastric cancers (eg. Zhang et al 2015 doi.org/10.3892/ol.2015.3875). Hence the increased utility and surprising advantages of the unnatural higher affinity antibodies of this invention over and above lower affinity variants are very clear.

Example 14: Dialing Up/Down Affinity on the EGFR Binding Arm of VD1×EGFR Multispecific Antibodies A series of multispecific antibodies were created wherein
(i) the affinity to EGFR was dialed up/down whilst
(ii) the affinity to Vδ1 was kept constant at about 0.2 nM.
The starting EGFR binding domain (FS1-67) for this exploration has previously been described (WO2018015448). One motivation to further modify this binding domain was an attempt to further fine-tune the affinity of this domain when employed in multispecific antibodies of this invention. In doing so the inventors have discovered that returning certain amino acids in the EGFR binding domains back to wild-type human immunoglobulin sequence impacted affinity to the EGFR target more so than others. This exploration resulted in the discovery of a panel of more finely-tuned binding domains with a range of affinity options ranging from about 1 nM binding to about 140 nM to EGFR. The differing EGFR binding domains conferred a variety of distinguishing properties when incorporated into multispecific antibodies of this invention. Accordingly, this panel of multispecific antibodies has also proved invaluable when exploring and determining the role of affinity.

Also included in this study—where indicated—is the multispecific D1.3×FS1-67 control (comprising a 1 nM affinity EGFR second binding domain and first binding domain comprised binding domain to chicken lysozyme)
(A) Affinity Summary The nomenclature and affinity of this panel of multispecific molecules is presented.

SPR method for example 14: For human EGFR, recombinant protein (Stratech; 10001-H08H-SIB-100 ug) was coupled to a Carboxylmethyl Dextran Sensor Chip (REICHERT TECHNOLOGIES®) to give an increase in baseline of approximately 500 uRIU. Concentration ranges of antibodies (7.5-200 nM) were injected in PBS-T buffer with the following parameters: 180s association, 660s dissociation, flow rate 25 μL/min, running buffer PBS-T. The chip surface was regenerated using 20 mM phosphoric acid following each injection. All experiments were performed at room temperature. Steady state fitting was determined according to Langmuir 1:1 binding using TraceDrawer software (REICHERT TECHNOLOGIES®).

Conclusions: The summary results are presented in FIG. 36A. For this study, the starting CH3-based FS1-67 binding module contains 5 modifications in the AB loop, 3 in the CD loop, and 5 in the EF loop. When attempting to modify the affinity of this molecule by varying degrees, some interesting discoveries were made. For example, it was discovered that returning all 5 amino acids in the AB loop back to wild-type sequence has the most significant impact on EGFR binding affinity (ADT1-4-2×LEE1 as indicated, broken line black rectangle). Certainly, when compared to the full return of the CD loop or (partial) return of the EF loop back to wild-type immunoglobulin sequence (ADT1-4-2× LEE2 and ADT1-4-2×LEE3 respectively), changes to the AB loop were the most impactful. Indeed, by some measures (see later) returning the AB loop to wild-type sequence resulted in loss of binding affinity and specificity. Hence it was unexpected that affinity was not impacted when a non-conservative amino acid found in the AB loop of FS1-67 was modified from threonine (polar) back to leucine (non-polar). This is highlighted by comparing the ADT1-4-2 LEE molecule (highlighted by solid line black rectangle, 1 change-negligible impact on affinity/function) with the ADT1-4-2 LEE1 molecule (highlighted by the dotted black rectangle, 5 changes-biggest impact on affinity/function). This said, the resulting ADT1-4-2×LEE now comprising only 4 changes to the AB loop did also incorporate additional modifications too. Hence it cannot be ruled out that these other (conservative) changes in the binding loop (D3659E, D360E) also contributed to the retention of high affinity; albeit surprisingly so. Either way, given returning such modifications back to wild-type may afford a reduced immunogenicity risk in the resulting multispecific antibodies of this invention, a wild-type Leucine at position 358—and as part of 4 amino-acid change to AB loop—is considered more preferred to 5 (or more) amino acid changes as found in the starting FS1-67, FS1-65 or 747 EGFR binding domains as incorporated into ADT1-4-2×FS1-67, ADT1-4-2×FS1-65 and ADT1-4-2×747 respectively.

(B)(C) Impact of EGFR Affinity on Multispecific Binding to EGFR+ Colon Cancer Cell Line HT-29.

Method: Example binding of EGFRxVδ1 multispecific antibodies was determined by incubating EGFR+HT-29 target cells with antibodies that were serially diluted in PBS to a range of concentrations from 500 nM to 0.13 pM for 20 minutes at 4 degrees. After washing, cells were incubated for a further 20 minutes with anti-human IgG secondary antibodies (Jackson Immunoresearch) and live/dead stain (eFluor 780, INVITROGEN®) before washing and fixing using CELLFIX™. The amount of antibody bound to each cell type was determined using flow cytometry (MACSQUANT® Analyser 10, MILTENYI BIOTEC®).

Conclusions: The data presented suggests a strong, direct and graduated correlation was observed between increased EGFR affinity and increased level of multispecific antibody binding to EGFR+HT-29 cancer cells. See FIG. 36B. FIG. 36C presents the results of FIG. 36B in tabulated form.

Further effects of these molecules were then studied in the following series of experiments. In brief, skin tissue-derived Vδ1+ effector cells were co-incubated with EGFR+A375 melanoma cancer cell line as follows; EGFR+ target cells were seeded into multi-well tissue-culture plates ~16 hours prior to assay setup. The following day antibodies were serially diluted to a range of concentrations in basal growth before adding to EGFR+ target cells. Skin derived Vδ1 γδ T-cells were detached from culture flasks and cell suspensions were seeded into assay plates and co-cultures incubated for the specified duration at 37° C., 5% CO2. Cells were processed and analyzed dependent on the chosen readout, as described in each case. The results of these studies are presented as follows:

(D)(E) Impact of EGFR Affinity on Vδ1 TCR Downregulation of Tissue-Resident Vδ1+ Cells.

This next analysis is focused on the induction of Vδ1 TCR internalization following multispecific antibody engagement.

Method: Co-cultures were established as above with 2.5×10^4 Vδ1 γδ T-cells added to 2.5×10^4 A375 EGFR+ target cells per well in U-bottomed 96-well plates. Prior to addition, Vδ1 γδ T-cells were stained with [0.5 µM] CELL-TRACE™ Violet live cell dye for 20 minutes. Final assay antibody concentrations ranged from 10 nM to 0.13 pM. Following incubation for 4 hours at 37° C., 5% CO2, cells were harvested and stained for dead cells (EFLOUR® 780, INVITROGEN®) and Vδ1 TCR (MILTENYI BIOTEC®) surface expression for 20 minutes at 4° C. The cells were washed in FACS buffer and resuspended in CELLFIX™ (BD® sciences) before analysis on a MACSQUANT® Analyser 10 flow cytometer (MILTENYI®).

Conclusions: The reduction in Vδ1 TCR MFI is indicative of increased TCR downregulation and specifically, it was discovered that the higher the affinity to EGFR, the greater the reduction in this signal. Remarkably, however, the relationship between EGFR affinity and induction of TCR downregulation did not appear to be a graduated correlation, but one dependent on a threshold affinity value. Specifically, three molecules (ADT1-4-2×LEE, ADT1-4-2×LEE2, and ADT1-4-2×LEE3) which respectively exhibited affinity of about 1 nM, about 9 nM and about 19 nM affinity to EGFR clustered closely together and conferred similar TCR downregulation effects and associated EC50 values. These three molecules contrasted significantly with ADT1-4-2×LEE1. As discussed previously, this molecule contains a wild-type immunoglobulin AB loop and exhibits the lowest affinity of about 140 nM. This molecule does not confer the desired TCR downregulation effects when compared to the other three molecules even when combined with the high-affinity anti-Vδ1 TCR ADT1-4-2 binding domain as is the case here. This would suggest there exists a threshold effect or steeply sloped gradient effect with multispecific antibodies such as ADT1-4-2×LEE, ADT1-4-2×LEE2, and ADT1-4-2×LEE3 clustered together and separate from lower EGFR affinity molecules such as ADT1-4-2×LEE1. This contrasts with the shallower, more graduated affinity/binding events previously seen (see FIG. 36B above) wherein the binding effects conferred by these multispecific antibodies were graded by their respective affinities to the EGFR second binding target rather than more clustered into two contrasting groups. See FIG. 36D. FIG. 36E presents the results of FIG. 36D in tabulated form.

(F)(G) Impact of EGFR Affinity on Degranulation of Tissue-Resident Vδ1+ Cells

This next analysis is focused on the degranulation effects conferred by multispecific antibodies of this invention.

Method: Co-cultures were established as above with 2.5×10^4 Vδ1 γδ T-cells added to 2.5×10^4 EGFR+ target cells per well in U-bottomed 96-well plates. Prior to addition, Vδ1 γδ T-cells were stained with [0.5 µM] CELL-TRACE™ Violet live cell dye for 20 minutes. Final assay multispecific antibody concentrations ranged from 10 nM to 0.13 pM. Additionally, a fluorophore-conjugated antibody specific for CD107a (MILTENYI BIOTEC®) was added at the start of the co-incubation. Following incubation for 4 hours at 37° C., 5% CO2, cells were harvested and stained for dead cells (EFLOUR® 780, INVITROGEN®) for 20 minutes at 4° C. The cells were washed in FACS buffer and resuspended in CELLFIX™ (BD® sciences) before analysis on a MACSQUANT® 16 flow cytometer (MILTENYI®).

Conclusions: These studies demonstrate once again that increased affinity for EGFR confers optimal effects wherein a correlation between increased CD107a upregulation and increased affinity is observed. This relationship is dependent on a threshold affinity value. As with TCR downregulation, multispecific antibodies with an affinity range of about EGFR of 1 to about 19 nM functionality clustered together and induced significantly higher levels of CD107a relative to the lower affinity molecule (ADT1-4-2×LEE1). This data suggests multispecific antibodies of this invention with high-to-medium affinities to EGFR drive remarkably differing, more favorable effects in certain scenarios which cannot be repeated with molecules with lower affinity to EGFR, even when dosed at much higher concentrations (eg. 1,000-fold). The results are shown in FIG. 36F, and are summarised in tabulated form in FIG. 36G.

(H)(I) Impact of EGFR Affinity on 41BB Activation Status of Tissue-Resident Vδ1+ Cells.

This next analysis is focused on the increase in activation-induced marker 41BB of Vδ1+ cells conferred by multispecific antibodies of this invention.

Method: Co-cultures were established as above with 2×10^4 Vδ1 γδ T-cells added to 2×10^4 EGFR+ target cells per well in U-bottomed 96-well plates. Prior to addition, Vδ1+γδ T-cells were stained with [0.5 µM] CELLTRACE™ Violet live cell dye for 20 minutes. Final assay multispecific antibody concentrations ranged from 100 pM to 0.13 pM. Following incubation for 24 hours at 37° C., 5% CO2, cells were harvested and stained for dead cells (EFLOUR® 780, INVITROGEN®) and 41BB (MILTENYI BIOTEC®) surface expression for 20 minutes at 4° C. The cells were washed in FACS buffer and resuspended in CELLFIX™ (BD® sciences) before analysis on a MACSQUANT® Analyser 10 flow cytometer (MILTENYI®).

Conclusions: The data presented here (see FIG. 36H and a tabulated summary in FIG. 36I) demonstrates that the multispecific antibodies of this invention with higher affinities to EGFR to be the most effective at stimulating increased 41BB activation of Vδ1+ cells. As with some other studies discussed previously, significant qualitative differences were again observed between the lowest EGFR affinity multispecific antibody about 140 nM and mid-to-high-EGFR affinity multispecific antibodies (those under about 20 nM threshold) wherein the lower affinity was unable to induce marked Vδ1+ cell activation. This suggests a threshold in which medium-to-high affinities are functionally clustered together—as measured by 41BB upregulation on this occasion. Once more, these effects cannot be repeated using molecules with lower affinity to EGFR, even when dosed at much higher (eg. 1,000-fold) concentrations. Interestingly however, it was also observed that the increased 41BB levels at saturation for the highest affinity molecule (ADT1-4-2×LEE, about 1 nM) was less than that observed for the mid-range multispecific molecules of this invention at between about 9 nM-19 nM (ADT1-4-2×LEE2 and ADT1-4-2 LEE3). This observation—that the highest affinity may not always be most preferred—is further discussed later herein.

(J)(K) Impact of EGFR Affinity on Multispecific Cytolytic Function Towards EGFR+ Cancer Cells.

This next analysis is focused on the cytolytic effect conferred by multispecific antibodies of this invention.

Method: Co-cultures were established as above with 4×10^3 Vδ1 γδ T-cells added to 4×10^3 EGFR+ target cells per well in 384-well CellCarrier Ultra plates (PERKINELMER®). Final assay antibody concentrations ranged from 5 nM to 0.03 pM. Following incubation for 24 hours at 37° C., 5% CO2, cells were stained with Hoechst 33342 (INVITROGEN®) and for dead cells (DRAQ7, ABCAM®) for 1 hour at 37° C. The cells were imaged on an Opera Phenix system (PERKINELMER®) and quantity of viable target cells determined using a linear regression model (Harmony 4.9) based on size, morphology, texture and intensity of live cell stains and the absence of DRAQ7 staining.

Conclusions: This data demonstrates that the higher EGFR affinity molecules are the most potent and cytolytic towards EGFR+ cancer cells. Once again, significant qualitative differences were observed between the lowest EGFR affinity multispecific antibody (at about 140 nM) and mid-to-high-EGFR affinity multispecific antibodies (at about 1 nM to 19 nM). Indeed, no measurable target killing was induced by the low EGFR affinity molecule (ADT1-4-2×LEE1). Hence this is another example wherein a threshold effect is observed whereby molecules at about 1 nM to about 19 nM (ADT1-4-2×LEE, ADT1-4-2×LEE3, ADT1-4-2×LEE2) confer a clustered more optimal functional effect. These effects cannot be repeated using molecules with lower affinity to EGFR, even when dosed at much higher (eg. 10,000-fold) concentrations. The results are shown in FIG. 36J, and are summarised in tabulated form in FIG. 36K.

(L)(M) Impact of EGFR Affinity on Proliferation of Tissue-Resident Vδ1+ Cells;

This next analysis is focused on the induction of proliferation of Vδ1+ cells conferred by multispecific antibodies of this invention.

Method: Co-cultures were established as above with 3×10^4 Vδ1 γδ T-cells added to 1.5×10^4 EGFR+ target cells per well in U-bottomed 96-well plates. Prior to addition, target cells were stained with [0.5 µM] CELLTRACE™ Violet live cell dye for 20 minutes. Final assay multispecific antibody concentrations ranged from 2 nM to 0.25 pM. The cells were incubated for 5 or 7 days at 37° C., 5% CO2. Complete media with the addition of cytokines (IL-2, IL-15, IL-4 and IL-21; need units) were added at day 3 and day 5. Cells were washed and stained for dead cells (EFLOUR® 780, INVITROGEN®) for 20 minutes at 4° C. The cells were washed in FACS buffer and resuspended in CELL-FIX™ (BD® sciences). The number of events was measured by flow cytometry the following day using the MACSQUANT® Analyzer 10.

Conclusions: These studies demonstrate once again that increased affinity confers more optimal effects wherein a direct correlation between increased induction of proliferation of Vδ1 T cells and increased affinity is observed. Once again, a clustering effect is observed wherein multispecific antibodies of this invention with mid-to-high affinities to EGFR in the range of about 1 nM to about 19 nM affinity (ADT1-4-2×LEE, ADT1-4-2×LEE3, ADT1-4-2LEE2) functionally cluster together whilst the lower affinity molecule with an affinity of about 140 nM (ADT1-4-2×LEE1) is significantly impaired and is equivalent to the non-binding (to TCR) control in this assay. Interestingly and similarly to 41BB effect (see FIG. 36H), the very highest affinity at about 1 nM affinity to EGFR does not confer the highest saturation effects. Rather, the mid-range affinity molecules at about 9 nM-19 nM (ADT1-4-2×LEE3 and ADT1-4-2×LEE2 respectively) confer the highest proliferative effects at saturating concentrations of the antibodies. This more optimal effect conferred by mid-range affinity multispecific antibodies of this invention is discussed later herein. The results are shown in FIG. 36L and are summarised in tabulated form in FIG. 36M.

(N) Affinity to EGFR and Impact of Cancer Cell TAA Copy Number

These studies highlight the impact of affinity towards EGFR for multispecific antibodies of this invention.

Next these effects were compared to the effects observed wherein extremely high-copy number A431 cell line rather than lower copy number A375 cell line is instead employed in Vδ1+ cell/EGFR+ cancer cell co-incubation studies.

A summary of this comparison is presented in FIG. 36N and it was discovered that for extremely high EGFR copy number cancers as represented by A431, some of the reduced effects observed by the lower affinity multispecific antibody of about 140 nM (ADT1-4-2×LEE1) could be 'recovered'. However, this recovery was still graduated, and the lower affinity molecule still do not 'cluster' with the mid-to-high affinity variants of ADT1-4-2×LEE, ADT1-4-2×LEE2 and ADT1-4-2×LEE3. Nevertheless, this observation is of interest and suggest lower affinity variants are more functional (and so more selective) for higher copy number EGFR bearing cancer cells.

Suitably, the functional properties of the antibodies when provided in a monospecific format are shared by the multispecific antibodies of the invention that additionally specifically bind to a second antigen.

Example 15: Impact of Affinity on Preferential Binding to Vδ1 Cells Versus EGFR Cells This following experiment explores how dialing up and down affinity on the respective binding domains impacts molecule distribution and preferential binding. Specifically, this study explored how varying binding affinity for the respective Vδ1 and EGFR targets then impacts the binding preferences for multispecific antibodies of this invention.

Method: Co-cultures were established with 2×10^4 Vδ1 T-cells added to 2×10^4 EGFR+ target cells per well in U-bottomed 96-well plates. A 'limiting' quantity (16 pM) of each multispecific antibodies as indicated were then added and the cells were incubated for 20 min at 4° C. Cells were incubated for a further 20 minutes with anti-human IgG secondary antibodies (Jackson Immunoresearch) and live/dead stain (eFluor 780, INVITROGEN®) before washing and fixing (BD® CELLFIX™). The amount of antibody bound to each cell type was determined using flow cytometry (MACSQUANT® Analyzer 10, MILTENYI BIOTEC®).

Conclusions: FIG. 37A shows the impact of affinity on preferential binding to Vδ1 versus EGFR cells as a bar chart format: The relative distribution between the two cell types is shown for each antibody as indicated. This data demonstrates that modification of Vδ1 affinity has only a marginal impact on binding ratios and distribution profiles. By contrast there appears to be a more profound effect when the affinity for EGFR binding domain is modified. Specifically, multispecific antibodies with lower EGFR affinities exhibit considerable preference towards Vδ1 binding—with the lowest EGFR binder ADT1-4-2×LEE1 (Kd, 140 nM) demonstrating the greatest preference for Vδ1 cells. In summary, these results demonstrate that by dialing up and down affinity of the respective binding domains, one can potential select and direct differing cell target/tissue distribution profiles. Moreover, when these findings are combined with others herein it suggests that whilst EGFR mid-affinity antibodies of this invention (of between about 9 nM and about 19 nM) exhibit similar effects in variety of ways to higher affinity variants (of about 1 nM affinity to EGFR) such mid-affinity multispecific antibodies of this invention do vary in other ways and may offer a more favorable tumour-mediated antibody clearance, distribution and EGF blocking profile in certain circumstances. This may in turn may offer greater potential to further reduce dose-limiting skin toxicities relative to higher affinity EGFR variants of this invention. FIG. 37B presents the results of FIG. 37A are presented in a tabulated format and FIG. 37C presents the results of part (A/B) as a ratio.

Example 16: Affinity to EGFR: Impact on Multispecific Antibody Internalization by A431 Tumour Cells (A)(B) This analysis is focused on the internalization of certain multispecific antibodies (and comparators). As described previously, a series of multispecific antibodies were created wherein
  (i) the affinity to EGFR was dialed up/down with a range of affinity options ranging from about 1 nM binding to about 140 nM to EGFR whilst
  (ii) (ii) the affinity to Vδ1 was kept constant at about 0.2 nM.

Also included in this study—where indicated—is the monospecific RSV IgG comparator (comprising binding domains to RSV protein), the multispecific D1.3×FS1-67 control (comprising a 1 nM affinity EGFR second binding domain and first binding domain comprised binding domain to chicken lysozyme).

Methods: Cultures were established with 4×10^3 EGFR+ A431 tumours cells per well in 384-well CellCarrier Ultra plates (PERKINELMER®). Antibodies were covalently labelled with Cy5 fluorophores using a Lightning Link antibody conjugation kit (ABCAM®), according to manufacturers instructions. Prior to addition of antibody, the cells were imaged on an Opera Phenix system (PERKINELMER®) using the Cy5 filter set. Labelled antibodies at final concentrations of 1 nM were then added and cells imaged by Opera Phenix for a further 8.5 hours at intervals of 15 minutes. The intensity of Cy5 within the intracellular regions was determined using Harmony 4.9 analysis.

Conclusions: This data demonstrates that the lower EGFR affinity multispecific molecules demonstrate the least EGFR-mediated internalization in target A431 tumour cells. Significant qualitative differences were observed between the lowest EGFR affinity multispecific antibody (at about 140 nM; equivalent to no antibody control) and high-EGFR affinity multispecific antibodies (at about 1 nM). Specifically, a positive correlation between EGFR target affinity and the observed level of antibody internalization was discovered. This represents an example of a graduated effect associated with EGFR affinity of molecules of this invention ranging from about 1 nM to about 140 nM to EGFR. The results are shown in FIG. 38A and tabulated in FIG. 38B.

(C)(D) This analysis is focused on the clearance of the multispecific antibodies described in this invention. Clearance in this case refers to the removal of antibody from the culture medium of A431 cell cultures by EGFR-mediated antibody internalisation.

Methods: Cultures were established with 2×10^4 EGFR+ A431 tumours cells per well in 96-well flat-bottom TC-treated plates. Final assay antibody concentrations ranged from 5 nM to 1.6 pM. Following incubation for 24 hours at 37° C., 5% CO2, supernatants were harvested and stored for further analysis. Multispecific antibody concentrations were determined by in-house ELISA. In brief, ELISAs was performed with 1 ug Vδ1 antigen directly coated to the plate, followed by blocking with blocking buffer. Harvested supernatants were added the plate, washed and anti-Human Fc-HRP was used as secondary antibody at ½000 dilution. Development was with 50 µL of TMB solution, and absorbance measured at 450 nM using a microplate reader (Tecan).

Conclusions: This data demonstrates that the lower EGFR affinity multispecific molecules demonstrate the least EGFR-mediated clearance of antibody. Significant differences were observed between the lowest EGFR affinity multispecific antibody (at about 140 nM; equivalent to no antibody control) and high-EGFR affinity multispecific antibodies (at about 1 nM). Further, this demonstrates a positive correlation between EGFR target affinity and the observed level of antibody clearance. Once again, these findings highlight the direct, graduated correlate between multispecific antibody affinity to EGFR and EGFR mediated internalization for molecules ranging from about 1 nM to about 140 nM to EGFR target. The results are shown in FIG. 38C and tabulated in FIG. 38D.

Example 17: Impact of EGFR Affinity on Multispecific Antibody Inhibition of EGF Ligand Binding and Tumour Cell Proliferation (A)(B) This analysis is focused on the inhibition (or blockade) of the binding of EGF to EGFR-positive tumour cells by the multispecific antibodies (and comparators) described in this invention. Also included in this study—where indicated—is the monospecific RSV IgG comparator (comprising binding domains to RSV protein).

Methods: EGF blockade mediated by EGFR×Vδ1 multispecific antibodies was determined by incubating 3×10^4 EGFR+A431 target cells with antibodies that were serially diluted in PBS to a range of concentrations from 250 nM to 3.2 pM for 30 minutes at 4 degrees. Cells were washed and a final concentration of 40 ug/mL EGF (EGF-AF647, LIFE TECH®) was added per well. Cells were then incubated for 1 hour at 4 degrees C., washed and stained with Live/dead dye (eFluor 520, THERMO FISHER™)) and incubated for a further 20 min at 4 degrees. The cells were washed in FACS buffer and resuspended in CELLFIX™ (BD® sciences) before incubating overnight at 4° C. in the dark. EGF blockage was measured by flow cytometry the following day using the MACSQUANT® Analyzer 10.

Conclusions: The reduction in MFI shown in FIGS. 39A-39B is indicative of increased blockade of EGF binding to EGFR-positive A431 cells. For the multispecific antibodies described, there is a direct correlation between EGFR target affinity and the observed level of EGF blockade. This represents a further example of graduated effects conferred by molecules with affinities to EGFR ranging from about 1 nM to about 140 nM.

(C)(D) This next analysis is focused on inhibition of tumour cell proliferation conferred by multispecific antibodies of this invention.

Method: Briefly, EGFR+A431 cells were seeded into 384-well imaging plates (PERKINELMER®) to give a final seeding density of 2×10^3 target cells per well before incubating overnight at 37° C., 5% CO2. Antibodies were diluted into basal growth media and serially diluted 1:5 before adding to the assay plates to give a final assay concentrations of 500 nM to 0.05 pM. Cells were cultured for 24 hours before staining with Hoechst (1:1000 final, INVITROGEN®) and DRAQ7 (1:300 final, ABCAM®). To determine the numbers of live target cells, confocal images were acquired using an Opera Phenix high content platform capturing nine fields of view at 10× magnification. Live cell counts were quantified base on size, morphology, texture and intensity of live cell stains and the absence of DRAQ7 staining.

Conclusions: The data presented in FIGS. 39C-39D demonstrates that the multispecific antibodies of this invention with higher affinities to EGFR to be the most effective at inhibiting proliferation of the EGFR-positive tumour cells. Again, this demonstrates a clear positive correlation between EGFR target affinity and the observed level of tumour proliferation inhibition. Hence this is another example that highlights graduated effects correlating with affinity towards the EGFR target (ranging from about 1 nM to about 140 nM).

Example 18: Sparing of Healthy EGFR+ Cells-VD1×EGFR Multispecific Antibodies

Methods: The effect of EGFR-Vδ1 bispecific antibodies on EGFR+ target cell cytotoxicity was determined using high content confocal imaging in the Opera Phenix (PERKINELMER®). Briefly, EGFR+A375 cells (melanoma) and HUVEC (human umbilical vein endothelial cells) were seeded into 384-well imaging plates (PERKINELMER®) to give a final seeding density of 5000 target cells per well before incubating overnight at 37° C., 5% CO2. Antibodies were diluted into basal growth media and serially diluted 1:5 before adding to the assay plates to give a final assay concentrations of 1 nM to 0.0005 pM. Expanded skin derived Vδ1 γδ T-cells were detached from tissue culture flasks and re-suspended in basal growth media before adding to the assay plate at 5000 cells per well at a 1:1 Effector: Target ratio. Cells were co-cultured for 24 hours before staining with Hoechst 33342 (1:1000 final, INVITROGEN®) and DRAQ7 (1:300 final, ABCAM®). To determine the numbers of live target cells, confocal images were acquired using an Opera Phenix high content platform capturing nine fields of view at 10× magnification. Live cell counts were quantified base on size, morphology, texture and intensity of live cell stains and the absence of DRAQ7 staining. The results are shown in FIGS. 40A-40C.

Dose titration effects are presented in FIG. 40A. This data helps highlight the innate capability of Vδ1 T cells to discriminate between healthy and malignant cells. A multispecific antibody of this invention redirects Vδ1 T cells to kill EGFR+ tumour cells, whilst 'sparing' healthy cells which express comparable EGFR copy numbers. Tabulated results of FIG. 40A are presented in FIG. 40C.

Representative microscopy images from the experiment described in FIG. 40A demonstrating the T cell-induced cytotoxicity of A375 tumours cells, alongside the 'sparing' of healthy HUVEC cells are presented in FIG. 40B. Images are shown in greyscale, with the cellular nuclei stained with Hoechst 33342.

Example 19: VD1×EGFR Multispecific Antibodies: Dose Response Comparison of ADT1-4-2×FS1-67 with Lower Affinity 'Parent' ADT1-4×FS1-67 (Alias G04 FS1-67)

The inventors have previously demonstrated that the "parental" (non-affinity matured) G04 FS1-67 multispecific antibody confers a variety of desired technical effects in co-cultures comprising Vδ1+ cells and target A431 cells (WO2021032963).

Specifically, the inventors observed that this multispecific antibody can enhance cytoxicity towards A431 cells by greater than 200%. In this series of experiments G04 FS1-67 (SEQ ID NO: 379)—which comprises a lower affinity 'parent' first Vδ1 binding domain (of about 126 nM) and a high affinity (of about 1 nM) EGFR binding—has been compared to an equivalent multispecific antibody but containing an affinity matured variant first Vδ1 binding domain ADT1-4-2 (affinity of about 0.2 nM) (SEQ ID NO: 414).

Method: In this analysis Vδ1+ effector cells are co-incubated with EGFR+ cancer cells as indicated, with the induction of Vδ1 TCR internalization following multispecific antibody engagement measured. Co-cultures were established with $2.5\times10^{\wedge}4$ Vδ1 γδ T-cells added to $2.5\times10^{\wedge}4$ EGFR+ target cells per well in U-bottomed 96-well plates. Prior to addition, Vδ1 γδ T-cells were stained with [0.5 μM] CELLTRACE™ Violet live cell dye for 20 minutes. Final assay antibody concentrations ranged from 10 nM to 0.13 pM. Following incubation for 4 hours at 37° C., 5% CO2, cells were harvested and stained for dead cells (EFLOUR® 780, INVITROGEN®) and Vδ1 TCR (MILTENYI BIOTEC®) surface expression for 20 minutes at 4° C. The cells were washed in FACS buffer and resuspended in CELLFIX™ (BD® sciences) before analysis on a MACSQUANT® Analyser 10 flow cytometer (MILTENYI®).

Conclusions: The results of this comparison are now presented in FIG. 41A (and in tabulated form in FIG. 41B) and concur with discoveries described elsewhere herein. The reduction in MFI (and so TCR downregulation) is presented and this comparison study further confirms that (i) unnaturally higher Vδ1 affinity multispecific antibody of this invention confer enhanced effects when compared to lower affinity variants (in this instance G04 FS1-67) and (ii) these enhanced effects are specifically noticeable in studies with lower copy number TAA target cancers cells such as A375. This data also highlights that once again, for the molecules with lower vd1 affinity (G04 FS1-67 comparator in this instance) no equivalent TCR downregulation effects can be achieved in Vδ1/A375 co-cultures even when 100-fold more of this molecule is added.

Example 20: VD1×EGFR Multispecific Antibodies: Comparison to a CD3×EGFR Multispecific Antibody A comparator multispecific antibody was created wherein
(i) the affinity to EGFR was kept constant at about 0.2 nM and
(ii) the variable domain targeting Vδ1 was substituted with a variable domain specific for CD3ε (derived from OKT3).

This molecule (termed CD3/ADT3-2) was then compared with the Vδ1×EGFR multispecific ADT1-4-2/ADT3-2 (alias ADT1-4-2×LEE) previously described elsewhere herein. One motivation for this comparison was to compare differences in T cell activation conferred by multispecific TCEs (T-cell engagers) which target the Vδ1 TCR versus those which engage via the CD3ε co-receptor. In doing so the inventors have discovered via that multispecific TCEs which engage T-cells the Vδ1 TCR confer distinguishing effects when compared to multispecific TCEs with engage T-cells via CD3ε. These effects are presented in the following set of experiments. Also included in these studies is the multispecific D1.3×FS1-67 control (comprising a 1 nM affinity EGFR second binding domain and first binding domain comprised binding domain to chicken lysozyme).

(A)(B) Differentiation to CD3×EGFR multispecific antibody; Impact of T cell target receptor on Vδ1 TCR and CD3ε downregulation. This following experiment determines how targeting different T cell receptors (Vδ1 or CD3ε) impacts the induction of Vδ1 TCR internalization following multispecific antibody engagement.

Method: A range of T cell populations were assayed as indicated in the key shown in FIG. 42A. These included PBMCs and purified Vδ1 γδ T-cells isolated either from skin tissue or directly from peripheral blood. Co-cultures were established as above with 2×10^4 T-cells added to 2×10^4 A375 EGFR+A375 tumour cells per well in U-bottomed 96-well plates. Antibodies at final concentrations of 1 nM were then added and cultures incubated for 4 at 37° C., 5% CO2. Cells were harvested and stained for dead cells (EFLOUR® 780, INVITROGEN®), Vδ1 TCR (MILTENYI®), CD3ε (MILTENYI®) surface expression for 20 minutes at 4° C. The cells were washed in FACS buffer and resuspended in CELLFIX™ (BD® sciences) before analysis on a MACSQUANT® Analyser 10 flow cytometer (MILTENYI®).

Conclusions: The reduction in MFI is presented in FIG. 42A. Remarkably, we observed more potent TCR down-regulation via antibody engagement of the TCR complex via Vδ1 than via CD3ε, as demonstrated with Vδ1 T-cells populations purified from both the skin and the peripheral blood. Conversely, T-cell engagement via CD3ε induced more potent CD3 down-regulation in PBMCs which contain only a minority population of Vδ1 cells (0.08% in this donation). The marked effect of CD3-based TCEs in PBMCs highlights the sledgehammer approach of this conventional strategy. Specifically, CD3-based TCEs will affect all CD3+ cells present in PBMCs inclusive of Tregs, CD4+ and CD8+ T-Cells. By contrast multispecific antibodies of this invention which engage T-cells via a first Vδ1 binding domain are selectively only for the highly desirable Vδ1+CD3 subset of cells typically more prevalent in tissues than blood.

(B) Impact of T cell target receptor on Vδ1 TCR down-regulation. Tabulated results of FIG. 42A are presented in FIG. 42B, highlighting the superior induction of TCR down-regulation by directly targeting Vδ1 TCR with a multispecific versus targeting this complex via CD3ε co-receptor.

(C) Impact of T cell target receptor on CD38 downregulation. Tabulated results of FIG. 42A are presented in FIG. 42C, highlighting the more pronounced impact of the CD3-based TCE on CD3 levels; particularly in unfractionated PBMCs.

(D)(E) Impact on multispecific cytolytic function towards EGFR+ cancer cells. This following experiment determines how engaging different T cell receptors (Vδ1 or CD3ε) impacts the stimulation of T cell populations to lyse tumour target cells.

Method: As previously, a range of T cell populations were evaluated including PBMC, or purified γδ T-cells isolated from skin tissue or directly from peripheral blood. Cultures were established by seeding 4×10^3 A375 EGFR+A375 tumour cells per well in 384-well CellCarrier Ultra plates (PERKINELMER®). Varying quantities of T-cells were added to vary effector-target ratios between 10 and 0.08. Antibodies at final concentrations of 1 nM were then added and cultures incubated for 24 at 37° C., 5% CO2. Cells were stained with Hoechst 33342 (INVITROGEN®) and for dead cells (DRAQ7, ABCAM®) for 1 hour at 37° C. and imaged on an Opera Phenix system (PERKINELMER®). The quantity of viable tumour cells was determined using a linear regression model (Harmony 4.9) based on size, morphology, texture and intensity of live cell stains and the absence of DRAQ7 staining.

Figures 42D, 42E:
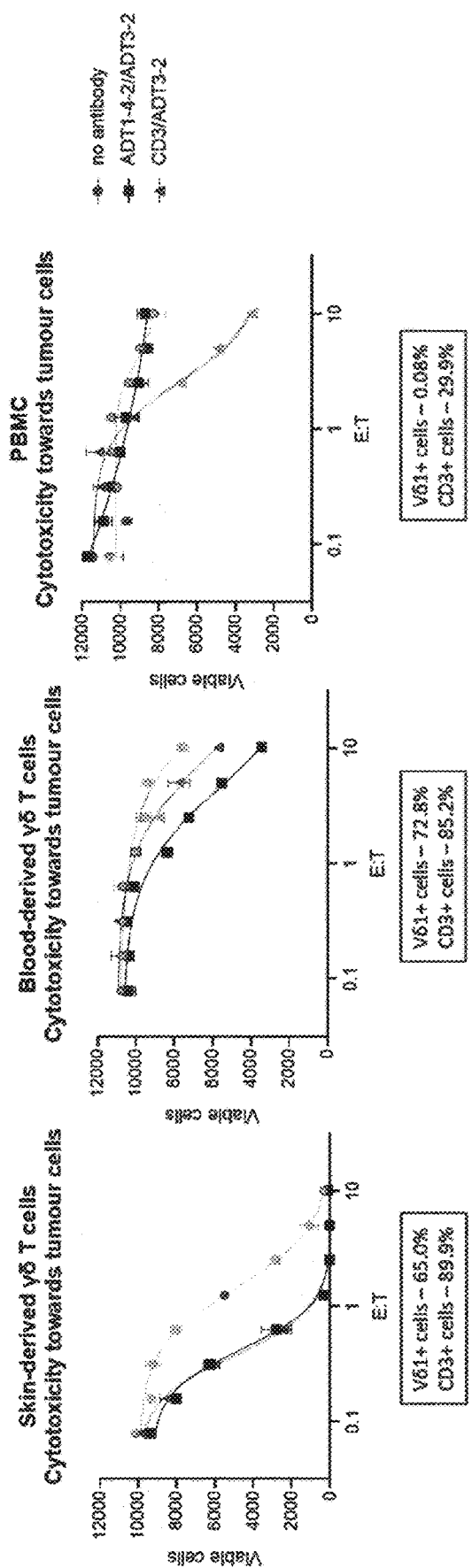
Figure 42F:
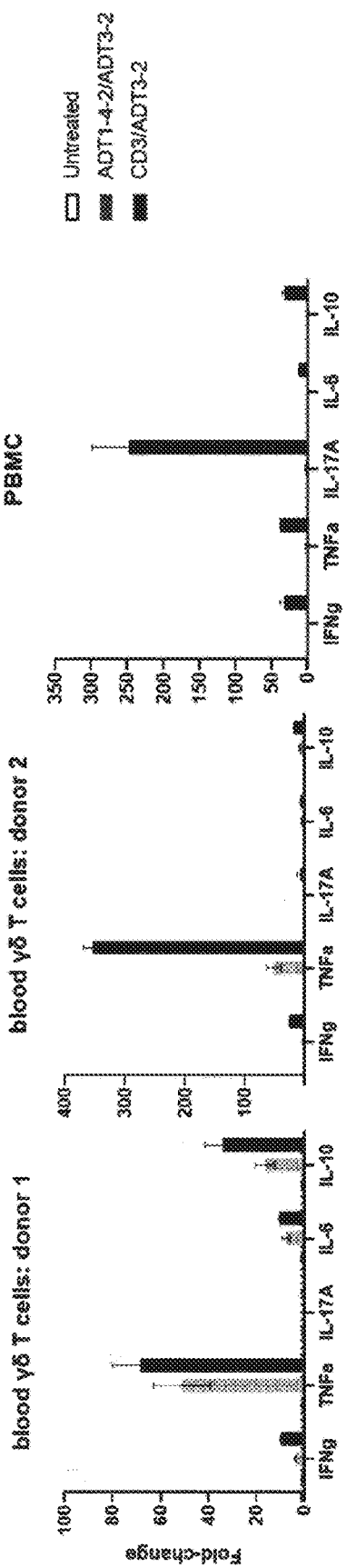
Figure 42G:
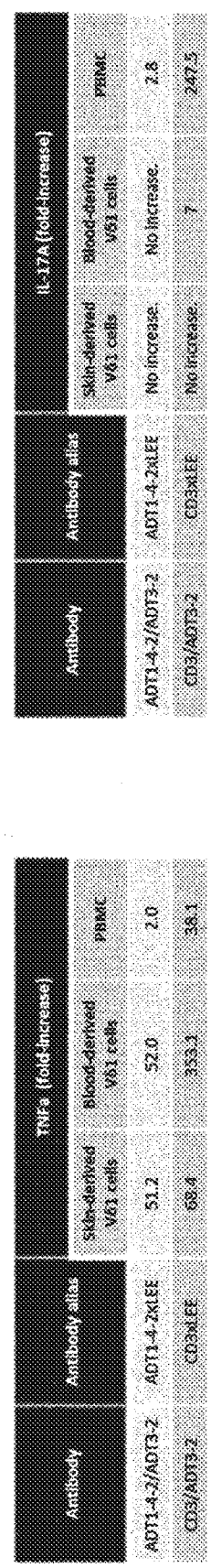
Figures 42H, 42I:
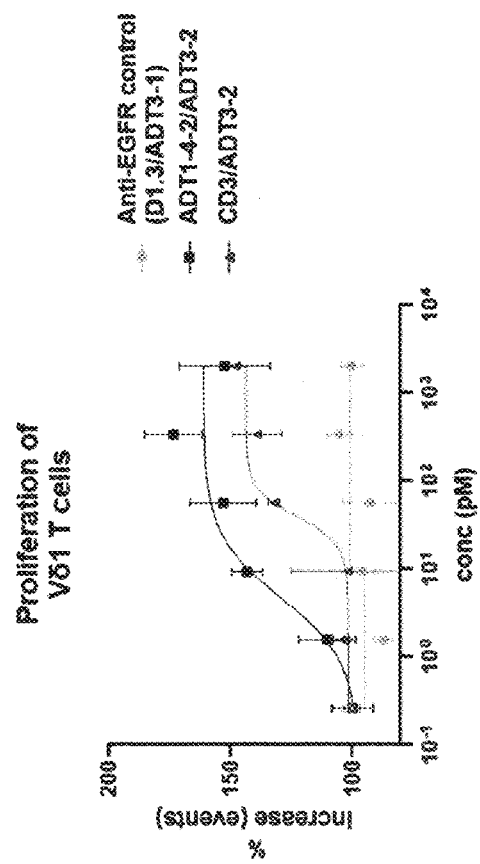

Conclusions: The data presented in FIG. 42D demonstrates the unique ability of the Vδ1-targeted multispecific antibody to specifically and only redirect Vδ1 T cell population to kill EGFR+ tumour cells. This contrasts with CD3-based TCEs which function more promiscuously as demonstrated by the observation here that such TCEs also re-direct unfractionated PBMCs towards EGFR+ cells. The tabulated results of FIG. 42D are presented in FIG. 42E. This further highlights the superior specificity of Vδ1-based TCEs versus CD3-based TCEs.

(F) Impact on induced cytokine secretion by activated T cells. This following experiment determines how targeting different T cell receptors (Vδ1 or CD3E) or target populations impacts the cytokine secretion profile of activated T cells.

Method: A range of T cell populations were assayed including PBMC, or purified γδ T-cells directly from the peripheral blood of two healthy donors. Co-cultures were established as above with 2×10^4 T-cells added to 2×10^4 A375 EGFR+A375 tumour cells per well in U-bottomed 96-well plates. Antibodies at final concentrations of 1 nM were then added and cultures incubated for 48 h at 37° C., 5% CO2. Supernatants were harvested, cells removed, and cytokine concentrations determined using a LEGENDplex cytokine beads array kit (BIOLEGEND®, CA, USA).

Conclusions: The data presented in FIGS. 42F-42G demonstrates significant quantitative and qualitative differences between the specific activation of Vδ1+ T cells and a wider activation of all CD3+ T cells within the unfractionated PBMCs. One striking difference is the 248-fold increase in the IL-17A levels induced only by CD3-based TCEs in PBMCs. By contrast, γδ T-cells stimulated with either the CD3-based or Vδ1-based TCEs do not produce IL-17A. IL17A is a cytokine which can enhance tumour growth and dampen the anti-cancer immune responses. This highlights the unique cytokine secretion profile of the Vδ1+ T-cell subset. Additionally, in all T cell populations, the CD3-based TCE induced significantly higher levels of many cytokines-most notably TNFα. Again, this highlights the less tailored, more sledgehammer like effects conferred by CD3-based TCEs involving more global induction effects on CD3+ cells.

(H) Impact on proliferation of tissue-resident Vδ1+ cells. This next analysis is focused on the induction of proliferation of Vδ1+ cells conferred by multispecific antibodies of this invention.

Method: Co-cultures were established as above with 3×10^4 Vδ1 γδ T-cells added to 1.5×10^4 EGFR+ target cells per well in U-bottomed 96-well plates. Prior to addition, target cells were stained with [0.5 μM] CELLTRACE™ Violet live cell dye for 20 minutes. Final assay multispecific antibody concentrations ranged from 2 nM to 0.25 pM. The cells were incubated for 5 or 7 days at 37° C., 5% CO2. Complete media with the addition of cytokines (IL-2, IL-15, IL-4 and IL-21; need units) were added at day 3 and day 5. Cells were washed and stained for dead cells (EFLOUR® 780, INVITROGEN®) for 20 minutes at 4° C. The cells were washed in FACS buffer and resuspended in CELLFIX™ (BD® sciences). The number of events was measured by flow cytometry the following day using the MACSQUANT® Analyzer 10.

Conclusions: This study demonstrated that the Vδ1-based TCE is demonstrably superior at inducing the proliferation of Vδ1 T cells relative to the equivalent CD3-based TCE with the Vδ1 bispecific inducing proliferation at 10-fold lower doses whilst also exhibiting more pronounced effects at saturating concentrations. See FIG. 42H and FIG. 42I which highlight the increased proliferative effects conferred by antibody-mediated stimulation of Vδ1 T cells when compared to stimulation via CD3ε.

The invention claimed is:

1. A multispecific antibody comprising:
a variable delta 1 (Vδ1) chain of a γδ T cell receptor (TCR) binding site, comprising:
   (i) a VHCDR1, a VHCDR2 and a VHCDR3 comprising the amino acid sequences of SEQ ID NO: 130, 131 and 133, respectively, and a VLCDR1, a VLCDR2 and a VLCDR3 comprising the amino acid sequences of SEQ ID NOs: 79, 80 and 83, respectively;
   (ii) a VHCDR1, a VHCDR2 and a VHCDR3 comprising the amino acid sequences of SEQ ID NO: 51, 53, and 68, respectively; and a VLCDR1, VLCDR2, and a VLCDR3 of SEQ ID NO: 79, 80 and 95, respectively; or
   (iii) a VHCDR1, a VHCDR2 and a VHCDR3 comprising the amino acid sequences of SEQ ID NO: 130, 131 and 136, respectively, and a VLCDR1, a VLCDR2 and a VLCDR3 comprising the amino acid sequences of SEQ ID NOs: 79, 80 and 86, respectively;
and
a fragment crystallizable (Fc) region that comprises an epidermal growth factor receptor (EGFR) binding site in the CH3 domain of the Fc region in which, according to EU antibody numbering:
   a. residues 359 to 362 comprise EEGP (SEQ ID NO: 523), residues 384 to 386 comprise TYG (SEQ ID NO:511), and residues 413 to 419 comprise SYWRWYK (SEQ ID NO: 512);
   b. residues 359 to 362 comprise EEGP (SEQ ID NO: 523), and residues 413 to 419 comprise SYWRWYK (SEQ ID NO: 512);
   c. residues 359 to 362 comprise EEGP (SEQ ID NO: 523) and residues 413 to 415 comprise SYW (SEQ ID NO: 533);
   d. residues 359 to 362 comprise EEGP (SEQ ID NO: 523), residues 384 to 386 comprise TYG (SEQ ID NO: 511), and residues 413 to 415 comprise SYW (SEQ ID NO: 533);
   e. residues 358 to 361, 361.1 and 362 comprise LDEGGP (SEQ ID NO: 542), residues 384 to 386 comprise TYG (SEQ ID NO: 511), and residues 413 to 419 comprise SYWRWVK (SEQ ID NO: 543);
   f. residues 384 to 386 comprise TYG (SEQ ID NO: 511), and residues 413 to 419 comprise SYWRWYK (SEQ ID NO: 512);
   g. residues 358 to 362 comprise TDDGP (SEQ ID NO: 560), residues 384 to 386 comprise TYG (SEQ ID NO: 511), and residues 413 to 419 comprise SYWRWYK (SEQ ID NO: 512); or
   h. residues 358 to 362 comprise TESGP (SEQ ID NO: 553), residues 384 to 386 comprise KFG (SEQ ID NO: 554), residues 413 to 421 comprise SNLRWTKGH (SEQ ID NO: 555), and residue 378 is valine.

2. The multispecific antibody of claim 1, wherein the EGFR binding site is in the CH3 domain in which, according to EU antibody numbering:
   a. residues 355 to 362 form an AB loop comprising RDELEEGP (SEQ ID NO: 524) and residues 413 to 422 form an EF loop comprising SYWRWYKGNV (SEQ ID NO: 515);

b. residues 355 to 362 form an AB loop comprising RDELEEGP (SEQ ID NO: 524), residues 383 to 391 form a CD loop comprising STYGPENNY (SEQ ID NO: 514) and residues 413 to 422 form an EF loop comprising SYWRWYKGNV (SEQ ID NO: 515);

c. residues 355 to 362 form an AB loop comprising RDELEEGP (SEQ ID NO: 524), residues 383 to 391 form a CD loop comprising SNGQPENNY (SEQ ID NO: 525) and residues 413 to 422 form an EF loop comprising SYWRWYKGNV (SEQ ID NO: 515);

d. residues 355 to 362 form an AB loop comprising RDELEEGP (SEQ ID NO: 524) residues 413 to 422 form an EF loop comprising SYWRWQQGNV (SEQ ID NO: 534);

e. residues 355 to 362 form an AB loop comprising RDELEEGP (SEQ ID NO: 524), residues 383 to 391 form a CD loop comprising STYGPENNY (SEQ ID NO: 514) and residues 413 to 422 form an EF loop comprising SYWRWQQGNV (SEQ ID NO: 534);

f. residues 355 to 362 form an AB loop comprising RDELDEGGP (SEQ ID NO: 544), residues 383 to 391 form a CD loop comprising STYGPENNY (SEQ ID NO: 514), and residues 413 to 422 form an EF loop comprising SYWRWVKGNV (SEQ ID NO: 545);

g. residues 355 to 362 form an AB loop comprising RDELTKNQ (SEQ ID NO: 513), residues 383 to 391 form a CD loop comprising STYGPENNY (SEQ ID NO: 514) and residues 413 to 422 form an EF loop comprising SYWRWYKGNV (SEQ ID NO: 515);

h. residues 355 to 362 form an AB loop comprising RDETDDGP (SEQ ID NO: 561), residues 383 to 391 according to form a CD loop comprising STYGPENNY (SEQ ID NO: 514), residues 413 to 422 form an EF loop comprising SYWRWYKGNV (SEQ ID NO: 515); or i. residues 355 to 362 form an AB loop comprising RDETESGP (SEQ ID NO: 556), residues 383 to 391 form a CD loop comprising SKFGPENNY (SEQ ID NO: 557), residues 413 to 422 form an EF loop comprising SNLRWTKGHV (SEQ ID NO: 558) and residue 378 is valine.

3. The multispecific antibody of claim 1, wherein the EGFR binding site CH3 domain does not comprise a CH3 domain in which, according to EU antibody numbering:

a. residues 358 to 362 comprise TDDGP (SEQ ID NO: 560), residues 384 to 386 comprise TYG (SEQ ID NO: 511), and residues 413 to 419 comprise SYWRWYK (SEQ ID NO: 512); or b. residues 355 to 362 form an AB loop comprising RDETDDGP (SEQ ID NO: 561), residues 383 to 391 form a CD loop comprising STYGPENNY (SEQ ID NO: 514), residues 413 to 422 form an EF loop comprising SYWRWYKGNV (SEQ ID NO: 515).

4. The multispecific antibody of claim 1, wherein the CH3 domain is a human IgG CH3 domain.

5. The multispecific antibody of claim 4, wherein the Fc region is a human IgG Fc region.

6. The multispecific antibody of claim 1, wherein the antibody is Fc enabled.

7. The multispecific antibody of claim 1, wherein the Vδ1 TCR binding site is in a Fab region of the multispecific antibody.

8. The multispecific antibody of claim 7, wherein the Fab region comprises an amino acid residue other than serine at position 74, according to the IMGT numbering system.

9. A pharmaceutical composition comprising the multispecific antibody of claim 1 and a pharmaceutically acceptable diluent or carrier.

10. A method of treating an EGFR expressing cancer in a subject, comprising administering to the subject the multispecific antibody of claim 1.

11. The multispecific antibody of claim 7, wherein the Vδ1 TCR binding site comprises the VHCDR1, the VHCDR2 and the VHCDR3 comprising the amino acid sequences of SEQ ID NO: 130, 131 and 133, respectively, and the VLCDR1, the VLCDR2 and the VLCDR3 comprising the amino acid sequences of SEQ ID NOs: 79, 80 and 83, respectively.

12. The multispecific antibody of claim 1, wherein the Vδ1 TCR binding site comprises the VHCDR1, the VHCDR2 and the VHCDR3 comprising the amino acid sequences of SEQ ID NO: 130, 131 and 136, respectively, and the VLCDR1, the VLCDR2 and the VLCDR3 comprising the amino acid sequences of SEQ ID NOs: 79, 80 and 86, respectively.

13. The multispecific antibody of claim 1, wherein the Vδ1 TCR binding site comprises the VHCDR1, the VHCDR2 and the VHCDR3 comprises the amino acid sequences of SEQ ID NO: 51, 53 and 68, respectively, and the VLCDR1, the VLCDR2 and the VLCDR3 comprises the amino acid sequences of SEQ ID NOs: 79, 80 and 95, respectively.

14. The multispecific antibody of claim 8, wherein the residue at position 74 according to the IMGT numbering system is a leucine residue.

* * * * *